(12) United States Patent
Iwaki et al.

(10) Patent No.: US 9,199,959 B2
(45) Date of Patent: Dec. 1, 2015

(54) HIV REPLICATION INHIBITOR

(71) Applicant: Shionogi & Co., Ltd., Osaka-shi (JP)

(72) Inventors: Tsutomu Iwaki, Toyonaka (JP); Kenji Tomita, Toyonaka (JP)

(73) Assignee: SHIONOGI & CO., LTD., Osaka-shi (JP)

(*) Notice: Subject to any disclaimer, the term of this patent is extended or adjusted under 35 U.S.C. 154(b) by 0 days.

(21) Appl. No.: 14/351,395

(22) PCT Filed: Oct. 25, 2012

(86) PCT No.: PCT/JP2012/077544
§ 371 (c)(1),
(2) Date: Apr. 11, 2014

(87) PCT Pub. No.: WO2013/062028
PCT Pub. Date: May 2, 2013

(65) Prior Publication Data
US 2014/0249306 A1    Sep. 4, 2014

(30) Foreign Application Priority Data

Oct. 25, 2011 (JP) ................................. 2011-233817
Dec. 1, 2011 (JP) ................................. 2011-263353

(51) Int. Cl.
*C07C 69/74* (2006.01)
*C07D 311/58* (2006.01)
*C07C 275/42* (2006.01)
*C07C 205/56* (2006.01)
(Continued)

(52) U.S. Cl.
CPC ............ *C07D 311/58* (2013.01); *C07C 205/56* (2013.01); *C07C 229/42* (2013.01); *C07C 233/54* (2013.01); *C07C 233/63* (2013.01); *C07C 233/81* (2013.01); *C07C 255/59* (2013.01); *C07C 271/28* (2013.01); *C07C 275/42* (2013.01); *C07C 311/10* (2013.01); *C07C 311/14* (2013.01); *C07C 311/21* (2013.01); *C07C 317/48* (2013.01); *C07D 215/14* (2013.01); *C07D 215/227* (2013.01); *C07D 235/26* (2013.01); *C07D 265/36* (2013.01); *C07D 277/82* (2013.01); *C07D 307/79* (2013.01); *C07D 307/83* (2013.01); *C07D 307/88* (2013.01); *C07D 307/89* (2013.01); *C07D 311/74* (2013.01); *C07D 317/60* (2013.01); *C07D 319/12* (2013.01); *C07D 319/16* (2013.01); *C07D 319/18* (2013.01); *C07D 319/20* (2013.01); *C07D 405/04* (2013.01); *C07D 405/10* (2013.01); *C07D 405/12* (2013.01); *C07D 405/14* (2013.01); *C07D 407/12* (2013.01); *C07D 409/12* (2013.01); *C07D 413/10* (2013.01); *C07D 413/12* (2013.01); *C07D 417/12* (2013.01); *C07D 491/06* (2013.01); *C07C 2101/02* (2013.01); *C07C 2101/08* (2013.01); *C07C 2101/14* (2013.01); *C07C 2101/16* (2013.01); *C07C 2101/18* (2013.01)

(58) Field of Classification Search
CPC .................................................... A61K 31/192
USPC ............................................................ 560/10
See application file for complete search history.

(56) References Cited

U.S. PATENT DOCUMENTS 3,978,071 A * 8/1976 Nakanishi et al. ............. 546/121
6,849,605 B1 * 2/2005 Shapiro .......................... 514/3.8
(Continued)

FOREIGN PATENT DOCUMENTS

EP        2 374 790 A1    10/2011
EP        2 402 305 A1     1/2012
(Continued)

OTHER PUBLICATIONS

Bradsher Journal of the American Chemical Society (1954), 76, 4140-3.*
STN Document No. 71:38611, Abstract of Duerr et al. Angewandte Chemie, International Edition in English (1969), 8(6), 446-7.*
Engle Journal of the American Chemical Society (2011), 133(45), 18183-18193.*
Bradsher Journal of Organic Chemistry (1957), 22, 1738-40.*
Duerr, Angewandte Chemie, International Edition in English (1969), 8(6), 446-7.*
Iwamura, Journal of the American Chemical Society (1974), 96(8), 2652-4.*
Kuendig, Organometallics (1993), 12(9), 3724-37.*
Grell, Journal of Medicinal Chemistry (1998), 41(26),5219-5246.*
(Continued)

*Primary Examiner* — Nizal Chandrakumar
(74) *Attorney, Agent, or Firm* — Oblon, McClelland, Maier & Neustadt, L.L.P.

(57) ABSTRACT

The present invention provides a novel compound having an antiviral action, in particular, an HIV replication inhibiting action, as well as a pharmaceutical composition, in particular, an anti-HIV agent.

Formula (I):

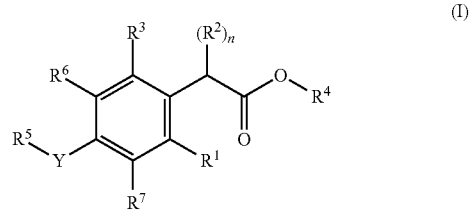

wherein, a broken line means the presence or absence of a bond; $R^1$ is substituted or unsubstituted alkyl etc., $R^2$ is substituted or unsubstituted alkyloxy etc.; n is 1 or 2; $R^3$ is a substituted or unsubstituted aromatic carbocyclic group; $R^4$ is a hydrogen atom etc.; $R^5$ is a substituted or unsubstituted aromatic carbocyclic group etc.; Y is a single bond etc.; $R^6$ is substituted or unsubstituted alkyl; $R^7$ is —Z—$R^{71}$ etc.; Z is —$NR^{72}$—CO— etc.; $R^{71}$ is substituted or unsubstituted alkyl etc.; $R^{72}$ is a hydrogen atom etc.

12 Claims, No Drawings

(51) Int. Cl.

| | | |
|---|---|---|
| C07C 311/14 | (2006.01) | |
| C07C 233/63 | (2006.01) | |
| C07C 233/81 | (2006.01) | |
| C07C 255/59 | (2006.01) | |
| C07C 271/28 | (2006.01) | |
| C07C 311/10 | (2006.01) | |
| C07C 311/21 | (2006.01) | |
| C07C 317/48 | (2006.01) | |
| C07C 229/42 | (2006.01) | |
| C07C 233/54 | (2006.01) | |
| C07D 405/14 | (2006.01) | |
| C07D 215/14 | (2006.01) | |
| C07D 215/227 | (2006.01) | |
| C07D 311/74 | (2006.01) | |
| C07D 317/60 | (2006.01) | |
| C07D 319/12 | (2006.01) | |
| C07D 319/16 | (2006.01) | |
| C07D 235/26 | (2006.01) | |
| C07D 405/04 | (2006.01) | |
| C07D 405/10 | (2006.01) | |
| C07D 405/12 | (2006.01) | |
| C07D 407/12 | (2006.01) | |
| C07D 409/12 | (2006.01) | |
| C07D 413/10 | (2006.01) | |
| C07D 413/12 | (2006.01) | |
| C07D 491/06 | (2006.01) | |
| C07D 265/36 | (2006.01) | |
| C07D 277/82 | (2006.01) | |
| C07D 307/79 | (2006.01) | |
| C07D 307/83 | (2006.01) | |
| C07D 307/88 | (2006.01) | |
| C07D 307/89 | (2006.01) | |
| C07D 319/18 | (2006.01) | |
| C07D 319/20 | (2006.01) | |
| C07D 417/12 | (2006.01) | |

(56) References Cited

U.S. PATENT DOCUMENTS

| 7,737,166 | B2* | 6/2010 | Kawakami et al. | 514/375 |
|---|---|---|---|---|
| 2009/0143353 | A1 | 6/2009 | Kawakami et al. | |
| 2009/0312323 | A1 | 12/2009 | Heemskerk et al. | |
| 2011/0082137 | A1* | 4/2011 | Giovannini et al. | 514/234.2 |
| 2012/0083495 | A1 | 4/2012 | Heemskerk et al. | |
| 2013/0203727 | A1* | 8/2013 | Babaoglu et al. | 514/210.01 |
| 2013/0210801 | A1* | 8/2013 | Babaoglu et al. | 514/210.21 |
| 2014/0031338 | A1* | 1/2014 | Chasset et al. | 514/211.05 |

FOREIGN PATENT DOCUMENTS

| JP | WO 2005035503 | * | 4/2005 | C07D 223/04 |
|---|---|---|---|---|
| JP | WO 2007029629 | * | 5/2007 | C07D 223/04 |
| JP | 2009-530306 A | | 8/2009 | |
| JP | 2010055911 | * | 5/2010 | C07C 233/11 |
| JP | 2010-195727 A | | 9/2010 | |
| WO | WO 2007/020936 A1 | | 2/2007 | |
| WO | WO 2007056366 | * | 5/2007 | C07D 223/04 |
| WO | WO 2007056497 | * | 5/2007 | C07D 223/04 |
| WO | WO 2007/131350 A1 | | 11/2007 | |
| WO | WO 2007146838 | * | 12/2007 | C07D 223/04 |
| WO | WO 2008/071587 A2 | | 6/2008 | |
| WO | WO 2008/071587 A3 | | 6/2008 | |
| WO | WO 2009/052319 A1 | | 4/2009 | |
| WO | WO 2009/062285 A1 | | 5/2009 | |
| WO | WO 2009/062288 A1 | | 5/2009 | |
| WO | WO 2009/062289 A1 | | 5/2009 | |
| WO | WO 2009/062308 A1 | | 5/2009 | |
| WO | WO 2009073620 | * | 6/2009 | |
| WO | WO 2010/055911 A1 | | 5/2010 | |
| WO | WO 2010/130034 A1 | | 11/2010 | |
| WO | WO 2010/130842 A1 | | 11/2010 | |
| WO | WO 2011/015641 A1 | | 2/2011 | |
| WO | WO 2011/076765 A1 | | 6/2011 | |
| WO | WO 2012/003497 A1 | | 1/2012 | |
| WO | WO 2012/003498 A1 | | 1/2012 | |
| WO | WO 2012/033735 A1 | | 3/2012 | |
| WO | WO 2012/066442 A1 | | 5/2012 | |
| WO | WO 2012/102985 A1 | | 8/2012 | |
| WO | WO 2012/137181 A1 | | 10/2012 | |
| WO | WO 2012/140243 A1 | | 10/2012 | |
| WO | WO 2013/103724 A1 | | 7/2013 | |
| WO | WO 2013/103788 A2 | | 7/2013 | |
| WO | WO 2013/103788 A3 | | 7/2013 | |
| WO | WO 2013/159064 A1 | | 10/2013 | |

OTHER PUBLICATIONS

Faigl, Synthetic Communications (2006), 36(19), 2841-2849.*
Newman Journal of the American Chemical Society (1938), 60, 2947-51.*
Newman Journal of Organic Chemistry (1944), 9, 518-28.*
J. Pharm. Sci. 89, 145-54 (2000) (p. 146, left column).*
International Preliminary Report on Patentability and Written Opinion issued May 8, 2014 in PCT/JP2012/077544 (submitting English translation only).
W. Dobler, "Die kombination von flash-chromatographie and MPLC—eine schnelle methode zur trennung präparativer mengen, The combination of flash-chromatography and mplc—a rapid technique for separations on a preparative scale", GIT Fachzeitschrift fuer das Laboratorium, vol. 27, 1983, pp. 1078-1080 (with English summary).
Suciati, et al., "Structures and anatomical distribution of oxygenated diterpenes in the Australian nudibranch Chromodoris reticulate", Australian Journal of Chemistry, vol. 64, 2011, pp. 757-765.
V. Manriquez, et al., "Structure of membranolide, a diterpene from the Antarctic sponge Dendrilla membranosa", Acta Crystallographica, Section C, vol. 46, 1990, pp. 2486-2487.
Sung-eun Yoo, et al., "Total synthesis of (±)-membranolide", Synlett, No. 11, 1990, pp. 697-699.
Tadeusz F. Molinski, et al., "Metabolites of the Antarctic sponge Dendrilla membranosa", Journal of Organic Chemistry, vol. 52, 1987, pp. 296-298.
Sridevi Ankisetty, et al., "Further membranolide diterpenes from the Antarctic sponge Dendrilla membranosa", Journal of Natural Products, vol. 67, 2004, pp. 1172-1174.

* cited by examiner

HIV REPLICATION INHIBITOR

CROSS REFERENCE TO RELATED APPLICATIONS

The present application is a 35 U.S.C. §371 national stage patent application of International patent application PCT/JP2012/077544, filed on Oct. 25, 2012, published as WO/2013/062028 on May 2, 2013, the text of which is incorporated by reference, and claims the benefit of the filing date of Japanese application nos. 2011-233817, filed on Oct. 25, 2011, and 2011-263353, filed on Dec. 1, 2011, the text of each of which is also incorporated by reference.

TECHNICAL FIELD

The present invention relates to a novel compound having an antiviral action, in more detail, an anti-HIV drug.

BACKGROUND ART

Among viruses, human immunodeficiency virus (hereinafter abbreviated as HIV) that is a type of retrovirus is known to be a cause of acquired immunodeficiency syndrome (hereinafter abbreviated as AIDS). As a therapeutic agent of the AIDS, reverse transcriptase inhibitors (AZT, 3TC, etc.), protease inhibitors (indinavir, etc.), and integrase inhibitors (raltegravir, etc.) are mainly used so far, but problems of side effects such as kidney problems and emergence of resistant viruses have been found, and development of anti-HIV drugs having a mechanism of action different from those is expected.

In addition, in the treatment of AIDS, because resistant viruses easily emerge, it is reported that, multiple drug therapy is currently effective. As the anti-HIV drugs, three types of reverse transcriptase inhibitors, protease inhibitors and integrase inhibitors have been used clinically, but the agents having the same mechanism of action often exhibit cross-resistance, or merely show additive effects, and there is a demand for the development of anti-HIV drugs having a different mechanism of action.

In Patent Document 1, a compound having a carboxymethyl benzene skeleton as an HIV reverse transcriptase inhibitor has been reported. In addition, as HIV replication inhibitors relatively similar to that of the present invention in structure, carboxymethyl pyridine derivatives (Patent Documents 2 to 8), carboxymethyl pyrimidine derivatives (Patent Documents 9 to 11), phenylacetic acid derivatives (Patent Documents 12 to 13), a tricyclic carboxymethyl pyridine derivative (Patent Document 14), a carboxymethyl pyridone derivative (Patent Document 15), a substituted five-membered ring compound (Patent Document 16), and a substituted six-membered ring compound (Patent Document 17) have been reported.

Patent Document 18 and Non-Patent Document 1 describe compounds relatively similar to that of the present invention in structure, but each document relates to an antiepileptic drug and an analytical technique. Non-Patent Documents 2 to 6 describe compounds relatively similar to that of the present invention in structure, but all the documents relate to antibiotics.

Further, the patent applications for HIV replication inhibitors (Japanese Patent Application No. 2011-146118, Japanese Patent Application No. 2011-176630, Japanese Patent Application No. 2012-095869) have been filed by the applicants.

PRIOR ART DOCUMENTS

Patent Documents

Patent Document 1: WO 2008/071587
Patent Document 2: WO 2007/131350
Patent Document 3: WO 2009/062285
Patent Document 4: WO 2009/062288
Patent Document 5: WO 2009/062289
Patent Document 6: WO 2009/062308
Patent Document 7: WO 2010/130034
Patent Document 8: WO 2010/130842
Patent Document 9: WO 2011/015641
Patent Document 10: WO 2011/076765
Patent Document 11: WO 2012/033735
Patent Document 12: WO 2012/003497
Patent Document 13: WO 2012/003498
Patent Document 14: WO 2012/066442
Patent Document 15: WO 2012/102985
Patent Document 16: WO 2012/137181
Patent Document 17: WO 2012/140243
Patent Document 18: WO 2010/055911

Non-Patent Documents

Non-Patent Document 1: GIT Fachzeitschrift fuer das Laboratorium, vol. 27,
No. 12, pages 1078 to 1080 (1983)
Non-Patent Document 2: Australian Journal of Chemistry, vol. 64, No. 6, pages 757 to 765 (2011)
Non-Patent Document 3: Acta Crystallographica, section C, vol. C46, No. 12, pages 2486 to 2487, (1990)
Non-Patent Document 4: Synlett, No. 11, pages 697 to 699, (1990)
Non-Patent Document 5: Journal of Organic Chemistry, vol. 52, No. 2, pages 296 to 298 (1987)
Non-Patent Document 6: Journal of Natural Products, vol. 67, No. 7, pages 1172 to 1174 (2004)

SUMMARY OF THE INVENTION

Problems to be Solved by the Invention

An object of the present invention is to provide a novel compound having antiviral activity. More preferably, the present invention provides an anti-HIV drug having an inhibitory effect on HIV replication.

Solutions to the Problems

As a result of intensive studies, the present inventors have found a novel HIV replication inhibitor. Furthermore, the present inventors have found that the compound of the present invention and a pharmaceutical containing the same are useful as an antiviral drug (examples: an antiretroviral drug, an anti-HIV drug, an anti-HTLV-1 (Human T cell leukemia virus type 1: human T-cell leukemia virus type 1) drug, an anti-FIV (Feline immunodeficiency virus: feline AIDS virus) drug, an anti-SIV (Simian immunodeficiency virus: simian AIDS virus) drug), particularly an anti-HIV drug, an anti-AIDS drug, a therapeutic agent of the related diseases or the like, thereby accomplishing the present invention.

(1) A compound represented by formula (I) or a pharmaceutically acceptable salt thereof:

[Formula I]:

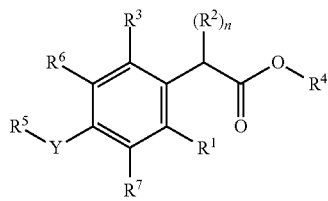

wherein
R$^1$ is halogen, cyano, nitro, or —X—R$^{11}$,
X is a single bond, —O—, —S—, —CO—, —SO$_2$—, —O—CO—, CO—O—, —NR$^{12}$—CO—, —CO—NR$^{12}$—, —NR$^{12}$—CO—O—, —NR$^{12}$—CO—NR$^{13}$—, —NR$^{12}$—SO$_2$—, or —SO$_2$—NR$^{12}$—,
R$^{11}$ is a hydrogen atom, substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group,
R$^{12}$ and R$^{13}$ are each independently a hydrogen atom, substituted or unsubstituted alkyl, substituted or unsubstituted alkenyl, or substituted or unsubstituted alkynyl,
when X is —NR$^{12}$—, —CO—NR$^{12}$—, or —SO$_2$—NR$^{12}$—, R$^{11}$ and R$^{12}$ may be taken together with an adjacent nitrogen atom to form a substituted or unsubstituted aromatic heterocyclic group or a substituted or unsubstituted nonaromatic heterocyclic group,
R$^2$ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, or substituted or unsubstituted alkynylsulfanyl,
n is 1 or 2,
R$^3$ is a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group,
R$^4$ is a hydrogen atom, substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group,
R$^5$ is a hydrogen atom, hydroxy, formyl, carboxy, carbamoyl, carbamoyloxy, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted monoalkylcarbamoyl, substituted or unsubstituted dialkylcarbamoyl, substituted or unsubstituted monoalkylcarbamoyloxy, substituted or unsubstituted dialkylcarbamoyloxy, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclicoxy, substituted or unsubstituted nonaromatic carbocyclicoxy, substituted or unsubstituted aromatic heterocyclicoxy, substituted or unsubstituted nonaromatic heterocyclicoxy, substituted or unsubstituted aromatic carbocyclic sulfanyl, substituted or unsubstituted nonaromatic carbocyclic sulfanyl, substituted or unsubstituted aromatic heterocyclic sulfanyl, substituted or unsubstituted nonaromatic heterocyclic sulfanyl, substituted or unsubstituted aromatic carbocyclic carbonyl, substituted or unsubstituted nonaromatic carbocyclic carbonyl, substituted or unsubstituted aromatic heterocyclic carbonyl, substituted or unsubstituted nonaromatic heterocyclic carbonyl, substituted or unsubstituted aromatic carbocyclic oxycarbonyl, substituted or unsubstituted nonaromatic carbocyclic oxycarbonyl, substituted or unsubstituted aromatic heterocyclic oxycarbonyl, substituted or unsubstituted nonaromatic heterocyclic oxycarbonyl, substituted or unsubstituted aromatic carbocyclic carbamoyl, substituted or unsubstituted nonaromatic carbocyclic carbamoyl, substituted or unsubstituted aromatic heterocyclic carbamoyl, substituted or unsubstituted nonaromatic heterocyclic carbamoyl, or —NR$^{51}$R$^{52}$ (R$^{51}$ and R$^{52}$ are each independently a hydrogen atom, formyl, carbamoyl, carboxy, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkylcarbamoyl, substituted or unsubstituted alkenylcarbamoyl, substituted or unsubstituted alkynylcarbamoyl, substituted or unsubstituted alkyloxycarbonyl, substituted or unsubstituted alkenyloxycarbonyl, substituted or unsubstituted alkynyloxycarbonyl, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclic carbonyl, substituted or unsubstituted nonaromatic carbocyclic carbonyl, substituted or unsubstituted aromatic heterocyclic carbonyl, substituted or unsubstituted nonaromatic heterocyclic carbonyl, substituted or unsubstituted aromatic carbocyclic carbamoyl, substituted or unsubstituted nonaromatic carbocyclic carbamoyl, substituted or unsubstituted aromatic heterocyclic carbamoyl, substituted or unsubstituted nonaromatic heterocyclic carbamoyl, substituted or unsubstituted aromatic carbocyclic oxycarbonyl, substituted or unsubstituted nonaromatic carbocyclic oxycarbonyl, substituted or unsubstituted aromatic heterocyclic oxycarbonyl, or substituted or unsubstituted nonaromatic heterocyclic oxycarbonyl),
Y is a single bond, alkylene, alkenylene, or alkynylene,
when R$^5$ is a hydrogen atom, substituted or unsubstituted alkyl, substituted or unsubstituted alkenyl, or substituted or unsubstituted alkynyl, Y is a single bond,
R$^6$ is a hydrogen atom, halogen, cyano, substituted or unsubstituted alkyl, substituted or unsubstituted alkenyl, substituted or unsubstituted alkynyl, a substituted or unsubstituted nonaromatic carbocyclic group, or substituted or unsubstituted alkyloxy, and
R$^7$ is halogen, cyano, nitro, or —Z—R$^{71}$,
wherein Z is a single bond, —O—, —S—, —NR$^{72}$—, —CO—, —SO$_2$—, —O—CO—, —CO—O—, —NR$^{72}$—CO—, —CO—NR$^{72}$—, —NR$^{72}$—CO—O—, —NR$^{72}$—CO—NR$^{73}$—, —NR$^{72}$—SO$_2$—, or —SO$_2$—NR$^{72}$—,
R$^{71}$ is a hydrogen atom, substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, $R^{72}$ and $R^{73}$ are each independently a hydrogen atom, substituted or unsubstituted alkyl, substituted or unsubstituted alkenyl, or substituted or unsubstituted alkynyl, when Z is —$NR^{72}$—, —CO—$NR^{72}$—, or —$SO_2$—$NR^{72}$—, $R^{71}$ and $R^{72}$ may be taken together with an adjacent nitrogen atom to form a substituted or unsubstituted aromatic heterocyclic group or a substituted or unsubstituted nonaromatic heterocyclic group, wherein $R^1$ and $R^7$ may be taken together with an adjacent atom to form ring A, ring A is an aromatic carbocyclic ring, a nonaromatic carbocyclic ring, an aromatic heterocyclic ring, or a nonaromatic heterocyclic ring, and may be substituted by 1 to 7 $R^4$s, $R^4$ is each independently halogen, cyano, nitro, oxo, or —$X^4$—$R^{41}$, wherein $X^4$ is a single bond, —O—, —S—, —$NR^{42}$—, —CO—, —$SO_2$—, —O—CO—, —CO—O—, —$NR^{42}$—CO—, —CO—$NR^{42}$—, —$NR^{42}$—CO—O—, —CO—O—$NR^{42}$—, —O—CO—$NR^{42}$—, —$NR^{42}$—O—CO—, —CO—$NR^{42}$—O—, —O—$NR^{42}$—CO—, —$NR^{42}$—CO—$NR^{43}$—, —$NR^{42}$—$SO_2$—, or —$SO_2$—$NR^{42}$—, $R^{41}$ is a hydrogen atom, substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, $R^{42}$ and $R^{43}$ are each independently a hydrogen atom, substituted or unsubstituted alkyl, substituted or unsubstituted alkenyl, or substituted or unsubstituted alkynyl, when $X^4$ is —$NR^{42}$—, —CO—$NR^{42}$—, CO—O—$NR^{42}$—, —O—CO—$NR^{42}$—, or —$SO_2$—$NR^{42}$—, $R^{41}$ and $R^{42}$ may be taken together with an adjacent nitrogen atom to form a substituted or unsubstituted aromatic heterocyclic group, or a substituted or unsubstituted nonaromatic heterocyclic group.

However, the following compounds are excluded:

[Formula 2]

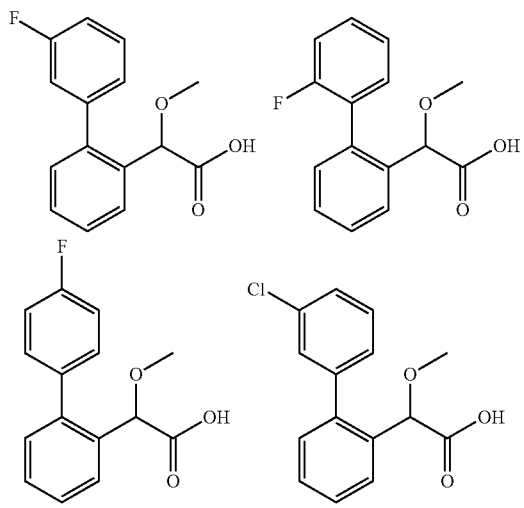

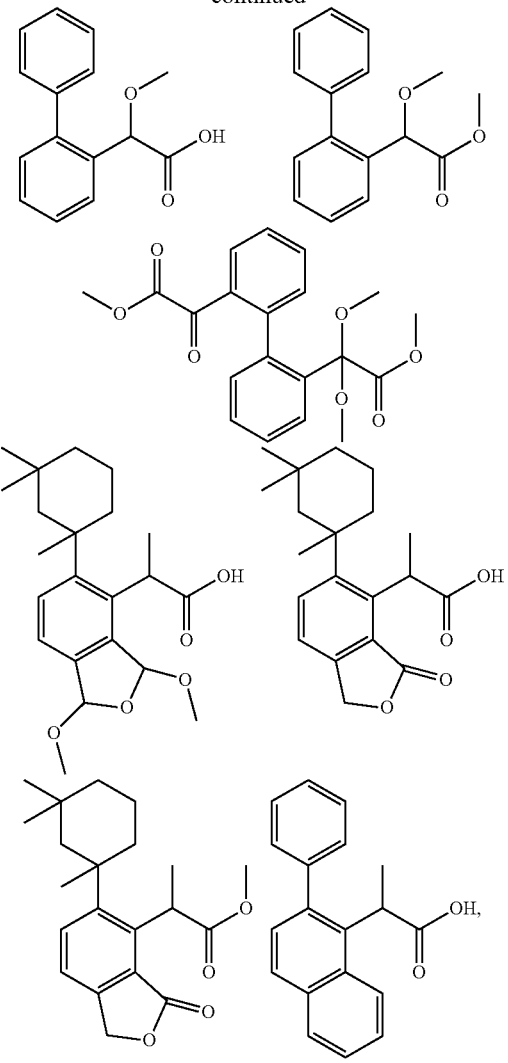

-continued (2) the compound according to the above (1) or a pharmaceutically acceptable salt thereof, wherein $R^4$ is a hydrogen atom, (3) the compound according to the above (1) or (2) or a pharmaceutically acceptable salt thereof, wherein n is 1, (4) the compound according to the above (3) or a pharmaceutically acceptable salt thereof, wherein $R^2$ is substituted or unsubstituted alkyloxy, (5) the compound as defined in the above (1) or a pharmaceutically acceptable salt thereof, wherein $R^1$ is halogen, cyano, nitro, or —X—$R^{11}$ (X is a single bond, —O—, —S—, —$NR^{12}$—, —CO—, —$SO_2$—, —O—CO—, —CO—O—, —$NR^{12}$—CO—, —CO—$NR^{12}$—, —$NR^{12}$—CO—O—, —$NR^{12}$—CO—$NR^{13}$—, —$NR^{12}$—$SO_2$—, or —$SO_2$—$NR^{12}$—; $R^{11}$ is a hydrogen atom, substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group; $R^{12}$ and $R^{13}$ are each independently a hydrogen atom, substituted or unsubstituted alkyl, substituted or unsubstituted alkenyl, or substituted or unsubstituted alkynyl. When X is —$NR^{12}$—, —CO—$NR^{12}$—, or —$SO_2$—$NR^{12}$—, $R^{11}$ and $R^{12}$ may be taken together with an adjacent nitrogen atom to form a substituted or unsubstituted aromatic heterocyclic group, or a substituted or unsubstituted nonaromatic heterocyclic group), $R^7$ is halogen, cyano, nitro, or —Z—$R^{71}$ (Z is a single bond, —O—, —S—, —$NR^{72}$—, —CO—, —$SO_2$—, —O—CO—, —CO—O—, —$NR^{72}$—CO—, —CO—$NR^{72}$—, —$NR^{72}$—CO—O—, —$NR^{72}$—CO—$NR^{73}$—, —$NR^{72}$—$SO_2$—, or —$SO_2$—$NR^{72}$—; $R^{71}$ is a hydrogen atom, substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group; $R^{72}$ and $R^{73}$ are each independently a hydrogen atom, substituted or unsubstituted alkyl, substituted or unsubstituted alkenyl, or substituted or unsubstituted alkynyl. When Z is —$NR^{72}$—, —CO—$NR^{72}$—, or —$SO_2$—$NR^{72}$—, $R^{71}$ and $R^{72}$ may be taken together with an adjacent nitrogen atom to form a substituted or unsubstituted aromatic heterocyclic group, or a substituted or unsubstituted nonaromatic heterocyclic group), (6) the compound as defined in the above (5) or a pharmaceutically acceptable salt thereof, wherein $R^4$ is a hydrogen atom, (7) the compound as defined in the above (5) or (6) or a pharmaceutically acceptable salt thereof, wherein n is 1, (8) the compound as defined in the above (7) or a pharmaceutically acceptable salt thereof, wherein $R^2$ is substituted or unsubstituted alkyloxy, (9) the compound as defined in any of the above (5) to (8) or a pharmaceutically acceptable salt thereof, wherein $R^4$ is a hydrogen atom, halogen, cyano, substituted or unsubstituted alkyl, substituted or unsubstituted alkenyl, or a substituted or unsubstituted aromatic carbocyclic group,

(10) the compound as defined in any of the above (5) to (9) or a pharmaceutically acceptable salt thereof, wherein $R^7$ is —Z—$R^{71}$, and Z is a single bond, —O—, —$NR^{72}$—, —$SO_2$—, —$NR^{72}$—CO—, —CO—$NR^{72}$—, —$NR^{72}$—CO—O—, —$NR^{72}$—CO—$NR^{73}$—, —$NR^{72}$—$SO_2$—, or —$SO_2$—$NR^{72}$—,

(11) the compound as defined in the above (10) or a pharmaceutically acceptable salt thereof, wherein $R^{71}$ is a hydrogen atom, substituted or unsubstituted alkyl, a substituted or unsubstituted aromatic carbocyclic group, or a substituted or unsubstituted nonaromatic carbocyclic group,

(12) the compound as defined in the above (10) or a pharmaceutically acceptable salt thereof, wherein $R^{71}$ is substituted or unsubstituted alkenyl, a substituted or unsubstituted aromatic heterocyclic group, or a substituted or unsubstituted nonaromatic heterocyclic group,

(13) the compound as defined in any of the above (10) to (12) or a pharmaceutically acceptable salt thereof, wherein Z is a single bond, —$NR^{72}$—, —$NR^{72}$—CO—, —CO—$NR^{72}$—, —$NR^{72}$—CO—O—, —$NR^{72}$—CO—NH—, —$NR^{72}$—$SO_2$—, or —$SO_2$—$NR^{72}$—,

(14) the compound as defined in the above (13) or a pharmaceutically acceptable salt thereof, wherein Z is a single bond, —$NR^{72}$—, —$NR^{72}$—CO—, —$NR^{72}$—CO—O—, —$NR^{72}$—CO—NH—, or —$NR^{72}$—$SO_2$—,

(15) the compound as defined in the above (5) or a pharmaceutically acceptable salt thereof, wherein $R^4$ is a hydrogen atom, n is 1, $R^2$ is substituted or unsubstituted alkyloxy, $R^6$ is substituted or unsubstituted alkyl, $R^1$ is a hydrogen atom, halogen, cyano, substituted or unsubstituted alkyl, substituted or unsubstituted alkenyl, or a substituted or unsubstituted aromatic carbocyclic group,

(16) the compound as defined in the above (5) or a pharmaceutically acceptable salt thereof, wherein $R^4$ is a hydrogen atom, n is 1, $R^2$ is substituted or unsubstituted alkyloxy, $R^6$ is substituted or unsubstituted alkyl, $R^1$ is a hydrogen atom, halogen, cyano, substituted or unsubstituted alkyl, substituted or unsubstituted alkenyl, or a substituted or unsubstituted aromatic carbocyclic group, $R^5$ is a hydrogen atom, substituted or unsubstituted alkyl, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclic carbamoyl, substituted or unsubstituted nonaromatic carbocyclic carbamoyl, or —$NR^{51}R^{52}$ ($R^{51}$ is substituted or unsubstituted aromatic carbocyclic carbonyl or substituted or unsubstituted nonaromatic carbocyclic carbonyl, and $R^{52}$ is a hydrogen atom), Y is a single bond, $R^7$ is —Z—$R^{71}$, Z is a single bond, —O—, —$NR^{72}$—, —$SO_2$—, —$NR^{72}$—CO—, —CO—$NR^{72}$—, —$NR^{72}$—CO—O—, —$NR^{72}$—CO—$NR^{73}$—, —$NR^{72}$—$SO_2$— or —$SO_2$—$NR^{72}$—, and $R^3$ is substituted or unsubstituted phenyl, substituted or unsubstituted cycloalkenyl, substituted or unsubstituted benzofuryl, substituted or unsubstituted benzodioxolyl, substituted or unsubstituted benzodioxanyl, substituted or unsubstituted dihydrobenzofuryl, substituted or unsubstituted chromanyl, or substituted or unsubstituted benzomorpholinyl,

(17) the compound as defined in the above (1) or a pharmaceutically acceptable salt thereof represented by formula (II):

[Formula 3]

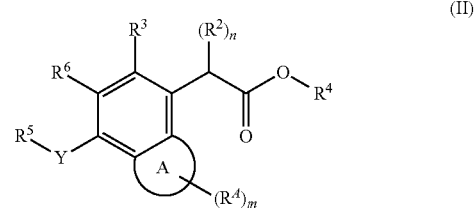

wherein m is any integer of 0 to 7, and other symbols have the same meaning as in claim 1,

(18) the compound as defined in the above (17) or a pharmaceutically acceptable salt thereof, wherein $R^4$ is a hydrogen atom,

(19) the compound as defined in the above (17) or (18) or a pharmaceutically acceptable salt thereof, wherein n is 1,

(20) the compound as defined in any of the above (17) to (19) or a pharmaceutically acceptable salt thereof, wherein $R^2$ is substituted or unsubstituted alkyloxy,

(21) the compound as defined in any of the above (17) to (20) or a pharmaceutically acceptable salt thereof, wherein ring A is a five-membered ring or a six-membered ring,

(22) the compound as defined in any of the above (17) to (21) or a pharmaceutically acceptable salt thereof, wherein ring A is an aromatic heterocyclic ring or a nonaromatic heterocyclic ring,

(23) the compound as defined in any of the above (17) to (22) or a pharmaceutically acceptable salt thereof, wherein m is any integer of 0 to 4,

(24) the compound as defined in any of the above (17) to (23) or a pharmaceutically acceptable salt thereof, wherein $R^4$ is halogen, cyano, oxo or —$X^A$—$R^{A1}$ ($X^A$ is a single bond, —O—, —S—, —$NR^{A2}$—, —CO—, $NR^{A2}$—CO—, CO—$NR^{A2}$—, —$NR^{A2}$—CO—$NR^{A3}$—, —$NR^{A2}$—$SO_2$—, or —$SO_2$—$NR^{A2}$—, $R^{A1}$ is a hydrogen atom, substituted or unsubstituted alkyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, and $R^{A2}$ and $R^{A3}$ are each independently a hydrogen atom or substituted or unsubstituted alkyl),

(25) the compound as defined in the above (17) or a pharmaceutically acceptable salt thereof, wherein $R^4$ is a hydrogen atom, n is 1, $R^2$ is substituted or unsubstituted alkyloxy, $R^6$ is substituted or unsubstituted alkyl, ring A is a five-membered or six-membered aromatic heterocyclic ring or nonaromatic heterocyclic ring, and m is any integer of 0 to 4,

(26) the compound as defined in the above (17) or a pharmaceutically acceptable salt thereof, wherein $R^4$ is a hydrogen atom, n is 1, $R^2$ is substituted or unsubstituted alkyloxy, $R^6$ is substituted or unsubstituted alkyl, ring A is a five-membered or six-membered aromatic heterocyclic ring or nonaromatic heterocyclic ring, and m is any integer of 0 to 4, $R^5$ is a hydrogen atom, substituted or unsubstituted alkyl, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclic carbamoyl, substituted or unsubstituted nonaromatic carbocyclic carbamoyl, or —$NR^{51}R^{52}$ ($R^{51}$ is substituted or unsubstituted aromatic carbocyclic carbonyl or substituted or unsubstituted nonaromatic carbocyclic carbonyl, and $R^{52}$ is a hydrogen atom), Y is a single bond, $R^4$ is each independently halogen, cyano, oxo or $X^A$—$R^{A1}$ ($X^A$ is a single bond, —O—, —S—, —$NR^{A2}$—, —CO—, —$SO_2$—, $NR^{A2}$—CO—, —CO—$NR^{A2}$—, —$NR^{A2}$—CO—$NR^{A3}$—, —$NR^{A2}$—$SO_2$—, or —$SO_2$—$NR^{A2}$—, $R^{A1}$ is a hydrogen atom, substituted or unsubstituted alkyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, and $R^{A2}$ and $R^{A3}$ are each independently a hydrogen atom or substituted or unsubstituted alkyl), and $R^3$ is substituted or unsubstituted phenyl, substituted or unsubstituted cycloalkenyl, substituted or unsubstituted benzofuryl, substituted or unsubstituted benzodioxolyl, substituted or unsubstituted benzodioxanyl, substituted or unsubstituted dihydrobenzofuryl, substituted or unsubstituted chromanyl, or substituted or unsubstituted benzomorpholinyl,

(27) the compound as defined in any of the above (1) to (26) or a pharmaceutically acceptable salt thereof, wherein $R^6$ is substituted or unsubstituted alkyl,

(28) the compound as defined in any of the above (1) to (27) or a pharmaceutically acceptable salt thereof, wherein $R^5$ is a hydrogen atom, substituted or unsubstituted alkyl, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclic carbamoyl, or —$NR^{51}H$ ($R^{51}$ is substituted or unsubstituted aromatic carbocyclic carbonyl),

(29) the compound as defined in the above (28) or a pharmaceutically acceptable salt thereof, wherein $R^5$ is a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group,

(30) the compound as defined in the above (28) or a pharmaceutically acceptable salt thereof, wherein $R^5$ is a hydrogen atom,

(31) the compound as defined in any of the above (1) to (27) or a pharmaceutically acceptable salt thereof, wherein $R^5$ is substituted or unsubstituted alkylcarbamoyl, substituted or unsubstituted alkenylcarbamoyl, substituted or unsubstituted alkyloxy, substituted or unsubstituted alkenyloxy, substituted or unsubstituted aromatic carbocyclic group carbonyl, substituted or unsubstituted nonaromatic carbocyclic group carbonyl, substituted or unsubstituted aromatic heterocyclic group carbonyl, substituted or unsubstituted nonaromatic heterocyclic group carbonyl, or substituted or unsubstituted nonaromatic carbocyclic carbamoyl,

(32) the compound as defined in any of the above (1) to (31) or a pharmaceutically acceptable salt thereof, wherein Y is a single bond,

(33) the compound as defined in any of the above (1) to (31) or a pharmaceutically acceptable salt thereof, wherein Y is alkylene,

(34) the compound as defined in any of the above (1) to (33) or a pharmaceutically acceptable salt thereof, wherein $R^3$ is substituted or unsubstituted phenyl, substituted or unsubstituted cycloalkenyl, substituted or unsubstituted benzofuryl, substituted or unsubstituted benzodioxolyl, substituted or unsubstituted benzodioxanyl, substituted or unsubstituted dihydrobenzofuryl, substituted or unsubstituted chromanyl, or substituted or unsubstituted benzomorpholinyl,

(35) A pharmaceutical composition comprising the compound as defined in any one of the above (1) to (34) or a pharmaceutically acceptable salt thereof,

(36) The pharmaceutical composition according to the above (35), having anti-HIV action,

(37) A method of treating a viral infection comprising administering to a human an antivirally effective amount of the compound as defined in any one of the above (1) to (34),

(38) The treatment method according to the above (37), for HIV infection,

(39) The compound according to any one of the above (1) to (34) or a pharmaceutically acceptable thereof, for the treatment of viral infection,

(40) The compound according to the above (39) or a pharmaceutically acceptable salt thereof, for the treatment of HIV infection.

(41) A use of the compound according to any one of the above (1) to (34) or a pharmaceutically acceptable salt thereof, for the production of a therapeutic agent for viral infection, and

(42) The use according to the above (41), for the production of a therapeutic agent for HIV infection.

Effects of the Invention

The compound of the present invention has a replication inhibitory activity on a virus, particularly HIV (example: HIV-1) and a resistant virus thereof. Accordingly, the compound of the present invention is useful in the prevention or treatment of viral infections (example: AIDS) and the like.

MODE FOR CARRYING OUT THE INVENTION

Each meaning of terms used herein is described below. Each term, alone or in combination with another word, is used in the same meaning.

The term of "halogen" includes a fluorine atom, a chlorine atom, a bromine atom and an iodine atom. A fluorine atom and a chlorine atom are preferable.

The term of "alkyl" includes a linear or branched hydrocarbon group having 1 to 15 carbon atom(s), preferably 1 to 10 carbon atom(s), more preferably 1 to 6 carbon atom(s), further preferably 1 to 4 carbon atom(s). For example, methyl, ethyl, n-propyl, isopropyl, n-butyl, isobutyl, sec-butyl, tert-butyl, n-pentyl, isopentyl, neo-pentyl, n-hexyl, isohexyl, n-heptyl, isoheptyl, n-octyl, isooctyl, n-nonyl, n-decyl and the like are exemplified.

In a preferable embodiment of "alkyl", methyl, ethyl, n-propyl, isopropyl, n-butyl, isobutyl, sec-butyl, tert-butyl and n-pentyl are exemplified. In another preferable embodiment, methyl, ethyl, n-propyl, isopropyl and tert-butyl are exemplified.

The term of "alkenyl" includes a linear or branched hydrocarbon group having 2 to 15 carbon atoms, preferably 2 to 10 carbon atoms, more preferably 2 to 6 carbon atoms, further preferably 2 to 4 carbon atoms, and one or more double bond(s) at any available position. For example, vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like are exemplified.

In one preferable embodiment of "alkenyl", vinyl, allyl, propenyl, isopropenyl and butenyl are exemplified.

The term of "alkynyl" includes a linear or branched hydrocarbon group having 2 to 10 carbon atoms, preferably 2 to 8 carbon atoms, more preferably 2 to 6 carbon atoms, further preferably 2 to 4 carbon atoms, and one or more triple bond(s) at any available position. For example, ethynyl, propynyl, butynyl, pentynyl, hexynyl, heptynyl, octynyl, nonynyl, decynyl and the like are exemplified. These may have further a double bond at any available position. Preferable embodiments of "alkynyl" include ethynyl, propynyl, butynyl, and pentynyl.

The term of "alkylene" includes a linear or branched divalent hydrocarbon group having 1 to 15 carbon atom(s), preferably 1 to 10 carbon atom(s), more preferably 1 to 6 carbon atom(s), most preferably 1 to 4 carbon atom(s). For example, methylene, ethylene, trimethylene, propylene, tetramethylene, panta methylene, hexamethylene and the like are exemplified.

The term of "alkenylene" includes a linear or branched divalent hydrocarbon group having 2 to 15 carbon atoms, preferably having 2 to 10 carbon atoms, more preferably 2 to 6 carbon atoms, most preferably 2 to 4 carbon atoms, and one or more double bond(s) at any available position. For example, vinylene, propenylene, butenylene, pentenylene and the like are exemplified.

The term of "alkynylene" includes a linear divalent hydrocarbon group having 2 to 15 carbon atoms, preferably having 2 to 10 carbon atoms, more preferably 2 to 6 carbon atoms, most preferably 2 to 4 carbon atoms, and one or more triple bond(s) at any available position. For example, ethynylene, propynylene, butynylene, pentynylene, hexynylene and the like are exemplified.

The term of "aromatic carboyclic group" includes a mono-, bi-, or more cyclic aromatic hydrocarbon group. For example, phenyl, naphthyl, anthryl, phenanthryl, and the like are exemplified.

In one preferable embodiment of "aromatic carbocyclic group", phenyl is exemplified.

The term of "non-aromatic carbocyclic group" includes a mono-, bi-, or more cyclic, non-aromatic saturated hydrocarbon group or non-aromatic unsaturated hydrocarbon group. A bi- or more cyclic non-aromatic carbocyclyl includes a fused ring wherein a non-aromatic carbocycle of monocyclic, or two or more rings is fused with a ring of the above "aromatic carbocycle".

In addition, the "non-aromatic carbocyclic group" also includes a cyclic group having a bridge or a cyclic group to form a spiro ring as follows:

[Chemical Formula 4]

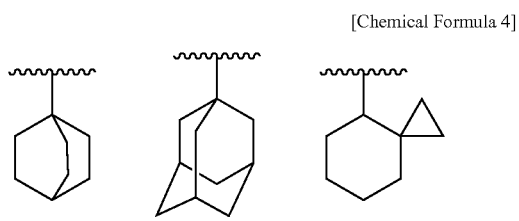 [SMILES: *C12CCC(CC1)CC2 ; *C12CC3CC(CC(C3)C1)C2 ; *C1CCCCC12CC2]

As a monocyclic non-aromatic carbocyclyl, 3 to 16 carbon atoms is preferred, more preferably 3 to 12 carbon atoms, further preferably 4 to 8 carbon atoms. For example, cycloalkyl, cycloalkenyl, and the like are exemplified.

Examples of "cycloalkyl" include cyclopropyl, cyclobutyl, cyclopentyl, cyclohexyl, cycloheptyl, cyclooctyl, cyclononyl, and cyclodecyl.

Examples of "cycloalkenyl" include cyclopropenyl, cyclobutenyl, cyclopentenyl, cyclohexenyl, cycloheptenyl, and cyclohexadienyl.

As a non-aromatic carbocyclyl of two or more rings, indanyl, indenyl, acenaphthyl, tetrahydronaphthyl, fluorenyl, dihydroindenyl and the like are exemplified.

The term of "aromatic heterocyclyl" includes an aromatic ring group which is monocyclic, or two or more rings, containing one or more the same or different of heteroatom(s) independently selected from oxygen, sulfur and nitrogen atom(s) in the ring.

An "aromatic heterocyclyl" of two or more rings includes a fused ring wherein an aromatic heterocycle of monocyclic, or two or more rings is fused with a ring of the above "aromatic carbocycle".

As a monocyclic aromatic heterocyclyl, a 5- to 8-membered ring is preferred, more preferably 5- to 6-membered. For example, pyrrolyl, imidazolyl, pyrazolyl, pyridyle, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl and the like are exemplified.

As a bicyclic aromatic heterocycle, indolyl, isoindolyl, indazoryl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridinyl, thiazolopyridyle and the like are exemplified.

As an aromatic heterocycle of three or more rings, carbazolyl, acridinyl, xanthenyl, phenothiazinyl, phenoxathiinyl, phenoxazinyl, dibenzofuryl and the like are exemplified.

The term of "non-aromatic heterocyclyl" includes a non-aromatic cyclic group which is monocyclic, or two or more rings, containing one or more the same or different of heteroatom(s) independently selected from oxygen, sulfur and nitrogen atoms.

A "non-aromatic heterocyclyl" of two or more rings includes a fused ring wherein a non-aromatic heterocyclyl of monocyclic, or two or more rings is fused with a ring of the above "aromatic carbocyclyl", "non-aromatic carbocyclyl" and/or "aromatic heterocyclyl".

In addition, the "non-aromatic heterocyclyl" also includes a cyclic group having a bridge or a cyclic group to form a spiro ring as follows:

[Chemical Formula 5]

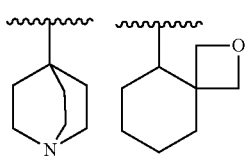

As a monocyclic non-aromatic heterocyclyl, a 3- to 8-membered ring is preferred, more preferably 5- to 6-membered. For example, dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiinyl, thiazinyl and the like are exemplified.

As a non-aromatic heterocyclyl of two or more rings, for example, indolinyl, isoindolinyl, chromanyl, isochromanyl, dihydrobenzofuryl, benzodioxazolyl, benzodioxanyl, benzomorpholinyl and the like are exemplified.

The term of "hydroxyalkyl" includes a group wherein hydrogen atom(s) attached to one or more carbon atom(s) of above "alkyl" is (are) replaced with one or more hydroxy group(s). For example, hydroxymethy, 1-hydroxyethyl, 2-hydroxyethyl, 1-hydroxypropyl, 2-hydroxypropyl, 1,2-dihydroxyethyl and the like are exemplified.

In one preferable embodiment of "hydroxyalkyl", hydroxymethyl is exemplified.

The term of "alkyloxy" includes a group wherein an oxygen atom is substituted with the above "alkyl". For example, methyloxy, ethyloxy, n-propyloxy, isopropyloxy, n-butyloxy, tert-butyloxy, isobutyloxy, sec-butyloxy, pentyloxy, isopentyloxy, hexyloxy and the like are exemplified.

In one preferable embodiment of "alkyloxy", methyloxy, ethyloxy, n-propyloxy, isopropyloxy and tert-butyloxy are exemplified.

The term of "alkenyloxy" includes a group wherein an oxygen atom is substituted with the above "alkenyl". For example, vinyloxy, allyloxy, 1-propenyloxy, 2-butenyloxy, 2-pentenyloxy, 2-hexenyloxy, 2-heptenyloxy, 2-octenyloxy and the like are exemplified.

The term of "alkynyloxy" includes a group wherein an oxygen atom is substituted with the above "alkynyl". For example, ethynyloxy, 1-propynyloxy, 2-propynyloxy, 2-butynyloxy, 2-pentynyloxy, 2-hexynyloxy, 2-heptynyloxy, 2-octynyloxy and the like are exemplified.

The term of "haloalkyl" includes a group wherein hydrogen atom(s) attached to one or more carbon atom(s) of the above "alkyl" is (are) replaced with one or more above "halogen". For example, monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropan-2-yl and the like are exemplified.

In one preferable embodiment of "haloalkyl", trifluoromethyl and trichloromethyl are exemplified.

The term of "haloalkyloxy" includes a group wherein an oxygen atom is substituted with one above "haloalkyl". For example, monofluoromethyloxy, monofluoroethyloxy, trifluoromethyloxy, trichloromethyloxy, trifluoroethyloxy, trichloroethyloxy and the like are exemplified.

In one preferable embodiment of "haloalkyloxy", trifluoromethyloxy and trichloromethyloxy are exemplified.

The term of "alkyloxyalkyl" includes a group wherein above "alkyl" is substituted with above "alkyloxy". For example, methyloxymethyl, methyloxyethyl, ethyloxymethyl and the like are exemplified.

The term of "alkyloxyalkyloxy" includes a group wherein above "alkyloxy" is substituted with above "alkyloxy". For example, methyloxymethyloxy, methyloxyethyloxy, ethyloxymethyloxy, ethyloxyethyloxy and the like are exemplified.

The term of "alkylcarbonyl" includes a group wherein a carbonyl is substituted with one above "alkyl". For example, methylcarbonyl, ethylcarbonyl, n-propylcarbonyl, isopropylcarbonyl, tert-butylcarbonyl, isobutylcarbonyl, sec-butylcarbonyl, pentylcarbonyl, isopentylcarbonyl, hexylcarbonyl and the like are exemplified.

In one preferable embodiment of "alkylcarbonyl", methylcarbonyl, ethylcarbonyl and n-propylcarbonyl are exemplified.

The term of "alkenylcarbonyl" includes a group wherein a carbonyl is substituted with one above "alkenyl". For example, ethylenylcarbonyl, propenylcarbonyl and the like are exemplified.

The term of "alkynylcarbonyl" includes a group wherein a carbonyl is substituted with one above "alkynyl". For example, ethynylcarbonyl, propynylcarbonyl and the like are exemplified.

The term of "monoalkylamino" includes a group wherein a hydrogen atom attached to a nitrogen atom of an amino group is replaced with above "alkyl". For example, methylamino, ethylamino, isopropylamino and the like are exemplified.

In one preferable embodiment of "monoalkylamino", methylamino and ethylamino are exemplified.

The term of "dialkylamino" includes a group wherein two hydrogen atoms attached to a nitrogen atom of an amino group are replaced with two above "alkyl". These two alkyl groups may be the same or different. For example, dimethylamino, diethylamino, N, N-diisopropylamino, N-methyl-N-ethylamino, N-isopropyl-N-ethylamino and the like are exemplified.

In one preferable embodiment of "dialkylamino", dimethylamino and diethylamino are exemplified.

The term of "alkylsulfonyl" includes a group wherein a sulfonyl is substituted with one above "alkyl". For example, methylsulfonyl, ethylsulfonyl, propylsulfonyl, isopropylsulfonyl, tert-butylsulfonyl, isobutylsulfonyl, sec-butylsulfonyl and the like are exemplified.

In one preferable embodiment of "alkylsulfonyl", methylsulfonyl and ethylsulfonyl are exemplified.

The term of "alkenylsulfonyl" includes a group wherein a sulfonyl is substituted with one above "alkenyl". For example, ethylenylsulfonyl, propenylsulfonyl and the like are exemplified.

The term of "alkynylsulfonyl" includes a group wherein a sulfonyl is substituted with one above "alkynyl". For example, ethynylsulfonyl, propynylsulfonyl and the like are exemplified.

The term of "monoalkylcarbonylamino" includes a group wherein a hydrogen atom attached to a nitrogen atom of an amino group is replaced with above "alkylcarbonyl". For example, methylcarbonylamino, ethylcarbonylamino, propylcarbonylamino, isopropylcarbonylamino, tert-butylcarbonylamino, isobutylcarbonylamino, sec-butylcarbonylamino and the like are exemplified.

In one preferable embodiment of "monoalkylcarbonylamino", methylcarbonylamino and ethylcarbonylamino are exemplified.

The term of "dialkylcarbonylamino" includes a group wherein two hydrogen atoms attached to a nitrogen atom of an amino group are replaced with above "alkylcarbonyl". The two "alkylcarbonyl" are identical or different. For example, dimethylcarbonylamino, diethylcarbonylamino, N, N-diisopropylcarbonylamino, and the like are exemplified.

In one preferable embodiment of "dialkylcarbonylamino", dimethylcarbonylamino and diethylcarbonylamino are exemplified.

The term of "monoalkylsulfonylamino" includes a group wherein a hydrogen atom attached to a nitrogen atom of an amino group is replaced with above "alkylsulfonyl". For example, methylsulfonylamino, ethylsulfonylamino, propylsulfonylamino, isopropylsulfonylamino, tert-butylsulfonylamino, isobutylsulfonylamino, sec-butylsulfonylamino and the like are exemplified.

In one preferable embodiment of "monoalkylsulfonylamino", methylsulfonylamino and ethylsulfonylamino are exemplified.

The term of "dilkylsulfonylamino" includes a group wherein two hydrogen atoms attached to a nitrogen atom of an amino group are replaced with above "alkylsulfonyl". For example, dimethylsulfonylamino, diethylsulfonylamino, N,N-diisopropylsulfonylamino and the like are exemplified.

In one preferable embodiment of "dialkylsulfonylamino", dimethylsulfonylamino and diethylsulfonylamino are exemplified.

The term of "alkylimino" includes a group wherein a hydrogen atom attached to a nitrogen atom of an imino group is replaced with above "alkyl". For example, methylimino, ethylimino, n-propylimino, isopropylimino and the like are exemplified.

The term of "alkenylimino" includes a group wherein a hydrogen atom attached to a nitrogen atom of an imino group is replaced with above "alkenyl". For example, ethylenylimino, propenylimino and the like are exemplified.

The term of "alkynylimino" includes a group wherein a hydrogen atom attached to a nitrogen atom of an imino group is replaced with above "alkynyl". For example, ethynylimino, propynylimino and the like are exemplified.

The term of "alkylcarbonylimino" includes a group wherein a hydrogen atom attached to a nitrogen atom of an imino group is replaced with above "alkylcarbonyl". For example, methylcarbonylimino, ethylcarbonylimino, n-propylcarbonylimino, isopropylcarbonylimino and the like are exemplified.

The term of "alkenylcarbonylimino" includes a group wherein a hydrogen atom attached to a nitrogen atom of an imino group is replaced with above "alkenylcarbonyl". For example, ethylenylcarbonylimino, propenylcarbonylimino and the like are exemplified.

The term of "alkynylcarbonylimino" includes a group wherein a hydrogen atom attached to a nitrogen atom of an imino group is replaced with above "alkynylcarbonyl". For example, ethynylcarbonylimino, propynylcarbonylimino and the like are exemplified.

The term of "alkyloxyimino" includes a group wherein a hydrogen atom attached to a nitrogen atom of an imino group is replaced with above "alkyloxy". For example, methyloxyimino, ethyloxyimino, n-propyloxyimino, isopropyloxyimino and the like are exemplified.

The term of "alkenyloxyimino" includes a group wherein a hydrogen atom attached to a nitrogen atom of an imino group is replaced with above "alkenyloxy". For example, ethylenyloxyimino, propenyloxyimino and the like are exemplified.

The term of "alkynyloxyimino" includes a group wherein a hydrogen atom attached to a nitrogen atom of an imino group is replaced with above "alkynyloxy". For example, ethynyloxyimino, propynyloxyimino and the like are exemplified.

The term of "alkylcarbonyloxy" includes a group wherein an oxygen atom is substituted with one above "alkylcarbonyl". For example, methylcarbonyloxy, ethylcarbonyloxy, propylcarbonyloxy, isopropylcarbonyloxy, tert-butylcarbonyloxy, isobutylcarbonyloxy, sec-butylcarbonyloxy and the like are exemplified.

In one preferable embodiment of "alkylcarbonyloxy", methylcarbonyloxy and ethylcarbonyloxy are exemplified.

The term of "alkenylcarbonyloxy" includes a group wherein an oxygen atom is substituted with one above "alkenylcarbonyl". For example, ethylenylcarbonyloxy, propenylcarbonyloxy and the like are exemplified.

The term of "alkynylcarbonyloxy" includes a group wherein an oxygen atom is substituted with one above "alkynylcarbonyl". For example, ethynylcarbonyloxy, propynylcarbonyloxy and the like are exemplified.

The term of "alkyloxycarbonyl" includes a group wherein a carbonyl is substituted with one above "alkyloxy". For example, methyloxycarbonyl, ethyloxycarbonyl, propyloxycarbonyl, isopropyloxycarbonyl, tert-butyloxycarbonyl, isobutyloxycarbonyl, sec-butyloxycarbonyl, pentyloxycarbonyl, isopentyloxycarbonyl, hexyloxycarbonyl and the like are exemplified.

In one preferable embodiment of "alkyloxycarbonyl", methyloxycarbonyl, ethyloxycarbonyl and propyloxycarbonyl are exemplified.

The term of "alkenyloxycarbonyl" includes a group wherein a carbonyl is substituted with one above "alkenyloxy". For example, ethylenyloxycarbonyl, propenyloxycarbonyl and the like are exemplified.

The term of "alkynyloxycarbonyl" includes a group wherein a carbonyl is substituted with one above "alkynyloxy". For example, ethynyloxycarbonyl, propynyloxycarbonyl, and the like are exemplified.

The term of "alkylsulfanyl" includes a group wherein a hydrogen atom attached to a sulfur atom of a sulfanyl is replaced with one above "alkyl". For example, methylsulfanyl, ethylsulfanyl, n-propylsulfanyl, isopropylsulfanyl, tert-butylsulfanyl, isobutylsulfanyl and the like are exemplified.

The term of "alkenylsulfanyl" includes a group wherein a hydrogen atom attached to a sulfur atom of sulfanyl is replaced with one above "alkenyl". For example, ethylenylsulfanyl, propenylsulfanyl and the like are exemplified.

The term of "alkynylsulfanyl" includes a group wherein a hydrogen atom attached to a sulfur atom of sulfanyl is replaced with one above "alkynyl". For example, ethynylsulfanyl, propynylsulfanyl, and the like are exemplified.

The term of "alkylsulfinyl" includes a group wherein a sulfinyl is substituted with one above "alkyl". For example, methylsulfinyl, ethylsulfinyl, n-propylsulfinyl, isopropylsulfinyl and the like are exemplified.

The term of "alkenylsulfinyl" includes a group wherein a sulfinyl is substituted with one above "alkenyl". For example, ethylenylsulfinyl, propenylsulfinyl, and the like are exemplified.

The term of "alkynylsulfinyl" includes a group in which a sulfinyl is substituted with one above "alkynyl". For example, ethynylsulfinyl, propynylsulfinyl and the like are exemplified.

The term of "monoalkylcarbamoyl" includes a group wherein a hydrogen atom attached to a nitrogen atom of a carbamoyl group is replaced with above "alkyl". For example, methylcarbamoyl, ethylcarbamoyl and the like are exemplified.

The term of "dialkylcarbamoyl" includes a group wherein two hydrogen atoms attached to a nitrogen atom of a carbamoyl group are replaced with two above "alkyl". These two alkyl groups may be the same or different. For example, dimethylcarbamoyl, diethylcarbamoyl, and the like are exemplified.

The term of "monoalkylsulfamoyl" includes a group wherein a hydrogen atom attached to a nitrogen atom of a sulfamoyl is replaced with one above "alkyl". For example, methylsulfamoyl and the like are exemplified.

The term of "dialkylsulfamoyl" includes a group wherein two hydrogen atoms attached to a nitrogen atom of a sulfamoyl are replaced with two above "alkyl". These two alkyl groups may be the same or different. For example, dimethylcarbamoyl, diethylcarbamoyl and the like are exemplified.

The term of "trialkylsilyl" includes a group wherein a silicon atom is substituted with three above "alkyl". These three alkyl groups may be the same or different. For example, trimethylsilyl, triethylsilyl, tert-butyldimethylsilyl and the like are exemplified.

The alkyl portion of "aromatic carbocyclyl alkyl", "non-aromatic carbocyclyl alkyl", "aromatic heterocyclyl alkyl" and "non-aromatic heterocyclyl alkyl", "aromatic carbocyclyl alkyloxy", "non-aromatic carbocyclyl alkyloxy", "aromatic heterocyclyl alkyloxy" and"non-aromatic heterocyclyl alkyloxy", "aromatic carbocyclyl alkylsulfanyl", "non-aromatic carbocyclyl alkylsulfanyl", "aromatic heterocyclyl alkylsulfanyl" and"non-aromatic heterocyclyl alkylsulfanyl", "aromatic carbocyclyl alkyloxycarbonyl", "non-aromatic carbocyclyl alkyloxycarbonyl", "aromatic heterocyclyl alkyloxycarbonyl" and"non-aromatic heterocyclyl alkyloxycarbonyl", "aromatic carbocyclyl alkyloxyalkyl", "non-aromatic carbocyclyl alkyloxyalkyl", "aromatic heterocyclyl alkyloxyalkyl" and"non-aromatic heterocyclyl alkyloxyalkyl", and "aromatic carbocyclyl alkylamino", "non-aromatic carbocyclyl alkylamino", "aromatic heterocyclyl alkylamino" and"non-aromatic heterocyclyl alkylamino" means the aforementioned "alkyl".

The term of "aromatic carbocyclyl alkyl" includes an alkyl substituted with one or more above "aromatic carbocyclyl". Examples thereof include such as benzyl, phenethyl, phenylpropyl, benzhydryl, trityl, naphthylmethyl and a group of the formula of

[Chemical Formula 6]

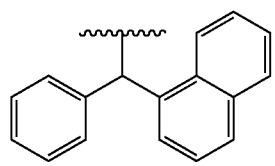

In one preferable embodiment of "aromatic carbocyclyl alkyl", benzyl, phenethyl and benzhydryl are exemplified.

The term of "non-aromatic carbocyclyl alkyl" includes an alkyl substituted with one or more above "non-aromatic carbocyclyl". Also, "non-aromatic carbocyclyl alkyl" includes a "non-aromatic carbocyclyl alkyl" wherein the alkyl portion thereof is substituted with one or more above "aromatic carbocyclyl". Examples thereof include cyclopropylmethyl, cyclobutylmethyl, cyclopentylmethyl, cyclohexylmethyl and a group of the formula of

[Chemical Formula 7]

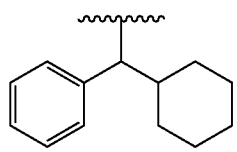

The term of "aromatic heterocyclyl alkyl" includes an alkyl substituted with one or more above "aromatic heterocyclyl". Also, "aromatic heterocyclyl alkyl" includes an "aromatic heterocyclyl alkyl" wherein the alkyl portion thereof is substituted with one or more above "aromatic carbocyclyl", and/or "non-aromatic carbocyclyl". Examples thereof include pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl and groups of the formula of

[Chemical Formula 8]

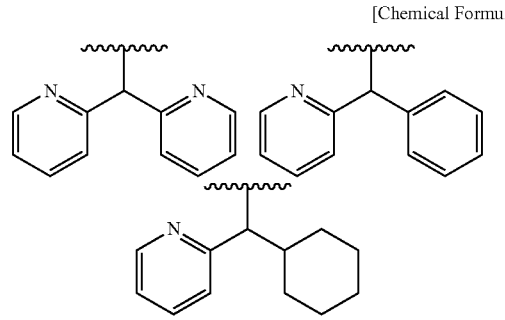

The term of "non-aromatic heterocyclyl alkyl" includes an alkyl substituted with one or more above "non-aromatic heterocyclyl". Also, "non-aromatic heterocyclyl alkyl" includes a "non-aromatic heterocyclyl alkyl" wherein the alkyl portion thereof is substituted with one or more above "aromatic carbocyclyl", "non-aromatic carbocyclyl" and/or "aromatic heterocyclyl". Examples thereof include tetrahydropyranylmethyl, morpholinylmethyl, morpholinylethyl, piperidinylmethyl, piperazinylmethyl and groups of the formula of

[Chemical Formula 9]

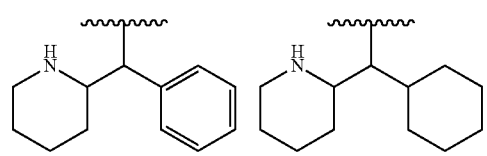

-continued

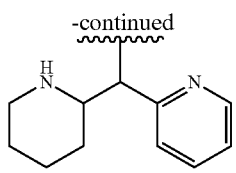

The term of "aromatic carbocyclyl alkyloxy" includes an alkyloxy substituted with one or more above "aromatic carbocyclyl". Examples thereof include such as benzyloxy, phenethyloxy, phenylpropynyloxy, benzhydryloxy, trityloxy, naphthylmethyloxy and a group of the formula of

[Chemical Formula 10]

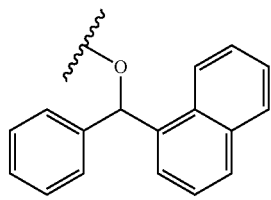

The term of "non-aromatic carbocyclyl alkyloxy" includes an alkyloxy substituted with one or more above "non-aromatic carbocyclyl". Also, "non-aromatic carbocyclyl alkyloxy" includes a "non-aromatic carbocyclyl alkyloxy" wherein the alkyl portion is substituted with one or more above "aromatic carbocyclyl". Examples thereof include cyclopropylmethyloxy, cyclobutylmethyloxy, cyclopentylmethyloxy, cyclohexylmethyloxy and a group of the formula of

[Chemical Formula 11]

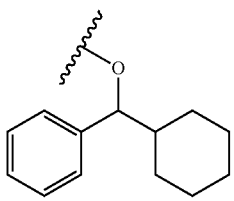

The term of "aromatic heterocyclyl alkyloxy" includes an alkyloxy substituted with one or more above "aromatic heterocyclyl". Also, "aromatic heterocyclyl alkyloxy" includes an "aromatic heterocyclyl alkyloxy" wherein the alkyl portion thereof is substituted with one or more above "aromatic carbocyclyl", and/or "non-aromatic carbocyclyl". Examples thereof include pyridylmethyloxy, furanylmethyloxy, imidazolylmethyloxy, indolylmethyloxy, benzothiophenylmethyloxy, oxazolylmethyloxy, isoxazolylmethyloxy, thiazolylmethyloxy, isothiazolylmethyloxy, pyrazolylmethyloxy, isopyrazolylmethyloxy, pyrrolidinylmethyloxy, benzoxazolylmethyloxy and groups of the formula of

[Chemical Formula 12]

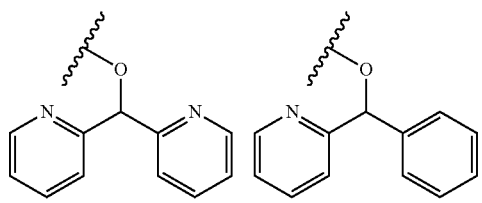

-continued

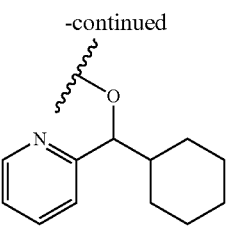

The term of "non-aromatic heterocyclyl alkyloxy" includes an alkyloxy substituted with one or more above "non-aromatic heterocyclyl". Also, "non-aromatic heterocyclyl alkyloxy" includes a "non-aromatic heterocyclyl alkyloxy" wherein the alkyl portion thereof is substituted with one or more above "aromatic carbocyclyl", "non-aromatic carbocyclyl" and/or "aromatic heterocyclyl". Examples thereof include tetrahydropyranylmethyloxy, morpholinylmethyloxy, morpholinylethyloxy, piperidinylmethyloxy, piperazinylmethyloxy and groups of the formula of

[Chemical Formula 13]

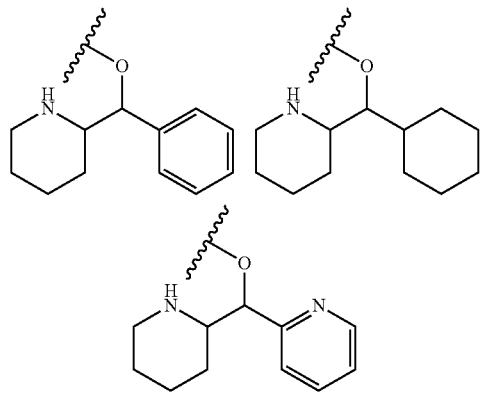

The term of "aromatic carbocyclyl alkylsulfanyl" includes an alkylsulfanyl substituted with one or more above "aromatic carbocyclyl". Examples thereof include benzylsulfanyl, phenethylsulfanyl, phenylpropynylsulfanyl, benzhydrylsulfanyl, tritylsulfanyl, naphthylmethylsulfanyl and the like.

The term of "non-aromatic carbocyclylalkylsulfanyl" includes an alkylsulfanyl substituted with one or more above "non-aromatic carbocyclyl". Also, "non-aromatic carbocyclyl alkylsulfanyl" includes a "non-aromatic carbocyclyl alkylsulfanyl" wherein the alkyl portion is substituted with one or more above "aromatic carbocyclyl". Examples thereof include cyclopropylmethylsulfanyl, cyclobutylmethylsulfanyl, cyclopentylmethylsulfanyl, and cyclohexylmethylsulfanyl.

The term of "aromatic heterocyclyl alkylsulfanyl" includes an alkylsulfanyl substituted with one or more above "aromatic heterocyclyl". Also, "aromatic heterocyclyl alkylsulfanyl" includes an "aromatic heterocyclyl alkylsulfanyl" wherein the alkyl portion is substituted with one or more above "aromatic carbocyclyl", and/or "non-aromatic carbocyclyl". Examples thereof include pyridylmethylsulfanyl, furanylmethylsulfanyl, imidazolylmethylsulfanyl, indolylmethylsulfanyl, benzothiophenylmethylsulfanyl, oxazolylmethylsulfanyl, isoxazolylmethylsulfanyl, thiazolylmethylsulfanyl, isothiazolylmethylsulfanyl, pyrazolylmethylsulfanyl, isopyrazolylmethylsulfanyl, pyrrolidinylmethylsulfanyl, benzoxazolylmethylsulfanyl and the like.

The term of "non-aromatic heterocyclyl alkylsulfanyl" includes an alkylsulfanyl substituted with one or more above "non-aromatic heterocyclyl". Also, "non-aromatic heterocyclyl alkylsulfanyl" includes a "non-aromatic heterocyclyl alkylsulfanyl" wherein the alkyl portion is substituted with one or more above "aromatic carbocyclyl", "non-aromatic carbocyclyl" and/or "aromatic heterocyclyl". Examples thereof include tetrahydropyranylmethylsulfanyl, morpholinylmethylsulfanyl, morpholinylethylsulfanyl, piperidinylmethylsulfanyl, piperazinylmethylsulfanyl and the like.

The term of "aromatic carbocyclyl alkyloxycarbonyl" includes an alkyloxycarbonyl substituted with one or more above "aromatic carbocyclyl". Examples thereof include benzyloxycarbonyl, phenethyloxycarbonyl, phenylpropynyloxycarbonyl, benzhydryloxycarbonyl, trityloxycarbonyl, naphthylmethyloxycarbonyl and a group of the formula of

[Chemical Formula 14]

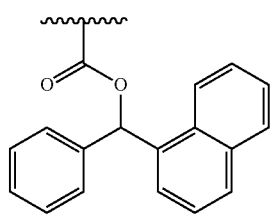

The term of "non-aromatic carbocyclyl alkyloxycarbonyl" includes an alkyloxycarbonyl substituted with one or more above "non-aromatic carbocyclyl". Also, "non-aromatic carbocyclyl alkyloxycarbonyl" includes a "non-aromatic carbocyclyl alkyloxycarbonyl" wherein the alkyl portion is substituted with one or more above "aromatic carbocyclyl". Examples thereof include cyclopropylmethyloxycarbonyl, cyclobutylmethyloxycarbonyl, cyclopentylmethyloxycarbonyl, cyclohexylmethyloxycarbonyl and a group of the formula of

[Chemical Formula 15]

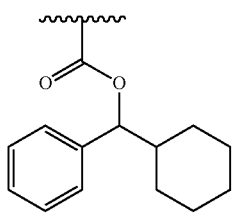

The term of "aromatic heterocyclyl alkyloxycarbonyl" includes an alkyloxycarbonyl substituted with one or more above "aromatic heterocyclyl". Also, "aromatic heterocyclyl alkyloxycarbonyl" includes an "aromatic heterocyclyl alkyloxycarbonyl" wherein the alkyl portion thereof is substituted with one or more above "aromatic carbocyclyl", and/or "non-aromatic carbocyclyl". Examples thereof include pyridylmethyloxycarbonyl, furanylmethyloxycarbonyl, imidazolylmethyloxycarbonyl, indolylmethyloxycarbonyl, benzothiophenylmethyloxycarbonyl, oxazolylmethyloxycarbonyl, isoxazolylmethyloxycarbonyl, thiazolylmethyloxycarbonyl, isothiazolylmethyloxycarbonyl, pyrazolylmethyloxycarbonyl, isopyrazolylmethyloxycarbonyl, pyrrolidinylmethyloxycarbonyl, benzoxazolylmethyloxycarbonyl and groups of the formula of

[Chemical Formula 16]

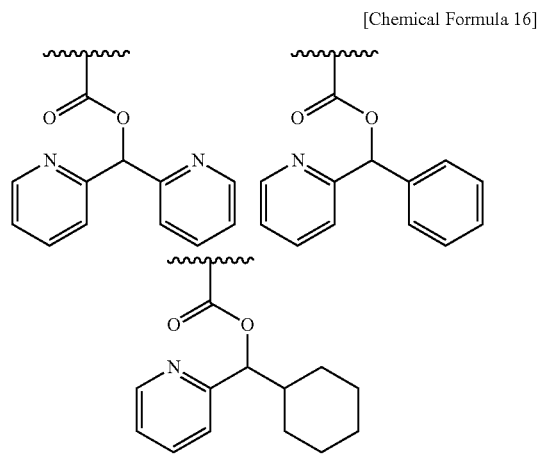

The term of "non-aromatic heterocyclyl alkyloxycarbonyl" includes an alkyloxycarbonyl substituted with one or more above "non-aromatic heterocyclyl". Also, "non-aromatic heterocyclyl alkyloxycarbonyl" includes a "non-aromatic heterocyclyl alkyloxycarbonyl" wherein the alkyl portion thereof is substituted with one or more above "aromatic carbocyclyl", "non-aromatic carbocyclyl" and/or "aromatic heterocyclyl". Examples thereof include tetrahydropyranylmethyloxy, morpholinylmethyloxy, morpholinylethyloxy, piperidinylmethyloxy, piperazinylmethyloxy and groups of the formula of

[Chemical Formula 17]

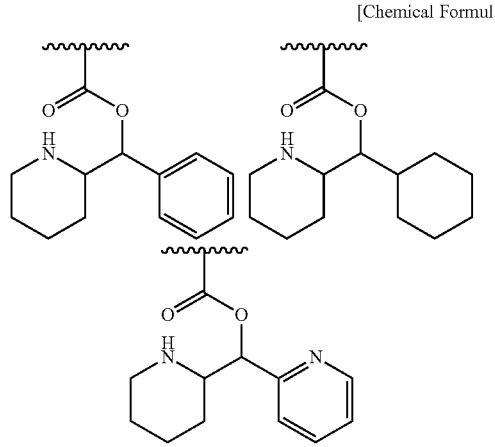

The term of "aromatic carbocyclyl alkyloxyalkyl" includes an alkyloxyalkyl substituted with one or more above "aromatic carbocyclyl". Examples thereof include benzyloxymethyl, phenethyloxymethyl, phenylpropynyloxymethyl, benzhydryloxymethyl, trityloxymethyl, naphthylmethyloxymethyl and a group of the formula of

[Chemical Formula 18]

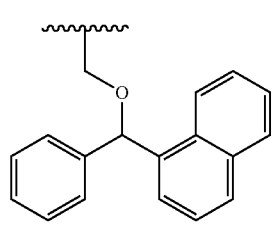

The term of "non-aromatic carbocyclyl alkyloxyalkyl" includes an alkyloxyalkyl substituted with one or more above "non-aromatic carbocyclyl". Also, "non-aromatic carbocyclyl alkyloxyalkyl" includes a "non-aromatic carbocyclyl alkyloxyalkyl" wherein the alkyl portion attached to a non-aromatic carbocycle is substituted with one or more above "aromatic carbocyclyl". Examples thereof include cyclopropylmethyloxymethyl, cyclobutylmethyloxymethyl, cyclopentylmethyloxymethyl, cyclohexylmethyloxymethyl and a group of the formula:

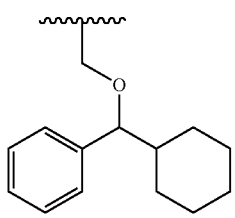

[Chemical Formula 19]

The term of "aromatic heterocyclyl alkyloxyalkyl" includes an alkyloxyalkyl substituted with one or more above "aromatic heterocyclyl". Also, "aromatic heterocyclyl alkyloxyalkyl" includes an "aromatic heterocyclyl alkyloxyalkyl" wherein the alkyl portion attached to aromatic heterocycle is substituted with one or more above "aromatic carbocyclyl" and/or "non-aromatic carbocyclyl". Examples thereof include pyridylmethyloxymethyl, furanylmethyloxymethyl, imidazolylmethyloxymethyl, indolylmethyloxymethyl, benzothiophenylmethyloxymethyl, oxazolylmethyloxymethyl, isoxazolylmethyloxymethyl, thiazolylmethyloxymethyl, isothiazolylmethyloxymethyl, pyrazolylmethyloxymethyl, isopyrazolylmethyloxymethyl, pyrrolidinylmethyloxymethyl, benzoxazolylmethyloxymethyl and groups of the formula of

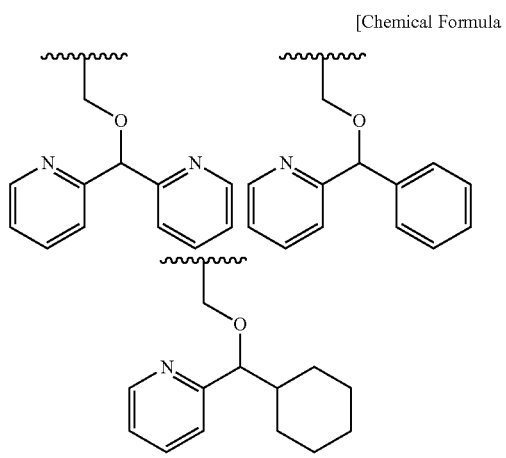

[Chemical Formula 20]

The term of "non-aromatic heterocyclyl alkyloxyalkyl" includes an alkyloxyalkyl substituted with one or more above "non-aromatic heterocyclyl". Also, "non-aromatic heterocyclyl alkyloxyalkyl" includes a "non-aromatic heterocyclyl alkyloxyalkyl" wherein the alkyl portion attached to non-aromatic heterocycle is substituted with one or more above "aromatic carbocyclyl", "non-aromatic carbocyclyl" and/or "aromatic heterocyclyl". Examples thereof include tetrahydropyranylmethyloxymethyl, morpholinylmethyloxymethyl, morpholinylethyloxymethyl, piperidinylmethyloxymethyl, piperazinylmethyloxymethyl and groups of the formula of

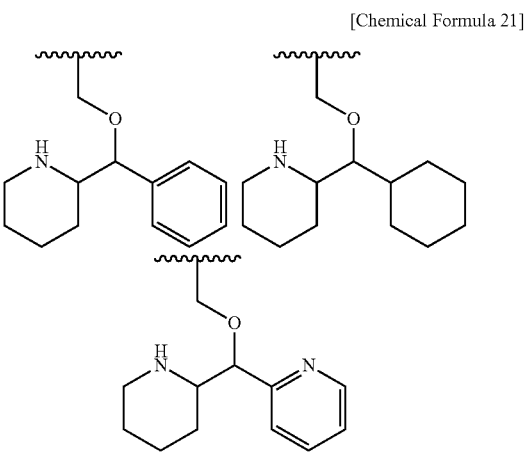

[Chemical Formula 21]

The term of "aromatic carbocyclyl alkylamino" includes a group wherein one or two hydrogen atom(s) attached to a nitrogen atom of an amino group is replaced with above "aromatic carbocyclyl alkyl". Examples include benzylamino, phenethylamino, phenylpropynylamino, benzhydrylamino, tritylamino, naphthylmethylamino, dibenzylamino and the like.

The term of "non-aromatic carbocyclyl alkylamino" includes a group wherein one or two hydrogen atom(s) attached to a nitrogen atom of an amino group is replaced with above "non-aromatic carbocyclyl alkyl". Examples include cyclopropylmethylamino, cyclobutylmethylamino, cyclopentylmethylamino, cyclohexylmethylamino and the like.

The term of "aromatic heterocyclyl alkylamino" includes a group wherein one or two hydrogen atom(s) attached to a nitrogen atom of an amino group is replaced with above "aromatic heterocyclyl alkyl". Examples include pyridylmethylamino, furanylmethylamino, imidazolylmethylamino, indolylmethylamino, benzothiophenylmethylamino, oxazolylmethylamino, isoxazolylmethylamino, thiazolylmethylamino, isothiazolylmethylamino, pyrazolylmethylamino, isopyrazolylmethylamino, pyrrolidinylmethylamino, benzoxazolylmethylamino and the like.

The term of "non-aromatic heterocyclyl alkylamino" includes a group wherein one or two hydrogen atom(s) attached to a nitrogen atom of an amino group is replaced with above "non-aromatic heterocyclyl alkyl". Examples include tetrahydropyranylmethylamino, morpholinylethylamino, piperidinylmethylamino, piperazinylmethyamino and the like.

The "aromatic carbocycle" portion of "aromatic carbocyclyl oxy", "aromatic carbocyclyl amino", "aromatic carbocyclyl carbonyl", "aromatic carbocyclyl oxycarbonyl", "aromatic carbocyclyl carbonylamino", "aromatic carbocyclyl sulfanyl" and "aromatic carbocyclyl sulfonyl" means the aforementioned "aromatic carbocyclyl".

The term of "aromatic carbocyclyl oxy" includes a group wherein an oxygen atom is substituted with one above "aromatic carbocycle". Examples include phenyloxy, naphthyloxy and the like.

The term of "aromatic carbocyclyl amino" includes a group wherein the nitrogen atom of amino is attached to above "aromatic carbocycle". Examples include phenylamino, naphthylamino and the like.

The term of "aromatic carbocyclyl carbonyl" includes a group wherein a carbonyl is substituted with one above "aromatic carbocycle". Examples include phenylcarbonyl, naphthylcarbonyl and the like.

The term of "aromatic carbocyclyl oxycarbonyl" includes a group wherein a carbonyl is substituted with one above "aromatic carbocyclyl oxy". Examples include phenyloxycarbonyl, naphthyloxycarbonyl and the like.

The term of "aromatic carbocyclyl carbonylamino" includes a group wherein the nitrogen atom of amino is attached to above "aromatic carbocycle carbonyl". Examples include phenylcarbonylamino, naphthylcarbonylamino and the like.

The term of "aromatic carbocyclyl sulfanyl" includes a group wherein a hydrogen atom attached to a sulfur atom of a sulfanyl is replaced with "aromatic carbocycle". Examples include phenylsulfanyl, naphthylsulfanyl and the like.

The term of "aromatic carbocyclyl sulfonyl" includes a group wherein a sulfonyl is substituted with one above "aromatic carbocycle". Examples include phenylsulfonyl, naphthylsulfonyl and the like.

The "non-aromatic carbocycle" portion of "non-aromatic carbocyclyl oxy", "non-aromatic carbocyclyl amino", "non-aromatic carbocyclyl carbonyl", "non-aromatic carbocyclyl oxycarbonyl", "non-aromatic carbocyclyl carbonylamino", "non-aromatic carbocyclyl sulfanyl" and "non-aromatic carbocyclyl sulfonyl" means the aforementioned "non-aromatic carbocyclyl".

The term of "non-aromatic carbocyclyl oxy" includes a group wherein an oxygen atom is substituted with one above "non-aromatic carbocycle". Examples include cyclopropyloxy, cyclohexyloxy, cyclohexenyloxy and the like.

The term of "non-aromatic carbocyclyl amino" includes a group wherein one or two hydrogen atom(s) attached to a nitrogen atom of an amino group is replaced with above "non-aromatic carbocycle". Examples include cyclopropylamino, cyclohexylamino, cyclohexenylamino, and the like.

The term of "non-aromatic carbocyclyl carbonyl" includes a group wherein a carbonyl is substituted with one above "non-aromatic carbocycle". Examples include cyclopropylcarbonyl, cyclohexylcarbonyl, cyclohexenylcarbonyl and the like.

The term of "non-aromatic carbocyclyl oxycarbonyl" includes a group wherein a carbonyl is substituted with one above "non-aromatic carbocyclyl oxy". Examples include cyclopropyloxycarbonyl, cyclohexyloxycarbonyl, cyclohexenyloxycarbonyl and the like.

The term of "non-aromatic carbocyclyl carbonylamino" includes a group wherein one or two hydrogen atom(s) attached to a nitrogen atom of an amino group is replaced with above "non-aromatic carbocyclecarbonyl". Examples include cyclopropylcarbonylamino, cyclohexylcarbonylamino, cyclohexenylcarbonylamino, and the like.

The term of "non-aromatic carbocyclyl sulfanyl" includes a group wherein a hydrogen atom attached to a sulfur atom of a sulfanyl is replaced with one above "non-aromatic carbocycle". Examples include cyclopropylsulfanyl, cyclohexylsulfanyl, cyclohexenylsulfanyl and the like.

The term of "non-aromatic carbocyclyl sulfonyl" includes a group wherein a sulfonyl is substituted with one above "non-aromatic carbocycle". Examples include cyclopropylsulfonyl, cyclohexylsulfonyl, cyclohexenylsulfonyl and the like.

The "aromatic heterocycle" portion of "aromatic heterocyclyl oxy", "aromatic heterocyclylamino", "aromatic heterocyclyl carbonyl", "aromatic heterocyclyl oxycarbonyl", "aromatic heterocyclylcarbonylamino", "aromatic heterocyclyl sulfanyl" and "aromatic heterocyclyl sulfonyl" means the aforementioned "aromatic heterocyclyl".

The term of "aromatic heterocyclyl oxy" includes a group wherein an oxygen atom is substituted with one above "aromatic heterocycle". Examples include pyridyloxy, oxazolyloxy and the like.

The term of "aromatic heterocyclyl amino" includes a group wherein one or two hydrogen atom(s) attached to a nitrogen atom of an amino group is replaced with "aromatic heterocycle". Examples include pyridylamino, oxazolylamino and the like.

The term of "aromatic heterocyclyl carbonyl" includes a group wherein a carbonyl is substituted with one above "aromatic heterocycle". Examples include pyridylcarbonyl, oxazolylcarbonyl and the like.

The term of "aromatic heterocyclyl oxycarbonyl" includes a group wherein a carbonyl is substituted with one above "aromatic heterocyclyl oxy". Examples include pyridyloxycarbonyl, oxazolyloxycarbonyl and the like.

The term of "aromatic heterocyclyl carbonylamino" includes a group wherein one or two hydrogen atom(s) attached to a nitrogen atom of an amino group is replaced with "aromatic heterocycle". Examples include pyridylcarbonylamino, oxazolylcarbonylamino and the like.

The term of "aromatic heterocyclyl sulfanyl" includes a group wherein a hydrogen atom attached to a sulfur atom of a sulfanyl is replaced with one above "aromatic heterocycle". Examples include pyridylsulfanyl, oxazolylsulfanyl and the like.

The term of "aromatic heterocyclyl sulfonyl" includes a group wherein a sulfonyl is substituted with one above "aromatic heterocycle". Examples include pyridylsulfonyl, oxazolylsulfonyl and the like.

The "non-aromatic heterocycle" portion of "non-aromatic heterocyclyl oxy", "non-aromatic heterocyclyl amino", "non-aromatic heterocyclyl carbonyl", "non-aromatic heterocyclyl oxycarbonyl", "non-aromatic heterocyclyl carbonylamio", "non-aromatic heterocyclyl sulfanyl" and "non-aromatic heterocyclyl sulfonyl" means the aforementioned "non-aromatic heterocyclyl".

The term of "non-aromatic heterocyclyl oxy" includes a group wherein an "non-aromatic heterocycle" is attached to an oxygen atom. Examples include piperidinyloxy, tetrahydrofuryloxy and the like.

The term of "non-aromatic heterocyclyl amino" includes a group wherein one hydrogen atom attached to the nitrogen atom of an amino group is replaced with above "non-aromatic heterocycle". Examples include piperidinylamino, tetrahydrofurylamino and the like.

The term of "non-aromatic heterocyclyl carbonyl" includes a group wherein above "non-aromatic heterocycle" is attached to a carbonyl group. Examples include piperidinylcarbonyl, tetrahydrofurylcarbonyl and the like are exemplified.

The term of "non-aromatic heterocyclyl oxycarbonyl" includes a group wherein "non-aromatic heterocyclyl oxy" is attached to a carbonyl group. Examples include piperidinyloxycarbonyl, tetrahydrofuryloxycarbonyl and the like.

The term of "non-aromatic heterocyclyl carbonylamino" includes a group wherein one or two hydrogen atom(s) attached to the nitrogen atom of an amino group is replaced with above "non-aromatic heterocyclecarbonyl". Examples include piperidinylcarbonylamino, tetrahydrofurylcarbonylamino and the like.

The term of "non-aromatic heterocyclyl sulfanyl" includes a group wherein a hydrogen atom attached to a sulfur atom of a sulfanyl is replaced with one above "non-aromatic heterocycle". Examples include piperidinylsulfanyl, tetrahydrofurylsulfanyl and the like.

The term of "non-aromatic heterocyclyl sulfonyl" includes a group wherein a "non-aromatic heterocycle" is attached to a sulfonyl group. Examples include piperidinylsulfonyl, tetrahydrofurylsulfonyl and the like.

The substituents of "substituted or unsubstituted alkyl", "substituted or unsubstituted alkenyl", "substituted or unsubstituted alkynyl", "substituted or unsubstituted haloalkyl", "substituted or unsubstituted alkyloxy", "substituted or unsubstituted alkenyloxy", "substituted or unsubstituted alkynyloxy", "substituted or unsubstituted haloalkyloxy", "substituted or unsubstituted alkylcarbonyl", "substituted or unsubstituted alkenylcarbonyl", "substituted or unsubstituted alkynylcarbonyl", "substituted or unsubstituted monoalkylamino", "substituted or unsubstituted dialkylamino", "substituted or unsubstituted alkylsulfonyl", "substituted or unsubstituted alkenylsulfonyl", "substituted or unsubstituted alkynylsulfonyl", "substituted or unsubstituted monoalkylcarbonylamino", "substituted or unsubstituted dialkylcarbonylamino", "substituted or unsubstituted monoalkylsulfonylamino", "substituted or unsubstituted dialkylsulfonylamino", "substituted or unsubstituted alkylimino", "substituted or unsubstituted alkenylimino", "substituted or unsubstituted alkynylimino", "substituted or unsubstituted alkylcarbonylimino", "substituted or unsubstituted alkenylcarbonylimino", "substituted or unsubstituted alkynylcarbonylimino", "substituted or unsubstituted alkyloxyimino", "substituted or unsubstituted alkenyloxyimino", "substituted or unsubstituted alkynyloxyimino", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfonyl", "substituted or unsubstituted alkenylsulfanyl", "substituted or unsubstituted alkynylsulfanyl", "substituted or unsubstituted alkylsulfinyl", "substituted or unsubstituted alkenylsulfinyl", "substituted or unsubstituted alkynylsulfinyl", "substituted or unsubstituted monoalkylcarbamoyl", "substituted or unsubstituted dialkylcarbamoyl", "substituted or unsubstituted monoalkylsulfamoyl", and "substituted or unsubstituted dialkylsulfamoyl" include the group as follows. A carbon atom at any possible position(s) can be substituted with one or more substituent(s) selected from the following group.

Substituent: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azido, hydrazino, ureido, amidino, guanidino, trialkylsilyl, alkyloxy, alkenyloxy, alkynyloxy, haloalkyloxy, alkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, monoalkylcarbamoyl, dialkylcarbamoyl, monoalkylsulfamoyl, dialkylsulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocylyloxy, substituted or unsubstituted non-aromatic carbocyclyl, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, aromatic carbocyclylcarbonylamino, non-aromatic carbocyclylcarbonylamino, aromatic heterocyclylcarbonylamino, non-aromatic heterocyclylcarbonylamino, aromatic carbocyclylalkyloxy, non-aromatic carbocyclylalkyloxy, aromatic heterocyclylalkyloxy, non-aromatic heterocyclylalkyloxy, aromatic carbocyclylalkylsulfanyl, non-aromatic carbocyclylalkylsulfanyl, aromatic heterocyclylalkylsulfanyl, non-aromatic heterocyclylalkylsulfanyl, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkylamino, non-aromatic carbocyclylalkylamino, aromatic heterocyclylalkylamino, non-aromatic heterocyclylalkylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfonyl, substituted or unsubstituted non-aromatic carbocyclylsulfonyl, substituted or unsubstituted aromatic heterocyclylsulfonyl, and substituted or unsubstituted non-aromatic heterocyclylsulfonyl.

The substituents on each ring of "substituted or unsubstituted aromatic carbocyclic group", "substituted or unsubstituted non-aromatic carbocyclic group", "substituted or unsubstituted aromatic heterocyclic group", "substituted or unsubstituted non-aromatic heterocyclic group", "substituted or unsubstituted aromatic carbocycleoxy", "substituted or unsubstituted non-aromatic carbocycleoxy", "substituted or unsubstituted aromatic heterocycleoxy", "substituted or unsubstituted non-aromatic heterocycleoxy", "substituted or unsubstituted aromatic carbocycleamino", "substituted or unsubstituted non-aromatic carbocycleamino", "substituted or unsubstituted aromatic heterocycle amino", "substituted or unsubstituted non-aromatic heterocycleamino", "substituted or unsubstituted aromatic carbocyclecarbonyl", "substituted or unsubstituted non-aromatic carbocyclecarbonyl", "substituted or unsubstituted aromatic heterocyclecarbonyl", "substituted or unsubstituted non-aromatic heterocyclecarbonyl", "substituted or unsubstituted aromatic carbocycleoxycarbonyl", "substituted or unsubstituted non-aromatic carbocycleoxycarbonyl", "substituted or unsubstituted aromatic heterocycleoxycarbonyl", "substituted or unsubstituted non-aromatic heterocycleoxycarbonyl", "substituted or unsubstituted aromatic carbocyclesulfanyl", "substituted or unsubstituted non-aromatic carbocyclesulfanyl", "substituted or unsubstituted aromatic heterocyclesulfanyl", "substituted or unsubstituted non-aromatic heterocyclesulfanyl", "substituted or unsubstituted aromatic carbocyclesulfonyl", "substituted or unsubstituted non-aromatic carbocyclesulfonyl", "substituted or unsubstituted aromatic heterocyclesulfonyl", "substituted or unsubstituted non-aromatic heterocyclesulfonyl", "aromatic carbocycle", "non-aromatic carbocycle", "aromatic heterocycle", and "non-aromatic heterocycle" include the following group, and a carbon atom at any possible position(s) can be substituted with one or more substituent(s) selected from the following group.

Substituent Group:

Substituent: halogen, hydroxy, carboxy, amino, imino, hydroxyamino, hydroxyimino, formyl, carbamoyl, sulfamoyl, sulfanyl, sulfino, sulfo, thioformyl, thiocarboxy, dithiocarboxy, thiocarbamoyl, cyano, nitro, azido, hydrazino, ureido, amidino, guanidino, trialkylsilyl, alkyl, alkenyl, alkynyl, haloalkyl, hydroxyalkyl, alkyloxy, alkenyloxy, alkynyloxy, haloalkyloxy, alkyloxyalkyl, alkyloxyalkyloxy, alkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, monoalkylcarbamoyl, dialkylcarbamoyl, monoalkylsulfamoyl, dialkylsulfamoyl, aromatic carbocyclic group, non-aromatic carbocyclic group, aromatic heterocyclic group, non-aromatic heterocyclic group, aromatic carbocycleoxy, non-aromatic carbocycleoxy, aromatic heterocycleoxy, non-aromatic heterocycleoxy, aromatic carbocycleamino, non-aromatic carbocycle amino, aromatic heterocycleamino, non-aromatic heterocycleamino, aromatic carbocyclecarbonyl, non-aromatic carbocyclecarbonyl, aromatic heterocyclecarbonyl, non-aromatic heterocyclecarbonyl, aromatic carbocycleoxycarbonyl, non-aromatic carbocycleoxycarbonyl, aromatic heterocycleoxycarbonyl, non-aromatic heterocycleoxycarbonyl, non-aromatic heterocycleoxycarbonyl, aromatic carbocyclecarbonylamino, non-aromatic carbocyclecarbonylamino, aromatic heterocyclecarbonylamino, non-aromatic heterocyclecarbonylamino, aromatic carbocyclealkyl, non-aromatic carbocyclealkyl, aromatic heterocyclealkyl, non-aromatic heterocyclealkyl, aromatic carbocyclealkyloxy, non-aromatic carbocyclealkyloxy, aromatic heterocyclealkyloxy, non-aromatic heterocyclealkyloxy, aromatic carbocyclealkylsukfanyl, non-aromatic carbocyclealkylsukfanyl, aromatic heterocyclealkylsukfanyl, non-aromatic heterocyclealkylsukfanyl, aromatic carbocyclealkyloxycarbonyl, non-aromatic carbocyclealkyloxycarbonyl, aromatic heterocyclealkyloxycarbonyl, non-aromatic heterocyclealkyloxycarbonyl, aromatic carbocyclealkyloxyalkyl, non-aromatic carbocyclealkyloxyalkyl, aromatic heterocyclealkyloxyalkyl, non-aromatic heterocyclealkyloxyalkyl, aromatic carbocyclealkylamino, non-aromatic carbocyclealkylamino, aromatic heterocyclealkylamino, non-aromatic heterocyclealkylamino, aromatic carbocyclesukfanyl, non-aromatic carbocyclesukfanyl, aromatic heterocyclesukfanyl, non-aromatic heterocyclesukfanyl, non-aromatic carbocyclesulfonyl, aromatic carbocyclesulfonyl, aromatic heterocyclesulfonyl, and non-aromatic heterocycle sulfonyl.

"Substituted or unsubstituted non-aromatic carbocyclyl" and "substituted or unsubstituted non-aromatic heterocyclyl" can be substituted with "oxo". Namely, two hydrogen atoms attached to a carbon atom are replaced with oxo as follows:

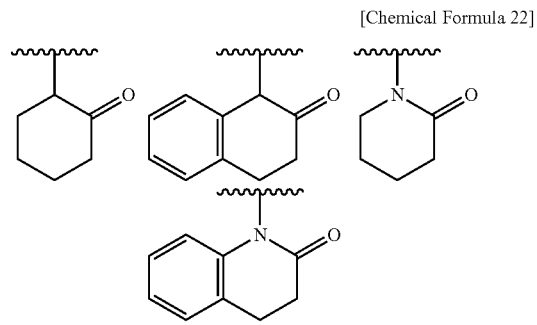

[Chemical Formula 22]

Further, "substituted or unsubstituted non-aromatic carbocyclic group" and "substituted or unsubstituted non-aromatic heterocyclic group" may be bridged with alkylene, alkenylene, or alkynylene, or form a Spiro ring together with another ring such as cycloalkane, cycloalkene, cycloalkyne, oxirane, oxetane, and thiolane, as shown below

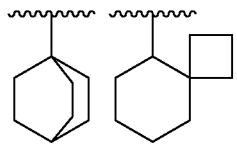

[Chemical Formula 23]

The above "non-aromatic carbocycle" and "non-aromatic heterocycle" of "substituted or unsubstituted non-aromatic carbocycleoxy", "substituted or unsubstituted non-aromatic heterocycleoxy", "substituted or unsubstituted non-aromatic carbocycleamino", "substituted or unsubstituted non-aromatic heterocycleamino", "substituted or unsubstituted non-aromatic carbocyclecarbonyl", "substituted or unsubstituted non-aromatic heterocyclecarbonyl", "substituted or unsubstituted non-aromatic carbocycleoxycarbonyl", "substituted or unsubstituted non-aromatic heterocycleoxycarbonyl", "substituted or unsubstituted non-aromatic carbocyclecarbonylamino", "substituted or unsubstituted non-aromatic heterocyclecarbonylamino", "substituted or unsubstituted non-aromatic carbocyclesukfanyl", "substituted or unsubstituted non-aromatic heterocyclesukfanyl", "substituted or unsubstituted non-aromatic carbocyclesulfonyl", and "substituted or unsubstituted non-aromatic heterocyclesulfonyl", may be substituted with "oxo" as mentioned above.

Preferred embodiment in the compound represented by the formula (I) is shown below.

[Formula 24]

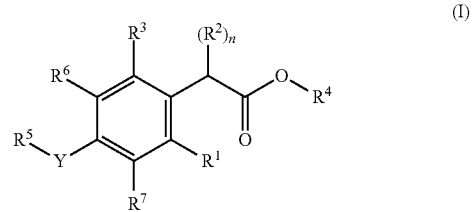

(I)

$R^1$ is preferably halogen, cyano, nitro, or —X—$R^{11}$ (X is a single bond, —O—, —S—, —$NR^{12}$—, —CO—, —$SO_2$—, —O—CO—, —CO—O—, —$NR^{12}$—CO—, —CO—

$NR^{12}$—, $-NR^{12}-CO-O-$, $-NR^{12}-CO-NR^{13}-$, $-NR^{12}-SO_2-$, or $-SO_2-NR^{12}-$, $R^{11}$ is a hydrogen atom, substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, and $R^{12}$ and $R^{13}$ are each independently a hydrogen atom, substituted or unsubstituted alkyl, substituted or unsubstituted alkenyl, or substituted or unsubstituted alkynyl).

When X is $-NR^{12}-$, $-CO-NR^{12}-$, or $-SO_2-NR^{12}-$, $R^{11}$ and $R^{12}$ may be taken together with an adjacent nitrogen atom to form a substituted or unsubstituted aromatic heterocyclic group or a substituted or unsubstituted nonaromatic heterocyclic group.

Here, X is preferably a single bond, $-O-$, $-NR^{12}-$, $-SO_2-$, $-NR^{12}-CO-$, $CO-NR^{12}-$, $-NR^{12}-CO-O-$, $-NR^{12}-CO-NR^{13}-$, $-NR^{12}-SO_2-$ or $-SO_2-NR^{12}-$, and more preferably a single bond.

$R^1$ is more preferably a hydrogen atom, halogen, cyano, substituted or unsubstituted alkyl, substituted or unsubstituted alkenyl, substituted or unsubstituted alkynyl, a substituted or unsubstituted aromatic carbocyclic group, or a substituted or unsubstituted nonaromatic carbocyclic group, further preferably a hydrogen atom, halogen, cyano, substituted or unsubstituted alkyl, substituted or unsubstituted alkenyl, or a substituted or unsubstituted aromatic carbocyclic group, further preferably a hydrogen atom, halogen, cyano, or substituted or unsubstituted alkyl, particularly preferably halogen, cyano, or alkyl having 1 to 4 carbon atoms, and most preferably bromo, cyano, or methyl.

$R^2$ is each independently preferably substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, or substituted or unsubstituted alkynylsulfanyl, more preferably substituted or unsubstituted alkyloxy, substituted or unsubstituted alkenyloxy, or substituted or unsubstituted alkynyloxy, further preferably substituted or unsubstituted alkyloxy, particularly preferably alkyloxy having 1 to 4 carbon atoms, and most preferably tert-butyloxy.

n is preferably 1 or 2, and particularly preferably 1.

$R^3$ is preferably a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, further preferably, substituted or unsubstituted phenyl, substituted or unsubstituted cycloalkenyl, substituted or unsubstituted benzofuryl, substituted or unsubstituted benzodioxolyl, substituted or unsubstituted benzodioxanyl, substituted or unsubstituted dihydrobenzofuryl, substituted or unsubstituted chromanyl, or substituted or unsubstituted benzomorpholinyl, and further preferably substituted or unsubstituted phenyl or substituted or unsubstituted chromanyl.

When $R^3$ is a substituted or unsubstituted aromatic heterocyclic group or substituted or unsubstituted nonaromatic heterocyclic group in which substituted or unsubstituted benzene is condensed, it is preferred that the aromatic heterocyclic group or nonaromatic heterocyclic group contains at least one oxygen atom.

When $R^3$ has a substituent, a preferred substituent is halogen, hydroxy, amino, cyano, oxo, alkyl, alkenyl, alkynyl, hydroxyalkyl, haloalkyl, alkyloxy, alkenyloxy, alkynyloxy, alkyloxyalkyl, haloalkyloxy, monoalkylamino, dialkylamino, alkylsulfanyl, alkenylsulfanyl, or alkynylsulfanyl, a more preferred substituent is halogen, hydroxy, amino, alkyl, or alkyloxy, a further preferred substituent is fluoro, chloro, bromo, hydroxy, amino, methyl, ethyl, or methyloxy, and a particularly preferred substituent is fluoro, chloro, hydroxy, amino, methyl, or methyloxy.

Specifically, $R^3$ preferably has any of the following structures.

[Formula 25]

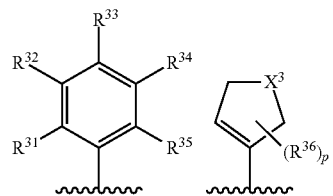

Here, $R^{31}$, $R^{32}$, $R^{33}$, $R^{34}$ and $R^{35}$ are each independently preferably a hydrogen atom, halogen, hydroxy, amino, alkyl, alkenyl, alkynyl, haloalkyl, alkyloxy, alkenyloxy, alkynyloxy, or haloalkyloxy, more preferably a hydrogen atom, halogen, hydroxy, amino, alkyl, or alkyloxy, further preferably fluoro, chloro, bromo, hydroxy, amino, methyl, ethyl, or methyloxy, and particularly preferably fluoro, chloro, hydroxy, amino, methyl, or methyloxy. $R^{31}$ and $R^{32}$, $R^{32}$ and $R^{33}$, $R^{33}$ and $R^{34}$ and $R^{34}$ and $R^{35}$ each independently may be taken together with an adjacent atom to form an aromatic carbocyclic ring, a nonaromatic carbocyclic ring, an aromatic heterocyclic ring, or a nonaromatic heterocyclic ring. The ring may be substituted by halogen, alkyl, or oxo, and a five-membered ring or a six-membered ring is preferred.

$R^{36}$ is each independently preferably alkyl, alkenyl, alkynyl, or haloalkyl, more preferably alkyl, and particularly methyl. p is preferably any integer of 0 to 6, and more preferably any integer of 0 to 2. $X^3$ is preferably alkylene, alkenylene, or alkynylene, more preferably alkylene, and particularly preferably methylene, ethylene, or propylene.

$R^3$ is further preferably a group shown below.

[Formula 26]

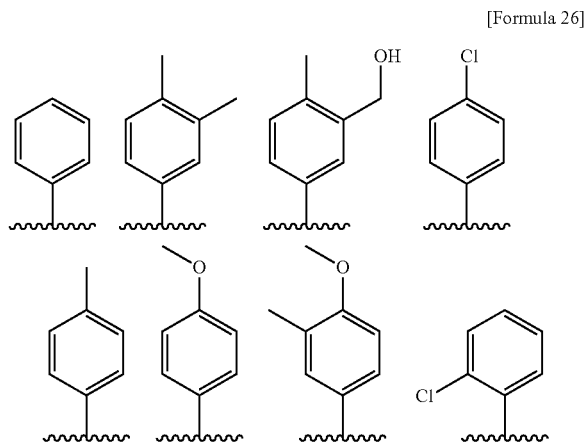

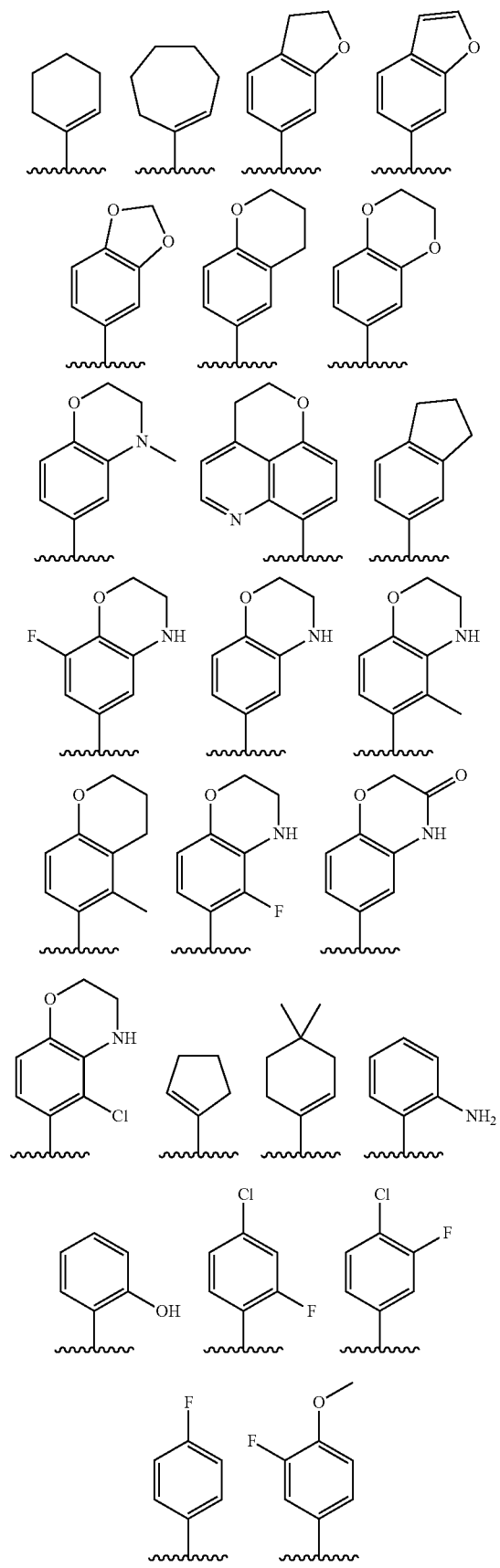
$R^3$ is particularly preferably a group shown below.
[Formula 27]
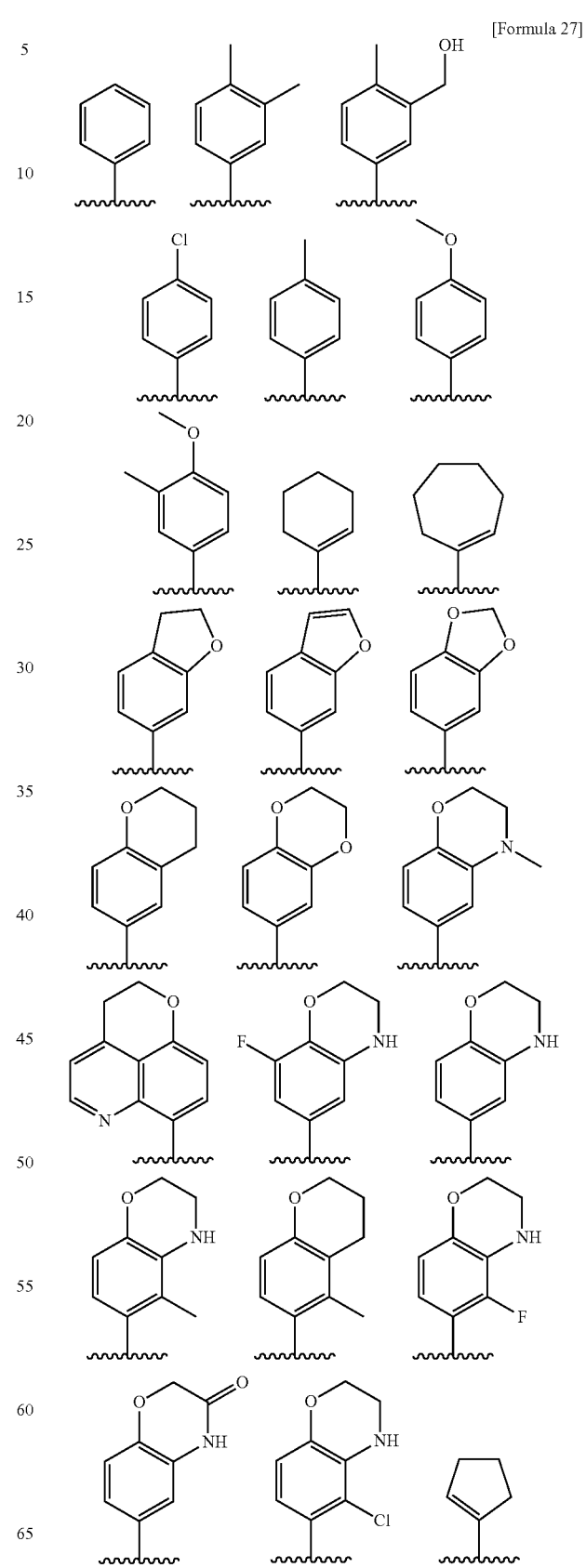

-continued

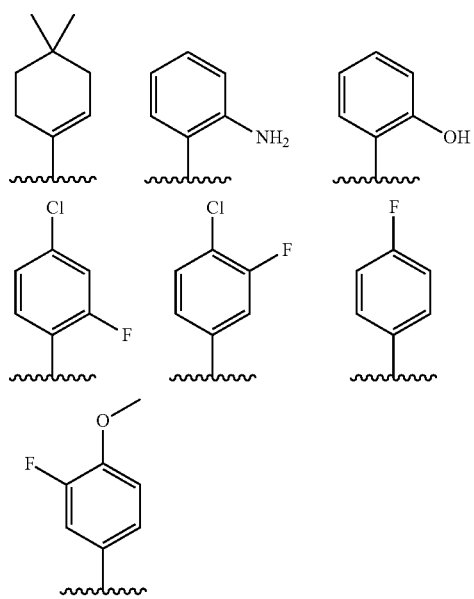

When $R^1$ and $R^7$ are not taken together with an adjacent atom to form ring A, $R^3$ is preferably a group shown below.

[Formula 28]

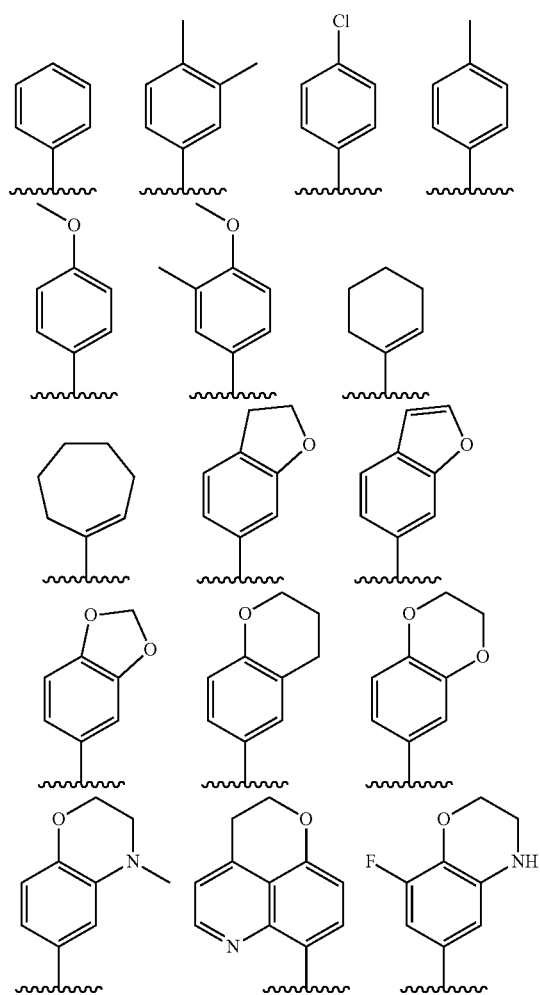

-continued $R^4$ is preferably a hydrogen atom, substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, and most preferably a hydrogen atom.

$R^5$ is preferably a hydrogen atom, hydroxy, formyl, carboxy, carbamoyl, carbamoyloxy, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted monoalkylcarbamoyl, substituted or unsubstituted dialkylcarbamoyl, substituted or unsubstituted monoalkylcarbamoyloxy, substituted or unsubstituted dialkylcarbamoyloxy, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclicoxy, substituted or unsubstituted nonaromatic carbocyclicoxy, substituted or unsubstituted aromatic heterocyclicoxy, substituted or unsubstituted nonaromatic heterocyclicoxy, substituted or unsubstituted aromatic carbocyclic sulfanyl, substituted or unsubstituted nonaromatic carbocyclic sulfanyl, substituted or unsubstituted aromatic heterocyclic sulfanyl, substituted or unsubstituted nonaromatic heterocyclic sulfanyl, substituted or unsubstituted aromatic carbocyclic carbonyl, substituted or unsubstituted nonaromatic carbocyclic carbonyl, substituted or unsubstituted aromatic heterocyclic carbonyl, substituted or unsubstituted nonaromatic heterocyclic carbonyl, substituted or unsubstituted aromatic carbocyclic oxycarbonyl, substituted or unsubstituted nonaromatic carbocyclic oxycarbonyl, substituted or unsubstituted aromatic heterocyclic oxycarbonyl, substituted or unsubstituted nonaromatic heterocyclic oxycarbonyl, substituted or unsubstituted aromatic carbocyclic carbamoyl, substituted or unsubstituted nonaromatic carbocyclic carbamoyl, substituted or unsubstituted aromatic heterocyclic carbamoyl, substituted or unsubstituted nonaromatic heterocyclic carbamoyl, or —NR$^{51}$R$^{52}$ (R$^{51}$ and R$^{52}$ are each independently a hydrogen atom, formyl, carbamoyl, carboxy, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkylcarbamoyl, substituted or unsubstituted alkenylcarbamoyl, substituted or unsubstituted alkynylcarbamoyl, substituted or unsubstituted alkyloxycarbonyl, substituted or unsubstituted alkenyloxycarbonyl, substituted or unsubstituted alkynyloxycarbonyl, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclic carbonyl, substituted or unsubstituted nonaromatic carbocyclic carbonyl, substituted or unsubstituted aromatic heterocyclic carbonyl, substituted or unsubstituted nonaromatic heterocyclic carbonyl, substituted or unsubstituted aromatic carbocyclic carbamoyl, substituted or unsubstituted nonaromatic carbocyclic carbamoyl, substituted or unsubstituted aromatic heterocyclic carbamoyl, substituted or unsubstituted nonaromatic heterocyclic carbamoyl, substituted or unsubstituted aromatic carbocyclic oxycarbonyl, substituted or unsubstituted nonaromatic carbocyclic oxycarbonyl, substituted or unsubstituted aromatic heterocyclic oxycarbonyl, or substituted or unsubstituted nonaromatic heterocyclic oxycarbonyl), more preferably a hydrogen atom, substituted or unsubstituted alkyl, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclic carbamoyl, or —NR$^{51}$R$^{52}$ (R$^{51}$ is substituted or unsubstituted aromatic carbocyclic carbonyl, and R$^{52}$ is a hydrogen atom), further preferably a hydrogen atom, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, and particularly preferably a hydrogen atom or a substituted or unsubstituted aromatic carbocyclic group.

R$^5$ is further preferably substituted or unsubstituted alkylcarbamoyl, substituted or unsubstituted alkenylcarbamoyl, substituted or unsubstituted alkyloxy, substituted or unsubstituted alkenyloxy, substituted or unsubstituted aromatic carbocyclic group carbonyl, substituted or unsubstituted nonaromatic carbocyclic group carbonyl, substituted or unsubstituted aromatic heterocyclic group carbonyl, substituted or unsubstituted nonaromatic heterocyclic group carbonyl, or substituted or unsubstituted nonaromatic carbocyclic carbamoyl.

When R$^5$ has a substituent, a preferred substituent is halogen, hydroxy, amino, cyano, oxo, alkyl, alkenyl, alkynyl, haloalkyl, hydroxyalkyl, alkyloxy, alkenyloxy, alkynyloxy, haloalkyloxy, alkyloxyalkyl, monoalkylamino, dialkylamino, alkylsulfanyl, alkenylsulfanyl, alkynylsulfanyl, alkylcarbonyl, alkenylcarbonyl, alkynylcarbonyl, an aromatic carbocyclic group, a nonaromatic carbocyclic group, an aromatic heterocyclic group, a nonaromatic heterocyclic group, aromatic carbocyclic group alkyl, nonaromatic carbocyclic group alkyl, aromatic heterocyclic group alkyl, or nonaromatic heterocyclic group alkyl, a more preferred substituent is halogen, alkyl, hydroxyalkyl, haloalkyl, haloalkyloxy, alkylcarbonyl, an aromatic carbocyclic group, or an aromatic heterocyclic group, and a further preferred substituent is fluoro, chloro, methyl, ethyl, hydroxymethyl, trifluoromethyl, trifluoromethyloxy, acetyl, phenyl, or pyridyl.

In addition, when R$^5$ is crosslinked or a Spiro ring is formed, preferably, R$^5$ is crosslinked by an alkylene, or the spiro ring is formed with a cycloalkyl ring.

R$^5$ is further preferably a group shown below.

[Formula 29]

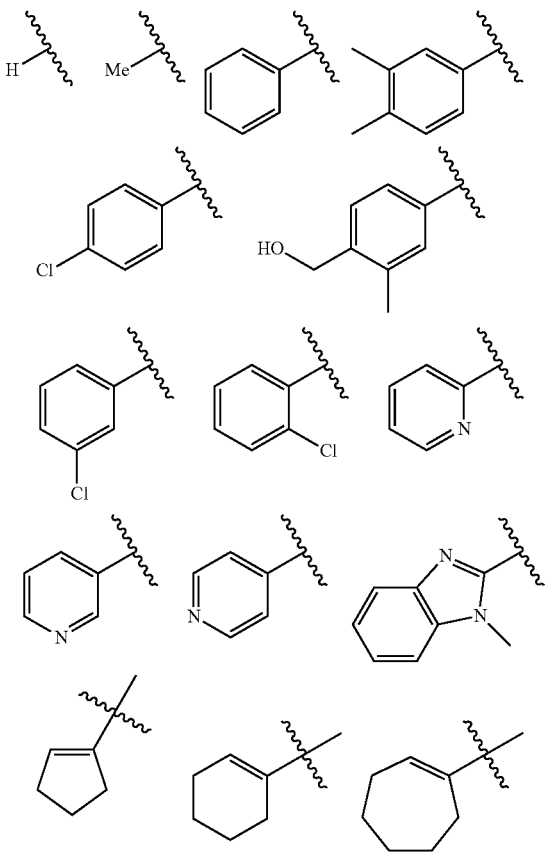

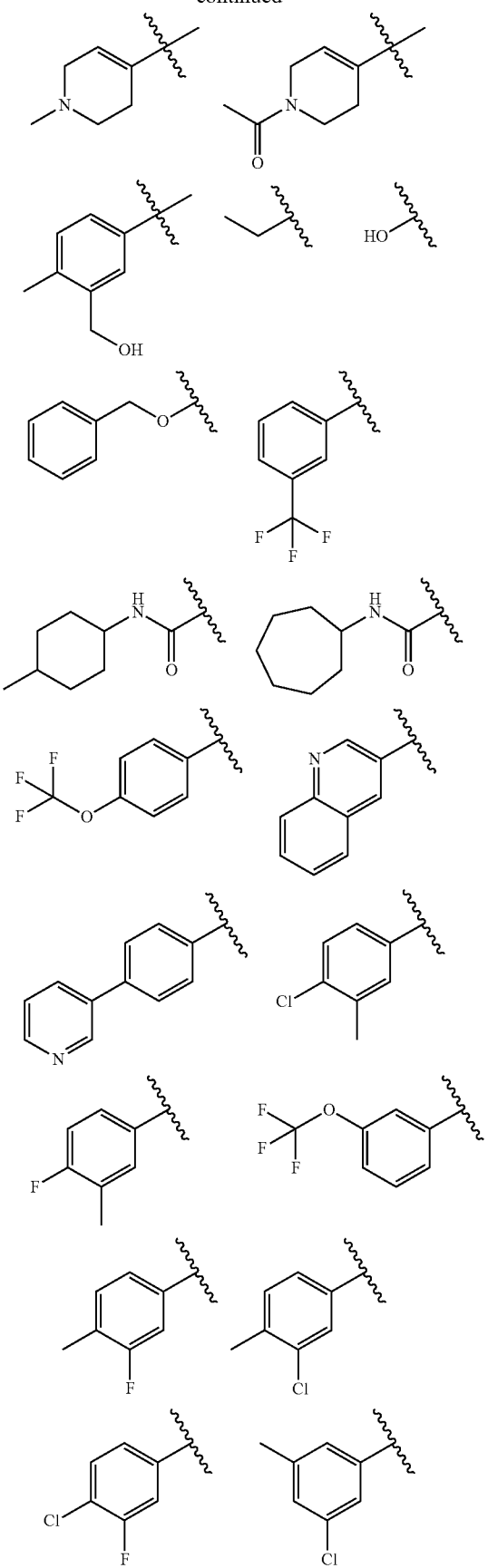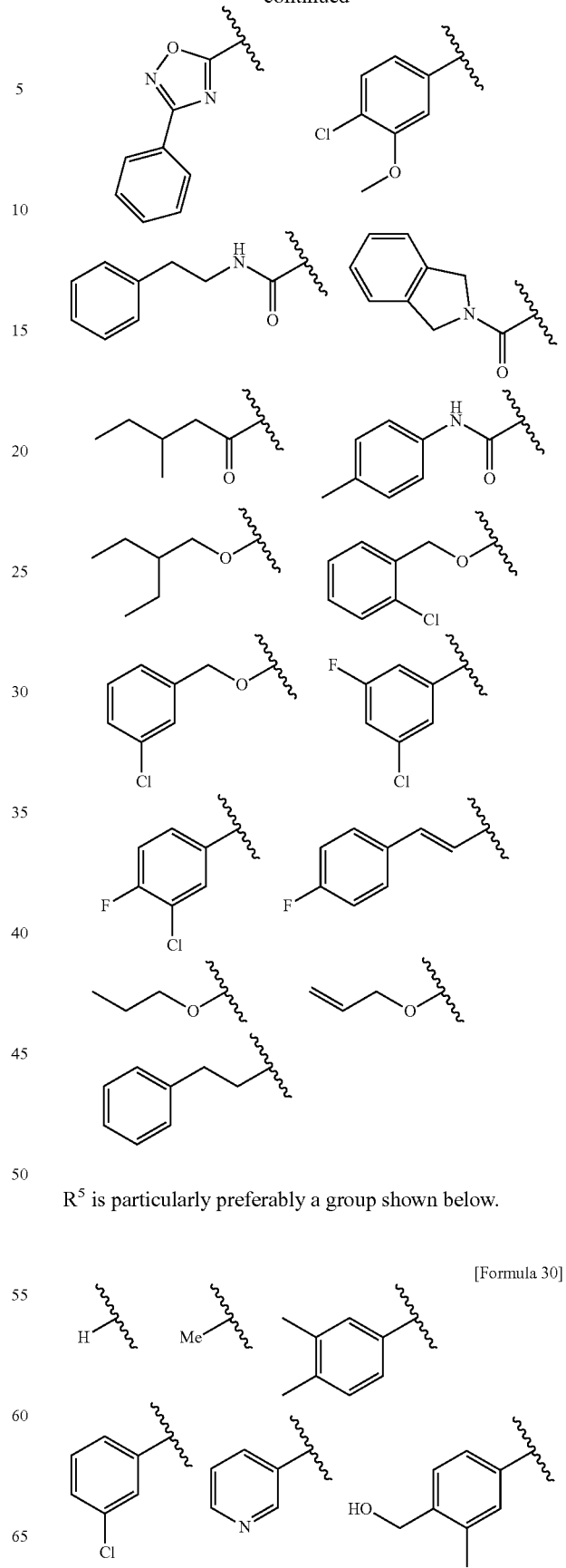
R[5] is particularly preferably a group shown below.
[Formula 30]
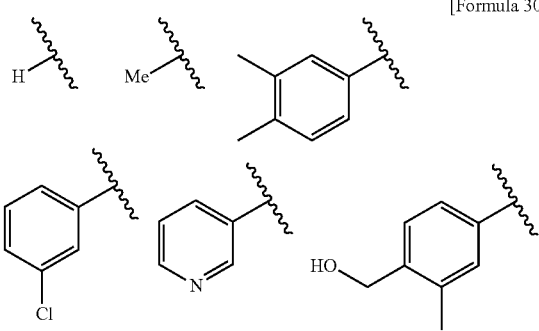

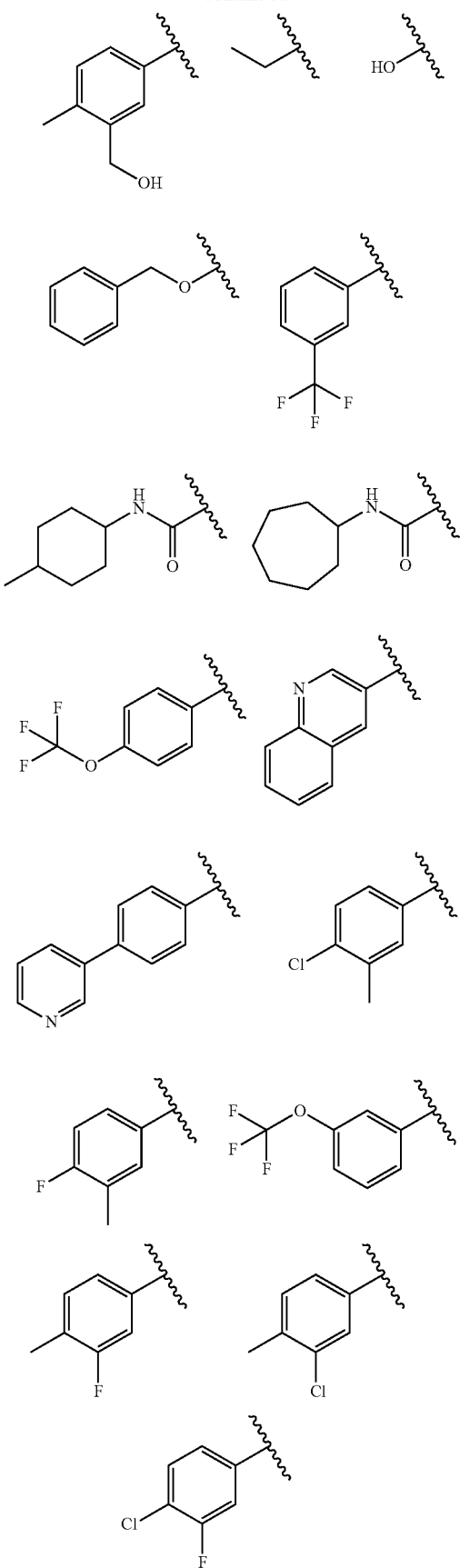
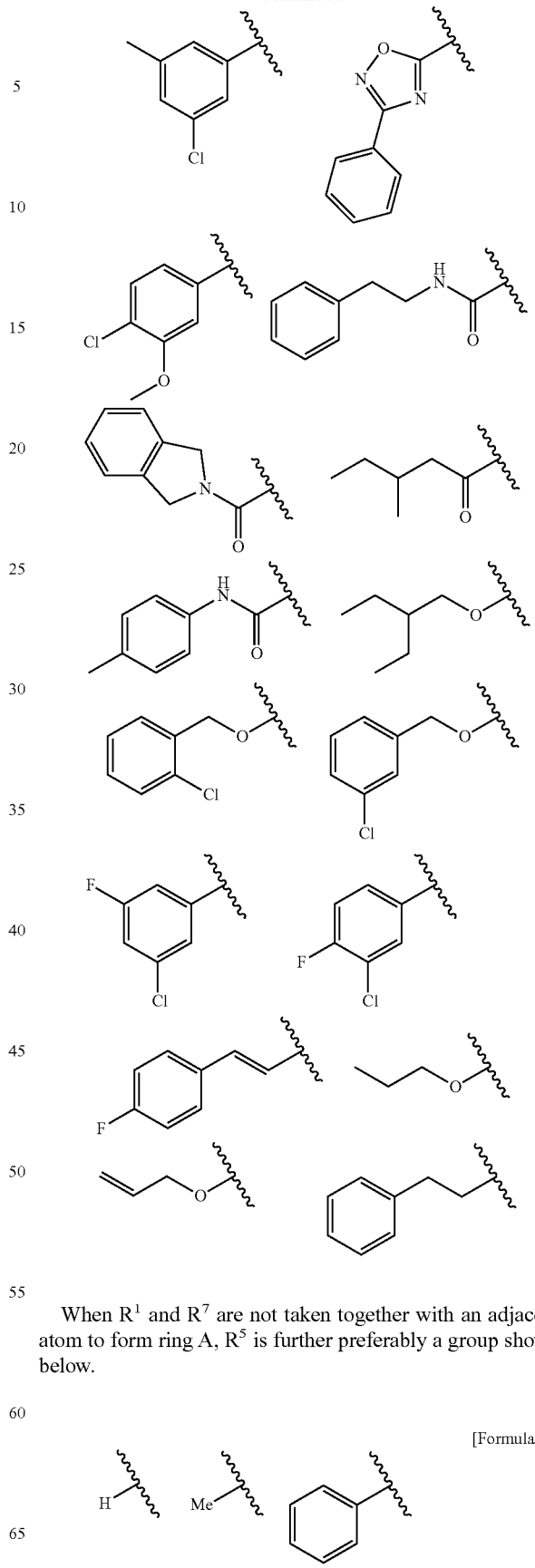
When R¹ and R⁷ are not taken together with an adjacent atom to form ring A, R⁵ is further preferably a group shown below.
[Formula 31]
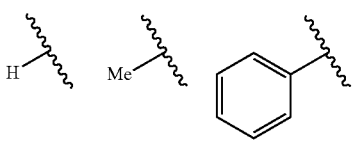

-continued
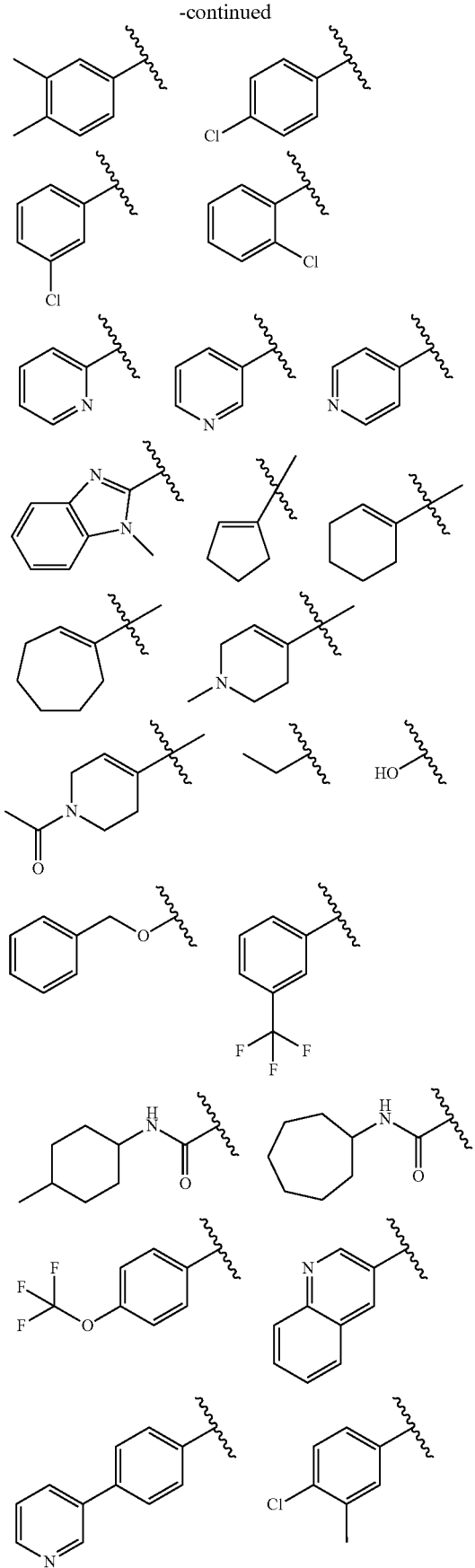
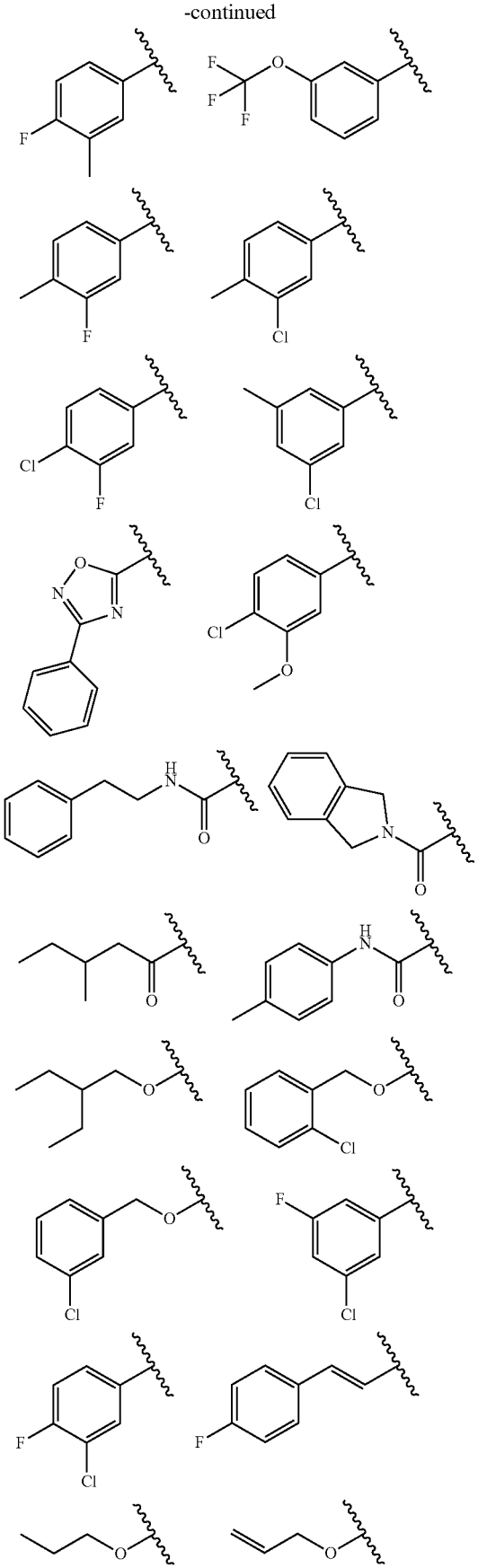

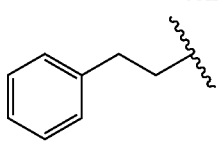
Here, when $R^1$ and $R^7$ are not taken together with an adjacent atom to form ring A, $R^5$ is particularly preferably a group shown below.
[Formula 32]
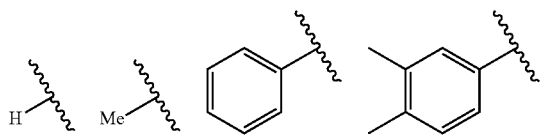
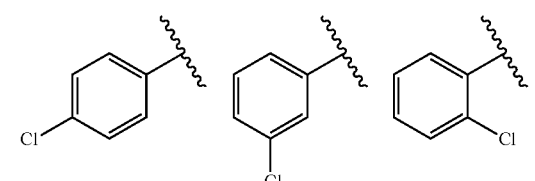
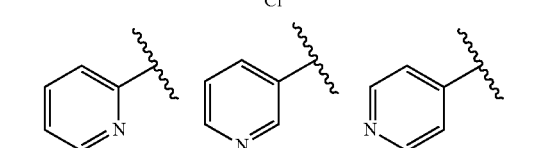
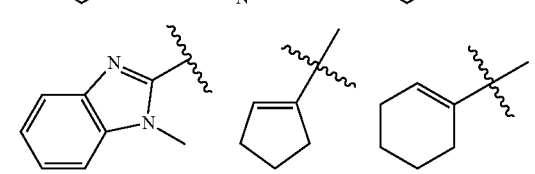
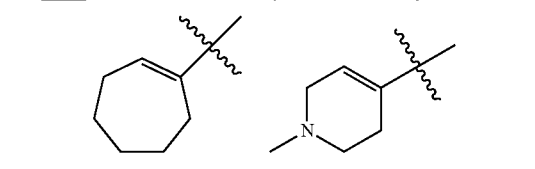
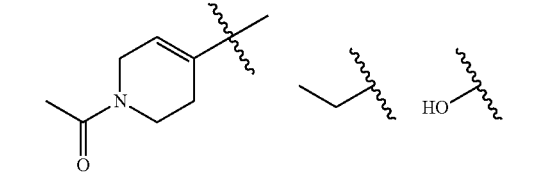
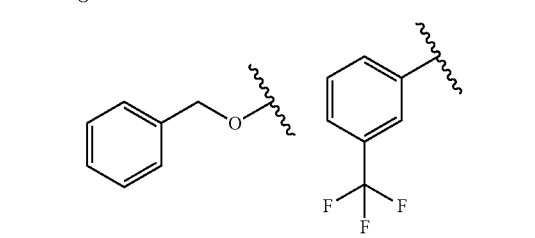
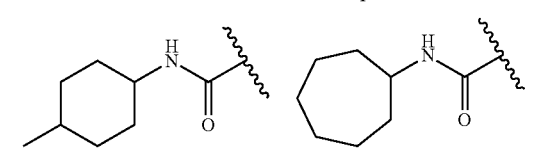
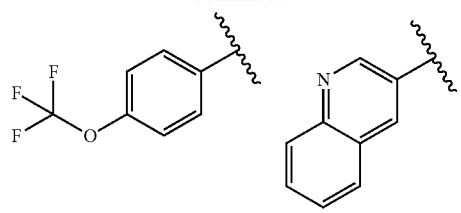
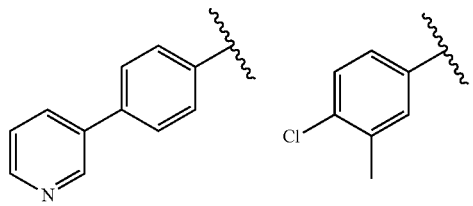
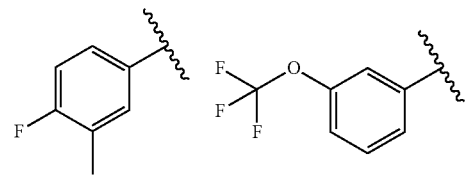
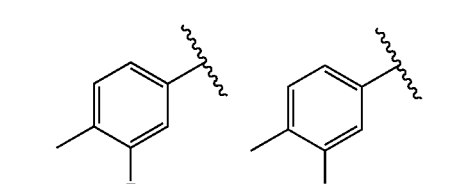
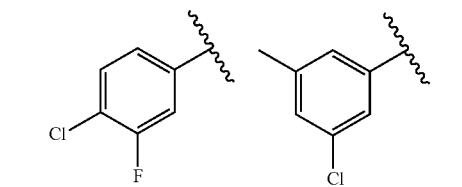
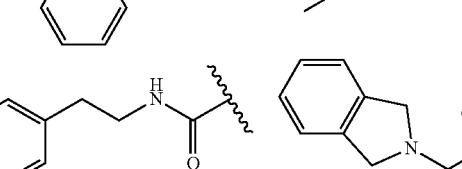
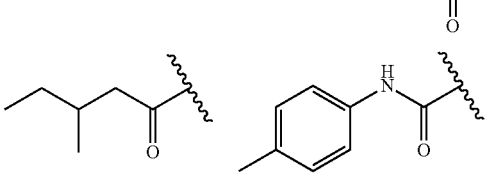
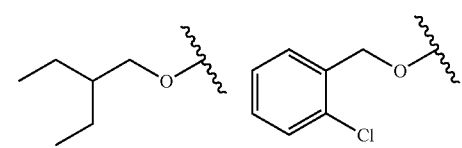

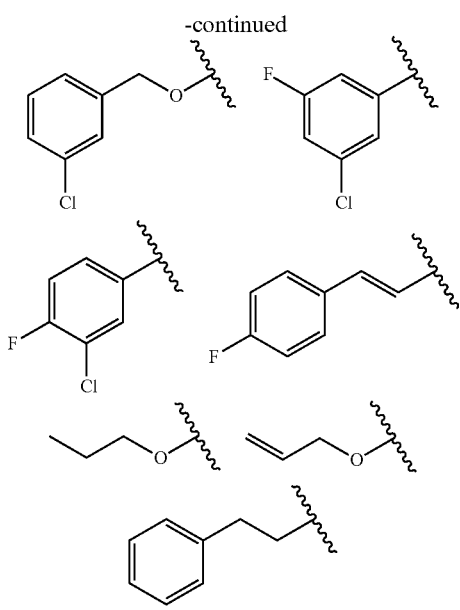

Y is preferably a single bond, alkylene, alkenylene, or alkynylene (however, when $R^5$ is a hydrogen atom, substituted or unsubstituted alkyl, substituted or unsubstituted alkenyl, or substituted or unsubstituted alkynyl, Y is a single bond), more preferably a single bond or alkenylene, further preferably a single bond or vinylene, and particularly preferably a single bond.

Y is also more preferably alkylene.

$R^6$ is preferably a hydrogen atom, halogen, cyano, substituted or unsubstituted alkyl, substituted or unsubstituted alkenyl, substituted or unsubstituted alkynyl, a substituted or unsubstituted nonaromatic carbocyclic group, or substituted or unsubstituted alkyloxy, more preferably a hydrogen atom, substituted or unsubstituted alkyl, substituted or unsubstituted alkenyl, or substituted or unsubstituted alkynyl, further preferably substituted or unsubstituted alkyl, or particularly preferably alkyl having 1 to 4 carbon atoms, and particularly preferably methyl.

$R^7$ is preferably halogen, cyano, nitro, or —Z—$R^{71}$ (Z is a single bond, —O—, —S—, —$NR^{72}$—, —CO—, —$SO_2$—, —O—CO—, —CO—O—, —$NR^{72}$—CO—, —CO—$NR^{72}$—, —$NR^{72}$—CO—O—, —$NR^{72}$—CO—$NR^{73}$—, —$NR^{72}$—$SO_2$—, or —$SO_2$—$NR^{72}$—, $R^{71}$ is a hydrogen atom, substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, $R^{72}$ and $R^{73}$ are each independently a hydrogen atom, substituted or unsubstituted alkyl, substituted or unsubstituted alkenyl, or substituted or unsubstituted alkynyl), and more preferably —Z—$R^{71}$.

When Z is —$NR^{72}$—, —CO—$NR^{72}$—, or —$SO_2$—$NR^{72}$—, $R^{71}$ and $R^{72}$ may be taken together with an adjacent nitrogen atom to form a substituted or unsubstituted aromatic heterocyclic group or a substituted or unsubstituted nonaromatic heterocyclic group.

Here, Z is preferably a single bond, —O—, —$NR^{72}$—, —$SO_2$—, —$NR^{72}$—CO—, —CO—$NR^{72}$—, —$NR^{72}$—CO—O—, —$NR^{72}$—CO—$NR^{73}$—, —$NR^{72}$—$SO_2$—, or —$SO_2$—$NR^{72}$—, more preferably a single bond, —$NR^{72}$—, —$NR^{72}$—CO—, —CO—$NR^{72}$—, —$NR^{72}$—CO—O—, —$NR^{72}$—CO—NH—, —$NR^{72}$—$SO_2$—, or —$SO_2$—$NR^{72}$—, and further preferably a single bond, —$NR^{72}$—, —$NR^{72}$—CO—, —$NR^{72}$—CO—O—, —$NR^{72}$—CO—NH—, or —$NR^{72}$—$SO_2$—. $R^{71}$ is preferably a hydrogen atom, substituted or unsubstituted alkyl, a substituted or unsubstituted aromatic carbocyclic group, or a substituted or unsubstituted nonaromatic carbocyclic group, and particularly preferably a hydrogen atom, methyl, ethyl, propyl, isopropyl, butyl, pentyl, hexyl, alkyl substituted by 1 to 3 halogens, (e.g., trifluoromethyl), cycloalkyl, or phenyl. $R^{72}$ is preferably a hydrogen atom or substituted or unsubstituted alkyl, and more preferably a hydrogen atom or methyl. $R^{73}$ is preferably a hydrogen atom.

$R^7$ is further preferably —Z—$R^{71}$ (Z is a single bond, —O—, —$NR^{72}$—, —$SO_2$—, —$NR^{72}$—CO—, —CO—$NR^{72}$—, —$NR^{72}$—CO—O—, —$NR^{72}$—CO—$NR^{73}$—, —$NR^{72}$—$SO_2$—, or —$SO_2$—$NR^{72}$—, $R^{71}$ is a hydrogen atom, substituted or unsubstituted alkyl, a substituted or unsubstituted aromatic carbocyclic group, or a substituted or unsubstituted nonaromatic carbocyclic group, and $R^{72}$ and $R^{73}$ are each independently a hydrogen atom, substituted or unsubstituted alkyl, substituted or unsubstituted alkenyl, or substituted or unsubstituted alkynyl), particularly preferably —Z—$R^{71}$ (Z is a single bond, —$NR^{72}$—, —$NR^{72}$—CO—, —CO—$NR^{72}$—, —$NR^{72}$—CO—O—, —$NR^{72}$—CO—NH—, —$NR^{72}$—$SO_2$—, or —$SO_2$—$NR^{72}$—, $R^{71}$ is a hydrogen atom, substituted or unsubstituted alkyl, a substituted or unsubstituted aromatic carbocyclic group, or a substituted or unsubstituted nonaromatic carbocyclic group, and $R^{72}$ is a hydrogen atom or substituted or unsubstituted alkyl), and most preferably —Z—$R^{71}$ (Z is a single bond, —$NR^{72}$—, —$NR^{72}$—CO—, —$NR^{72}$—CO—O—, —$NR^{72}$—CO—NH—, or —$NR^{72}$—$SO_2$—, $R^{71}$ is a hydrogen atom, substituted or unsubstituted alkyl, a substituted or unsubstituted aromatic carbocyclic group, or a substituted or unsubstituted nonaromatic carbocyclic group, and $R^{72}$ is a hydrogen atom or substituted or unsubstituted alkyl).

In addition, Z is preferably —O—, —$SO_2$—, —$NR^{72}$—CO—, —CO—$NR^{72}$—, —$NR^{72}$—CO—O—, —$NR^{72}$—CO—$NR^{73}$—, —$NR^{72}$—$SO_2$—, or —$SO_2$—$NR^{72}$—, more preferably —$NR^{72}$—CO—, —CO—$NR^{72}$—, —$NR^{72}$—CO—O—, —$NR^{72}$—CO—NH—, —$NR^{72}$—$SO_2$—, or —$SO_2$—$NR^{72}$—, and further preferably —$NR^{72}$—CO—, —$NR^{72}$—CO—O—, —$NR^{72}$—CO—NH—, or —$NR^{72}$—$SO_2$—.

Here, $R^{71}$ is preferably a hydrogen atom, substituted or unsubstituted alkyl, a substituted or unsubstituted aromatic carbocyclic group, or a substituted or unsubstituted nonaromatic carbocyclic group. Substituted or unsubstituted alkenyl, a substituted or unsubstituted aromatic heterocyclic group, or a substituted or unsubstituted nonaromatic heterocyclic group is also preferred.

$R^7$ is further preferably a group shown below.

[Formula 33]

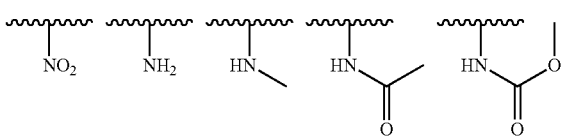

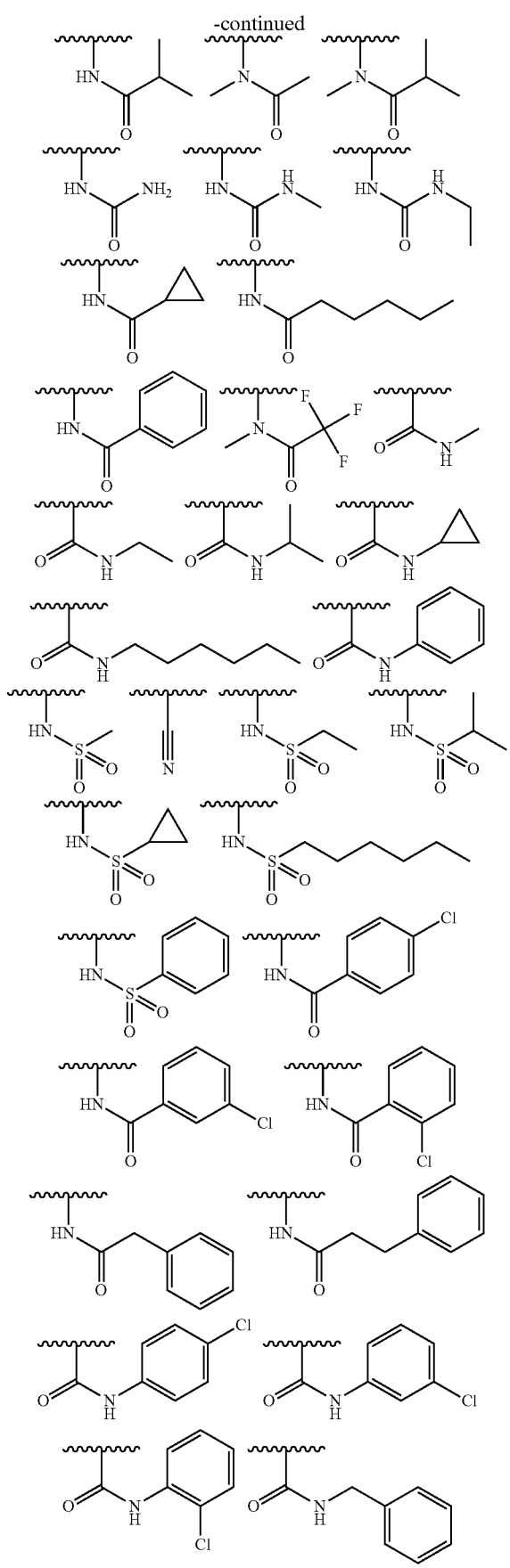
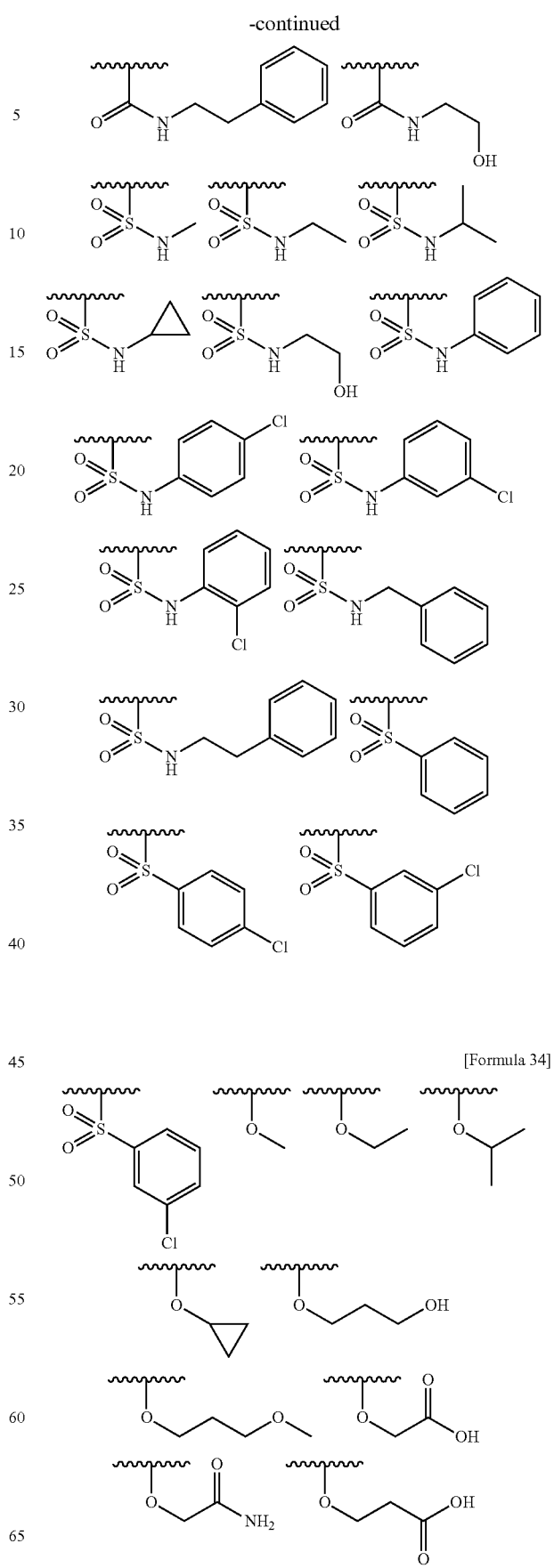

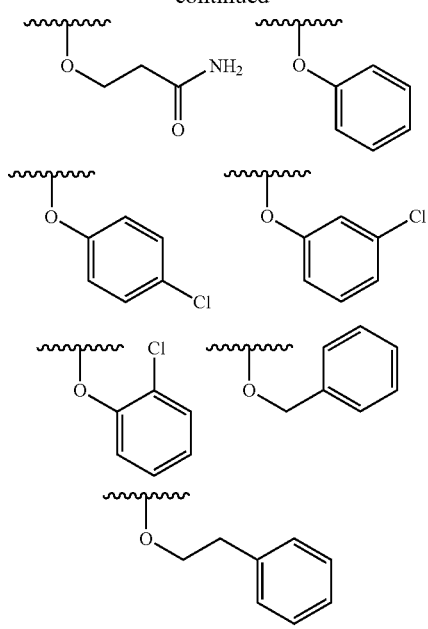
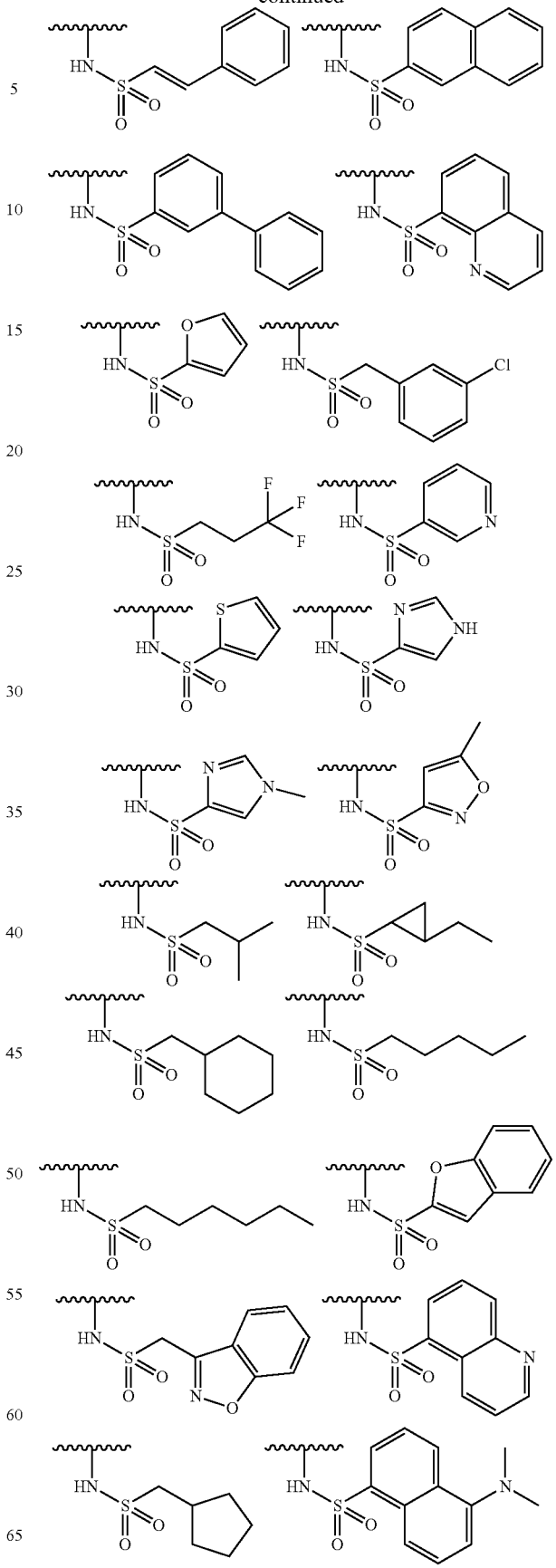
[Formula 35]

[Formula 36]
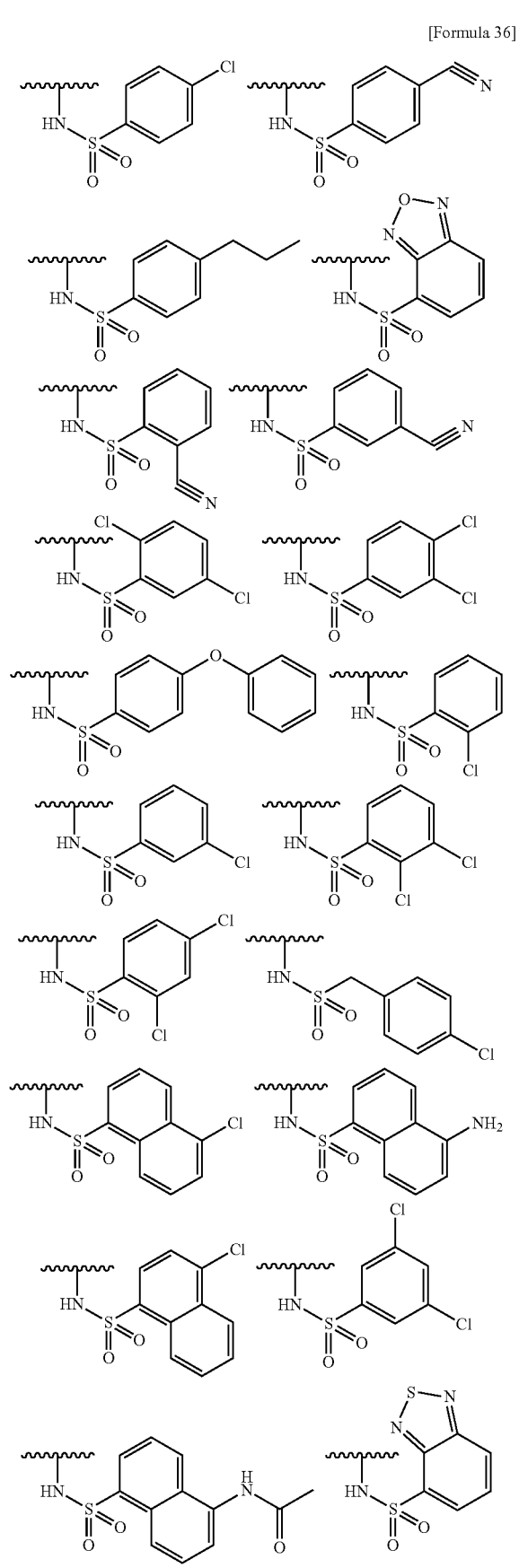
[Formula 37]
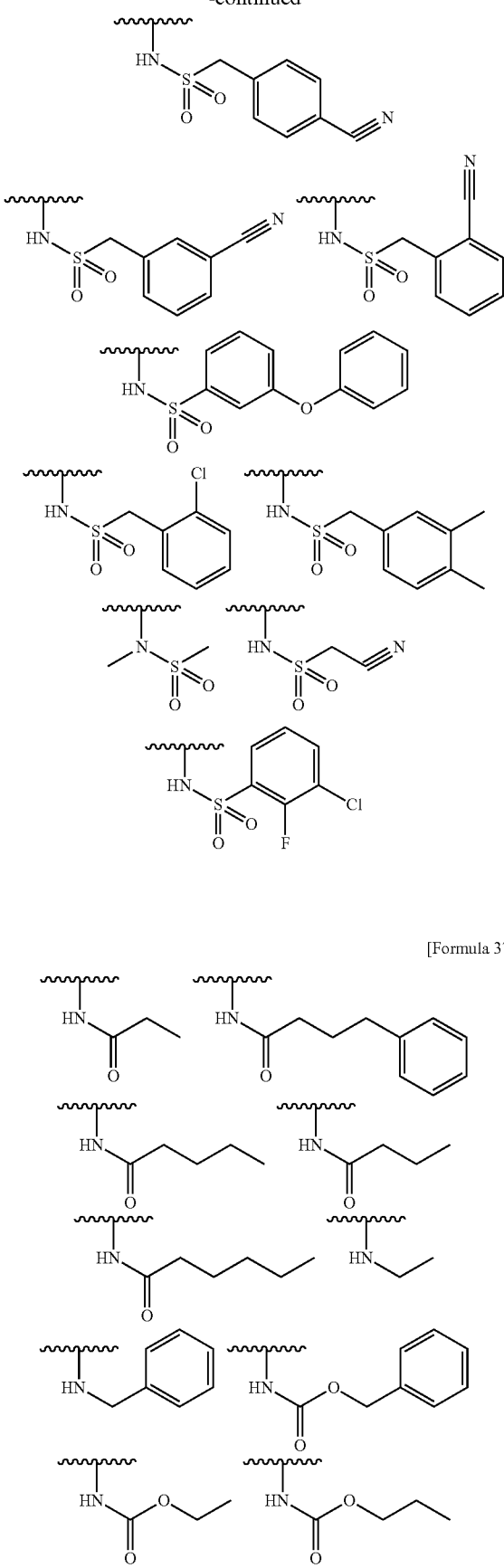

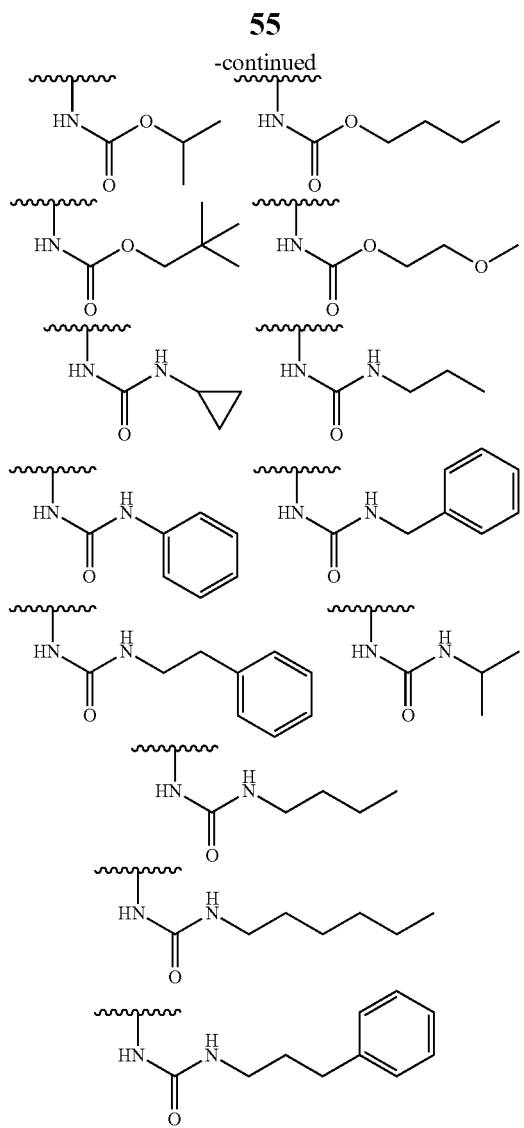
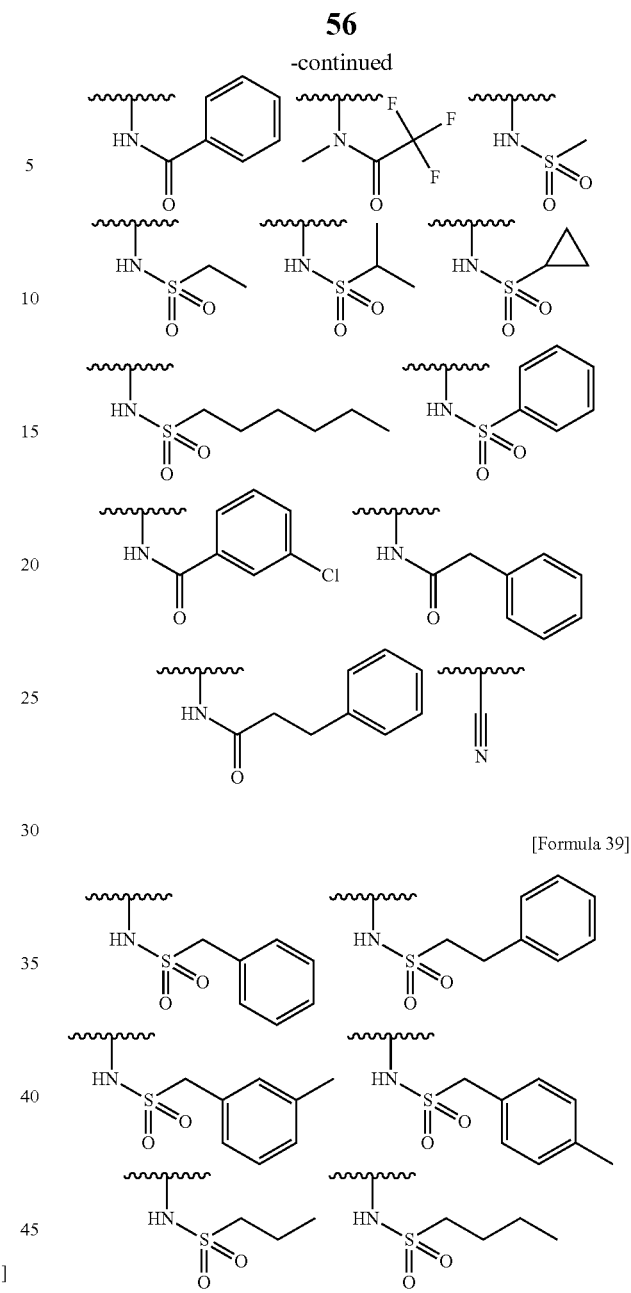
R[7] is particularly preferably a group shown below.
[Formula 38]
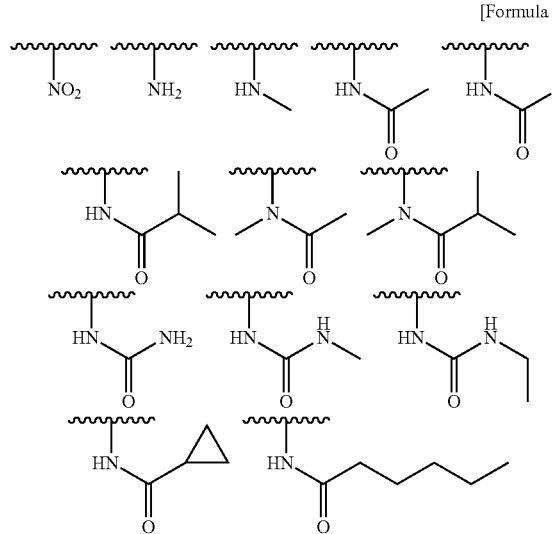
[Formula 39]
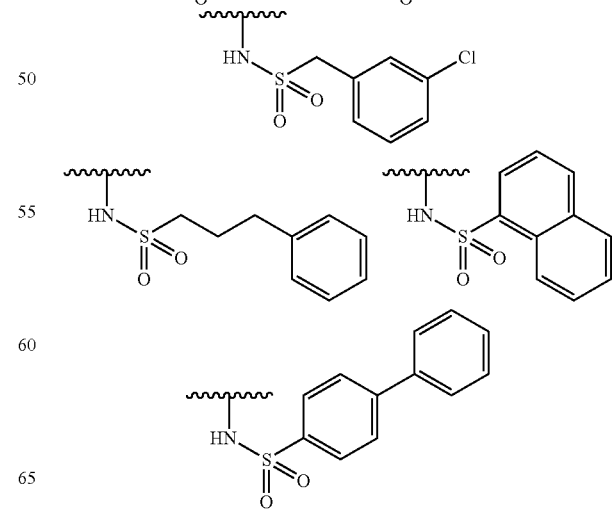

-continued
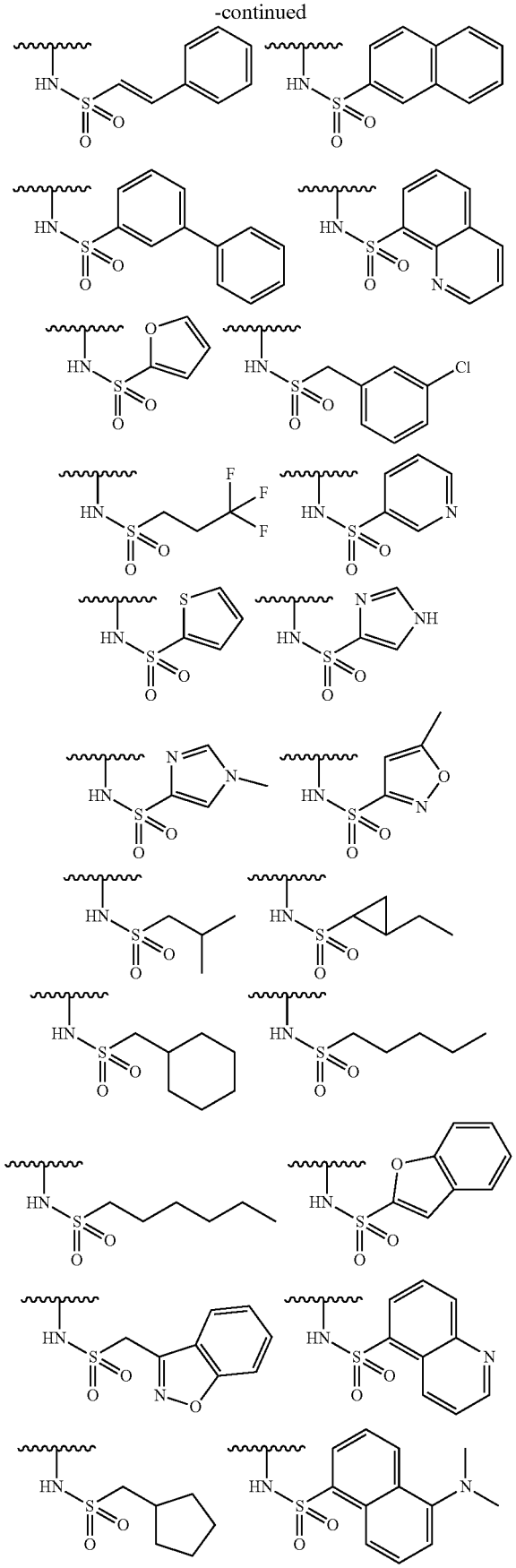
[Formula 40]
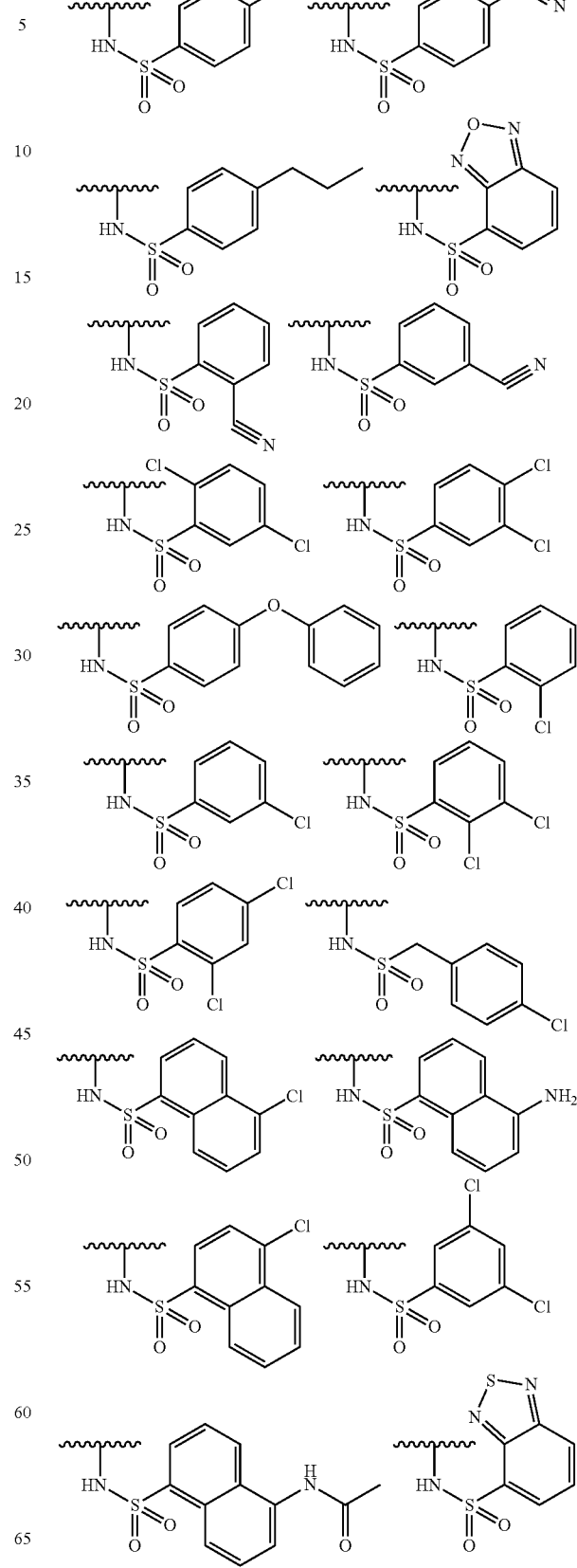

-continued

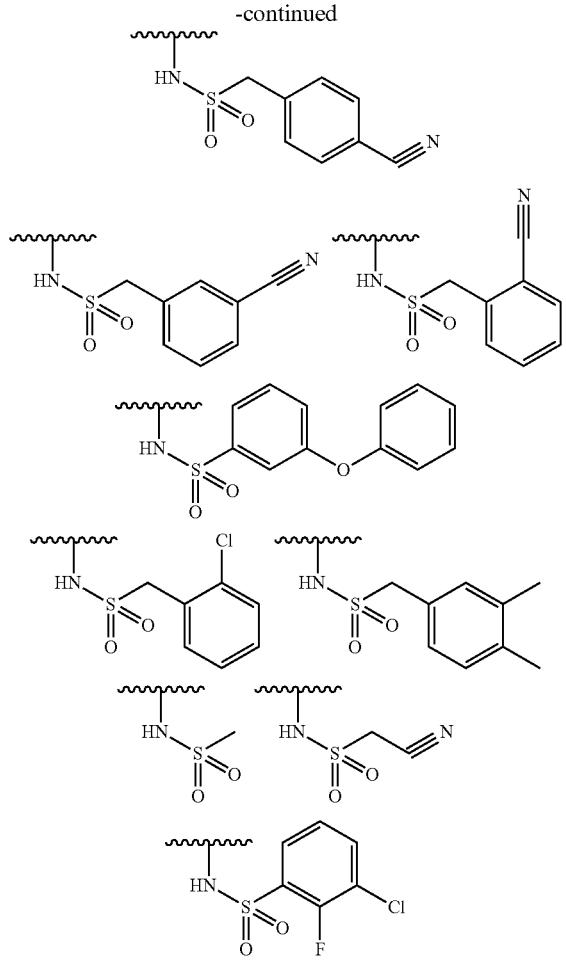

[Formula 41]

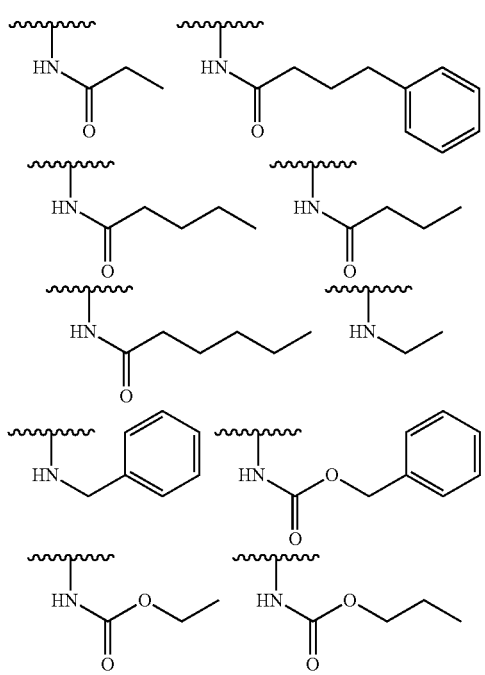

-continued

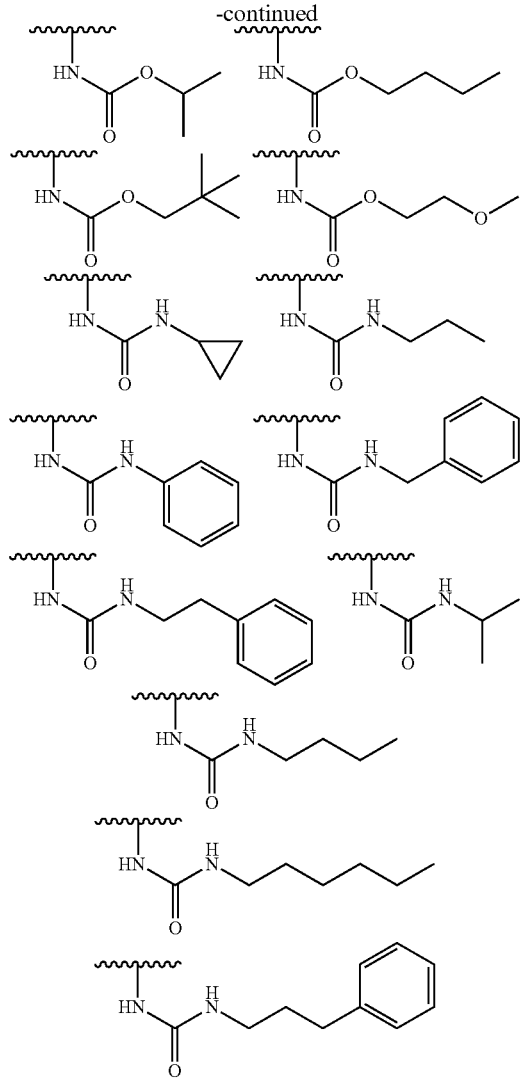

Here, $R^1$ and $R^7$ may be taken together with an adjacent atom to form ring A. Ring A may be substituted by 1 to a plurality of $R^A$s and preferably 1 to 7 $R^A$s. Specifically, the compound represented by the formula (I) may be a compound represented by following formula (II).

[Formula 42]

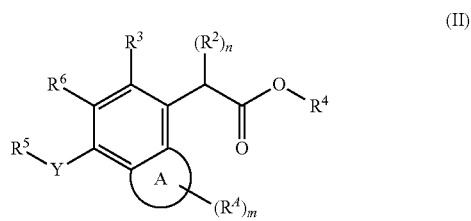

(II)

Preferred embodiment in the compound represented by the formula (II) is shown below.

Ring A is preferably an aromatic carbocyclic ring, a non-aromatic carbocyclic ring, an aromatic heterocyclic ring or a nonaromatic heterocyclic ring, and more preferably an aromatic heterocyclic ring or a nonaromatic heterocyclic ring. In addition, ring A is preferably a five-membered ring or a six-membered ring. Ring A is further preferably a five-membered or six-membered aromatic heterocyclic ring or nonaromatic heterocyclic ring, and particularly preferably thiazole, oxazole, imidazole, thiadiazole, oxadiazole, triazole, furan, thiophene, pyrrole, isothiazole, isoxazole, pyrazole, pyridine, pyridazine, pyrimidine, pyrazine, tetrahydropyran, thiane, piperidine, morpholine, thiomorpholine, piperazine, dioxane, hexahydropyrimidine, tetrahydrofuran, tetrahydrothiophene, pyrrolidine, dioxolane, oxazoline, thiazolidine, imidazoline, isothiadiazolidine, or thiadiazolidine, and most preferably thiazole, imidazole, pyrrole, pyridine, pyrrolidine, dioxolane, oxazoline, imidazoline, tetrahydropyran, piperidine, morpholine, thiomorpholine, dioxane, piperazine, or hexahydropyrimidine.

Two atoms of the portion in which ring A is fused with a benzene ring of the scaffold are carbon atoms.

$R^A$ is each independently, preferably halogen, cyano, nitro, oxo, or $-X^A-R^{A1}$, more preferably halogen, cyano, oxo, or $-X^A-R^{A1}$, and further preferably oxo or $-X^A-R^{A1}-$.

Here, $X^A$ is preferably a single bond, $-O-$, $-S-$, $-NR^{A2}$, $-CO-$, $-SO_2-$, $-O-CO-$, $-CO-O-$, $-NR^{A2}-CO-$, $-CO-NR^{A2}-$, $-NR^{A2}-CO-O-$, $-CO-O-NR^{A2}-$, $-O-CO-NR^{A2}-$, $-NR^{A2}-O-CO-$, $-CO-NR^{A2}-O-$, $-O-NR^{A2}-CO-$, $-NR^{A2}-CO-NR^{A3}-$, $-NR^{A2}-SO_2-$, or $-SO_2-NR^{A2}-$, more preferably a single bond, $-O-$, $-S-$, $-NR^{A2}-$, $-CO-$, $-SO_2-$, $-NR^{A2}-CO-$, $-CO-NR^{A2}-$, $-NR^{A2}-CO-NR^{A3}-$, $-NR^{A2}-SO_2-$, or $-SO_2-NR^{A2}-$, and further preferably a single bond, $-O-$, $-S-$, $-NR^{A2}-$, $-CO-$, $-SO_2-$, $-NR^{A2}-CO-$, $-CO-NR^{A2}-$, or $-NR^{A2}-CO-NR^{A3}-$.

$R^{A1}$ is preferably a hydrogen atom, substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, more preferably a hydrogen atom, substituted or unsubstituted alkyl, substituted or unsubstituted alkenyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, and further preferably a hydrogen atom, substituted or unsubstituted alkyl, substituted or unsubstituted alkenyl, a substituted or unsubstituted aromatic carbocyclic group, or a substituted or unsubstituted nonaromatic carbocyclic group. $R^{A2}$ and $R^{A3}$ are each independently, preferably a hydrogen atom, substituted or unsubstituted alkyl, substituted or unsubstituted alkenyl, or substituted or unsubstituted alkynyl, and when $X^A$ is $-NR^{A2}-$, $-CO-NR^{A2}-$, $CO-O-NR^{A2}-$, $-O-CO-NR^{A2}-$, or $-SO_2-NR^{A2}-$, $R^{A1}$ and $R^{A2}$ may be taken together with an adjacent nitrogen atom to form a substituted or unsubstituted aromatic heterocyclic group, or a substituted or unsubstituted nonaromatic heterocyclic group, and more preferably a hydrogen atom or substituted or unsubstituted alkyl.

$R^A$ is particularly preferably substituted or unsubstituted alkyl having 1 to 4 carbon atoms (examples: methyl, benzyl), substituted or unsubstituted alkenyl having 1 to 4 carbon atoms, substituted or unsubstituted alkylsulfonyl having 1 to 4 carbon atoms, substituted or unsubstituted alkylcarbonyl having 1 to 4 carbon atoms, substituted or unsubstituted monoalkylcarbamoyl having 1 to 4 carbon atoms, substituted or unsubstituted monoalkylcarbonylamino having 1 to 4 carbon atoms, substituted or unsubstituted alkylcarbamoylamino having 1 to 4 carbon atoms, hydroxy, amino, oxo, or substituted or unsubstituted aromatic carbocyclic sulfonyl, substituted or unsubstituted aromatic carbocyclic carbonyl, substituted or unsubstituted nonaromatic carbocyclic carbonyl, substituted or unsubstituted aromatic carbocyclic carbamoyl, substituted or unsubstituted nonaromatic carbocyclic carbamoyl, or substituted or unsubstituted aromatic carbocyclic carbonylamino. The aromatic carbocyclic ring is preferably benzene or naphthalene. The nonaromatic carbocyclic ring is preferably cycloalkyl.

m is preferably an integer of any of 0 to 7, more preferably an integer of any of 0 to 4, and further preferably an integer of any of 0 to 2.

$R^2$ is each independently preferably substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, or substituted or unsubstituted alkynylsulfanyl, more preferably substituted or unsubstituted alkyloxy, substituted or unsubstituted alkenyloxy, or substituted or unsubstituted alkynyloxy, further preferably substituted or unsubstituted alkyloxy, particularly preferably alkyloxy having 1 to 4 carbon atoms, and most preferably tert-butyloxy.

n is preferably 1 or 2, and particularly preferably 1.

$R^3$ is preferably a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, more preferably, substituted or unsubstituted phenyl, substituted or unsubstituted cycloalkenyl, substituted or unsubstituted benzofuryl, substituted or unsubstituted benzodioxolyl, substituted or unsubstituted benzodioxanyl, substituted or unsubstituted dihydrobenzofuryl, substituted or unsubstituted chromanyl, or substituted or unsubstituted benzomorpholinyl, and further preferably substituted or unsubstituted phenyl or substituted or unsubstituted chromanyl.

When $R^3$ is a substituted or unsubstituted aromatic heterocyclic group or substituted or unsubstituted nonaromatic heterocyclic group in which substituted or unsubstituted benzene is condensed, it is preferred that the aromatic heterocyclic group or nonaromatic heterocyclic group contains at least one oxygen atom.

When $R^3$ has a substituent, a preferred substituent is halogen, hydroxy, amino, cyano, oxo, alkyl, alkenyl, alkynyl, hydroxyalkyl, alkyloxy, alkenyloxy, alkynyloxy, alkyloxyalkyl, monoalkylamino, dialkylamino, alkylsulfanyl, alkenylsulfanyl, or alkynylsulfanyl, a more preferred substituent is halogen, alkyl, or alkyloxy, a further preferred substituent is fluoro, chloro, bromo, alkyl having 1 to 4 carbon atoms (examples: methyl, ethyl), or alkyloxy having 1 to 4 carbon atoms (example: methyloxy), and a particularly preferred substituent is chloro or methyl.

$R^3$ is further preferably a group shown below.

[Formula 43]

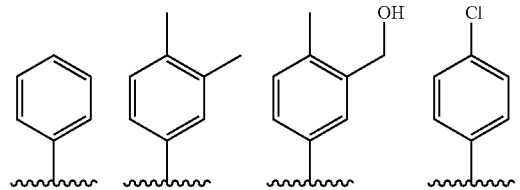

-continued

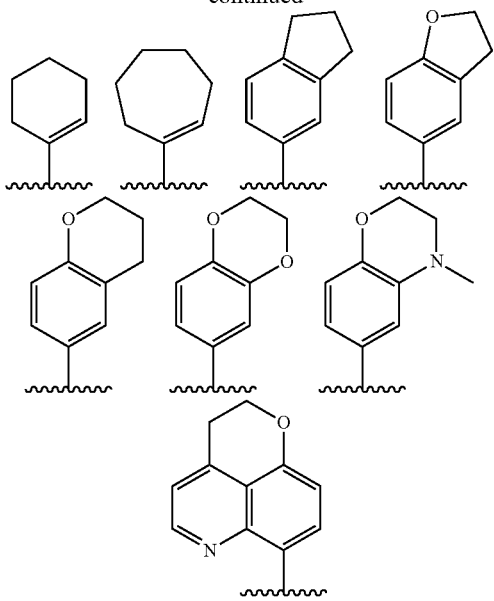

R³ is particularly preferably a group shown below.

[Formula 44]

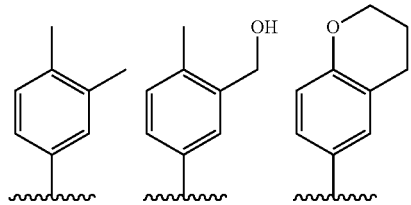

R⁴ is preferably a hydrogen atom, substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, and most preferably a hydrogen atom.

R⁵ is preferably a hydrogen atom, hydroxy, formyl, carboxy, carbamoyl, carbamoyloxy, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted monoalkylcarbamoyl, substituted or unsubstituted dialkylcarbamoyl, substituted or unsubstituted monoalkylcarbamoyloxy, substituted or unsubstituted dialkylcarbamoyloxy, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclicoxy, substituted or unsubstituted nonaromatic carbocyclicoxy, substituted or unsubstituted aromatic heterocyclicoxy, substituted or unsubstituted nonaromatic heterocyclicoxy, substituted or unsubstituted aromatic carbocyclic sulfanyl, substituted or unsubstituted nonaromatic carbocyclic sulfanyl, substituted or unsubstituted aromatic heterocyclic sulfanyl, substituted or unsubstituted nonaromatic heterocyclic sulfanyl, substituted or unsubstituted aromatic carbocyclic carbonyl, substituted or unsubstituted nonaromatic carbocyclic carbonyl, substituted or unsubstituted aromatic heterocyclic carbonyl, substituted or unsubstituted nonaromatic heterocyclic carbonyl, substituted or unsubstituted aromatic carbocyclic oxycarbonyl, substituted or unsubstituted nonaromatic carbocyclic oxycarbonyl, substituted or unsubstituted aromatic heterocyclic oxycarbonyl, substituted or unsubstituted nonaromatic heterocyclic oxycarbonyl, substituted or unsubstituted aromatic carbocyclic carbamoyl, substituted or unsubstituted nonaromatic carbocyclic carbamoyl, substituted or unsubstituted aromatic heterocyclic carbamoyl, substituted or unsubstituted nonaromatic heterocyclic carbamoyl, or —NR⁵¹R⁵² (R⁵¹ and R⁵² are each independently a hydrogen atom, formyl, carbamoyl, carboxy, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkylcarbamoyl, substituted or unsubstituted alkenylcarbamoyl, substituted or unsubstituted alkynylcarbamoyl, substituted or unsubstituted alkyloxycarbonyl, substituted or unsubstituted alkenyloxycarbonyl, substituted or unsubstituted alkynyloxycarbonyl, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclic carbonyl, substituted or unsubstituted nonaromatic carbocyclic carbonyl, substituted or unsubstituted aromatic heterocyclic carbonyl, substituted or unsubstituted nonaromatic heterocyclic carbonyl, substituted or unsubstituted aromatic carbocyclic carbamoyl, substituted or unsubstituted nonaromatic carbocyclic carbamoyl, substituted or unsubstituted aromatic heterocyclic carbamoyl, substituted or unsubstituted nonaromatic heterocyclic carbamoyl, substituted or unsubstituted aromatic carbocyclic oxycarbonyl, substituted or unsubstituted nonaromatic carbocyclic oxycarbonyl, substituted or unsubstituted aromatic heterocyclic oxycarbonyl, or substituted or unsubstituted nonaromatic heterocyclic oxycarbonyl), more preferably a hydrogen atom, substituted or unsubstituted alkyl, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclic carbamoyl, or —NR⁵¹R⁵² (R⁵¹ is substituted or unsubstituted aromatic carbocyclic carbonyl, and R⁵² is a hydrogen atom), and further preferably a substituted or unsubstituted aromatic carbocyclic group.

When R⁵ has a substituent, a preferred substituent is halogen, hydroxy, amino, cyano, oxo, alkyl, alkenyl, alkynyl, hydroxyalkyl, alkyloxy, alkenyloxy, alkynyloxy, alkyloxyalkyl, monoalkylamino, dialkylamino, alkylsulfanyl, alkenylsulfanyl, alkenylsulfanyl, alkylcarbonyl, alkenylcarbonyl, alkynylcarbonyl, an aromatic carbocyclic group, a nonaromatic carbocyclic group, an aromatic heterocyclic group, a nonaromatic heterocyclic group, aromatic carbocyclic group alkyl, nonaromatic carbocyclic group alkyl, aromatic heterocyclic group alkyl, or nonaromatic heterocyclic group alkyl, a more preferred substituent is halogen, alkyl, or alkylcarbonyl, and a further preferred substituent is chloro or alkyl having 1 to 4 carbon atoms (example: methyl).

In addition, when $R^5$ is crosslinked or a Spiro ring is formed, preferably, $R^5$ is crosslinked by an alkylene, or the Spiro ring is formed with a cycloalkyl ring.

$R^5$ is further preferably a group shown below.

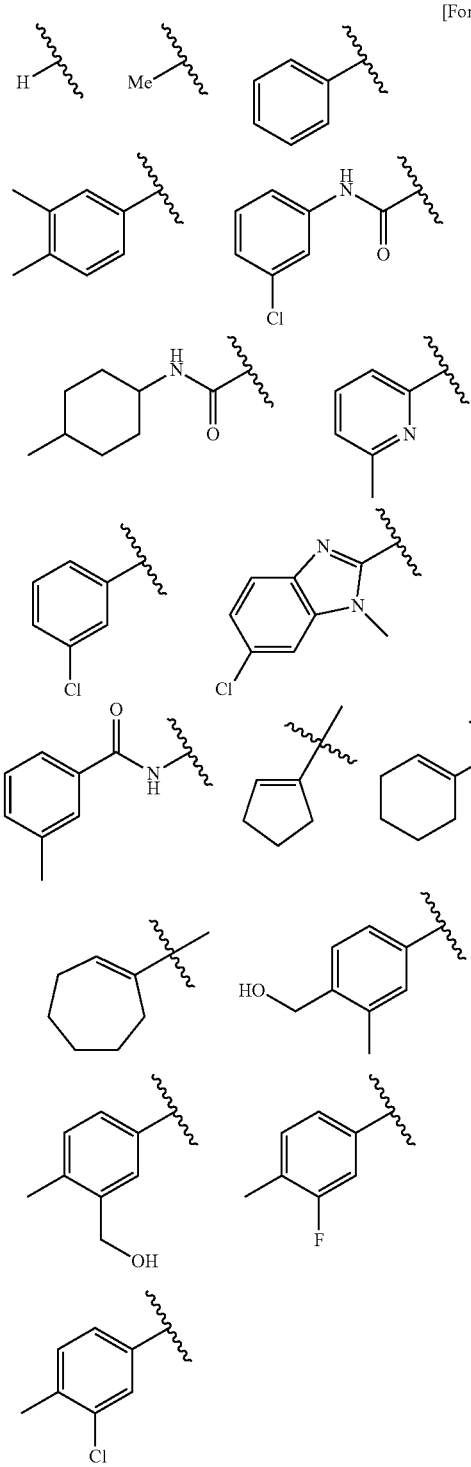

[Formula 45]

$R^5$ is particularly preferably a group shown below.

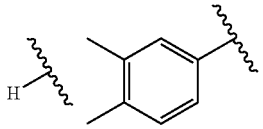

[Formula 46]

Y is preferably a single bond, alkylene, alkenylene, or alkynylene, more preferably a single bond or alkenylene, further preferably a single bond or vinylene, and particularly preferably a single bond.

However, when $R^5$ is a hydrogen atom, substituted or unsubstituted alkyl, substituted or unsubstituted alkenyl, or substituted or unsubstituted alkynyl, Y is a single bond.

$R^6$ is preferably a hydrogen atom, halogen, cyano, substituted or unsubstituted alkyl, substituted or unsubstituted alkenyl, substituted or unsubstituted alkynyl, a substituted or unsubstituted nonaromatic carbocyclic group, or substituted or unsubstituted alkyloxy, more preferably a hydrogen atom, substituted or unsubstituted alkyl, substituted or unsubstituted alkenyl, or substituted or unsubstituted alkynyl, further preferably substituted or unsubstituted alkyl, or particularly preferably alkyl having 1 to 4 carbon atoms, and particularly preferably methyl.

Preferred embodiments of the compound represented by the formula (I) include 1) to 180) and 201) to 240) as follows.

[Formula 47]

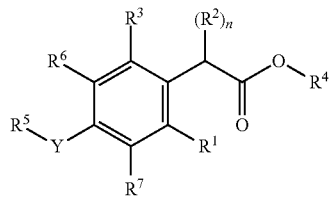

(I)

1) Compound wherein $R^1$ is a hydrogen atom, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is a hydrogen atom, and $R^{72}$ is a hydrogen atom).

2) Compound wherein $R^1$ is halogen, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is a hydrogen atom, and $R^{72}$ is a hydrogen atom).

3) Compound wherein $R^1$ is substituted or unsubstituted alkyl, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is a hydrogen atom, and $R^{72}$ is a hydrogen atom).

4) Compound wherein $R^1$ is a hydrogen atom, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is a hydrogen atom, and $R^{72}$ is a hydrogen atom).

5) Compound wherein $R^1$ is halogen, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is a hydrogen atom, and $R^{72}$ is a hydrogen atom).

6) Compound wherein $R^1$ is substituted or unsubstituted alkyl, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is a hydrogen atom, and $R^{72}$ is a hydrogen atom).

7) Compound wherein $R^1$ is a hydrogen atom, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is a hydrogen atom, and $R^{72}$ is a hydrogen atom).

8) Compound wherein $R^1$ is halogen, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is a hydrogen atom, and $R^{72}$ is a hydrogen atom).

9) Compound wherein $R^1$ is substituted or unsubstituted alkyl, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is a hydrogen atom, and $R^{72}$ is a hydrogen atom).

10) Compound wherein $R^1$ is a hydrogen atom, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is a hydrogen atom, and $R^{72}$ is a hydrogen atom).

11) Compound wherein $R^1$ is halogen, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is a hydrogen atom, and $R^{72}$ is a hydrogen atom).

12) Compound wherein $R^1$ is substituted or unsubstituted alkyl, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is a hydrogen atom, and $R^{72}$ is a hydrogen atom).

13) Compound wherein $R^1$ is a hydrogen atom, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is a hydrogen atom).

14) Compound wherein $R^1$ is halogen, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is a hydrogen atom).

15) Compound wherein $R^1$ is substituted or unsubstituted alkyl, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is a hydrogen atom).

16) Compound wherein $R^1$ is a hydrogen atom, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is a hydrogen atom).

17) Compound wherein $R^1$ is halogen, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is a hydrogen atom).

18) Compound wherein $R^1$ is substituted or unsubstituted alkyl, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is a hydrogen atom).

19) Compound wherein $R^1$ is a hydrogen atom, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is a hydrogen atom).

20) Compound wherein $R^1$ is halogen, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is a hydrogen atom).

21) Compound wherein $R^1$ is substituted or unsubstituted alkyl, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is a hydrogen atom).

22) Compound wherein $R^1$ is a hydrogen atom, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is a hydrogen atom).

23) Compound wherein $R^1$ is halogen, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is a hydrogen atom).

24) Compound wherein $R^1$ is substituted or unsubstituted alkyl, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is a hydrogen atom).

25) Compound wherein $R^1$ is a hydrogen atom, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is substituted or unsubstituted alkyl).

26) Compound wherein $R^1$ is halogen, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is substituted or unsubstituted alkyl).

27) Compound wherein $R^1$ is substituted or unsubstituted alkyl, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is substituted or unsubstituted alkyl).

28) Compound wherein $R^1$ is a hydrogen atom, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is substituted or unsubstituted alkyl).

29) Compound wherein $R^1$ is halogen, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is substituted or unsubstituted alkyl).

30) Compound wherein $R^1$ is substituted or unsubstituted alkyl, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is substituted or unsubstituted alkyl).

31) Compound wherein $R^1$ is a hydrogen atom, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is substituted or unsubstituted alkyl).

32) Compound wherein $R^1$ is halogen, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is substituted or unsubstituted alkyl).

33) Compound wherein $R^1$ is substituted or unsubstituted alkyl, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is substituted or unsubstituted alkyl).

34) Compound wherein $R^1$ is a hydrogen atom, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is substituted or unsubstituted alkyl).

35) Compound wherein $R^1$ is halogen, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is substituted or unsubstituted alkyl).

36) Compound wherein $R^1$ is substituted or unsubstituted alkyl, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—, $R^{71}$ is substituted or unsubstituted alkyl, and $R^{72}$ is substituted or unsubstituted alkyl).

37) Compound wherein $R^1$ is a hydrogen atom, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is a hydrogen atom, and $R^{72}$ is a hydrogen atom).

38) Compound wherein $R^1$ is halogen, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is a hydrogen atom, and $R^{72}$ is a hydrogen atom).

39) Compound wherein $R^1$ is substituted or unsubstituted alkyl, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is a hydrogen atom, and $R^{72}$ is a hydrogen atom).

40) Compound wherein $R^1$ is a hydrogen atom, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is a hydrogen atom, and $R^{72}$ is a hydrogen atom).

41) Compound wherein $R^1$ is halogen, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is a hydrogen atom, and $R^{72}$ is a hydrogen atom).

42) Compound wherein $R^1$ is substituted or unsubstituted alkyl, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is a hydrogen atom, and $R^{72}$ is a hydrogen atom).

43) Compound wherein $R^1$ is a hydrogen atom, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is a hydrogen atom, and $R^{72}$ is a hydrogen atom).

44) Compound wherein $R^1$ is halogen, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is a hydrogen atom, and $R^{72}$ is a hydrogen atom).

45) Compound wherein $R^1$ is substituted or unsubstituted alkyl, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is a hydrogen atom, and $R^{72}$ is a hydrogen atom).

46) Compound wherein $R^1$ is a hydrogen atom, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is a hydrogen atom, and $R^{72}$ is a hydrogen atom).

47) Compound wherein $R^1$ is halogen, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is a hydrogen atom, and $R^{72}$ is a hydrogen atom).

48) Compound wherein $R^1$ is substituted or unsubstituted alkyl, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is a hydrogen atom, and $R^{72}$ is a hydrogen atom).

49) Compound wherein $R^1$ is a hydrogen atom, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is a hydrogen atom).

50) Compound wherein $R^1$ is halogen, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is a hydrogen atom).

51) Compound wherein $R^1$ is substituted or unsubstituted alkyl, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is a hydrogen atom).

52) Compound wherein $R^1$ is a hydrogen atom, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is a hydrogen atom).

53) Compound wherein $R^1$ is halogen, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is a hydrogen atom).

54) Compound wherein $R^1$ is substituted or unsubstituted alkyl, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z 55) Compound wherein $R^1$ is a hydrogen atom, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is a hydrogen atom).

56) Compound wherein $R^1$ is halogen, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is a hydrogen atom).

57) Compound wherein $R^1$ is substituted or unsubstituted alkyl, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is a hydrogen atom).

58) Compound wherein $R^1$ is a hydrogen atom, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is a hydrogen atom).

59) Compound wherein $R^1$ is halogen, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is a hydrogen atom).

60) Compound wherein $R^1$ is substituted or unsubstituted alkyl, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is a hydrogen atom).

61) Compound wherein $R^1$ is a hydrogen atom, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is substituted or unsubstituted alkyl).

62) Compound wherein $R^1$ is halogen, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is substituted or unsubstituted alkyl).

63) Compound wherein $R^1$ is substituted or unsubstituted alkyl, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is substituted or unsubstituted alkyl).

64) Compound wherein $R^1$ is a hydrogen atom, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is substituted or unsubstituted alkyl).

65) Compound wherein $R^1$ is halogen, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is substituted or unsubstituted alkyl).

66) Compound wherein $R^1$ is substituted or unsubstituted alkyl, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is substituted or unsubstituted 67) Compound wherein $R^1$ is a hydrogen atom, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is substituted or unsubstituted alkyl).

68) Compound wherein $R^1$ is halogen, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is substituted or unsubstituted alkyl).

69) Compound wherein $R^1$ is substituted or unsubstituted alkyl, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is substituted or unsubstituted alkyl).

70) Compound wherein $R^1$ is a hydrogen atom, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is substituted or unsubstituted alkyl).

71) Compound wherein $R^1$ is halogen, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is substituted or unsubstituted alkyl).

72) Compound wherein $R^1$ is substituted or unsubstituted alkyl, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—, $R^{71}$ is substituted or unsubstituted alkyl, and $R^{72}$ is substituted or unsubstituted alkyl).

73) Compound wherein $R^1$ is a hydrogen atom, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is a hydrogen atom, and $R^{72}$ is a hydrogen atom).

74) Compound wherein $R^1$ is halogen, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is a hydrogen atom, and $R^{72}$ is a hydrogen atom).

75) Compound wherein $R^1$ is substituted or unsubstituted alkyl, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is a hydrogen atom, and $R^{72}$ is a hydrogen atom).

76) Compound wherein $R^1$ is a hydrogen atom, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is a hydrogen atom, and $R^{72}$ is a hydrogen atom).

77) Compound wherein $R^1$ is halogen, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is a hydrogen atom, and $R^{72}$ is a hydrogen atom).

78) Compound wherein $R^1$ is substituted or unsubstituted alkyl, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is a hydrogen atom, and $R^{72}$ is a hydrogen atom).

79) Compound wherein $R^1$ is a hydrogen atom, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is a hydrogen atom, and $R^{72}$ is a hydrogen atom).

80) Compound wherein $R^1$ is halogen, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is a hydrogen atom, and $R^{72}$ is a hydrogen atom).

81) Compound wherein $R^1$ is substituted or unsubstituted alkyl, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is a hydrogen atom, and $R^{72}$ is a hydrogen atom).

82) Compound wherein $R^1$ is a hydrogen atom, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is a hydrogen atom, and $R^{72}$ is a hydrogen atom).

83) Compound wherein $R^1$ is halogen, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is a hydrogen atom, and $R^{72}$ is a hydrogen atom).

84) Compound wherein $R^1$ is substituted or unsubstituted alkyl, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is a hydrogen atom, and $R^{72}$ is a hydrogen atom).

85) Compound wherein $R^1$ is a hydrogen atom, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is a hydrogen atom).

86) Compound wherein $R^1$ is halogen, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is a hydrogen atom).

87) Compound wherein $R^1$ is substituted or unsubstituted alkyl, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is a hydrogen atom).

88) Compound wherein $R^1$ is a hydrogen atom, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is a hydrogen atom).

89) Compound wherein $R^1$ is halogen, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is a hydrogen atom).

90) Compound wherein $R^1$ is substituted or unsubstituted alkyl, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is a hydrogen atom).

91) Compound wherein $R^1$ is a hydrogen atom, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is a hydrogen atom).

92) Compound wherein $R^1$ is halogen, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is a hydrogen atom).

93) Compound wherein $R^1$ is substituted or unsubstituted alkyl, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is a hydrogen atom).

94) Compound wherein $R^1$ is a hydrogen atom, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is a hydrogen atom).

95) Compound wherein $R^1$ is halogen, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is a hydrogen atom).

96) Compound wherein $R^1$ is substituted or unsubstituted alkyl, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is a hydrogen atom).

97) Compound wherein $R^1$ is a hydrogen atom, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is substituted or unsubstituted alkyl).

98) Compound wherein $R^1$ is halogen, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is substituted or unsubstituted alkyl).

99) Compound wherein $R^1$ is substituted or unsubstituted alkyl, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is substituted or unsubstituted alkyl).

100) Compound wherein $R^1$ is a hydrogen atom, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is substituted or unsubstituted alkyl).

101) Compound wherein $R^1$ is halogen, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is substituted or unsubstituted alkyl).

102) Compound wherein $R^1$ is substituted or unsubstituted alkyl, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is substituted or unsubstituted alkyl).

103) Compound wherein $R^1$ is a hydrogen atom, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is substituted or unsubstituted alkyl).

104) Compound wherein $R^1$ is halogen, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—

105) Compound wherein $R^1$ is substituted or unsubstituted alkyl, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is substituted or unsubstituted alkyl).

106) Compound wherein $R^1$ is a hydrogen atom, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is substituted or unsubstituted alkyl).

107) Compound wherein $R^1$ is halogen, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is substituted or unsubstituted alkyl).

108) Compound wherein $R^1$ is substituted or unsubstituted alkyl, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—O—, $R^{71}$ is substituted or unsubstituted alkyl, and $R^{72}$ is substituted or unsubstituted alkyl).

109) Compound wherein $R^1$ is a hydrogen atom, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is a hydrogen atom, and $R^{72}$ is a hydrogen atom).

110) Compound wherein $R^1$ is halogen, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is a hydrogen atom, and $R^{72}$ is a hydrogen atom).

111) Compound wherein $R^1$ is substituted or unsubstituted alkyl, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is a hydrogen atom, and $R^{72}$ is a hydrogen atom).

112) Compound wherein $R^1$ is a hydrogen atom, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is a hydrogen atom, and $R^{72}$ is a hydrogen atom).

113) Compound wherein $R^1$ is halogen, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is a hydrogen atom, and $R^{72}$ is a hydrogen atom).

114) Compound wherein $R^1$ is substituted or unsubstituted alkyl, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is a hydrogen atom, and $R^{72}$ is a hydrogen atom).

115) Compound wherein $R^1$ is a hydrogen atom, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is a hydrogen atom, and $R^{72}$ is a hydrogen atom).

116) Compound wherein $R^1$ is halogen, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is a hydrogen atom, and $R^{72}$ is a hydrogen atom).

117) Compound wherein $R^1$ is substituted or unsubstituted alkyl, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is a hydrogen atom, and $R^{72}$ is a hydrogen atom).

118) Compound wherein $R^1$ is a hydrogen atom, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is a hydrogen atom, and $R^{72}$ is a hydrogen atom).

119) Compound wherein $R^1$ is halogen, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is a hydrogen atom, and $R^{72}$ is a hydrogen atom).

120) Compound wherein $R^1$ is substituted or unsubstituted alkyl, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is a hydrogen atom, and $R^{72}$ is a hydrogen atom).

121) Compound wherein $R^1$ is a hydrogen atom, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is a hydrogen atom).

122) Compound wherein $R^1$ is halogen, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is a hydrogen atom).

123) Compound wherein $R^1$ is substituted or unsubstituted alkyl, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is a hydrogen atom).

124) Compound wherein $R^1$ is a hydrogen atom, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is a hydrogen atom).

125) Compound wherein $R^1$ is halogen, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is a hydrogen atom).

126) Compound wherein $R^1$ is substituted or unsubstituted alkyl, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is a hydrogen atom).

127) Compound wherein $R^1$ is a hydrogen atom, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is a hydrogen atom).

128) Compound wherein $R^1$ is halogen, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is a hydrogen atom).

129) Compound wherein $R^1$ is substituted or unsubstituted alkyl, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is a hydrogen atom).

130) Compound wherein $R^1$ is a hydrogen atom, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is a hydrogen atom).

131) Compound wherein $R^1$ is halogen, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is a hydrogen atom).

132) Compound wherein $R^1$ is substituted or unsubstituted alkyl, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is a hydrogen atom).

133) Compound wherein $R^1$ is a hydrogen atom, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is substituted or unsubstituted alkyl).

134) Compound wherein $R^1$ is halogen, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is substituted or unsubstituted alkyl).

135) Compound wherein $R^1$ is substituted or unsubstituted alkyl, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is substituted or unsubstituted alkyl).

136) Compound wherein $R^1$ is a hydrogen atom, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is substituted or unsubstituted alkyl).

137) Compound wherein $R^1$ is halogen, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is substituted or unsubstituted alkyl).

138) Compound wherein $R^1$ is substituted or unsubstituted alkyl, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is substituted or unsubstituted alkyl).

139) Compound wherein $R^1$ is a hydrogen atom, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is substituted or unsubstituted alkyl).

140) Compound wherein $R^1$ is halogen, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is substituted or unsubstituted alkyl).

141) Compound wherein $R^1$ is substituted or unsubstituted alkyl, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is substituted or unsubstituted alkyl).

142) Compound wherein $R^1$ is a hydrogen atom, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is substituted or unsubstituted alkyl).

143) Compound wherein $R^1$ is halogen, $R^2$ is, substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is substituted or unsubstituted alkyl).

144) Compound wherein $R^1$ is substituted or unsubstituted alkyl, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—CO—NH—, $R^{71}$ is substituted or unsubstituted alkyl, and $R^{72}$ is substituted or unsubstituted alkyl).

145) Compound wherein $R^1$ is a hydrogen atom, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is a hydrogen atom, and $R^{72}$ is a hydrogen atom).

146) Compound wherein $R^1$ is halogen, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is a hydrogen atom, and $R^{72}$ is a hydrogen atom).

147) Compound wherein $R^1$ is substituted or unsubstituted alkyl, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is a hydrogen atom, and $R^{72}$ is a hydrogen atom).

148) Compound wherein $R^1$ is a hydrogen atom, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is a hydrogen atom, and $R^{72}$ is a hydrogen atom).

149) Compound wherein $R^1$ is halogen, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is a hydrogen atom, and $R^{72}$ is a hydrogen atom).

150) Compound wherein $R^1$ is substituted or unsubstituted alkyl, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is a hydrogen atom, and $R^{72}$ is a hydrogen atom).

151) Compound wherein $R^1$ is a hydrogen atom, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is a hydrogen atom, and $R^{72}$ is a hydrogen atom).

152) Compound wherein $R^1$ is halogen, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is a hydrogen atom, and $R^{72}$ is a hydrogen atom).

153) Compound wherein $R^1$ is substituted or unsubstituted alkyl, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is a hydrogen atom, and $R^{72}$ is a hydrogen atom).

154) Compound wherein $R^1$ is a hydrogen atom, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is a hydrogen atom, and $R^{72}$ is a hydrogen atom).

155) Compound wherein $R^1$ is halogen, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is a hydrogen atom, and $R^{72}$ is a hydrogen atom).

156) Compound wherein $R^1$ is substituted or unsubstituted alkyl, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is a hydrogen atom, and $R^{72}$ is a hydrogen atom).

157) Compound wherein $R^1$ is a hydrogen atom, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is substituted or unsubstituted alkyl, and $R^{72}$ is a hydrogen atom).

158) Compound wherein $R^1$ is halogen, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is substituted or unsubstituted alkyl, and $R^{72}$ is a hydrogen atom).

159) Compound wherein $R^1$ is substituted or unsubstituted alkyl, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is substituted or unsubstituted alkyl, and $R^{72}$ is a hydrogen atom).

160) Compound wherein $R^1$ is a hydrogen atom, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is substituted or unsubstituted alkyl, and $R^{72}$ is a hydrogen atom).

161) Compound wherein $R^1$ is halogen, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is substituted or unsubstituted alkyl, and $R^{72}$ is a hydrogen atom).

162) Compound wherein $R^1$ is substituted or unsubstituted alkyl, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is substituted or unsubstituted alkyl, and $R^{72}$ is a hydrogen atom).

163) Compound wherein $R^1$ is a hydrogen atom, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is substituted or unsubstituted alkyl, and $R^{72}$ is a hydrogen atom).

164) Compound wherein $R^1$ is halogen, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is substituted or unsubstituted alkyl, and $R^{72}$ is a hydrogen atom).

165) Compound wherein $R^1$ is substituted or unsubstituted alkyl, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is substituted or unsubstituted alkyl, and $R^{72}$ is a hydrogen atom).

166) Compound wherein $R^1$ is a hydrogen atom, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is substituted or unsubstituted alkyl, and $R^{72}$ is a hydrogen atom).

167) Compound wherein $R^1$ is halogen, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is substituted or unsubstituted alkyl, and $R^{72}$ is a hydrogen atom).

168) Compound wherein $R^1$ is substituted or unsubstituted alkyl, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is substituted or unsubstituted alkyl, and $R^{72}$ is a hydrogen atom).

169) Compound wherein $R^1$ is a hydrogen atom, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is substituted or unsubstituted alkyl, and $R^{72}$ is substituted or unsubstituted alkyl).

170) Compound wherein $R^1$ is halogen, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —$NR^{72}$—$SO_2$—, $R^{71}$ is substituted or unsubstituted alkyl, and $R^{72}$ is substituted or unsubstituted alkyl).

171) Compound wherein $R^1$ is substituted or unsubstituted alkyl, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, $R^6$ is substituted or unsubstituted alkyl, and $R^7$ is —Z—$R^{71}$ (Z is —NR$^{72}$—SO$_2$—, R$^{71}$ is substituted or unsubstituted alkyl, and R$^{72}$ is substituted or unsubstituted alkyl).

172) Compound wherein R$^1$ is a hydrogen atom, R$^2$ is substituted or unsubstituted alkyloxy, n is 1, R$^3$ is a substituted or unsubstituted nonaromatic carbocyclic group, R$^4$ is a hydrogen atom, R$^5$ is a substituted or unsubstituted aromatic carbocyclic group, Y is a single bond, R$^6$ is substituted or unsubstituted alkyl, and R$^7$ is —Z—R$^{71}$ (Z is —NR$^{72}$—SO$_2$—, R$^{71}$ is substituted or unsubstituted alkyl, and R$^{72}$ is substituted or unsubstituted alkyl).

173) Compound wherein R$^1$ is halogen, R$^2$ is substituted or unsubstituted alkyloxy, n is 1, R$^3$ is a substituted or unsubstituted nonaromatic carbocyclic group, R$^4$ is a hydrogen atom, R$^5$ is a substituted or unsubstituted aromatic carbocyclic group, Y is a single bond, R$^6$ is substituted or unsubstituted alkyl, and R$^7$ is —Z—R$^{71}$ (Z is —NR$^{72}$—SO$_2$—, R$^{71}$ is substituted or unsubstituted alkyl, and R$^{72}$ is substituted or unsubstituted alkyl).

174) Compound wherein R$^1$ is substituted or unsubstituted alkyl, R$^2$ is substituted or unsubstituted alkyloxy, n is 1, R$^3$ is a substituted or unsubstituted nonaromatic carbocyclic group, R$^4$ is a hydrogen atom, R$^5$ is a substituted or unsubstituted aromatic carbocyclic group, Y is a single bond, R$^6$ is substituted or unsubstituted alkyl, and R$^7$ is —Z—R$^{71}$ (Z is —NR$^{72}$—SO$_2$—, R$^{71}$ is substituted or unsubstituted alkyl, and R$^{72}$ is substituted or unsubstituted alkyl).

175) Compound wherein R$^1$ is a hydrogen atom, R$^2$ is substituted or unsubstituted alkyloxy, n is 1, R$^3$ is a substituted or unsubstituted aromatic heterocyclic group, R$^4$ is a hydrogen atom, R$^5$ is a substituted or unsubstituted aromatic carbocyclic group, Y is a single bond, R$^6$ is substituted or unsubstituted alkyl, and R$^7$ is —Z—R$^{71}$ (Z is —NR$^{72}$—SO$_2$—, R$^{71}$ is substituted or unsubstituted alkyl, and R$^{72}$ is substituted or unsubstituted alkyl).

176) Compound wherein R$^1$ is halogen, R$^2$ is substituted or unsubstituted alkyloxy, n is 1, R$^3$ is a substituted or unsubstituted aromatic heterocyclic group, R$^4$ is a hydrogen atom, R$^5$ is a substituted or unsubstituted aromatic carbocyclic group, Y is a single bond, R$^6$ is substituted or unsubstituted alkyl, and R$^7$ is —Z—R$^{71}$ (Z is —NR$^{72}$—SO$_2$—, R$^{71}$ is substituted or unsubstituted alkyl, and R$^{72}$ is substituted or unsubstituted alkyl).

177) Compound wherein R$^1$ is substituted or unsubstituted alkyl, R$^2$ is substituted or unsubstituted alkyloxy, n is 1, R$^3$ is a substituted or unsubstituted aromatic heterocyclic group, R$^4$ is a hydrogen atom, R$^5$ is a substituted or unsubstituted aromatic carbocyclic group, Y is a single bond, R$^6$ is substituted or unsubstituted alkyl, and R$^7$ is —Z—R$^{71}$ (Z is —NR$^{72}$—SO$_2$—, R$^{71}$ is substituted or unsubstituted alkyl, and R$^{72}$ is substituted or unsubstituted alkyl).

178) Compound wherein R$^1$ is a hydrogen atom, R$^2$ is substituted or unsubstituted alkyloxy, n is 1, R$^3$ is a substituted or unsubstituted nonaromatic heterocyclic group, R$^4$ is a hydrogen atom, R$^5$ is a substituted or unsubstituted aromatic carbocyclic group, Y is a single bond, R$^6$ is substituted or unsubstituted alkyl, and R$^7$ is —Z—R$^{71}$ (Z is —NR$^{72}$—SO$_2$—, R$^{71}$ is substituted or unsubstituted alkyl, and R$^{72}$ is substituted or unsubstituted alkyl).

179) Compound wherein R$^1$ is halogen, R$^2$ is substituted or unsubstituted alkyloxy, n is 1, R$^3$ is a substituted or unsubstituted nonaromatic heterocyclic group, R$^4$ is a hydrogen atom, R$^5$ is a substituted or unsubstituted aromatic carbocyclic group, Y is a single bond, R$^6$ is substituted or unsubstituted alkyl, and R$^7$ is —Z—R$^{71}$ (Z is —NR$^{72}$—SO$_2$—, R$^{71}$ is substituted or unsubstituted alkyl, and R$^{72}$ is substituted or unsubstituted alkyl).

180) Compound wherein R$^1$ is substituted or unsubstituted alkyl, R$^2$ is substituted or unsubstituted alkyloxy, n is 1, R$^3$ is a substituted or unsubstituted nonaromatic heterocyclic group, R$^4$ is a hydrogen atom, R$^5$ is a substituted or unsubstituted aromatic carbocyclic group, Y is a single bond, R$^6$ is substituted or unsubstituted alkyl, and R$^7$ is —Z—R$^{71}$ (Z is —NR$^{72}$—SO$_2$—, R$^{71}$ is substituted or unsubstituted alkyl, and R$^{72}$ is substituted or unsubstituted alkyl).

Other preferred embodiments of the compound represented by the formula (I) include compounds of 1) to 180) described above in which R$^2$ is replaced by substituted or unsubstituted alkyl, substituted or unsubstituted alkenyl, substituted or unsubstituted alkynyl, substituted or unsubstituted alkenyloxy, substituted or unsubstituted alkynyloxy, substituted or unsubstituted alkylsulfanyl, substituted or unsubstituted alkenylsulfanyl, or substituted or unsubstituted alkynylsulfanyl.

When the compound of the formula (I) is represented by the formula (II), preferred embodiments include 201) to 240) as follows.

[Formula 48]

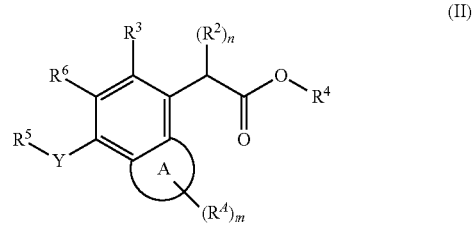

(II)

201) Compound wherein ring A is an aromatic heterocyclic ring, m is 0, R$^2$ is substituted or unsubstituted alkyloxy, n is 1, R$^3$ is a substituted or unsubstituted aromatic carbocyclic group, R$^4$ is a hydrogen atom, R$^5$ is a substituted or unsubstituted aromatic carbocyclic group, Y is a single bond, and R$^6$ is substituted or unsubstituted alkyl.

202) Compound wherein ring A is an aromatic heterocyclic ring, m is 1, R$^2$ is substituted or unsubstituted alkyloxy, n is 1, R$^3$ is a substituted or unsubstituted aromatic carbocyclic group, R$^4$ is a hydrogen atom, R$^5$ is a substituted or unsubstituted aromatic carbocyclic group, Y is a single bond, and R$^6$ is substituted or unsubstituted alkyl.

203) Compound wherein ring A is an aromatic heterocyclic ring, m is 2, R$^2$ is substituted or unsubstituted alkyloxy, n is 1, R$^3$ is a substituted or unsubstituted aromatic carbocyclic group, R$^4$ is a hydrogen atom, R$^5$ is a substituted or unsubstituted aromatic carbocyclic group, Y is a single bond, and R$^6$ is substituted or unsubstituted alkyl.

204) Compound wherein ring A is an aromatic heterocyclic ring, m is 3, R$^2$ is substituted or unsubstituted alkyloxy, n is 1, R$^3$ is a substituted or unsubstituted aromatic carbocyclic group, R$^4$ is a hydrogen atom, R$^5$ is a substituted or unsubstituted aromatic carbocyclic group, Y is a single bond, and R$^6$ is substituted or unsubstituted alkyl.

205) Compound wherein ring A is an aromatic heterocyclic ring, m is 4, R$^2$ is substituted or unsubstituted alkyloxy, n is 1, R$^3$ is a substituted or unsubstituted aromatic carbocyclic group, R$^4$ is a hydrogen atom, R$^5$ is a substituted or unsubstituted aromatic carbocyclic group, Y is a single bond, and R$^6$ is substituted or unsubstituted alkyl.

206) Compound wherein ring A is a nonaromatic heterocyclic ring, m is 0, R$^2$ is substituted or unsubstituted alkyloxy, n is 1, R$^3$ is a substituted or unsubstituted aromatic carbocyclic 207) Compound wherein ring A is a nonaromatic heterocyclic ring, m is 1, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, and $R^6$ is substituted or unsubstituted alkyl.

208) Compound wherein ring A is a nonaromatic heterocyclic ring, m is 2, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, and $R^6$ is substituted or unsubstituted alkyl.

209) Compound wherein ring A is a nonaromatic heterocyclic ring, m is 3, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, and $R^6$ is substituted or unsubstituted alkyl.

210) Compound wherein ring A is a nonaromatic heterocyclic ring, m is 4, $R^2$ is substituted or unsubstituted alkyloxy, n is 1, $R^3$ is a substituted or unsubstituted aromatic carbocyclic group, $R^4$ is a hydrogen atom, $R^5$ is a substituted or unsubstituted aromatic carbocyclic group, Y is a single bond, and $R^6$ is substituted or unsubstituted alkyl.

211) Compound wherein ring A is an aromatic heterocyclic ring, m is 0, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, and $R^6$ is substituted or unsubstituted alkyl.

212) Compound wherein ring A is an aromatic heterocyclic ring, m is 1, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, and $R^6$ is substituted or unsubstituted alkyl.

213) Compound wherein ring A is an aromatic heterocyclic ring, m is 2, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, and $R^6$ is substituted or unsubstituted alkyl.

214) Compound wherein ring A is an aromatic heterocyclic ring, m is 3, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, and $R^6$ is substituted or unsubstituted alkyl.

215) Compound wherein ring A is an aromatic heterocyclic ring, m is 4, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, and $R^6$ is substituted or unsubstituted alkyl.

216) Compound wherein ring A is a nonaromatic heterocyclic ring, m is 0, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, and $R^6$ is substituted or unsubstituted alkyl.

217) Compound wherein ring A is a nonaromatic heterocyclic ring, m is 1, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, and $R^6$ is substituted or unsubstituted alkyl.

218) Compound wherein ring A is a nonaromatic heterocyclic ring, m is 2, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, and $R^6$ is substituted or unsubstituted alkyl.

219) Compound wherein ring A is a nonaromatic heterocyclic ring, m is 3, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, and $R^6$ is substituted or unsubstituted alkyl.

220) Compound wherein ring A is a nonaromatic heterocyclic ring, m is 4, $R^2$ is substituted or unsubstituted alkyloxy, n is 1, $R^3$ is a substituted or unsubstituted nonaromatic carbocyclic group, $R^4$ is a hydrogen atom, $R^5$ is a substituted or unsubstituted aromatic carbocyclic group, Y is a single bond, and $R^6$ is substituted or unsubstituted alkyl.

221) Compound wherein ring A is an aromatic heterocyclic ring, m is 0, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, and $R^6$ is substituted or unsubstituted alkyl.

222) Compound wherein ring A is an aromatic heterocyclic ring, m is 1, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, and $R^6$ is substituted or unsubstituted alkyl.

223) Compound wherein ring A is an aromatic heterocyclic ring, m is 2, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, and $R^6$ is substituted or unsubstituted alkyl.

224) Compound wherein ring A is an aromatic heterocyclic ring, m is 3, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, and $R^6$ is substituted or unsubstituted alkyl.

225) Compound wherein ring A is an aromatic heterocyclic ring, m is 4, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, and $R^6$ is substituted or unsubstituted alkyl.

226) Compound wherein ring A is a nonaromatic heterocyclic ring, m is 0, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, and $R^6$ is substituted or unsubstituted alkyl.

227) Compound wherein ring A is a nonaromatic heterocyclic ring, m is 1, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, and $R^6$ is substituted or unsubstituted alkyl.

228) Compound wherein ring A is a nonaromatic heterocyclic ring, m is 2, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, and $R^6$ is substituted or unsubstituted alkyl.

229) Compound wherein ring A is a nonaromatic heterocyclic ring, m is 3, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, and $R^6$ is substituted or unsubstituted alkyl.

230) Compound wherein ring A is a nonaromatic heterocyclic ring, m is 4, $R^2$ is substituted or unsubstituted alkyloxy, n is 1, $R^3$ is a substituted or unsubstituted aromatic heterocyclic group, $R^4$ is a hydrogen atom, $R^5$ is a substituted or unsubstituted aromatic carbocyclic group, Y is a single bond, and $R^6$ is substituted or unsubstituted alkyl.

231) Compound wherein ring A is an aromatic heterocyclic ring, m is 0, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, and $R^6$ is substituted or unsubstituted alkyl.

232) Compound wherein ring A is an aromatic heterocyclic ring, m is 1, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, and $R^6$ is substituted or unsubstituted alkyl.

233) Compound wherein ring A is an aromatic heterocyclic ring, m is 2, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, and $R^6$ is substituted or unsubstituted alkyl.

234) Compound wherein ring A is an aromatic heterocyclic ring, m is 3, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, and $R^6$ is substituted or unsubstituted alkyl.

235) Compound wherein ring A is an aromatic heterocyclic ring, m is 4, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, and $R^6$ is substituted or unsubstituted alkyl.

236) Compound wherein ring A is a nonaromatic heterocyclic ring, m is 0, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, and $R^6$ is substituted or unsubstituted alkyl.

237) Compound wherein ring A is a nonaromatic heterocyclic ring, m is 1, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, and $R^6$ is substituted or unsubstituted alkyl.

238) Compound wherein ring A is a nonaromatic heterocyclic ring, m is 2, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, and $R^6$ is substituted or unsubstituted alkyl.

239) Compound wherein ring A is a nonaromatic heterocyclic ring, m is 3, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, and $R^6$ is substituted or unsubstituted alkyl.

240) Compound wherein ring A is a nonaromatic heterocyclic ring, m is 4, $R^2$ is substituted or unsubstituted alkyloxy, n is 1, $R^3$ is a substituted or unsubstituted nonaromatic heterocyclic group, $R^4$ is a hydrogen atom, $R^5$ is a substituted or unsubstituted aromatic carbocyclic group, Y is a single bond, and $R^6$ is substituted or unsubstituted alkyl.

In 201) to 240) described above, when m is not 0, $R^4$ is each independently halogen, cyano, oxo, or $—X^A—R^{41}$ ($X^A$ is a single bond, $—O—$, $—S—$, $—NR^{42}—$, $—CO—$, $—SO_2—$, $NR^{42}—CO—$, $—CO—NR^{42}—$, $—NR^{42}—CO—NR^{43}—$, $NR^{42}—SO_2—$, or $—SO_2—NR^{42}—$, $R^{41}$ is a hydrogen atom, substituted or unsubstituted alkyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, and $R^{42}$ and $R^{43}$ are each independently a hydrogen atom or substituted or unsubstituted alkyl).

Other preferred embodiments of the compound represented by the formula (II) include compounds of 201) to 240) described above in which $R^5$ is replaced by a hydrogen atom, substituted or unsubstituted alkyl, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclic carbamoyl, substituted or unsubstituted nonaromatic carbocyclic carbamoyl, or $—NR^{51}R^{52}$ ($R^{51}$ is substituted or unsubstituted aromatic carbocyclic carbonyl or substituted or unsubstituted nonaromatic carbocyclic carbonyl, and $R^{52}$ is a hydrogen atom).

In addition, other preferred embodiments of the compound represented by the formula (II) include compounds of 201) to 240) described above in which $R^2$ is replaced by substituted or unsubstituted alkyl, substituted or unsubstituted alkenyl, substituted or unsubstituted alkynyl, substituted or unsubstituted alkenyloxy, substituted or unsubstituted alkynyloxy, substituted or unsubstituted alkylsulfanyl, substituted or unsubstituted alkenylsulfanyl, or substituted or unsubstituted alkynylsulfanyl.

A characteristic of the compound according to the present invention is to have an inhibitory effect on HIV replication, in which, in the formula (I), (1) the benzene ring, the main skeleton, is substituted with at least one cyclic group ($R^3$), and (2) the benzene ring has a side chain represented by $—C(R^2)nCOOR^4$ (n=1, 2)

Another characteristic of the compound according to the present invention is that a substituted or unsubstituted alkyloxy group is preferably introduced as $R^2$ in the formula (I), and/or $R^4$ is a hydrogen atom, thereby having a high inhibitory effect on HIV replication.

The compound represented by the formula (I) is not limited to a specific isomer, and includes all possible isomers (e.g., keto-enol isomers, imine-enamine isomers, diastereoisomers, atropisomers, optical isomers, rotamers, etc.), racemates or mixtures thereof.

One or more hydrogens, carbons and/or other atoms of the compounds represented by the formula (I) may be substituted by an isotope of hydrogen, carbon and/or other atom. Examples of the isotope include hydrogen, carbon, nitrogen, oxygen, phosphorus, sulfur, fluorine, iodine and chlorine, like $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$. The compound represented by the formula (I) also includes compounds substituted with the isotope. The compound substituted with the isotope is also useful as a pharmaceutical, and includes all radiolabeled materials of the compounds represented by the formula (I). Also, a "radiolabeling method" for producing the "radiolabeled material" is also included in the present invention, and it is useful as a research and/or diagnostic tool in metabolism pharmacokinetic studies and binding assays.

The radiolabeled material of the compound represented by the formula (I) can be prepared by a method well known in the art. For example, a tritium-labeled compound represented by the formula (I) can be prepared, for example, by introducing tritium into a particular compound represented by the formula (I) by catalytic dehalogenation using tritium. This method includes reacting a precursor in which the compound represented by the formula (I) is properly substituted with halogen with tritium gas, in the presence of an appropriate catalyst, for example, Pd/C, in the presence or absence of a base. As the appropriate method for preparing other tritium-labeled compound, document of Isotopes in the Physical and Biomedical Sciences, Vol. 1, Labeled Compounds (Part A), Chapter 6 (1987) can be referred. A $^{14}C$-labeled compound can be prepared by using a raw material having a $^{14}C$ carbon.

Examples of the pharmaceutically acceptable salt of the compound represented by the formula (I) include salts of the compound represented by the formula (I) with an alkali metal (e.g., lithium, sodium, potassium, etc.), an alkaline earth metal (e.g., calcium, barium, etc.), magnesium, a transition metal (e.g., zinc, iron, etc.), ammonia, an organic base (e.g., trimethylamine, triethylamine, dicyclohexylamine, ethanolamine, diethanolamine, triethanolamine, meglumine, diethanolamine, ethylenediamine, pyridine, picoline, quinolone, etc.) and an amino acid, or salts with an inorganic acid (e.g., hydrochloric acid, sulfuric acid, nitric acid, carbonic acid, hydrobromic acid, phosphoric acid, hydroiodic acid, etc.) and an organic acid (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid, etc.). Examples include, particularly, salts with hydrochloric acid, sulfuric acid, phosphoric acid, tartaric acid, or methanesulfonic acid, and the like. These salts can be formed by a method usually carried out.

The compound represented by the formula (I) of the present invention and a pharmaceutically acceptable salt thereof may form a solvate (e.g., hydrate, etc.) and/or a crystalline polymorph, and the present invention also includes various kinds of solvates and crystalline polymorphs. "Solvate" may be coordinated with solvent molecules (e.g., water molecules, etc.) in any number, relative to the compound represented by the formula (I). The compound represented by the formula (I) or a pharmaceutically acceptable salt thereof is left in the air, whereby it may absorb water and the adsorbed water may attach thereto, or it may form a hydrate. In addition, there is a case that the compound represented by the formula (I) or a pharmaceutically acceptable salt thereof is recrystallized to form a crystalline polymorph thereof.

The compound represented by the formula (I) of the present invention or a pharmaceutically acceptable salt thereof may form a prodrug, and the present invention also includes such various prodrugs. The prodrug is a derivative of the compound of the present invention having a group that can chemically or metabolically decompose, and is a compound to be the pharmaceutically active compound of the present invention in vivo by solvolysis or under physiological conditions. The prodrug includes compounds which are converted to a compound represented by the formula (I) in response to enzymatic oxidation, reduction, hydrolysis, or the like, under physiological conditions in vivo, compounds which are converted to a compound represented by the formula (I) by being hydrolyzed by gastric acid or the like, and the like. A method for selecting an appropriate prodrug derivative and a method for producing the same are described, for example, in Design of Prodrugs, Elsevier, Amsterdam 1985. The prodrugs themselves may have an activity.

When the compound represented by the formula (I) or a pharmaceutically acceptable salt thereof has a hydroxyl group, for example, prodrugs such as acyloxy derivatives and sulfonyloxy derivatives produced by reacting a compound having a hydroxyl group with an appropriate acyl halide, an appropriate acid anhydride, an appropriate sulfonyl chloride, an appropriate sulfonyl anhydride and a mixed anhydrides or by reacting using a condensing agent are exemplified. Examples include $CH_3COO-$, $C_2H_5COO-$, $t-BuCOO-$, $C_{15}H_{31}COO-$, $PhCOO-$, $(m-NaOOCPh)COO-$, $NaOOCCH2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3$, $CF_3CH_2SO_3-$, $p-CH_3-O-PhSO_3-$, $PhSO_3-$, $p-CH_3PhSO_3-$, and the like.

(Method for Producing Compound of Present Invention)

The compound represented by the formula (I) according to the present invention can be produced, for example, according to the general synthesis method described below. In addition, extraction, purification and the like may be performed by a treatment performed in a normal experiment of organic chemistry.

The synthesis of the compound of the present invention can be carried out while referring to the method known in the art.

1) Synthesis of Compounds A-1 and A-2

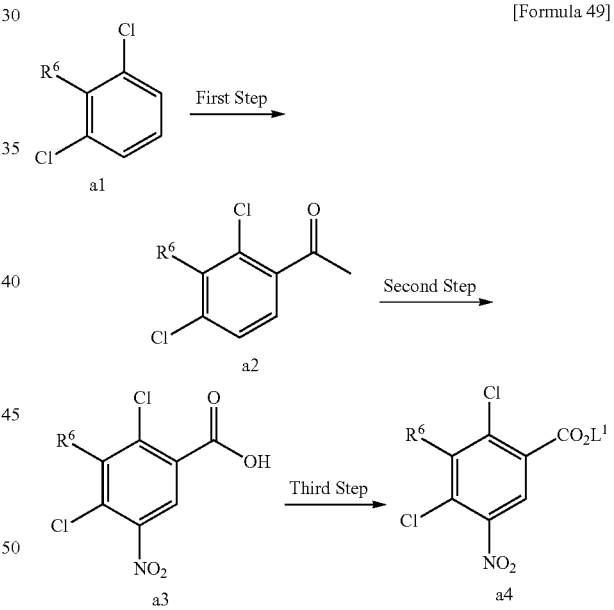

[Formula 49]

wherein $R^6$ has the same meaning as described above, and $L^1$ is substituted or unsubstituted alkyl.

First Step

Compound a1 that is commercially available or synthesized by a known method is reacted with an acid halide or acid anhydride such as acetyl chloride or acetic anhydride, by Friedel-Crafts-acylation, in a solvent of methylene chloride, dichloroethane or the like, in the presence of a Lewis acid such as aluminum chloride, at 0° C. to 150° C., and preferably 60° C. to 120° C., for 1 hour to 48 hours, and preferably 12 hours to 24 hours, whereby compound a2 can be obtained.

Second Step

In a mixed acid of sulfuric acid and nitric acid, compound a2 is reacted at −30° C. to 100° C., and preferably at 0° C. to 50° C., for 0.5 hours to 48 hours, and preferably 6 hours to 24 hours, whereby compound a3 can be obtained.

Third Step

In $L^1OH$, an acid such as concentrated sulfuric acid or concentrated hydrochloric acid is added to compound a3, and the mixture is reacted at 0° C. to 150° C., and preferably at 80° C. to 110° C., for 1 hour to 24 hours, and preferably 6 hours to 12 hours, whereby compound a4 can be obtained.

[Formula 50]

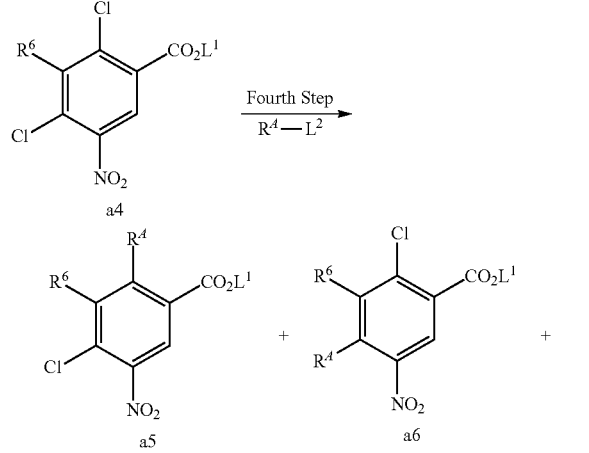

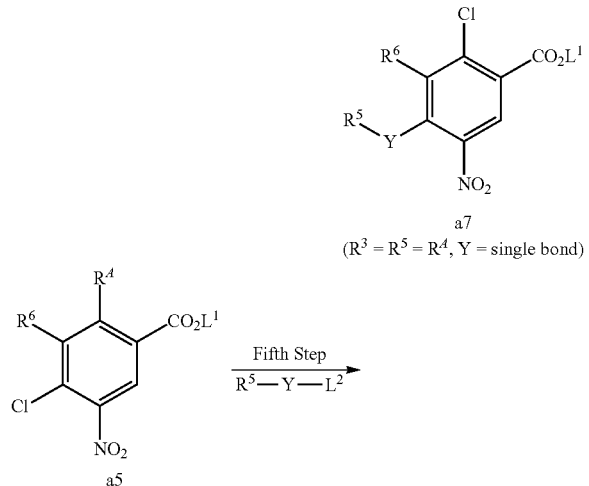

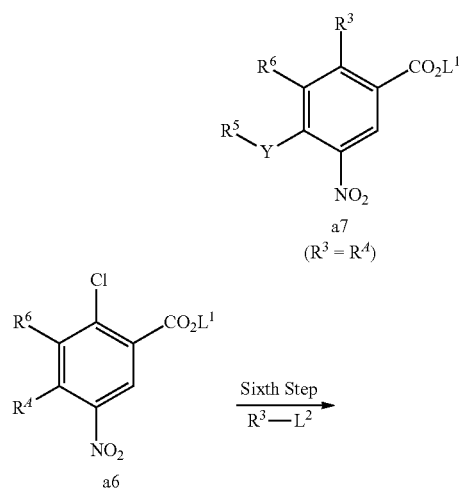

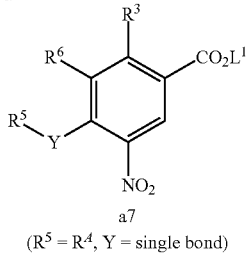

wherein $R^3$, $R^5$, $R^6$, Y, and $L^1$ have the same meaning as described above, $R^4$ is a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, and $L^2$ is boronic acid, a boronic acid ester, an alkyltin, a zinc halide, or the like.

Fourth Step

Compounds a5, a6, and a7 can be obtained by a coupling reaction of compound a4 with $R^4$-$L^2$. As the reaction, Suzuki cross-coupling, Ullmann cross-coupling, Negishi cross-coupling, Stille coupling, and the like are exemplified.

In a solvent such as dioxane, DMF, DME, THF or water or a mixed solvent, a palladium catalyst such as $Pd(PPh_3)_4$, $Pd(OAc)_2$, $Pd(PPh_3)_2Cl_2$ or $Pd(dppf)_2Cl_2$, a base such as potassium carbonate, sodium carbonate or potassium phosphate, and boronic acid, a boronic acid ester, an alkyltin or a zinc halide that is commercially available or synthesized by a known method, are added to compound a4, and the mixture is reacted under a nitrogen atmosphere at 0° C. to 150° C., and preferably at 60° C. to 120° C., for 0.5 hours to 24 hours, and preferably 1 hour to 12 hours, whereby compounds a5, a6 and a7 ($R^3$=$R^5$=$R^4$, and Y is a single bond) can be obtained.

Fifth Step

From compound a5, compound a7 ($R^3$=$R^4$) can be obtained in the same manner as in the fourth step.

Sixth Step

From compound a6, compound a7 ($R^5$=$R^4$, and Y is a single bond) can be obtained in the same manner as in the fourth step.

[Formula 51]

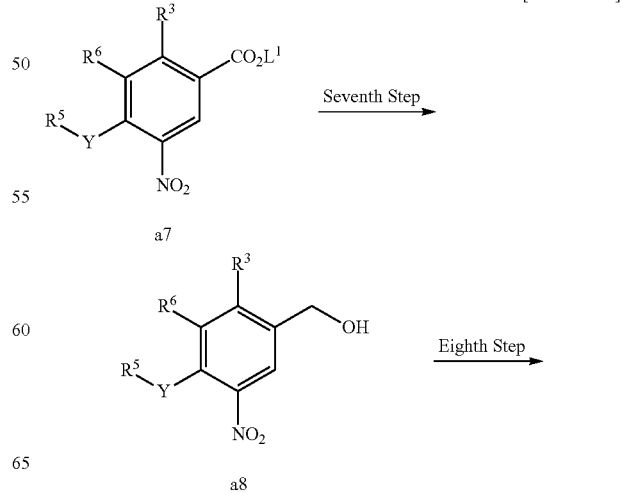

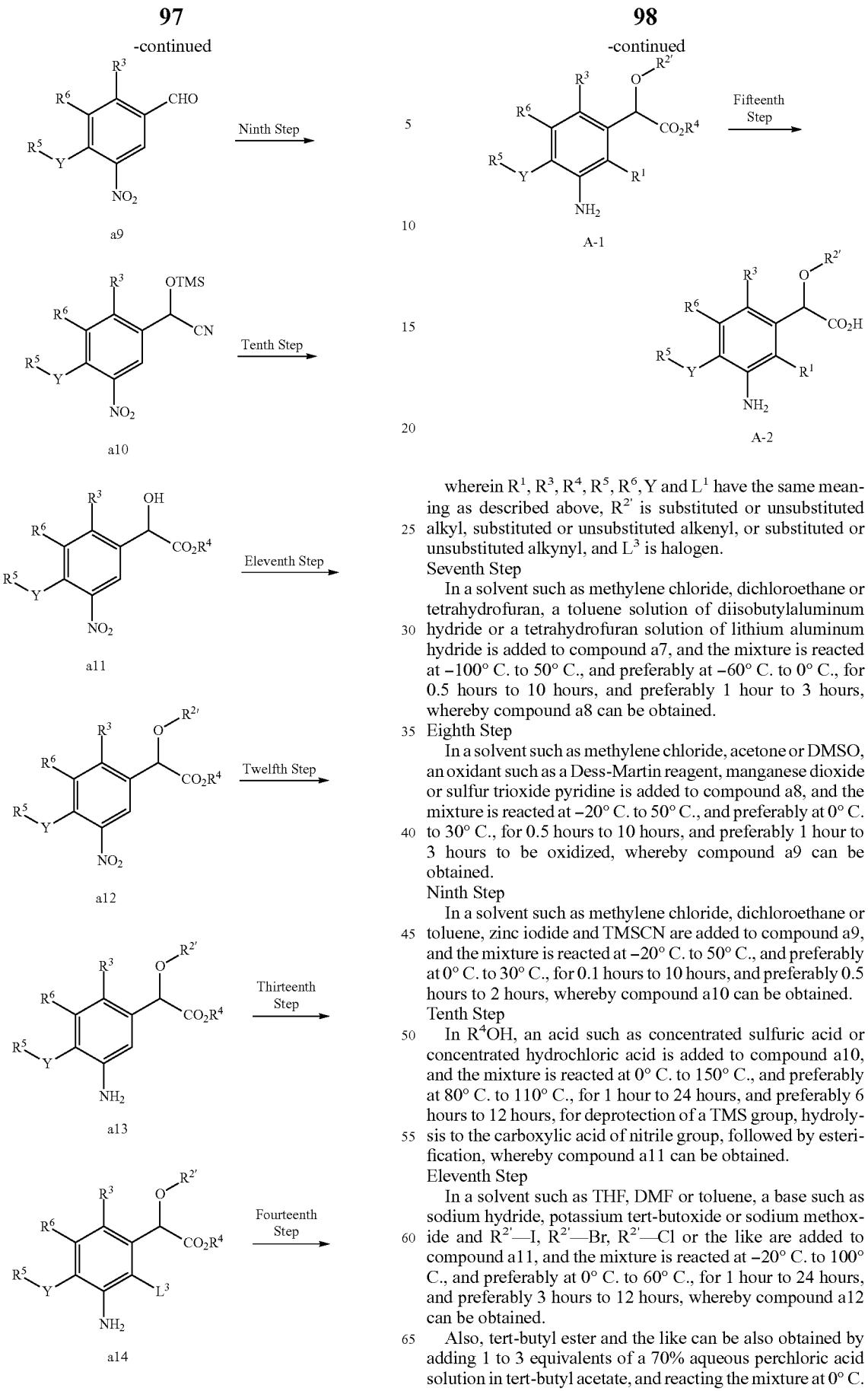

wherein $R^1$, $R^3$, $R^4$, $R^5$, $R^6$, Y and $L^1$ have the same meaning as described above, $R^{2'}$ is substituted or unsubstituted alkyl, substituted or unsubstituted alkenyl, or substituted or unsubstituted alkynyl, and $L^3$ is halogen.

Seventh Step

In a solvent such as methylene chloride, dichloroethane or tetrahydrofuran, a toluene solution of diisobutylaluminum hydride or a tetrahydrofuran solution of lithium aluminum hydride is added to compound a7, and the mixture is reacted at −100° C. to 50° C., and preferably at −60° C. to 0° C., for 0.5 hours to 10 hours, and preferably 1 hour to 3 hours, whereby compound a8 can be obtained.

Eighth Step

In a solvent such as methylene chloride, acetone or DMSO, an oxidant such as a Dess-Martin reagent, manganese dioxide or sulfur trioxide pyridine is added to compound a8, and the mixture is reacted at −20° C. to 50° C., and preferably at 0° C. to 30° C., for 0.5 hours to 10 hours, and preferably 1 hour to 3 hours to be oxidized, whereby compound a9 can be obtained.

Ninth Step

In a solvent such as methylene chloride, dichloroethane or toluene, zinc iodide and TMSCN are added to compound a9, and the mixture is reacted at −20° C. to 50° C., and preferably at 0° C. to 30° C., for 0.1 hours to 10 hours, and preferably 0.5 hours to 2 hours, whereby compound a10 can be obtained.

Tenth Step

In $R^4OH$, an acid such as concentrated sulfuric acid or concentrated hydrochloric acid is added to compound a10, and the mixture is reacted at 0° C. to 150° C., and preferably at 80° C. to 110° C., for 1 hour to 24 hours, and preferably 6 hours to 12 hours, for deprotection of a TMS group, hydrolysis to the carboxylic acid of nitrile group, followed by esterification, whereby compound a11 can be obtained.

Eleventh Step

In a solvent such as THF, DMF or toluene, a base such as sodium hydride, potassium tert-butoxide or sodium methoxide and $R^{2'}$—I, $R^{2'}$—Br, $R^{2'}$—Cl or the like are added to compound a11, and the mixture is reacted at −20° C. to 100° C., and preferably at 0° C. to 60° C., for 1 hour to 24 hours, and preferably 3 hours to 12 hours, whereby compound a12 can be obtained.

Also, tert-butyl ester and the like can be also obtained by adding 1 to 3 equivalents of a 70% aqueous perchloric acid solution in tert-butyl acetate, and reacting the mixture at 0° C.

to 60° C., and preferably at 15° C. to 30° C., for 0.1 hours to 10 hours, and preferably 0.5 hours to 2 hours.

Twelfth Step

In a solvent such as methanol, ethanol, THF or ethyl acetate, a catalyst such as 5% or 10% palladium carbon, palladium hydroxide or platinum dioxide is added to compound a12, and the mixture is reacted under a hydrogen atmosphere at 0° C. to 50° C., and preferably at 15° C. to 25° C., for 0.1 hours to 48 hours, and preferably 1 hour to 24 hours, whereby compound a13 can be obtained.

In this condition, the reaction may be promoted by adding acetic acid, hydrochloric acid or the like. In a mixed solvent of an organic solvent such as methanol, ethanol or THF and water, a metal such as iron, zinc or tin is added to compound a12, under acidic conditions of hydrochloric acid or acetic acid, under alkaline conditions of potassium hydroxide or sodium hydroxide, or under neutral conditions of ammonium chloride, and the mixture is reacted at 0° C. to 120° C., and preferably at 25° C. to 80° C., for 0.1 hours to 24 hours, and preferably 1 hour to 12 hours, whereby compound a13 can be also obtained.

Thirteenth Step

In a solvent such as dichloromethane, THF, toluene, acetonitrile or DMF, bromine or a halogenating reagent such as NBS, NCS and NIS is added to compound a13, and when $L^3$ is bromo, the mixture is reacted at −30° C. to 50° C., and preferably at −10° C. to 20° C., for 0.1 hours to 10 hours, and preferably 0.5 hours to 2 hours, whereby compound a14 can be obtained.

When $L^3$ is chloro or iodine, the mixture is reacted at 10° C. to 150° C., and preferably at 60° C. to 120° C., for 0.5 hours to 24 hours, and preferably 1 hour to 6 hours, whereby compound a14 can be obtained.

Fourteenth Step

From compound a14, compound A-1 can be obtained in the same manner as in the fourth step.

Fifteenth Step

In a solvent such as methanol, ethanol, THF or DMSO, potassium hydroxide, sodium hydroxide, lithium hydroxide or the like is added to compound A-1, and the mixture is reacted at 0° C. to 100° C., and preferably at 20° C. to 50° C., for 0.1 hours to 24 hours, and preferably 1 hour to 6 hours, whereby compound A-2 can be obtained.

In a solvent such as methanol, ethanol, THF or DMSO, hydrochloric acid, TFA or the like is added to compound A-1, and the mixture is reacted at 0° C. to 100° C., and preferably at 20° C. to 50° C., for 0.1 hours to 24 hours, and preferably 1 hour to 6 hours, whereby compound A-2 can be also obtained.

Synthesis of compound A-1 is also possible by the method shown below.

[Formula 52]

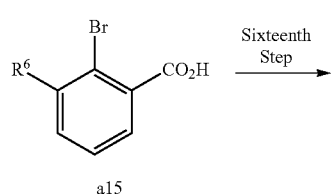

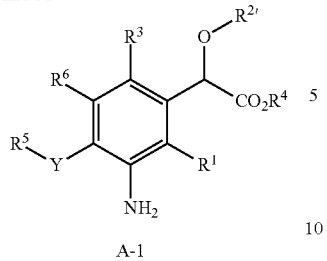

wherein $R^1$, $R^{2'}$, $R^3$, $R^4$, $R^5$, $R^6$, Y and $L^1$ have the same meaning as described above, $L^4$ is halogen, and $L^5$ is halogen.

Sixteenth Step

To compound a15 that is commercially available or synthesized by a known method is added, in a solvent such as concentrated sulfuric acid or acetic acid, nitric acid, fuming nitric acid or the like under ice-cooling, and the mixture is reacted at −20° C. to 60° C., and preferably at 0° C. to 25° C., for 0.5 hours to 6 hours, and preferably 1 hour to 3 hours, whereby a nitro compound can be obtained. This compound is reacted in a solvent such as thionyl chloride and phosphorus oxychloride, at 20° C. to 120° C., and preferably at 80° C. to 100° C., for 0.5 hours to 6 hours, and preferably 1 hour to 3 hours, and the solvent is concentrated under reduced pressure, whereby a crude acid chloride can be obtained. Subsequently, in a $L^1$-OH solvent, the crude chloride is reacted at 20° C. to 120° C., and preferably at 50° C. to 80° C., for 0.5 hours to 6 hours, and preferably 1 hour to 3 hours, whereby compound a16 can be obtained.

Seventeenth Step

From compound a16, compound a17 can be obtained in the same manner as in the fourth step.

Eighteenth Step

From compound a17, compound a18 can be obtained in the same manner as in the twelfth step.

Nineteenth Step

From compound a18, compound a19 can be obtained in the same manner as in the thirteenth step.

Twentieth Step

From compound a19, compound a20 can be obtained in the same manner as in the fourth step.

Twenty First Step

From compound a20, compound a21 can be obtained in the same manner as in the thirteenth step.

Twenty Second Step

From compound a21, compound a22 can be obtained in the same manner as in the fourth step.

Twenty Third Step

From compound a22, compound A-1 can be obtained in the same manner as in the seventh to eleventh steps.

Here, from compound a20, synthesis of compound A-1 is possible also by the method shown below.

[Formula 53]

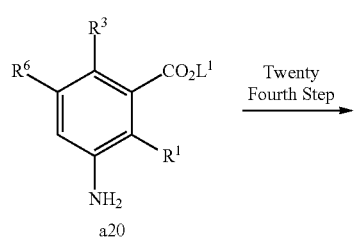

wherein $R^1$, $R^{2'}$, $R^3$, $R^4$, $R^5$, $R^6$, Y and $L^1$ have the same meaning as described above, $L^6$ is an amino group-protecting group such as tert-butyloxycarbonyl, and trifluoroacetyl, and $L^7$ is halogen.

Twenty Fourth Step

In a solvent such as THF or DMSO, an amino group protecting reagent such as a tert-butyloxycarbonylating reagent or a trifluoroacetylating reagent such as trifluoroacetyl chloride or trifluoroacetic acid anhydride, and a base such as triethylamine or N-methylmorpholine are added to compound a20, and the mixture is reacted at 0° C. to 100° C., and preferably at 20° C. to 50° C., for 0.1 hours to 24 hours, and preferably 1 hour to 6 hours, whereby compound a23 that is an amino group protector can be obtained.

Twenty Fifth Step

From compound a23, after reacting in the same manner as in the seventh step to the eleventh step, compound a24 can be obtained in the same manner as in the thirteenth step.

Twenty Sixth Step

From compound a24, compound A-1 can be obtained in the same manner as in the fourth step.

Furthermore, synthesis of compound A-1 is also possible by the method shown below.

[Formula 54]

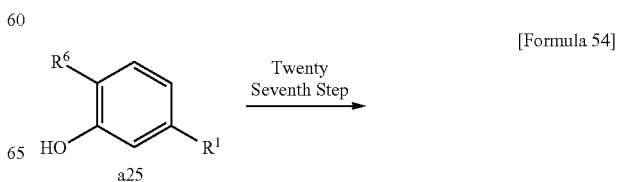

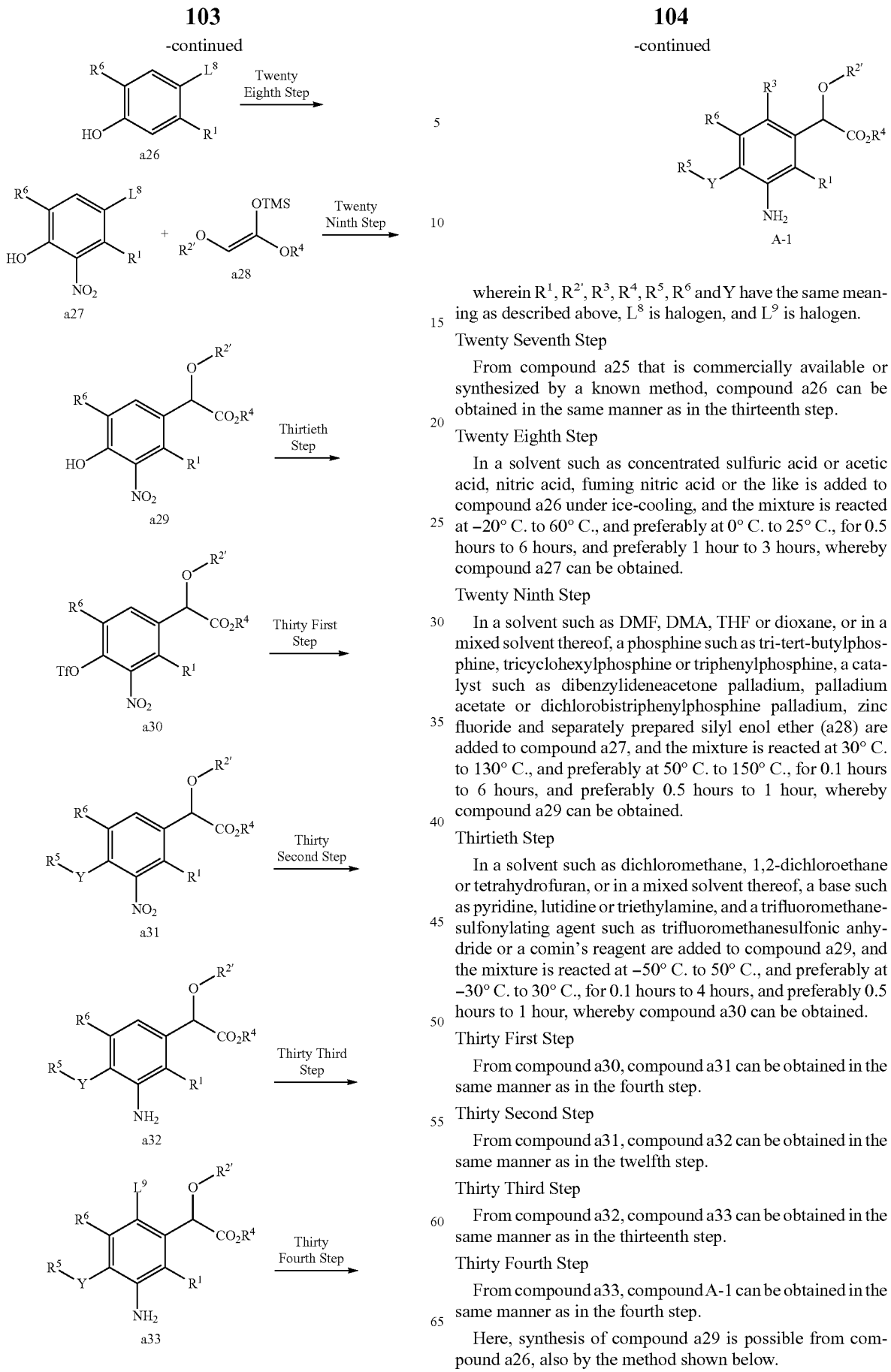

wherein $R^1$, $R^{2'}$, $R^3$, $R^4$, $R^5$, $R^6$ and Y have the same meaning as described above, $L^8$ is halogen, and $L^9$ is halogen.

Twenty Seventh Step

From compound a25 that is commercially available or synthesized by a known method, compound a26 can be obtained in the same manner as in the thirteenth step.

Twenty Eighth Step

In a solvent such as concentrated sulfuric acid or acetic acid, nitric acid, fuming nitric acid or the like is added to compound a26 under ice-cooling, and the mixture is reacted at −20° C. to 60° C., and preferably at 0° C. to 25° C., for 0.5 hours to 6 hours, and preferably 1 hour to 3 hours, whereby compound a27 can be obtained.

Twenty Ninth Step

In a solvent such as DMF, DMA, THF or dioxane, or in a mixed solvent thereof, a phosphine such as tri-tert-butylphosphine, tricyclohexylphosphine or triphenylphosphine, a catalyst such as dibenzylideneacetone palladium, palladium acetate or dichlorobistriphenylphosphine palladium, zinc fluoride and separately prepared silyl enol ether (a28) are added to compound a27, and the mixture is reacted at 30° C. to 130° C., and preferably at 50° C. to 150° C., for 0.1 hours to 6 hours, and preferably 0.5 hours to 1 hour, whereby compound a29 can be obtained.

Thirtieth Step

In a solvent such as dichloromethane, 1,2-dichloroethane or tetrahydrofuran, or in a mixed solvent thereof, a base such as pyridine, lutidine or triethylamine, and a trifluoromethanesulfonylating agent such as trifluoromethanesulfonic anhydride or a comin's reagent are added to compound a29, and the mixture is reacted at −50° C. to 50° C., and preferably at −30° C. to 30° C., for 0.1 hours to 4 hours, and preferably 0.5 hours to 1 hour, whereby compound a30 can be obtained.

Thirty First Step

From compound a30, compound a31 can be obtained in the same manner as in the fourth step.

Thirty Second Step

From compound a31, compound a32 can be obtained in the same manner as in the twelfth step.

Thirty Third Step

From compound a32, compound a33 can be obtained in the same manner as in the thirteenth step.

Thirty Fourth Step

From compound a33, compound A-1 can be obtained in the same manner as in the fourth step.

Here, synthesis of compound a29 is possible from compound a26, also by the method shown below.

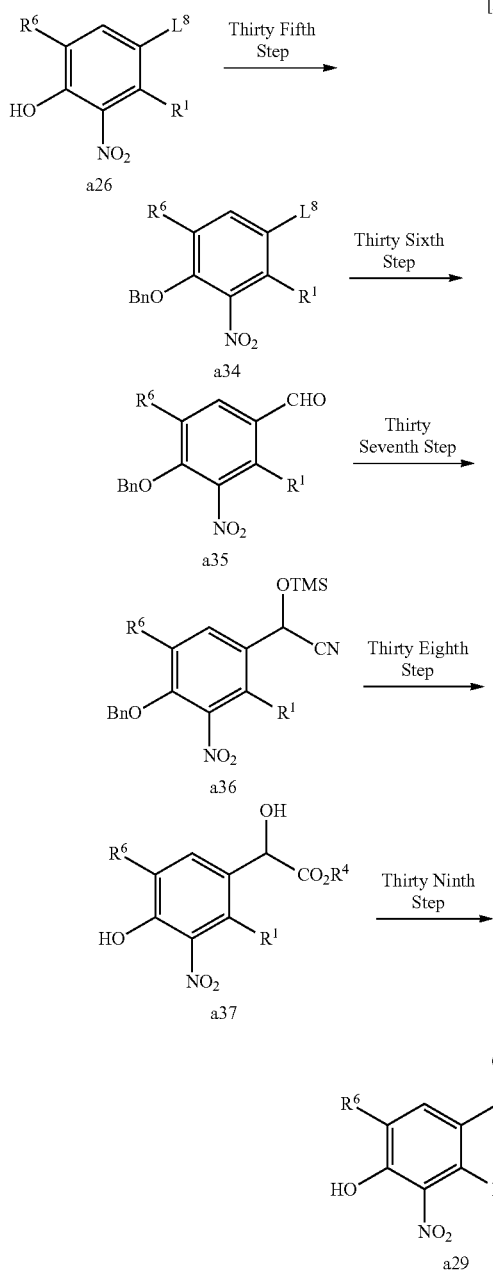

[Formula 55]

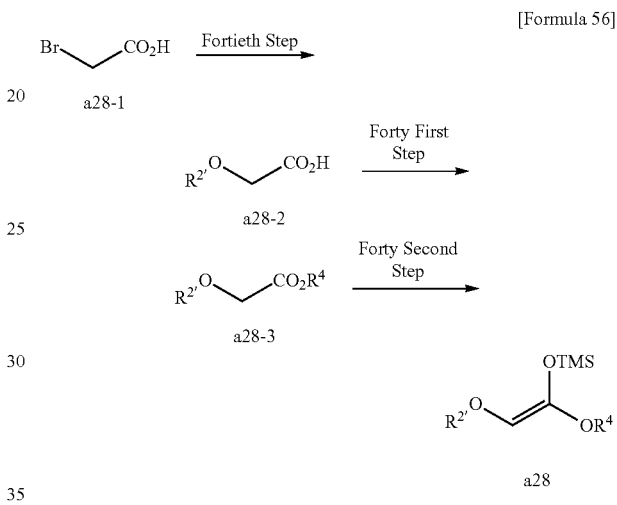

[Formula 56]

wherein each definition has the same meaning as described above.

Thirty Fifth Step

In a solvent such as dioxane, DMF, DME, THF, acetone or acetonitrile, a base such as potassium carbonate or sodium carbonate and benzyl bromide or benzyl chloride are added to compound a26, and the mixture is reacted at 0° C. to 100° C., and preferably at 20° C. to 50° C., for 0.5 hours to 24 hours, and preferably 1 hour to 5 hours, whereby compound a34 can be obtained.

Thirty Sixth Step

In a solvent such as diethyl ether or THF, $L^8$ of compound a34 is converted to a Grignard reagent or a lithium compound by metal magnesium or n-butyl lithium, and a reagent such as dimethylformamide, N-formyl piperidine, and N-formyl morpholine is added, and the mixture is reacted at −20° C. to 50° C., and preferably at 0° C. to 20° C., for 0.5 hours to 6 hours, and preferably 1 hour to 3 hours, whereby compound a35 can be obtained.

Thirty Seventh Step

From compound a35, compound a36 can be obtained in the same manner as in the ninth step.

Thirty Eighth Step

From compound a36, compound a37 can be obtained in the same manner as in the tenth step.

Thirty Ninth Step

From compound a37, compound a29 can be obtained in the same manner as in the eleventh step.

Incidentally, synthesis of compound a28 is possible by the method shown below.

wherein each definition has the same meaning as described above.

Fortieth Step

To compound a28-1 that is commercially available or synthesized by a known method are added, in a solvent such as THF, diethyl ether or dioxane, or in a mixed solvent thereof, $R^{2'}OH$ and a metal reagent such as sodium hydride, lithium hydride or potassium hydride, and the mixture is reacted at 20° C. to 120° C., and preferably at 40° C. to 100° C., for 0.1 hours to 12 hours, and preferably 0.5 hours to 6 hours, whereby compound a28-2 can be obtained.

Forty First Step

In a solvent such as DMF, DMA, THF or dioxane, or in a mixed solvent thereof, a base such as potassium carbonate, sodium carbonate or potassium phosphate, and an alkylating agent such as an alkyl iodide, alkyl bromide or alkyl sulfate are added to compound a28-2, and the mixture is reacted at −30° C. to 70° C., and preferably at −10° C. to 50° C., for 0.1 hours to 5 hours, and preferably 0.5 hours to 1 hour, whereby compound a28-3 can be obtained.

Forty Second Step

In a solvent such as THF, diethyl ether or dioxane, or in a mixed solvent thereof, a base such as potassium hexamethyldisilazide, lithium hexamethyldisilazide or lithium diisopropylamide, and a silylating agent such as TMSCl and TMSOTf are added to compound a28-3, and the mixture is reacted at −130° C. to −20° C., and preferably at −110° C. to −50° C., for 0.1 hours to 5 hours, and preferably 0.5 hours to 1 hour, whereby compound a28 can be obtained.

Also, as shown below, optically active forms of compounds A-1 and A-2 can be synthesized by using compound a28', instead of compound a28. Synthesis of compound a28' is possible by the method shown below.

[Formula 57]

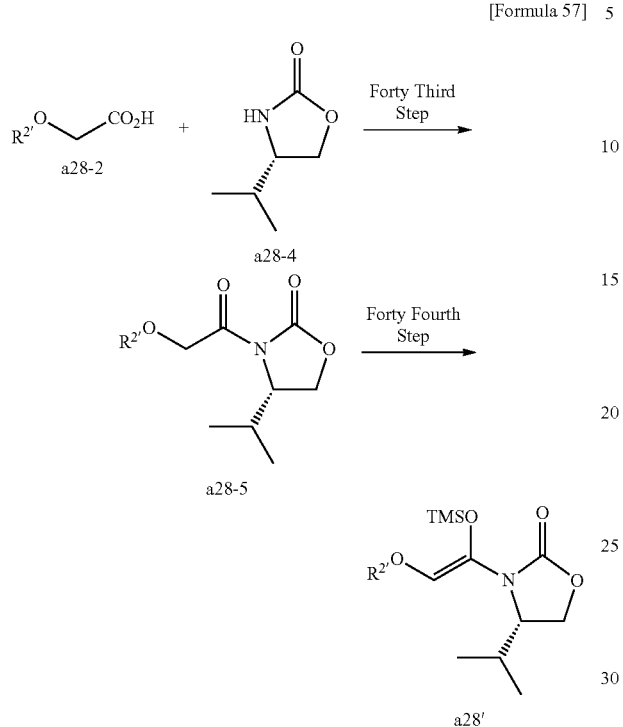

wherein each definition has the same meaning as described above.

Forty Third Step

In a solvent such as dichloromethane, toluene or dichloroethane, or in a mixed solvent thereof, a reagent such as oxalyl chloride or thionyl chloride and oxazolidinone (a28-4) are added to compound a28-2, and the mixture is reacted at −50° C. to 50° C., and preferably at −30° C. to 30° C., for 0.1 hours to 4 hours, and preferably 0.5 hours to 1 hour, whereby compound a28-5 can be obtained.

Forty Fourth Step

From compound a28-5, compound a28' can be obtained in the same manner as in the forty second step.

Here, synthesis of compound a29 is also possible from compound a28', by the method shown below. Compound a29 to be obtained is an optical isomer. Furthermore, from the optical isomer of compound a29, optical isomers of compounds A-1 and A-2 can be synthesized by the method described above.

[Formula 58]

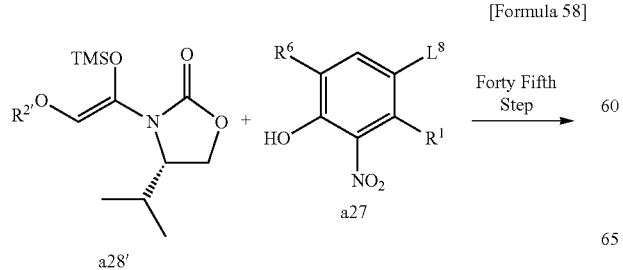

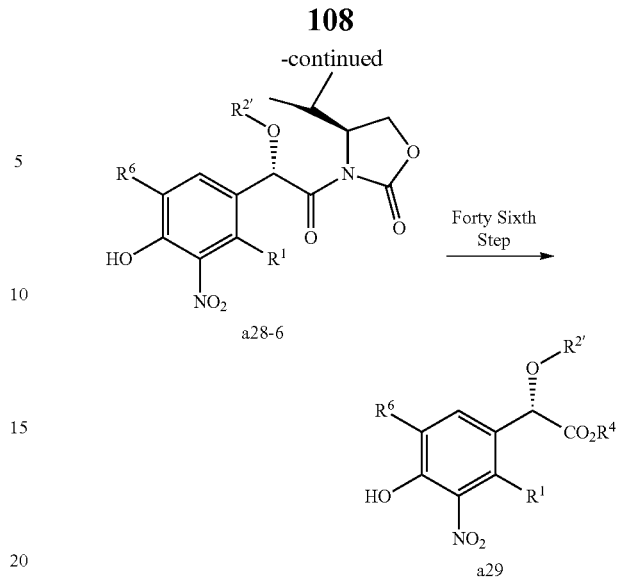

wherein each definition has the same meaning as described above.

Forty Fifth Step

From compound a28', compound a28-6 can be obtained in the same manner as in the twenty ninth step.

Forty Sixth Step

In a tetrahydrofuran-water mixed solvent, a mixed liquid of hydrogen peroxide and an aqueous solution of lithium hydroxide is added to compound a28-6, and the mixture is reacted at −20° C. to 10° C., and preferably at −10° C. to 10° C., for 0.1 hours to 5 hours, and preferably 0.1 hours to 1 hour, to obtain a carboxylate form, and thereafter, without purification, the carboxylate form is directly esterified by the addition of a $R^{4N}{}_2$/diethyl ether solution or the like, whereby compound a29 can be obtained.

It is also possible to synthesize optical isomers of compounds A-1 and A-2 from compound a16, by the method shown below.

[Formula 59]

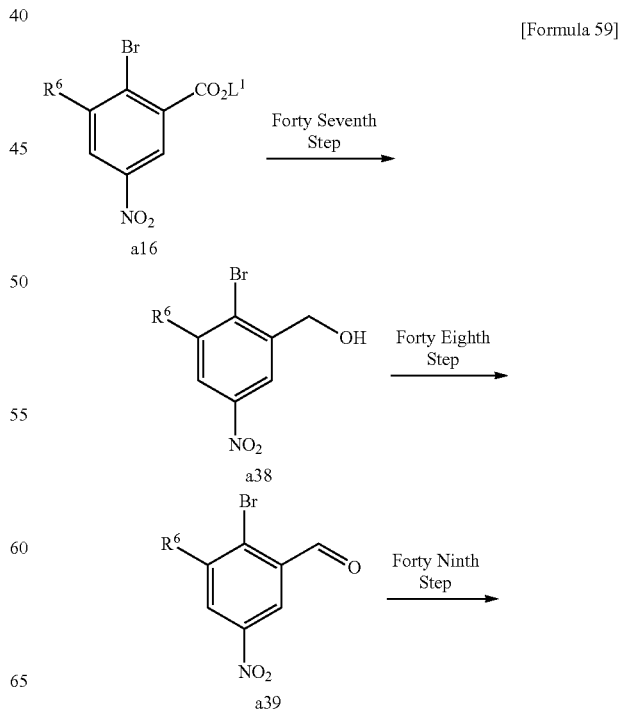

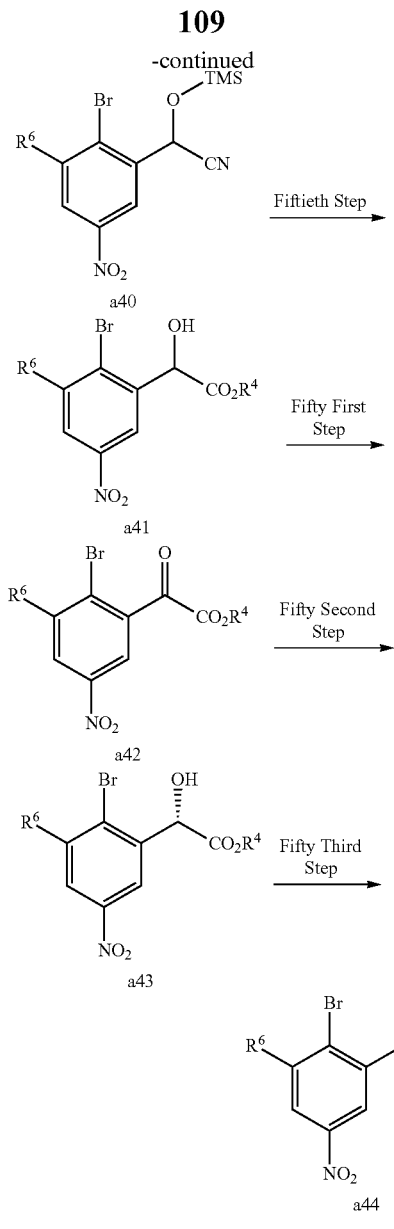

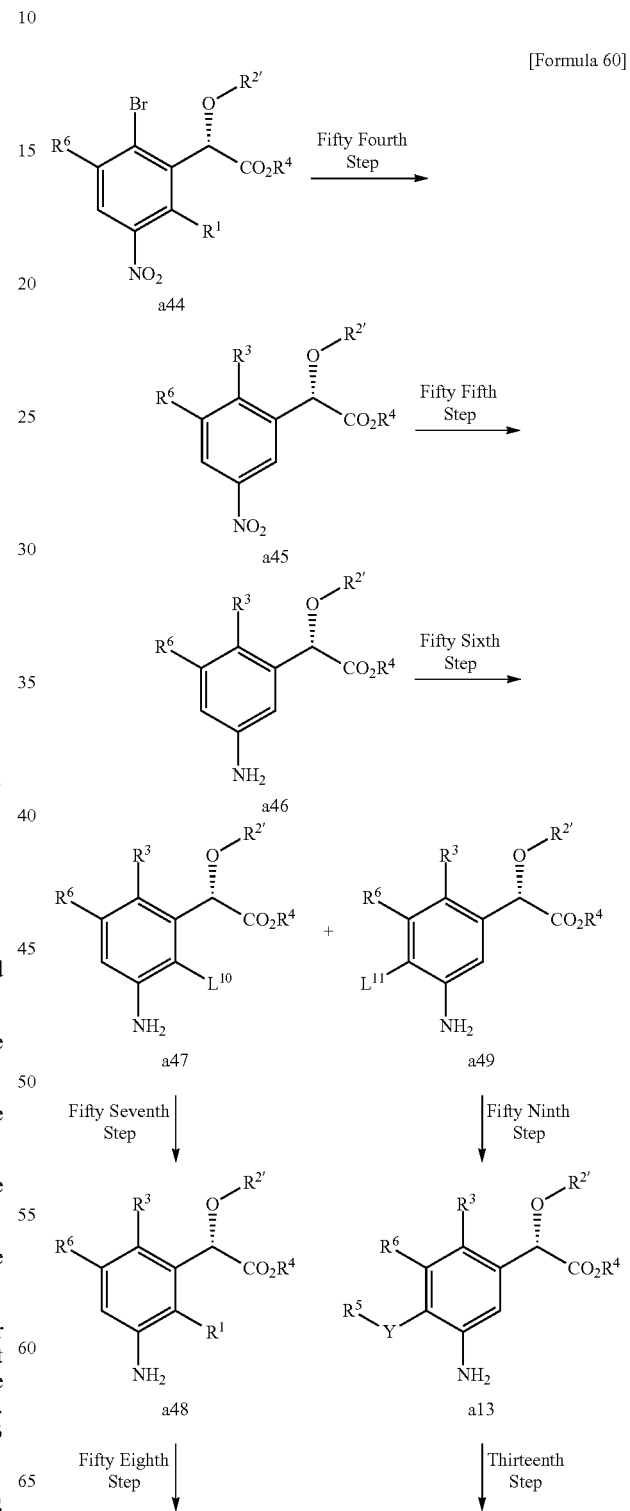

wherein each definition has the same meaning as described above.

Forty Seventh Step
From compound a16, compound a38 can be obtained in the same manner as in the seventh step.

Forty Eighth Step
From compound a38, compound a39 can be obtained in the same manner as in the eighth step.

Forty Ninth Step
From compound a39, compound a40 can be obtained in the same manner as in the ninth step.

Fiftieth Step
From compound a40, compound a41 can be obtained in the same manner as in the tenth step.

Fifty First Step
In a solvent such as dichloromethane, dichloroethane or chloroform, an oxidizing agent such as a Dess-Martin reagent or manganese dioxide is added to compound a41, and the mixture is reacted at 0° C. to 80° C., and preferably at 20° C. to 45° C., for 0.5 hours to 5 hours, and preferably 1 hour to 3 hours, whereby compound a42 can be obtained.

Fifty Second Step
In a solvent such as benzene, toluene or xylene, a (R)-CBS reagent is added to compound a42 as an asymmetric source, and a reducing agent such as catechol borane or 9-borabicyclo [3.3.1]nonane is sequentially added, and the mixture is reacted at −50° C. to 0° C., and preferably at −35° C. to −10° C., for 0.5 hours to 6 hours, and preferably 1 hour to 3 hours, whereby compound a43 can be obtained.

Fifty Third Step
From compound a43, compound a44 can be obtained in the same manner as in the eleventh step.

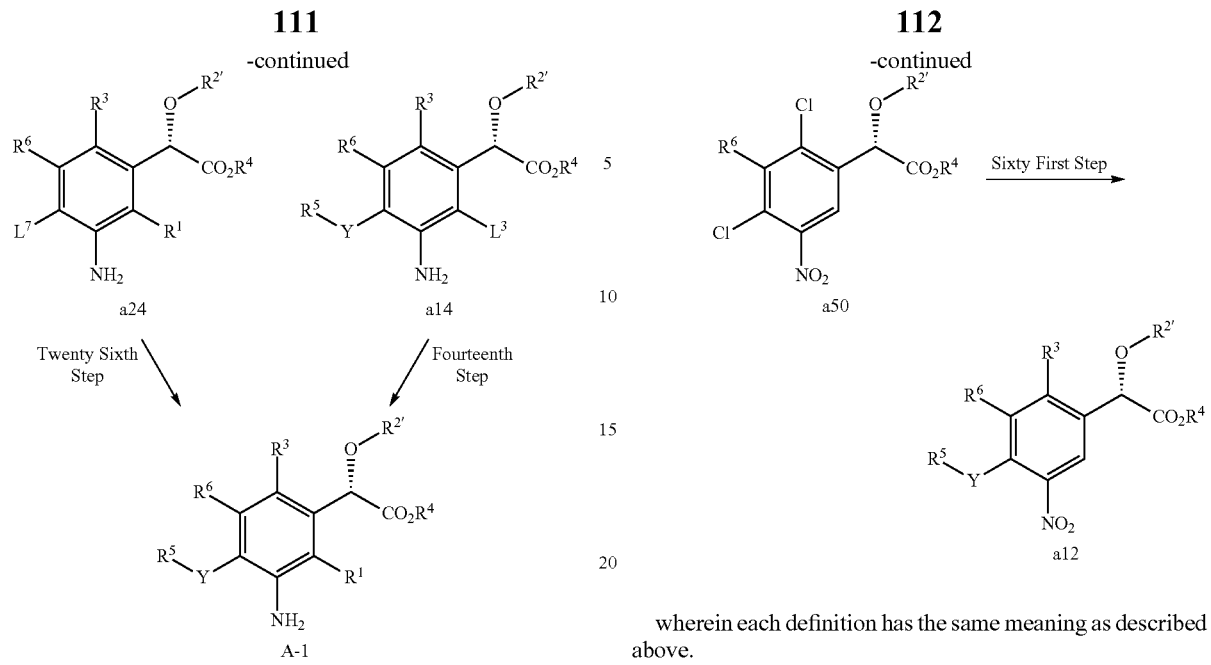

a24 a14

Twenty Sixth Step / Fourteenth Step

A-1 wherein $R^1, R^{2'}, R^3, R^4, R^5, R^6, Y, L^3$, and $L^7$ have the same meaning as described above, $L^{10}$ is halogen, and $L^{11}$ is halogen.

Fifty Fourth Step

From compound a44, compound a45 can be obtained in the same manner as in the seventeenth step.

Fifty Fifth Step

From compound a45, compound a46 can be obtained in the same manner as in the eighteenth step.

Fifty Sixth Step

From compound a46, compounds a47 and a49 can be obtained in the same manner as in the nineteenth step.

Fifty Seventh Step

From compound a47, compound a48 can be obtained in the same manner as in the twentieth step.

Fifty Eighth Step

From compound a48, compound a24 can be obtained in the same manner as in the twenty first step.

Fifty Ninth Step

From compound a49, compound a13 can be obtained in the same manner as in the twentieth step.

In the same manner, as shown below, an optical isomer of compound a12 can be synthesized from compound a4. Furthermore, from the optical isomer of compound a12, optical isomers of compounds A-1 and A-2 can be synthesized by the method described above.

[Formula 61]

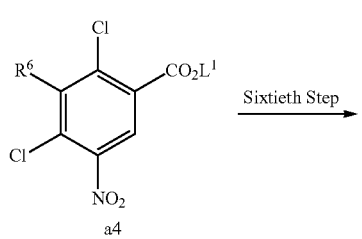

a4

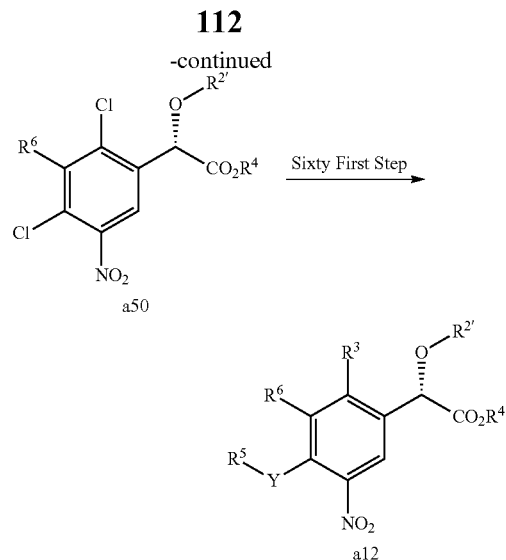

a50 wherein each definition has the same meaning as described above.

Sixtieth Step

From compound a4, compound a50 can be obtained in the same manner as in the forty seventh step to the fifty third step.

Sixty First Step

From compound a50, compound a11 can be obtained in the same manner as in the fourth step to the sixth step.

Here, synthesis of compound a44 is possible from compound a41, also by the method shown below.

[Formula 62]

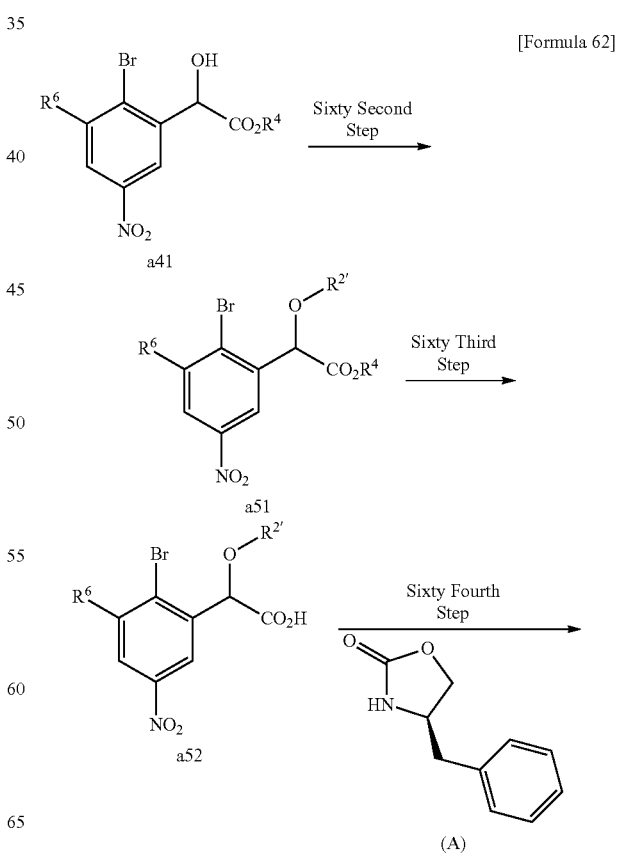

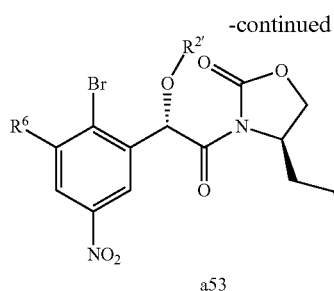

a53

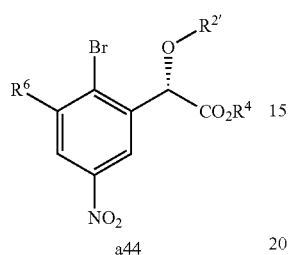

a44 wherein each definition has the same meaning as described above.

Sixty Second Step

From compound a41, compound a51 can be obtained in the same manner as in the eleventh step.

Sixty Third Step

From compound a51, compound a52 can be obtained in the same manner as in the fifteenth step.

Sixty Fourth Step

Compound a53 can be synthesized by condensing compound a52 with an enantiopure chiral auxiliary compound like R-(+)-4-benzyl-2-oxazolidinone (compound (A)) to produce a diastereomeric mixture and separating the diastereomeric mixture by silica gel column chromatography.

Specifically, compound a52 is dissolved in a solvent such as anhydrous dichloromethane, anhydrous chloroform or anhydrous THF, and thereafter a small amount of anhydrous DMF is added, and a chlorinating reagent such as thionyl chloride or oxalyl chloride is added dropwise at −30° C. to 50° C., and preferably at −10° C. to 20° C. Thereafter, the mixture is stirred at −30° C. to 50° C., and preferably at −10° C. to 20° C., for 0.1 hours to 10 hours, and preferably 0.5 hours to 2 hours and concentrated, and the obtained foamy solid is dissolved in anhydrous tetrahydrofuran, anhydrous dichloromethane, or the like. A solution of anhydrous tetrahydrofuran, anhydrous dichloromethane or the like of compound (A) is stirred at −100° C. to −30° C., and preferably at −80° C. to −60° C., a n-BuLi/hexane solution is added, and the mixture is stirred at −100° C. to −30° C., and preferably at −80° C. to −60° C., for 0.1 hours to 1 hour, and preferably 0.1 hours to 0.5 hours, and is further stirred at −20° C. to 60° C., and preferably at 0° C. to 30° C., for 0.1 hours to 5 hours, and preferably 0.1 hours to 2 hours. Thereafter, the mixture is mixed with the prepared acid chloride solution at −60° C. to −10° C., and preferably at −40° C. to −20° C., and then heated to −10° C. to 60° C., and preferably to 10° C. to 30° C. After the reaction, the mixture is quenched with a saturated aqueous ammonium chloride solution, and extracted with dichloromethane, and then separated and purified by silica gel chromatography, whereby compound a53 can be obtained.

Sixty Fifth Step

In a tetrahydrofuran-water mixed solvent, a mixed liquid of hydrogen peroxide and an aqueous solution of lithium hydroxide is added to compound a53, and the mixture is reacted at −20° C. to 10° C., and preferably at −10° C. to 10° C., to obtain a carboxylate form, and thereafter, the carboxylate form is esterified by a diazomethane/diethyl ether solution or the like, whereby compound a44 can be obtained.

It is also possible to obtain an optical isomer of compound a29, by the method shown below.

[Formula 63]

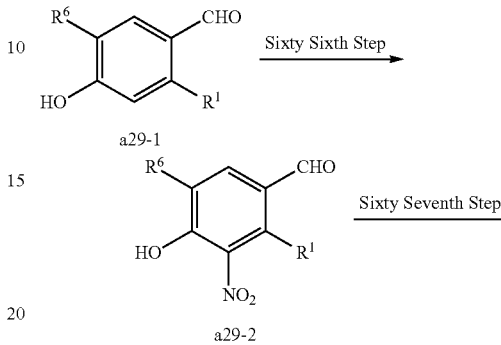

a29-1

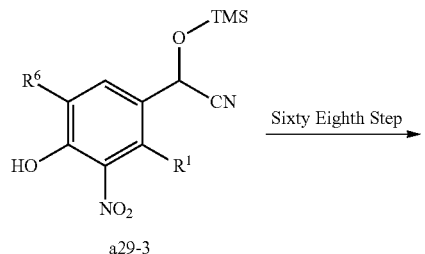

a29-2

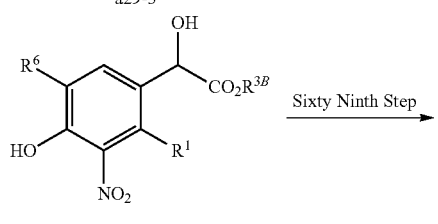

a29-3

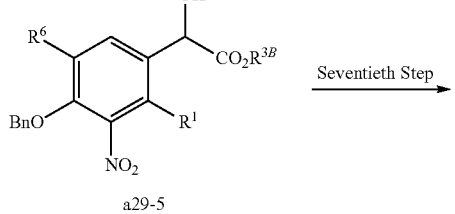

a29-4

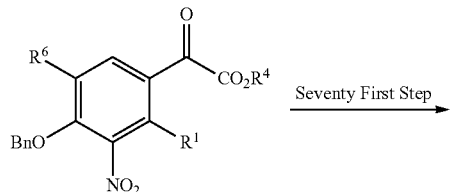

a29-5

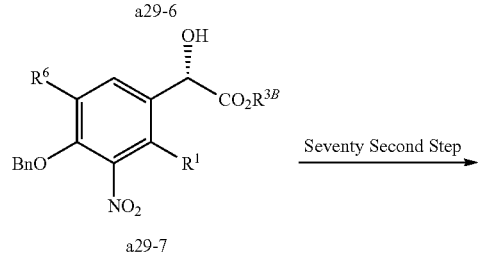

a29-6 a29-7

-continued

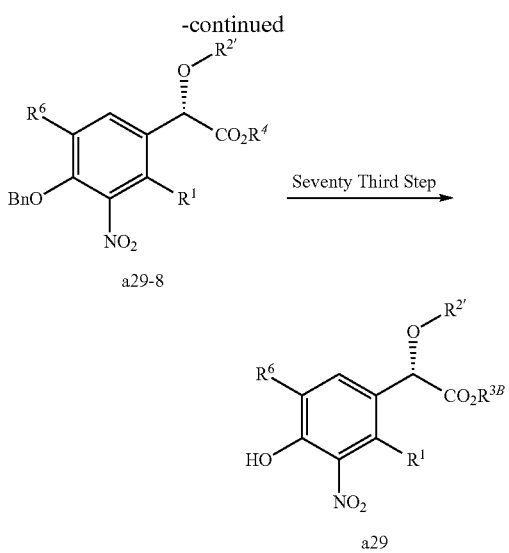

wherein each definition has the same meaning as described above.

Sixty Sixth Step

To compound a29-1 that is commercially available or prepared by a known method is added, in a solvent such as concentrated sulfuric acid or acetic acid, nitric acid, fuming nitric acid or the like under ice-cooling, and the mixture is reacted at −20° C. to 60° C., and preferably at 0° C. to 25° C., for 0.5 hours to 6 hours, and preferably 1 hour to 3 hours, whereby compound a29-2 can be obtained. Also, compound a29-2 can be obtained by adding a metal salt such as potassium nitrate or sodium nitrate under ice-cooling in concentrated sulfuric acid, and reacting the mixture at −20° C. to 60° C., and preferably at 0° C. to 25° C., for 0.5 hours to 6 hours, and preferably 1 hour to 3 hours.

Sixty Seventh Step

In a solvent such as dichloromethane, dichloroethane or toluene, zinc iodide and TMSCN are added to compound a29-2, and the mixture is reacted at −20° C. to 50° C., and preferably at 0° C. to 30° C., for 0.1 hours to 10 hours, and preferably 0.5 hours to 2 hours, whereby compound a29-3 can be obtained. Also, compound a29-3 can be obtained by reacting a metal salt such as zinc iodide, TMSCI, sodium cyanide or potassium cyanide in a solvent such as acetonitrile and DMF at −20° C. to 50° C., and preferably at 0° C. to 30° C., for 0.1 hours to 10 hours, and preferably 0.5 hours to 2 hours.

Sixty Eighth Step

In $R^4OH$ of compound a29-3, an acid such as concentrated sulfuric acid or concentrated hydrochloric acid is added, and the mixture is reacted at 0° C. to 150° C., and preferably at 80° C. to 110° C., for 1 hour to 24 hours, and preferably 6 hours to 12 hours, for deprotection of a TMS group, hydrolysis to the carboxylic acid of nitrile group, followed by esterification, whereby compound 1-4 can be obtained.

Sixty Ninth Step

In a solvent such as DMF, DME, tetrahydrofuran, acetone or acetonitrile, a base such as potassium carbonate, sodium carbonate, cesium carbonate or sodium hydride, and benzyl bromide or benzyl chloride are added to compound a29-4, and the mixture is reacted at 0° C. to 100° C., and preferably at 20° C. to 50° C., for 0.5 hours to 24 hours, and preferably 1 hour to 5 hours, whereby compound a29-5 can be obtained. Also, compound a29-5 can be obtained by adding diethyl azodicarboxylate or diisopropyl azodicarboxylate, and benzyl alcohol in a solvent such as tetrahydrofuran, toluene or dichloromethane, and reacting the mixture at 0° C. to 100° C., and preferably at 20° C. to 50° C., for 0.5 hours to 24 hours, and preferably 1 hour to 5 hours.

Seventieth Step

In a solvent such as dichloromethane, dichloroethane or chloroform of compound a29-5, an oxidizing agent such as a Dess-Martin reagent, manganese dioxide or pyridinium chlorochromate is added, and the mixture is reacted at 0° C. to 80° C., and preferably at 20° C. to 45° C., for 0.5 hours to 5 hours, and preferably 1 hour to 3 hours, whereby compound a29-6 can be obtained. Also, compound a29-6 can be obtained by general Swern oxidation.

Seventy First Step

In a solvent such as benzene, toluene, xylene, dichloromethane or dichloroethane of compound a29-6, a (R)-CBS reagent is added as an asymmetric source, and a reducing agent such as catechol borane or 9-borabicyclo[3.3.1]nonane is sequentially added, and the mixture is reacted at −100° C. to 0° C., and preferably at −78° C. to −50° C., for 0.5 hours to 6 hours, and preferably 1 hour to 3 hours, whereby compound a29-7 can be obtained.

Seventy Second Step

In a solvent such as tetrahydrofuran, DMF or toluene, a base such as sodium hydride, potassium tert-butoxide or sodium methoxide and $R^{2'}$—I, $R^{2'}$—Br, $R^{2'}$—Cl or the like that is commercially available or prepared by a known method are added to compound a29-7, and the mixture is reacted at −20° C. to 100° C., and preferably at 0° C. to 60° C., for 1 hour to 24 hours, and preferably 3 hours to 12 hours, whereby compound a29-8 can be obtained.

Also, tert-butyl ester and the like can be also obtained by adding 1 to 3 equivalents of a 70% aqueous perchloric acid solution in tert-butyl acetate, and reacting the mixture at 0° C. to 60° C., and preferably at 15° C. to 30° C., for 0.1 hours to 10 hours, and preferably 0.5 hours to 2 hours.

Seventy Third Step

In a solvent such as methanol, ethanol or tetrahydrofuran, a catalyst such as 5% or 10% palladium carbon, palladium hydroxide or platinum dioxide is added to compound a29-8, and the mixture is reacted under a hydrogen atmosphere at 0° C. to 60° C., and preferably at 20° C. to 40° C., for 0.1 hours to 24 hours, and preferably 1 hour to 12 hours, whereby compound a29 can be obtained.

Also, compound a29 can be obtained by adding tribromoboron and trimethylsilyliodide in a solvent such as dichloromethane, dichloroethane or chloroform, and reacting the mixture at −20° C. to 100° C., and preferably at 0° C. to 30° C., for 1 hour to 24 hours, and preferably 3 hours to 12 hours.

2) Synthesis of Compounds A-3 and A-4

[Formula 64]

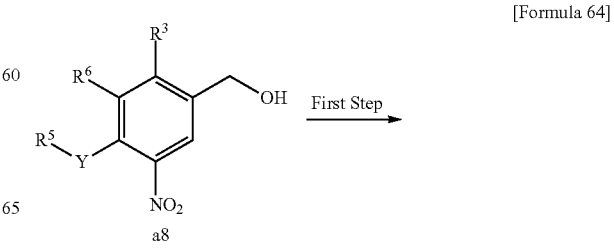

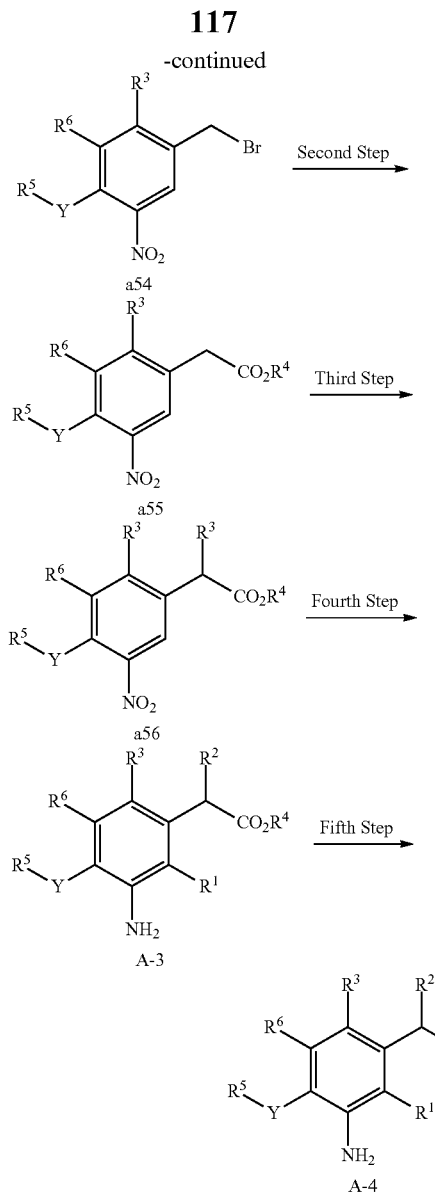

to compound a55, and the mixture is reacted at −70° C. to 50° C., and preferably at −20° C. to 20° C., for 1 hour to 24 hours, and preferably 3 hours to 10 hours, whereby compound a56 can be obtained.

Fourth Step

From compound a56, compound A-3 can be obtained in the same manner as in the twelfth to fourteenth steps in "1) Synthesis of Compounds A-1 and A-2" described above.

Fifth Step

From compound A-3, compound A-4 can be obtained in the same manner as in the fifteenth step in "1) Synthesis of Compounds A-1 and A-2" described above.

3) Synthesis of Compounds A-5 and A-6

[Formula 65]

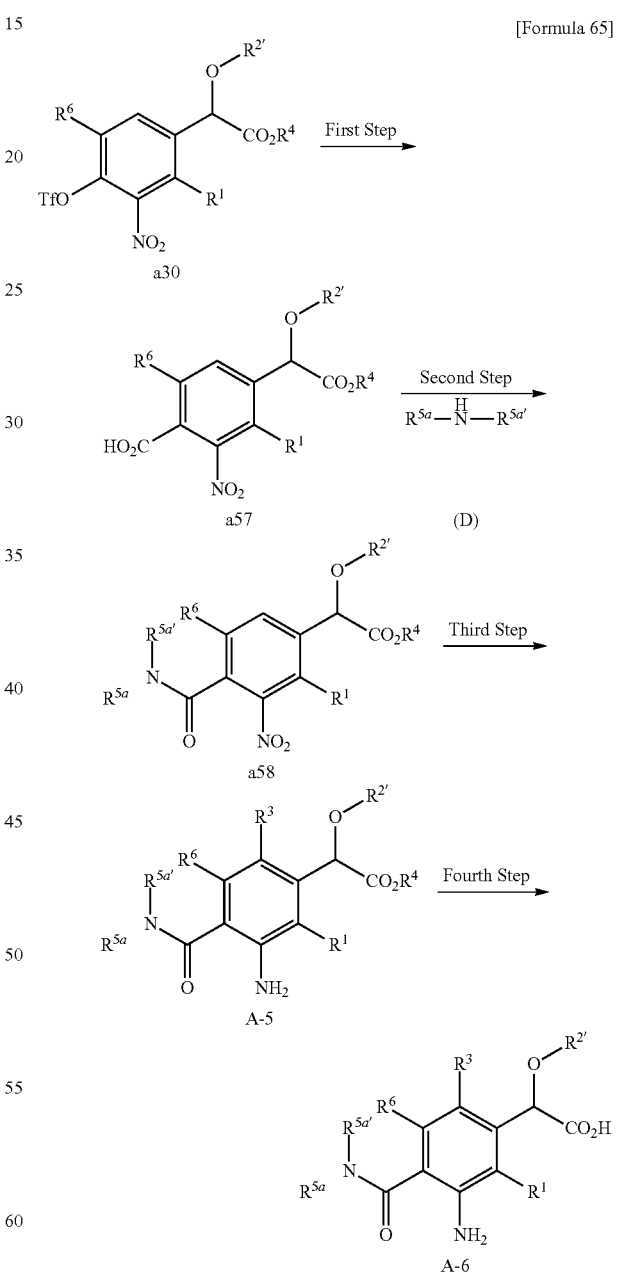

wherein each definition has the same meaning as described above.

First Step

In a solvent such as methylene chloride, toluene or THF, phosphorus tribromide, thionyl bromide or the like is added to compound a8, and the mixture is reacted at −20° C. to 120° C., and preferably at 0° C. to 60° C., for 0.1 hours to 12 hours, and preferably 1 hour to 4 hours, whereby compound a54 can be obtained.

Second Step

In a solvent such as DMF, DMSO, dioxane or toluene, a palladium catalyst such as $Pd(PPh_3)_4$, $Pd(OAc)_2$, $Pd(PPh_3)_2Cl_2$ or $PdCl_2(dppf)_2$, a base such as triethylamine or N-methylmorpholine, and $R^4OH$ are added to compound a54, and the mixture is reacted under a carbon monoxide atmosphere at 0° C. to 150° C., and preferably at 50° C. to 100° C., for 1 hour to 24 hours, and preferably 3 hours to 12 hours, whereby compound a55 can be obtained.

Third Step

In a solvent such as THF, diethyl ether or toluene, a base such as lithium diisopropylamide, potassium hexamethyldisilazide, lithium hexamethyldisilazide or sodium hexamethyldisilazide, and $R^2$—I, $R^2$—Br, $R^2$—Cl, or the like are added wherein $R^1$, $R^{2'}$, $R^3$, $R^4$, and $R^6$ have the same meaning as described above, and $R^{5a}$ and $R^{5a'}$ are each independently substituted or unsubstituted alkyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, wherein $R^{5a}$ and $R^{5a'}$ may be taken together with an adjacent nitrogen atom to form a substituted or unsubstituted aromatic heterocyclic group or a substituted or unsubstituted nonaromatic heterocyclic group.

First Step

In a solvent such as DMF, DMSO, dioxane or toluene, a palladium catalyst such as $Pd(PPh_3)_4$, $Pd(OAc)_2$, $Pd(PPh_3)_2Cl_2$ or $PdCl_2(dppf)_2$, a base such as triethylamine or N-methylmorpholine, and further allyl alcohol are added to compound a30, and the mixture is reacted under a carbon monoxide atmosphere at 0° C. to 150° C., and preferably at 50° C. to 100° C., for 1 hour to 24 hours, and preferably 3 hours to 12 hours, whereby an allyl ester form can be synthesized. Thereafter, in a solvent such as ethanol, MeCN or THF, morpholine, pyrrolidine, or the like is added, and the mixture is reacted, in the presence of $Pd(Ph_3P)_4$, at 0° C. to 100° C., and preferably at 25° C. to 75° C., for 0.1 hours to 24 hours, and preferably 1 hour to 12 hours, whereby compound a57 can be obtained.

Second Step

In DMF, DMA, THF, acetonitrile, or the like, or a mixed solvent thereof, 1-hydroxy-7-azabenzotriazole, 1-hydroxybenzotriazole or the like, and/or a condensing agent such as dicyclohexylcarbodiimide or diisopropylcarbodiimide, and a base such as triethylamine, diisopropylethylamine or N-methylmorpholine are added to compound a57 and an amine derivative (D) that is commercially available or prepared by a known method, and the mixture is reacted at 0° C. to 100° C., and preferably at 20° C. to 50° C., for 1 hour to 48 hours, and preferably 2 hours to 24 hours, whereby compound a58 can be obtained.

Third Step

From compound a58, compound A-5 can be obtained in the same manner as in the thirty second to thirty fourth steps in "1) Synthesis of Compounds A-1 and A-2" described above.

Fourth Step

From compound A-5, compound A-6 can be obtained in the same manner as in the fifteenth step in "1) Synthesis of Compounds A-1 and A-2" described above.

It is also possible to synthesize compound a57, by the method shown below.

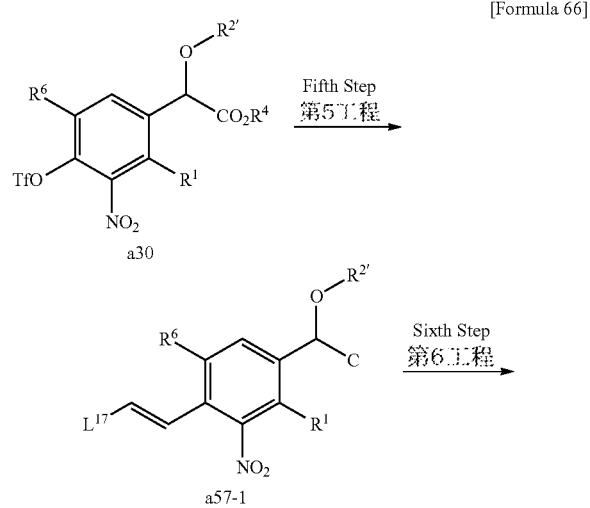

[Formula 66]

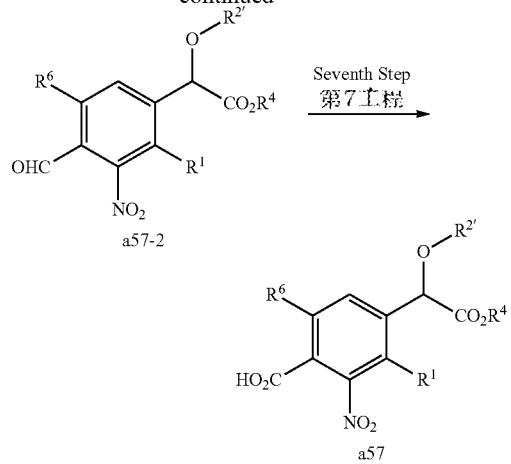

wherein $R^1$, $R^{2'}$, $R^4$, and $R^6$ have the same meaning as described above, and $L^{17}$ is hydrogen or phenyl.

Fifth Step

In a solvent such as dioxane, DMF, DME, tetrahydrofuran or water, or a mixed solvent, a palladium catalyst such as $Pd(PPh_3)_4$, $Pd(OAc)_2$, $Pd(PPh_3)_2Cl_2$, $Pd(dppf)_2Cl_2$ or $Pd(dt-bpf)$, a base such as potassium carbonate, sodium carbonate, cesium carbonate or potassium phosphate, and trans-ethynylboronic acid, vinyl boronate, vinyl trialkyltin, or the like are added to compound a30, and the mixture is reacted under a nitrogen atmosphere at 0° C. to 150° C., and preferably at 60° C. to 120° C., for 0.5 hours to 24 hours, and preferably 1 hour to 12 hours, whereby compound a57-1 can be obtained.

Sixth Step

In dichloromethane or methanol or a mixed solvent thereof, an ozone gas is passed through compound a57-1 at −100° C. to 0° C., and preferably at −78° C. to 50° C., for 0.5 hours to 6 hours, and preferably 1 hour to 3 hours, and thereafter dimethylsulfide, trimethylphosphite, or the like is added, and the mixture is stirred at the same temperature for 0.1 hours to 3 hours, and preferably 0.5 hours to 1 hour, whereby compound a57-2 can be obtained.

Seventh Step

In a solvent such as acetone or methyl ethyl ketone, potassium permanganate is added to compound a57-2, and the mixture is reacted at −20° C. to 50° C., and preferably at 0° C. to 20° C., for 0.5 hours to 6 hours, and preferably 1 hour to 3 hours, whereby compound a57 can be obtained. Also, compound a57 can be also obtained by adding pyridinium dichromate in a DMF solvent, and reacting the mixture at 0° C. to 60° C., and preferably at 20° C. to 40° C., for 2 hours to 24 hours, and preferably 6 hours to 12 hours.

4) Synthesis of Compounds A-7 and A-8

[Formula 67]

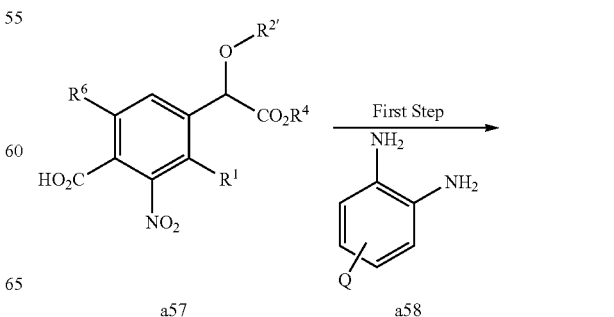

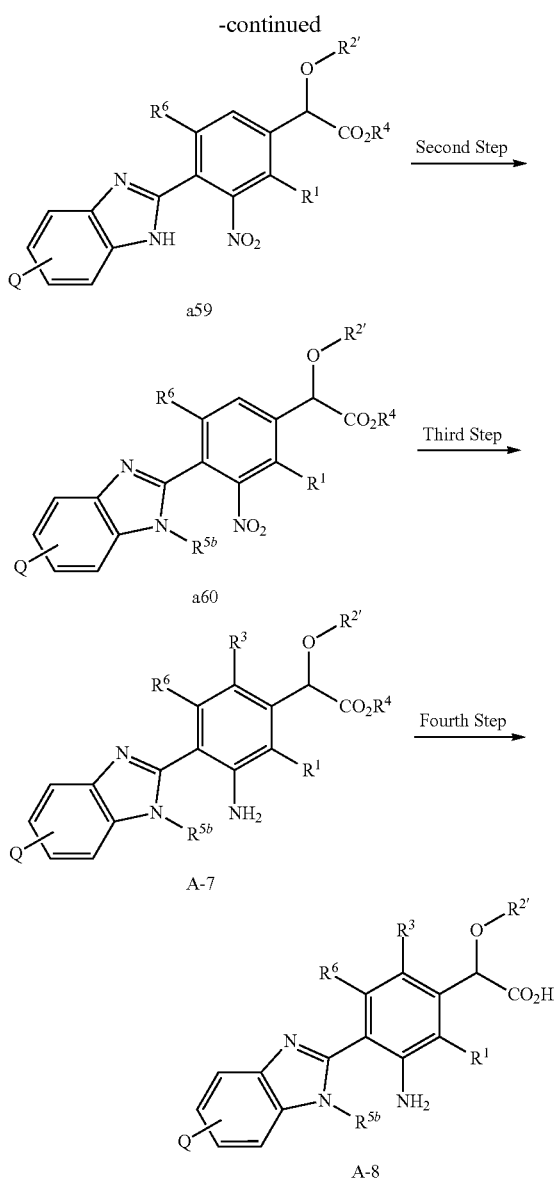

wherein $R^4$, $R^{2'}$, $R^3$, $R^4$, and $R^6$ have the same meaning as described above, $R^{5b}$ is alkyl, and Q is halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azido, hydrazino, ureido, amidino, guanidino, trialkylsilyl, alkyl, alkenyl, alkynyl, haloalkyl, hydroxyalkyl, alkyloxy, alkenyloxy, alkynyloxy, haloalkyloxy, alkyloxyalkyl, alkyloxyalkyloxy, alkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, an aromatic carbocyclic group, a nonaromatic carbocyclic group, an aromatic heterocyclic group, a nonaromatic heterocyclic group, aromatic carbocyclicoxy, nonaromatic carbocyclicoxy, aromatic heterocyclicoxy, nonaromatic heterocyclicoxy, aromatic carbocyclic amino, nonaromatic carbocyclic amino, aromatic heterocyclic amino, nonaromatic heterocyclic amino, aromatic carbocyclic carbonyl, nonaromatic carbocyclic carbonyl, aromatic heterocyclic carbonyl, nonaromatic heterocyclic carbonyl, aromatic carbocyclic oxycarbonyl, nonaromatic carbocyclic oxycarbonyl, aromatic heterocyclic oxycarbonyl, nonaromatic heterocyclic oxycarbonyl, aromatic carbocyclic carbonylamino, nonaromatic carbocyclic carbonylamino, aromatic heterocyclic carbonylamino, nonaromatic heterocyclic carbonylamino, aromatic carbocyclic alkyl, nonaromatic carbocyclic alkyl, aromatic heterocyclic alkyl, nonaromatic heterocyclic alkyl, aromatic carbocyclic alkyloxy, nonaromatic carbocyclic alkyloxy, aromatic heterocyclic alkyloxy, nonaromatic heterocyclic alkyloxy, aromatic carbocyclic alkylsulfanyl, nonaromatic carbocyclic alkylsulfanyl, aromatic heterocyclic alkylsulfanyl, nonaromatic heterocyclic alkylsulfanyl, aromatic carbocyclic alkyloxycarbonyl, nonaromatic carbocyclic alkyloxycarbonyl, aromatic heterocyclic alkyloxycarbonyl, nonaromatic heterocyclic alkyloxycarbonyl, aromatic carbocyclic alkyloxyalkyl, nonaromatic carbocyclic alkyloxyalkyl, aromatic heterocyclic alkyloxyalkyl, nonaromatic heterocyclic alkyloxyalkyl, aromatic carbocyclic alkylamino, nonaromatic carbocyclic alkylamino, aromatic heterocyclic alkylamino, nonaromatic heterocyclic alkylamino, aromatic carbocyclic sulfanyl, nonaromatic carbocyclic sulfanyl, aromatic heterocyclic sulfanyl, nonaromatic heterocyclic sulfanyl, nonaromatic carbocyclic sulfonyl, aromatic carbocyclic sulfonyl, aromatic heterocyclic sulfonyl, or nonaromatic heterocyclic sulfonyl.

First Step

In DMF, DMA, THF, acetonitrile, or the like, or a mixed solvent thereof, 1-hydroxy-7-azabenzotriazole, 1-hydroxybenzotriazole, and/or a condensing agent such as dicyclohexylcarbodiimide or diisopropylcarbodiimide, and a base such as triethylamine, diisopropylethylamine or N-methylmorpholine are added to compound a57 and a phenylenediamine derivative (a58) that is commercially available or prepared by a known method, and the mixture is reacted at 0° C. to 100° C., and preferably at 20° C. to 50° C., for 1 hour to 48 hours, and preferably 2 hours to 24 hours, whereby compound a59 can be obtained.

Second Step

In DMF, DMA, THF, acetonitrile, or the like, or a mixed solvent thereof, a base such as sodium hydride or cesium carbonate, and halogenated alkyl that is commercially available or prepared by a known method are added to compound a59, and the mixture is reacted at 20° C. to 140° C., and preferably at 40° C. to 80° C., for 1 hour to 48 hours, and preferably 2 hours to 24 hours, whereby compound a60 can be obtained.

Third Step

From compound a60, compound A-7 can be obtained in the same manner as in the thirty second to thirty fourth steps in "1) Synthesis of Compounds A-1 and A-2" described above.

Fourth Step

From compound A-7, compound A-8 can be obtained in the same manner as in the fifteenth step in "1) Synthesis of Compounds A-1 and A-2" described above.

5) Synthesis of Compounds A-9 and A-10

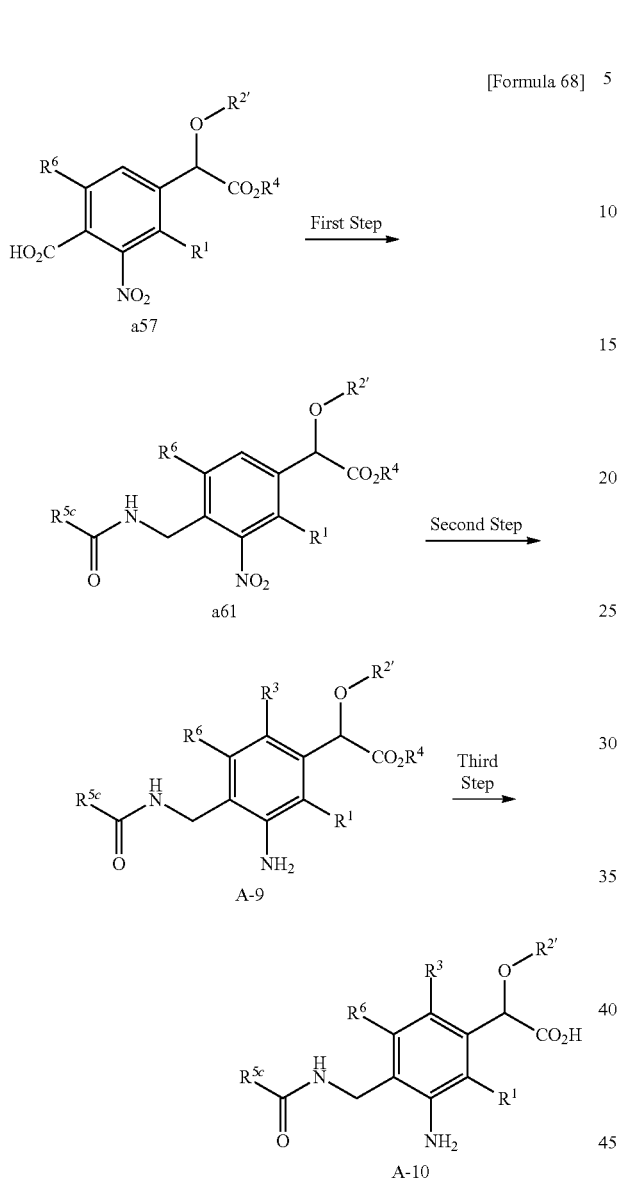

6) Synthesis of Compounds A-11 and A-12

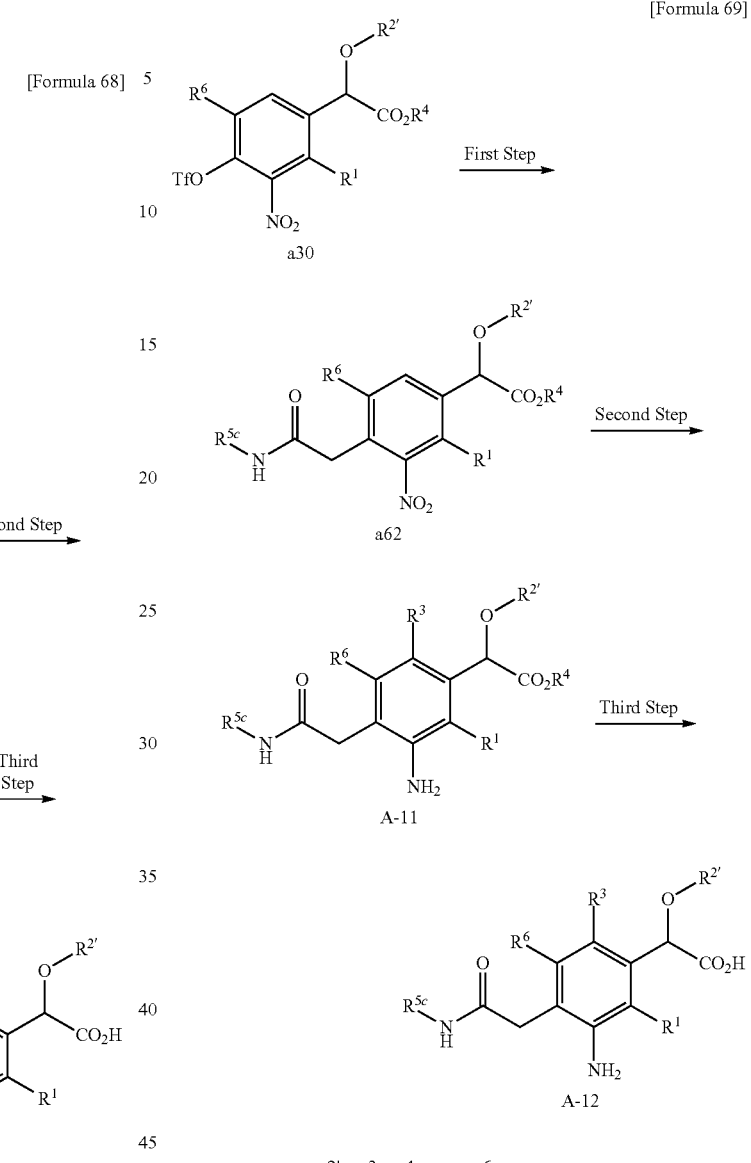

wherein $R^1$, $R^{2'}$, $R^3$, $R^4$, and $R^6$ have the same meaning as described above, and $R^{5c}$ is alkyl, alkenyl, alkynyl, an aromatic carbocyclic group, a nonaromatic carbocyclic group, an aromatic heterocyclic group, or a nonaromatic heterocyclic group.

First Step

From compound a57, compound a61 can be obtained in the same manner as in the first to sixth steps in "30) Synthesis of Compounds N-1 and N-2" described below.

Second Step

From compound a61, compound A-9 can be obtained in the same manner as in the thirty second to thirty fourth steps in "1) Synthesis of Compounds A-1 and A-2" described above.

Third Step

From compound A-9, compound A-10 can be obtained in the same manner as in the fifteenth step in "1) Synthesis of Compounds A-1 and A-2" described above.

wherein R', $R^{2'}$, $R^3$, $R^4$, and $R^6$ have the same meaning as described above, and $R^{5d}$ is substituted or unsubstituted alkyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group.

First Step

From compound a30, compound a62 can be obtained in the same manner as in the first to fifth steps in "31) Synthesis of Compounds O-1 and O-2" described below.

Second Step

From compound a62, compound A-11 can be obtained in the same manner as in the thirty second to thirty fourth steps in "1) Synthesis of Compounds A-1 and A-2" described above.

Third Step

From compound A-9, compound A-12 can be obtained in the same manner as in the fifteenth step in "1) Synthesis of Compounds A-1 and A-2" described above.

125

7) Synthesis of Compounds A-13 and A-14

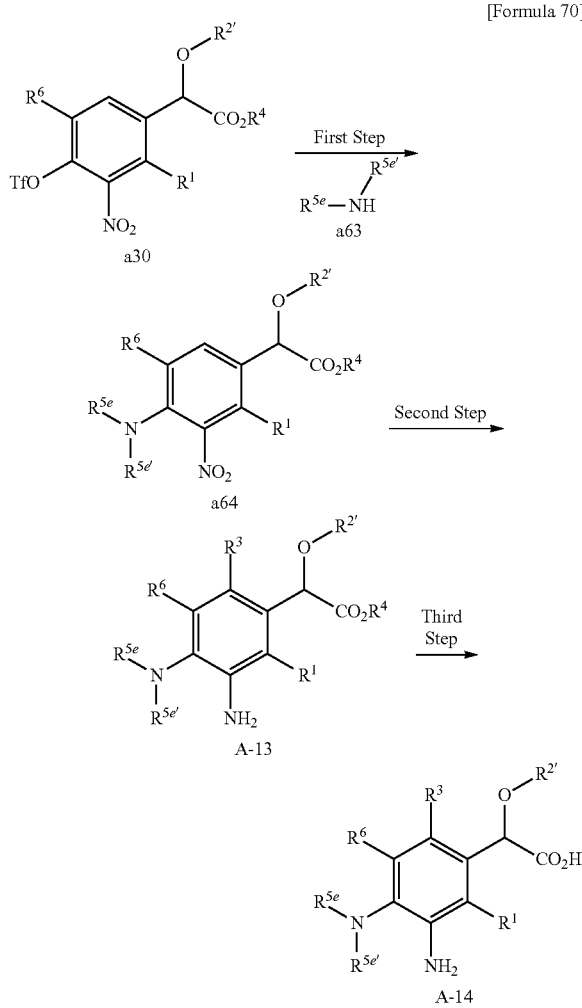

[Formula 70]

wherein $R^1$, $R^{2'}$, $R^3$, $R^4$, and $R^6$ have the same meaning as described above, and $R^{5e}$ and $R^{5e'}$ are each independently a hydrogen atom, formyl, carbamoyl, carboxy, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkylcarbamoyl, substituted or unsubstituted alkenylcarbamoyl, substituted or unsubstituted alkynylcarbamoyl, substituted or unsubstituted alkyloxycarbonyl, substituted or unsubstituted alkenyloxycarbonyl, substituted or unsubstituted alkynyloxycarbonyl, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclic carbonyl, substituted or unsubstituted nonaromatic carbocyclic carbonyl, substituted or unsubstituted aromatic heterocyclic carbonyl, substituted or unsubstituted nonaromatic heterocyclic carbonyl, substituted or unsubstituted aromatic carbocyclic carbamoyl, substituted or unsubstituted nonaromatic carbocyclic carbamoyl, substituted or unsubstituted aromatic heterocyclic carbamoyl, substituted or unsubstituted nonaromatic heterocyclic carbamoyl, substituted or unsubstituted aromatic carbocyclic oxycarbonyl, substituted or unsubstituted nonaromatic carbocyclic oxycarbonyl, substituted or unsubstituted aromatic heterocyclic oxycarbonyl, or substituted or unsubstituted nonaromatic heterocyclic oxycarbonyl, wherein $R^{5e}$ and $R^{5e'}$ may be taken together with an adjacent nitrogen atom to form a substituted or unsubstituted aromatic heterocyclic group or a substituted or unsubstituted nonaromatic heterocyclic group.

First Step

In a solvent such as dimethylformamide, dimethylacetamide, tetrahydrofuran or dioxane, or in a mixed solvent thereof, a base such as sodium carbonate, potassium carbonate, cesium carbonate or potassium phosphate, a substituted amine a63 that is commercially available or prepared by a known method, a palladium catalyst such as $Pd(PPh_3)_4$, $Pd(OAc)_2$, $Pd(PPh_3)_2Cl_2$, $Pd(dppf)_2Cl_2$ or tris(dibenzylideneacetone)dipalladium, and a ligand such as 2,2'-bis(diphenylphosphino)-1,1'-binaphthyl or Xantphos are added to compound a30, and the mixture is reacted at 50° C. to 180° C., and preferably at 70° C. to 150° C., for 0.1 hours to 8 hours, and preferably 0.5 to 2 hours, whereby compound a64 can be obtained.

Second Step

From compound a64, compound A-13 can be obtained in the same manner as in the thirty second to thirty fourth steps in "1) Synthesis of Compounds A-1 and A-2" described above.

Third Step

From compound A-13, compound A-14 can be obtained in the same manner as in the fifteenth step in "1) Synthesis of Compounds A-1 and A-2" described above.

8) Synthesis of Compounds A-15 and A-16

[Formula 71]

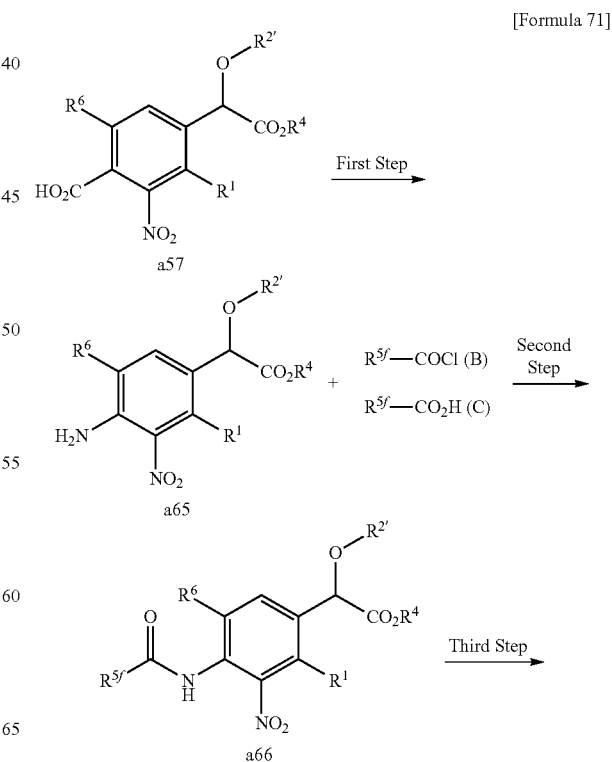

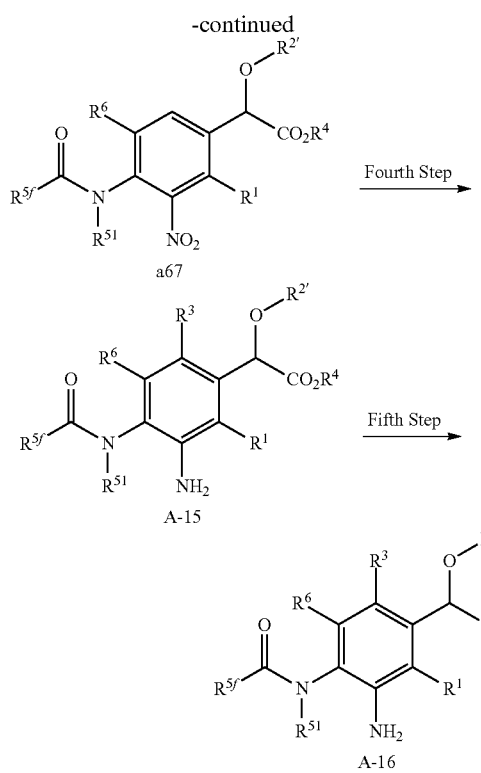

a67

A-15

A-16 wherein $R^1$, $R^{2'}$, $R^3$, $R^4$, $R^{51}$, and $R^6$ have the same meaning as described above, and $R^{5f}$ is substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group.

First Step

In DMF, toluene, benzene or the like, or a mixed solvent of those and water, diphenylphosphoryl azide and a base such as triethylamine, diisopropylethylamine or N-methylmorpholine are added to compound a57, and the mixture is reacted at 20° C. to 100° C., and preferably at 50° C. to 80° C., for 1 hour to 24 hours, and preferably 2 hours to 6 hours, and thereafter potassium hydroxide, sodium hydroxide, lithium hydroxide or the like is added, and the mixture is reacted at 0° C. to 100° C., and preferably at 20° C. to 50° C., for 1 hour to 24 hours, and preferably 2 hours to 6 hours, whereby compound a65 can be obtained.

Second Step

In a solvent such as dichloromethane, dichloroethane or THF, pyridine, triethylamine or N-methylmorpholine is added to compound a65 as a base, and then an acylating reagent such as an acid chloride or acid anhydride that is commercially available or synthesized by a known method is sequentially added, and the mixture is reacted at −20° C. to 50° C., and preferably at 0° C. to 20° C., for 0.1 hours to 6 hours, and preferably 1 hour to 3 hours, whereby compound a66 can be obtained.

Third Step

In a solvent such as THF, dimethylformamide or dimethylacetamide, a base such as sodium hydride, tert-butoxypotassium or lithium diisopropylamide, and then $R^{51}$—I, $R^{51}$—Br, $R^{51}$—Cl or the like that is commercially available or synthesized by a known method are added to compound a66, and the mixture is reacted at 0° C. to 50° C., and preferably at 20° C. to 35° C., for 0.1 hours to 3 hours, and preferably 0.5 hours to 1 hour, whereby compound a67 can be obtained.

Fourth Step

From compound a67, compound A-15 can be obtained in the same manner as in the thirty second to thirty fourth steps in "1) Synthesis of Compounds A-1 and A-2" described above.

Fifth Step

From compound A-15, compound A-16 can be obtained in the same manner as in the fifteenth step in "1) Synthesis of Compounds A-1 and A-2" described above.

9) Synthesis of Compounds A-17 and A-18

[Formula 72]

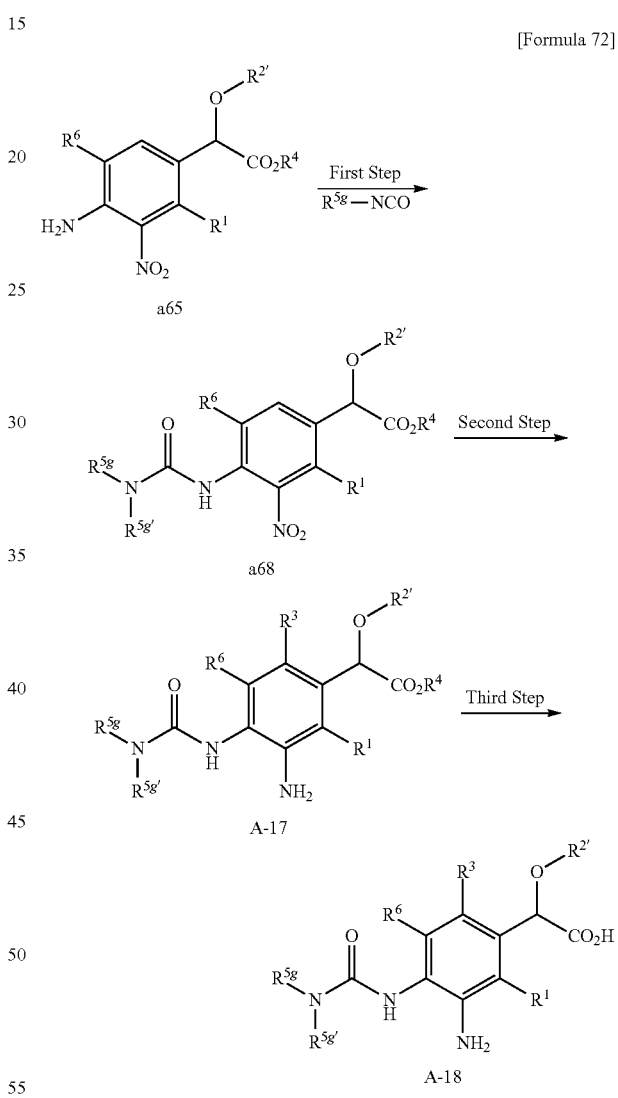

a65 a68

A-17

A-18 wherein $R^1$, $R^{2'}$, $R^3$, $R^4$, and $R^6$ have the same meaning as described above, $R^{5g}$ is substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, and $R^{5g'}$ is a hydrogen atom.

First Step

In a solvent such as toluene, acetonitrile or dichloroethane, $R^{5g}$—NCO that is commercially available or synthesized by a known method is added to compound a65, and the mixture is reacted at 25° C. to 120° C., and preferably at 60° C. to 80° C., for 0.5 hours to 4 hours, and preferably 1 hour to 2 hours, whereby compound a68 can be obtained.

In a solvent such as dichloromethane, THF or toluene, a base such as triethylamine or N-methylmorpholine is added to compound a65, and reacted with triphosgene, thereby synthesizing an isocyanate form in the system. $R^{5g}NH_2$ that is commercially available or synthesized by a known method is added without taking out the isocyanate form from the reaction mixture, and the mixture is reacted at 0° C. to 50° C., and preferably at 20° C. to 35° C., for 0.1 hours to 6 hours, and preferably 0.5 hours to 2 hours, whereby compound a68 can be obtained.

Second Step

From compound a68, compound A-17 can be obtained in the same manner as in the thirty second to thirty fourth steps in "1) Synthesis of Compounds A-1 and A-2" described above.

Third Step

From compound A-17, compound A-18 can be obtained in the same manner as in the fifteenth step in "1) Synthesis of Compounds A-1 and A-2" described above.

In addition, from compound a57, in the same manner as in the first step in "8) Synthesis of Compounds A-15 and A-16" described above, in DMF, toluene, benzene, or the like, or a mixed solvent of those and water, diphenylphosphoryl azide and a base such as triethylamine, diisopropylethylamine or N-methylmorpholine are added, and the mixture is reacted at 20° C. to 100° C., and preferably at 50° C. to 80° C., for 1 hour to 24 hours, and preferably 2 hours to 6 hours, and thereafter, $R^{5g}$—N—$R^{5g'}$ (wherein $R^{5g'}$ is substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group) is added, and the mixture is reacted at 0° C. to 100° C., and preferably at 20° C. to 50° C., for 1 hour to 24 hours, and preferably 2 hours to 6 hours, whereby compound a68 can be obtained.

10) Synthesis of Compounds A-19 and A-20

[Formula 73]

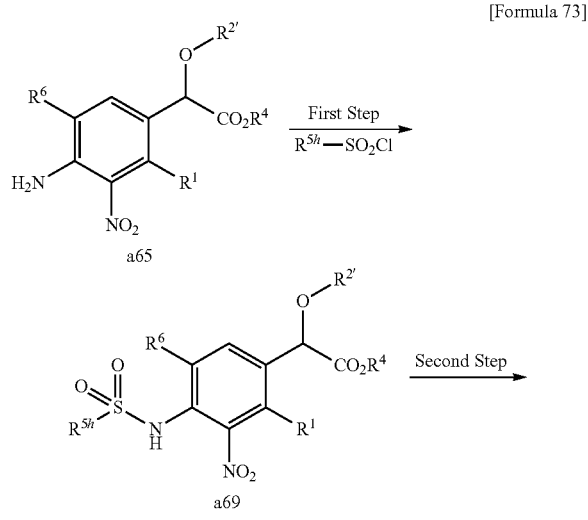

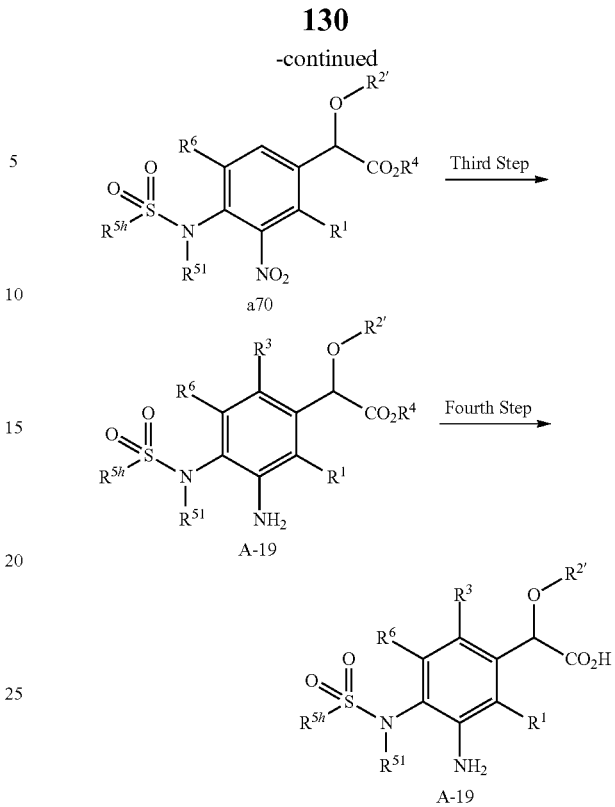

wherein $R^1$, $R^{2'}$, $R^3$, $R^4$, $R^{51}$, and $R^6$ have the same meaning as described above, and $R^{5h}$ is substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group.

First Step

In a solvent such as pyridine or lutidine, a substituted sulfonyl chloride that is commercially available or synthesized by a known method is added to compound a65, and the mixture is reacted at 20° C. to 100° C., and preferably at 50° C. to 70° C., for 1 hour to 24 hours, and preferably 5 hours to 10 hours, whereby compound a69 can be obtained.

Second Step

In a solvent such as dichloromethane, THF or dimethylformamide, a base such as sodium carbonate, potassium carbonate or cesium carbonate is added to compound a69, and then $R^{51}$—I, $R^{51}$—Br, $R^{51}$—Cl or the like that is commercially available or synthesized by a known method is added, and the mixture is reacted at 0° C. to 80° C., and preferably at 25° C. to 50° C., for 1 hour to 12 hours, and preferably 3 hours to 6 hours, whereby compound a70 can be obtained.

Third Step

From compound a70, compound A-19 can be obtained in the same manner as in the thirty second to thirty fourth steps in "1) Synthesis of Compounds A-1 and A-2" described above.

Fourth Step

From compound A-19, compound A-20 can be obtained in the same manner as in the fifteenth step in "1) Synthesis of Compounds A-1 and A-2" described above.

11) Synthesis of Compounds A-21 and A-22

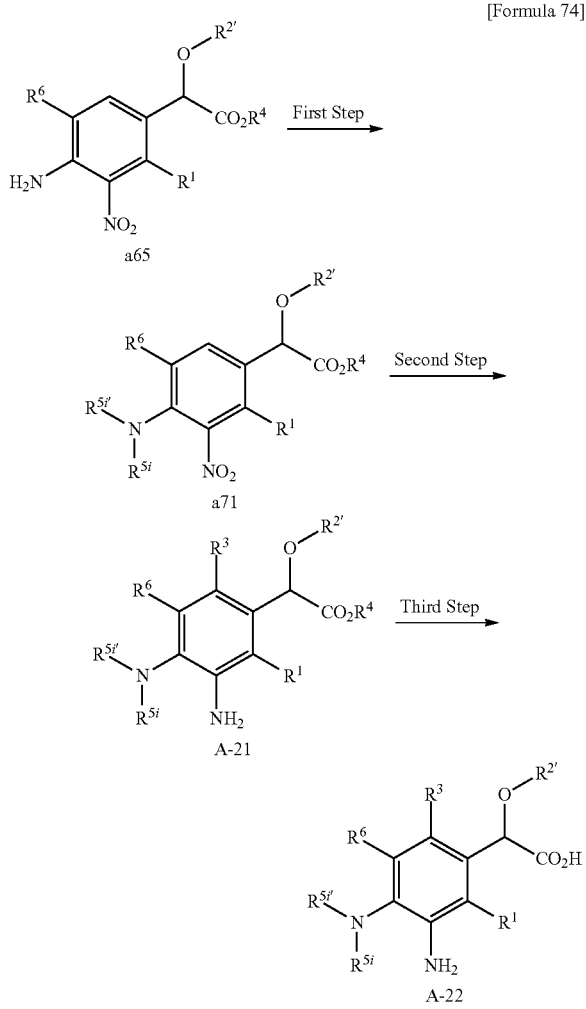

[Formula 74]

wherein $R^1$, $R^{2'}$, $R^3$, $R^4$, and $R^6$ have the same meaning as described above, and $R^{5i}$ and $R^{5i'}$ are each independently a hydrogen atom, formyl, carbamoyl, carboxy, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkylcarbamoyl, substituted or unsubstituted alkenylcarbamoyl, substituted or unsubstituted alkynylcarbamoyl, substituted or unsubstituted alkyloxycarbonyl, substituted or unsubstituted alkenyloxycarbonyl, substituted or unsubstituted alkynyloxycarbonyl, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclic carbonyl, substituted or unsubstituted nonaromatic carbocyclic carbonyl, substituted or unsubstituted aromatic heterocyclic carbonyl, substituted or unsubstituted nonaromatic heterocyclic carbonyl, substituted or unsubstituted aromatic carbocyclic carbamoyl, substituted or unsubstituted nonaromatic carbocyclic carbamoyl, substituted or unsubstituted aromatic heterocyclic carbamoyl, substituted or unsubstituted nonaromatic heterocyclic carbamoyl, substituted or unsubstituted aromatic carbocyclic oxycarbonyl, substituted or unsubstituted nonaromatic carbocyclic oxycarbonyl, substituted or unsubstituted aromatic heterocyclic oxycarbonyl, or substituted or unsubstituted nonaromatic heterocyclic oxycarbonyl, wherein $R^{5i}$ and $R^{5i'}$ may be taken together with an adjacent nitrogen atom to form a substituted or unsubstituted aromatic heterocyclic group or a substituted or unsubstituted nonaromatic heterocyclic group.

First Step

In a solvent such as dichloromethane, THF or dimethylformamide, an acid such as acetic acid or trifluoroacetic acid is added to compound a65, and an aldehyde or ketone that is commercially available or synthesized by a known method is sequentially added, and the mixture is stirred at 0° C. to 100° C., and preferably at 25° C. to 60° C., for 0.5 hours to 24 hours, and preferably 3 hours to 12 hours, and thereafter, a reducing agent such as $NaBH_4$, $NaBH_3CN$ or $NaBH(OAc)_3$ is added, and the mixture is reacted at 0° C. to 100° C., and preferably at 25° C. to 60° C., for 0.5 hours to 24 hours, and preferably 3 hours to 12 hours, whereby compound a71 can be obtained.

Second Step

From compound a71, compound A-21 can be obtained in the same manner as in the thirty second to thirty fourth steps in "1) Synthesis of Compounds A-1 and A-2" described above.

Third Step

From compound A-21, compound A-22 can be obtained in the same manner as in the fifteenth step in "1) Synthesis of Compounds A-1 and A-2" described above.

12) Synthesis of Compounds A-23 and A-24

[Formula 75]

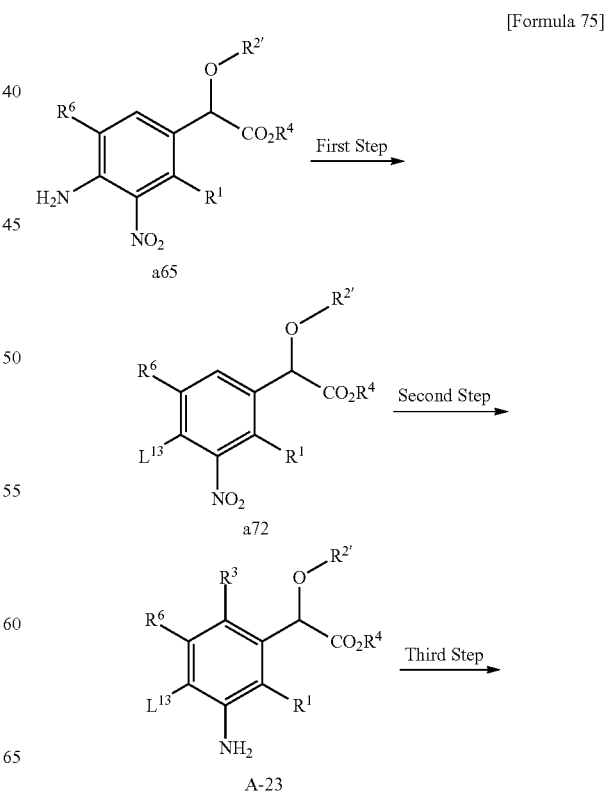

-continued

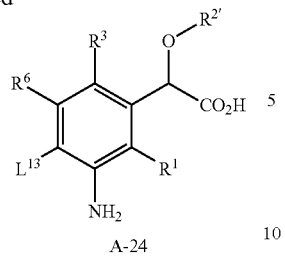

A-24 wherein $R^1$, $R^{2'}$, $R^3$, $R^4$, and $R^6$ have the same meaning as described above, and $L^{13}$ is halogen.

First Step

In a solvent such as acetonitrile, tetrahydrofuran or dimethylformamide, a diazotization reagent such as tert-butyl nitrite or isopentyl nitrite is added to compound a65, and then a cupric halide such as cupric chloride, cupric bromide or cupric iodide is sequentially added, and the mixture is reacted at 0° C. to 80° C., and preferably at 20° C. to 50° C., for 0.1 hours to 6 hours, and preferably 0.5 hours to 3 hours, whereby compound a72 can be obtained as a chloride, a bromide or an iodide, respectively.

Second Step

From compound a72, compound A-23 can be obtained in the same manner as in the thirty second to thirty fourth steps in "1) Synthesis of Compounds A-1 and A-2" described above.

Third Step

From compound A-23, compound A-24 can be obtained in the same manner as in the fifteenth step in "1) Synthesis of Compounds A-1 and A-2" described above.

13) Synthesis of Compounds A-25 and A-26

-continued

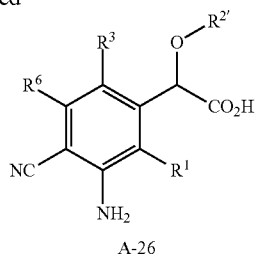

A-26 wherein each definition has the same meaning as described above.

First Step

In a solvent such as acetonitrile, dimethylformamide or dimethylsulfoxide, a diazotization reagent such as tert-butyl nitrite or isopentyl nitrite is added to compound a65, and then a cyanide such as cuprous cyanide, sodium cyanide or potassium cyanide is added, and the mixture is reacted at 0° C. to 100° C., and preferably at 40° C. to 70° C., for 1 hour to 12 hours, and preferably 3 hours to 6 hours, whereby compound a73 can be obtained.

Second Step

From compound a73, compound A-25 can be obtained in the same manner as in the thirty second to thirty fourth steps in "1) Synthesis of Compounds A-1 and A-2" described above.

Third Step

From compound A-25, compound A-26 can be obtained in the same manner as in the fifteenth step in "1) Synthesis of Compounds A-1 and A-2" described above.

14) Synthesis of Compounds A-27 and A-28

[Formula 76]

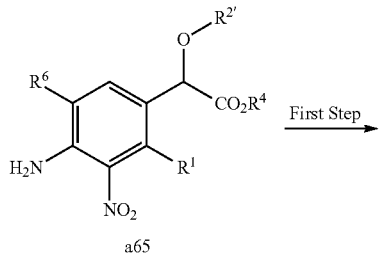

a65

First Step →

[Formula 77]

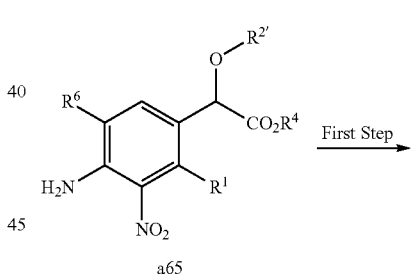

a65

First Step →

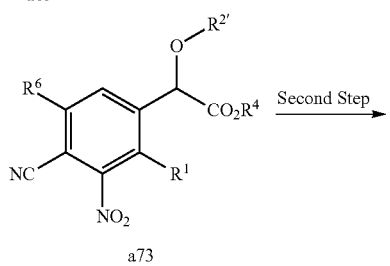

a73

Second Step →

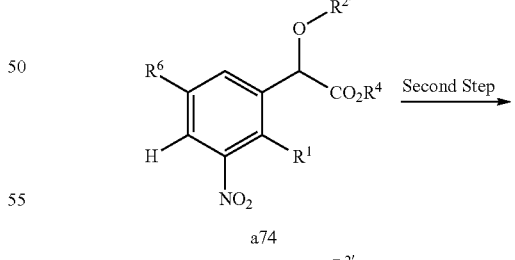

a74

Second Step →

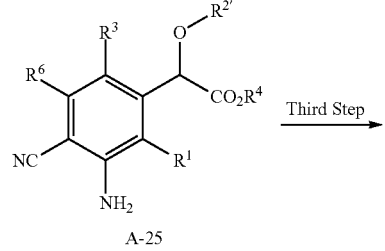

A-25

Third Step →

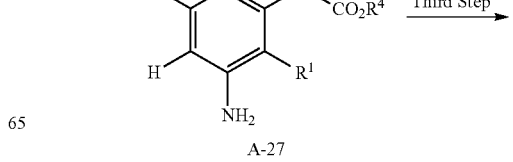

A-27

Third Step →

-continued

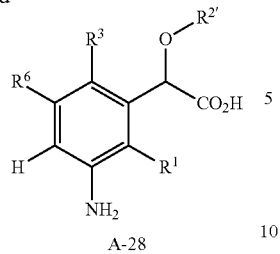

A-28 wherein each definition has the same meaning as described above.

First Step

In a solvent such as tetrahydrofuran, acetonitrile or dimethylformamide, a diazotization reagent such as tert-butyl nitrite or isopentyl nitrite is added to compound a65, and the mixture is reacted at 20° C. to 100° C., and preferably at 50° C. to 70° C., for 0.1 hours to 6 hours, and preferably 1 hour to 3 hours, whereby compound a74 can be obtained as a deamination product.

Second Step

From compound a74, compound A-27 can be obtained in the same manner as in the thirty second to thirty fourth steps in "1) Synthesis of Compounds A-1 and A-2" described above.

Third Step

From compound A-27, compound A-28 can be obtained in the same manner as in the fifteenth step in "1) Synthesis of Compounds A-1 and A-2" described above.

15) Synthesis of Compounds A-29 and A-30

[Formula 78]

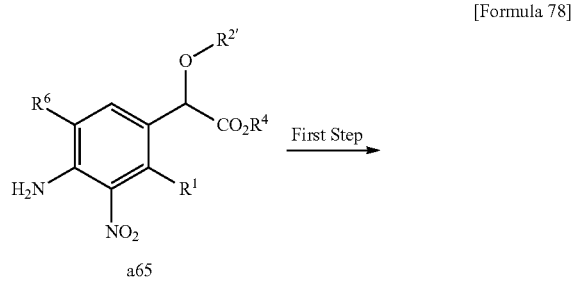

a65

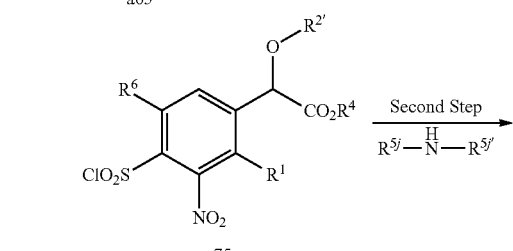

a75

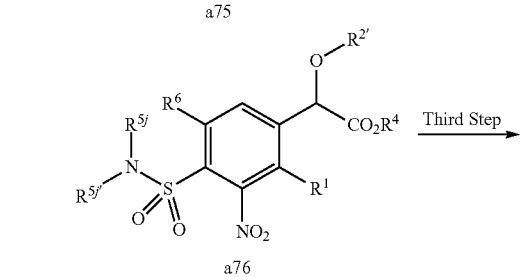

a76

-continued

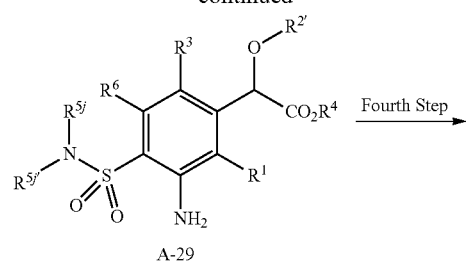

A-29

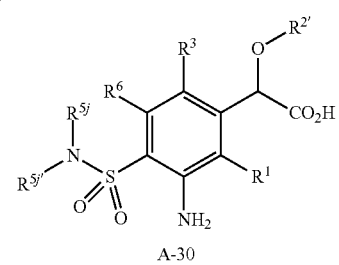

A-30 wherein $R^1$, $R^{2'}$, $R^3$, $R^4$, and $R^6$ have the same meaning as described above, and $R^{5j}$ and $R^{5j'}$ are each independently substituted or unsubstituted alkyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, wherein $R^{5j}$ and $R^{5j'}$ may be taken together with an adjacent nitrogen atom to form a substituted or unsubstituted aromatic heterocyclic group or a substituted or unsubstituted nonaromatic heterocyclic group.

First Step

Compound a65 is suspended in concentrated hydrochloric acid, and diazotized with sodium nitrite according to a known method, and then sulfurous acid and an acetic acid solution of cuprous chloride are added, and the mixture is reacted at −20° C. to 20° C., and preferably at −5° C. to 10° C., for 0.1 hours to 6 hours, and preferably 0.5 hours to 3 hours, whereby compound a75 can be obtained.

Also, compound a75 can be obtained as well by using thionyl chloride, instead of sulfurous acid and the acetic acid solution of cuprous chloride.

Second Step

In a solvent such as dichloromethane, toluene or tetrahydrofuran, a base such as triethylamine, N-methylmorpholine or pyridine is added to compound a75, and then an amine that is commercially available or synthesized by a known method is sequentially added, and the mixture is reacted at 0° C. to 100° C., and preferably at 25° C. to 60° C., for 0.5 hours to 24 hours, and preferably 2 hours to 12 hours, whereby compound a76 can be obtained.

Third Step

From compound a76, compound A-29 can be obtained in the same manner as in the thirty second to thirty fourth steps in "1) Synthesis of Compounds A-1 and A-2" described above.

Fourth Step

From compound A-29, compound A-30 can be obtained in the same manner as in the fifteenth step in "1) Synthesis of Compounds A-1 and A-2" described above.

137

16) Synthesis of Compounds A-31 and A-32

[Formula 79]

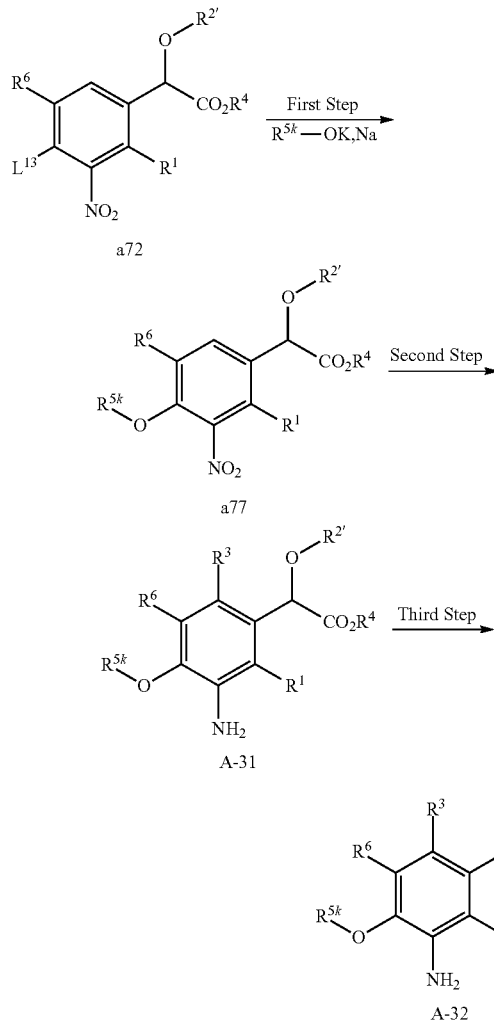

wherein $R^1$, $R^{2'}$, $R^3$, $R^4$, $R^6$, and $L^{13}$ have the same meaning as described above, and $R^{5k}$ is substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group.

First Step

In DMF, DMA, THF, dioxane, or the like, or a mixed solvent thereof, $R^{5k}$—OK or $R^{5k}$—ONa that is commercially available or prepared by a known method is added to compound a72, and the mixture is reacted at 20° C. to 200° C., and preferably at 50° C. to 100° C., for 1 hour to 48 hours, and preferably 2 hours to 24 hours, whereby compound a77 can be obtained.

Second Step

From compound a77, compound A-31 can be obtained in the same manner as in the thirty second to thirty fourth steps in "1) Synthesis of Compounds A-1 and A-2" described above.

138

Third Step

From compound A-31, compound A-32 can be obtained in the same manner as in the fifteenth step in "1) Synthesis of Compounds A-1 and A-2" described above.

17) Synthesis of Compounds A-33 and A-34

[Formula 80]

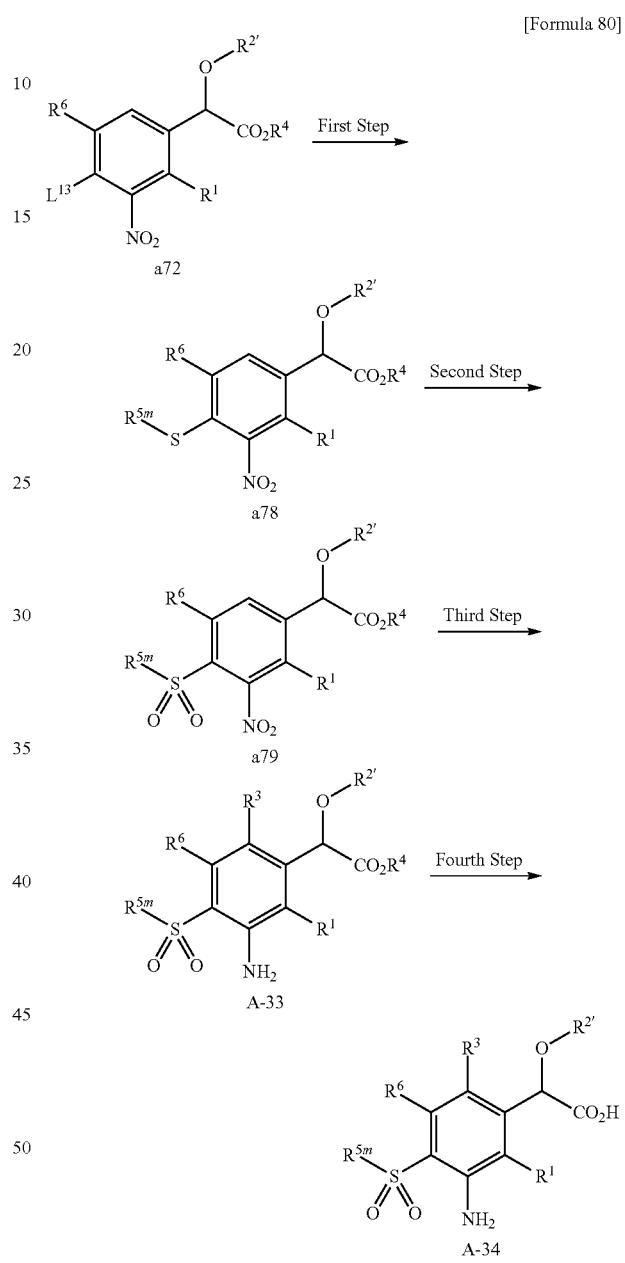

wherein $R^1$, $R^{2'}$, $R^3$, $R^4$, $R^6$, and $L^{13}$ have the same meaning as described above, and $R^{5m}$ is a substituted or unsubstituted aromatic carbocyclic group.

First Step

In a solvent such as dichloromethane, tetrahydrofuran or dimethylformamide, a base such as potassium carbonate, sodium carbonate or cesium carbonate is added to compound a72, and then $R^{5m}$SH that is commercially available or synthesized by a known method is sequentially added, and the mixture is reacted at 0° C. to 100° C., and preferably at 25° C. to 60° C., for 0.1 hours to 12 hours, and preferably 0.5 hours to 3 hours, whereby compound a78 can be obtained.

Second Step

In a solvent such as dichloromethane or chloroform, mCPBA is added to compound a78, and the mixture is reacted at −20° C. to 50° C., and preferably at 0° C. to 25° C., for 0.1 hours to 3 hours, and preferably 0.5 hours to 2 hours, whereby compound a79 can be obtained.

Also, compound a79 can be obtained by adding oxone to compound a78 in a mixed solvent of a solvent such as acetone or tetrahydrofuran and water, and reacting the mixture at 0° C. to 100° C., and preferably at 25° C. to 60° C., for 0.5 hours to 24 hours, and preferably 3 hours to 12 hours.

Third Step

From compound a79, compound A-33 can be obtained in the same manner as in the thirty second to thirty fourth steps in "1) Synthesis of Compounds A-1 and A-2" described above.

Fourth Step

From compound A-33, compound A-34 can be obtained in the same manner as in the fifteenth step in "1) Synthesis of Compounds A-1 and A-2" described above.

18) Synthesis of Compounds B-1, B-2, B-3, and B-4 (Amide Derivatives)

[Formula 81]

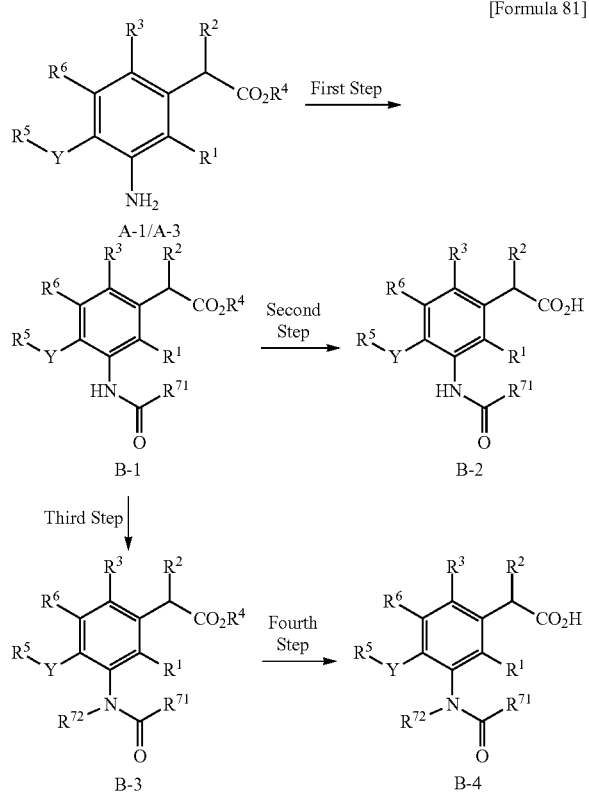

wherein each definition has the same meaning as described above. However, in compound A-1, $R^2$ is $OR^{2'}$, and $R^{2'}$ has the same meaning as described above.

First Step

In a solvent such as dichloromethane, dichloroethane or THF, pyridine, triethylamine or N-methylmorpholine is added to compound A-1 or compound A-3 as a base, and then an acylating reagent such as an acid chloride or acid anhydride that is commercially available or synthesized by a known method is sequentially added, and the mixture is reacted at −20° C. to 50° C., and preferably at 0° C. to 20° C., for 0.1 hours to 6 hours, and preferably 1 hour to 3 hours, whereby compound B-1 can be obtained.

Second Step

From compound B-1, compound B-2 can be obtained in the same manner as in the fifteenth step in "1) Synthesis of Compounds A-1 and A-2" described above.

Third Step

In a solvent such as THF, dimethylformamide or dimethylacetamide, a base such as sodium hydride, tert-butoxypotassium or lithium diisopropylamide, and then $R^{72}$—I, $R^{72}$—Br, $R^{72}$—Cl or the like that is commercially available or synthesized by a known method are added to compound B-1, and the mixture is reacted at 0° C. to 50° C., and preferably at 20° C. to 35° C., for 0.1 hours to 3 hours, and preferably 0.5 hours to 1 hour, whereby compound B-3 can be obtained.

Fourth Step

From compound B-3, compound B-4 can be obtained in the same manner as in the fifteenth step in "1) Synthesis of Compounds A-1 and A-2" described above.

It is also possible to synthesize compounds B-1 to B-4, by the method shown below.

[Formula 82]

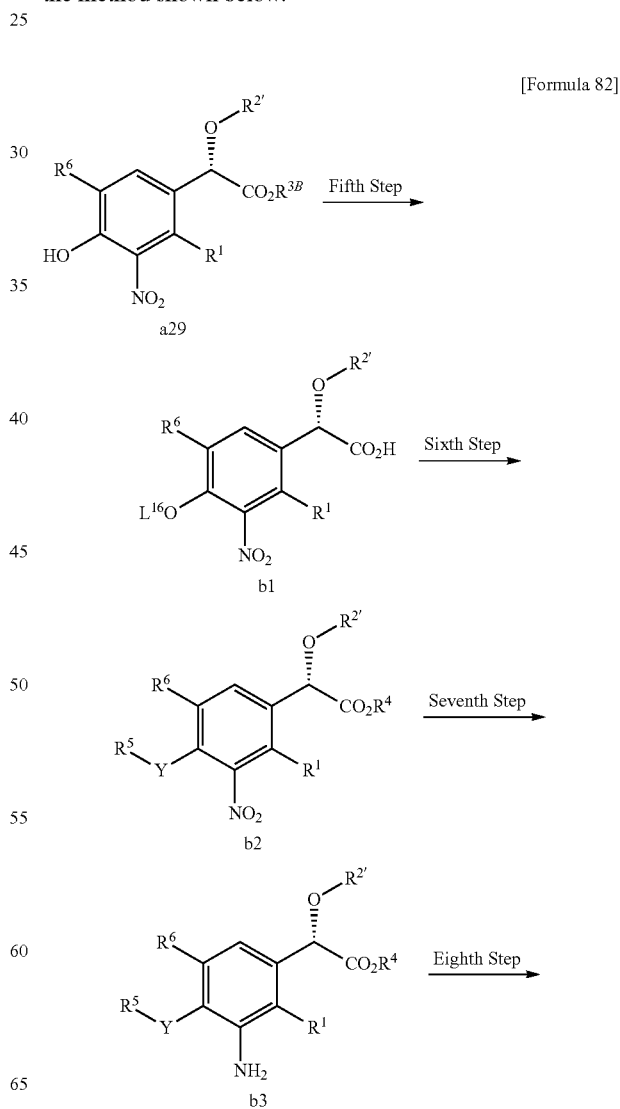

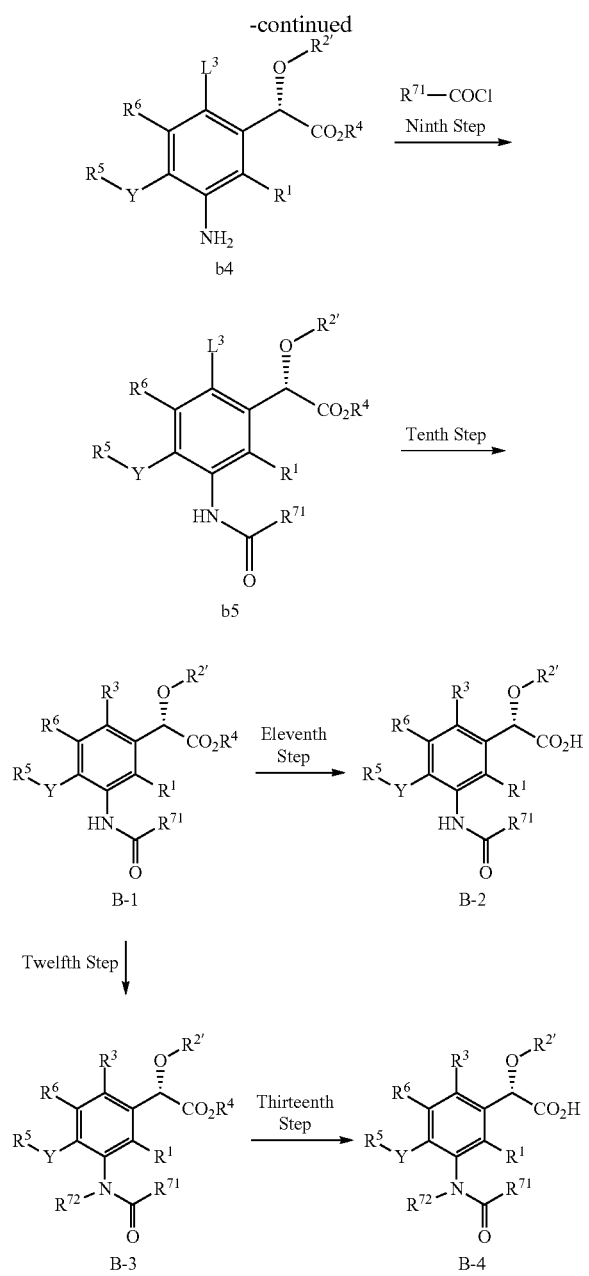

wherein $R^1$, $R^{2'}$, $R^3$, $R^4$, $R^5$, $R^6$, $R^{71}$, $R^{72}$, $L^2$ and $L^3$ have the same meaning as described above, and $L^{16}$ is substituted or unsubstituted alkylsulfonyl.

Fifth Step

In a solvent such as dichloromethane, dichloroethane or tetrahydrofuran, or in a mixed solvent thereof, a base such as pyridine, lutidine or triethylamine, and a trifluoromethanesulfonylating reagent such as trifluoromethanesulfonyl chloride, trifluoromethanesulfonic anhydride or N-phenylbistrifluoromethanesulfonimide or a nonaflating reagent such as nonafluorobutanesulfonyl chloride or nonafluorobutanesulfonic anhydride are added to compound a29, and the mixture is reacted at −50° C. to 50° C., and preferably at −30° C. to 30° C., for 0.1 hours to 4 hours, and preferably 0.5 hours to 1 hour, whereby compound b1 can be obtained.

Sixth Step

Compound b2 can be obtained by a coupling reaction of compound b1 with $R^5$—Y-$L^2$. As the reaction, Suzuki cross-coupling, Ullmann cross-coupling, Negishi cross-coupling, Stille coupling, and the like are exemplified.

In a solvent such as dioxane, DMF, DME, tetrahydrofuran or water, or a mixed solvent, a palladium catalyst such as $Pd(PPh_3)_4$, $Pd(OAc)_2$, $Pd(PPh_3)_2Cl_2$, $Pd(dppf)_2Cl_2$ or $Pd(dt\text{-}bpf)$, a base such as potassium carbonate, sodium carbonate, cesium carbonate or potassium phosphate, and boronic acid, a boronic acid ester, an alkyltin or a zinc halide that is commercially available or prepared by a known method are added to compound b1, and the mixture is reacted under a nitrogen atmosphere at 0° C. to 150° C., and preferably at 60° C. to 120° C., for 0.5 hours to 24 hours, and preferably 1 hour to 12 hours, whereby compound b2 can be obtained.

Seventh Step

In a solvent such as methanol, ethanol, ethyl acetate or tetrahydrofuran, a catalyst such as 5% or 10% palladium carbon, palladium hydroxide or platinum dioxide is added to compound b2, and the mixture is reacted under a hydrogen atmosphere and under 1 to 10 atmospheres, and preferably 2 to 5 atmospheres, at 0° C. to 60° C., and preferably at 20° C. to 40° C., for 0.1 hours to 24 hours, and preferably 1 hour to 12 hours, whereby compound b3 can be obtained.

In a mixed solvent of an organic solvent such as methanol, ethanol or tetrahydrofuran and water, a metal such as iron, zinc or tin is added to compound b2, under acidic conditions of hydrochloric acid or acetic acid, under alkaline conditions of potassium hydroxide or sodium hydroxide, or under neutral conditions of ammonium chloride, and the mixture is reacted at 0° C. to 120° C., and preferably at 25° C. to 80° C., for 0.1 hours to 24 hours, and preferably 1 hour to 12 hours, whereby compound b3 can be also obtained.

Eighth Step

In a solvent such as dichloromethane, dichloroethane, acetonitrile or DMF, bromine or a halogenating reagent such as NBS, NCS and NIS is added to compound b3, and when $L^3$ is bromo, the mixture is reacted at −30° C. to 50° C., and preferably at −10° C. to 20° C., for 0.1 hours to 10 hours, and preferably 0.5 hours to 2 hours, whereby compound b4 can be obtained. When $L^3$ is chloro or iodine, the mixture is reacted at 10° C. to 150° C., and preferably at 60° C. to 120° C., for 0.5 hours to 24 hours, and preferably 1 hour to 6 hours, whereby compound b4 can be obtained.

Ninth Step

From compound b4, compound b5 can be obtained in the same manner as in the first step.

Tenth Step

From compound b5, compound B-1 can be obtained in the same manner as in the sixth step.

Eleventh Step

From compound B-1, compound B-2 can be obtained in the same manner as in the fifteenth step in "1) Synthesis of Compounds A-1 and A-2" described above.

Twelfth Step

From compound B-1, compound B-3 can be obtained in the same manner as in the third step.

Thirteenth Step

From compound B-3, compound B-4 can be obtained in the same manner as in the fifteenth step in "1) Synthesis of Compounds A-1 and A-2" described above.

Furthermore, it is also possible to synthesize compound B-1 in which $R^5$ is a hydrogen atom and Y is a single bond, by the method shown below.

[Formula 83]

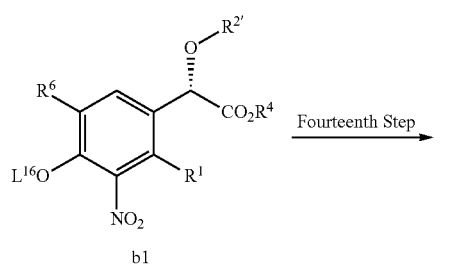

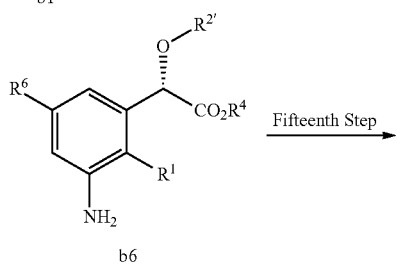

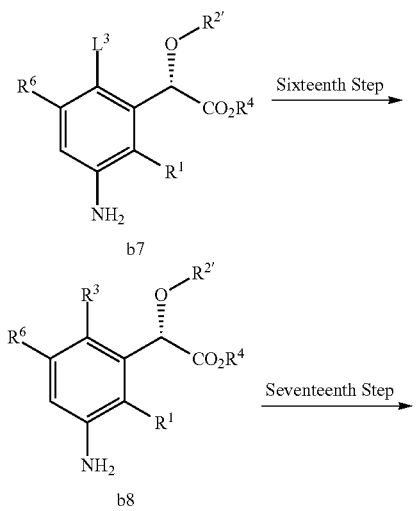

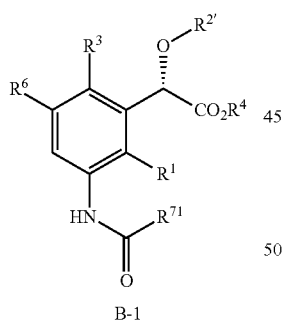

wherein each definition has the same meaning as described above.

Fourteenth Step

In a solvent such as methanol, ethanol, ethyl acetate or tetrahydrofuran, a base such as triethylamine, N-methylmorpholine or DIEA and a catalyst such as 5% or 10% palladium carbon, palladium hydroxide or platinum dioxide are added to compound b1, and the mixture is reacted under a hydrogen atmosphere and under 1 to 10 atmospheres, and preferably 2 to 5 atmospheres, at 0° C. to 60° C., and preferably at 20° C. to 40° C., for 0.1 hours to 24 hours, and preferably 1 hour to 12 hours, whereby compound b6 can be obtained.

Also, compound b6 can be also obtained by adding formic acid, a base such as triethylamine or tributylamine, a ligand such as triphenylphosphine, dppf or dppp, and a palladium catalyst such as $Pd(OAc)_2$, $Pd(PPh_3)_4$ or bistriphenylphosphine palladium dichloride to compound b1, in a solvent such as toluene, DMF or dioxane, and reacting the mixture at 20° C. to 200° C., and preferably at 60° C. to 120° C., for 0.1 hours to 24 hours, and preferably 1 hour to 12 hours.

Fifteenth Step

From compound b6, compound b7 can be obtained in the same manner as in the eighth step.

Sixteenth Step

From compound b7, compound b8 can be obtained in the same manner as in the sixth step.

Seventeenth Step

From compound b8, compound B-1 can be obtained in the same manner as in the ninth step.

Compound B-1 in which $R^1$ and $R^6$ are methyl, and $R^5$ is —O—$R^{5k}$ ($R^{5k}$ has the same meaning as described above) can be synthesized by the method described below.

[Formula 84]

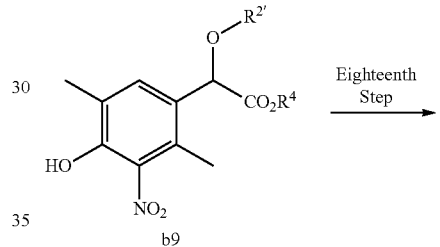

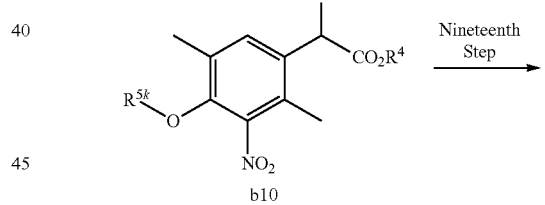

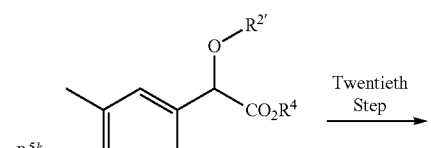

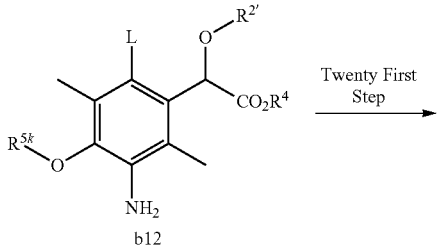

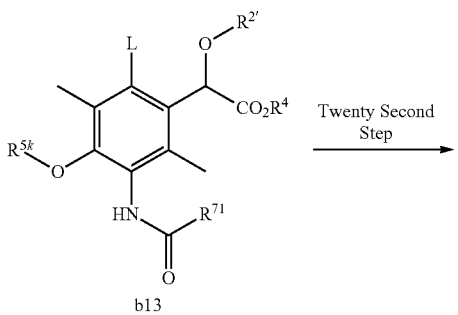

b13

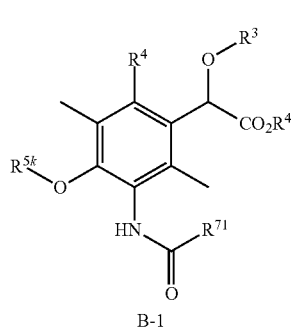

B-1 wherein each definition has the same meaning as described above.

Eighteenth Step

From compound b9, compound b10 can be obtained in the same manner as in the fifth step in "27) Synthesis of Compounds K-1 and K-2 (Phenol Derivatives)" described below.

Nineteenth Step

From compound b10, compound b11 can be obtained in the same manner as in the twelfth step in "1) Synthesis of Compounds A-1 and A-2" described above.

Twentieth Step

From compound b11, compound b12 can be obtained in the same manner as in the thirteenth step in "1) Synthesis of Compounds A-1 and A-2" described above.

Twenty First Step

From compound b12, compound b13 can be obtained in the same manner as in the first step.

Twenty Second Step

From compound b13, compound B-1 can be obtained in the same manner as in the fourth step in "1) Synthesis of Compounds A-1 and A-2" described above.

19) Synthesis of Compounds C-1 and C-2 (Urea Derivatives)

[Formula 85]

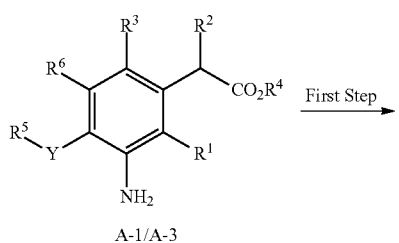

A-1/A-3

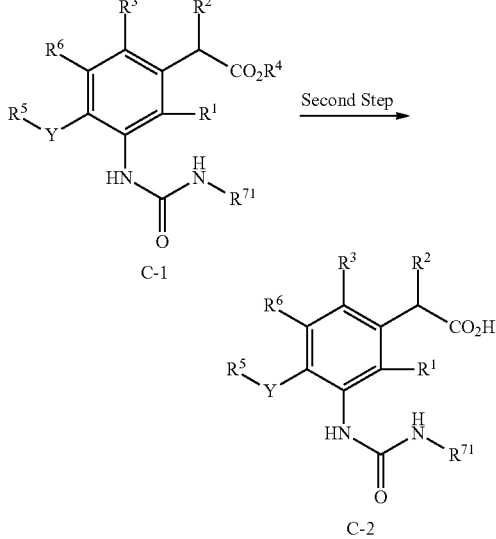

C-1

C-2 wherein each definition has the same meaning as described above. However, in compound A-1, $R^2$ is $OR^{2'}$, and $R^{2'}$ has the same meaning as described above.

First Step

In a solvent such as toluene, acetonitrile or dichloroethane, $R^{71}$—NCO that is commercially available or synthesized by a known method is added to compound A-1 or compound A-3, and the mixture is reacted at 25° C. to 120° C., and preferably at 60° C. to 80° C., for 0.5 hours to 4 hours, and preferably 1 hour to 2 hours, whereby compound C-1 can be obtained.

In a solvent such as dichloromethane, THF or toluene, a base such as triethylamine or N-methylmorpholine is added to compound A-1 or compound A-3, and reacted with triphosgene, thereby synthesizing an isocyanate form in the system. $R^{71}NH_2$ that is commercially available or synthesized by a known method is added without taking out the isocyanate form from the reaction mixture, and the mixture is reacted at 0° C. to 50° C., and preferably at 20° C. to 35° C., for 0.1 hours to 6 hours, and preferably 0.5 hours to 2 hours, whereby compound C-1 can be obtained.

Second Step

From compound C-1, compound C-2 can be obtained in the same manner as in the fifteenth step in "1) Synthesis of Compounds A-1 and A-2" described above.

A N—$R^{72}$-substituted urea derivative can be synthesized by using compound E-1 ($R^{71}$=H) described below, instead of compound A-1 and compound A-3.

Also, compound C-1 and compound C-2 can be obtained from compound b1, in the same manner as in the sixth to eleventh steps in "18) Synthesis of Compounds B-1, B-2, B-3, and B-4 (Amide Derivatives)" described above (however, among the above steps, the ninth step in "18) Synthesis of Compounds B-1, B-2, B-3, and B-4 (Amide Derivatives)" is replaced with the first step in "19) Synthesis of Compounds C-1 and C-2 (Urea Derivatives)").

Compound C-1 in which $R^1$ and $R^6$ are methyl, and $R^5$ is —O—$R^{5k}$ ($R^{5k}$ has the same meaning as described above) can be obtained from compound b9, in the same manner as in the eighteenth to twenty second steps in "18) Synthesis of Compounds B-1, B-2, B-3, and B-4 (Amide Derivatives)" described above (however, among the above steps, the twenty first step in "18) Synthesis of Compounds B-1, B-2, B-3, and B-4 (Amide Derivatives)" is replaced with the first step in "19) Synthesis of Compounds C-1 and C-2 (Urea Derivatives)").-

20) Synthesis of Compounds D-1, D-2, D-3, and D-4 (Sulfonamide Derivatives)

[Formula 86]

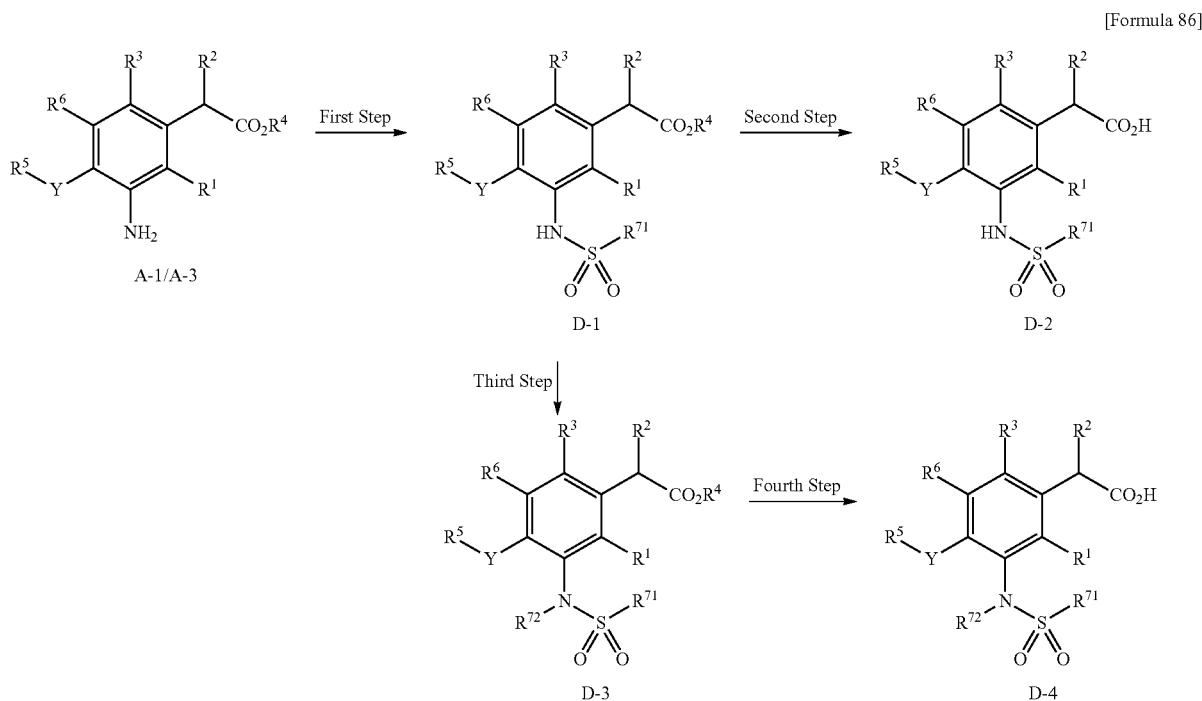

wherein each definition has the same meaning as described above. However, in compound A-1, $R^2$ is $OR^{2'}$, and $R^{2'}$ has the same meaning as described above.

First Step

In a solvent such as pyridine or lutidine, a substituted sulfonyl chloride that is commercially available or synthesized by a known method is added to compound A-1 or compound A-3, and the mixture is reacted at 20° C. to 100° C., and preferably at 50° C. to 70° C., for 1 hour to 24 hours, and preferably 5 hours to 10 hours, whereby compound D-1 can be obtained.

Second Step

From compound D-1, compound D-2 can be obtained in the same manner as in the fifteenth step in "1) Synthesis of Compounds A-1 and A-2" described above.

Third Step

In a solvent such as dichloromethane, THF or dimethylformamide, a base such as sodium carbonate, potassium carbonate or cesium carbonate is added to compound D-1, and then $R^{72}$—I, $R^{72}$—Br, $R^{72}$—Cl or the like that is commercially available or synthesized by a known method is added, and the mixture is reacted at 0° C. to 80° C., and preferably at 25° C. to 50° C., for 1 hour to 12 hours, and preferably 3 hours to 6 hours, whereby compound D-3 can be obtained.

Fourth Step

From compound D-3, compound D-4 can be obtained in the same manner as in the fifteenth step in "1) Synthesis of Compounds A-1 and A-2" described above.

Also, compounds D-1, D-2, D-3 and D-4 can be obtained from compound b1, in the same manner as in the sixth to thirteenth steps in "18) Synthesis of Compounds B-1, B-2, B-3, and B-4 (Amide Derivatives)" described above (however, among the above steps, the ninth step and the twelfth step in "18) Synthesis of Compounds B-1, B-2, B-3, and B-4 (Amide Derivatives)" are replaced with the first step and the third step, respectively, in "20) Compounds D-1, D-2, D-3 and D-4 (Sulfonamide Derivatives)").

Compound D-1 in which $R^1$ and $R^6$ are methyl, and $R^5$ is —O—$R^{5k}$ ($R^{5k}$ has the same meaning as described above) can be obtained from compound b9, in the same manner as in the eighteenth to twenty second steps in "18) Synthesis of Compounds B-1, B-2, B-3, and B-4 (Amide Derivatives)" described above (however, among the above steps, the twenty first step in "18) Synthesis of Compounds B-1, B-2, B-3, and B-4 (Amide Derivatives)" is replaced with the first step in "20) Compounds D-1, D-2, D-3 and D-4 (Sulfonamide Derivatives)").

21) Synthesis of Compounds E-1 and E-2 (Amine Derivatives)

[Formula 87]

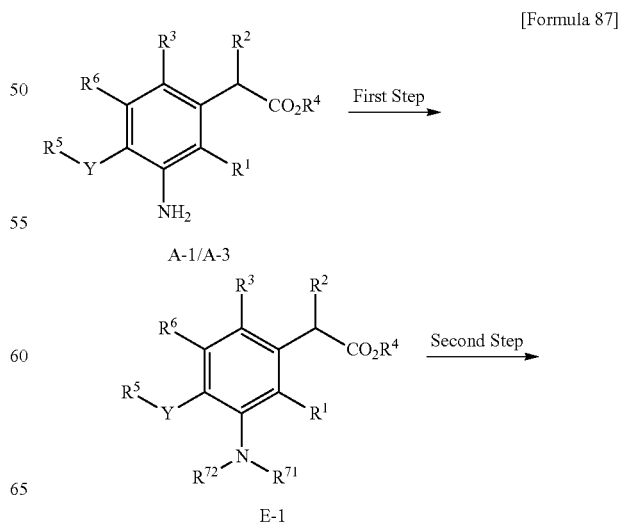

149

-continued

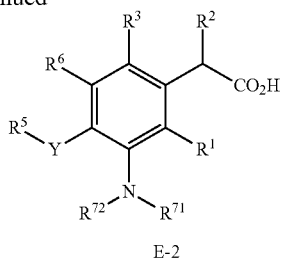

E-2 wherein each definition has the same meaning as described above. However, in compound A-1, $R^2$ is $OR^{2'}$, and $R^{2'}$ has the same meaning as described above.

First Step

In a solvent such as dichloromethane, THF or dimethylformamide, an acid such as acetic acid or trifluoroacetic acid is added to compound A-1 or compound A-3, and an aldehyde or ketone that is commercially available or synthesized by a known method is sequentially added, and the mixture is stirred at 0° C. to 100° C., and preferably at 25° C. to 60° C., for 0.5 hours to 24 hours, and preferably 3 hours to 12 hours, and thereafter, a reducing agent such as NaBH$_4$, NaBH$_3$CN or NaBH(OAc)$_3$ is added, and the mixture is reacted at 0° C. to 100° C., and preferably at 25° C. to 60° C., for 0.5 hours to 24 hours, and preferably 3 hours to 12 hours, whereby compound E-1 can be obtained.

Second Step

From compound E-1, compound E-2 can be obtained in the same manner as in the fifteenth step in "1) Synthesis of Compounds A-1 and A-2" described above.

22) Synthesis of Compounds F-1 and F-2 (Halogen Derivatives)

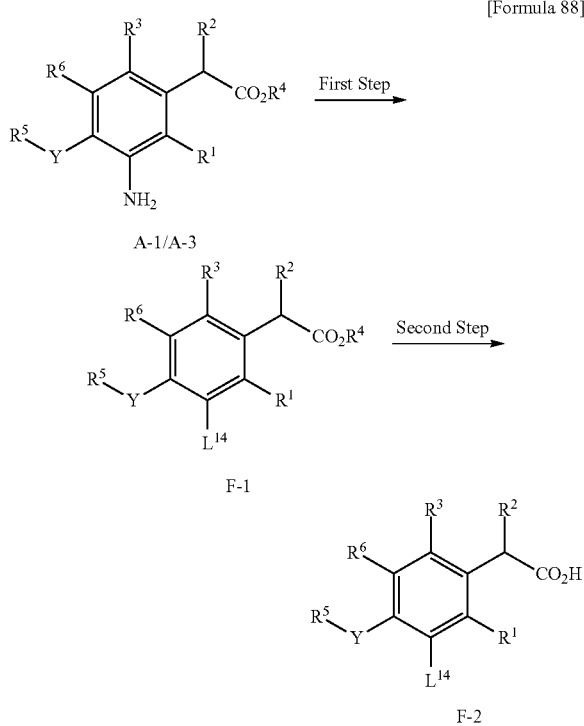

[Formula 88]

wherein $R^1$, $R^2$, $R^3$, $R^4$, $R^5$, $R^6$, and Y have the same meaning as described above, and $L^{14}$ is halogen. However, in compound A-1, $R^2$ is $OR^{2'}$, and $R^{2'}$ has the same meaning as described above.

First Step

In a solvent such as acetonitrile, tetrahydrofuran or dimethylformamide, a diazotization reagent such as tert-butyl nitrite or isopentyl nitrite is added to compound A-1 or compound A-3, and then a cupric halide such as cupric chloride, cupric bromide or cupric iodide is sequentially added, and the mixture is reacted at 0° C. to 80° C., and preferably at 20° C. to 50° C., for 0.1 hours to 6 hours, and preferably 0.5 hours to 3 hours, whereby compound F-1 can be obtained as a chloride, a bromide or an iodide, respectively.

Second Step

From compound F-1, compound F-2 can be obtained in the same manner as in the fifteenth step in "1) Synthesis of Compounds A-1 and A-2" described above.

23) Synthesis of Compounds G-1 and G-2 (Cyano Derivatives)

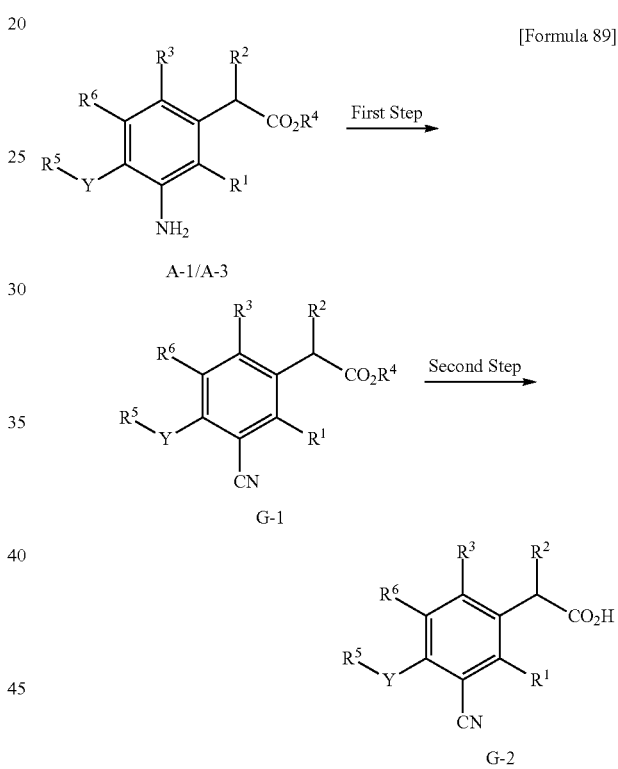

[Formula 89]

wherein each definition has the same meaning as described above. However, in compound A-1, $R^2$ is $OR^{2'}$, and $R^{2'}$ has the same meaning as described above.

First Step

In a solvent such as acetonitrile, dimethylformamide or dimethylsulfoxide, a diazotization reagent such as tert-butyl nitrite or isopentyl nitrite is added to compound A-1 or compound A-3, and then a cyanide such as cuprous cyanide, sodium cyanide or potassium cyanide is added, and the mixture is reacted at 0° C. to 100° C., and preferably at 40° C. to 70° C., for 1 hour to 12 hours, and preferably 3 hours to 6 hours, whereby compound G-1 can be obtained.

Second Step

From compound G-1, compound G-2 can be obtained in the same manner as in the fifteenth step in "1) Synthesis of Compounds A-1 and A-2" described above.

24) Synthesis of Compounds H-1 and H-2 (Hydrogenation Reductant)

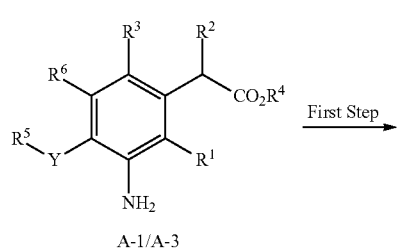

A-1/A-3

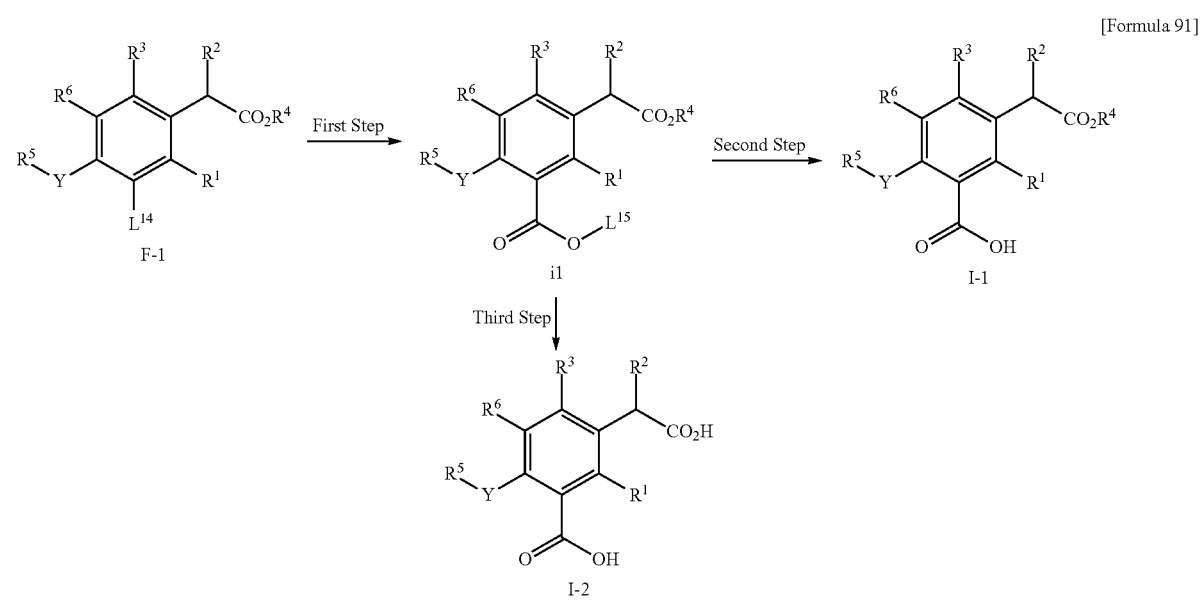

wherein each definition has the same meaning as described above. However, in compound A-1, $R^2$ is $OR^{2'}$, and $R^{2'}$ has the same meaning as described above.

First Step

In a solvent such as tetrahydrofuran, acetonitrile or dimethylformamide, a diazotization reagent such as tert-butyl nitrite or isopentyl nitrite is added to compound A-1 or compound A-3, and the mixture is reacted at 20° C. to 100° C., and preferably at 50° C. to 70° C., for 0.1 hours to 6 hours, and preferably 1 hour to 3 hours, whereby compound H-1 can be obtained as a deamination product.

Second Step

From compound H-1, compound H-2 can be obtained in the same manner as in the fifteenth step in "1) Synthesis of Compounds A-1 and A-2" described above.

25) Synthesis of Compounds I-1 and I-2 (Carboxy Derivatives)

wherein $R^1$, $R^2$, $R^3$, $R^4$, $R^5$, $R^6$, $L^{14}$, and Y have the same meaning as described above, and $L^{15}$ is alkyl or benzyl (however, L is benzyl in the second step)

First Step

In an alkyl alcohol such as methanol or ethanol or a benzyl alcohol, or a mixed solvent of these alcohols and dimethylformamide, dimethylsulfoxide or the like, a base such as triethylamine, N-methylmorpholine or pyridine is added to compound F-1, and then a palladium catalyst such as $Pd(PPh_3)_4$, $Pd(OAc)_2$ or $PdCl_2(dppf)$ is added, and the reaction mixture is well degassed, and reacted under a carbon monoxide atmosphere at 30° C. to 120° C., and preferably at 70° C. to 100° C., for 1 hour to 24 hours, and preferably 3 hours to 12 hours, whereby compound i1 can be obtained.

Second Step

In a solvent such as methanol, ethanol or tetrahydrofuran, a catalyst such as 5% or 10% palladium carbon, palladium hydroxide or platinum dioxide is added to compound i1 in which $L^{15}$ is benzyl, and the mixture is reacted under a hydrogen atmosphere at 0° C. to 60° C., and preferably at 20° C. to 40° C., for 0.1 hours to 24 hours, and preferably 1 hour to 12 hours, whereby compound I-1 can be obtained.

Third Step

From compound i1 compound I-2 can be obtained in the same manner as in the fifteenth step in "1) Synthesis of Compounds A-1 and A-2" described above.

26) Synthesis of Compounds J-1 and J-2 (Reverse Amide Derivatives)

[Formula 92]

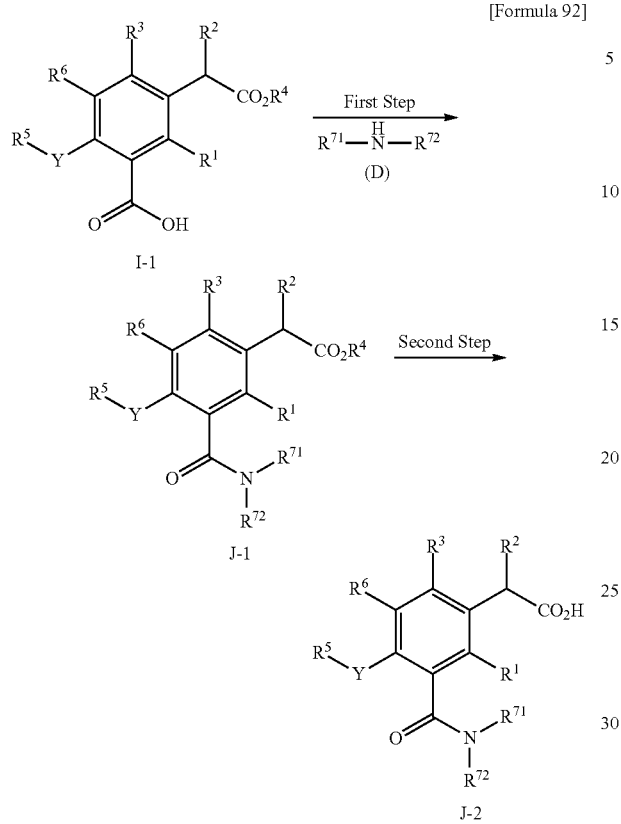

wherein each definition has the same meaning as described above. However, in compound A-1, $R^2$ is $OR^{2'}$, and $R^{2'}$ has the same meaning as described above.

First Step

In a solvent such as dichloromethane, tetrahydrofuran or dimethylformamide, a condensing agent such as 1-ethyl-3-(3-dimethylaminopropyl)carbodiimide, dicyclohexylcarbodiimide or O-(benzotriazol-1-yl)-N,N,N',N'-tetramethyluronium hexafluorophosphate is added to compound I-1, and an additive such as 1-hydroxy-7-azabenzotriazole, 1-hydroxybenzotriazole or N-hydroxysuccinimide is further added as necessary, and then a substituted amine (D) that is commercially available or prepared by a known method is sequentially added, and the mixture is reacted at 0° C. to 100° C., and preferably at 25° C. to 60° C., for 0.5 hours to 24 hours, and preferably 2 hours to 12 hours, whereby compound J-1 can be obtained.

Second Step

From compound J-1, compound J-2 can be obtained in the same manner as in the fifteenth step in "1) Synthesis of Compounds A-1 and A-2" described above.

27) Synthesis of Compounds K-1 and K-2 (Phenol Derivatives)

[Formula 93]

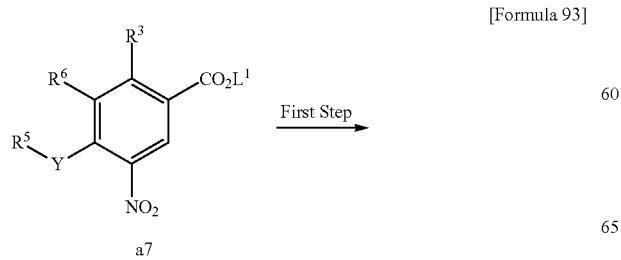

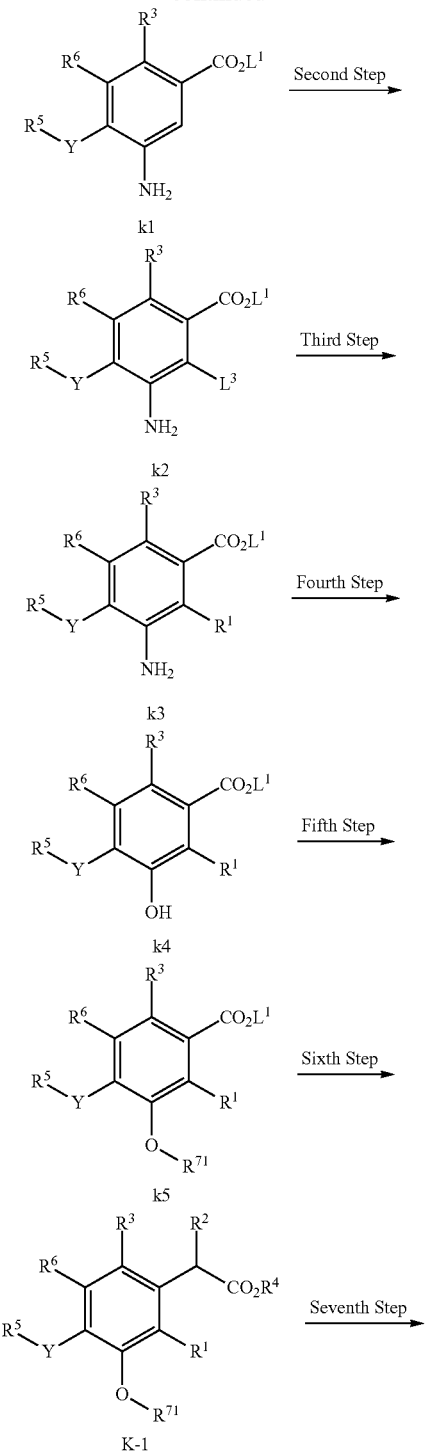

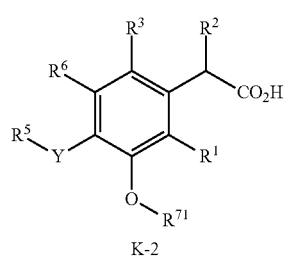

wherein each definition has the same meaning as described above.

First Step

From compound a7, compound k1 can be obtained in the same manner as in the twelfth step in "1) Synthesis of Compounds A-1 and A-2" described above.

Second Step

From compound k1, compound k2 can be obtained in the same manner as in the thirteenth step in "1) Synthesis of Compounds A-1 and A-2" described above.

Third Step

From compound k2, compound k3 can be obtained in the same manner as in the fourth step in "1) Synthesis of Compounds A-1 and A-2" described above.

Fourth Step

Compound k3 is diazotized with sodium nitrite in dilute sulfuric acid or the like according to a known method, and the mixture is reacted at 25° C. to 100° C., and preferably at 50° C. to 80° C., for 0.5 hours to 6 hours, and preferably 1 hour to 3 hours, whereby compound k4 can be obtained.

Fifth Step

In a solvent such as tetrahydrofuran, dimethylformamide or dimethylacetamide, a base such as potassium carbonate, sodium carbonate or sodium hydride is added to compound k4, and then $R^{71}$—Cl, $R^{71}$—Br, $R^{71}$—I or the like that is commercially available or synthesized by a known method is added, and the mixture is reacted at 0° C. to 100° C., and preferably at 25° C. to 60° C., for 0.5 hours to 24 hours, and preferably 1 hour to 12 hours, whereby compound k5 can be obtained.

Sixth Step i) When $R^2$ is $OR^{2'}$ ($R^{2'}$ has the same meaning as described above)

From compound k5, compound K-1 can be obtained in the same manner as in the seventh to tenth steps in "1) Synthesis of Compounds A-1 and A-2" described above.

ii) When $R^2$ is other

Compound k5 is reacted in the same manner as in the seventh step in "1) Synthesis of Compounds A-1 and A-2" described above, and then in the same manner as in the first to third steps in "2) Synthesis of Compounds A-3 and A-4" described above, whereby compound K-1 can be obtained.

Seventh Step

From compound K-1, compound K-2 can be obtained in the same manner as in the fifteenth step in "1) Synthesis of Compounds A-1 and A-2" described above.

28) Synthesis of Compounds L-1 and L-2 (Reverse Sulfonamide Derivatives)

[Formula 94]

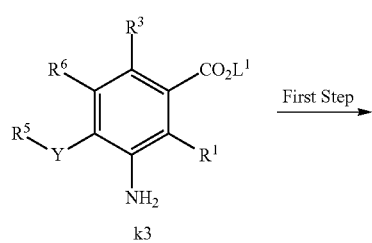

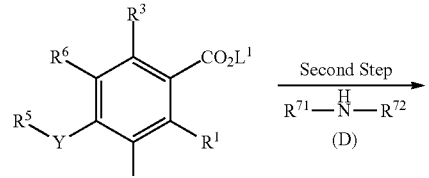

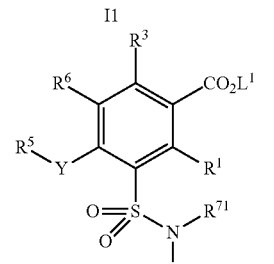

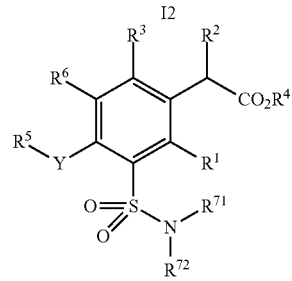

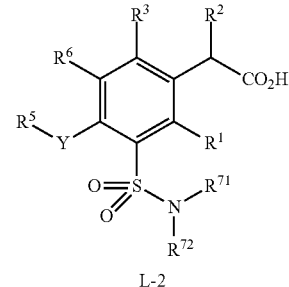

wherein each definition has the same meaning as described above.

First Step

Compound k3 is suspended in concentrated hydrochloric acid, and diazotized with sodium nitrite according to a known method, and then sulfurous acid and an acetic acid solution of cuprous chloride are added, and the mixture is reacted at −20° C. to 20° C., and preferably at −5° C. to 10° C., for 0.1 hours to 6 hours, and preferably 0.5 hours to 3 hours, whereby compound l1 can be obtained.

Also, compound l1 can be obtained as well by using thionyl chloride, instead of sulfurous acid and the acetic acid solution of cuprous chloride.

Second Step

In a solvent such as dichloromethane, toluene or tetrahydrofuran, a base such as triethylamine, N-methylmorpholine or pyridine is added to compound l1, and then amine (D) that is commercially available or synthesized by a known method is sequentially added, and the mixture is reacted at 0° C. to 100° C., and preferably at 25° C. to 60° C., for 0.5 hours to 24 hours, and preferably 2 hours to 12 hours, whereby compound l2 can be obtained.

Third Step i) When $R^2$ is $OR^{2'}$ ($R^{2'}$ has the same meaning as described above)

From compound l2, compound L-1 can be obtained in the same manner as in the seventh to tenth steps in "1) Synthesis of Compounds A-1 and A-2" described above.

ii) When $R^2$ is other

Compound l2 is reacted in the same manner as in the seventh step in "1) Synthesis of Compounds A-1 and A-2" described above, and then in the same manner as in the first to third steps in "2) Synthesis of Compounds A-3 and A-4" described above, whereby compound L-1 can be obtained.

Fourth Step

From compound L-1, compound L-2 can be obtained in the same manner as in the fifteenth step in "1) Synthesis of Compounds A-1 and A-2" described above.

29) Synthesis of Compounds M-1 and M-2 (Sulfonyl Derivatives)

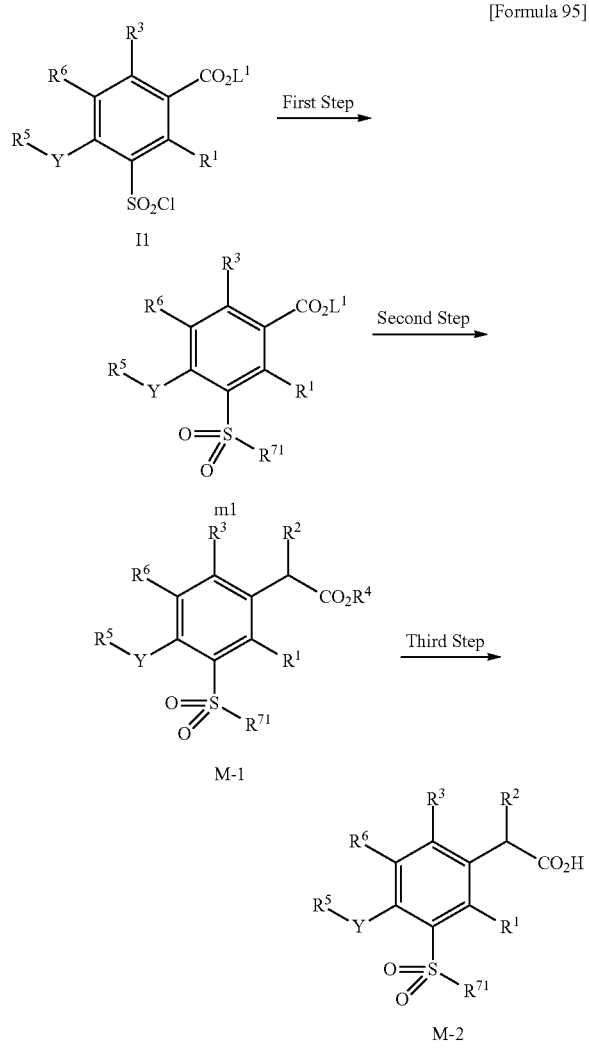

[Formula 95]

wherein each definition has the same meaning as described above.

First Step

In a mixed solvent of tetrahydrofuran, dioxane or acetone and water, sodium sulfite and sodium bicarbonate are added to compound l1, and the mixture is reacted at 25° C. to 100° C., and preferably at 50° C. to 80° C., for 0.1 hours to 6 hours, and preferably 1 hour to 3 hours, and cooled to room temperature. Next, $R^{71}$—Cl, $R^{71}$—Br, $R^{71}$—I or the like that is commercially available or synthesized by a known method is added, and the mixture is reacted at 10° C. to 100° C., and preferably at 40° C. to 70° C., for 6 hours to 48 hours, and preferably 12 hours to 24 hours, whereby compound m1 can be obtained.

Second Step i) When $R^2$ is $OR^{2'}$ ($R^{2'}$ has the same meaning as described above)

From compound m1, compound M-1 can be obtained in the same manner as in the seventh to tenth steps in "1) Synthesis of Compounds A-1 and A-2" described above.

ii) When $R^2$ is other

Compound m1 is reacted in the same manner as in the seventh step in "1) Synthesis of Compounds A-1 and A-2" described above, and then in the same manner as in the first to third steps in "2) Synthesis of Compounds A-3 and A-4" described above, whereby compound M-1 can be obtained.

Third Step

From compound M-1, compound M-2 can be obtained in the same manner as in the fifteenth step in "1) Synthesis of Compounds A-1 and A-2" described above.

30) Synthesis of Compounds N-1 and N-2

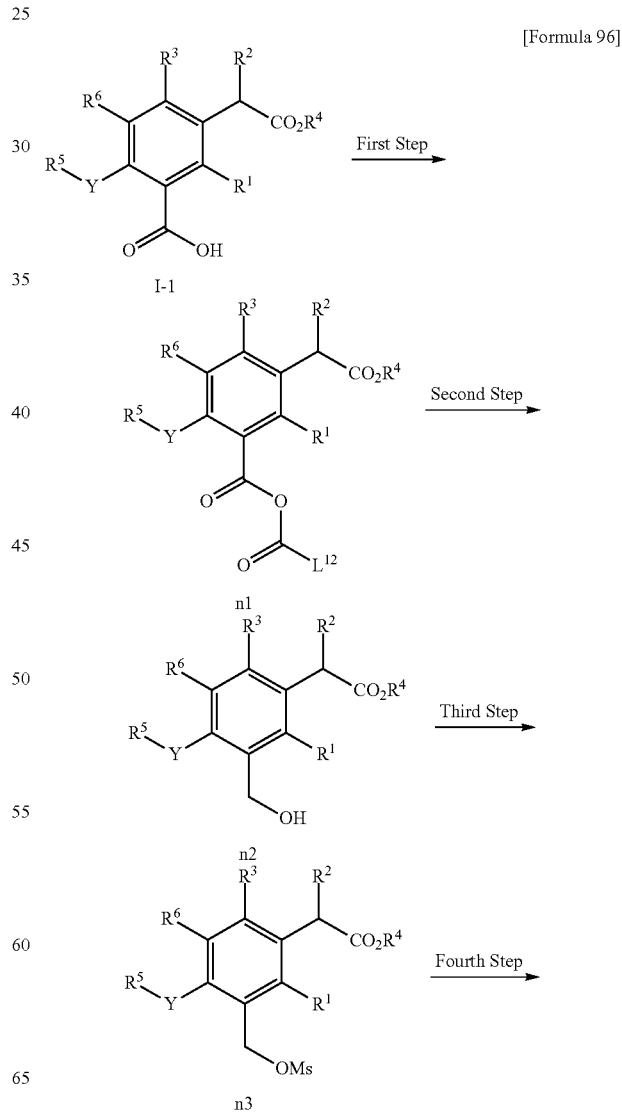

[Formula 96]

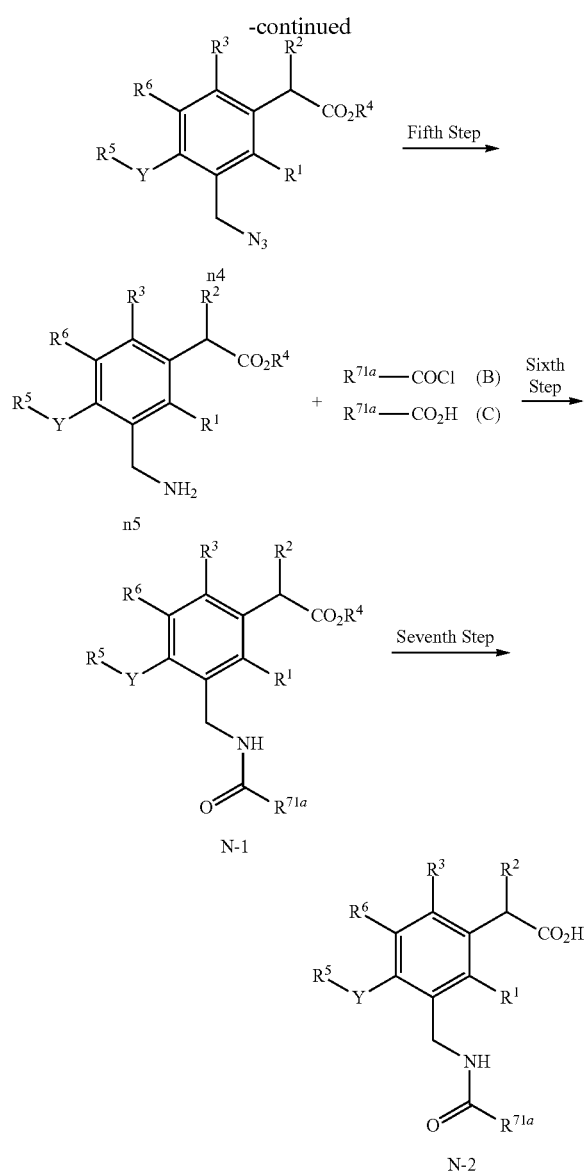

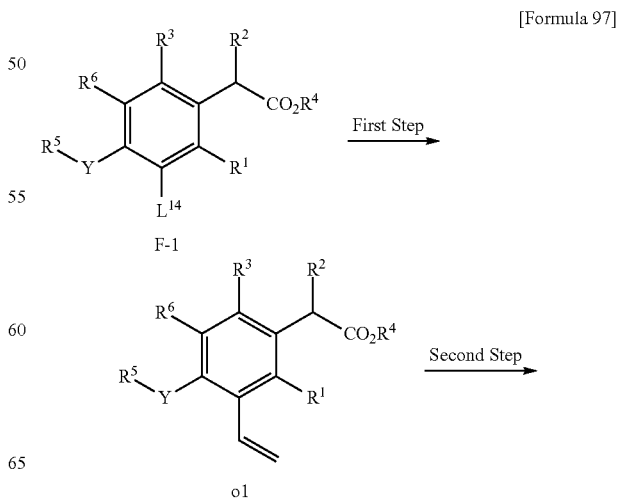

[Formula 97]

wherein $R^1$, $R^2$, $R^3$, $R^4$, $R^5$, $R^6$ and Y have the same meaning as described above, $L^{12}$ is alkyl, and $R^{71a}$ is alkyl, alkenyl, alkynyl, an aromatic carbocyclic group, a nonaromatic carbocyclic group, an aromatic heterocyclic group, or a nonaromatic heterocyclic group.

First Step

In THF, DMF, dichloromethane or the like, water, or a mixed solvent thereof, a base such as triethylamine, diisopropylethylamine or N-methylmorpholine, and a carboxylic acid derivative such as isobutyl chloroformate, an acid chloride such as pivaloyl chloride, or the like are added to compound I-1, and the mixture is reacted at −20° C. to 60° C., and preferably at −5° C. to 20° C., for 0.5 hours to 24 hours, and preferably 1 hour to 4 hours, whereby compound n1 can be obtained.

Second Step

In THF, DMF, DMA, or the like, or a mixed solvent thereof, a reducing agent such as sodium borohydride or lithium borohydride is added to compound n1, and the mixture is reacted at −20° C. to 80° C., and preferably at 0° C. to 50° C., for 1 hour to 24 hours, and preferably 2 hours to 6 hours, whereby compound n2 can be obtained.

Third Step

In THF, DMF, DMA, or the like, or a mixed solvent thereof, a base such as triethylamine, lutidine or N-methylmorpholine is added to compound n2 and methanesulfonic acid chloride, and the mixture is reacted at 0° C. to 80° C., and preferably at 20° C. to 40° C., for 1 hour to 24 hours, and preferably 2 hours to 6 hours, whereby compound n3 can be obtained.

Fourth Step

In THF, DMF, DMA, or the like, or a mixed solvent thereof, sodium azide is added to compound n3, and the mixture is reacted at 0° C. to 100° C., and preferably at 20° C. to 50° C., for 1 hour to 24 hours, and preferably 2 hours to 6 hours, whereby compound n4 can be obtained.

Fifth Step

In ethanol, methanol, DMF, or the like, or a mixed solvent thereof, a palladium carbon is added to compound n4, and the mixture is reacted under a hydrogen atmosphere at 0° C. to 100° C., and preferably at 20° C. to 50° C., for 1 hour to 24 hours, and preferably 2 hours to 6 hours, whereby compound n5 can be obtained.

Sixth Step

In DMF, DMA, dichloromethane, or the like, or a mixed solvent thereof, a base such as pyridine or lutidine is added to compound n5 and an acid chloride derivative (B) that is commercially available or prepared by a known method, and the mixture is reacted at 0° C. to 100° C., and preferably at 20° C. to 50° C., for 1 hour to 24 hours, and preferably 2 hours to 6 hours, whereby compound N-1 can be obtained.

Alternatively, compound N-1 can be obtained by adding 1-hydroxy-7-azabenzotriazole, 1-hydroxybenzotriazole, or the like, and/or a condensing agent such as dicyclohexylcarbodiimide or diisopropylcarbodiimide, and a base such as triethylamine, diisopropylethylamine or N-methylmorpholine to compound n5 and a carboxylic acid derivative (C) that is commercially available or prepared by a known method, in DMF, DMA, THF, acetonitrile, or the like, or a mixed solvent thereof, and reacting the mixture at 0° C. to 100° C., and preferably at 20° C. to 50° C., for 1 hour to 48 hours, and preferably 2 hours to 24 hours.

Seventh Step

From compound N-1, compound N-2 can be obtained in the same manner as in the fifteenth step in "1) Synthesis of Compounds A-1 and A-2" described above.

31) Synthesis of Compounds O-1 and O-2

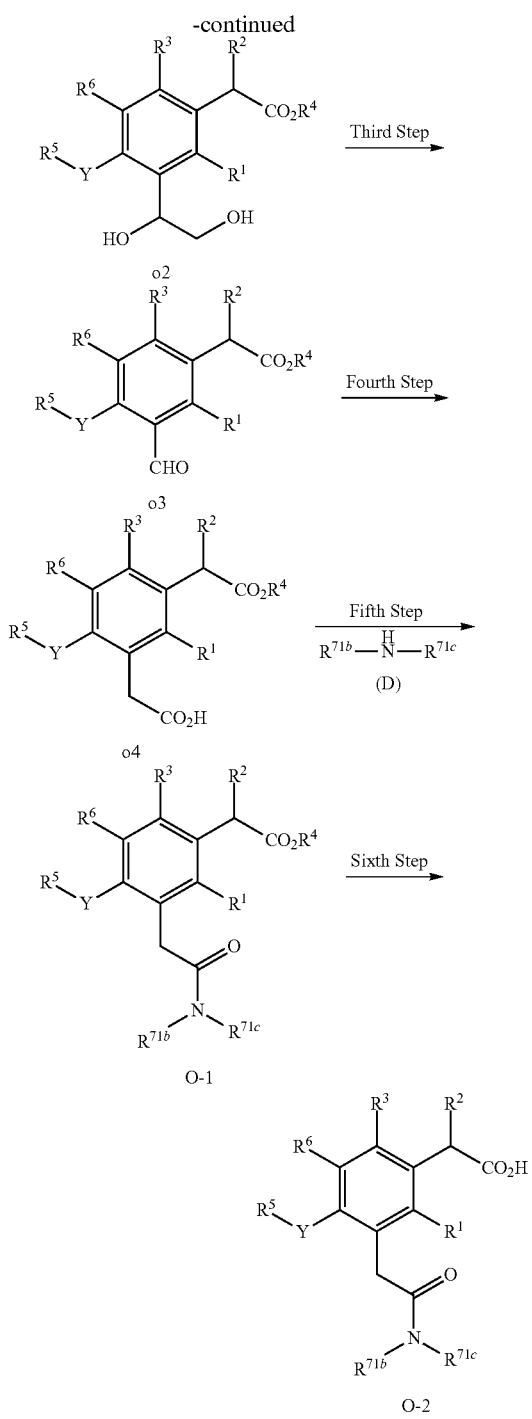

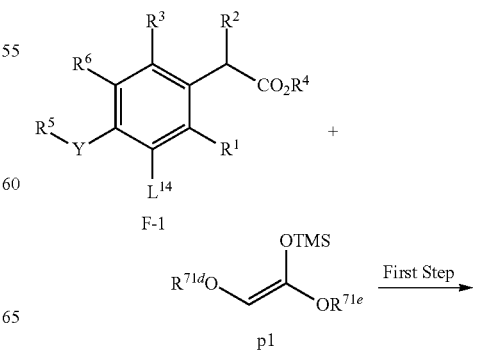

wherein $R^1$, $R^2$, $R^3$, $R^4$, $R^5$, $R^6$, $L^{14}$, and Y have the same meaning as described above, and $R^{71b}$ and $R^{71c}$ are each independently alkyl, alkenyl, or alkynyl, wherein $R^{71b}$ and $R^{71c}$ may be taken together with an adjacent nitrogen atom to form an aromatic heterocyclic group or a nonaromatic heterocyclic group.

First Step

In a solvent such as DMF, DMA, THF or acetonitrile, or in a mixed solvent thereof, a phosphine such as tri-tert-butylphosphine, tricyclohexylphosphine or triphenylphosphine, a palladium catalyst such as dibenzylideneacetone palladium, palladium acetate or dichlorobistriphenylphosphine palladium, and a base such as N-methylmorpholine are added to compound F-1, and the mixture is reacted with ethylene gas at 30° C. to 180° C., and preferably at 50° C. to 150° C., for 1 hour to 48 hours, and preferably 4 hours to 24 hours, whereby compound o1 can be obtained.

Second Step

In a mixed solvent of THF, acetonitrile, acetone, tert-butyl alcohol or the like and water or a phosphate buffer solution, an oxidizing agent such as N-methylmorpholine oxide or $K_3Fe(CN)_6$ and a catalytic amount of osmium tetroxide or dipotassium osmate dihydrate are added to compound o1, and the mixture is reacted at 0° C. to 100° C., and preferably at 20° C. to 50° C., for 1 hour to 48 hours, and preferably 2 hours to 24 hours, whereby compound o2 can be obtained.

Third Step

In a mixed solvent of THF, acetonitrile, chloroform or the like and water, sodium periodate is added to compound o2, and the mixture is reacted at 0° C. to 100° C., and preferably at 0° C. to 30° C., for 1 hour to 48 hours, and preferably 2 hours to 6 hours, whereby compound o3 can be obtained.

Fourth Step

In a solvent such as diethyl ether of sodium hydride or THF, or in a mixed solvent thereof, methoxymethyl triphenylphosphonium chloride is added, and the mixture is stirred at 0° C. to 80° C., and preferably at 25° C. to 50° C., for 0.1 hours to 6 hours, and preferably 0.5 hours to 2 hours, and thereafter, compound o3 is added, and the mixture is reacted at 0° C. to 80° C., and preferably at 50° C. to 60° C., for 1 hour to 48 hours, and preferably 6 hours to 24 hours, to give a methoxyvinyl form. In a solvent such as THF or dioxane, or a mixed solvent thereof, an aqueous solution of hydrochloric acid or sulfuric acid was added to the methoxyvinyl form, and the mixture is reacted at 0° C. to 100° C., and preferably at 50° C. to 80° C., for 0.1 hours to 6 hours, and preferably 0.5 hours to 2 hours, to give an acetaldehyde form. Furthermore, the acetaldehyde form is oxidized under Jones oxidation conditions by $CrO_3$, whereby compound o4 can be obtained.

Fifth Step

From compound o4, compound O-1 can be obtained in the same manner as in the first step in "26) Synthesis of Compounds J-1 and J-2 (Reverse Amide Derivatives)" described above.

Sixth Step

From compound O-1, compound O-2 can be obtained in the same manner as in the fifteenth step in "1) Synthesis of Compounds A-1 and A-2" described above.

32) Synthesis of Compounds P-1 and P-2

[Formula 98]

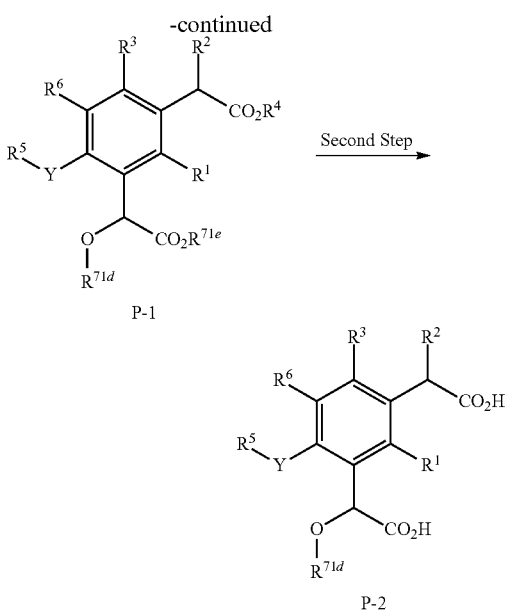

wherein $R^1$, $R^2$, $R^3$, $R^4$, $R^5$, $R^6$, $L^{14}$, and Y have the same meaning as described above, and $R^{71d}$ and $R^{71e}$ are each independently alkyl, alkenyl, alkynyl, an aromatic carbocyclic group, a nonaromatic carbocyclic group, an aromatic heterocyclic group, or a nonaromatic heterocyclic group.

First Step

From compound F-1 and compound p1, compound P-1 can be obtained in the same manner as in the twenty ninth step in "1) Synthesis of Compounds A-1 and A-2" described above.

Here, compound p1 can be obtained in the same manner as in the fortieth to forty second steps in "1) Synthesis of Compounds A-1 and A-2" described above.

Second Step

From compound P-1, compound P-2 can be obtained in the same manner as in the fifteenth step in "1) Synthesis of Compounds A-1 and A-2" described above.

33) Synthesis of Compounds A'-1 to A'-4

First Step

Compound a'1 that is commercially available or synthesized by a known method is reacted with an acid halide such as acetyl chloride or acid anhydride such as acetic anhydride, by Friedel-Crafts-acylation, in a solvent of methylene chloride, dichloroethane or the like, in the presence of a Lewis acid such as aluminum chloride, at 0° C. to 150° C., and preferably 60° C. to 120° C., for 1 hour to 48 hours, and preferably 12 hours to 24 hours, whereby compound a'2 can be obtained.

Second Step

In a mixed acid of sulfuric acid and nitric acid, compound a'2 is reacted at −30° C. to 100° C., and preferably at 0° C. to 50° C., for 0.5 hours to 48 hours, and preferably 6 hours to 24 hours, whereby compound a'3 can be obtained.

Third Step

In $L^{1'}OH$, an acid such as concentrated sulfuric acid or concentrated hydrochloric acid is added to compound a'3, and the mixture is reacted at 0° C. to 150° C., and preferably at 80° C. to 110° C., for 1 hour to 24 hours, and preferably 6 hours to 12 hours, whereby compound a'4 can be obtained.

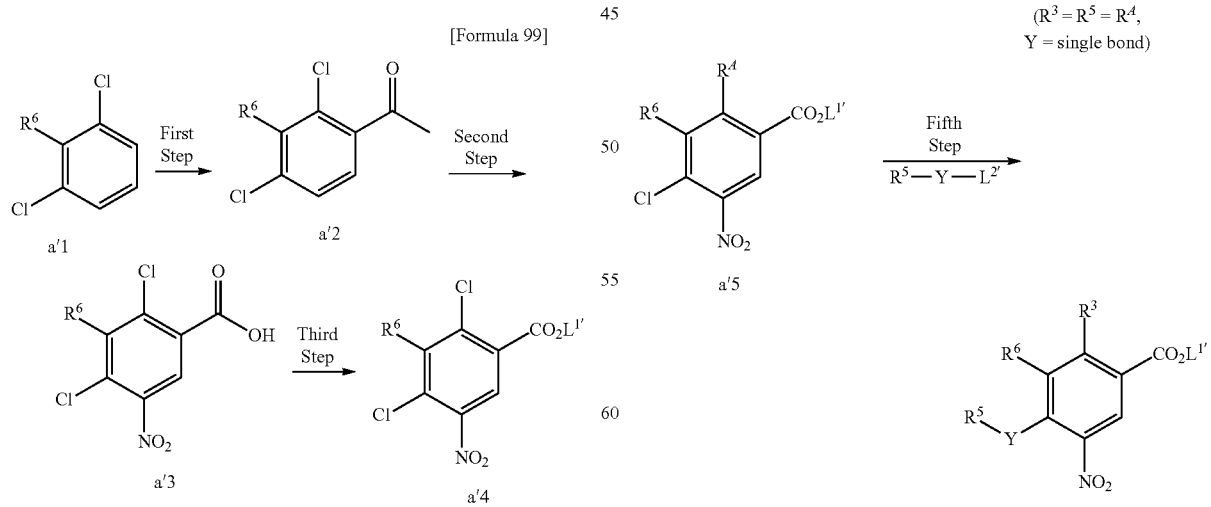

wherein $R^6$ has the same meaning as described above, and $L^{1'}$ is substituted or unsubstituted alkyl.

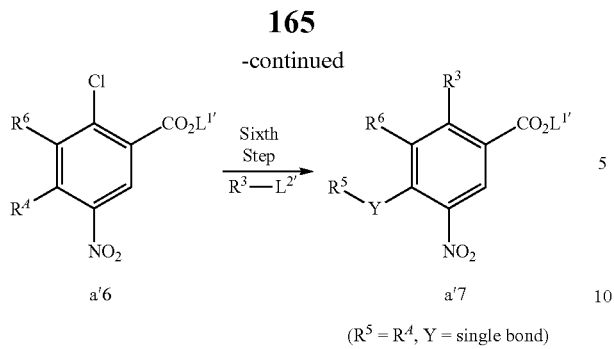

(R⁵ = R⁴, Y = single bond)

wherein $R^3$, $R^5$, $R^6$, Y, and $L^{1'}$ have the same meaning as described above, $R^4$ is a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, and $L^{2'}$ is boronic acid, a boronic acid ester, an alkyltin, or a zinc halide.

Fourth Step

Compounds a'5, a'6, and a'7 can be obtained by a coupling reaction of compound a'4 with $R^4$-$L^{2'}$. As the reaction, Suzuki cross-coupling, Ullmann cross-coupling, Negishi cross-coupling, Stille coupling, and the like are exemplified.

In a solvent such as dioxane, DMF, DME, THF or water or a mixed solvent, a palladium catalyst such as $Pd(PPh_3)_4$, $Pd(OAc)_2$, $Pd(PPh_3)_2Cl_2$ or $Pd(dppf)_2Cl_2$, a base such as potassium carbonate, sodium carbonate or potassium phosphate, and boronic acid or a boronic acid ester, and an alkyltin or a zinc halide, that are commercially available or synthesized by a known method, are added to compound a4, and the mixture is reacted under a nitrogen atmosphere at 0° C. to 150° C., and preferably at 60° C. to 120° C., for 0.5 hours to 24 hours, and preferably 1 hour to 12 hours, whereby compounds a'5, a'6 and a'7 ($R^3$=$R^5$=$R^4$, and Y is a single bond) can be obtained.

Fifth Step

From compound a'5, compound a'7 ($R^3$=$R^4$) can be obtained in the same manner as in the fourth step.

Sixth Step

From compound a'6, compound a'7 ($R^5$=$R^4$, Y is a single bond) can be obtained in the same manner as in the fourth step.

[Formula 101]

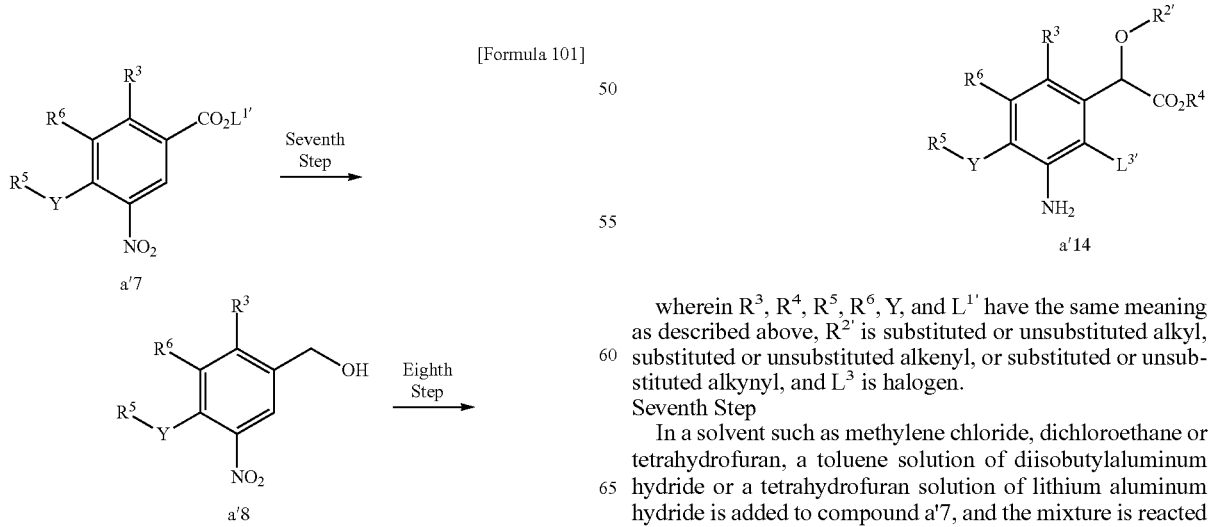

wherein $R^3$, $R^4$, $R^5$, $R^6$, Y, and $L^{1'}$ have the same meaning as described above, $R^{2'}$ is substituted or unsubstituted alkyl, substituted or unsubstituted alkenyl, or substituted or unsubstituted alkynyl, and $L^3$ is halogen.

Seventh Step

In a solvent such as methylene chloride, dichloroethane or tetrahydrofuran, a toluene solution of diisobutylaluminum hydride or a tetrahydrofuran solution of lithium aluminum hydride is added to compound a'7, and the mixture is reacted at −100° C. to 50° C., and preferably at −60° C. to 0° C., for 0.5 hours to 10 hours, and preferably 1 hour to 3 hours, whereby compound a'8 can be obtained.

Eighth Step

In a solvent such as methylene chloride, acetone or DMSO, an oxidant such as Dess-Martin reagent, manganese dioxide or sulfur trioxide pyridine is added to compound a'8, and the mixture is reacted at −20° C. to 50° C., and preferably at 0° C. to 30° C., for 0.5 hours to 10 hours, and preferably 1 hour to 3 hours to be oxidized, whereby compound a'9 can be obtained.

Ninth Step

In a solvent such as methylene chloride, dichloroethane or toluene, zinc iodide and TMSCN are added to compound a'9, and the mixture is reacted at −20° C. to 50° C., and preferably at 0° C. to 30° C., for 0.1 hours to 10 hours, and preferably 0.5 hours to 2 hours, whereby compound a'10 can be obtained.

Tenth Step

In $R^4OH$, an acid such as concentrated sulfuric acid or concentrated hydrochloric acid is added to compound a'10, and the mixture is reacted at 0° C. to 150° C., and preferably at 80° C. to 110° C., for 1 hour to 24 hours, and preferably 6 hours to 12 hours, for deprotection of a TMS group, hydrolysis to the carboxylic acid of nitrile group, followed by esterification, whereby compound a'11 can be obtained.

Eleventh Step

In a solvent such as THF, DMF or toluene, a base such as sodium hydride, potassium tert-butoxide or sodium methoxide and a halide such as $R^{2'}$—I, $R^{2'}$—Br or $R^{2'}$—Cl are added to compound a'11, and the mixture is reacted at −20° C. to 100° C., and preferably at 0° C. to 60° C., for 1 hour to 24 hours, and preferably 3 hours to 12 hours, whereby compound a'12 can be obtained.

Also, tert-butyl ester and the like can be also obtained by adding 1 to 3 equivalents of a 70% aqueous perchloric acid solution in tert-butyl acetate, and reacting the mixture at 0° C. to 60° C., and preferably at 15° C. to 30° C., for 0.1 hours to 10 hours, and preferably 0.5 hours to 2 hours.

Twelfth Step

In a solvent such as methanol, ethanol, THF or ethyl acetate, a catalyst such as 5% or 10% palladium carbon, palladium hydroxide or platinum dioxide is added to compound a'12, and the mixture is reacted under a hydrogen atmosphere at 0° C. to 50° C., and preferably at 15° C. to 25° C., for 0.1 hours to 48 hours, and preferably 1 hour to 24 hours, whereby compound a'13 can be obtained.

In this condition, the reaction may be promoted by adding an acid such as acetic acid or hydrochloric acid. In a mixed solvent of an organic solvent such as methanol, ethanol or THF and water, a metal such as iron, zinc or tin is added to compound a'12, under acidic conditions of hydrochloric acid or acetic acid, under alkaline conditions of potassium hydroxide or sodium hydroxide, or under neutral conditions of ammonium chloride, and the mixture is reacted at 0° C. to 120° C., and preferably at 25° C. to 80° C., for 0.1 hours to 24 hours, and preferably 1 hour to 12 hours, whereby compound a'13 can be also obtained.

Thirteenth Step

In a solvent such as dichloromethane, THF, toluene, acetonitrile or DMF, bromine or a halogenating reagent such as NBS, NCS and NIS is added to compound a'13, and when $L^{3'}$ is bromo, the mixture is reacted at −30° C. to 50° C., and preferably at −10° C. to 20° C., for 0.1 hours to 10 hours, and preferably 0.5 hours to 2 hours, whereby compound a'14 can be obtained.

When $L^{3'}$ is chloro or iodine, the mixture is reacted at 10° C. to 150° C., and preferably at 60° C. to 120° C., for 0.5 hours to 24 hours, and preferably 1 hour to 6 hours, whereby compound a'14 can be obtained.

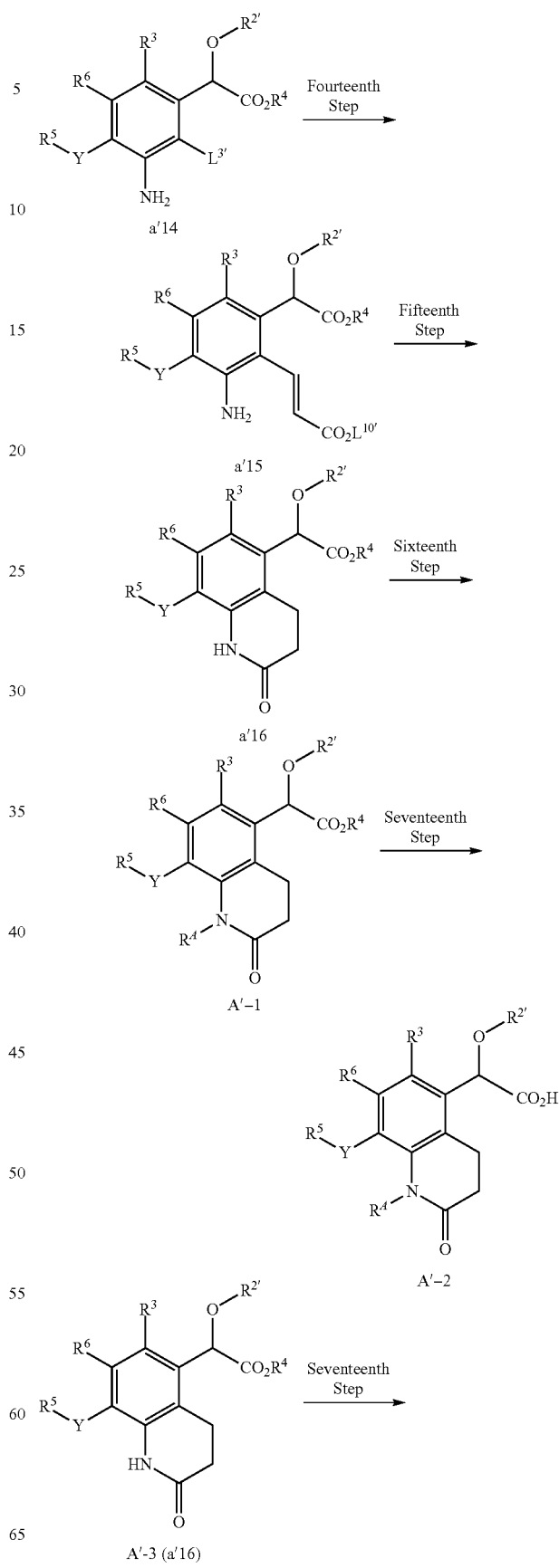

[Formula 102]

-continued

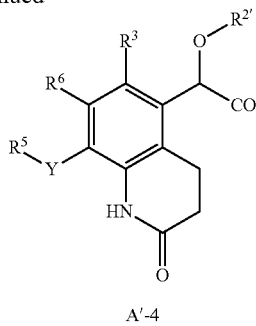

A'-4 wherein $R^{2'}$, $R^3$, $R^4$, $R^5$, $R^6$, $R^{4}$, Y, and $L^{3'}$ have the same meaning as described above, and $L^{10'}$ is substituted or unsubstituted alkyl.

Fourteenth Step

In a solvent such as DMF, DMA, THF, dioxane or water, or in a mixed solvent thereof, an aqueous solution of a base such as $K_2CO_3$, $Na_2CO_3$ or $K_3PO_4$ and (E)-3-boranyl acrylate that is commercially available or prepared by a known method are added to compound a'14, and the mixture is reacted at 50° C. to 150° C., and preferably at 70° C. to 130° C., for 0.1 hours to 8 hours, and preferably 0.5 to 2 hours, whereby compound a'15 can be obtained.

Fifteenth Step

In a solvent such as ethanol, methanol, DMF or acetic acid, or in a mixed solvent thereof, a palladium carbon is added to compound a'15, and the mixture is reacted under a hydrogen atmosphere at 0° C. to 100° C., and preferably at 20° C. to 50° C., for 1 hour to 24 hours, and preferably 2 hours to 6 hours, whereby compound a'16 can be obtained.

Sixteenth Step

In a solvent such as DMF, DMA, THF or acetonitrile, or in a mixed solvent thereof, a base such as sodium hydride or cesium carbonate, and a haloalkane that is commercially available or prepared by a known method are added to compound a'16, and the mixture is reacted at 20° C. to 140° C., and preferably at 40° C. to 80° C., for 1 hour to 48 hours, and preferably 2 hours to 24 hours, whereby compound A'-1 can be obtained.

Seventeenth Step

In a solvent such as methanol, ethanol, THF or DMSO, potassium hydroxide, sodium hydroxide, lithium hydroxide or the like is added to compound A'-1, and the mixture is reacted at 0° C. to 100° C., and preferably at 20° C. to 50° C., for 0.1 hours to 24 hours, and preferably 1 hour to 6 hours, whereby compound A'-2 can be obtained.

Also, compound A'-2 can be obtained by adding hydrochloric acid, TFA or the like to compound A'-1, in a solvent such as methanol, ethanol, THF or DMSO, and reacting the mixture at 0° C. to 100° C., and preferably at 20° C. to 50° C., for 0.1 hours to 24 hours, and preferably 1 hour to 6 hours.

In the same manner, compound A'-4 can be obtained from compound A'-3 (a'16).

Here, as shown below, compound a'12' that is an optical isomer of compound a'12 can be synthesized from compound a'4. Furthermore, from compound a'12', compounds A'-1' and A'-2' that are optical isomers of compounds A'-1 and A'-2, respectively, can be synthesized by the method described above.

[Formula 103]

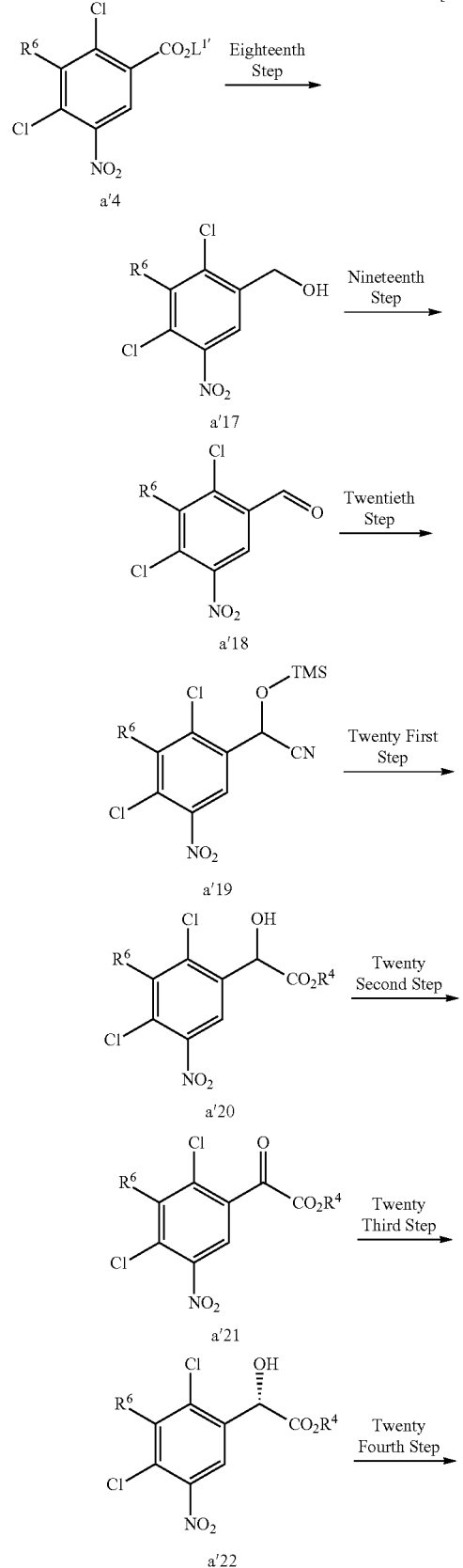

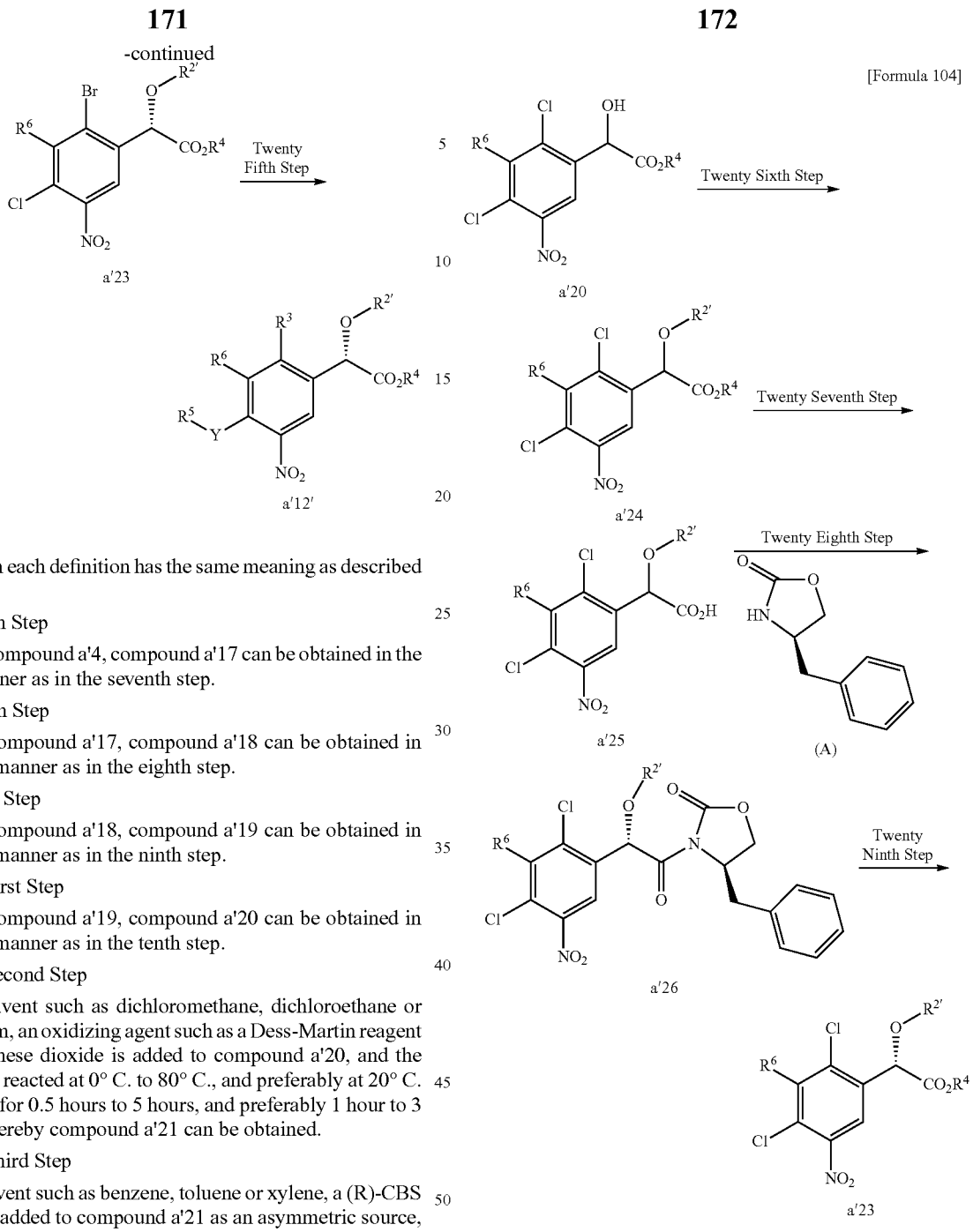

wherein each definition has the same meaning as described above.

Eighteenth Step

From compound a'4, compound a'17 can be obtained in the same manner as in the seventh step.

Nineteenth Step

From compound a'17, compound a'18 can be obtained in the same manner as in the eighth step.

Twentieth Step

From compound a'18, compound a'19 can be obtained in the same manner as in the ninth step.

Twenty First Step

From compound a'19, compound a'20 can be obtained in the same manner as in the tenth step.

Twenty Second Step

In a solvent such as dichloromethane, dichloroethane or chloroform, an oxidizing agent such as a Dess-Martin reagent or manganese dioxide is added to compound a'20, and the mixture is reacted at 0° C. to 80° C., and preferably at 20° C. to 45° C., for 0.5 hours to 5 hours, and preferably 1 hour to 3 hours, whereby compound a'21 can be obtained.

Twenty Third Step

In a solvent such as benzene, toluene or xylene, a (R)-CBS reagent is added to compound a'21 as an asymmetric source, and a reducing agent such as catechol borane or 9-borabicyclo[3.3.1]nonane is sequentially added, and the mixture is reacted at −50° C. to 0° C., and preferably at −35° C. to −10° C., for 0.5 hours to 6 hours, and preferably 1 hour to 3 hours, whereby compound a'22 can be obtained.

Twenty Fourth Step

From compound a'22, compound a'23 can be obtained in the same manner as in the eleventh step.

Twenty Fifth Step

Compound a'12' that is an optical isomer of compound a'12 can be obtained from compound a'23 in the same manner as in the fourth to sixth steps.

Here, synthesis of compound a'23 is also possible from compound a'20, by the method shown below.

wherein each definition has the same meaning as described above.

Twenty Sixth Step

From compound a'20, compound a'24 can be obtained in the same manner as in the eleventh step.

Twenty Seventh Step

From compound a'24, compound a'25 can be obtained in the same manner as in the seventeenth step.

Twenty Eighth Step

Compound a'26 can be synthesized by condensing compound a'25 with an enantiopure chiral auxiliary compound like R-(+)-4-benzyl-2-oxazolidinone (compound (A)) to produce a diastereomeric mixture and separating the diastereomeric mixture by silica gel column chromatography.

Specifically, compound a'25 is dissolved in a solvent such as anhydrous dichloromethane, anhydrous chloroform or anhydrous THF, and thereafter a small amount of anhydrous DMF was added, and a chlorinating reagent such as thionyl chloride or oxalyl chloride is added dropwise at −30° C. to 50° C., and preferably at −10° C. to 20° C. Thereafter, the mixture was stirred at −30° C. to 50° C., and preferably at −10° C. to 20° C., for 0.1 hours to 10 hours, and preferably 0.5 hours to 2 hours and concentrated, and the obtained foamy solid is dissolved in anhydrous tetrahydrofuran, anhydrous dichloromethane, or the like. A solution of anhydrous tetrahydrofuran, anhydrous dichloromethane or the like of compound (A) is stirred at −100° C. to 30° C., and preferably at −80° C. to 60° C., a n-BuLi/hexane solution is added, and the mixture is stirred at −100° C. to −30° C., and preferably at −80° C. to −60° C., for 0.1 hours to 1 hour, and preferably 0.1 hours to 0.5 hours, and is further stirred at −20° C. to 60° C., and preferably at 0° C. to 30° C., for 0.1 hours to 5 hours, and preferably 0.1 hours to 2 hours. Thereafter, the mixture is mixed with the prepared acid chloride solution at −60° C. to −10° C., and preferably at −40° C. to −20° C., and then heated to −10° C. to 60° C., and preferably to 10° C. to 30° C. After the reaction, the mixture is quenched with a saturated aqueous ammonium chloride solution, and extracted with dichloromethane, and then separated and purified by silica gel chromatography, whereby compound a'26 can be obtained.

Twenty Ninth Step

In a tetrahydrofuran-water mixed solvent, a mixed liquid of hydrogen peroxide and an aqueous solution of lithium hydroxide is added to compound a'26, the mixture is reacted at −20° C. to 10° C., and preferably at −10° C. to 10° C., to obtain a carboxylate form, and thereafter, the carboxylate form is esterified by a diazomethane/diethyl ether solution or the like, whereby compound a'23 can be obtained.

Synthesis of compound A'-1 is also possible by the method shown below.

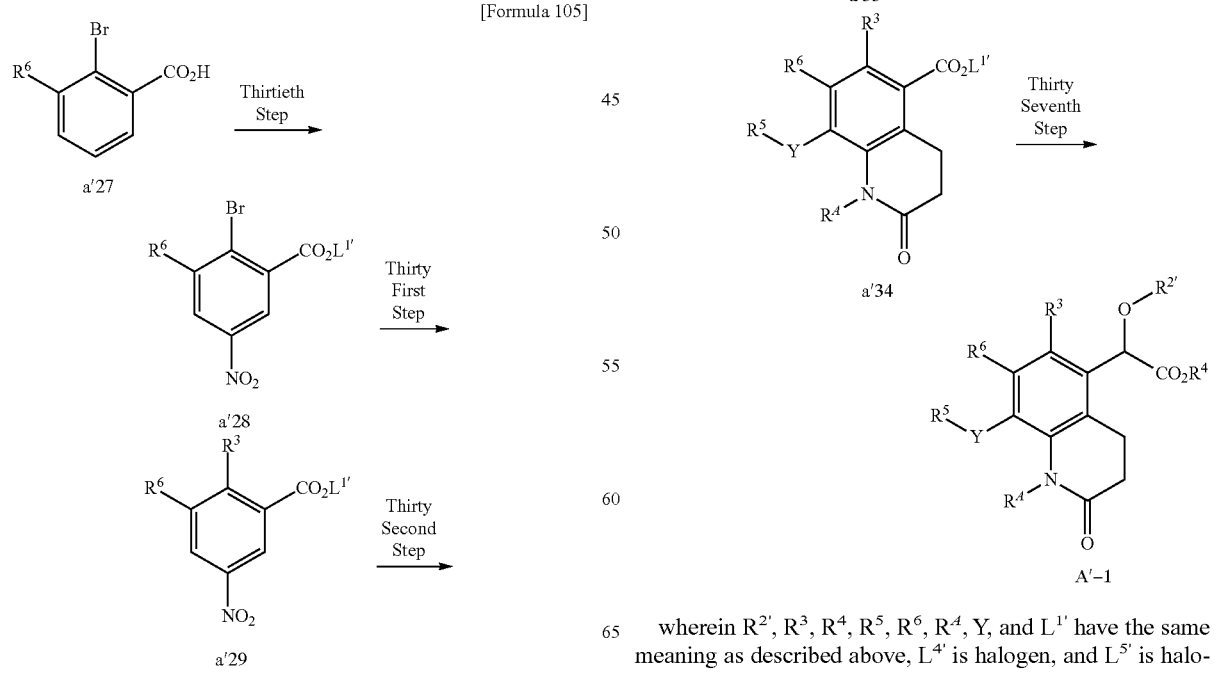

wherein $R^{2'}$, $R^3$, $R^4$, $R^5$, $R^6$, $R^{4'}$, Y, and $L^{1'}$ have the same meaning as described above, $L^{4'}$ is halogen, and $L^{5'}$ is halogen.

Thirtieth Step

To compound a'27 that is commercially available or synthesized by a known method is added, in a solvent such as concentrated sulfuric acid or acetic acid, nitric acid, fuming nitric acid or the like under ice-cooling, and the mixture is reacted at −20° C. to 60° C., and preferably at 0° C. to 25° C., for 0.5 hours to 6 hours, and preferably 1 hour to 3 hours, whereby a nitro compound can be obtained. This compound is reacted in a solvent such as thionyl chloride and phosphorus oxychloride, at 20° C. to 120° C., and preferably at 80° C. to 100° C., for 0.5 hours to 6 hours, and preferably 1 hour to 3 hours, and the solvent is concentrated under reduced pressure, whereby a crude acid chloride can be obtained. Subsequently, in a $L^1OH$ solvent, the crude chloride is reacted at 20° C. to 120° C., and preferably at 50° C. to 80° C., for 0.5 hours to 6 hours, and preferably 1 hour to 3 hours, whereby compound a'28 can be obtained.

Thirty First Step

From compound a'28, compound a'29 can be obtained in the same manner as in the fourth step.

Thirty Second Step

From compound a'29, compound a'30 can be obtained in the same manner as in the twelfth step.

Thirty Third Step

From compound a'30, compound a'31 can be obtained in the same manner as in the thirteenth step.

Thirty Fourth Step

From compound a'31, compound a'32 can be obtained in the same manner as in the fourteenth to sixteenth steps.

Thirty Fifth Step

From compound a'32, compound a'33 can be obtained in the same manner as in the thirteenth step.

Thirty Sixth Step

From compound a'33, compound a'34 can be obtained in the same manner as in the fourth step.

Thirty Seventh Step

From compound a'34, compound A-1 can be obtained in the same manner as in the seventh to eleventh steps.

Here, as shown below, compound A-1' that is an optical isomer of compound A-1 can be synthesized from compound a'28.

[Formula 106]

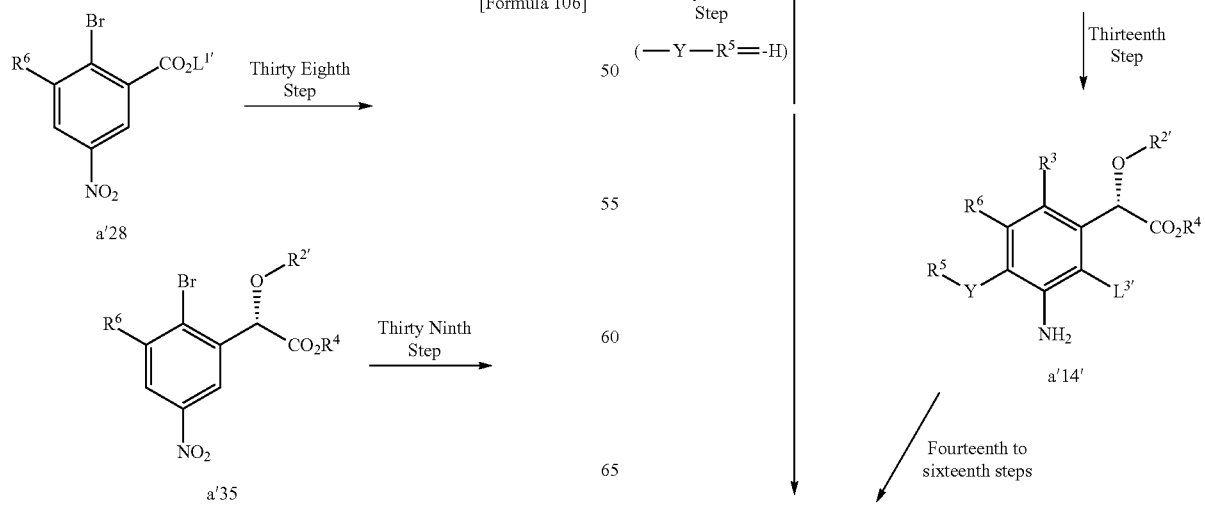

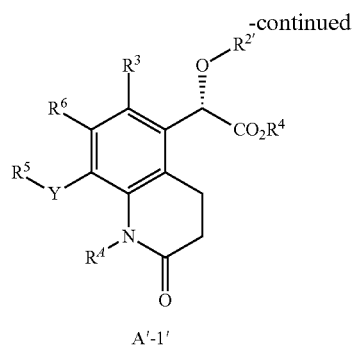

A'-1' wherein $R^{2'}$, $R^3$, $R^4$, $R^5$, $R^6$, $R^A$, Y, and $L^{3'}$ have the same meaning as described above, $L^{6'}$ is halogen, and $L^{7'}$ is halogen.

Thirty Eighth Step

From compound a'28, compound a'35 can be obtained in the same manner as in the eighteenth to twenty fourth steps.

Thirty Ninth Step

From compound a'35, compound a'36 can be obtained in the same manner as in the thirty first step.

Fortieth Step

From compound a'36, compound a'37 can be obtained in the same manner as in the thirty second step.

Forty First Step

From compound a'37, compounds a'38 and a'39 can be obtained in the same manner as in the thirty third step.

Forty Second Step

When Y is a single bond, and $R^5$ is a hydrogen atom, compound A'-1' that is an optical isomer of compound A'-1 can be obtained from compound a'38 in the same manner as in the fourteenth to sixteenth steps.

Forty Third Step

Compound a'13' that is an optical isomer of compound a'13 can be obtained from compound a'39 in the same manner as in the thirty sixth step.

The method of introducing various substituents into —Y—$R^5$ will be shown below.

[Formula 107]

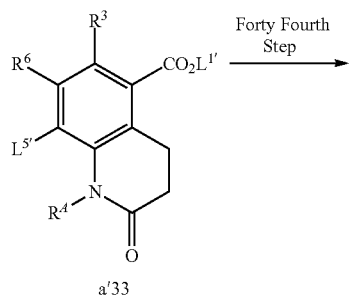

a'33

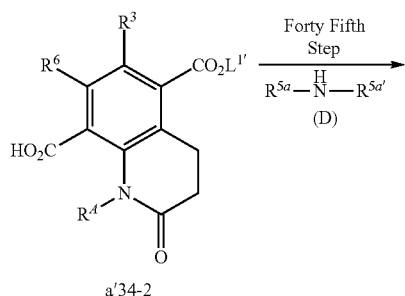

a'34-2

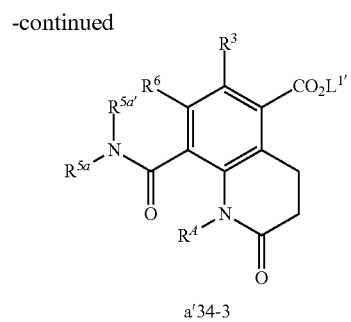

a'34-3 wherein $R^3$, $R^6$, $R^A$, $L^{1'}$, and $L^{5'}$ have the same meaning as described above, and $R^{5a}$ and $R^{5a'}$ are each independently substituted or unsubstituted alkyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, wherein $R^{5a}$ and $R^{5a'}$ may be taken together with an adjacent nitrogen atom to form a substituted or unsubstituted aromatic heterocyclic group or a substituted or unsubstituted nonaromatic heterocyclic group.

Forty Fourth Step

In a solvent such as DMF, DMSO, dioxane or toluene, a palladium catalyst such as $Pd(PPh_3)_4$, $Pd(OAc)_2$, $Pd(PPh_3)_2Cl_2$ or $PdCl_2(dppf)_2$, a base such as triethylamine or N-methylmorpholine, and allyl alcohol are added to compound a'33, and the mixture is reacted under a carbon monoxide atmosphere at 0° C. to 150° C., and preferably at 50° C. to 100° C., for 1 hour to 24 hours, and preferably 3 hours to 12 hours, whereby an allyl ester form can be synthesized. Thereafter, in a solvent such as ethanol, MeCN or THF, morpholine, pyrrolidine, or the like is added, and the mixture is reacted, in the presence of $Pd(Ph_3P)_4$, at 0° C. to 100° C., and preferably at 25° C. to 75° C., for 0.1 hours to 24 hours, and preferably 1 hour to 12 hours, whereby compound a'34-2 can be obtained.

Forty Fifth Step

In DMF, DMA, THF, acetonitrile or the like, or a mixed solvent thereof, 1-hydroxy-7-azabenzotriazole, 1-hydroxybenzotriazole or the like, and/or a condensing agent such as dicyclohexylcarbodiimide or diisopropylcarbodiimide, and a base such as triethylamine, diisopropylethylamine or N-methylmorpholine are added to compound a'34-2 and an amine derivative (D) that is commercially available or prepared by a known method, and the mixture is reacted at 0° C. to 100° C., and preferably at 20° C. to 50° C., for 1 hour to 48 hours, and preferably 2 hours to 24 hours, whereby compound a'34-3 can be obtained.

[Formula 108]

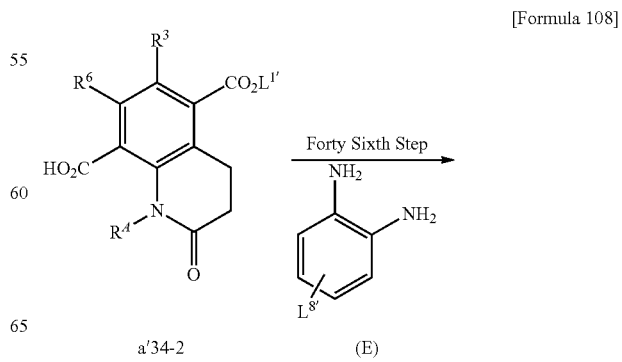

a'34-2    (E)

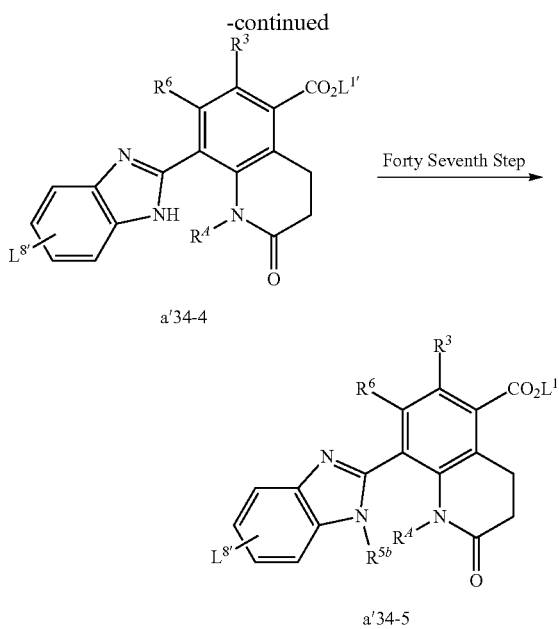

a'34-4 a'34-5 wherein $R^3$, $R^6$, $R^4$, and $L^{1'}$ have the same meaning as described above, $R^{5b}$ is alkyl, and $L^{8'}$ is halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azido, hydrazino, ureido, amidino, guanidino, trialkylsilyl, alkyl, alkenyl, alkynyl, haloalkyl, hydroxyalkyl, alkyloxy, alkenyloxy, alkynyloxy, halo alkyloxy, alkyloxyalkyl, alkyloxyalkyloxy, alkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, an aromatic carbocyclic group, a nonaromatic carbocyclic group, an aromatic heterocyclic group, a nonaromatic heterocyclic group, aromatic carbocyclicoxy, nonaromatic carbocyclicoxy, aromatic heterocyclicoxy, nonaromatic heterocyclicoxy, aromatic carbocyclic amino, nonaromatic carbocyclic amino, aromatic heterocyclic amino, nonaromatic heterocyclic amino, aromatic carbocyclic carbonyl, nonaromatic carbocyclic carbonyl, aromatic heterocyclic carbonyl, nonaromatic heterocyclic carbonyl, aromatic carbocyclic oxycarbonyl, nonaromatic carbocyclic oxycarbonyl, aromatic heterocyclic oxycarbonyl, nonaromatic heterocyclic oxycarbonyl, nonaromatic heterocyclic oxycarbonyl, aromatic carbocyclic carbonylamino, nonaromatic carbocyclic carbonylamino, aromatic heterocyclic carbonylamino, nonaromatic heterocyclic carbonylamino, aromatic carbocyclic alkyl, nonaromatic carbocyclic alkyl, aromatic heterocyclic alkyl, nonaromatic heterocyclic alkyl, aromatic carbocyclic alkyloxy, nonaromatic carbocyclic alkyloxy, aromatic heterocyclic alkyloxy, nonaromatic heterocyclic alkyloxy, aromatic carbocyclic alkylsulfanyl, nonaromatic carbocyclic alkylsulfanyl, aromatic heterocyclic alkylsulfanyl, nonaromatic heterocyclic alkylsulfanyl, aromatic carbocyclic alkyloxycarbonyl, nonaromatic carbocyclic alkyloxycarbonyl, aromatic heterocyclic alkyloxycarbonyl, nonaromatic heterocyclic alkyloxycarbonyl, aromatic carbocyclic alkyloxyalkyl, nonaromatic carbocyclic alkyloxyalkyl, aromatic heterocyclic alkyloxyalkyl, nonaromatic heterocyclic alkyloxyalkyl, aromatic carbocyclic alkylamino, nonaromatic carbocyclic alkylamino, aromatic heterocyclic alkylamino, nonaromatic heterocyclic alkylamino, aromatic carbocyclic sulfanyl, nonaromatic carbocyclic sulfanyl, aromatic heterocyclic sulfanyl, nonaromatic heterocyclic sulfanyl, nonaromatic carbocyclic sulfonyl, aromatic carbocyclic sulfonyl, aromatic heterocyclic sulfonyl, or nonaromatic heterocyclic sulfonyl.

Forty Sixth Step

In DMF, DMA, THF, acetonitrile, or the like, or a mixed solvent thereof, 1-hydroxy-7-azabenzotriazole, 1-hydroxybenzotriazole or the like, and/or a condensing agent such as dicyclohexylcarbodiimide or diisopropylcarbodiimide, and a base such as triethylamine, diisopropylethylamine or N-methylmorpholine are added to compound a'34-2 and a phenylenediamine derivative (E) that is commercially available or prepared by a known method, and the mixture is reacted at 0° C. to 100° C., and preferably at 20° C. to 50° C., for 1 hour to 48 hours, and preferably 2 hours to 24 hours, whereby compound a'34-4 can be obtained.

Forty Seventh Step

In DMF, DMA, THF, acetonitrile, or the like, or a mixed solvent thereof, a base such as sodium hydride or cesium carbonate, and halogenated alkyl that is commercially available or prepared by a known method are added to compound a'34-4, and the mixture is reacted at 20° C. to 140° C., and preferably at 40° C. to 80° C., for 1 hour to 48 hours, and preferably 2 hours to 24 hours, whereby compound a'34-5 can be obtained.

[Formula 109]

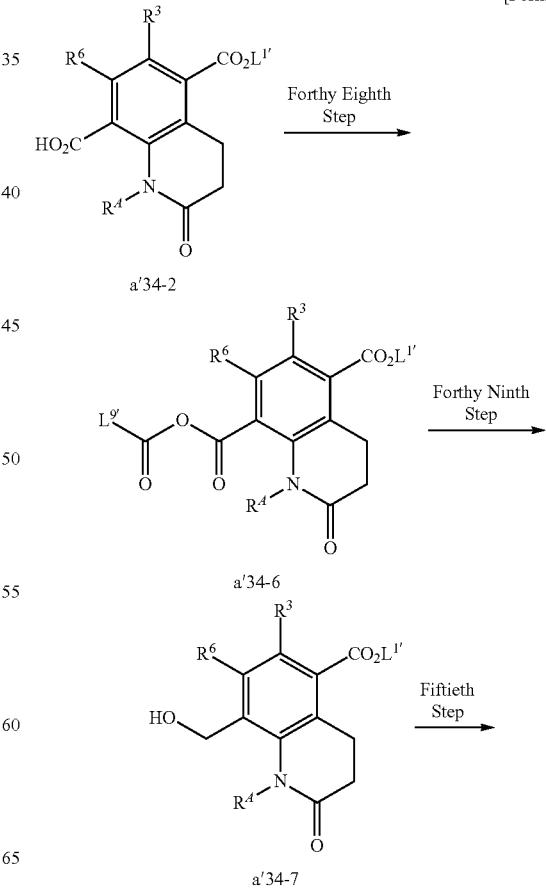

a'34-2 a'34-6 a'34-7

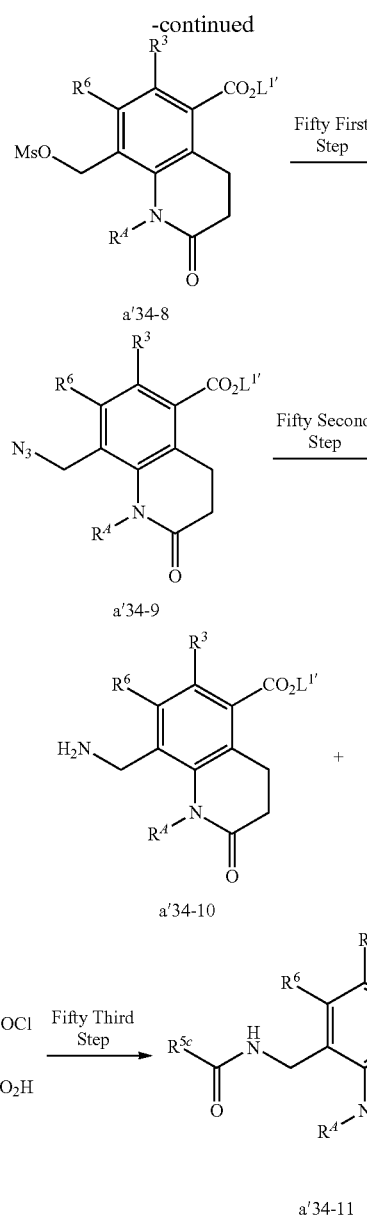

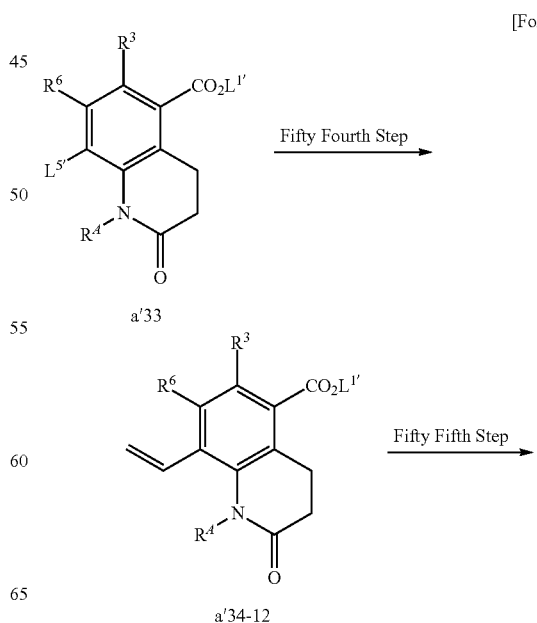

wherein $R^3$, $R^6$, $R^4$, and $L^{1'}$ have the same meaning as described above, $R^{5c}$ is alkyl, alkenyl, alkynyl, an aromatic carbocyclic group, a nonaromatic carbocyclic group, an aromatic heterocyclic group, or a nonaromatic heterocyclic group, and $L^{9''}$ is alkyl.

Forty Eighth Step

In THF, DMF, dichloromethane, water, or the like, or a mixed solvent thereof, a base such as triethylamine, diisopropylamine or N-methylmorpholine, and isobutyl chloroformate, pivaloyl chloride, or the like are added to compound a'34-2, and the mixture is reacted at −20° C. to 60° C., and preferably at −5° C. to 20° C., for 0.5 hours to 24 hours, and preferably 1 hour to 4 hours, whereby compound a'34-6 can be obtained.

Forty Ninth Step

In THF, DMF, DMA, or the like, or a mixed solvent thereof, a reducing agent such as sodium borohydride or lithium borohydride is added to compound a'34-6, and the mixture is reacted at −20° C. to 80° C., and preferably at 0° C. to 50° C., for 1 hour to 24 hours, and preferably 2 hours to 6 hours, whereby compound a'34-7 can be obtained.

Fiftieth Step

In THF, DMF, DMA, or the like of methanesulfonic acid chloride, or a mixed solvent thereof, a base such as triethylamine, lutidine or N-methylmorpholine is added to compound a'34-7, and the mixture is reacted at 0° C. to 80° C., and preferably at 20° C. to 40° C., for 1 hour to 24 hours, and preferably 2 hours to 6 hours, whereby compound a'34-8 can be obtained.

Fifty First Step

In THF, DMF, DMA, or the like, or a mixed solvent thereof, sodium azide is added to compound a'34-8, and the mixture is reacted at 0° C. to 100° C., and preferably at 20° C. to 50° C., for 1 hour to 24 hours, and preferably 2 hours to 6 hours, whereby compound a'34-9 can be obtained.

Fifty Second Step

In ethanol, methanol, DMF, or the like, or a mixed solvent thereof, a palladium carbon is added to compound a'34-9, and the mixture is reacted under a hydrogen atmosphere at 0° C. to 100° C., and preferably at 20° C. to 50° C., for 1 hour to 24 hours, and preferably 2 hours to 6 hours, whereby compound a'34-10 can be obtained.

Fifty Third Step

In DMF, DMA, dichloromethane, or the like, or a mixed solvent thereof, an acid chloride derivative (B) that is commercially available or prepared by a known method and a base such as pyridine or lutidine are added to compound a'34-10, and the mixture is reacted at 0° C. to 100° C., and preferably at 20° C. to 50° C., for 1 hour to 24 hours, and preferably 2 hours to 6 hours, whereby compound a'34-11 can be obtained.

Alternatively, compound a'34-11 can be also obtained by adding a carboxylic acid derivative (C) that is commercially available or prepared by a known method and a condensing agent such as 1-hydroxy-7-azabenzotriazole, 1-hydroxybenzotriazole, cyclohexylcarbodiimide or diisopropylcarbodiimide, and a base such as triethylamine, diisopropylethylamine or N-methylmorpholine to compound a'34-10, in DMF, DMA, THF, acetonitrile, or the like, or a mixed solvent thereof, and reacting the mixture at 0° C. to 100° C., and preferably at 20° C. to 50° C., for 1 hour to 48 hours, and preferably 2 hours to 24 hours.

[Formula 110]

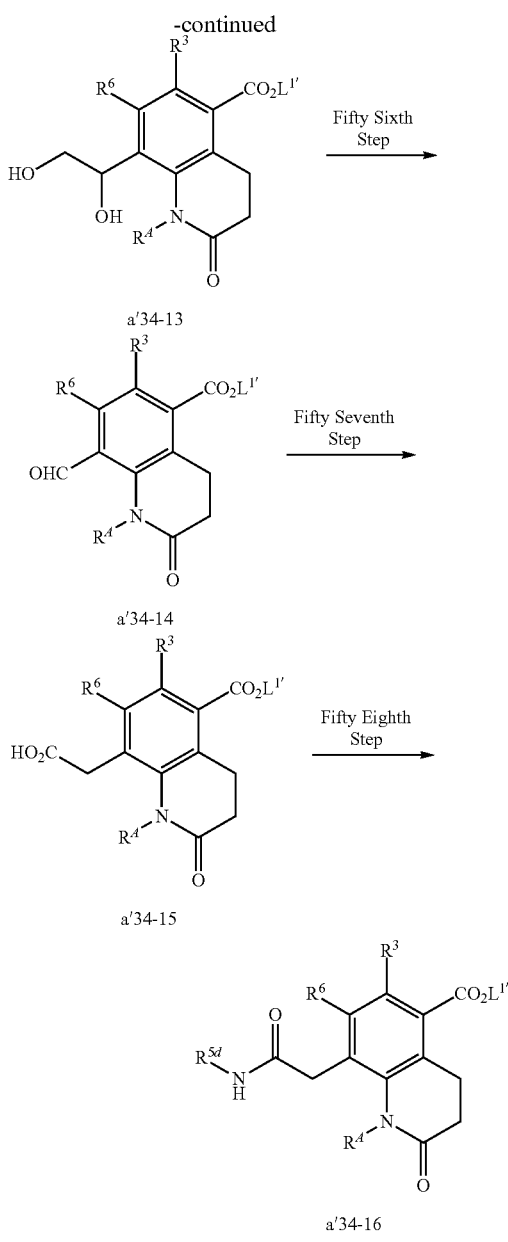

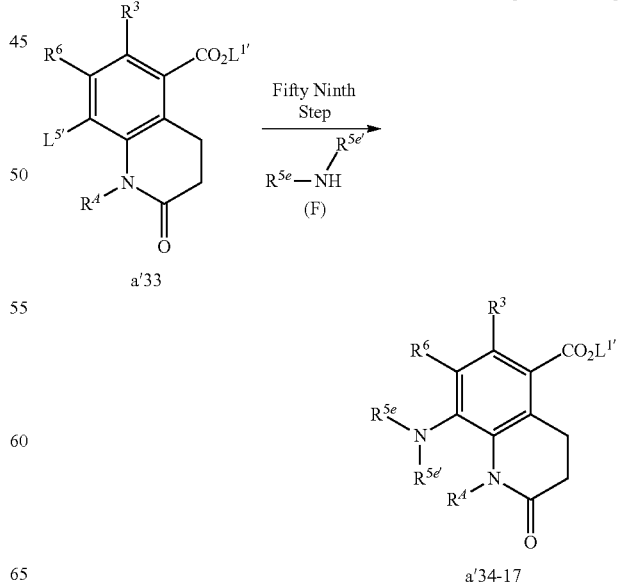

wherein $R^3$, $R^6$, $R^4$, $L^{1'}$, and $L^{5'}$ have the same meaning as described above, and $R^{5d}$ is substituted or unsubstituted alkyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group.

Fifty Fourth Step

In a solvent such as DMF, DMA, THF or acetonitrile, or in a mixed solvent thereof, a phosphine such as tri-tert-butylphosphine, tricyclohexylphosphine or triphenylphosphine, a catalyst such as dibenzylideneacetone palladium, palladium acetate or dichlorobistriphenylphosphine palladium, and a base such as N-methylmorpholine are added to compound a'33, and the mixture is reacted with ethylene gas at 30° C. to 180° C., and preferably at 50° C. to 150° C., for 1 hour to 48 hours, and preferably 4 hours to 24 hours, whereby compound a'34-12 can be obtained.

Fifty Fifth Step

In a mixed solvent of THF, acetonitrile, acetone, tert-butyl alcohol or the like and water or a phosphate buffer solution, an oxidizing agent such as N-methylmorpholine oxide or $K_3Fe(CN)_6$ and a catalytic amount of osmium tetroxide or dipotassium osmate dihydrate are added to compound a'34-12, and the mixture is reacted at 0° C. to 100° C., and preferably at 20° C. to 50° C., for 1 hour to 48 hours, and preferably 2 hours to 24 hours, whereby compound a'34-13 can be obtained.

Fifty Sixth Step

In a mixed solvent of THF, acetonitrile, chloroform or the like and water, sodium periodate is added to compound a'34-13, and the mixture is reacted at 0° C. to 100° C., and preferably at 0° C. to 30° C., for 1 hour to 48 hours, and preferably 2 hours to 6 hours, whereby compound a'34-14 can be obtained.

Fifty Seventh Step

In a mixed solvent of a buffer such as an aqueous sodium dihydrogen phosphate solution or a THF solution thereof and tert-butyl alcohol or the like, sodium chlorite, and amide sulfate, 2-methyl-2-butene, and the like are added to compound a'34-14, and the mixture is reacted at 0° C. to 80° C., and preferably at 0° C. to 50° C., for 1 hour to 48 hours, and preferably 2 hours to 24 hours, whereby compound a'34-15 can be obtained.

Fifty Eighth Step

In a solvent such as dichloromethane, tetrahydrofuran or dimethylformamide, a condensing agent such as 1-ethyl-3-(3-dimethylaminopropyl)carbodiimide, dicyclohexylcarbodiimide or O-(benzotriazol-1-yl)-N,N,N',N'-tetramethyluronium hexafluorophosphate is added to compound a'34-15, and an additive such as 1-hydroxy-7-azabenzotriazole, 1-hydroxybenzotriazol or N-hydroxysuccinimide is further added as necessary, and then a substituted amine (D) that is commercially available or prepared by a known method is sequentially added, and the mixture is reacted at 0° C. to 100° C., and preferably at 25° C. to 60° C., for 0.5 hours to 24 hours, and preferably 2 hours to 12 hours, whereby compound a'34-16 can be obtained.

[Formula 111]

wherein $R^3$, $R^6$, $R^4$, $L^{1'}$, and $L^{5'}$ have the same meaning as described above, and $R^{5e}$ and $R^{5e'}$ are each independently a hydrogen atom, formyl, carbamoyl, carboxy, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkylcarbamoyl, substituted or unsubstituted alkenylcarbamoyl, substituted or unsubstituted alkynylcarbamoyl, substituted or unsubstituted alkyloxycarbonyl, substituted or unsubstituted alkenyloxycarbonyl, substituted or unsubstituted alkynyloxycarbonyl, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclic carbonyl, substituted or unsubstituted nonaromatic carbocyclic carbonyl, substituted or unsubstituted aromatic heterocyclic carbonyl, substituted or unsubstituted nonaromatic heterocyclic carbonyl, substituted or unsubstituted aromatic carbocyclic carbamoyl, substituted or unsubstituted nonaromatic carbocyclic carbamoyl, substituted or unsubstituted aromatic heterocyclic carbamoyl, substituted or unsubstituted nonaromatic heterocyclic carbamoyl, substituted or unsubstituted aromatic carbocyclic oxycarbonyl, substituted or unsubstituted nonaromatic carbocyclic oxycarbonyl, substituted or unsubstituted aromatic heterocyclic oxycarbonyl, or substituted or unsubstituted nonaromatic heterocyclic oxycarbonyl, wherein $R^{5e}$ and $R^{5e'}$ may be taken together with an adjacent nitrogen atom to form a substituted or unsubstituted aromatic heterocyclic group or a substituted or unsubstituted nonaromatic heterocyclic group.

Fifty Ninth Step

In a solvent such as dimethylformamide, dimethylacetamide, tetrahydrofuran or dioxane, or in a mixed solvent thereof, a base such as sodium carbonate, potassium carbonate, cesium carbonate or potassium phosphate, a substituted amine (F) that is commercially available or prepared by a known method, a palladium catalyst such as Pd(PPh$_3$)$_4$, Pd(OAc)$_2$, Pd(PPh$_3$)$_2$Cl$_2$, Pd(dppf)$_2$Cl$_2$ or tris(dibenzylideneacetone)dipalladium, and a ligand such as 2,2'-bis(diphenylphosphino)-1,1'-binaphthyl or Xantphos are added to compound a'33, and the mixture is reacted at 50° C. to 180° C., and preferably at 70° C. to 150° C., for 0.1 hours to 8 hours, and preferably 0.5 to 2 hours, whereby compound a'34-17 can be obtained.

[Formula 112]

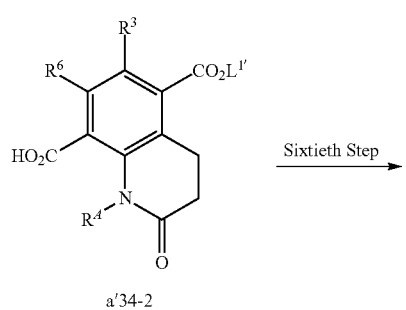

a'34-2

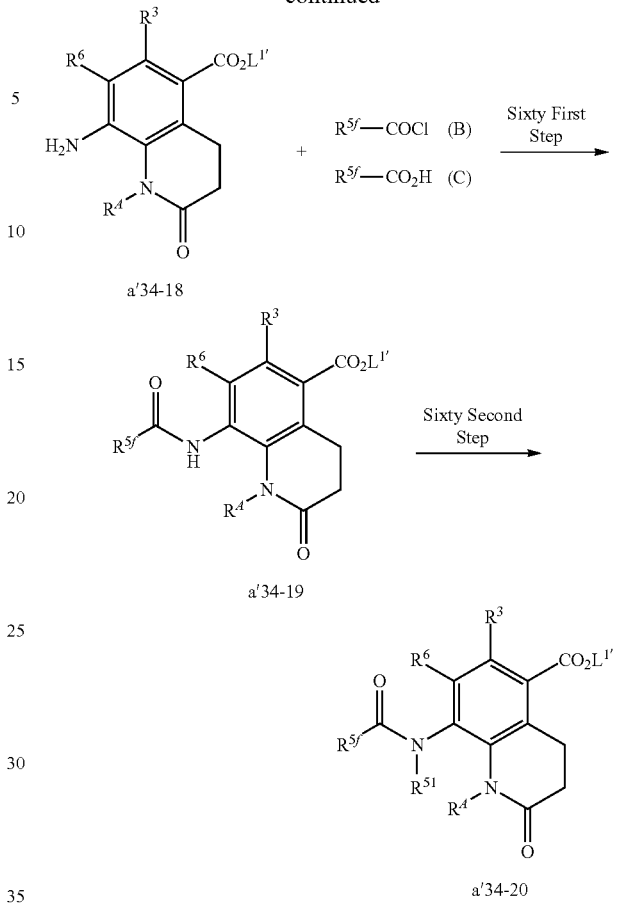

wherein $R^3$, $R^{51}$, $R^6$, $R^4$, and $L^{1'}$ have the same meaning as described above, and $R^{5f}$ is substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group.

Sixtieth Step

In DMF, toluene, benzene or the like, or a mixed solvent of those and water, diphenylphosphoryl azide and a base such as triethylamine, diisopropylethylamine or N-methylmorpholine are added to compound a'34-2, and the mixture is reacted at 20° C. to 100° C., and preferably at 50° C. to 80° C., for 1 hour to 24 hours, and preferably 2 hours to 6 hours, and thereafter, potassium hydroxide, sodium hydroxide, lithium hydroxide or the like is added, and the mixture is reacted at 0° C. to 100° C., and preferably at 20° C. to 50° C., for 1 hour to 24 hours, and preferably 2 hours to 6 hours, whereby compound a'34-18 can be obtained.

Sixty First Step

In a solvent such as dichloromethane, dichloroethane or THF, pyridine, triethylamine or N-methylmorpholine is added to compound a'34-18 as a base, and then an acylating reagent such as an acid chloride or acid anhydride that is commercially available or synthesized by a known method is sequentially added, and the mixture is reacted at −20° C. to 50° C., and preferably at 0° C. to 20° C., for 0.1 hours to 6 hours, and preferably 1 hour to 3 hours, whereby compound a'34-19 can be obtained.

Sixty Second Step

In a solvent such as THF, dimethylformamide or dimethylacetamide, a base such as sodium hydride, tert-butoxypotassium or lithium diisopropylamide, and then $R^{51}$—I, $R^{51}$—Br, $R^{51}$—Cl or the like that is commercially available or synthesized by a known method are added to compound a'34-19, and the mixture is reacted at 0° C. to 50° C., and preferably at 20° C. to 35° C., for 0.1 hours to 3 hours, and preferably 0.5 hours to 1 hour, whereby compound a'34-20 can be obtained.

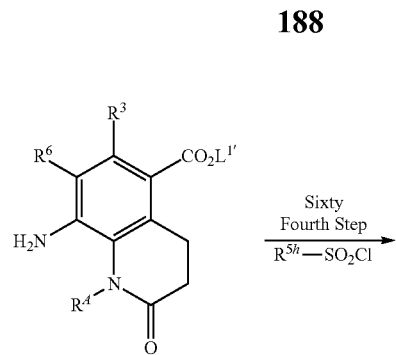

a'34-18

[Formula 114]

Sixty Fourth Step
$R^{5h}$—SO$_2$Cl

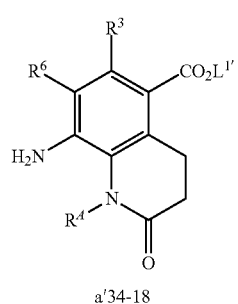

a'34-18

[Formula 113]

Sixty Third Step
$R^{5g}$—NCO

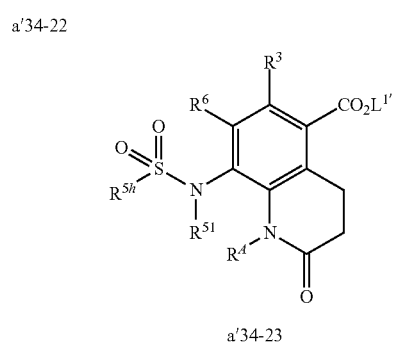

a'34-22

Sixty Fifth Step

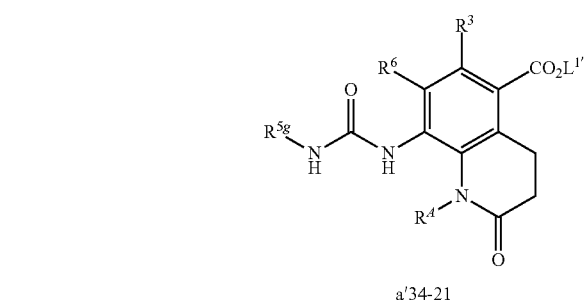

a'34-21

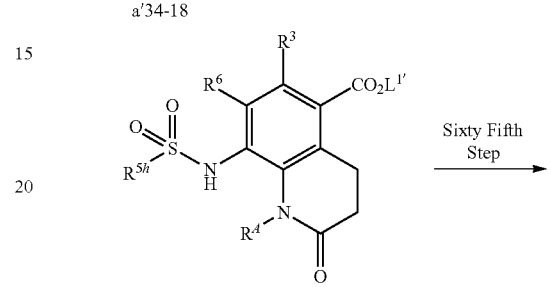

a'34-23 wherein $R^3$, $R^6$, $R^A$, and $L^{1'}$ have the same meaning as described above, and $R^{5g}$ is substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group.

Sixty Third Step

In a solvent such as toluene, acetonitrile or dichloroethane, $R^{5g}$—NCO that is commercially available or synthesized by a known method is added to compound a'34-18, and the mixture is reacted at 25° C. to 120° C., and preferably at 60° C. to 80° C., for 0.5 hours to 4 hours, and preferably 1 hour to 2 hours, whereby compound a'34-21 can be obtained.

In a solvent such as dichloromethane, THF or toluene, a base such as triethylamine or N-methylmorpholine is added to compound a'34-18, and reacted with triphosgene, thereby synthesizing an isocyanate form in the system. $R^{5g}NH_2$ that is commercially available or synthesized by a known method is added without taking out the isocyanate form from the reaction mixture, and the mixture is reacted at 0° C. to 50° C., and preferably at 20° C. to 35° C., for 0.1 hours to 6 hours, and preferably 0.5 hours to 2 hours, whereby compound a'34-21 can be obtained.

wherein $R^3$, $R^{51}$, $R^6$, $R^A$, and $L^{1'}$ have the same meaning as described above, and $R^{5h}$ is substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group or a substituted or unsubstituted nonaromatic heterocyclic group.

Sixty Fourth Step

In a solvent such as pyridine or lutidine, a substituted sulfonyl chloride that is commercially available or synthesized by a known method is added to compound a'34-18, and the mixture is reacted at 20° C. to 100° C., and preferably at 50° C. to 70° C., for 1 hour to 24 hours, and preferably 5 hours to 10 hours, whereby compound a'34-22 can be obtained.

Sixty Fifth Step

In a solvent such as dichloromethane, THF or dimethylformamide, a base such as sodium carbonate, potassium carbonate or cesium carbonate is added to compound a'34-22, and then $R^{51}$—I, $R^{51}$—Br, $R^{51}$—Cl or the like that is commercially available or synthesized by a known method is added, and the mixture is reacted at 0° C. to 80° C., and preferably at 25° C. to 50° C., for 1 hour to 12 hours, and preferably 3 hours to 6 hours, whereby compound a'34-23 can be obtained.

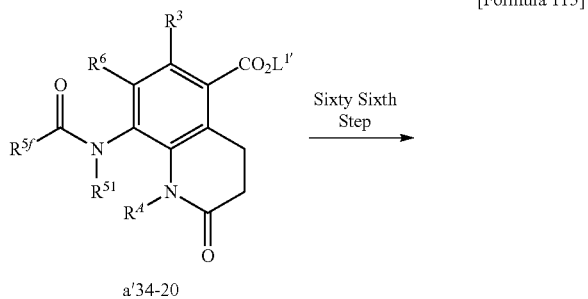

a'34-20

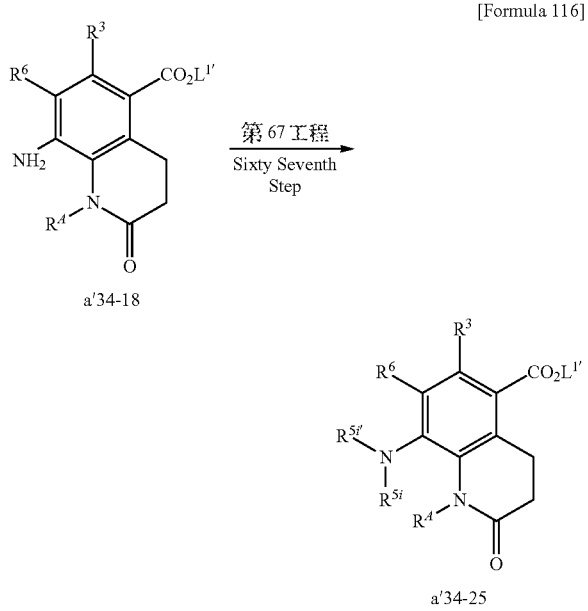

a'34-18 wherein each definition has the same meaning as described above.

Sixty Sixth Step

Compound a'34-20 in which $R^{5f}$ is trifluromethyl is dissolved in dimethyl sulfoxide, and an aqueous solution of a base such as sodium hydroxide, potassium hydroxide or lithium hydroxide is added, and the mixture is reacted at 30° C. to 150° C., and preferably at 80° C. to 120° C., for 1 hour to 10 hours, and preferably 3 hours to 6 hours, whereby compound a'34-24 can be obtained.

a'34-25 wherein $R^3$, $R^6$, $R^4$, and $L^{1'}$ have the same meaning as described above, and $R^{5i}$ and $R^{5i'}$ are each independently a hydrogen atom, formyl, carbamoyl, carboxy, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkylcarbamoyl, substituted or unsubstituted alkenylcarbamoyl, substituted or unsubstituted alkynylcarbamoyl, substituted or unsubstituted alkyloxycarbonyl, substituted or unsubstituted alkenyloxycarbonyl, substituted or unsubstituted alkynyloxycarbonyl, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclic carbonyl, substituted or unsubstituted nonaromatic carbocyclic carbonyl, substituted or unsubstituted aromatic heterocyclic carbonyl, substituted or unsubstituted nonaromatic heterocyclic carbonyl, substituted or unsubstituted aromatic carbocyclic carbamoyl, substituted or unsubstituted nonaromatic carbocyclic carbamoyl, substituted or unsubstituted aromatic heterocyclic carbamoyl, substituted or unsubstituted nonaromatic heterocyclic carbamoyl, substituted or unsubstituted aromatic carbocyclic oxycarbonyl, substituted or unsubstituted nonaromatic carbocyclic oxycarbonyl, substituted or unsubstituted aromatic heterocyclic oxycarbonyl, or substituted or unsubstituted nonaromatic heterocyclic oxycarbonyl, wherein $R^{5i}$ and $R^{5i'}$ may be taken together with an adjacent nitrogen atom to form a substituted or unsubstituted aromatic heterocyclic group or a substituted or unsubstituted nonaromatic heterocyclic group.

Sixty Seventh Step

In a solvent such as dichloromethane, THF or dimethylformamide, an acid such as acetic acid or trifluoroacetic acid and an aldehyde or ketone that is commercially available or synthesized by a known method are added to compound a'34-18, and the mixture is stirred at 0° C. to 100° C., and preferably at 25° C. to 60° C., for 0.5 hours to 24 hours, and preferably 3 hours to 12 hours, and thereafter, a reducing agent such as $NaBH_4$, $NaBH_3CN$ or $NaBH(OAc)_3$ is added, and the mixture is reacted at 0° C. to 100° C., and preferably at 25° C. to 60° C., for 0.5 hours to 24 hours, and preferably 3 hours to 12 hours, whereby compound a'34-25 can be obtained.

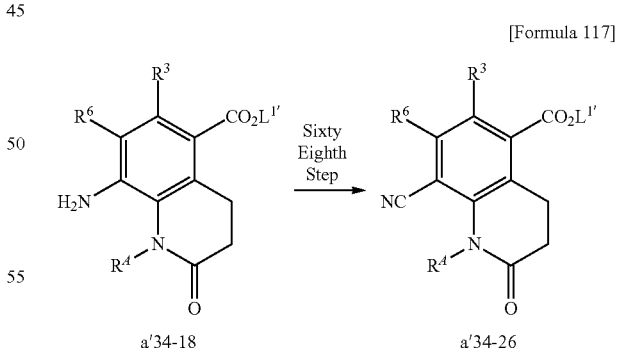

a'34-18            a'34-26 wherein each definition has the same meaning as described above.

Sixty Eighth Step

In a solvent such as acetonitrile, dimethylformamide or dimethylsulfoxide, a diazotization reagent such as tert-butyl nitrite or isopentyl nitrite and a cyanide such as cuprous cyanide, sodium cyanide or potassium cyanide are added to compound a'34-18, and the mixture is reacted at 0° C. to 100°

C., and preferably at 40° C. to 70° C., for 1 hour to 12 hours, and preferably 3 hours to 6 hours, whereby compound a'34-26 can be obtained.

[Formula 118]

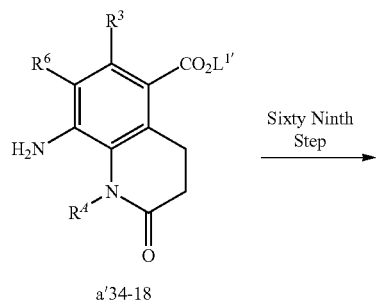

a'34-18

Sixty Ninth Step

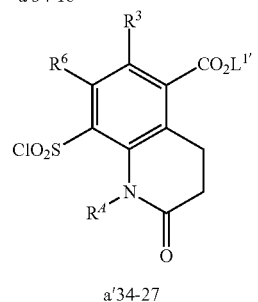

a'34-27

Seventieth Step
$R^{5j}-\overset{H}{N}-R^{5j'}$

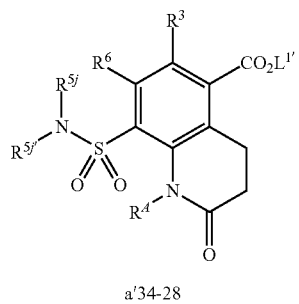

a'34-28 wherein $R^3$, $R^6$, $R^4$, and $L^{1'}$ have the same meaning as described above, and $R^{5j}$ and $R^{5j'}$ are each independently substituted or unsubstituted alkyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, wherein $R^{5j}$ and $R^{5j'}$ may be taken together with an adjacent nitrogen atom to form a substituted or unsubstituted aromatic heterocyclic group or a substituted or unsubstituted nonaromatic heterocyclic group.

Sixty Ninth Step

Compound a'34-18 is suspended in concentrated hydrochloric acid, and diazotized with sodium nitrite according to a known method, and then sulfurous acid and an acetic acid solution of cuprous chloride are added, and the mixture is reacted at −20° C. to 20° C., and preferably at −5° C. to 10° C., for 0.1 hours to 6 hours, and preferably 0.5 hours to 3 hours, whereby compound a'34-27 can be obtained.

Also, compound a'34-27 can be obtained as well by using thionyl chloride, instead of sulfurous acid and the acetic acid solution of cuprous chloride.

Seventieth Step

In a solvent such as dichloromethane, toluene or tetrahydrofuran, a base such as triethylamine, N-methylmorpholine or pyridine is added to compound a'34-27, and then an amine that is commercially available or synthesized by a known method is sequentially added, and the mixture is reacted at 0° C. to 100° C., and preferably at 25° C. to 60° C., for 0.5 hours to 24 hours, and preferably 2 hours to 12 hours, whereby compound a'34-28 can be obtained.

[Formula 119]

![Structure of a'33 with Sixty First Step arrow labeled $R^{5k}$—OK, Na]

a'33

![Structure of a'34-29]

a'34-29 wherein $R^3$, $R^6$, $R^4$, $L^{1'}$, and $L^{5'}$ have the same meaning as described above, and $R^{5k}$ is substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group.

Seventy First Step

In DMF, DMA, THF, dioxane, or the like, or a mixed solvent thereof, $R^{5k}$—OK or $R^{5k}$—ONa that is commercially available or prepared by a known method is added to compound '33, and the mixture is reacted at 20° C. to 200° C., and preferably at 50° C. to 100° C., for 1 hour to 48 hours, and preferably 2 hours to 24 hours, whereby compound '34-29 can be obtained.

[Formula 120]

![Structure of a'33 with Seventy Second Step arrow]

a'33

[Formula 121]

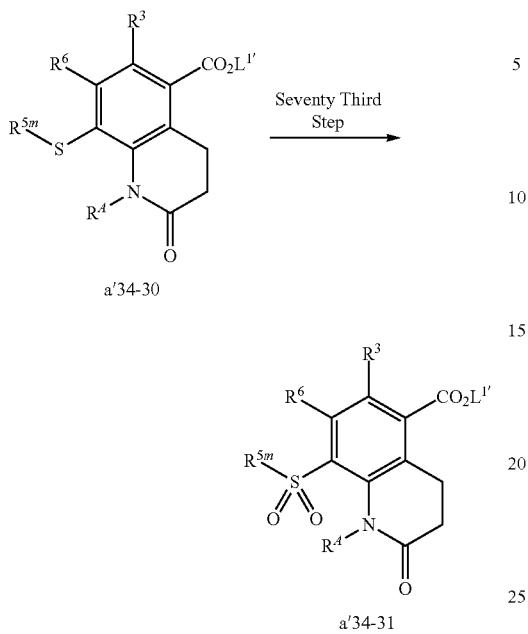

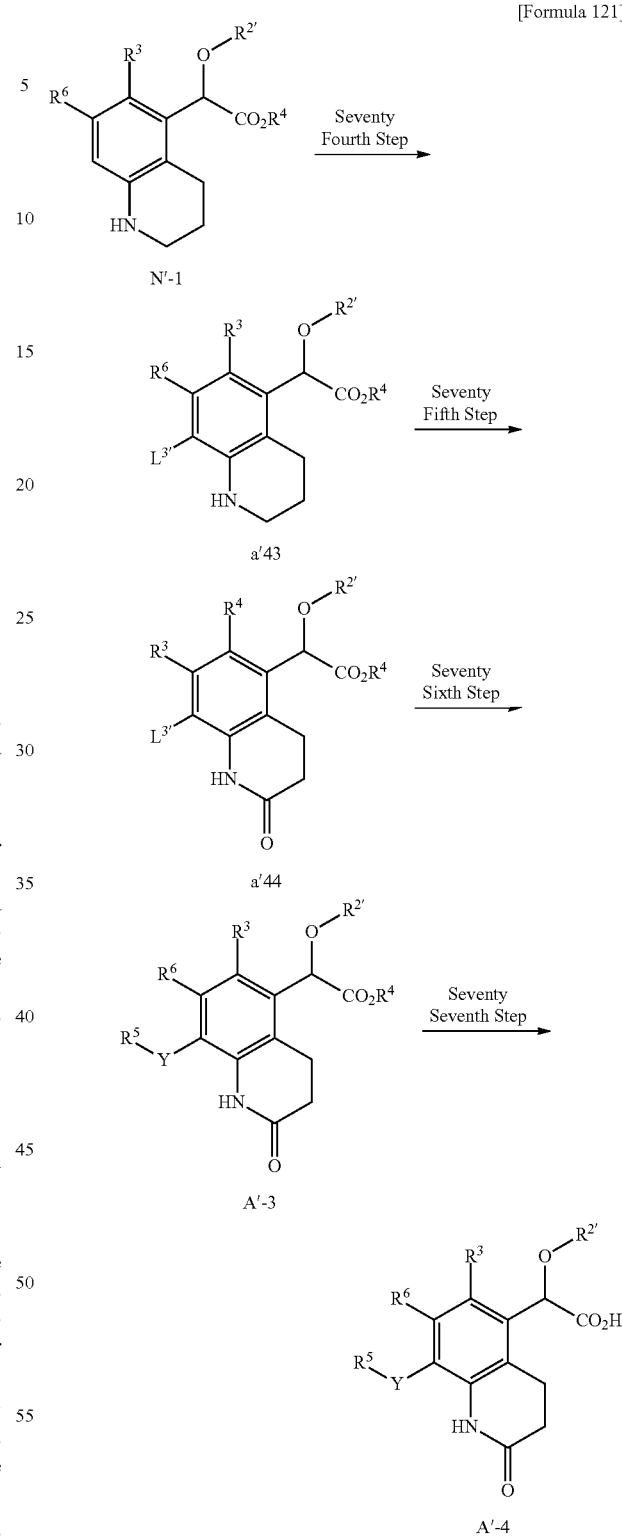

wherein $R^3$, $R^6$, $R^4$, $L^{1'}$, and $L^{5'}$ have the same meaning as described above, and $R^{5m}$ is a substituted or unsubstituted aromatic carbocyclic group.

Seventy Second Step

In a solvent such as dichloromethane, tetrahydrofuran or dimethylformamide, a base such as potassium carbonate, sodium carbonate or cesium carbonate is added to compound a'33, and then $R^{5m}$SH that is commercially available or synthesized by a known method is sequentially added, and the mixture is reacted at 0° C. to 100° C., and preferably at 25° C. to 60° C., for 0.1 hours to 12 hours, and preferably 0.5 hours to 3 hours, whereby compound a'34-30 can be obtained.

Seventy Third Step

In a solvent such as dichloromethane or chloroform, m-chloroperoxybenzoic acid is added to compound a'34-30, and the mixture is reacted at −20° C. to 50° C., and preferably at 0° C. to 25° C., for 0.1 hours to 3 hours, and preferably 0.5 hours to 2 hours, whereby compound a'34-31 can be obtained.

Also, compound a'34-31 can be obtained by adding oxone to compound a'34-30 in a mixed solvent of a solvent such as acetone or tetrahydrofuran and water, and reacting the mixture at 0° C. to 100° C., and preferably at 25° C. to 60° C., for 0.5 hours to 24 hours, and preferably 3 hours to 12 hours.

From compounds a'34-2 to a'34-31 obtained by any method described above, introduction of various substituents into —Y—$R^5$ is possible in compound A'-1 by the same method as in the thirty seventh step.

Also, introduction of various substituents into —Y—$R^5$ is possible in compound A'-1 by synthesizing, from compound a'5, a compound in which various substituents are introduced into —Y—$R^5$ of compound a'7 in the same manner as any method described above, and further by the same method as in the seventh to sixteenth steps.

From compound N'-1 described below, A'-3 and A'-4 can be also synthesized using the method shown below.

wherein each definition has the same meaning as described above.

Seventy Fourth Step

From compound N'-1, compound a'43 can be obtained in the same manner as in the thirteenth step.

Seventy Fifth Step

In a mixed solvent of tert-butanol and water, an acid such as acetic acid or a base such as sodium bicarbonate, and potassium permanganate are added to compound a'43, and the mixture is reacted at 0° C. to 100° C., and preferably at 20° C. to 60° C., for 0.25 hours to 24 hours, and preferably 0.5 hours to 2 hours, whereby compound a'44 can be obtained.

Seventy Sixth Step

From compound a'44, compound A'-3 can be obtained in the same manner as in the fourth step.

Seventy Seventh Step

From compound A'-3, compound A'-4 can be obtained in the same manner as in the seventeenth step.

34) Synthesis of Compounds A'-5 and A'-6

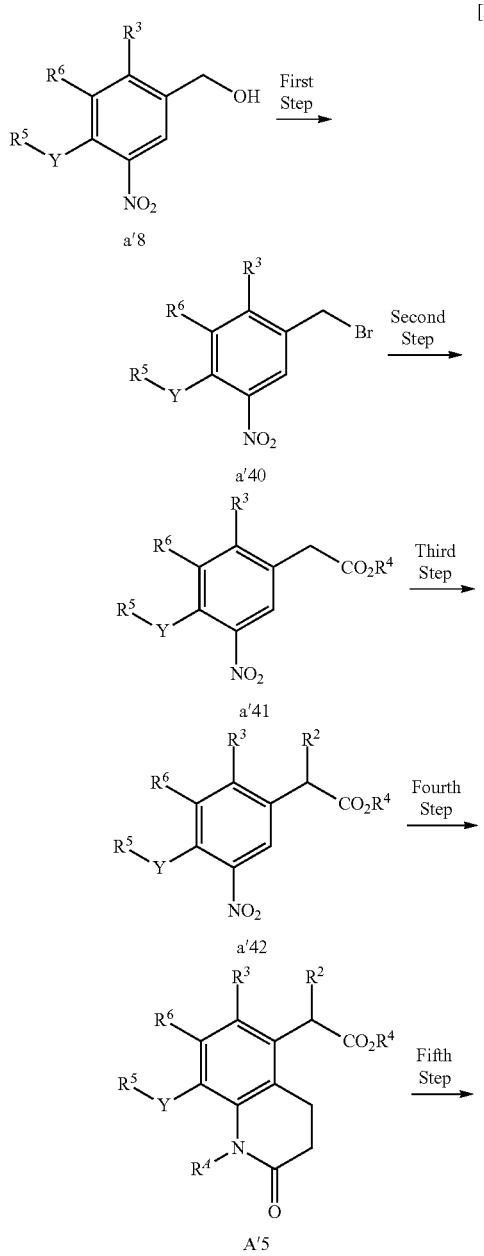

[Formula 122]

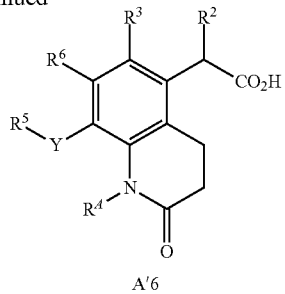

A'6 wherein each definition has the same meaning as described above.

First Step

In a solvent such as methylene chloride, toluene or THF, phosphorus tribromide, thionyl bromide or the like is added to compound a'8, and the mixture is reacted at −20° C. to 120° C., and preferably at 0° C. to 60° C., for 0.1 hours to 12 hours, and preferably 1 hour to 4 hours, whereby compound a'40 can be obtained.

Second Step

In a solvent such as DMF, DMSO, dioxane or toluene, a palladium catalyst such as $Pd(PPh_3)_4$, $Pd(OAc)_2$, $Pd(PPh_3)_2Cl_2$ or $PdCl_2(dppf)_2$, a base such as triethylamine or N-methylmorpholine, and $R^4OH$ are added to compound a'40, and the mixture is reacted under a carbon monoxide atmosphere at 0° C. to 150° C., and preferably at 50° C. to 100° C., for 1 hour to 24 hours, and preferably 3 hours to 12 hours, whereby compound a'41 can be obtained.

Third Step

In a solvent such as THF, diethyl ether or toluene, a base such as lithium diisopropylamide, potassium hexamethyldisilazide, lithium hexamethyldisilazide or sodium hexamethyldisilazide, and an alkyl halide such as $R^2$—I, $R^2$—Br or $R^2$—Cl are added to compound a'41, and the mixture is reacted at −70° C. to 50° C., and preferably at −20° C. to 20° C., for 1 hour to 24 hours, and preferably 3 hours to 10 hours, whereby compound a'42 can be obtained.

Fourth Step

From compound a'42, compound A'5 can be obtained in the same manner as in the twelfth to sixteenth steps in "33) Synthesis of Compounds A'-1 to A'-4" described above.

Fifth Step

From compound A'-5, compound A'-6 can be obtained in the same manner as in the seventeenth step in "33) Synthesis of Compounds A'-1 to A'-4" described above.

35) Synthesis of Compounds B'-1 and B'-2

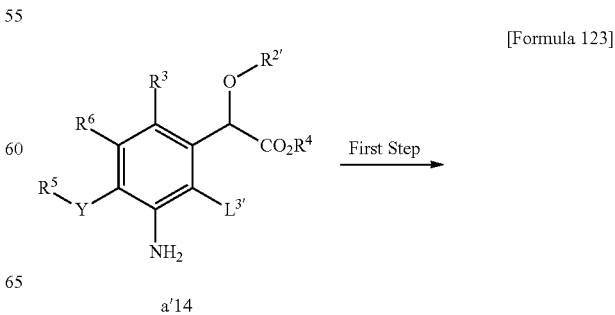

[Formula 123]

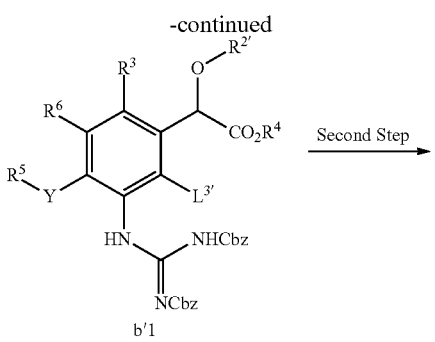

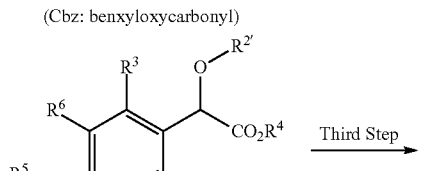

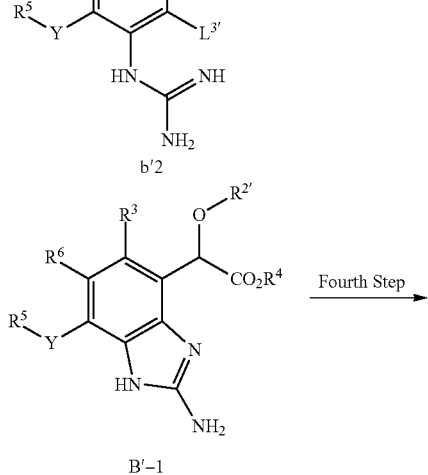

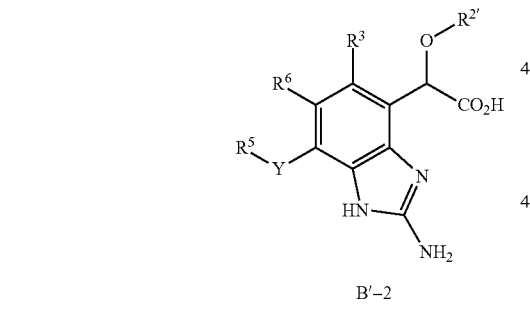

wherein each definition has the same meaning as described above.

First Step

In a solvent such as DMF, DMA, THF or dioxane, or in a mixed solvent thereof, a base such as triethylamine or diisopropylethylamine, and 1,3-dibenzyloxycarbonylamino-2-methyl-isothiourea synthesized by a known method are added to compound a'14, and the mixture is reacted at 0° C. to 80° C., and preferably at 20° C. to 60° C., for 0.5 hours to 8 hours, and preferably 1 to 2 hours, whereby compound b'1 can be obtained.

Second Step

In a solvent such as methanol, ethanol, propanol or butanol, or in a mixed solvent thereof, Pd/C is added to compound b'1 under a hydrogen atmosphere, and the mixture is reacted at 0° C. to 80° C., and preferably at 20° C. to 60° C., for 1 hour to 8 hours, and preferably 2 to 4 hours, whereby compound b'2 can be obtained.

Third Step

In a solvent such as DMF, DMA, THF or dioxane, or in a mixed solvent thereof, a base such as triethylamine or diisopropylethylamine, and copper iodide are added to compound b'2, and the mixture is reacted at 50° C. to 200° C., and preferably at 80° C. to 170° C., for 0.5 hours to 8 hours, and preferably 2 to 4 hours, whereby compound B'-1 can be obtained.

Fourth Step

In a solvent such as methanol, ethanol, propanol, butanol or water, or in a mixed solvent thereof, lithium hydroxide, sodium hydroxide, potassium hydroxide, or the like is added to compound B'-1, and the mixture is reacted at 20° C. to 100° C., and preferably at 40° C. to 80° C., for 0.5 hours to 8 hours, and preferably 1 to 4 hours, whereby compound B'-2 can be obtained.

36) Synthesis of Compounds C'-1 and C'-2

[Formula 124]

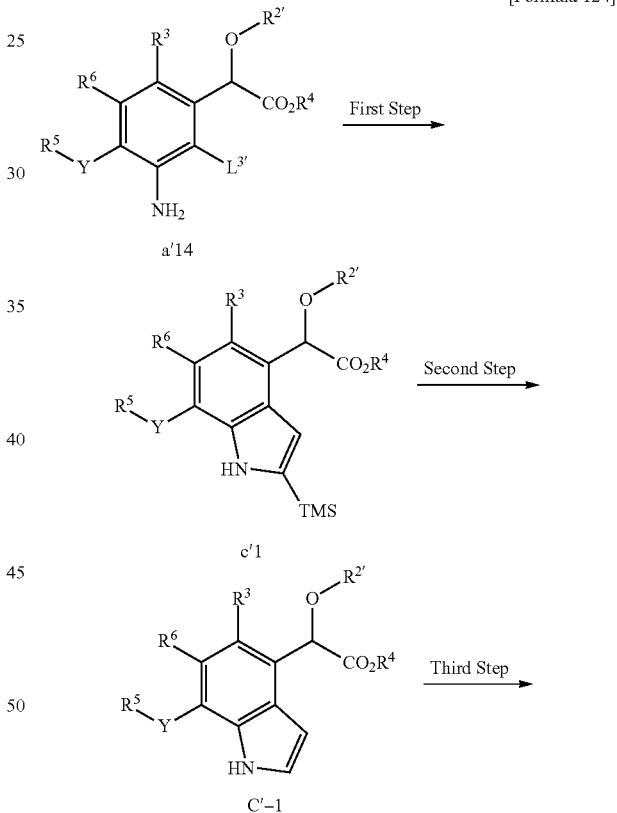

wherein each definition has the same meaning as described above.

First Step

In a solvent such as DMF, DMA, THF or dioxane, or in a mixed solvent thereof, silylacetylene, a base such as $Na_2CO_3$, $K_2CO_3$, $Cs_2CO_3$ or $K_3PO_4$, a catalyst such as dibenzylideneacetone palladium, palladium acetate or dichlorobistriphenylphosphine palladium, and an additive such as lithium chloride or tetrabutylammonium chloride are added to trimethyl compound a'14, and the mixture is reacted at 20° C. to 150° C., and preferably at 50° C. to 120° C., for 0.5 hours to 8 hours, and preferably 1 to 2 hours, whereby compound c'1 can be obtained.

Second Step

In a solvent such as DMF, DMA, THF or dioxane, or in a mixed solvent thereof, tetrabutylammonium fluoride is added to compound c'1, and the mixture is reacted at 0° C. to 80° C., and preferably at 20° C. to 60° C., for 0.5 hours to 8 hours, and preferably 1 to 4 hours, whereby compound C'-1 can be obtained.

Third Step

In a solvent such as methanol, ethanol, propanol, butanol or water, or in a mixed solvent thereof, a base such as lithium hydroxide, sodium hydroxide or potassium hydroxide is added to compound C'-1, and the mixture is reacted at 20° C. to 100° C., and preferably at 40° C. to 80° C., for 0.5 hours to 8 hours, and preferably 1 to 4 hours, whereby compound C'-2 can be obtained.

37) Synthesis of Compounds D'-1 and D'-2

[Formula 125]

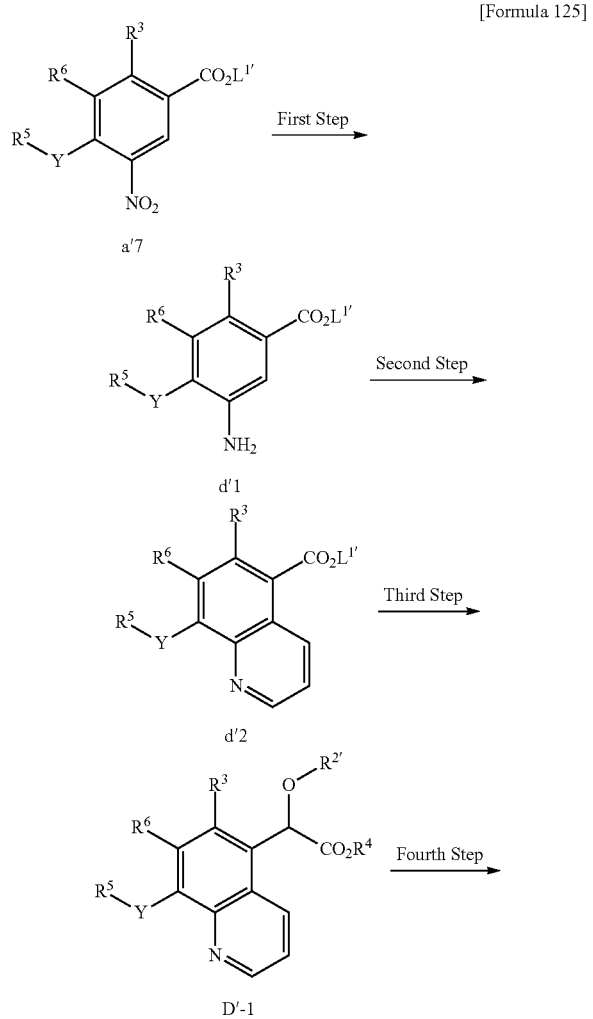

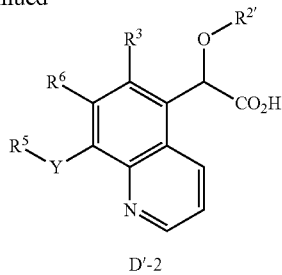

wherein each definition has the same meaning as described above.

First Step

From compound a'7, compound d'1 can be obtained in the same manner as in the twelfth step in "33) Synthesis of Compounds A'-1 to A'-4" described above.

Second Step

Compound d'1 is mixed with glycerin, nitrobenzene, and a 75% sulfuric acid aqueous solution, and the mixture is reacted at 80° C. to 180° C., and preferably at 120° C. to 150° C., for 1 hour to 12 hours, and preferably 2 hours to 6 hours, whereby compound d'2 can be obtained.

Third Step

From compound d'2, compound D'-1 can be obtained in the same manner as in the seventh to eleventh steps in "33) Synthesis of Compounds A'-1 to A'-4" described above.

Fourth Step

From compound D'-1, compound D'-2 can be obtained in the same manner as in the seventeenth step in "33) Synthesis of Compounds A'-1 to A'-4" described above.

38) Synthesis of Compounds D'-3 and D'-4

[Formula 126]

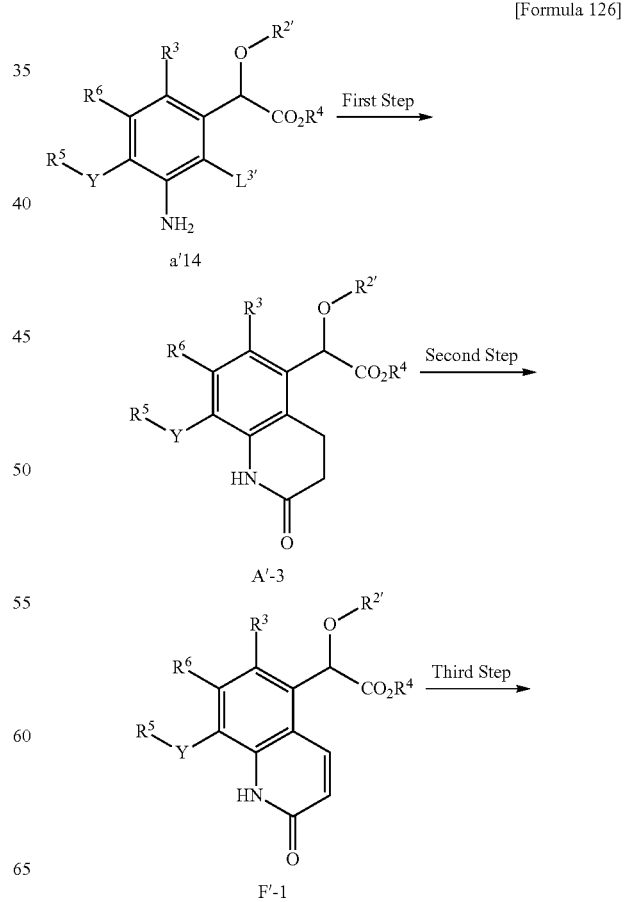

201

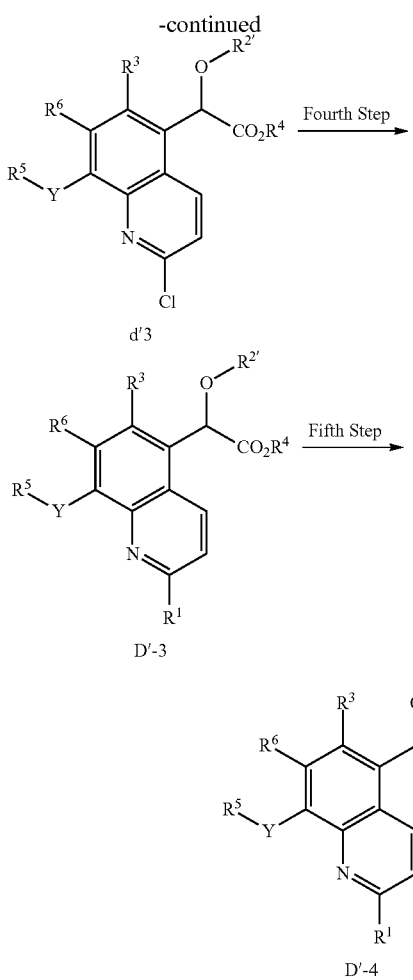

wherein each definition has the same meaning as described above.

First Step

From compound a'14, compound A'-3 can be obtained in the same manner as in the fourteenth to fifteenth steps in "33) Synthesis of Compounds A'-1 to A'-4" described above.

Second Step

From compound A'-3, compound F'-1 can be obtained in the same manner as in the first step in "40) Synthesis of Compounds F'-1 to F'-6" described below.

Third Step

In a solvent such as toluene, acetonitrile, chloroform or dichloromethane, or in a mixed solvent thereof, phosphorus trichloride is added to compound F'-1, and the mixture is reacted at 0° C. to 150° C., and preferably at 20° C. to 110° C., for 0.1 hours to 8 hours, and preferably 0.5 to 2 hours, whereby compound d'3 can be obtained.

Fourth Step

From compound d'3, compound D'-3 can be obtained in the same manner as in the fourth step in "33) Synthesis of Compounds A'-1 to A'-4" described above.

Fifth Step

From compound D'-3, compound D'-4 can be obtained in the same manner as in the seventeenth step in "33) Synthesis of Compounds A'-1 to A'-4" described above.

202

39) Synthesis of Compounds E'-1 to E'-4

[Formula 127]

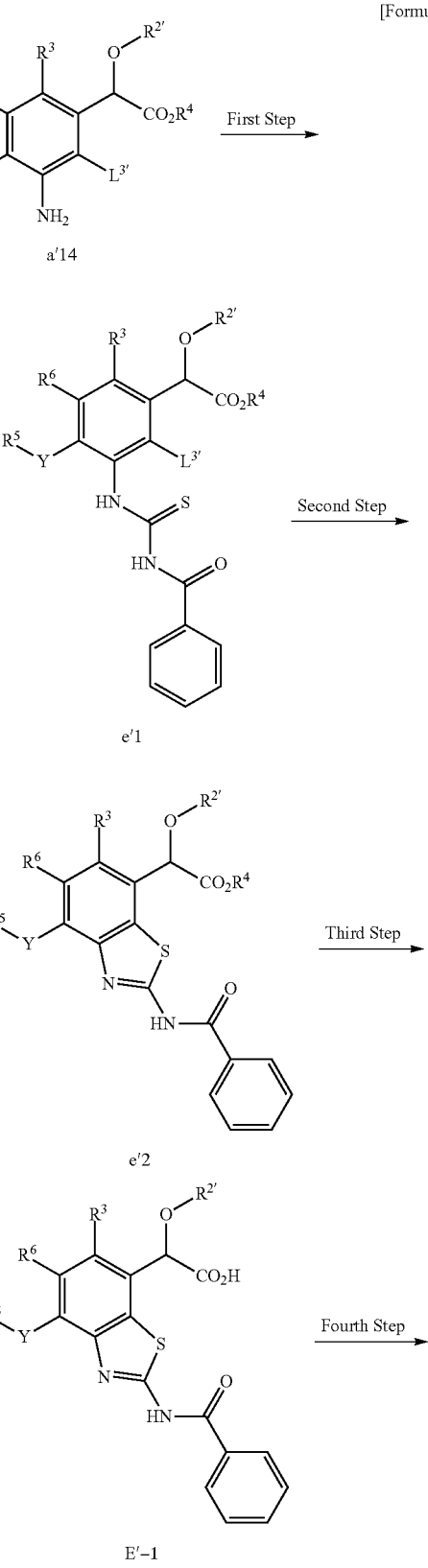

E'-2 wherein each definition has the same meaning as described above.

First Step

In a solvent such as acetone, tetrahydrofuran or ethyl acetate, benzoyl isothiocyanate that is commercially available or synthesized by a known method is added to compound a'14, and the mixture is reacted at 0° C. to 80° C., and preferably at 25° C. to 50° C., for 0.1 hours to 6 hours, and preferably 0.5 hours to 3 hours, whereby compound e'1 can be obtained.

Second Step

In a solvent such as tetrahydrofuran or dimethylformamide, a base such as sodium hydride, potassium tert-butoxide or sodium methoxide is added to compound e'1, and the mixture is reacted at 25° C. to 140° C., and preferably at 50° C. to 100° C., for 0.5 hours to 12 hours, and preferably 1 hour to 6 hours, whereby compound e'2 can be obtained.

Third Step

In a solvent such as methanol, ethanol, THF or DMSO, or in a mixed solvent thereof, a base such as potassium hydroxide, sodium hydroxide or lithium hydroxide is added to compound e'2, and the mixture is reacted at 0° C. to 100° C., and preferably at 20° C. to 50° C., for 0.1 hours to 24 hours, and preferably 1 hour to 6 hours, whereby compound E'-1 can be obtained.

Fourth Step

In a solvent such as methanol, ethanol, THF or DMSO, or in a mixed solvent thereof, a base such as potassium hydroxide, sodium hydroxide or lithium hydroxide is added to compound E'-1, and the mixture is reacted at 25° C. to 120° C., and preferably at 70° C. to 100° C., for 1 hour to 48 hours, and preferably 2 hours to 12 hours, whereby compound E'-2 can be obtained.

[Formula 128]

E'-2

E'-3

E'-2

E'-4 wherein each definition has the same meaning as described above.

Fifth Step

In a solvent such as DMF, THF or acetonitrile, a base such as potassium carbonate, sodium carbonate, cesium carbonate, pyridine or triethylamine and halogenated alkyl such as $R^{41}$—I, $R^{41}$—Br or $R^{41}$—Cl that is commercially available or synthesized by a known method or an acylating reagent such as an acid chloride or acid anhydride are added to compound E'-2, and the mixture is reacted at −10° C. to 80° C., and preferably at 0° C. to 50° C., for 0.1 hours to 6 hours, and preferably 0.5 hours to 3 hours, whereby compound E'-3 can be obtained.

Sixth Step

In a solvent such as tetrahydrofuran or ethyl acetate, substituted isothiocyanate that is commercially available or synthesized by a known method is added to compound E'-2, and the mixture is reacted at 0° C. to 80° C., and preferably at 25° C. to 50° C., for 0.1 hours to 6 hours, and preferably 0.5 hours to 3 hours, whereby compound E'-4 can be obtained.

40) Synthesis of Compounds F'-1 to F'-6

[Formula 129]

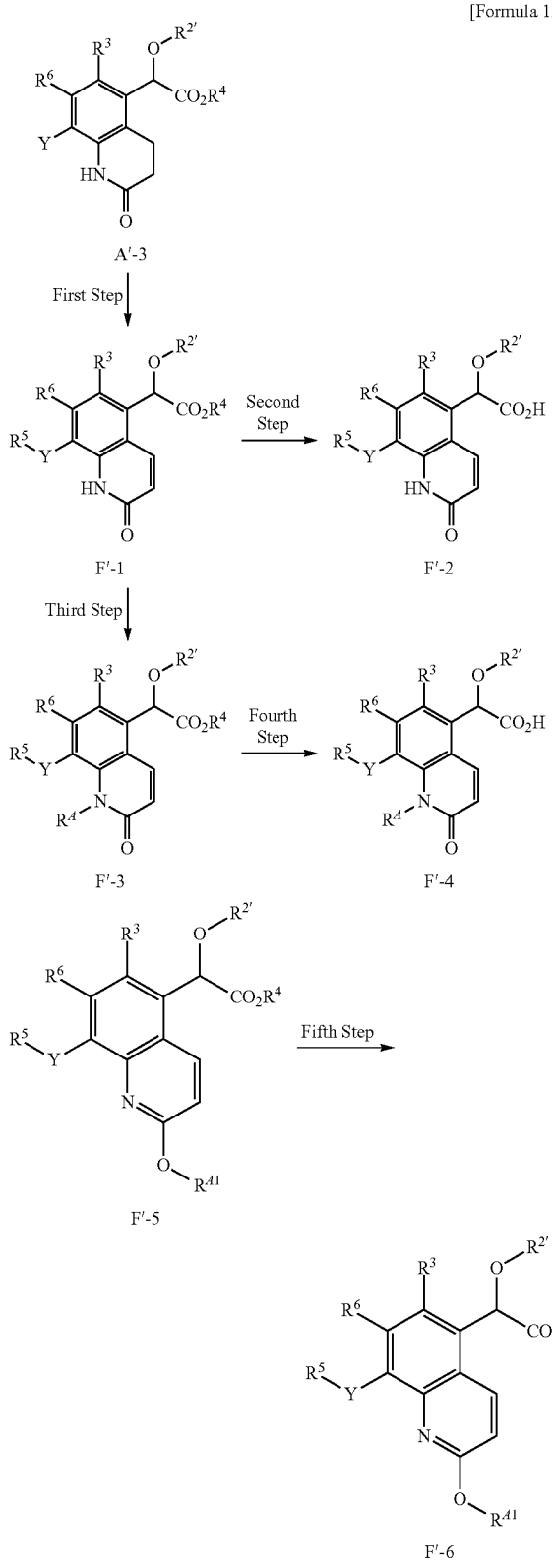

wherein each definition has the same meaning as described above.

First Step

In a solvent such as DMF, acetone, dioxane, toluene or 2-propanol, 2,3-dichloro-5,6-dicyano-p-benzoquinone is added to compound A'-3, and the mixture is reacted at 0° C. to 150° C., and preferably at 50° C. to 100° C., for 1 hour to 72 hours, and preferably 6 hours to 48 hours, whereby compound F'-1 can be obtained.

Second Step

From compound F'-1, compound F'-2 can be obtained in the same manner as in the seventeenth step in "33) Synthesis of Compounds A'-1 to A'-4" described above.

Third Step

From compound F'-1, compounds F'-3 and F'-5 can be obtained in the same manner as in the third step in "39) Synthesis of Compounds E'-1 to E'-4" described above.

Fourth Step

From compound F'-3, compound F'-4 can be obtained in the same manner as in the seventeenth step in "33) Synthesis of Compounds A'-1 to A'-4" described above.

Fifth Step

From compound F'-5, compound F'-6 can be obtained in the same manner as in the seventeenth step in "33) Synthesis of Compounds A'-1 to A'-4" described above.

41) Synthesis of Compounds G'-1 and G'-2

[Formula 130]

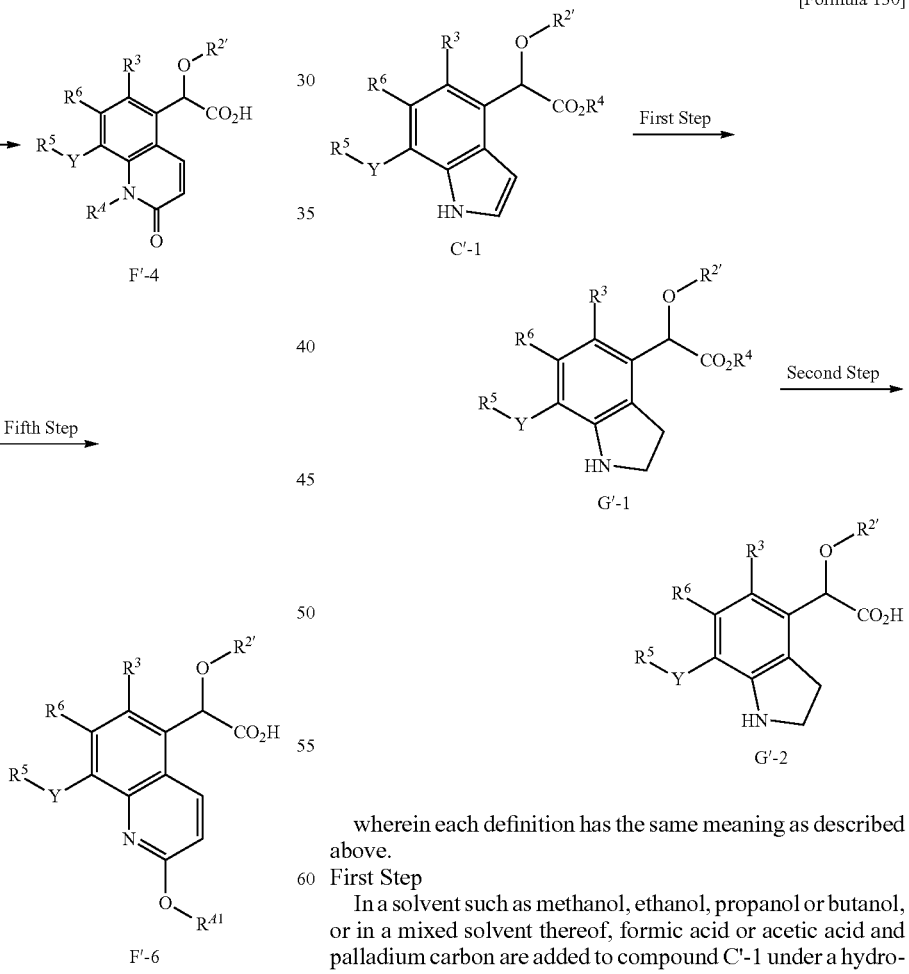

wherein each definition has the same meaning as described above.

First Step

In a solvent such as methanol, ethanol, propanol or butanol, or in a mixed solvent thereof, formic acid or acetic acid and palladium carbon are added to compound C'-1 under a hydrogen atmosphere, and the mixture is reacted at 20° C. to 100° C., and preferably at 40° C. to 80° C., for 1 hour to 24 hours, and preferably 3 to 8 hours, whereby compound G'-1 can be obtained.

Second Step

In a solvent such as methanol, ethanol, propanol, butanol or water, or in a mixed solvent thereof, a base such as lithium hydroxide, sodium hydroxide or potassium hydroxide is added to compound G'-1, and the mixture is reacted at 20° C. to 100° C., and preferably at 40° C. to 80° C., for 0.5 hours to 8 hours, and preferably 1 to 4 hours, whereby compound G'-2 can be obtained.

42) Synthesis of Compounds H'-1 and H'-2

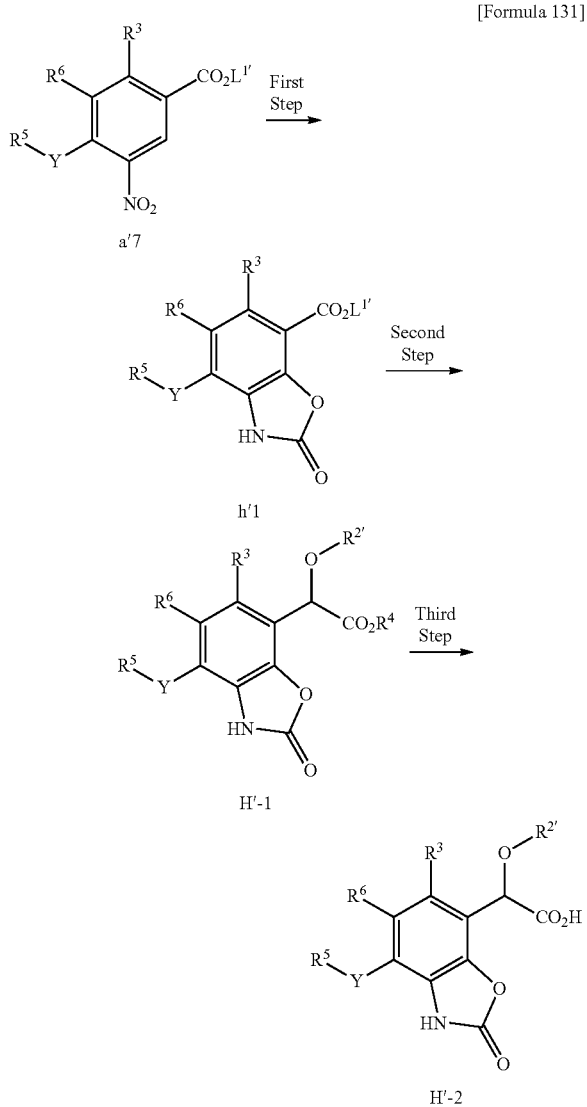

[Formula 131]

wherein each definition has the same meaning as described above.

First Step

In a mixed solvent of water and tetrahydrofuran, benzyl chlorocarbonate, zinc, and ammonium chloride are added to compound a'7, and the mixture is reacted at 0° C. to 80° C., and preferably at 25° C. to 50° C., for 0.1 hours to 6 hours, and preferably 0.5 hours to 3 hours, to give N,O-biscarbonate form of hydroxyamine. In a solvent of toluene or xylene, the resulting substance is reacted at 80° C. to 180° C., and preferably at 120° C. to 180° C., for 0.5 hours to 12 hours, and preferably 1 hour to 6 hours, whereby compound h'1 can be obtained.

Second Step

From compound h'1, compound H'-1 can be obtained in the same manner as in the seventh to eleventh steps in "33) Synthesis of Compounds A'-1 to A'-4" described above.

Third Step

From compound H'-1, compound H'-2 can be obtained in the same manner as in the seventeenth step in "33) Synthesis of Compounds A'-1 to A'-4" described above.

43) Synthesis of Compounds I'-1 and I'-2

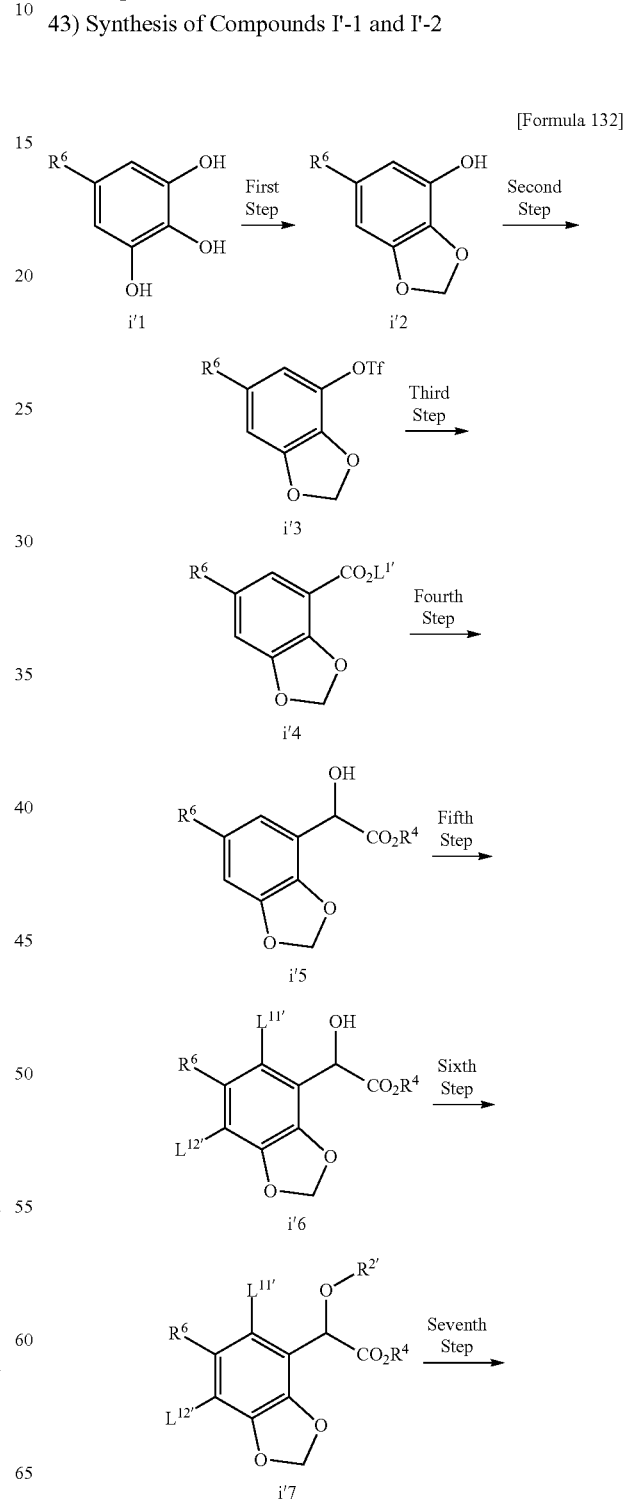

[Formula 132]

-continued

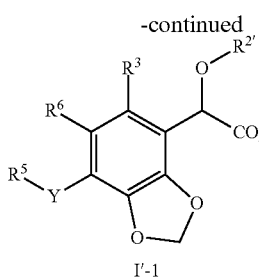

I'-1

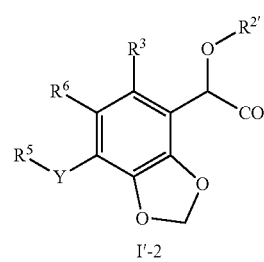

I'-2 wherein $R^{2'}$, $R^3$, $R^4$, $R^5$, $R^6$, Y, and $L^{1'}$ have the same meaning as described above, $L^{11'}$ is halogen, and $L^{12'}$ is halogen.

First Step

In a solvent such as DMF, DMSO, acetone, dioxane, acetonitrile or water, or in a mixed solvent thereof, a base such as potassium carbonate, cesium carbonate or potassium fluoride, and dihalomethane such as dibromomethane or diiodomethane are added to compound i'1 that is commercially available or synthesized by a known method, and the mixture is reacted at 0° C. to 150° C., and preferably at 20° C. to 100° C., for 1 hour to 72 hours, and preferably 6 to 24 hours, whereby compound i'2 can be obtained.

Second Step

In a solvent such as dichloromethane, 1,2-dichloroethane or THF, or in a mixed solvent thereof, a base such as pyridine, lutidine or triethylamine, and a trifluoromethanesulfonylating agent such as trifluoromethanesulfonic anhydride or a comin's reagent are added to compound i'2, and the mixture is reacted at −50° C. to 50° C., and preferably at −30° C. to 30° C., for 0.1 hours to 4 hours, and preferably 0.5 hours to 1 hour, whereby compound i'3 can be obtained.

Third Step

From compound i'3, compound i'4 can be obtained in the same manner as in the second step in "34) Synthesis of Compounds A'-5 and A'-6" described above.

Fourth Step

From compound i'4, compound i'5 can be obtained in the same manner as in the seventh to tenth steps in "33) Synthesis of Compounds A'-1 to A'-4" described above.

Fifth Step

From compound i'5, compound i'6 can be obtained in the same manner as in the thirteenth step in "33) Synthesis of Compounds A'-1 to A'-4" described above.

Sixth Step

From compound i'6, compound i'7 can be obtained in the same manner as in the eleventh step in "33) Synthesis of Compounds A'-1 to A'-4" described above.

Seventh Step

From compound i'7, compound I'-1 can be obtained in the same manner as in the fourth to sixth steps in "33) Synthesis of Compounds A'-1 to A'-4" described above.

Eighth Step

From compound I'-1, compound I'-2 can be obtained in the same manner as in the seventeenth step in "33) Synthesis of Compounds A'-1 to A'-4" described above.

44) Synthesis of Compounds J'-1 and J'-2

[Formula 133]

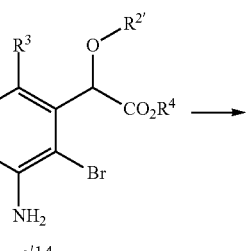

a'14

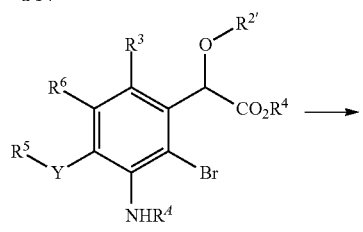

j'1

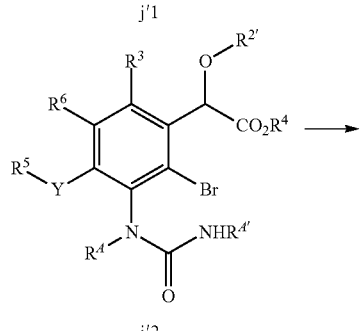

j'2

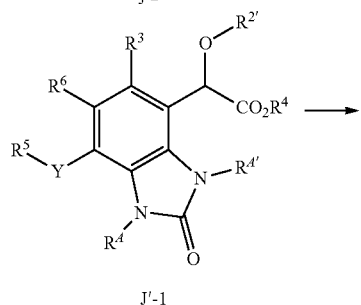

J'-1

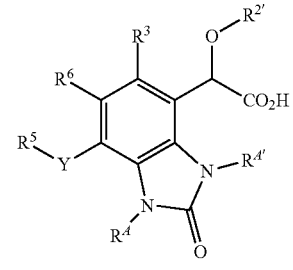

J'-2 wherein $R^{2'}$, $R^3$, $R^4$, $R^5$, $R^6$, $R^A$, and Y have the same meaning as described above, and $R^{A'}$ has the same meaning as $R^A$.

First Step

In a solvent such as benzene or toluene, or in a mixed solvent thereof, various alkylaldehydes and a molecular sieve are added to compound a'14, and the mixture is reacted at 20°

C. to 120° C., and preferably at 60° C. to 100° C., for 1 hour to 8 hours, and preferably 2 to 4 hours, whereby compound j'1 can be obtained.

Second Step

In a solvent such as dichloromethane, 1,2-dichloroethane or chloroform, or in a mixed solvent thereof, a base such as triethylamine or diisopropylethylamine, and phosgene are added to compound j'1, and the mixture is reacted at 0° C. to 80° C., and preferably at 20° C. to 60° C., for 0.1 hours to 2 hours, and preferably 0.5 to 1 hour. Furthermore, various primary amines are added, and the mixture is reacted at 0° C. to 80° C., and preferably at 20° C. to 60° C., for 0.1 hours to 2 hours, and preferably 0.5 to 1 hour, whereby compound j'2 can be obtained.

Third Step

In a solvent such as DMF, DMA, THF or dioxane, or in a mixed solvent thereof, a base such as triethylamine or diisopropylethylamine, and copper iodide are added to compound j'2, and the mixture is reacted at 50° C. to 200° C., and preferably at 80° C. to 170° C., for 0.5 hours to 8 hours, and preferably 2 to 4 hours, whereby compound J'-1 can be obtained.

Fourth Step

In a solvent such as methanol, ethanol, propanol, butanol or water, or in a mixed solvent thereof, a base such as lithium hydroxide, sodium hydroxide or potassium hydroxide is added to compound J'-1, and the mixture is reacted at 20° C. to 100° C., and preferably at 40° C. to 80° C., for 0.5 hours to 8 hours, and preferably 1 to 4 hours, whereby compound J'-2 can be obtained.

45) Synthesis of Compounds K'-1 and K'-2

[Formula 134]

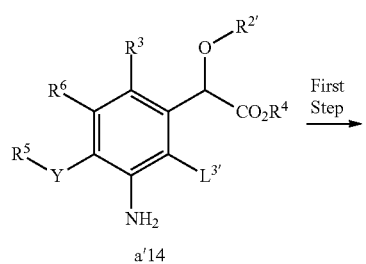

a'14

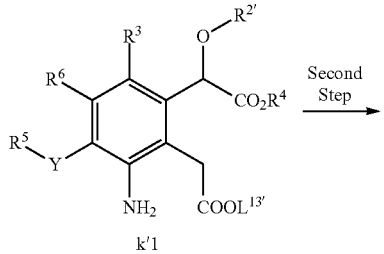

k'1

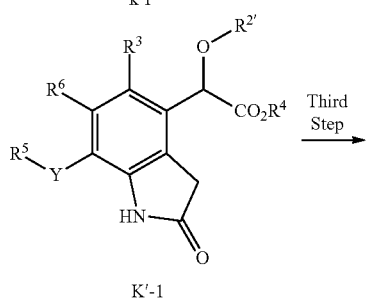

K'-1

-continued

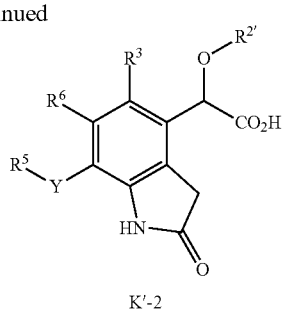

K'-2 wherein $R^{2'}$, $R^3$, $R^4$, $R^5$, $R^6$, Y, and $L^{3'}$ have the same meaning as described above, and $L^{13'}$ is substituted or unsubstituted alkyl.

First Step

In a solvent such as DMF, DMA, THF or dioxane, or in a mixed solvent thereof, 2-(tri-n-butylstannyl)alkyl acetate synthesized by a known method, $ZnBr_2$, and a catalyst such as palladium acetate, dichlorobistriphenylphosphine palladium or dichlorobis(tri-o-toluylphosphine)palladium are added to compound a'14, and the mixture is reacted at 20° C. to 150° C., and preferably at 50° C. to 120° C., for 0.5 hours to 8 hours, and preferably 1 to 4 hours, whereby compound k'1 can be obtained.

Second Step

Compound k'1 is dissolved in a solvent such as DMF, DMA, THF or dioxane, or in a mixed solvent thereof, and the mixture is stirred at 20° C. to 150° C., and preferably at 50° C. to 120° C., for 0.5 hours to 8 hours, and preferably 1 to 4 hours, whereby compound K'-1 can be obtained.

Third Step

In a solvent such as methanol, ethanol, propanol, butanol or water, or in a mixed solvent thereof, lithium hydroxide, sodium hydroxide, potassium hydroxide, or the like is added to compound K'-1, and the mixture is reacted at 20° C. to 100° C., and preferably at 40° C. to 80° C., for 0.5 hours to 8 hours, and preferably 1 to 4 hours, whereby compound K'-2 can be obtained.

46) Synthesis of Compounds L'-1 and L'-2

[Formula 135]

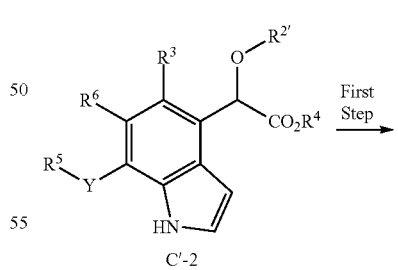

C'-2

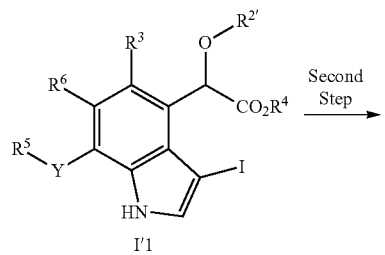

I'1

-continued

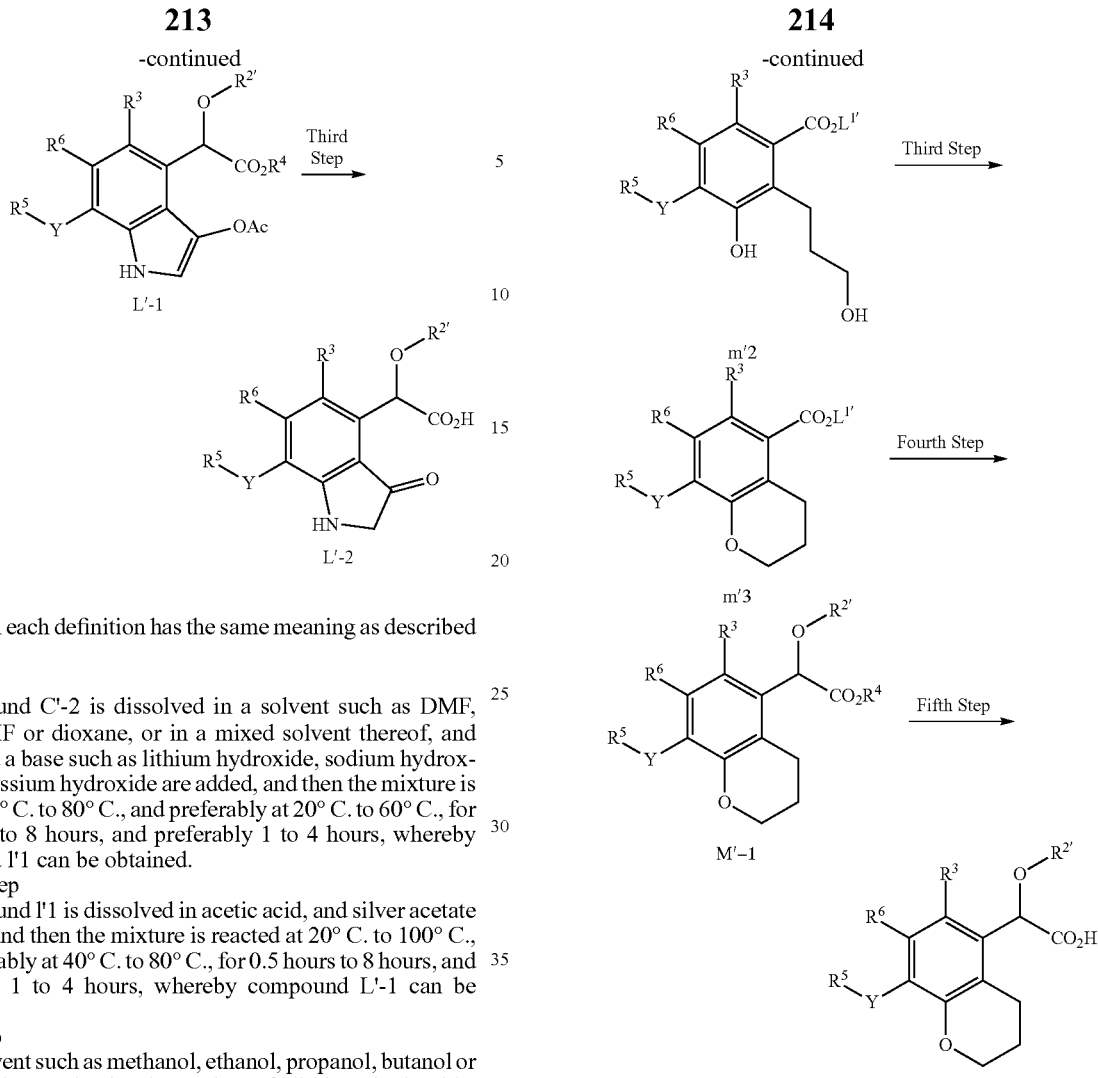

wherein each definition has the same meaning as described above.

First Step

Compound C'-2 is dissolved in a solvent such as DMF, DMA, THF or dioxane, or in a mixed solvent thereof, and iodine and a base such as lithium hydroxide, sodium hydroxide or potassium hydroxide are added, and then the mixture is stirred at 0° C. to 80° C., and preferably at 20° C. to 60° C., for 0.5 hours to 8 hours, and preferably 1 to 4 hours, whereby compound l'1 can be obtained.

Second Step

Compound l'1 is dissolved in acetic acid, and silver acetate is added, and then the mixture is reacted at 20° C. to 100° C., and preferably at 40° C. to 80° C., for 0.5 hours to 8 hours, and preferably 1 to 4 hours, whereby compound L'-1 can be obtained.

Third Step

In a solvent such as methanol, ethanol, propanol, butanol or water, or in a mixed solvent thereof, lithium hydroxide, sodium hydroxide, potassium hydroxide, or the like is added to compound L'-1, and the mixture is reacted at 20° C. to 100° C., and preferably at 40° C. to 80° C., for 0.5 hours to 8 hours, and preferably 1 to 4 hours, whereby compound L'-2 can be obtained.

47) Synthesis of Compounds M'-1 and M'-2

[Formula 136]

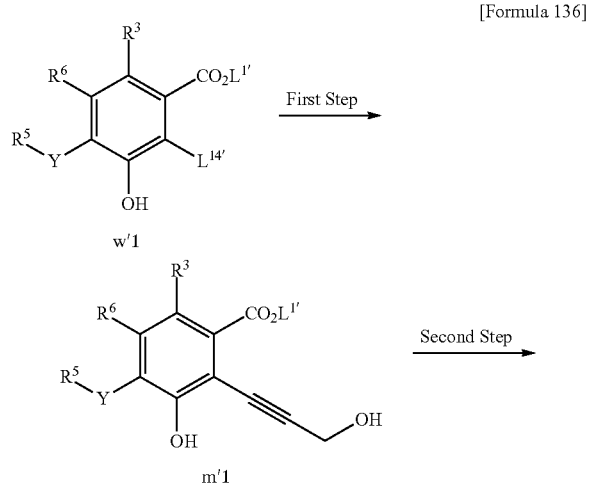

wherein $R^{2'}$, $R^3$, $R^4$, $R^5$, $R^6$, Y, and $L^{1'}$ have the same meaning as described above, and $L^{14'}$ is halogen.

First Step

In a solvent such as DMF, THF or acetonitrile or a mixed solvent, a palladium catalyst such as $Pd(PPh_3)_4$, $Pd(PPh_3)_2Cl_2$ or $Pd(dppf)_2Cl_2$, copper iodide, a base such as triethylamine or diisopropylethylamine, and 2-propyn-1-ol are added to compound w'1 described below, and the mixture is reacted under a nitrogen atmosphere at 0° C. to 100° C., and preferably at 25° C. to 80° C., for 0.5 hours to 24 hours, and preferably 1 hour to 12 hours, whereby compound m'1 can be obtained.

Second Step

In a solvent such as methanol, ethanol, THF or ethyl acetate, 5% or 10% palladium carbon and palladium hydroxide are added to compound m'1, and the mixture is reacted under a hydrogen atmosphere at 0° C. to 50° C., and preferably at 15° C. to 25° C., for 0.1 hours to 48 hours, and preferably 1 hour to 24 hours, whereby compound m'2 can be obtained.

In this condition, the reaction may be promoted by adding acetic acid, hydrochloric acid or the like.

Third Step

In a solvent such as dichloromethane, benzene, THF or DMF, triphenylphosphine is added to compound m'2, and an azo compound such as diethyl azodicarboxylate or diisopropyl azodicarboxylate is added dropwise at 0° C. to 35° C., and preferably at 5° C. to 25° C., and the mixture is reacted at 0° C. to 80° C., and preferably at 15° C. to 35° C., for 0.1 hours to 24 hours, and preferably 1 hour to 12 hours, whereby compound m'3 can be obtained.

Fourth Step

From compound m'3, compound M'-1 can be obtained in the same manner as in the seventh to eleventh steps in "33) Synthesis of Compounds A'-1 to A'-4" described above.

Fifth Step

From compound M'-1, compound M'-2 can be obtained in the same manner as in the seventeenth step in "33) Synthesis of Compounds A'-1 to A'-4" described above.

48) Synthesis of Compounds N'-1 to N'-4

[Formula 137]

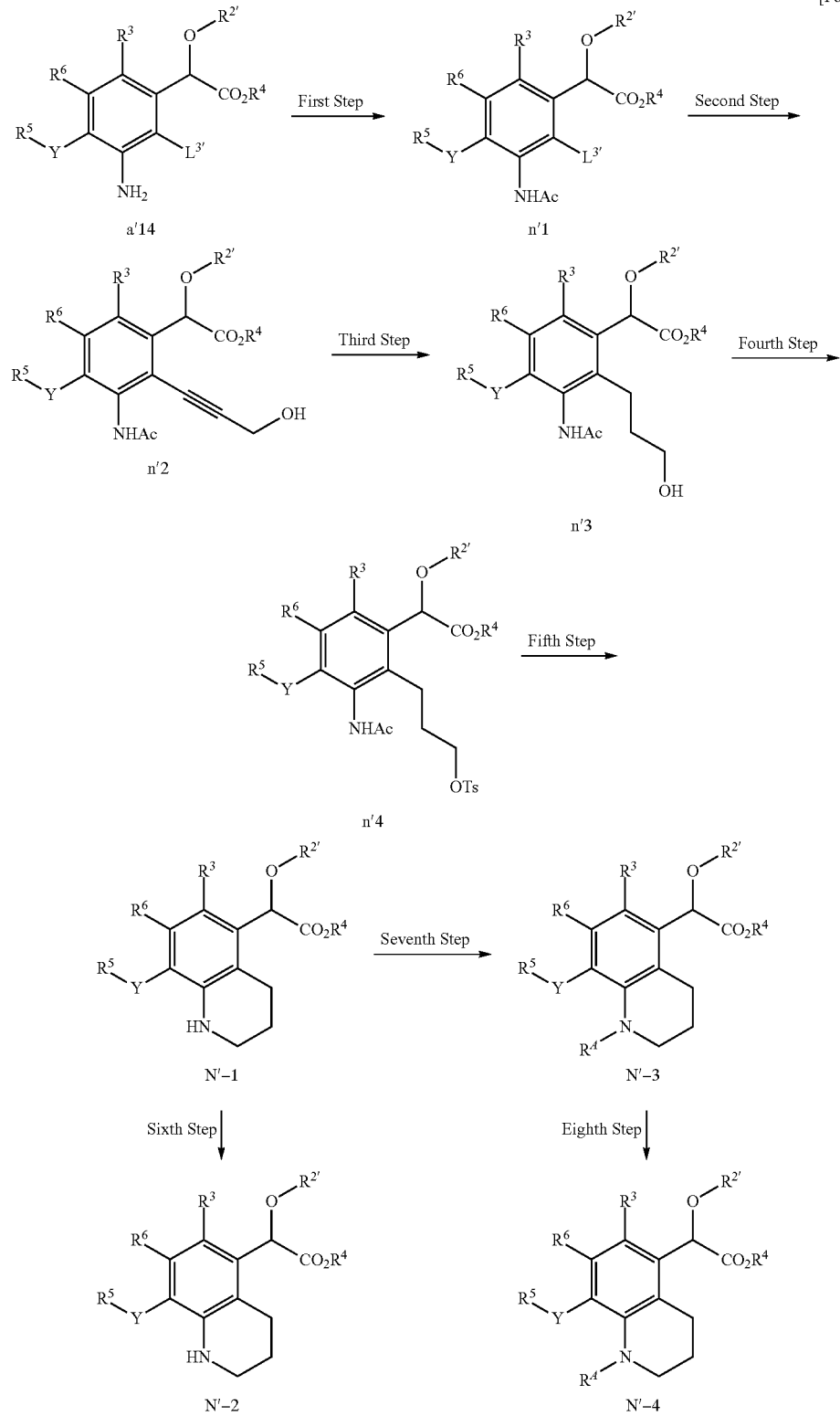

wherein each definition has the same meaning as described above.

First Step

In a solvent such as dichloromethane, dichloroethane or THF, a base such as pyridine, triethylamine or N-methylmorpholine as a base, and an acylating reagent such as an acetyl chloride or acetic anhydride are sequentially added to compound a'14, and the mixture is reacted at −20° C. to 50° C., and preferably at 0° C. to 20° C., for 0.1 hours to 6 hours, and preferably 1 hour to 3 hours, whereby compound n'1 can be obtained.

Second Step

From compound n'1, compound n'2 can be obtained in the same manner as in the first step in "47) Synthesis of Compounds M'-1 and M'-2" described above.

Third Step

From compound n'2, compound n'3 can be obtained in the same manner as in the second step in "47) Synthesis of Compounds M'-1 and M'-2" described above.

Fourth Step

In a solvent such as dichloromethane, dichloroethane or THF, a base such as pyridine or triethylamine, and p-toluenesulfonyl chloride are sequentially added to compound n'3, and the mixture is reacted at −20° C. to 50° C., and preferably at 0° C. to 20° C., for 1 hour to 48 hours, and preferably 6 hours to 12 hours, whereby compound n'4 can be obtained.

Fifth Step

In a solvent of toluene or xylene, compound n'4 is reacted at 25° C. to 150° C., and preferably at 70° C. to 100° C., for 1 hour to 48 hours, and preferably 6 hours to 12 hours, whereby compound N'-1 can be obtained.

Sixth Step

From compound N'-1, compound N'-2 can be obtained in the same manner as in the seventeenth step in "33) Synthesis of Compounds A'-1 to A'-4" described above.

Seventh Step

From compound N'-1, compound N'-3 can be obtained in the same manner as in the sixth step in "39) Synthesis of Compounds E'-1 to E'-4" described above.

Eighth Step

From compound N'-3, compound N'-4 can be obtained in the same manner as in the seventeenth step in "33) Synthesis of Compounds A'-1 to A'-4" described above.

49) Synthesis of Compounds O'-1 to O'-4

[Formula 138]

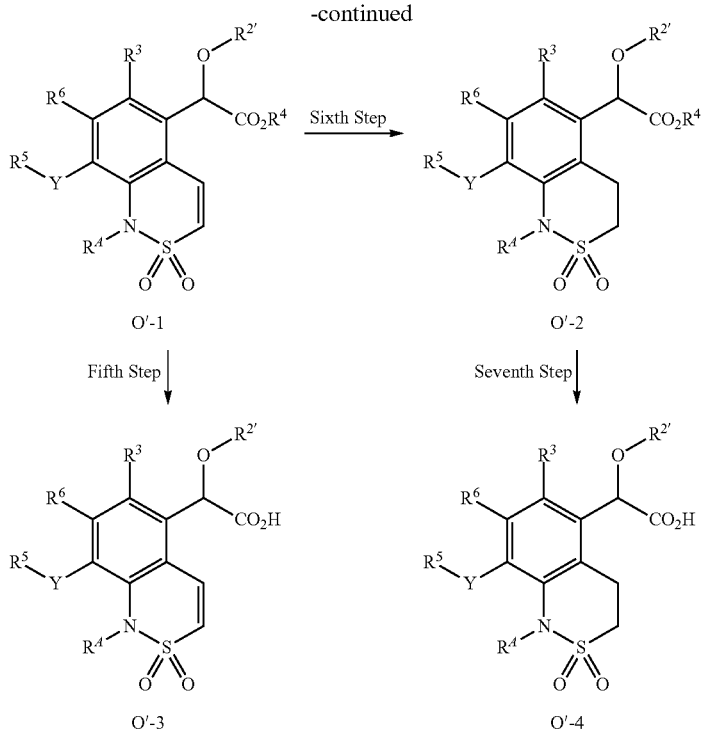

O'-1 O'-2

Fifth Step | Seventh Step |

O'-3 O'-4 wherein each definition has the same meaning as described above.

First Step

In a solvent such as dioxane, DMF or DMSO, an inorganic base such as sodium formate or sodium acetate is added to compound a'14, and in the presence of a palladium catalyst such as $Pd(OAc)_2$, diphenylphosphinoferrocene, diphenylphosphinopropane or $PdCl_2(dppf)$, the mixture is subjected to carbon monoxide insertion, under a carbon monoxide atmosphere, at 50° C. to 150° C., and preferably at 90° C. to 120° C., for 0.5 hours to 24 hours, and preferably 2 hours to 12 hours, whereby compound o'1 can be obtained.

Second Step

In a solvent such as dichloromethane or tetrahydrofuran, in the presence of a base such as pyridine or triethylamine, compound o'1 is reacted with methanesulfonyl chloride at −20° C. to 100° C., and preferably at 0° C. to 50° C., for 0.5 hours to 24 hours, and preferably 6 hours to 12 hours, whereby compound o'2 can be obtained.

Third Step

In a solvent such as tetrahydrofuran, DMF or DMA, in the presence of a base such as sodium hydride or tert-butoxypotassium, $R^4$—Cl, $R^4$—Br or $R^4$—I that is commercially available or synthesized by a known method is added to compound o'2, and the mixture is reacted at 0° C. to 100° C., and preferably at 20° C. to 50° C., for 1 hour to 24 hours, and preferably 6 hours to 12 hours, whereby compound o'3 can be obtained.

Fourth Step

In a solvent such as DMF or DMA, in the presence of a base such as sodium hydride or tert-butoxypotassium, compound o'3 is reacted at 0° C. to 100° C., and preferably at 20° C. to 50° C., for 1 hour to 24 hours, and preferably 6 hours to 12 hours, whereby compound O'-1 can be obtained.

Fifth Step

From compound O'-1, compound O'-2 can be obtained in the same manner as in the seventeenth step in "33) Synthesis of Compounds A'-1 to A'-4" described above.

Sixth Step

In a solvent such as methanol, ethanol or tetrahydrofuran, in the presence of a palladium catalyst such as 5% or 10% palladium carbon or palladium hydroxide, compound O'-1 is subjected to a catalytic reduction under a hydrogen atmosphere at 0° C. to 60° C., and preferably at 20° C. to 30° C., for 1 hour to 24 hours, and preferably 2 hours to 12 hours, whereby compound O'-3 can be obtained.

Seventh Step

From compound O'-3, compound O'-4 can be obtained in the same manner as in the seventeenth step in "33) Synthesis of Compounds A'-1 to A'-4" described above.

50) Synthesis of Compounds P'-1 to P'-4

[Formula 139]

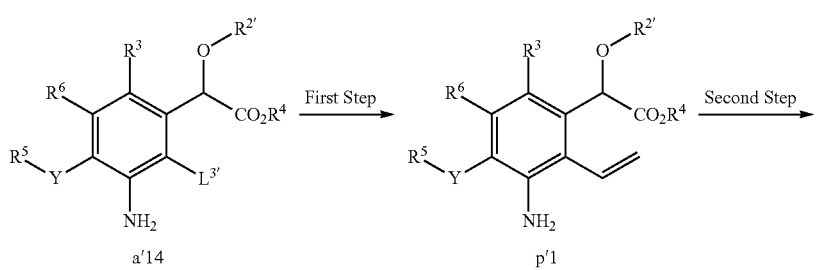

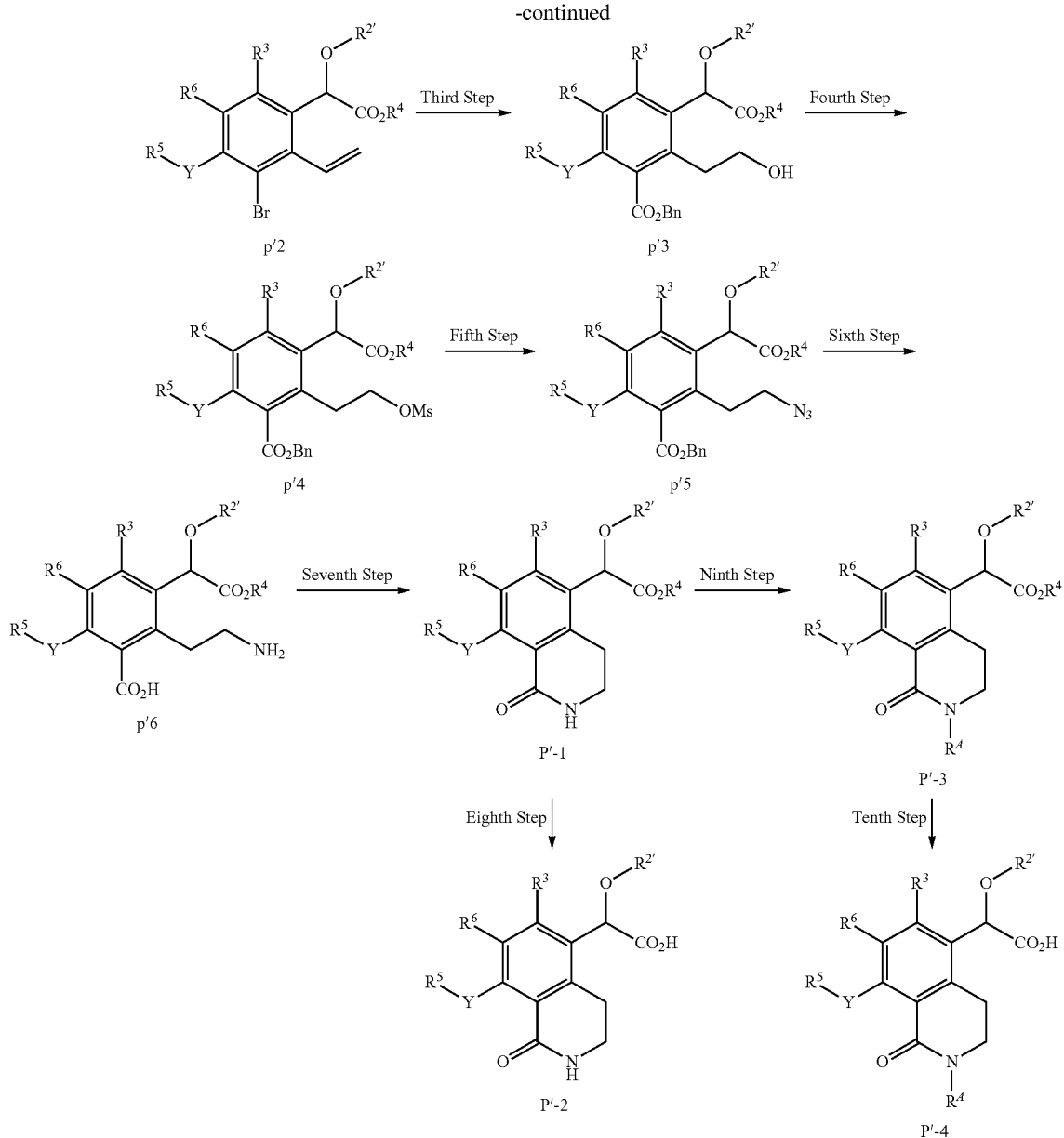

wherein each definition has the same meaning as described above.

First Step

In a solvent such as dioxane, DMF, DME, tetrahydrofuran or water, or a mixed solvent, a base such as potassium carbonate, sodium carbonate or potassium phosphate, a palladium catalyst such as Pd(PPh$_3$)$_4$, Pd(PPh$_3$)$_2$Cl$_2$ or PdCl$_2$(dppf)$_2$, and vinyl boronate, vinyl tin, and the like are added to compound a'14, and the reaction solution is well degassed, and then subjected to a coupling reaction under a nitrogen atmosphere at 0° C. to 150° C., and preferably at 60° C. to 120° C., for 0.5 hours to 24 hours, and preferably 1 hour to 12 hours, whereby compound p'1 can be obtained.

Second Step

In a solvent such as tetrahydrofuran, acetonitrile or DMF, cuprous bromide, cupric bromide or the like and a diazotization reagent such as tert-butyl nitrite or isoamyl nitrate are added to compound p'1, and the mixture is reacted at −20° C. to 80° C., and preferably at 0° C. to 25° C., for 1 hour to 12 hours, and preferably 3 hours to 6 hours, whereby compound p'2 can be obtained.

Third Step

In a solvent such as tetrahydrofuran or dioxane, a borane reagent such as borane-tetrahydrofuran complex, thexylborane or 9-borabicyclo[3.3.1]nonane is added to compound p'2, and the mixture is stirred at −20° C. to 80° C., and preferably at 0° C. to 25° C., for 1 hour to 12 hours, and preferably 3 hours to 6 hours, and then 30% hydrogen peroxide aqueous solution and 1 to 10 mol/L sodium hydroxide or potassium hydroxide aqueous solution are added, and the mixture is subjected to a hydroboration reaction at −20° C. to 80° C., and preferably at 0° C. to 25° C., for 1 hour to 12 hours, and preferably 3 hours to 6 hours, whereby compound p'3 can be obtained.

Fourth Step

In a solvent such as dichloromethane, toluene or tetrahydrofuran, a base such as pyridine, triethylamine or N-methylmorpholine and methanesulfonyl chloride or methanesulfonic anhydride are added to compound p'3, and the mixture is reacted at −20° C. to 60° C., and preferably at 0° C. to 25° C., for 0.5 hours to 12 hours, and preferably 1 hour to 6 hours, whereby compound p'4 can be obtained.

Fifth Step

In a solvent such as acetone, tetrahydrofuran or DMF, a azidation reagent such as sodium azide or trimethylsilyl azide is added to compound p'4, and the mixture is reacted at 0° C. to 100° C., and preferably at 20° C. to 50° C., for 0.5 hours to 12 hours, and preferably 1 hour to 6 hours, whereby compound p'5 can be obtained.

Sixth Step

In a solvent such as methanol, ethanol or tetrahydrofuran, in the presence of a palladium catalyst such as 5% or 10% palladium carbon or palladium hydroxide, compound p'5 is subjected to a catalytic reduction under a hydrogen atmosphere at 0° C. to 60° C., and preferably at 20° C. to 30° C., for 0.5 hours to 24 hours, and preferably 2 hours to 12 hours, whereby compound p'6 can be obtained.

Seventh Step

In a solvent such as dichloromethane, tetrahydrofuran or DMF, a condensing agent such as 1-ethyl-3-(3-dimethylaminopropyl)carbodiimide, dicyclohexylcarbodiimide or benzotriazol-1-yl-oxytripyrrolidinophosphonium hexafluorophosphate, an additive such as 1-hydroxybenzotriazol or N-hydroxysuccinimide, and a base such as triethylamine or N-methylmorpholine, are added to compound p'6, and the mixture is reacted at 0° C. to 100° C., and preferably at 20° C. to 50° C., for 0.5 hours to 12 hours, and preferably 1 hour to 6 hours, whereby compound P'-1 can be obtained.

Eighth Step

From compound P'-1, compound P'-2 can be obtained in the same manner as in the seventeenth step in "33) Synthesis of Compounds A'-1 to A'-4" described above.

Ninth Step

From compound P'-1, compound P'-3 can be obtained in the same manner as in the third step in "49) Synthesis of Compounds O'-1 to O'-4" described above.

Tenth Step

From compound P'-3, compound P'-4 can be obtained in the same manner as in the seventeenth step in "33) Synthesis of Compounds A'-1 to A'-4" described above.

51) Synthesis of Compounds Q'-1 to Q'-4

[Formula 140]

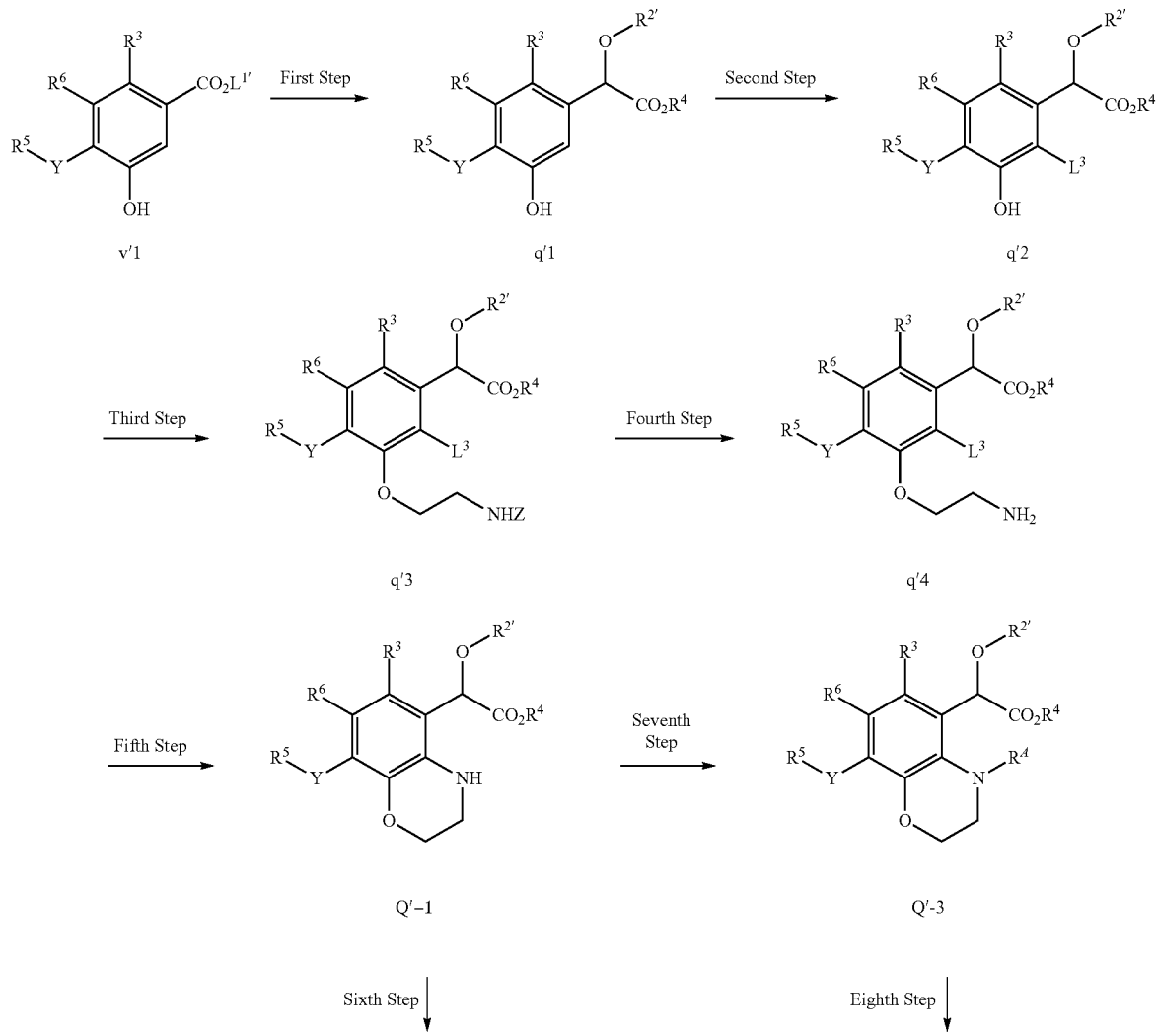

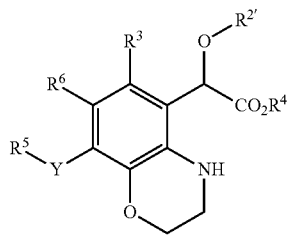

Q'-2

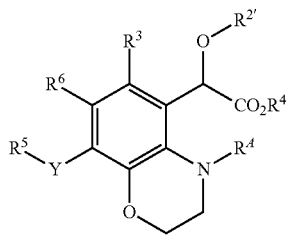

Q'-4 wherein each definition has the same meaning as described above.

First Step

From compound v'1 described below, compound q'1 can be obtained in the same manner as in the seventh to eleventh steps in "33) Synthesis of Compounds A'-1 to A'-4" described above.

Second Step

From compound q'1, compound q'2 can be obtained in the same manner as in the thirteenth step in "33) Synthesis of Compounds A'-1 to A'-4" described above.

Third Step

In a tetrahydrofuran solvent, a phosphine such as benzyl N-(2-hydroxyethyl)carbamate, triphenylphosphine, tri n-butylphosphine or tri-tert-butylphosphine, a base such as N-methylmorpholine or triethylamine, and an azodicarboxylic acid ester such as diethyl azodicarboxylate or diisopropyl azodicarboxylate are added to compound q'2, and the mixture is reacted at 0° C. to 60° C., and preferably at 20° C. to 40° C., for 1 hour to 24 hours, and preferably 6 hours to 12 hours, whereby compound q'3 can be obtained.

Fourth Step

From compound q'3, compound q'4 can be obtained in the same manner as in the sixth step in "49) Synthesis of Compounds O'-1 to O'-4" described above.

Fifth Step

In a solvent such as toluene, dioxane or DMF, a base such as sodium tert-butoxide or potassium tert-butoxide, and a palladium catalyst such as $Pd(dba)_3$ or $PdCl_2(dppf)_2$ are added to compound q'4, and the reaction solution is well degassed, and then subjected to a coupling reaction under a nitrogen atmosphere at 0° C. to 150° C., and preferably at 60° C. to 120° C., for 0.5 hours to 24 hours, and preferably 1 hour to 12 hours, whereby compound Q'-1 can be obtained.

Sixth Step

From compound Q'-1, compound Q'-2 can be obtained in the same manner as in the seventeenth step in "33) Synthesis of Compounds A'-1 to A'-4" described above.

Seventh Step

From compound Q'-1, compound Q'-3 can be obtained in the same manner as in the third step in "49) Synthesis of Compounds O'-1 to O'-4" described above.

Eighth Step

From compound Q'-3, compound Q'-4 can be obtained in the same manner as in the seventeenth step in "33) Synthesis of Compounds A'-1 to A'-4" described above.

52) Synthesis of Compounds R'-1 to R'-4

[Formula 141]

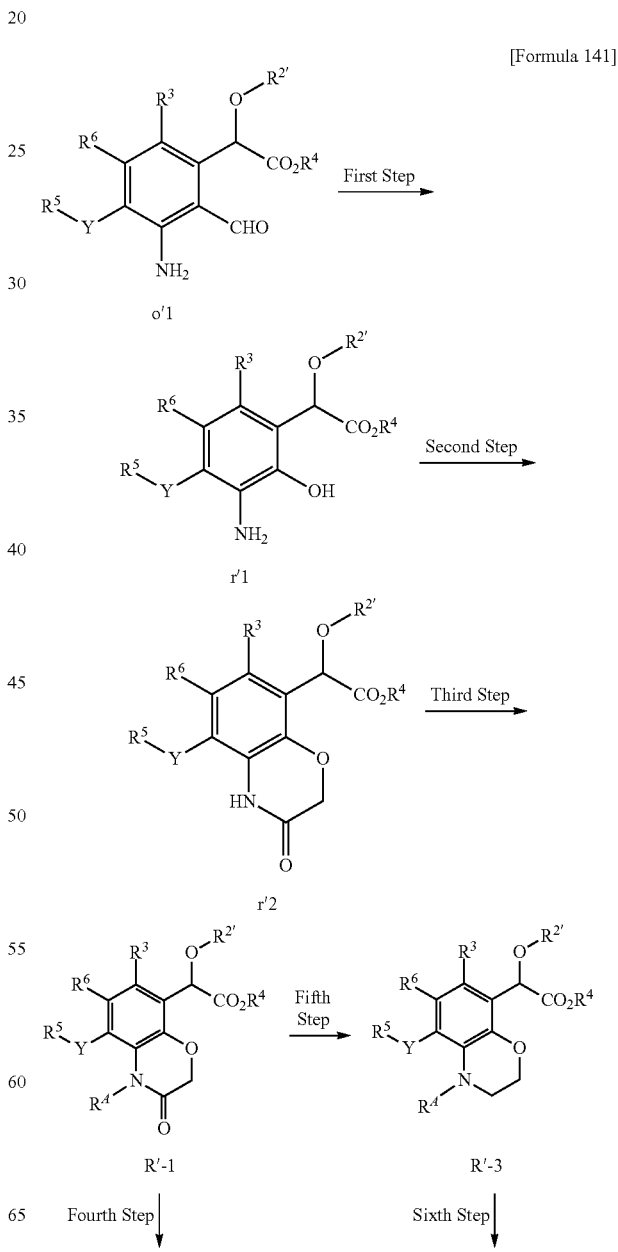

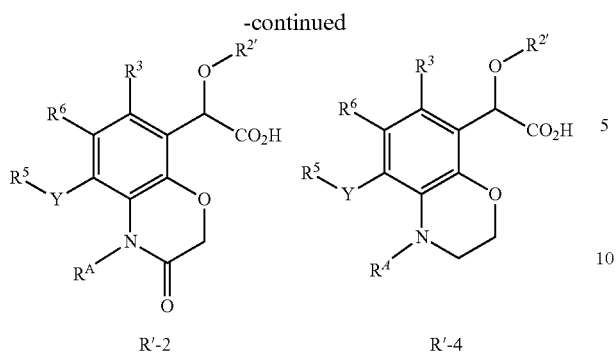

wherein each definition has the same meaning as described above.

First Step

In a solvent such as methanol or ethanol, an aqueous solution such as sodium hydroxide or potassium hydroxide and a 3 to 31% hydrogen peroxide aqueous solution are added to compound o'1, and the mixture is reacted at −20° C. to 100° C., and preferably at 0° C. to 50° C., for 1 hour to 24 hours, and preferably 3 hours to 12 hours, whereby compound r'1 can be obtained.

Second Step

In a halogenated solvent such as dichloromethane, dichloroethane or chloroform, a phase transfer catalyst such as benzyltriethylammonium chloride or benzyltriethylammonium bromide, an inorganic base such as sodium bicarbonate or potassium bicarbonate, and chloroacetyl chloride, bromoacetyl bromide or the like are added to compound r'1, and the mixture is reacted at −20° C. to 100° C., and preferably at 0° C. to 50° C., for 1 hour to 24 hours, and preferably 3 hours to 12 hours, whereby compound r'2 can be obtained.

Third Step

From compound r'2, compound R'-1 can be obtained in the same manner as in the sixth step in "49) Synthesis of Compounds O'-1 to O'-4" described above.

Fourth Step

From compound R'-1, compound R'-2 can be obtained in the same manner as in the seventeenth step in "33) Synthesis of Compounds A'-1 to A'-4" described above.

Fifth Step

In a solvent such as tetrahydrofuran or diethyl ether, a reducing agent such as borane-tetrahydrofuran or borane-dimethylsulfide complex is added to compound R'-1, and the mixture is reacted at 20° C. to 150° C., and preferably at 50° C. to 100° C., for 1 hour to 24 hours, and preferably 3 hours to 12 hours, whereby compound R'-3 can be obtained.

Sixth Step From compound R'-3, compound R'-4 can be obtained in the same manner as in the seventeenth step in "33) Synthesis of Compounds A'-1 to A'-4" described above.

53) Synthesis of Compounds S'-1 and S'-2

[Formula 142]

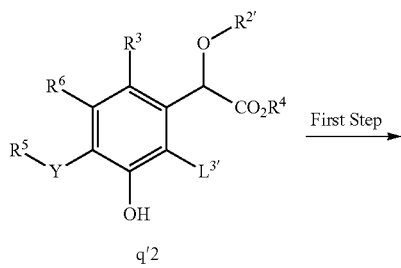

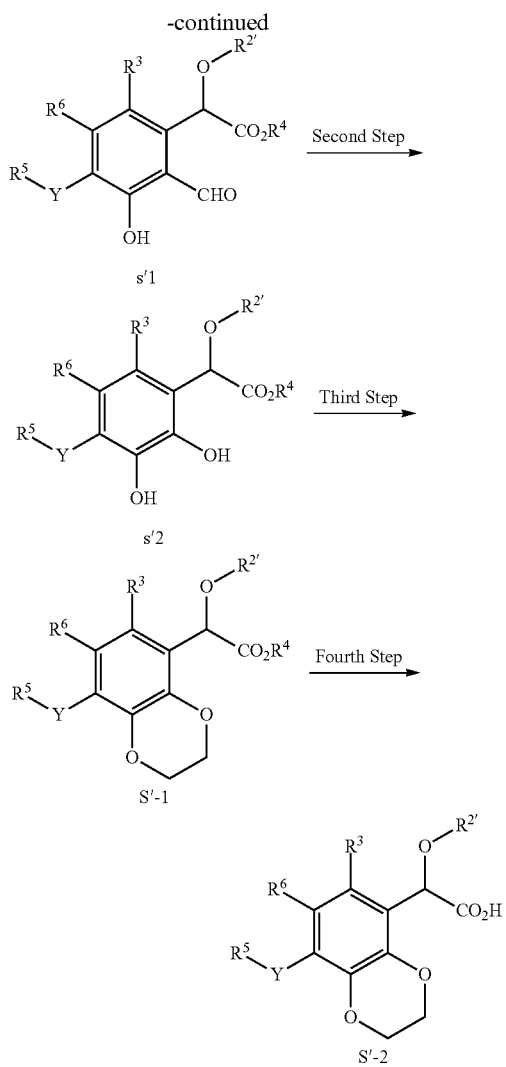

wherein each definition has the same meaning as described above.

First Step

From compound q'2, compound s'1 can be obtained in the same manner as in the first step in "49) Synthesis of Compounds O'-1 to O'-4" described above.

Second Step

From compound s'1, compound s'2 can be obtained in the same manner as in the first step in "50) Synthesis of Compounds P'-1 to P'-4" described above.

Third Step

In a solvent such as DMF, DMA or acetonitrile, an inorganic base such as potassium carbonate, sodium carbonate or cesium carbonate, and a halogenating reagent such as 1,2-dibromoethane or 1,2-diiodoethane are added to compound s'2, and the mixture is reacted at 20° C. to 150° C., and preferably at 60° C. to 100° C., for 1 hour to 24 hours, and preferably 3 hours to 12 hours, whereby compound S'-1 can be obtained.

Fourth Step

From compound S'-1, compound S'-2 can be obtained in the same manner as in the seventeenth step in "33) Synthesis of Compounds A'-1 to A'-4" described above.

It is also possible to synthesize compounds S'-1 and S'-2 in which $R^6$ is methyl, and —$R^3$ is —Y—$R^5$, by the method shown below.

[Formula 143]

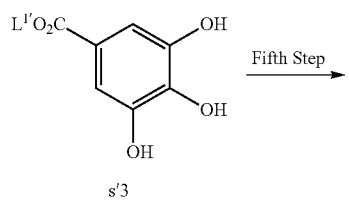

s'3

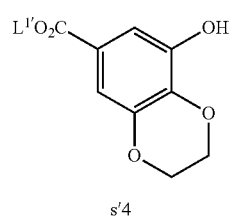

s'4

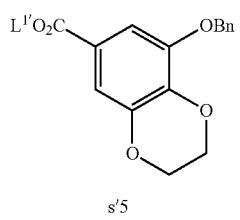

s'5

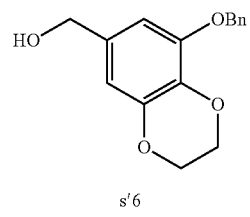

s'6

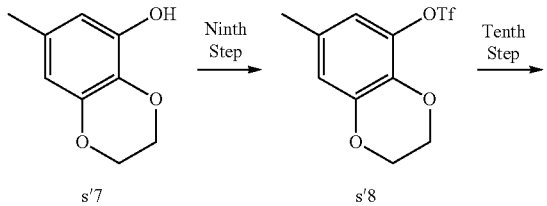

s'7    s'8

[structure] s'9

[structure] s'10

[structure] s'11

[structure] S'-1

[structure] S'-2 wherein each definition has the same meaning as described above.

Fifth Step

In a solvent such as dioxane, DMF, DME, THF, acetone or acetonitrile, a base such as potassium carbonate or sodium carbonate and dibromoethane or diiodoethane are added to compound s'3, and the mixture is reacted at 0° C. to 140° C., and preferably at 50° C. to 120° C., for 0.5 hours to 48 hours, and preferably 6 hours to 24 hours, whereby compound s'4 can be obtained.

Sixth Step

In a solvent such as dioxane, DMF, DME, THF, acetone or acetonitrile, a base such as potassium carbonate or sodium carbonate and benzyl bromide or benzyl chloride are added to compound s'4, and the mixture is reacted at 0° C. to 100° C., and preferably at 20° C. to 50° C., for 0.5 hours to 24 hours, and preferably 1 hour to 5 hours, whereby compound s'5 can be obtained.

Seventh Step

From compound s'5, compound s'6 can be obtained in the same manner as in the seventh step in "33) Synthesis of Compounds A'-1 to A-4" described above.

Eighth Step

In a solvent such as methanol, ethanol or tetrahydrofuran, a catalyst such as 5% or 10% palladium carbon, palladium hydroxide or platinum dioxide is added to compound s'6, and the mixture is reacted under a hydrogen atmosphere at 0° C. to 60° C., and preferably at 20° C. to 40° C., for 0.1 hours to 24 hours, and preferably 1 hour to 12 hours, whereby compound s'7 can be obtained.

Ninth Step

In a solvent such as dichloromethane, 1,2-dichloroethane or tetrahydrofuran, or in a mixed solvent thereof, a base such as pyridine, lutidine or triethylamine, and a trifluoromethanesulfonylating agent such as trifluoromethanesulfonic anhydride or a comin's reagent are added to compound s'7, and the mixture is reacted at −50° C. to 50° C., and preferably at −30° C. to 30° C., for 0.1 hours to 4 hours, and preferably 0.5 hours to 1 hour, whereby compound s'8 can be obtained.

Tenth Step

In an alkyl alcohol such as methanol or ethanol or a benzyl alcohol, or a mixed solvent of these alcohols and dimethylformamide, dimethylsulfoxide or the like, a base such as triethylamine, N-methylmorpholine or pyridine is added to compound s'8, and then a palladium catalyst such as Pd(PPh$_3$)$_4$, Pd(OAc)$_2$ or PdCl$_2$(dppf) is added, and the reaction mixture is well degassed, and reacted under a carbon monoxide atmosphere at 30° C. to 120° C., and preferably at 70° C. to 100° C., for 1 hour to 24 hours, and preferably 3 hours to 12 hours, whereby compound s'9 can be obtained.

Eleventh Step

From compound s'9, compound s'10 can be obtained in the same manner as in the seventh step in "33) Synthesis of Compounds A'-1 to A-4" described above.

Twelfth Step

From compound s'10, compound s'11 can be obtained in the same manner as in the thirteenth step in "33) Synthesis of Compounds A'-1 to A-4" described above.

Thirteenth Step

From compound s'11, compound S'-1 can be obtained in the same manner as in the eighth to eleventh steps in "33) Synthesis of Compounds A'-1 to A-4" described above.

Fourteenth Step

From compound S'-1, compound S'-2 can be obtained in the same manner as in the seventeenth step in "33) Synthesis of Compounds A'-1 to A-4" described above.

54) Synthesis of Compounds T'-1 to T'-4

[Formula 144]

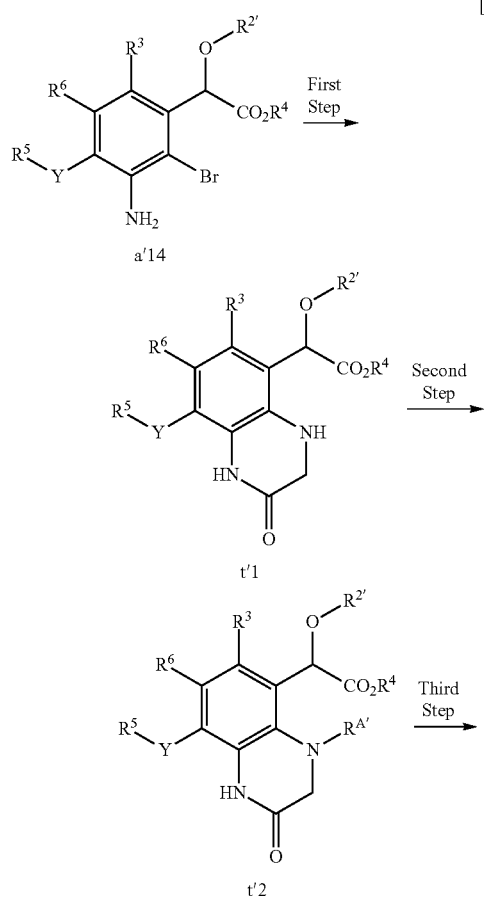

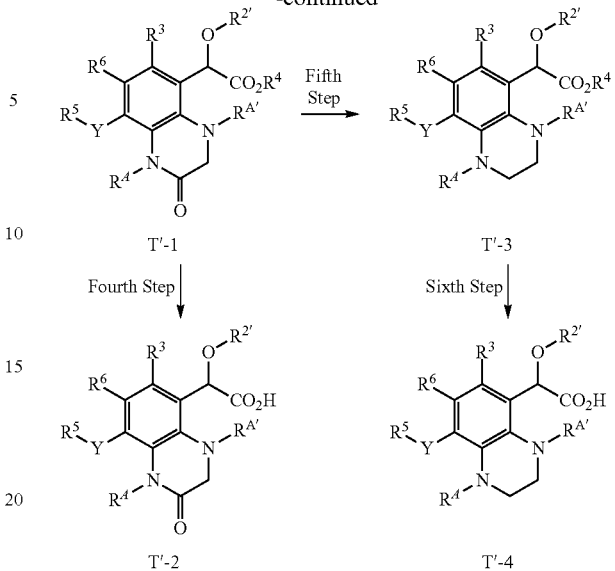

wherein $R^{2'}$, $R^3$, $R^4$, $R^5$, $R^6$, $R^A$, and Y have the same meaning as described above, and $R^{A'}$ has the same meaning as $R^A$.

First Step

In a solvent such as DMF, DMA or DMSO, an inorganic base such as potassium carbonate or cesium carbonate, a catalyst such as cuprous bromide or cuprous iodide and glycine are added to compound a'14, and the mixture is reacted at 50° C. to 200° C., and preferably at 80° C. to 150° C., for 1 hour to 24 hours, and preferably 3 hours to 12 hours, whereby compound t'1 can be obtained.

Second Step

In a solvent such as acetone, tetrahydrofuran or DMF, an inorganic base such as potassium carbonate or cesium carbonate, or an organic base such as pyridine or triethylamine, and $R^{A'}$—Cl, $R^{A'}$—Br or $R^{A'}$—I that is commercially available or synthesized by a known method are added to compound t'1, and the mixture is reacted at 0° C. to 100° C., and preferably at 20° C. to 50° C., for 1 hour to 24 hours, and preferably 6 hours to 12 hours, whereby compound t'2 can be obtained.

Third Step

From compound t'2, compound T'-1 can be obtained in the same manner as in the third step in "49) Synthesis of Compounds O'-1 to O'-4" described above.

Fourth Step

From compound T'-1, compound T'-2 can be obtained in the same manner as in the seventeenth step in "33) Synthesis of Compounds A'-1 to A-4" described above.

Fifth Step

From compound T'-1, compound T'-3 can be obtained in the same manner as in the fifth step in "52) Synthesis of Compounds R'-1 to R'-4" described above.

Sixth Step

From compound T'-3, compound T'-4 can be obtained in the same manner as in the seventeenth step in "33) Synthesis of Compounds A'-1 to A-4" described above.

55) Synthesis of Compounds U'-1 and U'-2

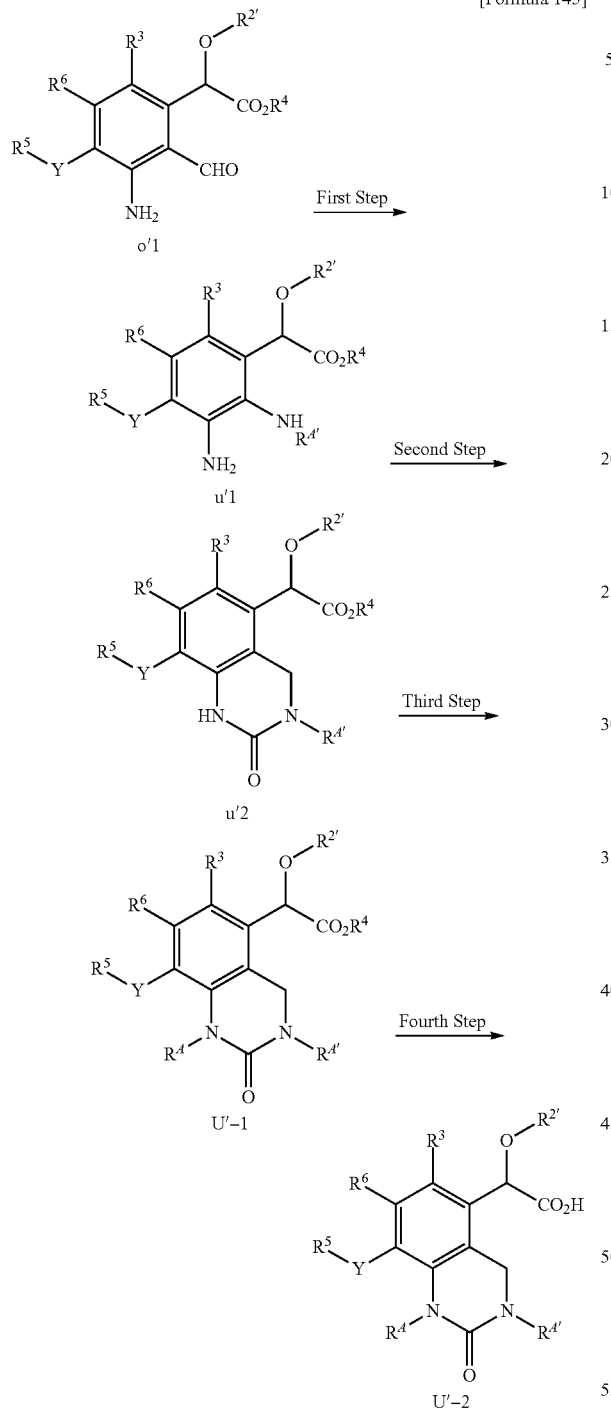

[Formula 145]

wherein $R^{2'}$, $R^3$, $R^4$, $R^5$, $R^6$, $R^4$, and Y have the same meaning as described above, and $R^{4'}$ has the same meaning as $R^4$.

First Step

In a solvent such as dichloromethane, tetrahydrofuran or ethyl acetate, an organic acid such as acetic acid or trifluoroacetic acid, a reducing agent such as sodium cyanoborohydride or sodium triacetoxyborohydride, and $R^{4'}$—$NH_2$ that is commercially available or synthesized by a known method are added to compound o'1, and the mixture is reacted at 0° C. to 100° C., and preferably at 20° C. to 50° C., for 0.5 hours to 12 hours, and preferably 1 hour to 6 hours, whereby compound u'1 can be obtained.

Second Step

In a solvent such as dichloromethane, tetrahydrofuran or DMF, sodium hydride as an inorganic base and 1-1'-carbonyldiimidazole are added to compound u'1, and the mixture is reacted at 0° C. to 100° C., and preferably at 20° C. to 50° C., for 1 hour to 48 hours, and preferably 6 hours to 24 hours, whereby compound u'2 can be obtained.

Third Step

From compound u'2, compound U'-1 can be obtained in the same manner as in the third step in "49) Synthesis of Compounds O'-1 to O'-4" described above.

Fourth Step

From compound U'-1, compound U'-2 can be obtained in the same manner as in the seventeenth step in "33) Synthesis of Compounds A'-1 to A-4" described above.

56) Synthesis of Compounds V'-1 and V'-2

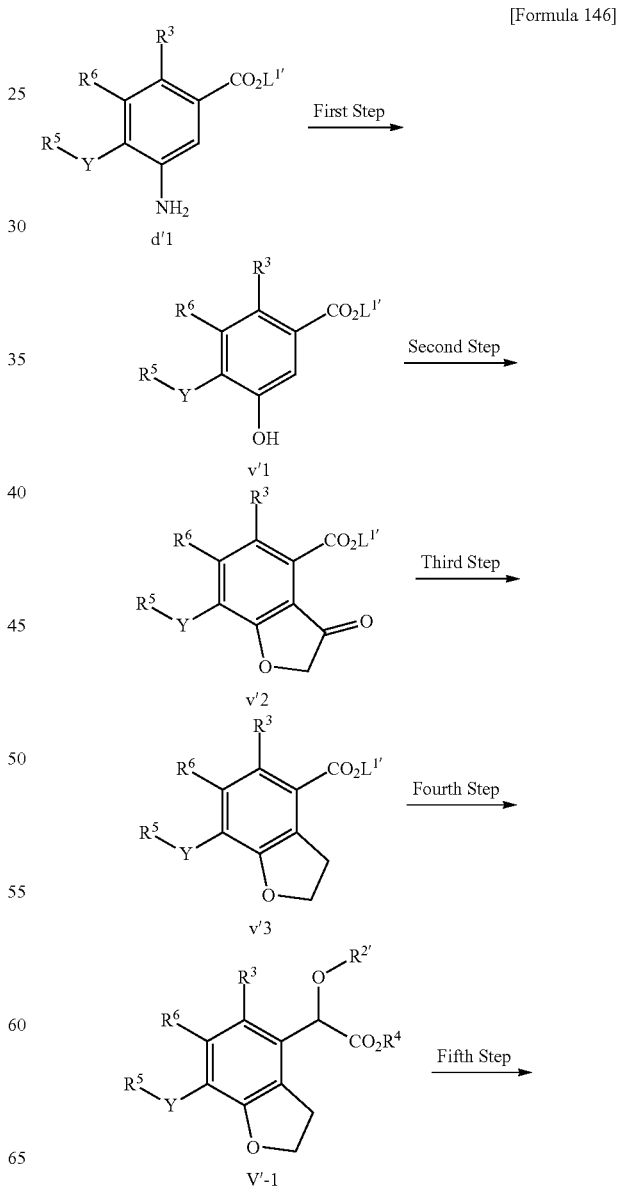

[Formula 146]

-continued

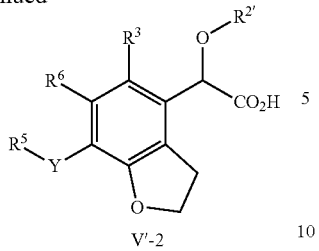

V'-2 wherein each definition has the same meaning as described above.

First Step

In a sulfuric acid solvent, a diazotization reagent such as tert-butyl nitrite or isopentyl nitrite is added to compound d'1, and the mixture is reacted at 0° C. to 100° C., and preferably at 25° C. to 80° C., for 0.5 hours to 12 hours, and preferably 1 hour to 6 hours, whereby compound v'1 can be obtained.

Second Step

In a nitrobenzene solvent, chloroacetyl chloride and aluminum chloride are added to compound v'1, and the mixture is reacted at 0° C. to 80° C., and preferably at 25° C. to 50° C., for 0.1 hours to 6 hours, and preferably 0.5 hours to 3 hours, whereby compound v'2 can be obtained.

Third Step

In a solvent such as methanol, ethanol or tetrahydrofuran, a catalyst such as 5% or 10% palladium carbon, palladium hydroxide or platinum dioxide is added to compound v'2, and the mixture is reacted under a hydrogen atmosphere and at 0° C. to 60° C., and preferably at 20° C. to 40° C., at 1 to 10 atmospheres, and preferably 1 to 6 atmospheres, for 0.1 hours to 24 hours, and preferably 1 hour to 12 hours, whereby compound v'3 can be obtained.

Fourth Step

From compound v'3, compound V'-1 can be obtained in the same manner as in the seventh to eleventh steps in "33) Synthesis of Compounds A'-1 to A'-4" described above.

Fifth Step

From compound V'-1, compound V'-2 can be obtained in the same manner as in the seventeenth step in "33) Synthesis of Compounds A'-1 to A'-4" described above.

57) Synthesis of Compounds W'-1 and W'-2

[Formula 147]

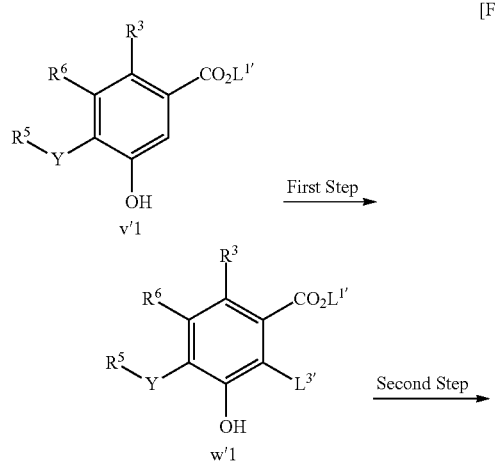

-continued

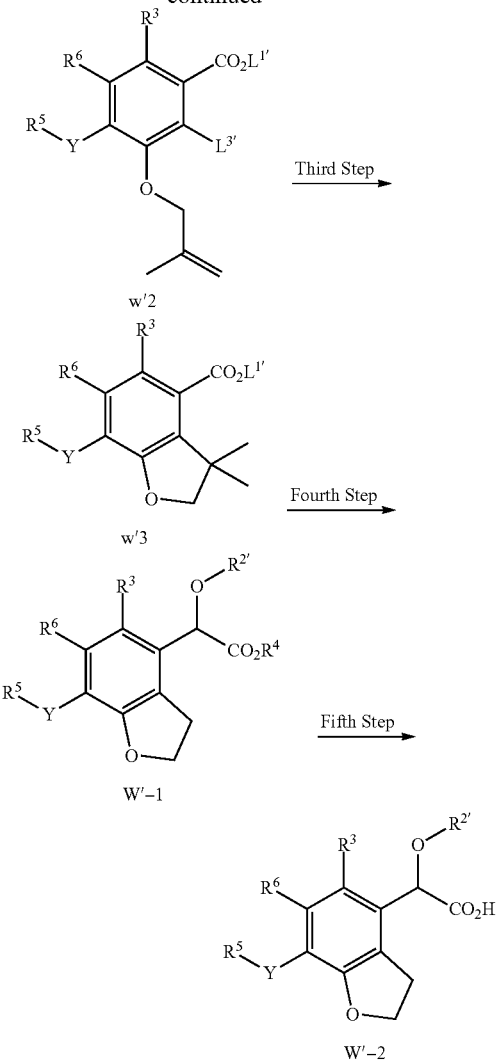

wherein each definition has the same meaning as described above.

First Step

From compound v'1, compound w'1 can be obtained in the same manner as in the seventh step in "33) Synthesis of Compounds A'-1 to A'-4" described above.

Second Step

In a solvent such as dimethylformamide or dimethylacetamide, a base such as potassium carbonate, sodium carbonate or cesium carbonate and 3-bromo-2-methylpropene are added to compound w'1, and the mixture is reacted at 0° C. to 80° C., and preferably at 25° C. to 50° C., for 0.1 hours to 6 hours, and preferably 0.5 hours to 3 hours, whereby compound w'2 can be obtained.

Third Step

In a solvent such as toluene or xylene, azobisisobutyronitrile, tributyltin hydride or the like, and 3-bromo-2-methylpropene are added to compound w'2, and the mixture is reacted at 25° C. to 130° C., and preferably at 80° C. to 110° C., for 0.5 hours to 6 hours, and preferably 1 hour to 3 hours, whereby compound w'3 can be obtained.

Fourth Step

From compound w'3, compound W'-1 can be obtained in the same manner as in the seventh to eleventh steps in "33) Synthesis of Compounds A'-1 to A'-4" described above.

Fifth Step

From compound W'-1, compound W'-2 can be obtained in the same manner as in the seventeenth step in "33) Synthesis of Compounds A'-1 to A'-4" described above.

As for each compound synthesized by the method described from "35) Synthesis of Compounds B'-1 and B'-2" to "57) Synthesis of Compounds W'-1 and W'-2" described above, it is possible to synthesize an optical isomer and synthesize a compound in which various substituents are introduced into —Y—$R^5$, in the same manner as in the method described in "33) Synthesis of Compounds A'-1 to A'-4" described above. In addition, it is possible to introduce a substituent other than the substituent represented by $OR^{2'}$ into $R^2$, in the method described in "33) Synthesis of Compounds A'-1 to A'-4" described above and the same manner as in "34) Synthesis of Compounds A'-5 and A'-6".

The compound of the present invention has an inhibitory effect on HIV replication, thus is useful as a therapeutic agent and/or prophylactic agent of viral infections such as AIDS.

The compound of the present invention has, not only an inhibitory effect on HIV replication, but also utility as a medicament, and preferably has any or all of excellent characteristics described below.
a) Has a weak inhibitory effect on CYP enzymes (e.g., CYP1A2, CYP2C9, CYP2C19, CYP2D6, CYP3A4, etc.).
b) Shows good pharmacokinetics such as high bioavailability and moderate clearance.
c) Has high metabolic stability.
d) Shows no irreversible inhibitory effect on a CYP enzyme (e.g., CYP3A4) within a concentration range in the measurement conditions described herein.
e) Has no mutagenicity.
f) Has low risk on the cardiovascular system.
g) Shows high solubility.
h) Shows strong efficacy also against resistant viruses.

When administering the pharmaceutical composition of the present invention, it can be administered in any method of orally and parenterally methods. For oral administration, the pharmaceutical composition may be prepared into a commonly used dosage form such as tablets, granules, powders and capsules, according to a conventional method, and administered. In parenteral administration, the pharmaceutical composition can be suitably administered in any commonly used dosage form such as injections. The compound of the present invention preferably has high oral absorbability, thus can be suitably used as an oral agent.

Various pharmaceutical additives such as excipients, binders, disintegrating agents and lubricants suitable for the dosage form can be mixed as necessary in an effective amount of the compound of the present invention, to make the compound into a pharmaceutical composition.

It is desirable that the dosage amount of the pharmaceutical composition of the present invention is set in consideration of the patient's age, weight, the type and degree of disease, the route of administration, and the like, and when orally administered to an adult, the dosage amount is normally in the range of 0.05 to 100 mg/kg/day, and preferably 0.1 to 10 mg/kg/day. In the case of parenteral administration, the dosage amount greatly varies depending on the route of administration, but is normally in the range of 0.005 to 10 mg/kg/day, and preferably 0.01 to 1 mg/kg/day. This dosage amount may be administered in once to several times a day.

The compound of the present invention can be used in combination with a reverse transcriptase inhibitor, a protease inhibitor, an integrase inhibitor, other anti-HIV drug, or the like (hereinafter, abbreviated as concomitant drug), for the purpose of enhancement of action of the compound, reduction of the dosage amount of the compound, or the like. At this time, the time of administration of the compound of the present invention and the concomitant drug is not limited, and, these may be administered simultaneously, or may be administered with a time difference, to the administration subject. Furthermore, the compound of the present invention and the concomitant drug may be administered as two types of preparations containing each active ingredient, or may be administered as a single preparation containing both active ingredients.

The dosage amount of the concomitant drug can be appropriately selected based on the clinically used dose. In addition, the blending ratio of the compound of the present invention to the concomitant drug can be appropriately selected depending on the administration subject, administration route, target disease, symptoms, combination and the like. For example, when the administration subject is a human, 0.01 to 100 parts by weight of the concomitant drug may be used, based on 1 part by weight of the compound of the present invention.

In addition, the compound of the present invention can be used, in the field of gene therapy, to prevent infection of retroviral vectors from spreading to other parts than the object tissues when using a retroviral vector based on HIV and MLV. In particular, when a vector is transmitted to cells and the like in a test tube and then returned to the body, by administering the compound of the present invention in advance, it is possible to prevent unnecessary infection in the body.

Examples of the reverse transcriptase inhibitor include AZT, 3TC, didanosine, zalcitabine, Sanirubujin, abacavir, tenofovir, emtricitabine, Nebirabin, efavirenz, capravirine, etravirine, delavirdine, and the like.

Examples of the protease inhibitor include indinavir, ritonavir, saquinavir, nelfinavir, amprenavir, Atanazabiru, lopinavir, fosamprenavir, darunavir, atazanavir, Burekanabiru, Tipuranabiru, and the like.

Examples of the integrase inhibitor include raltegravir, Erubitegurabiru, JTK-656, S-349572, S-265744, and the like.

Examples of other anti-HIV drugs include entry inhibitors such as maraviroc and Bikuribiroku, fusion inhibitors such as enfuvirtide, sifuvirtide, albuvirtide, and the like.

EXAMPLES

Hereinbelow, the present invention will be described in more detail with reference to examples and reference examples of the present invention and test examples, but the present invention is not limited by these examples.

In addition, abbreviations used herein represent the following meanings.
Ac: acetyl
n-Bu: n-butyl
t-Bu: tert-butyl
Bn: benzyl
DMA: N, N-dimethylacetamide
DME: dimethoxyethane
DMF: N, N-dimethylformamide
DCM: dichloromethane
DMSO: dimethylsulfoxide
dppf: 1,1'-bis(diphenylphosphino)ferrocene
dppp: 1,3-bis(diphenylphosphino)propane
dtbpf: 1,1'-di-tert-butyl phosphinoferrocene
Et: ethyl
Me: methyl
MsOH: methane sulfonic acid
NBS: N-bromosuccinimide
NCS: N-chlorosuccinimide NIS: N-iodosuccinimide Ph: phenyl TBS: tert-butyldimethylsilyl THF: tetrahydrofuran Tf: trifluoromethanesulfonyl TFA: trifluoroacetic acid TMS: trimethylsilyl Ts: p-toluenesulfonyl The NMR analysis obtained in each example was carried out in 300 MHz or 400 Mhz, and was measured using DMSO-$d_6$, CDCl$_3$.

The term RT in the table represents a retention time at LC/MS: liquid chromatography/mass spectrometry, and was measured under the following conditions. For the compound that may exist as two isomers in the mobile phase, two measurement peaks may be obtained.

(Measurement Conditions)

Column: ACQUITY UPLC BEH C18 (1.7 μm, i.d. 2.1×50 mm) (Waters)

Flow rate: 0.8 mL/min

UV detection wavelength: 254 nm

Mobile phase: [A]: a 0.1% formic acid-containing aqueous solution, [B]: a 0.1% formic acid-containing acetonitrile solution Gradient: a linear gradient of 10% to 100% solvent [B] was carried out in 3.5 minutes, and 100% solvent [B] was kept for 0.5 minutes.

Example 1

Synthesis of Compound I-6

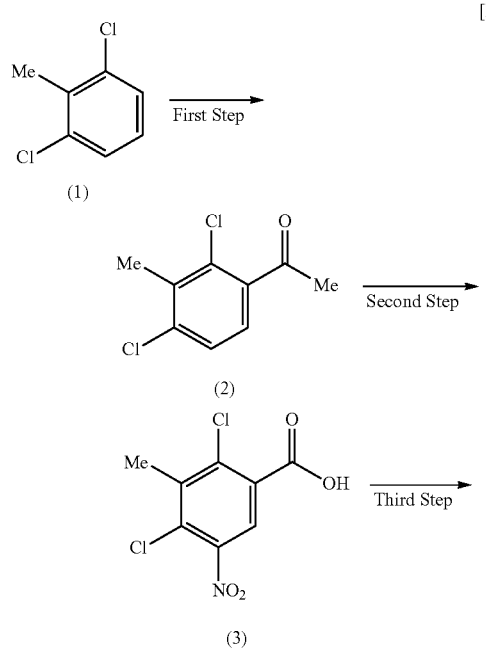

[Formula 148]

-continued

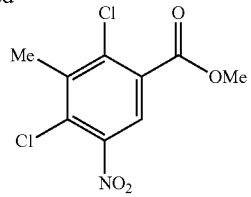

(4)

First Step Synthesis of Compound (2)

Compound (1) (190 g, 1.19 mol) was dissolved in dichloromethane (2 L), and aluminum chloride (313 g, 2.38 mol) was added at room temperature. Acetyl chloride (186 g, 2.38 mol) was added dropwise at room temperature, and the mixture was heated under reflux for 16 hours. After cooling to room temperature, the mixture was flown into ice water (2 L), and extracted with dichloromethane (1 L×2 times). The organic layer was washed with saturated saline (1 L), dried over anhydrous sodium sulfate and concentrated, and then purified by silica gel column chromatography to give compound (2) (180 g, 75% yield) as a yellow solid.

$^1$H NMR (CDCl$_3$) δ: 2.51 (s, 3H), 2.61 (s, 3H), 7.23 (d, J=8.4 Hz, 1H), 7.34 (d, J=8.4 Hz, 1H)

Second Step Synthesis of Compound (3)

Compound (2) (120 g, 0.594 mol) was dissolved in sulfuric acid (600 mL, 98%), and nitric acid (120 mL, 70%) was added dropwise under ice-cooling, and stirred at room temperature for 16 hours. After completion of the reaction, the mixture was flown into ice water (3 L), and an insoluble matter was filtered. The filtered matter was dissolved in ethyl acetate (1.5 L) and a 5% aqueous sodium hydroxide solution (2 L), and the aqueous layer was adjusted to pH 2 with 1 N hydrochloric acid and separated, and then the aqueous layer was extracted with ethyl acetate (1 L×2 times). The organic layer was washed with saturated saline (1 L) and then dried over anhydrous sodium sulfate and concentrated to give compound (3) as a yellow solid (94 g, 63% yield).

$^1$H NMR (CDCl$_3$) δ: 2.67 (s, 3H), 8.26 (s, 1H)

Third Step Synthesis of Compound (4)

Compound (3) (93 g, 0.372 mol) was dissolved in methanol (1 L), and sulfuric acid (20 mL, 98%) was added at room temperature, and then the mixture was heated under reflux for 16 hours. After cooling to room temperature, the mixture was concentrated, and the residue was dissolved in ethyl acetate (1 L) and sequentially washed with saturated aqueous sodium bicarbonate (500 mL) and saturated saline (500 mL). Thereafter, the mixture was dried over anhydrous sodium sulfate and concentrated, and then purified by silica gel column chromatography to give compound (4) as a yellow solid (58.7 g, 60% yield).

$^1$H NMR (CDCl$_3$) δ: 2.64 (s, 3H), 3.96 (s, 3H), 8.07 (s, 1H)

[Formula 149]

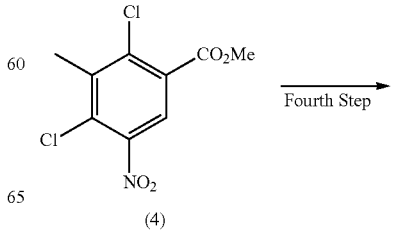

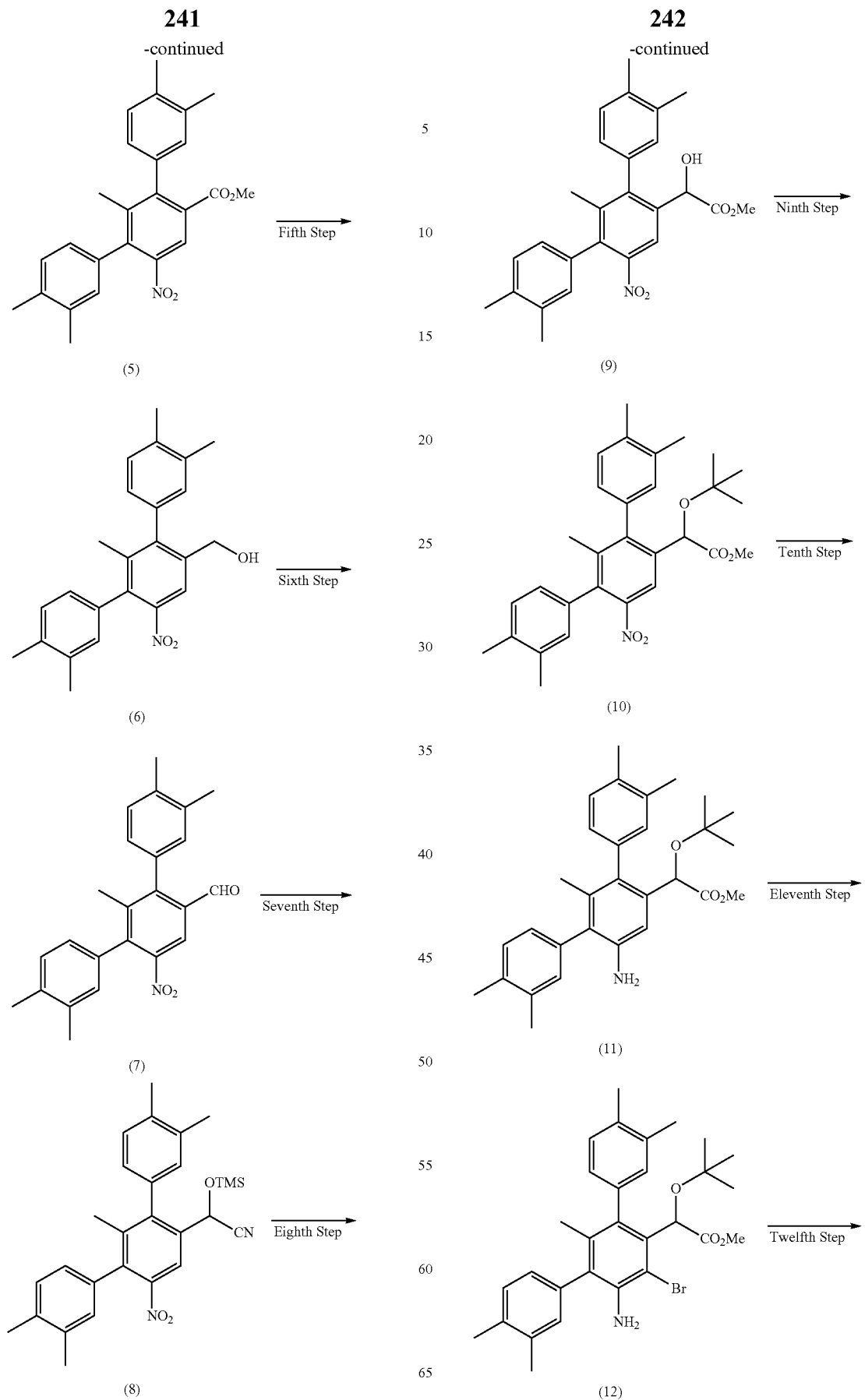

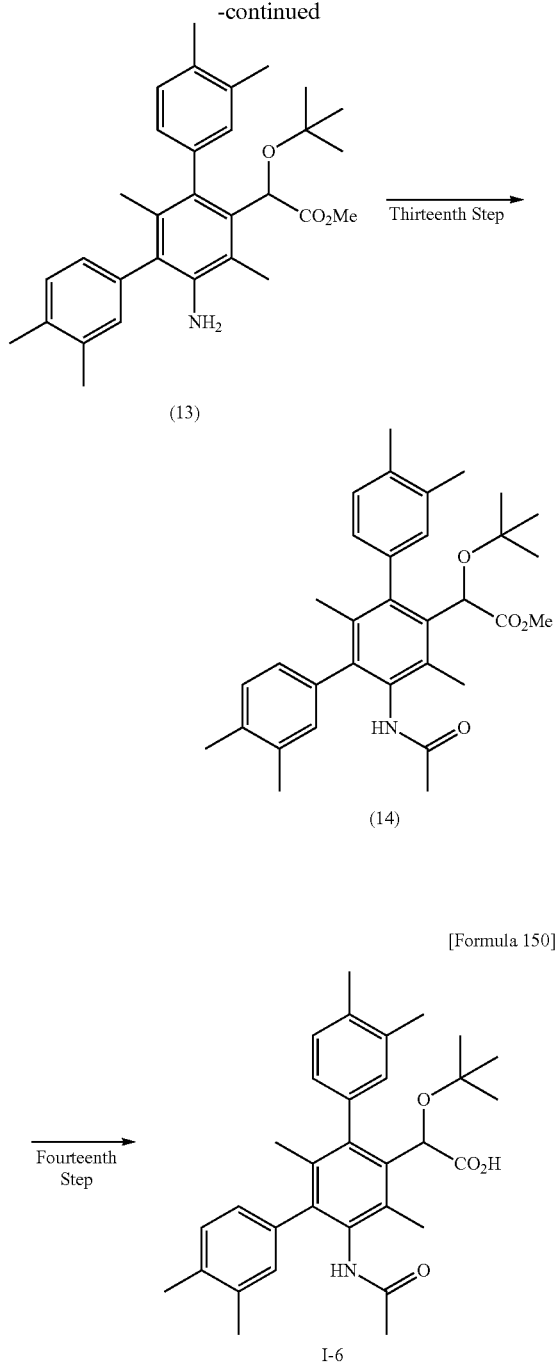

Fourth Step Synthesis of Compound (5)

Compound (4) (18.5 g, 70.1 mmol) and 3,4-dimethylphenylboronic acid (22.07 g, 147 mmol) were dissolved in dioxane (315 mL), and a 2 mol/L aqueous potassium carbonate solution (105 mL, 210 mmol) was added, and then the operation of degassing and nitrogen substitution was repeated three times. Pd(PPh$_3$)$_4$ (810 mg, 0.701 mmol) was added, and the operation of degassing and nitrogen substitution was again repeated three times, and then the mixture was stirred at 100° C. for 22 hours. The reaction solution was poured into ice water (450 mL) and a 2 mol/L aqueous hydrochloric acid solution (150 mL), and extracted with ethyl acetate. The organic layer was sequentially washed with a saturated aqueous sodium bicarbonate solution and a saturated aqueous sodium chloride solution, and dried over anhydrous sodium sulfate, and then the solvent was evaporated under reduced pressure using an evaporator. The resulting residue was purified by silica gel chromatography (hexane-ethyl acetate) to give compound (5) as yellow foam (20.06 g, 71.0% yield).

$^1$H NMR (CDCl$_3$) δ: 1.85 (s, 3H), 2.27 (s, 3H), 2.29 (s, 3H), 2.30 (s, 3H), 2.31 (s, 3H), 3.64 (s, 3H), 6.80-6.98 (m, 4H), 7.15-7.21 (m, 2H), 8.08 (s, 1H).

Fifth Step Synthesis of Compound (6)

Compound (5) (20.06 g, 49.7 mmol) was dissolved in dichloromethane (300 mL), and the solution was cooled to an internal temperature of −78° C. in a dry ice bath. A 1 mmol/L toluene solution (149 mL, 149 mmol) of diisobutylaluminum hydride was added dropwise at the same temperature over a period of about 1 hour. Next, the solution was stirred at an internal temperature of −30° C. for 1 hour and again cooled to −78° C., and a 2 mol/L aqueous hydrochloric acid solution (150 mL) was added, and then the mixture was stirred for a while. The reaction solution was poured into ice water (200 mL), and extracted with chloroform. The organic layer was sequentially washed with a saturated aqueous sodium bicarbonate solution and water, and dried over anhydrous sodium sulfate, and then the solvent was evaporated under reduced pressure using an evaporator. The resulting residue was purified by silica gel chromatography (hexane-ethyl acetate) to give compound (6) as yellow foam (16.80 g, 90.0% yield).

$^1$H NMR (CDCl$_3$) δ: 1.80 (s, 3H), 2.27 (s, 3H), 2.29 (s, 3H), 2.30 (s, 3H), 2.32 (s, 3H), 4.42 (s, 2H), 6.85-6.98 (m, 4H), 7.14-7.27 (m, 2H), 7.83 (s, 1H).

Sixth Step Synthesis of Compound (7)

Compound (6) (16.80 g, 44.7 mmol) was dissolved in dichloromethane (170 mL), and manganese dioxide (38.9 g, 447 mmol) was added, and then the mixture was stirred at 70° C. for 2.5 hours. After cooled to room temperature, the reaction solution was filtered through celite, and then the filtrate was evaporated under reduced pressure using an evaporator. The resulting residue was purified by silica gel chromatography (hexane-ethyl acetate) to give compound (7) as pale orange crystalline powder (13.95 g, 83.5% yield).

$^1$H NMR (CDCl$_3$) δ: 1.91 (s, 3H), 2.28 (s, 3H), 2.30 (s, 3H), 2.32 (s, 3H), 2.35 (s, 3H), 6.90-7.03 (m, 4H), 7.17-7.25 (m, 2H), 8.18 (m, 1H), 9.65 (s, 1H).

Seventh Step Synthesis of Compound (8)

Compound (7) (13.95 g, 37.4 mmol) was dissolved in dichloromethane (140 mL), and the solution was cooled to an internal temperature of 0° C. in an ice bath. Zinc iodide (12.55 g, 37.4 mmol) and trimethylsilyl cyanide (15.65 mL, 112 mmol) were sequentially added at the same temperature, the ice bath was removed, and the mixture was stirred at room temperature for 1.5 hours. The reaction solution was poured into ice water and a saturated aqueous sodium bicarbonate solution, and extracted with chloroform. The organic layer was washed with water and dried over anhydrous sodium sulfate, and then the solvent was evaporated under reduced pressure using an evaporator. Compound (8) (18.80 g) obtained as red foam was used in the next reaction without purification.

$^1$H NMR (CDCl$_3$) δ: 0.10 (s, 3H), 0.11 (s, 3H), 1.80 (s, 3H), 2.25-2.36 (m, 12H), 5.17 (m, 1H), 6.80-7.02 (m, 4H), 7.14-7.29 (m, 2H), 8.01 (s, 1H).

Eighth Step Synthesis of Compound (9)

Compound (8) (18.80 g) was dissolved in methanol (83.1 mL), and the solution was cooled to an internal temperature of 0° C. in an ice bath. Concentrated sulfuric acid (20.8 mL, 374 mmol) was added, and the ice bath was removed, and then the mixture was stirred at 90° C. for 21 hours. The reaction solution was poured into ice water, and extracted with ethyl acetate. The organic layer was sequentially washed with a saturated aqueous sodium bicarbonate solution and a saturated aqueous sodium chloride solution, and dried over anhydrous sodium sulfate, and then the solvent was evaporated under reduced pressure using an evaporator. The resulting residue was purified by silica gel chromatography (hexane-ethyl acetate) to give compound (9) as pale yellow foam (14.38 g, 88.7% yield (seventh to eighth steps)).

$^1$H NMR (CDCl$_3$) δ: 1.80 (s, 3H), 2.25-2.33 (m, 12H), 3.37 (br s, 1H), 3.73 (s, 3H), 4.99 (m, 1H), 6.86-7.03 (m, 4H), 7.13-7.25 (m, 2H), 7.65 (s, 1H).

Ninth Step Synthesis of Compound (10)

Compound (9) (14.38 g, 33.2 mmol) was dissolved in tert-butyl acetate (144 mL), and a 70% aqueous perchloric acid solution (5.70 mL, 66.3 mmol) was added, and then the mixture was stirred at room temperature for 2 hours. The reaction solution was poured into ice water and a saturated aqueous sodium bicarbonate solution, and extracted with ethyl acetate. The organic layer was washed with a saturated aqueous sodium chloride solution and dried over anhydrous sodium sulfate, and then the solvent was evaporated under reduced pressure using an evaporator. The resulting residue was purified by silica gel chromatography (hexane-ethyl acetate) to give compound (10) as pale orange foam (9.77 g, 60.2% yield).

$^1$H NMR (CDCl$_3$) δ: 1.08 (s, 9H), 1.78 (s, 3H), 2.25-2.36 (m, 12H), 3.64 (s, 3H), 4.85 (m, 1H), 6.85-7.00 (m, 4H), 7.15-7.26 (m, 2H), 7.98 (m, 1H).

Tenth Step Synthesis of Compound (11)

Compound (10) (2.448 g, 5 mmol) was dissolved in methanol (25 mL), and 20% by weight palladium hydroxide (490 mg) was added, and then the mixture was stirred under a hydrogen atmosphere at room temperature for 7 hours. The reaction solution was filtered through celite, and then the filtrate was evaporated under reduced pressure using an evaporator. The resulting residue was purified by silica gel chromatography (hexane-ethyl acetate) to give compound (11) as pale pink foam (2.033 g, 88.5% yield).

$^1$H NMR (DMSO-d$_6$) δ: 0.92-0.95 (m, 9H), 1.51-1.54 (m, 3H), 2.21 (s, 3H), 2.23 (s, 3H), 2.25 (s, 3H), 2.26 (s, 3H), 3.55 (s, 3H), 4.69 (s, 2H), 4.31 (s, 1H), 6.75-6.98 (m, 5H), 7.12-7.24 (m, 2H).

Eleventh Step Synthesis of Compound (12)

Compound (11) (460 mg, 1 mmol) was dissolved in DMF (4.6 mL), and the solution was cooled to an internal temperature of 0° C. in an ice bath. NBS (178 mg, 1 mmol) was added, and the ice bath was removed, and then the mixture was stirred at room temperature for 1.5 hours. The reaction solution was poured into ice water and a saturated aqueous sodium bicarbonate solution, and extracted with ethyl acetate. The organic layer was washed with a saturated aqueous sodium chloride solution, and dried over anhydrous sodium sulfate, and then the solvent was evaporated under reduced pressure using an evaporator. The resulting residue was purified by silica gel chromatography (hexane-ethyl acetate) to give compound (12) as white foam (481 mg, 89.3% yield).

$^1$H NMR (DMSO-d$_6$) δ: 0.92-0.96 (m, 9H), 1.48-1.51 (m, 3H), 2.18-2.20 (m, 12H), 3.58 (s, 3H), 4.31 (s, 3H), 5.14 (br s, 1H), 6.90-7.30 (in, 6H).

Twelfth Step Synthesis of Compound (13)

Compound (12) (369 mg, 0.685 mmol) and trimethylboroxine (258 mg, 2.06 mmol) were dissolved in a mixed solvent of dioxane (7.4 mL) and water (0.74 mL), and the operation of degassing and nitrogen substitution was repeated three times. PdCl$_2$(dppf)$_2$ (56.0 mg, 0.069 mmol) was added, and the operation of degassing and nitrogen substitution was again repeated three times, and then the mixture was stirred at 120° C. for 7.5 hours. The reaction solution was poured into ice water, and extracted with ethyl acetate. The organic layer was washed with a saturated aqueous sodium chloride solution, and dried over anhydrous sodium sulfate, and then the solvent was evaporated under reduced pressure using an evaporator. The resulting residue was purified by silica gel chromatography (hexane-ethyl acetate) to give compound (13) as white foam (188 mg, 57.9% yield).

$^1$H NMR (DMSO-d$_6$) δ: 0.88-0.91 (m, 9H), 1.47-1.51 (m, 2H), 2.06-2.10 (m, 2H), 2.18-2.28 (m, 12H), 3.59-3.63 (m, 3H), 3.89 (s, 2H), 4.95 (m, 1H), 6.84-7.27 (m, 6H).

Thirteenth Step Synthesis of Compound (14)

Compound (13) (100 mg, 0.211 mmol) was dissolved in dichloromethane (1 mL), and the solution was cooled to an internal temperature of 0° C. in an ice bath. Pyridine (0.034 mL, 0.422 mmol) and acetyl chloride (0.023 mL, 0.317 mmol) were sequentially added, the ice bath was removed, and the mixture was stirred at room temperature for 1.5 hours. The reaction solution was poured into ice water and a 2 mol/L aqueous hydrochloric acid solution, and extracted with ethyl acetate. The organic layer was sequentially washed with a saturated aqueous sodium bicarbonate solution and a saturated aqueous sodium chloride solution, and dried over anhydrous sodium sulfate, and then the solvent was evaporated under reduced pressure using an evaporator. The resulting residue was purified by silica gel chromatography (hexane-ethyl acetate) to give compound (14) as white foam (79 mg, 72.6% yield).

$^1$H NMR (CDCl$_3$) δ: 0.98-1.01 (m, 9H), 1.64-1.67 (m, 3H), 1.83 (s, 3H), 2.23-3.24 (m, 15H), 3.67-3.70 (m, 3H), 5.06 (s, 1H), 6.31 (s, 1H), 6.78-7.22 (m, 6H).

Fourteenth Step Synthesis of Compound I-6

Compound (14) (79 mg, 0.153 mmol) was dissolved in a mixed solvent of tetrahydrofuran (0.8 mL) and methanol (1.6 mL), and a 2 mol/L aqueous sodium hydroxide solution (0.383 mL) was added, and then the mixture was stirred at 60° C. for 4 hours. The reaction solution was poured into ice water, and the aqueous layer was washed with diethyl ether, the pH was adjusted to nearly equal to 3 with a 2 mol/L aqueous hydrochloric acid solution, and the reaction solution was extracted with ethyl acetate. The organic layer was washed with a saturated aqueous sodium chloride solution, and dried over anhydrous sodium sulfate, and then the solvent was evaporated under reduced pressure using an evaporator. The resulting residue was dried at 60° C. under reduced pressure, thereby obtaining compound I-6 as pale white powder (58 mg, 75.5% yield).

$^1$H NMR (DMSO-d$_6$) δ: 0.90 (s, 9H), 1.55-1.60 (m, 3H), 1.66 (s, 3H), 2.15-2.29 (m, 15H), 4.92 (m, 1H), 6.77-7.27 (m, 6H). FABMS m/z [M+H]$^+$=502.

Example 2

Synthesis of Compound I-12

[Formula 151]

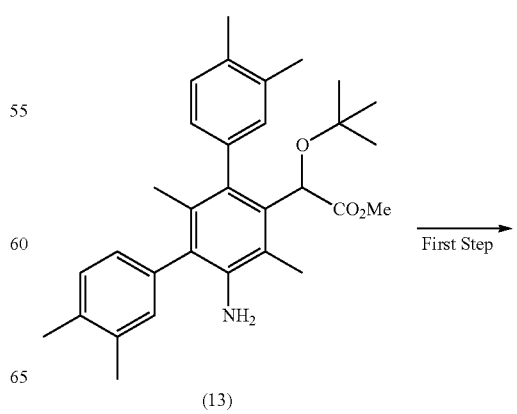

Example 3

Synthesis of Compound I-11

[Formula 152]

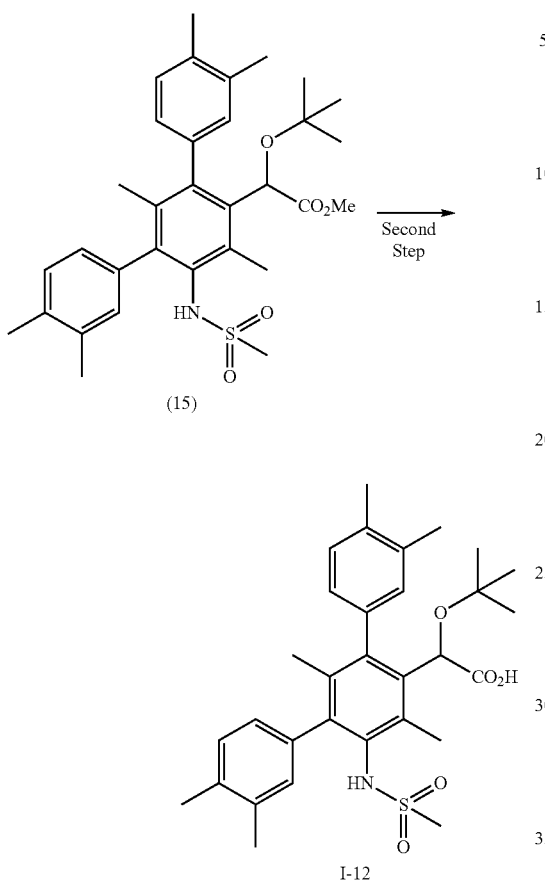

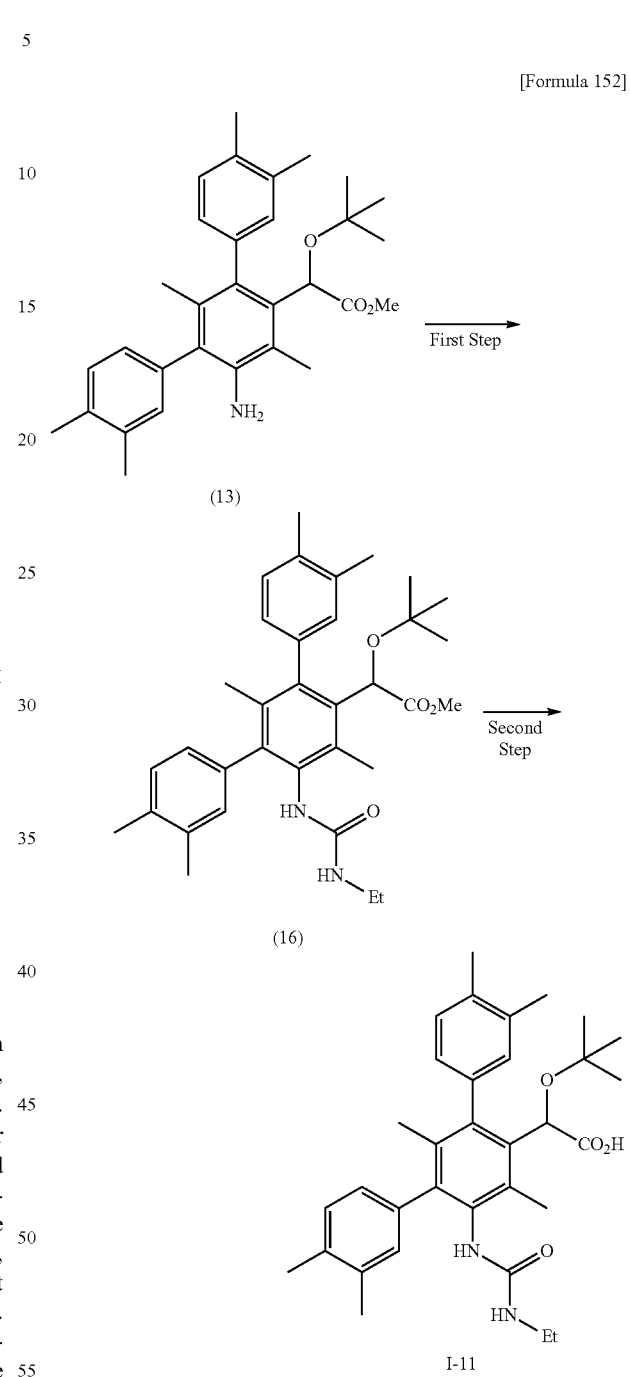

First Step Synthesis of Compound (15)

Compound (13) (100 mg, 0.211 mmol) was dissolved in pyridine (1 mL), and methanesulfonyl chloride (0.025 mL, 0.317 mmol) was added, and the mixture was stirred at 50° C. for 12 hours. The reaction solution was poured into ice water and a 2 mol/L aqueous hydrochloric acid solution, and extracted with ethyl acetate. The organic layer was sequentially washed with a saturated aqueous sodium bicarbonate solution and a saturated aqueous sodium chloride solution, and dried over anhydrous sodium sulfate, and then the solvent was evaporated under reduced pressure using an evaporator. The resulting residue was purified by silica gel chromatography (hexane-ethyl acetate) to give compound (15) as white foam (84 mg, 72.1% yield).

$^1$H NMR (CDCl$_3$) δ: 0.98-1.00 (m, 9H), 1.64-1.67 (m, 3H), 2.26-2.52 (m, 18H), 3.67-3.71 (m, 3H), 5.05 (s, 1H), 5.71 (m, 1H), 6.90-7.21 (m, 6H).

Second Step Synthesis of Compound I-12

In the same manner as in the fourteenth step in Example 1, from compound (15) (85 mg, 0.156 mmol), compound I-12 was obtained as white powder (71 mg, 85.6% yield).

$^1$H NMR (DMSO-d$_6$) δ: 0.88-0.90 (m, 9H), 1.57-1.61 (m, 3H), 2.01 (s, 3H), 2.21-2.40 (m, 15H), 4.91 (m, 1H), 6.85-7.25 (m, 6H), 8.43 (s, 1H). FABMS m/z [M]$^+$=537.

First Step Synthesis of Compound (16)

Compound (13) (100 mg, 0.211 mmol) was dissolved in toluene (1 mL), and ethyl isocyanate (0.025 mL, 0.317 mmol) was added, and the mixture was stirred at 70° C. for 4 hours. The reaction solution was poured into ice water, and extracted with ethyl acetate. The organic layer was washed with a saturated aqueous sodium chloride solution, and dried over anhydrous sodium sulfate, and then the solvent was evaporated under reduced pressure using an evaporator. The resulting residue was purified by silica gel chromatography (hexane-ethyl acetate) to give compound (16) as white crystalline powder (87 mg, 75.6% yield).

¹H NMR (CDCl₃) δ: 0.98-1.01 (m, 9H), 1.07 (t, J=7.2 Hz, 3H), 1.66-1.70 (m, 3H), 2.22-2.38 (m, 15H), 3.10-3.28 (m, 2H), 3.68-3.72 (m, 3H), 4.31 (br s, 1H), 5.07 (s, 1H), 5.48 (br s, 1H), 6.80-7.20 (m, 6H).

Second Step Synthesis of Compound I-11

In the same manner as in the fourteenth step in Example 1, from compound (16) (82 mg, 0.149 mmol), compound I-11 was obtained as white powder (48 mg, 60.1% yield).

¹H NMR (DMSO-d₆) δ: 0.88-0.91 (m, 9H), 1.17 (t, J=7.2 Hz, 3H), 1.54-1.57 (m, 3H), 2.18-2.29 (m, 15H), 2.85-3.00 (m, 2H), 4.91 (m, 1H), 5.71 (br s, 1H), 6.75 (s, 1H), 6.80-7.25 (m, 6H). FABMS m/z [M+H]⁺=531.

Example 4

Synthesis of Compound I-14

[Formula 153]

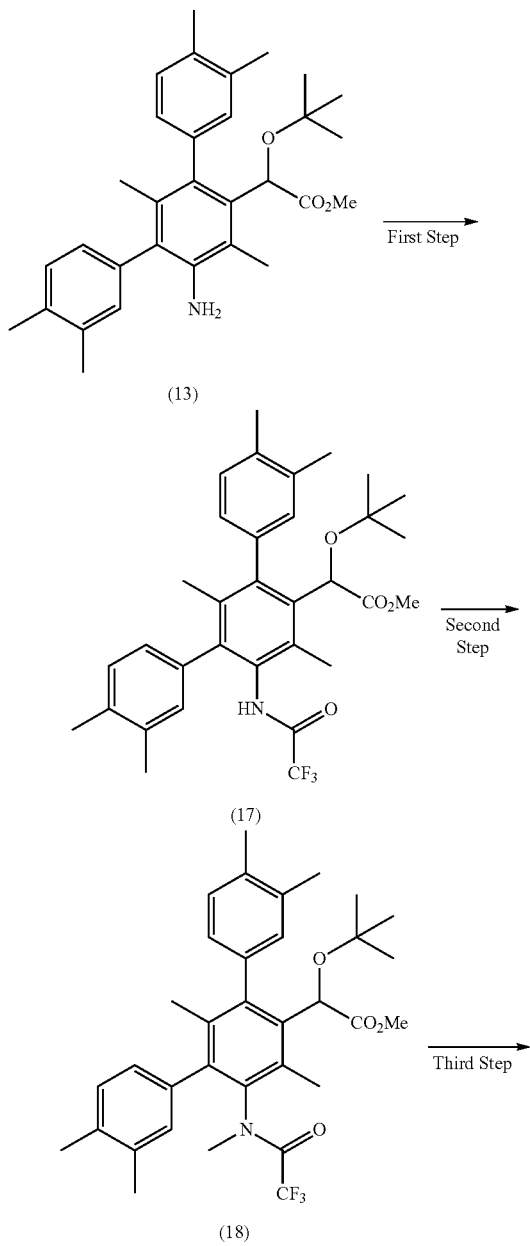

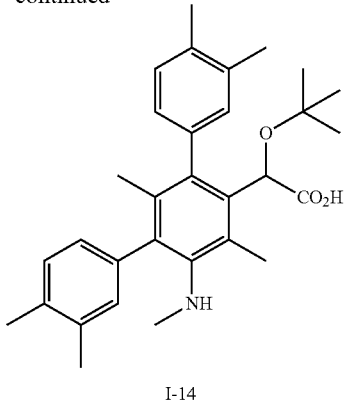

I-14

First Step Synthesis of Compound (17)

Compound (13) (550 mg, 1.61 mmol) was dissolved in dichloromethane (5.5 mL), and the solution was cooled to an internal temperature of 0° C. in an ice bath. Pyridine (0.187 mL, 2.32 mmol) and trifluoroacetic anhydride (0.187 mL, 1.74 mmol) were sequentially added, and the mixture was stirred at the same temperature for 1.5 hours. The reaction solution was poured into ice water and a 2 mol/L aqueous hydrochloric acid solution, and extracted with ethyl acetate. The organic layer was sequentially washed with a saturated aqueous sodium bicarbonate solution and a saturated aqueous sodium chloride solution, and dried over anhydrous sodium sulfate, and then the solvent was evaporated under reduced pressure using an evaporator. The resulting residue was purified by silica gel chromatography (hexane-ethyl acetate) to give compound (17) as white foam (648 mg, 98.0% yield).

¹H NMR (CDCl₃) δ: 1.00 (s, 9H), 1.68-1.71 (m, 3H), 2.24-2.33 (m, 15H), 3.67-3.71 (m, 3H), 5.07 (m, 1H), 6.85-7.20 (m, 7H).

Second Step Synthesis of Compound (18)

Compound (17) (147 mg, 0.258 mmol) was dissolved in dimethylformamide (1.5 mL), potassium carbonate (71.3 mg, 0.516 mmol) and iodomethane (0.081 mL, 1.29 mmol) were sequentially added, and the mixture was stirred at room temperature for 2 hours. The reaction solution was poured into ice water and a 2 mol/L aqueous hydrochloric acid solution, and extracted with ethyl acetate. The organic layer was sequentially washed with a saturated aqueous sodium bicarbonate solution and a saturated aqueous sodium chloride solution, and dried over anhydrous sodium sulfate, and then the solvent was evaporated under reduced pressure using an evaporator. The resulting residue was purified by silica gel chromatography (hexane-ethyl acetate) to give compound (18) as white foam (121 mg, 80.3% yield).

¹H NMR (CDCl₃) δ: 0.97-1.00 (m, 9H), 1.62-1.71 (m, 3H), 2.21-2.33 (m, 15H), 2.90-3.00 (m, 3H), 3.63-3.74 (m, 3H), 5.05 (m, 1H), 6.80-7.20 (m, 6H).

Third Step Synthesis of Compound I-14

Compound (18) (30.2 mg, 0.053 mmol) was dissolved in dimethylsulfoxide (1.0 mL), and a 2 mol/L aqueous sodium hydroxide solution (0.25 mL) was added, and then the mixture was stirred at 60° C. for 2 hours, and at 100° C. for 3 hours. The reaction solution was poured into ice water, and the pH was adjusted to about 3 with a 2 mol/L aqueous hydrochloric acid solution, and then the reaction solution was extracted with ethyl acetate. The organic layer was washed with a saturated aqueous sodium chloride solution, and dried over anhydrous sodium sulfate, and then the solvent was evaporated under reduced pressure using an evaporator. The resulting residue was purified by silica gel chromatography (chloroform-methanol) to give compound I-14 as pale white powder (22 mg, 88.2% yield).

$^1$H NMR (DMSO-$d_6$) δ: 0.89 (s, 9H), 1.48-1.51 (m, 3H), 2.20-2.30 (m, 15H), 2.36 (s, 3H), 4.89 (m, 1H), 6.85-7.25 (m, 6H). FABMS m/z [M+H]$^+$=474.

Example 5

Synthesis of Compound I-15

[Formula 154]

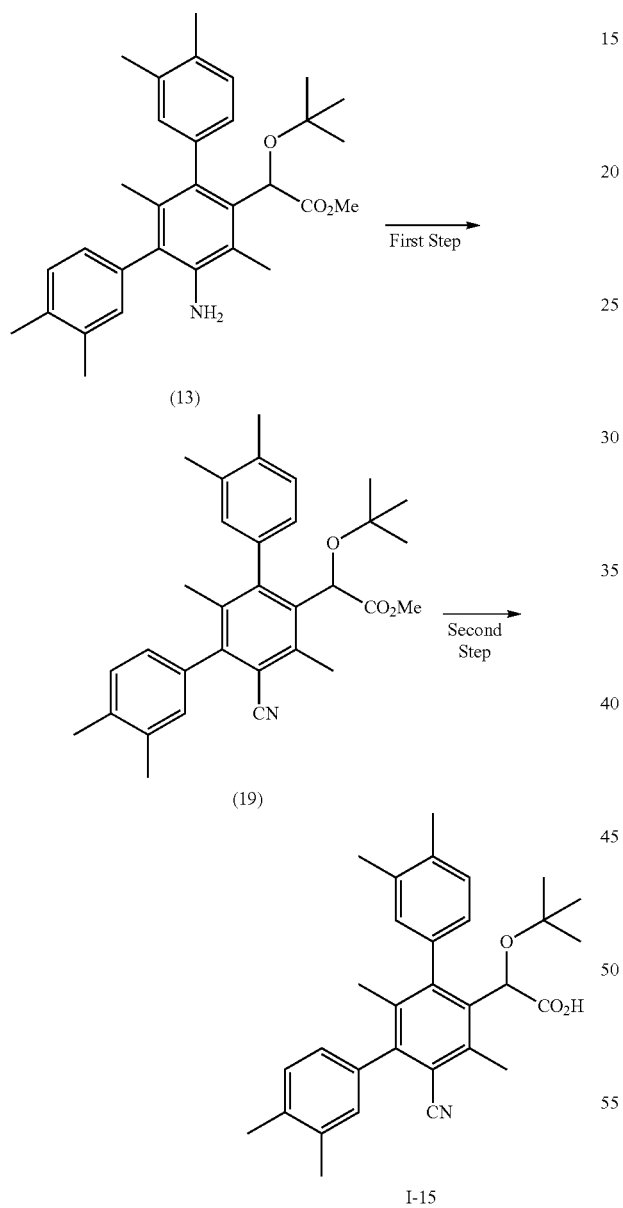

First Step Synthesis of Compound (19)

Compound (13) (30 mg, 0.063 mmol) and copper cyanide (7.37 mg, 0.082 mmol) were dissolved in DMSO (0.6 mL), and tert-butyl nitrite (0.25 mL, 0.190 mmol) was added, and then the mixture was stirred at 50° C. for 1.5 hours. Water was added, and the mixture was extracted with ethyl acetate. The organic layer was washed with water and saturated saline, and then dried over anhydrous magnesium sulfate. The solvent was evaporated under reduced pressure, and the resulting residue was purified by silica gel column chromatography (hexane-ethyl acetate) to give compound (19) (10 mg, 33% yield).

$^1$H-NMR (CDCl$_3$) δ: 7.24-7.22 (m, 3H), 7.05-7.03 (m, 3H), 5.03 (s, 1H), 3.71 (d, J=6.6 Hz, 3H), 2.65 (s, 3H), 2.31 (s, 12H), 1.72 (d, J=4.5 Hz, 3H), 1.24 (s, 3H), 0.99 (s, 9H).

Second Step Synthesis of Compound I-15

In the same manner as in the fourteenth step in Example 1, from compound (19) (6.0 mg, 0.012 mmol), compound I-15 (5.6 mg, 96% yield) was obtained.

$^1$H-NMR (CDCl$_3$) δ: 7.23-7.20 (m, 3H), 7.04-6.96 (m, 3H), 5.16 (s, 1H), 2.62 (s, 3H), 2.30 (s, 12H), 1.75 (s, 3H), 1.24 (s, 3H), 1.03 (s, 9H)

Example 6

Synthesis of Compound I-44

[Formula 155]

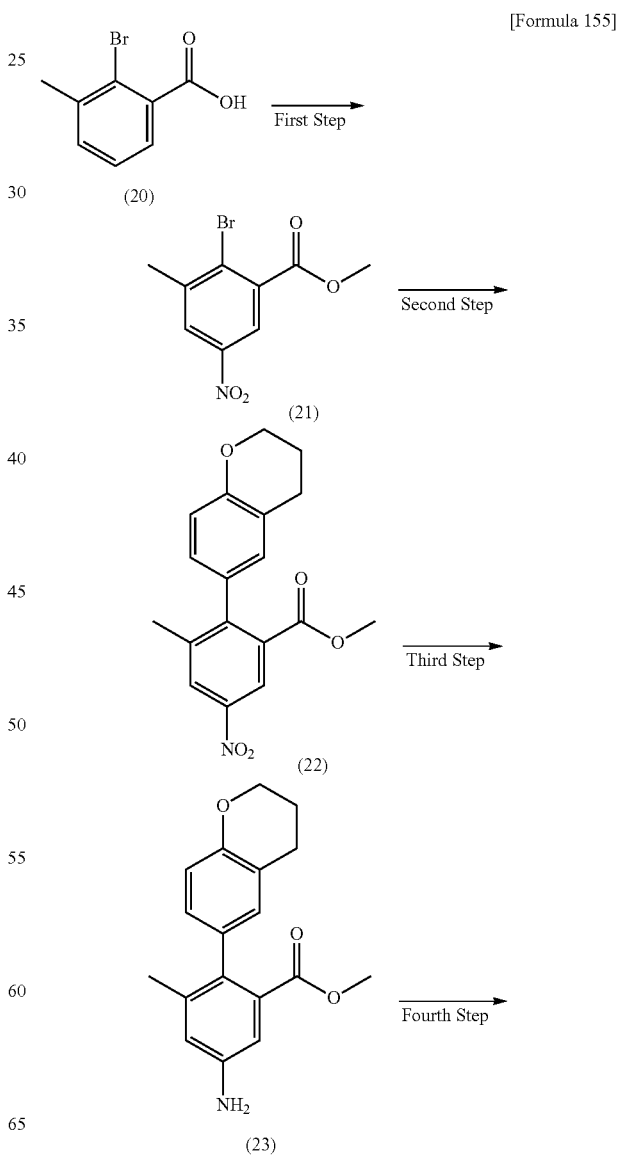

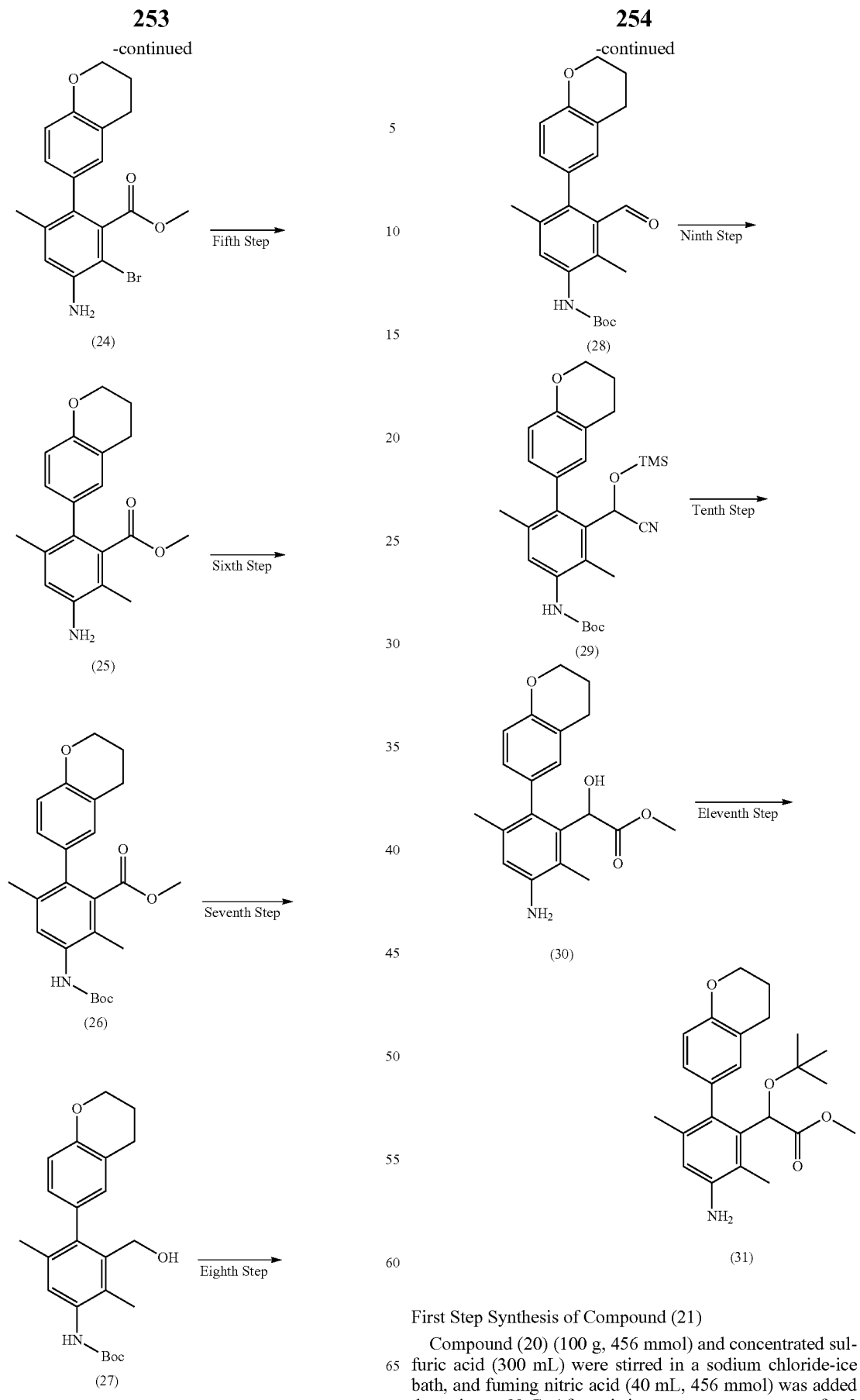
First Step Synthesis of Compound (21)
Compound (20) (100 g, 456 mmol) and concentrated sulfuric acid (300 mL) were stirred in a sodium chloride-ice bath, and fuming nitric acid (40 mL, 456 mmol) was added dropwise at 0° C. After stirring at room temperature for 2 hours, the reaction mixture was added to ice, and the precipitated solid was filtered. The precipitated solid was dissolved in ethyl acetate (500 mL), and washed with water and saline, and then dried over sodium sulfate to be concentrated and dried. The concentrated residue was dissolved in thionyl chloride (270 mL), and heated under reflux for 1 hour to be concentrated and dried. Furthermore, methanol (400 mL) was slowly added to the concentrated residue, and heated under reflux for 1 hour to be concentrated and dried. The concentrated residue was recrystallized from ethyl acetate, thereby obtaining compound (21) (72 g).

$^1$H-NMR (CD3OD) δ: 2.59 (s, 3H), 3.98 (s, 3H), 8.32 (s, 2H)

Second Step Synthesis of Compound (22)

Compound (21) (50 g, 183 mmol), 2-(chroman-6-yl)-4,4,5,5-tetramethyl-1,3,2-dioxaborolane (57.8 g, 220 mmol) and $Cs_2CO_3$ (178 g, 550 mmol) were dissolved in dioxane (400 mL)-water (80 mL), and Pd(dppf)$Cl_2$ (2 g, 2.4 mmol) was added under a nitrogen atmosphere, and then the mixture was heated and stirred at 90° C. for 14 hours. After cooling to room temperature, ethyl acetate and water were added, and the organic layer was washed with saturated saline, dried over sodium sulfate, and purified by silica gel column chromatography (petroleum ether:ethyl acetate=8:1), thereby obtaining compound (22) (47.2 g).

LC-MS (ESI): m/z=328 [M+H]$^+$.

Third Step Synthesis of Compound (23)

Compound (22) (47.2 g, 145 mmol) was dissolved in methanol (200 mL), and 10% palladium carbon (20 g) was added under a nitrogen atmosphere. The reaction vessel was replaced by hydrogen, and the mixture was stirred at room temperature for 14 hours. Palladium was filtered through celite, and the filtrate was concentrated and dried, thereby obtaining compound (23) (42 g). The concentrated residue was used for next reaction without purification.

1HNMR (CDCl$_3$): 2.04-2.06 (m, 2H), 2.24 (s, 3H), 2.80 (s, 2H), 3.66 (s, 3H), 4.23-4.25 (m, 2H), 6.80-6.85 (m, 3H), 8.23 (s, 1H), 8.46 (s, 1 H).

Fourth Step Synthesis of Compound (24)

Compound (23) (42 g, 142 mmol) was dissolved in DMF (200 mL), and a DMF (50 mL) solution of NBS (25.2 g, 142 mmol) was added dropwise under ice cooling, and then the mixture was stirred for 10 minutes. Ethyl acetate and water were added, and the organic layer was washed with saturated saline and dried over sodium sulfate to be concentrated. The residue was purified by silica gel column chromatography (petroleum ether:ethyl acetate=8:1), thereby obtaining compound (24) (23 g).

LC-MS (ESI): m/z=376 [M+H]+.

1HNMR (CDCl$_3$): 2.01-2.04 (m, 5H), 2.75-2.78 (m, 2H), 3.59 (s, 3H), 4.19-4.21 (m, 2H), 6.71-6.76 (m, 2H), 6.85-6.89 (m, 2 H).

Fifth Step Synthesis of Compound (25)

Compound (24) (36.9 g, 98 mmol), trimethylboroxine (50%, 36.9 g, 148 mmol) and $Cs_2CO_3$ (96 g, 295 mmol) were dissolved in dioxane (400 mL)-water (80 mL), and Pd(dppf)$Cl_2$ (4 g, 4.9 mmol) was added under a nitrogen atmosphere, and then the mixture was heated and stirred at 90° C. for 14 hours. After cooling to room temperature, ethyl acetate and water were added, and the organic layer was washed with saturated saline, dried over sodium sulfate, and purified by silica gel column chromatography (petroleum ether:ethyl acetate=5:1), thereby obtaining compound (25) (28.1 g).

LC-MS (ESI): m/z=312 [M+H]+.

Sixth Step Synthesis of Compound (26)

$Boc_2O$ (50 mL) was added to compound (25) (28.1 g, 90 mmol), and the mixture was stirred at 80° C. for 4 hours. The concentrated residue was purified by silica gel column chromatography (petroleum ether:ethyl acetate=10:1), thereby obtaining compound (26) (32.1 g).

LC-MS (ESI): m/z=429 [M+18]+.

1H-NMR (CDCl$_3$) δ: 1.54 (s, 9H), 2.00-2.03 (m, 2H), 2.10 (s, 3H), 2.16 (s, 3H), 2.76-2.79 (m, 2H), 3.51 (s, 3H), 4.19-4.22 (m, 2H), 6.27 (s, 1H), 6.75-6.89 (m, 3H), 7.75 (s, 1H)

Seventh Step Synthesis of Compound (27)

Compound (26) (32.1 g, 78 mmol) was dissolved in dichloromethane (400 mL), and a 1 M diisobutylaluminium hydride/toluene solution (345 mL, 345 mmol) was added at −78° C., and then the mixture was stirred at −78° C. for 1.5 hours and at 0° C. for 30 minutes. 1 M hydrochloric acid (500 mL) was added and the mixture was stirred for 1 hour, and the dichloromethane was separated. The organic layer was washed with water (500 mL) and saturated saline (200 mL), and dried over magnesium sulfate. The mixture was concentrated and dried, thereby obtaining compound (27) (26.8 g).

LC-MS (ESI): m/z=789 [2M+Na]+.

1H-NMR (CDCl$_3$) δ: 1.53 (s, 9H), 2.00-2.06 (m, 5H), 2.34 (s, 3H), 2.78-2.81 (m, 2H), 4.22-4.24 (m, 2H), 4.43 (s, 2H), 6.29 (s, 1H), 6.79-6.82 (m, 3H), 7.59 (s, 1H)

Eighth Step Synthesis of Compound (28)

Compound (27) (26.8 g, 70 mmol) was dissolved in dichloromethane (100 mL), and pyridinium chlorochromate (22.3 g, 104 mmol) was added, and then the mixture was stirred at room temperature for 3 hours. The concentrated residue was purified by silica gel column chromatography (petroleum ether:ethyl acetate=8:1), thereby obtaining compound (28) (23.7 g).

LC-MS (ESI): m/z=785 [2M+Na]+.

1H-NMR (CDCl$_3$) δ: 1.54 (s, 9H), 2.03-2.06 (m, 2H), 2.11 (s, 3H), 2.45 (s, 3H), 2.78-2.81 (m, 2H), 4.22-4.24 (m, 2H), 6.37 (s, 1H), 6.79-6.87 (m, 3H), 7.88 (s, 1H), 9.76 (s, 1H)

Ninth Step Synthesis of Compound (29)

Compound (28) (23.7 g, 62 mmol) was dissolved in dichloromethane (300 mL), and zinc iodide (19.8 g, 62 mmol) and TMSCN (18.4 g, 186 mmol) were added under ice cooling and a nitrogen atmosphere, and then the mixture was stirred at room temperature for 1 hour. Dichloromethane (100 mL) and water (200 mL) were added, and the mixture was separated. The organic layer was washed with water and saturated saline, and dried over sodium sulfate to be concentrated and dried, thereby obtaining compound (29) (27.2 g). The concentrated residue was used for next reaction without purification.

Tenth Step Synthesis of Compound (30)

Concentrated sulfuric acid (70 mL) was slowly added to methanol (300 mL) under ice cooling, and compound (29) (27.2 g, 56 mmol) was added, and then the mixture was stirred at 90° C. for 14 hours. The mixture was diluted with water (300 mL) under ice cooling, and neutralized with 1 M NaOH, and then the precipitate was filtered. The residue was purified by silica gel column chromatography (petroleum ether:ethyl acetate=3:1), thereby obtaining compound (30) (13.5 g).

LC-MS (ESI): m/z=342 [M+H]+.

1H-NMR (CDCl$_3$) δ: 1.94 (s, 3H), 2.03-2.07 (m, 5H), 2.77-2.81 (m, 2H), 3.71 (s, 3H), 4.21-4.23 (m, 2H), 5.15 (s, 1H), 6.62 (s, 1H), 6.77-6.81 (m, 1H), 6.86-6.90 (m, 2H)

Eleventh Step Synthesis of Compound (31)

Compound (30) (13.5 g, 39 mmol) was dissolved in t-butylacetate (100 mL), and perchloric acid (70%, 6.2 g, 43 mmol) was added at room temperature. The mixture was stirred at room temperature for 2 hours, and the pH was adjusted to 8 with saturated aqueous sodium bicarbonate, and then the mixture was extracted with ethyl acetate (150 mL). The mixture was dried over sodium sulfate, and the concentrated residue was purified by silica gel column chromatography (petroleum ether:ethyl acetate=5:1), thereby obtaining compound (31) (7.2 g).

LC-MS (ESI): m/z=398 [M+H]+.

1H-NMR (CDCl₃) δ: 0.98 (s, 9H), 1.92-2.05 (m, 5H), 2.2 (s, 3H), 2.77-2.81 (m, 2H), 3.64-3.67 (d, 3H), 4.23-4.24 (m, 2H), 5.03-5.05 (d, 1H), 6.58 (s, 1H), 6.76-6.89 (m, 2H), 6.97-7.02 (m, 1H).

romethane (10 mL), and triethylamine (80 mg, 0.7 mmol) was added. The mixture was stirred at room temperature for 14 hours, and water (10 mL) was added, and then the mixture was separated. The organic layer was washed with 1 M hydrochloric acid and saturated saline, and then dried over sodium sulfate to be concentrated and dried, thereby obtaining compound (32) (300 mg). The concentrated residue was used for next reaction without purification.

LC-MS (ESI): m/z=476 [M+H]+.

Thirteenth Step Synthesis of Compound I-49

Compound (32) (300 mg, 0.5 mmol) was dissolved in methanol (5 mL) and a 1 M aqueous sodium hydroxide solution (5 mL) was added, and then the mixture was stirred at 45° C. for 14 hours. The pH was adjusted to 3 with 1 M hydrochloric acid, and the mixture was extracted with ethyl acetate, and fractionated by HPLC, thereby obtaining compound I-49 (20 mg).

LC-MS (ESI): m/z=1065 [2M+Na]+.

1H-NMR (CDCl₃) δ: 0.94 (s, 9H), 1.96 (s, 5H), 2.19 (s, 3H), 2.71-2.74 (m, 2H), 4.17 (s, 2H), 5.18 (s, 1H), 6.77-6.79 (m, 2H), 7.05 (s, 1H), 7.39-7.48 (m, 3H), 7.76-7.78 (m, 3H).

Example 7

Synthesis of Compound I-44

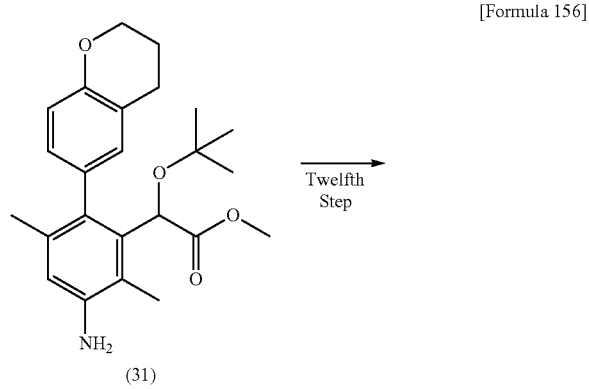

[Formula 156]

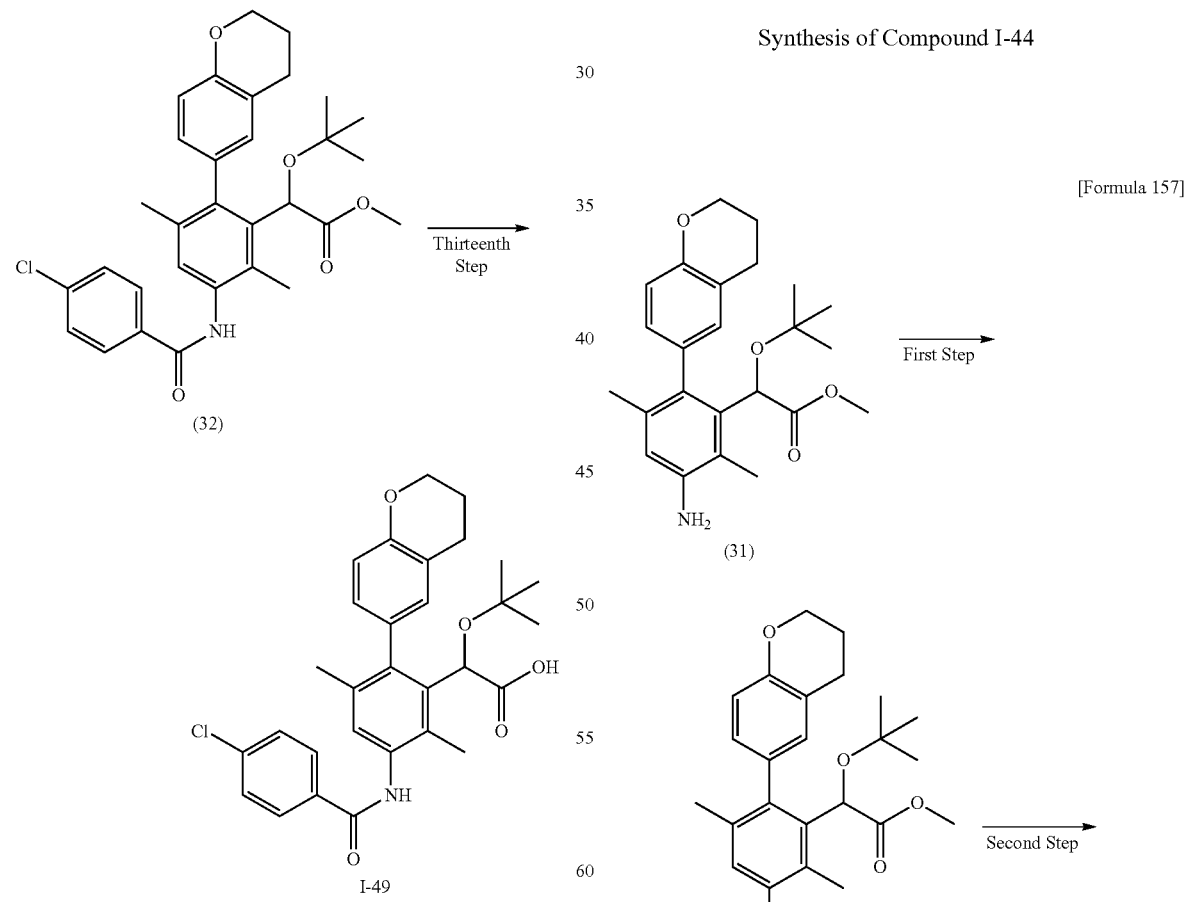

[Formula 157]

Twelfth Step Synthesis of Compound (32)

Compound (31) (200 mg, 0.5 mmol), p-chlorobenzoic acid (94 mg, 0.6 mmol), 1-ethyl-3-(3-dimethylaminopropyl)carbocarbodiimide (144 mg, 0.7 mmol) and 1-hydroxybenzotriazole (100 mg, 0.7 mmol) were dissolved in dichlo-

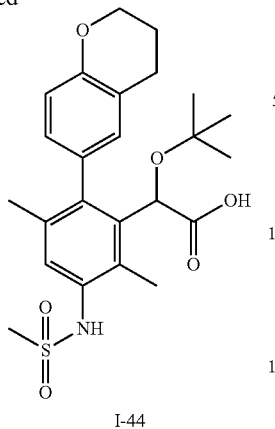

I-44

First Step Synthesis of Compound (33)

Compound (31) (200 mg, 0.5 mmol) was dissolved in pyridine (2 mL), and methanesulfonyl chloride (114 mg, 1 mmol) was added, and then the mixture was stirred at room temperature for 14 hours. Water (10 mL) was added, and the pH was adjusted to 2 with 1 M hydrochloric acid. The mixture was extracted with ethyl acetate and dried over sodium sulfate to be concentrated and dried, thereby obtaining compound (33) (300 mg). The concentrated residue was used for next reaction without purification.

LC-MS (ESI): m/z=475 [M+H]$^+$.

Second Step Synthesis of Compound I-44

Compound (33) (300 mg) was dissolved in methanol (5 mL), and a 1 N aqueous sodium hydroxide solution (5 mL) was added, and then the mixture was stirred at 45° C. for 14 hours. The pH was adjusted to 3 with 1 M hydrochloric acid, and the mixture was extracted with ethyl acetate, and then the concentrated residue was fractionated by HPLC, thereby obtaining compound I-44 (60 mg).

LC-MS (ESI): m/z=945 [2M+Na]$^+$.

1H-NMR (DMSO-d6) δ: 0.87 (s, 9H), 1.95 (s, 5H), 2.08 (s, 3H), 2.55-2.70 (m, 2H), 3.00 (s, 3H), 4.18 (s, 2H), 4.93-4.97 (d, 1H), 6.80-6.99 (m, 3H), 7.13 (s, 1H), 8.97 (s, 1H), 12.50 (s, 1H)

Example 8

Synthesis of Compound I-76

[Formula 158]

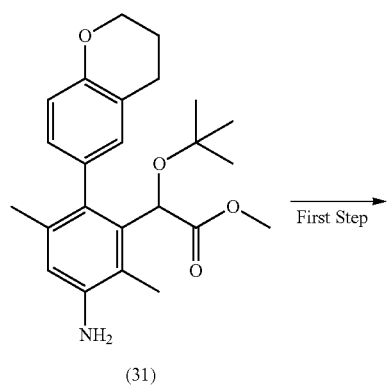

(31)

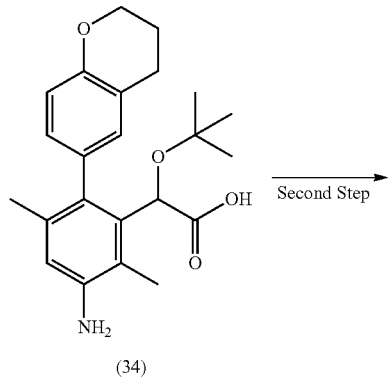

(34)

First Step Synthesis of Compound (34)

Compound (31) (2 g, 5.0 mmol) was dissolved in methanol (10 mL), and a 2 M aqueous sodium hydroxide solution (10 mL) was added, and then the mixture was stirred at 45° C. for 14 hours. The pH was adjusted to 3 with 1 M hydrochloric acid, and the mixture was extracted with ethyl acetate to be concentrated and dried, thereby obtaining compound (34) (1.5 g). The concentrated residue was used for next reaction without purification.

LC-MS (ESI): m/z=384 [M+H]$^+$.

Second Step Synthesis of Compound I-76

Compound (34) (200 mg, 0.52 mmol) was dissolved in pyridine (2 mL), and trifluoromethylmethanesulfonyl chloride (189 mg, 1.04 mmol) was added, and then the mixture was stirred at room temperature for 14 hours. Water (10 mL) was added, and the pH was adjusted to 2 with 1 N hydrochloric acid. The mixture was extracted with ethyl acetate, dried over sodium sulfate, and then the concentrated residue was fractionated by HPLC, thereby obtaining compound I-76 (40 mg).

LC-MS (ESI): m/z=1081 [2M+Na]$^+$.

1H-NMR (DMSO-d6) δ: 0.87 (s, 9H), 1.95-1.96 (m, 5H), 2.29 (s, 3H), 2.60-2.80 (m, 2H), 4.18 (s, 2H), 4.51-4.54 (m, 2H), 4.93-4.97 (d, 1H), 6.70-6.89 (m, 2H), 6.90-7.10 (m, 1H), 7.17 (s, 1H), 9.63 (s, 1H).

Example 9

Synthesis of Compound I-78

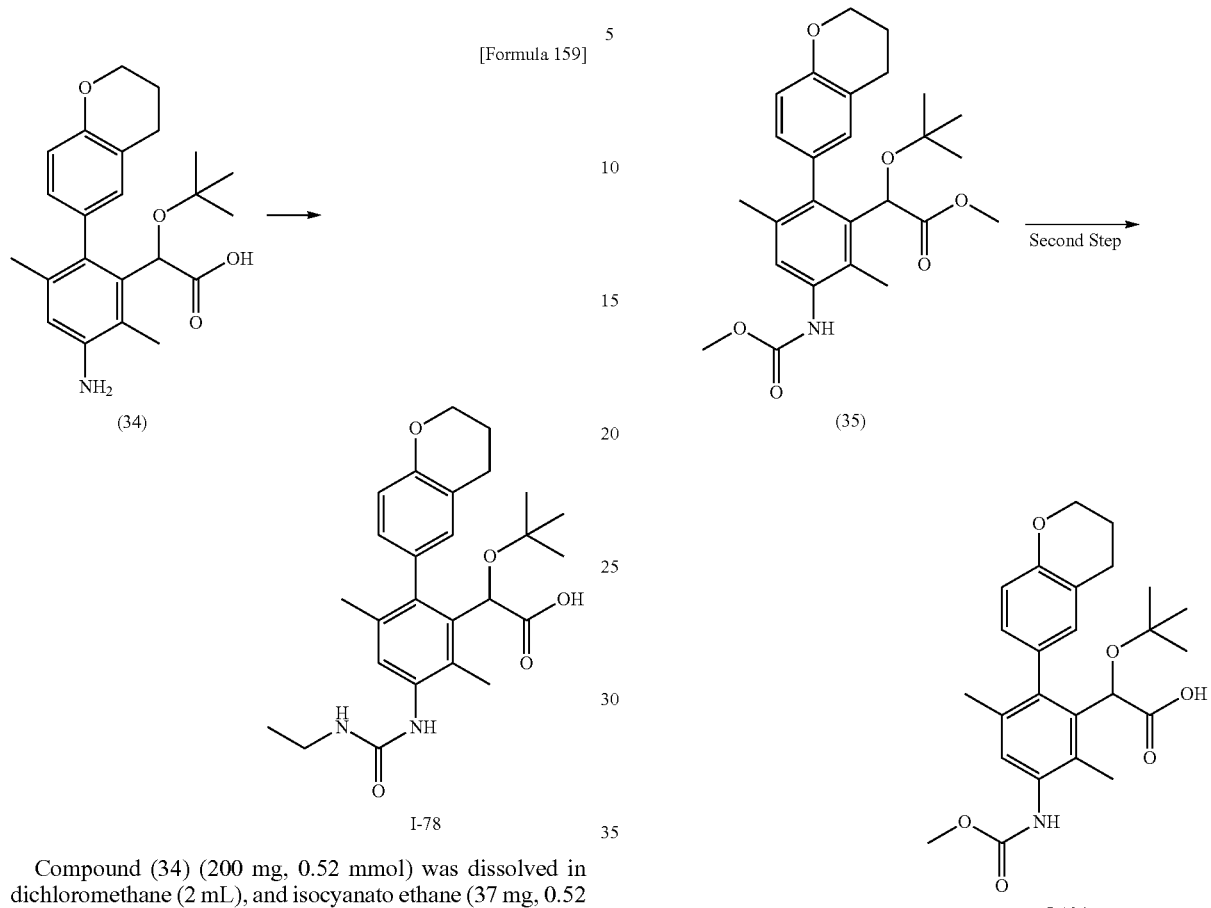

[Formula 159]

Compound (34) (200 mg, 0.52 mmol) was dissolved in dichloromethane (2 mL), and isocyanato ethane (37 mg, 0.52 mmol) was added, and then the mixture was stirred at room temperature for 14 hours. Water (10 mL) was added and the mixture was extracted with dichloromethane, and then dried over sodium sulfate. The concentrated residue was fractionated by HPLC, thereby obtaining compound I-78 (32 mg).

LC-MS (ESI): m/z=455 [M+1]$^+$

1H-NMR (CDCl$_3$) δ: 1.00 (s, 9H), 1.10-1.14 (t, 3H), 2.01-2.06 (m, 5H), 2.25 (s, 3H), 2.80-2.81 (m, 2H), 3.26-3.29 (m, 2H), 4.23-4.25 (t, 2l1H), 5.22 (s, 1H), 6.83-6.87 (m, 2H), 7.13 (d, 1H), 7.14 (s, 2H)

Example 10

Synthesis of Compound I-104

[Formula 160]

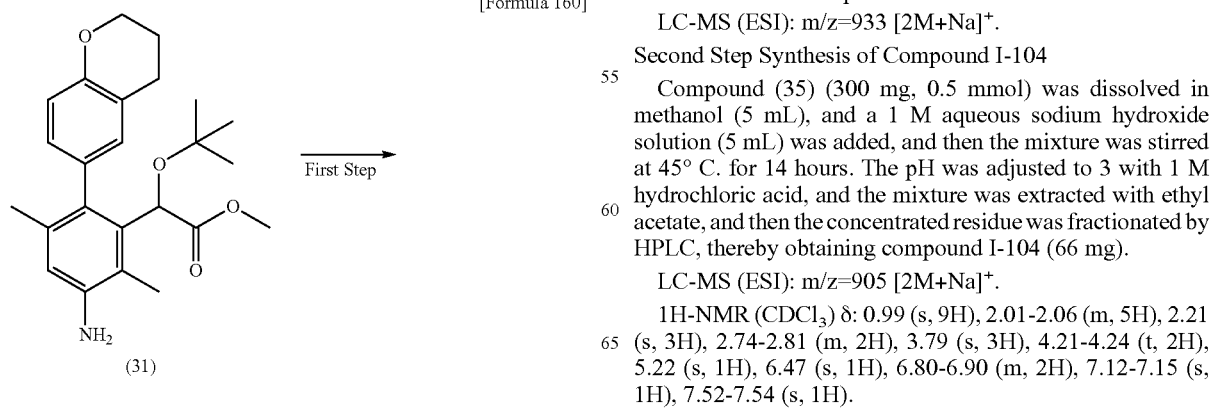

First Step Synthesis of Compound (35)

Compound (31) (200 mg, 0.5 mmol) was dissolved in pyridine (2 mL), and methyl chlorocarbonate (94 mg, 1 mmol) was added, and then the mixture was stirred at room temperature for 14 hours. Water (10 mL) was added, and the pH was adjusted to 2 with 1 N hydrochloric acid. The mixture was extracted with ethyl acetate, and dried over sodium sulfate to be concentrated and dried, thereby obtaining compound (35) (300 mg). The concentrated residue was used for next reaction without purification.

LC-MS (ESI): m/z=933 [2M+Na]$^+$.

Second Step Synthesis of Compound I-104

Compound (35) (300 mg, 0.5 mmol) was dissolved in methanol (5 mL), and a 1 M aqueous sodium hydroxide solution (5 mL) was added, and then the mixture was stirred at 45° C. for 14 hours. The pH was adjusted to 3 with 1 M hydrochloric acid, and the mixture was extracted with ethyl acetate, and then the concentrated residue was fractionated by HPLC, thereby obtaining compound I-104 (66 mg).

LC-MS (ESI): m/z=905 [2M+Na]$^+$.

1H-NMR (CDCl$_3$) δ: 0.99 (s, 9H), 2.01-2.06 (m, 5H), 2.21 (s, 3H), 2.74-2.81 (m, 2H), 3.79 (s, 3H), 4.21-4.24 (t, 2H), 5.22 (s, 1H), 6.47 (s, 1H), 6.80-6.90 (m, 2H), 7.12-7.15 (s, 1H), 7.52-7.54 (s, 1H).

Example 11

Synthesis of Compound I-99

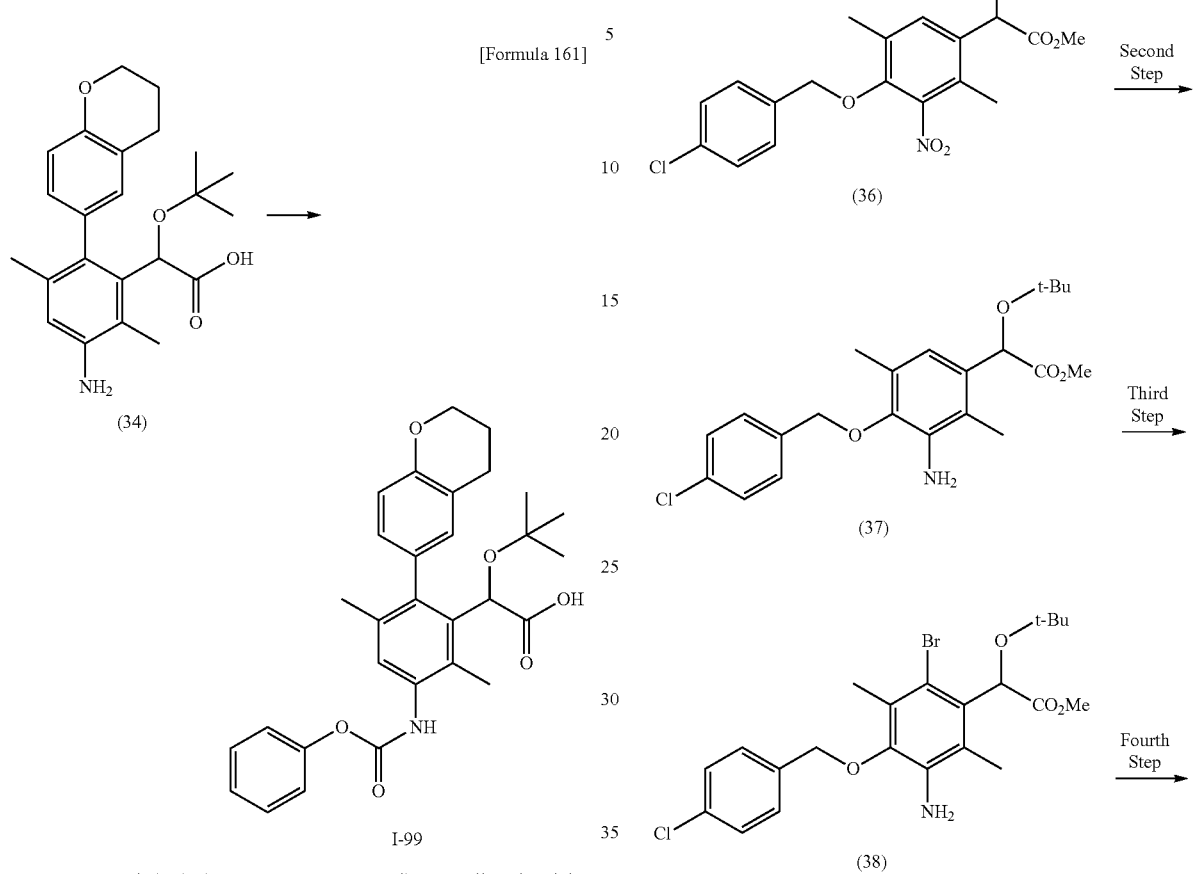

[Formula 161]

Compound (34) (200 mg, 0.52 mmol) was dissolved in pyridine (2 mL), and phenyl chlorocarbonate (162 mg, 1.04 mmol) was added under ice cooling, and then the mixture was stirred at 0° C. for 2 hours. Water (10 mL) was added, and the pH was adjusted to 2 with 1 M hydrochloric acid. The mixture was extracted with ethyl acetate, and dried over sodium sulfate, and then the concentrated residue was fractionated by HPLC, thereby obtaining compound I-99 (50 mg).

LC-MS (ESI): m/z=1030 [2M+Na]$^+$.

1H-NMR (CDCl$_3$) δ: 1.04 (s, 9H), 2.01-2.05 (m, 5H), 2.29 (s, 3H), 2.73-2.81 (m, 2H), 4.22-4.24 (t, 2H), 5.24 (s, 1H), 6.73-6.91 (m, 3H), 7.13-7.24 (m, 4H), 7.38-7.43 (m, 2H), 7.64 (s, 1H).

Example 12

Synthesis of Compound I-296

[Formula 162]

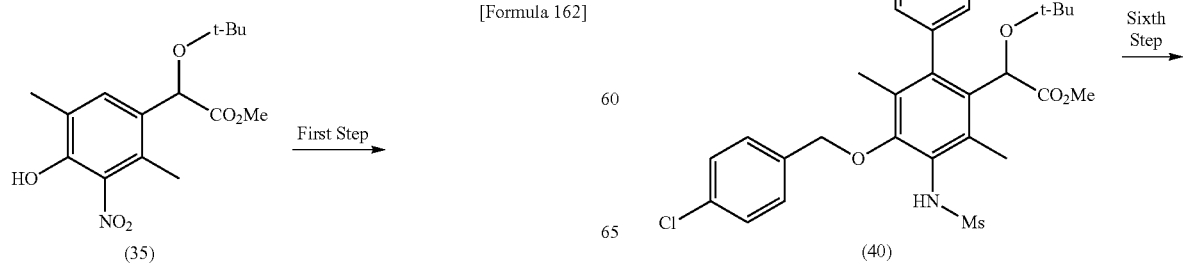

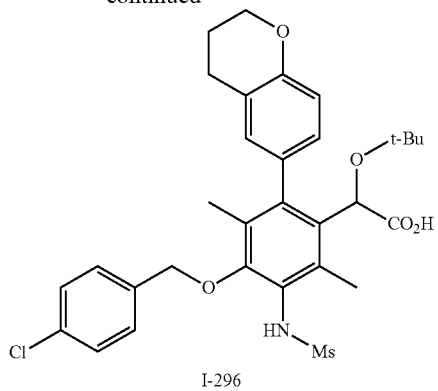

I-296

First Step Synthesis of Compound (36)

Compound (35) (200 mg, 0.642 mmol) was dissolved in DMF (2 mL), and potassium carbonate (178 mg, 1.29 mmol) was added at room temperature, and then the mixture was stirred at room temperature for 5 minutes. 4-Chlorobenzyl bromide (198 mg, 0.964 mmol) was added at room temperature, and the mixture was stirred for 14 hours. 1 mol/L hydrochloric acid (20 mL) was added, and the mixture was extracted with ethyl acetate (50 mL). The organic layer was washed with saturated saline (20 mL), dried over anhydrous magnesium sulfate and concentrated, and then purified by silica gel column chromatography (hexane-ethyl acetate), thereby obtaining compound (36) (281 mg, 100% yield) as a colorless oily substance.

$^1$H-NMR (CDCl$_3$) δ: 1.24 (s, 9H), 2.30 (s, 3H), 2.32 (s, 3H), 3.70 (s, 3H), 4.89 (s, 2H), 5.17 (s, 1H), 7.32-7.37 (m, 4.0H), 7.53 (s, 1H)

Second Step Synthesis of Compound (37)

Compound (36) (265 mg, 0.608 mmol) was dissolved in acetic acid (2.65 mL), and zinc (199 mg, 3.04 mmol) was added at room temperature, and then the mixture was stirred at 60° C. for 1 hour. After cooling to room temperature, a saturated aqueous sodium bicarbonate solution (100 mL) was added, and the mixture was extracted with ethyl acetate (100 mL). The organic layer was washed with saturated saline (50 mL), dried over anhydrous magnesium sulfate and concentrated, and then purified by silica gel column chromatography (hexane-ethyl acetate), thereby obtaining compound (37) (215 mg, 87% yield) as a brown oily substance.

$^1$H-NMR (CDCl$_3$) δ: 1.24 (s, 9H), 2.20 (s, 3H), 2.24 (s, 3H), 3.67 (s, 3H), 3.73 (s, 2H), 4.79 (s, 2H), 5.17 (s, 1H), 6.80 (s, 1H), 7.31-7.42 (m, 4H)

Third Step Synthesis of Compound (38)

Compound (37) (201 mg, 0.495 mmol) was dissolved in DMF (2.1 mL), and the solution was cooled to an internal temperature of 0° C. in an ice bath. NBS (88.0 mg, 0.495 mmol) was added, and the ice bath was removed, and then the mixture was stirred at room temperature for 45 minutes. Water (50 mL) was added, and the mixture was extracted with ethyl acetate (50 mL). The organic layer was washed with water (50 mL×2 times) and saturated saline (30 mL), dried over anhydrous magnesium sulfate and concentrated, and then purified by silica gel column chromatography (hexane-ethyl acetate), thereby obtaining compound (38) (173 mg, 72% yield) as a brown oily substance.

$^1$H-NMR (CDCl$_3$) δ: 1.22 (s, 9H), 2.21 (s, 3H), 2.37 (s, 3H), 3.68 (s, 3H), 3.76 (s, 2H), 4.78 (s, 2H), 5.94 (s, 1H), 7.33-7.41 (m, 4H)

Fourth Step Synthesis of Compound (39)

Compound (38) (166 mg, 0.343 mmol) was dissolved in pyridine (1.7 mL), and methanesulfonyl chloride (0.133 mL, 1.713 mmol) was added, and the mixture was stirred at room temperature for 17 hours. Water (50 mL) was added, and the mixture was extracted with ethyl acetate (50 mL). The organic layer was washed with 1 mol/L hydrochloric acid (50 mL), water (50 mL), a saturated aqueous sodium bicarbonate solution (50 mL) and saturated saline (30 mL), dried over anhydrous magnesium sulfate and concentrated, and then purified by silica gel column chromatography (hexane-ethyl acetate), thereby obtaining compound (39) (167 mg, 87% yield) as a colorless foam substance.

$^1$H-NMR (CDCl$_3$) δ: 1.22 (d, 9H), 2.45 (s, 6H), 3.06 (s, 3H), 3.70 (s, 3H), 4.81-4.94 (m, 2H), 5.87 (s, 1H), 5.96 (s, 1H), 7.37-7.49 (m, 4H)

Fifth Step Synthesis of Compound (40)

Compound (39) (112 mg, 0.199 mmol) was dissolved in DMA (2.3 mL), and 6-chromaneboronic acid (38.9 mg, 0.219 mmol), [1,1'-bis(di-tert-butylphosphino)ferrocene]palladium dichloride (25.9 mg, 0.040 mmol), and a 2 mol/L aqueous potassium carbonate solution (0.199 mL, 0.398 mmol) were added, and the mixture was sealed and stirred at 110° C. for 1.5 hours. Water (50 mL) was added, and the mixture was extracted with ethyl acetate (50 mL). The organic layer was washed with 1 mol/L hydrochloric acid (40 mL×2 times) and saturated saline (40 mL), and then dried over anhydrous magnesium sulfate. The mixture was concentrated and purified by silica gel column chromatography (hexane-ethyl acetate), thereby obtaining compound (40) (62.7 mg, 51% yield) as a brown foam substance.

MS: m/z=614.3 [M−H]$^-$

Sixth Step Synthesis of Compound I-296

A 2 mol/L aqueous sodium hydroxide solution (0.252 mL, 0.503 mmol) was added to an ethanol (1 mL) solution of compound (40) (62.0 mg, 0.101 mmol), and the mixture was stirred under heat reflux for 2 hours. 1 mol/L hydrochloric acid (30 mL) was added, and the mixture was extracted with ethyl acetate (50 mL). The organic layer was washed with saturated saline (30 mL), and then dried over anhydrous magnesium sulfate. The mixture was concentrated, and then purified by silica gel column chromatography (chloroform-methanol), thereby obtaining compound I-296 (60.2 mg, 99% yield) as a colorless foam substance.

MS: m/z=600.3 [M−H]$^-$

Example 13

Synthesis of Compounds I-300 and I-301

[Formula 163]

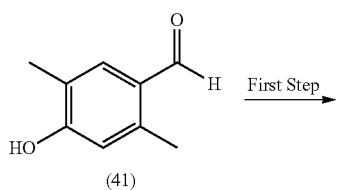

(41)    First Step →

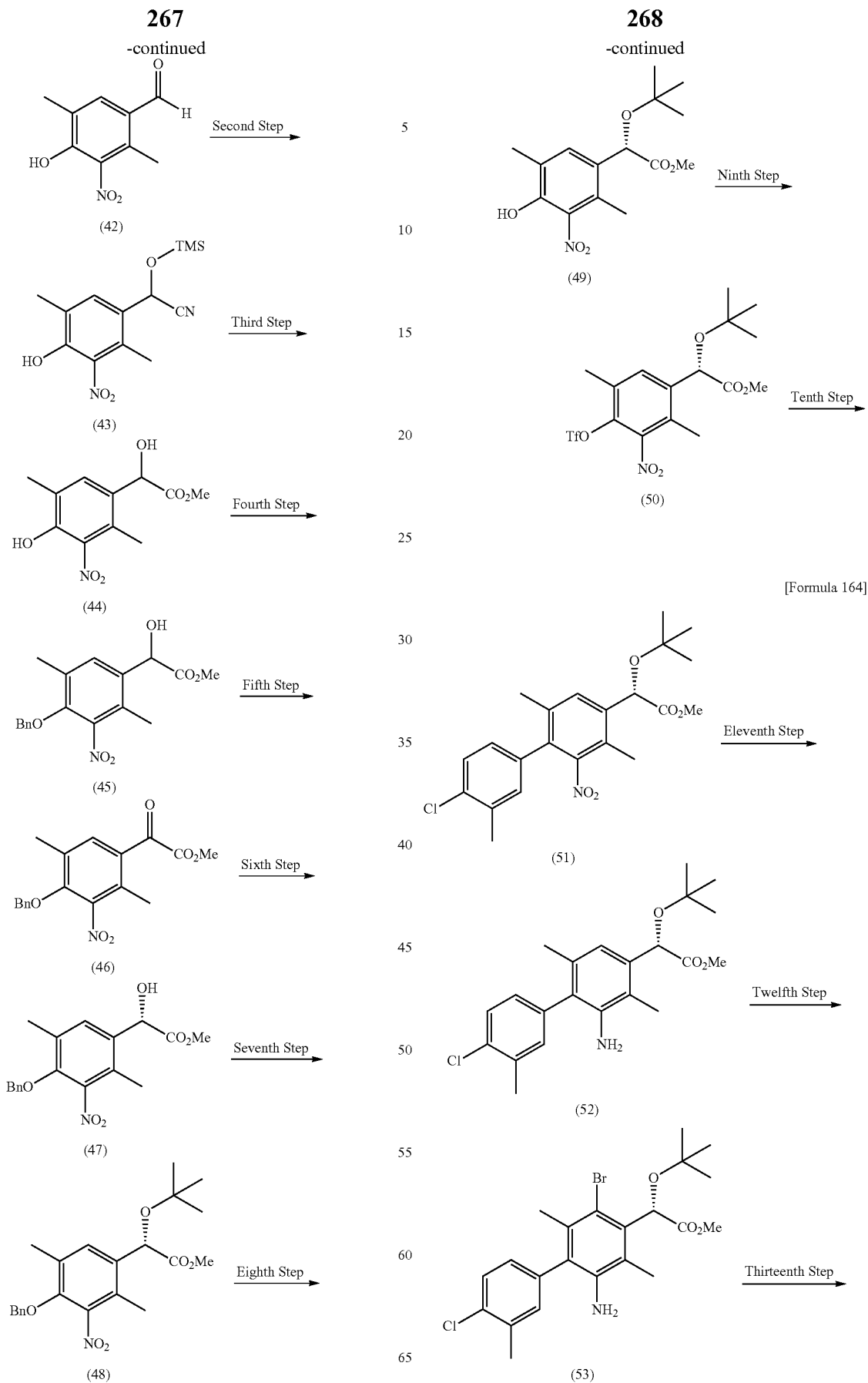

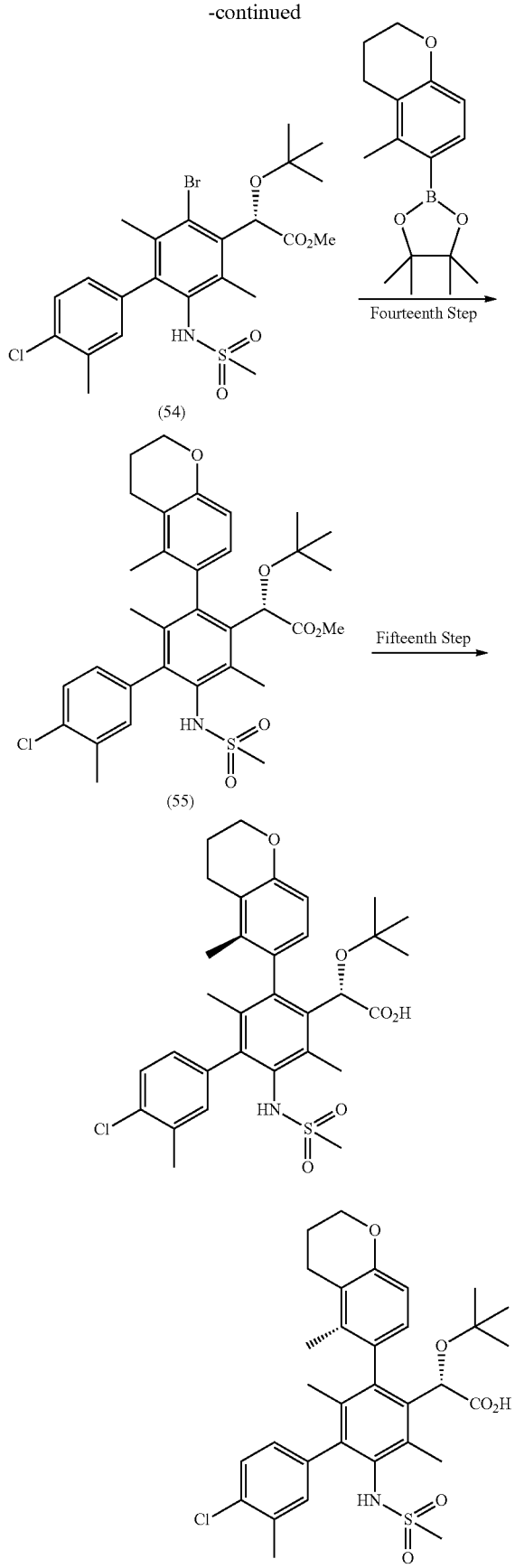

First Step Synthesis of Compound (42)

Potassium nitrate (18.5 g, 183 mmol) was added to a sulfuric acid (350 mL) solution of compound (41) (25.0 g, 166 mmol) under ice cooling. The mixture was stirred at 0° C. for 1.5 hours, and the reaction solution was poured into ice water. The precipitated solid was filtered, to give compound (42) (31.8 g, 98%) as a yellow solid.

$^1$H-NMR (CDCl$_3$, 400 MHz) δ: 2.81 (s, 3H), 7.88 (s, 1H), 10.03 (s, 1H), 10.28 (s, 1H)

MS (ESI) m/z: 194.30 [M−H]−

Second Step Synthesis of Compound (43)

Zinc chloride (40.9 g, 128 mmol) and TMSCN (51.5 mL, 384 mmol) were added to a dichloromethane (750 mL) solution of compound (42) (25.0 g, 128 mmol) under ice cooling. The mixture was stirred at 0° C. for 20 minutes, and saturated aqueous sodium bicarbonate (100 mL) and water (600 mL) were added. The mixture was extracted with dichloromethane (500 mL×3), and the organic layer was washed with water and saturated saline, and then dried over sodium sulfate and concentrated, thereby obtaining a crude product (47 g) of brown oily compound (43).

MS (ESI) m/z: 292.95 [M−H]−

Third Step Synthesis of Compound (44)

A 5 to 10% hydrogen chloride/methanol solution (456 mL), water (2.2 mL, 123 mmol) were added to the crude product (45.6 g) of compound (43), and the mixture was stirred under heat reflux for 20 hours. Methanol was distilled away under reduced pressure, and water (300 mL) was added. The mixture was extracted with ethyl acetate (300 mL×3), and the organic layer was washed with water and saturated saline, and then dried over sodium sulfate and concentrated. Diisopropyl ether and hexane were added to the residue to precipitate a solid, and the solid was filtered, thereby obtaining yellow solid compound (44) (28.6 g, 91% 2 steps).

$^1$H-NMR (CDCl$_3$, 400 MHz) δ: 2.28 (s, 3H), 2.50 (s, 3H), 3.41 (s, 1H), 3.78 (s, 3H), 5.37 (s, 1H), 7.33 (s, 1H), 9.48 (s, 1H)

MS (ESI) m/z: 254.05 [M−H]−

Fourth Step Synthesis of Compound (45)

Potassium carbonate (31.4 g, 227 mmol) and benzyl bromide (14.9 mL, 125 mmol) were added to a DMF (290 mL) solution of compound (44) (29.0 g, 114 mmol). The mixture was stirred at room temperature for 45 minutes, and 2 mol/L hydrochloric acid (300 mL) and water (300 mL) were added. The mixture was extracted with ethyl acetate (300 mL×3), the organic layer was washed with water and saturated saline and dried over sodium sulfate and concentrated, and then purified by column chromatography, thereby obtaining yellow oily compound (45) (38.0 g, 97%).

$^1$H-NMR (CDCl$_3$, 400 MHz) δ: 2.30 (s, 3H), 2.32 (s, 3H), 3.46 (d, 1H, J=4.3 Hz), 3.80 (s, 3H), 4.93 (s, 2H), 5.33 (d, 1H, J=4.3 Hz), 7.30 (s, 1H), 7.37-7.44 (m, 5H)

Fifth Step Synthesis of Compound (46)

Manganese dioxide (47.8 g, 550 mmol) was added to a dichloromethane (380 mL) solution of Compound (45) (38.0 g, 110 mmol), and the mixture was stirred under heat reflux for 2 hours. The reaction solution was filtered through celite, and then concentrated, thereby obtaining yellow solid compound (46) (32.9 g, 87%).

$^1$H-NMR (CDCl$_3$, 400 MHz) δ: 2.37 (s, 3H), 2.45 (s, 3H), 3.98 (s, 3H), 5.00 (s, 2H), 7.40 (s, 5H), 7.65 (s, 1H)

Sixth Step Synthesis of Compound (47)

A 1 M-(R)-CBS reagent (18.9 mL, 18.9 mmol) and catecholborane (20.2 mL, 189 mmol) were added to a dichloromethane (325 mL) solution of compound (46) (32.5 g, 95 mmol) under cooling to −78° C. The mixture was stirred at −78° C. for 20 minutes, and a saturated aqueous ammonium chloride solution (100 mL) was added, and then the mixture was extracted with ethyl acetate (200 mL×3). The organic layer was washed with saturated aqueous sodium bicarbonate and saturated saline, dried over sodium sulfate and concentrated, and then purified by column chromatography, thereby obtaining yellow oily compound (47) (24.8 g, 76%).

$^1$H-NMR (CDCl$_3$, 400 MHz) δ: 2.30 (s, 3H), 2.32 (s, 3H), 3.46 (d, 1H, J=4.3 Hz), 3.80 (s, 3H), 4.93 (s, 2H), 5.33 (d, 1H, J=4.3 Hz), 7.30 (s, 1H), 7.37-7.44 (m, 5H)

Seventh Step Synthesis of Compound (48)

Perchloric acid (18.3 mL, 213 mmol) was added to a tert-butyl acetate (245 mL) solution of compound (47) (24.5 g, 70.9 mmol) under ice cooling. The mixture was stirred at 0° C. for 10 minutes, and saturated aqueous sodium bicarbonate (400 mL) was added. The mixture was extracted with ethyl acetate (300 mL×3), and the organic layer was washed with water and saturated saline. The mixture was dried over sodium sulfate and concentrated, and then purified by column chromatography, thereby obtaining yellow oily compound (48) (21.2 g, 74%).

$^1$H-NMR (CDCl$_3$, 400 MHz) δ: 1.24 (s, 9H), 2.31 (s, 3H), 2.34 (s, 3H), 3.70 (s, 3H), 4.93 (s, 2H), 5.17 (s, 1H), 7.37-7.40 (m, 5H), 7.53 (s, 1H)

Eighth Step Synthesis of Compound (49)

10% wt, 50% wet, Pd/C (2.12 g) was added to an ethyl acetate (212 mL) solution of compound (48) (21.2 g, 52.8 mmol). The mixture was stirred under a hydrogen atmosphere at room temperature for 6 hours, and the reaction solution was filtered through celite. The filtrate was concentrated, and then purified by column chromatography, thereby obtaining yellow oily compound (49) (16.2 g, 99%).

$^1$H-NMR (CDCl$_3$, 400 MHz) δ 1.23 (s, 9H), 2.29 (s, 3H), 2.51 (s, 3H), 3.68 (s, 3H), 5.22 (s, 1H), 7.60 (s, 1H), 9.51 (s, 1H)

MS (ESI) m/z: 315.35 [M−H]−

Ninth Step Synthesis of Compound (50)

Pyridine (8.42 mL, 104 mmol) and trifluoromethanesulfonic anhydride (13.2 mL, 78 mmol) were added to a dichloromethane (160 mL) solution of compound (49) (16.2 g, 52 mmol) under ice cooling. The mixture was stirred at 0° C. for 10 minutes, and a saturated aqueous ammonium chloride (100 mL) was added. The mixture was extracted with dichloromethane (100 mL×2), and the organic layer was washed with water and saturated saline. The mixture was dried over sodium sulfate and concentrated, and then purified by column chromatography, thereby obtaining pale pink solid compound (50) (21.2 g, 92%).

$^1$H-NMR (CDCl$_3$, 400 MHz) δ: 1.24 (s, 9H), 2.36 (s, 3H), 2.47 (s, 3H), 3.71 (s, 3H), 5.20 (s, 1H), 7.69 (s, 1H)

Tenth Step Synthesis of Compound (51)

A 2 mol/L aqueous potassium carbonate solution (10.2 mL, 20.3 mmol) was added to a dioxane (101 mL) solution of compound (50) (3.0 g, 6.77 mmol), and degassing and nitrogen substitution was repeated three times. Subsequently, 4-chloro-3-methylphenylboronic acid (1.73 g, 10.2 mmol) and PdCl$_2$(dppf) (553 mg, 0.68 mmol) were added, and the mixture was stirred under a nitrogen atmosphere at 80° C. for 5 hours. A 2 mol/L hydrochloric acid (50 mL) was added, and the mixture was extracted with ethyl acetate (50 mL×3), and then the organic layer was washed with water and saturated saline. The mixture was dried over sodium sulfate and concentrated, and then purified by column chromatography, thereby obtaining white foam compound (51) (1.08 g, 31%).

$^1$H-NMR (CDCl$_3$, 400 MHz) δ: 1.27 (s, 9H), 2.09 (s, 3H), 2.31 (s, 3H), 2.37 (s, 3H), 3.73 (s, 3H), 5.24 (s, 1H), 6.96 (d, 1H, J=8.2 Hz), 7.05 (s, 1H), 7.36 (d, 1H, J=8.2 Hz), 7.59 (s, 1H)

Eleventh Step Synthesis of Compound (52)

Zinc (841 mg, 12.86 mmol) was added to an acetic acid (10.8 mL) solution of compound (51) (1.08 g, 2.57 mmol), and the mixture was stirred at 60° C. for 20 minutes. Saturated aqueous sodium bicarbonate (50 mL) was added, and the mixture was extracted with ethyl acetate (50 mL×3), and then the organic layer was washed with water and saturated saline. The mixture was dried over sodium sulfate and concentrated, and then purified by column chromatography, thereby obtaining white solid compound (52) (727 mg, 73%).

$^1$H-NMR (CDCl$_3$, 400 MHz) δ: 1.26 (s, 9H), 1.95 (s, 3H), 2.20 (s, 3H), 2.40, (s, 3H), 3.40 (s, 2H), 3.70 (s, 3H), 5.24 (s, 1H), 6.89 (s, 1H), 7.00 (d, 1H, J=7.8 Hz), 7.10 (s, 1H), 7.42 (d, 1H, J=7.8 Hz)

MS (ESI) m/z: 390.10 [M+H]+

Twelfth Step Synthesis of Compound (53)

NBS (329 mg, 1.85 mmol) was added to a DMF (7.2 mL) solution of compound (52) (720 mg, 1.85 mmol) under ice cooling, and the mixture was stirred at 0° C. for 30 minutes. Saturated aqueous sodium bicarbonate (5 mL) was added, the mixture was extracted with ethyl acetate (10 mL×3), and then the organic layer was washed with water and saturated saline. The mixture was dried over sodium sulfate and concentrated, and then purified by column chromatography, thereby obtaining white solid compound (53) (703 mg, 81%).

$^1$H-NMR (CDCl$_3$, 400 MHz) δ: 1.25 (s, 9H), 2.09 (s, 3H), 2.21 (s, 3H), 2.40 (s, 3H), 3.40 (s, 2H), 3.71 (s, 3H) 6.03 (s, 1H), 6.98 (dd, 1H, J=8.0, 6.3 Hz), 7.08 (d, 1H, J=6.3 Hz), 7.44 (d, 1H, J=8.0 Hz)

MS (ESI) m/z: 468.25 [M+H]+

Thirteenth Step Synthesis of Compound (54)

Methanesulfonic anhydride (361 mg, 2.08 mmol) was added to a pyridine (3.2 mL) solution of compound (53) (324 mg, 0.69 mmol), and the mixture was stirred at 80° C. for 4 hours. A 2 mol/L hydrochloric acid (20 mL) was added, and the mixture was extracted with ethyl acetate (10 mL×3), and then the organic layer was washed with water and saturated saline. The mixture was dried over sodium sulfate and concentrated, and then purified by column chromatography, thereby obtaining white foam compound (54) (220 mg, 58%).

$^1$H-NMR (CDCl$_3$, 400 MHz) δ: 1.25 (s, 9H), 2.17 (s, 3H), 2.42 (s, 3H), 2.48 (s, 3H), 2.49 (s, 3H), 3.73 (s, 3H), 5.55 (s, 0.5 H), 5.56 (s, 0.5H), 6.06 (s, 1H), 7.01 (dd, 1H, J=9.4, 8.0 Hz), 7.11 (d, 1H, J=9.4 Hz), 7.44 (d, 1H, J=8.0 Hz)

MS (ESI) m/z: 544.00 [M−H]−

Fourteenth Step Synthesis of Compound (55)

A 2 mol/L aqueous potassium carbonate solution (0.073 mL, 0.15 mmol) was added to a DMF (1 mL) solution of compound (54) (20 mg, 0.037 mmol), and degassing and nitrogen substitution was repeated three times. Subsequently, a boronic acid ester (30.1 mg, 0.11 mmol) and PdCl$_2$(dtbpf) (4.8 mg, 0.007 mmol) were added, and the mixture was stirred under a nitrogen atmosphere at 80° C. for 40 minutes. A 2 mol/L hydrochloric acid (1 mL) was added, and the mixture was extracted with ethyl acetate (1 mL×3), and then the organic layer was washed with water and saturated saline. The mixture was dried over sodium sulfate and concentrated, and then purified by column chromatography, thereby obtaining white foam diastereomeric mixture of compound (55) (17.9 mg, 80%).

MS (ESI) m/z: 612.10 [M−H]−

Fifteenth Step Synthesis of Compounds I-300 and I-301

A 2 M aqueous sodium hydroxide solution (1.9 mL) was added to an ethanol (1.2 mL) solution of diastereomeric mixture of compound (55) (120 mg, 0.195 mmol), and the mixture was stirred at 80° C. for 1 hour. A 2 mol/L hydrochloric acid (1 mL) was added, the mixture was extracted with ethyl acetate (1 mL×3), and then the organic layer was washed with water and saturated saline. The mixture was dried over sodium sulfate and concentrated, and then purified by column chromatography, thereby obtaining white foam compound I-300 (64.1 mg, 55%) and white foam compound I-301 (21.4 mg, 18%).

(Compound I-300)

$^1$H-NMR (CDCl$_3$, 400 MHz) δ: 1.15 (s, 9H), 1.95 (s, 3H), 2.09-2.07 (m, 2H), 2.49-2.53 (m, 9H), 2.60-2.74 (m, 2H), 4.18 (t, 2H, J=4.0 Hz), 5.67-5.80 (m, 1H), 6.72 (d, 1H, J=8.0 Hz), 6.80-6.90 (m, 1H), 6.99 (d, 0.5H, J=8.0 Hz), 7.10 (s, 1H), 7.19 (s, 0.5 H), 7.43 (dd, 1H, J=8.0, 4.0 Hz)

MS (ESI) m/z: 598.10 [M−H]−

(Compound I-301)

$^1$H-NMR (CDCl$_3$, 400 MHz) δ: 1.05 (s, 9H), 1.61 (s, 3H), 1.92 (s, 3H), 2.00-2.12 (m, 2H), 2.42 (s, 3H), 2.49 (s, 3H), 2.51 (s, 3H), 2.64 (d, 2H, J=6.0 Hz), 4.17 (t, 2H, J=6.0 Hz), 5.68 (s, 0.5H), 5.72 (s, 0.5H), 6.74 (d, 1H, J=8.0 Hz), 7.00-7.24 (m, 3H), 7.44 (dd, 1H, J=8.0, 4.0 Hz)

MS (ESI) m/z: 598.10 [M−H]−

Example 14

Synthesis of I-283 and I-284

[Formula 165]

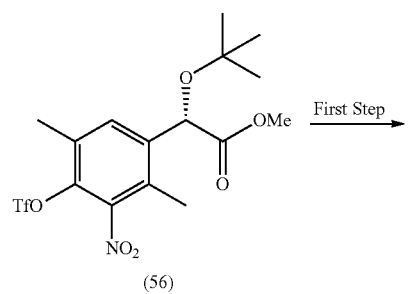

(56) First Step →

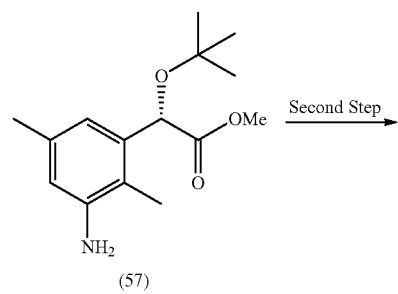

(57) Second Step →

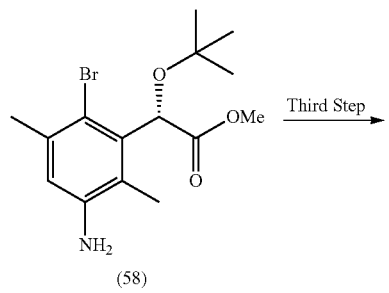

(58) Third Step →

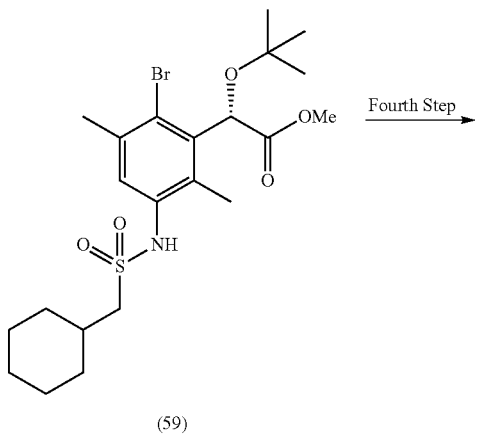

(59) Fourth Step →

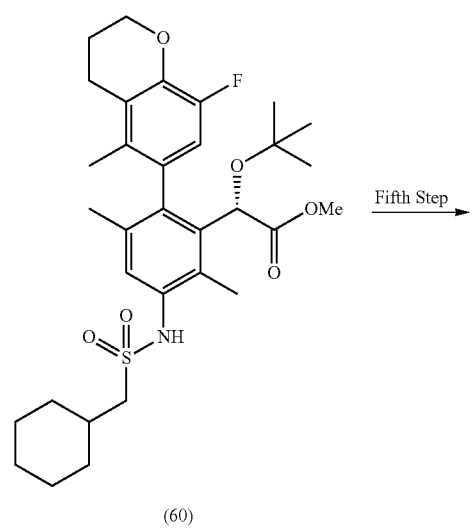

(60) Fifth Step →

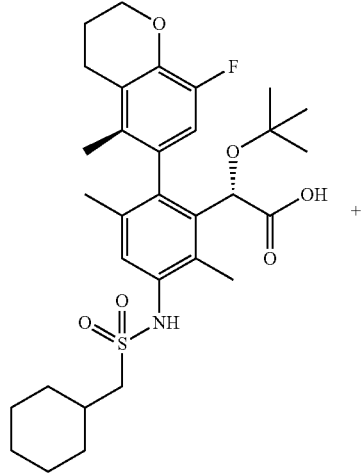

+

-continued

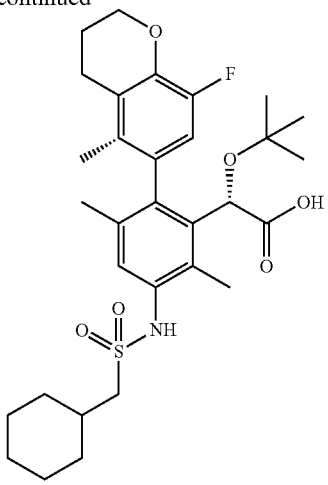

First Step Synthesis of Compound (57)

Compound (56) (10.0 g, 22.6 mmol) was dissolved in ethanol (150 ml), and 10% Pd(OH)$_2$ carbon powder (3.17 g, 2.26 mmol) and triethylamine (3.13 ml, 22.6 mmol) were added. The mixture was stirred under a hydrogen atmosphere of 5 atmospheres, at room temperature for 18 hours. The reaction solution was filtered through celite, and the filtrate was concentrated under reduced pressure. The crude product was purified by silica gel column chromatography (hexane-ethyl acetate), to give 5.02 g of white solid compound (57) (84% yield).

$^1$H-NMR (CDCl$_3$) δ: 1.25 (s, 9H), 2.17 (s, 3H), 2.23 (s, 3H), 3.55 (br s, 2H), 3.66 (s, 3H), 5.20 (s, 1H), 6.47 (s, 1H), 6.81 (s, H).

Second Step Synthesis of Compound (58)

Compound (57) (5.02 g, 18.9 mmol)) was dissolved in acetonitrile (60 ml), and N-bromosuccinimide (3.40 g, 18.9 mmol) was added at 0° C., and then the mixture was stirred for 2 hours. The reaction solution was poured into water, extracted with ethyl acetate, and the organic layer was washed with water and then dried over anhydrous sodium sulfate. The crude product obtained by evaporating the solvent under reduced pressure was purified by silica gel column chromatography (hexane-ethyl acetate), to give 4.95 g of white solid compound (58) (76% yield).

$^1$H-NMR (CDCl$_3$) δ: 1.25 (s, 9H), 2.18 (s, 3H), 2.34 (s, 3H), 3.57 (br s, 2H), 3.67 (s, 3H), 5.95 (s, 1H), 6.57 (s, 1H).

Third Step Synthesis of Compound (59)

Compound (58) (500 mg, 1.45 mmol) was dissolved in pyridine (5 mL) and cyclohexylmethylsulfonyl chloride (371 mg, 1.89 mmol) was added, and then the mixture was stirred at room temperature for 48 hours. Cyclohexylmethylsulfonyl chloride (143 mg, 0.726 mmol) was further added, and the mixture was stirred at room temperature for 5 hours. The reaction solution was poured into water, and extracted with ethyl acetate, and the organic layer was washed with 1 normal hydrochloric acid and then dried over anhydrous sodium sulfate. The crude product obtained by evaporating the solvent under reduced pressure was purified by silica gel column chromatography (hexane-ethyl acetate), to give 644 mg of colorless gummy substance of compound (59) (88% yield).

$^1$H-NMR (CDCl$_3$) δ: 1.04-1.33 (m, 5H), 1.21 (s, 9H), 1.63-1.96 (m, 6H), 2.30 (s, 3H), 2.43 (s, 3H), 2.96 (dd, J=6.1, 2.1 Hz, 2H), 3.68 (s, 3H), 5.99 (s, 1H), 6.12 (s, 1H), 7.38 (s, 1H).

Fourth Step Synthesis of Compound (60)

Compound (59) (200 mg, 0.396 mmol) was dissolved in N,N-dimethylformamide (2 mL), and 8-fluoro-5-methyl-chroman-6-ylboronic acid (250 mg, 1.19 mmol), potassium carbonate (219 mg, 1.59 mmol), water (0.2 ml), and 1,1'-bis(di-tert-butylphosphino)ferrocene]palladium(II) dichloride (78 mg, 0.119 mmol) were added. The mixture was stirred under a nitrogen atmosphere, at 120° C. for 10 minutes. The reaction solution was poured into water, extracted with ethyl acetate, and the organic layer was washed with water and then dried over anhydrous sodium sulfate. The crude product obtained by evaporating the solvent under reduced pressure was purified by silica gel column chromatography (hexane-ethyl acetate), to give 152 mg of a colorless foam substance of compound (60) (65% yield).

MS: m/z=588 [M−H]$^-$

Fifth Step Synthesis of Compounds I-283 and I-284

Methanol (2 ml), tetrahydrofuran (1 mL) and 2 mol/L sodium hydroxide (1.29 ml, 2.58 mmol) were added to compound (60) (152 mg, 0.258 mmol), and the mixture was stirred at 80° C. for 12 hours. The reaction solution was poured into 1 mol/L hydrochloric acid, extracted with ethyl acetate, and then dried over anhydrous sodium sulfate. The crude product obtained by evaporating the solvent under reduced pressure was purified by silica gel column chromatography (chloroform-methanol), to give 30 mg of colorless foam compound I-283 (20% yield) and 5 mg of colorless foam compound I-284 (3% yield).

(Compound I-283)

MS: m/z=574 [M−H]$^-$ $^1$H-NMR (CDCl$_3$) δ: 0.97-2.13 (m, 13H), 1.12 (s, 9H), 1.85 (s, 3H), 1.89 (s, 3H), 2.30 (s, 3H), 2.66 (m, 2H), 3.02 (m, 2H), 4.26 (t, J=4.8 Hz, 2H), 5.10 (s, 1H), 6.13 (s, 1H), 6.70 (d, J=11.4 Hz, 1H), 7.39 (s, 1H).

(Compound I-284)

MS: m/z=574 [M−H]$^-$ $^1$H-NMR (CDCl$_3$) δ: 0.93-2.14 (m, 13H), 1.04 (s, 9H), 1.92 (s, 6H), 2.33 (s, 3H), 2.65 (m, 2H), 3.02 (m, 2H), 4.23-4.29 (m, 2H), 5.21 (s, 1H), 6.13 (s, 1H), 7.02 (m, 1H), 7.37 (s, 1H).

Example 15

Synthesis of I-152

[Formula 166]

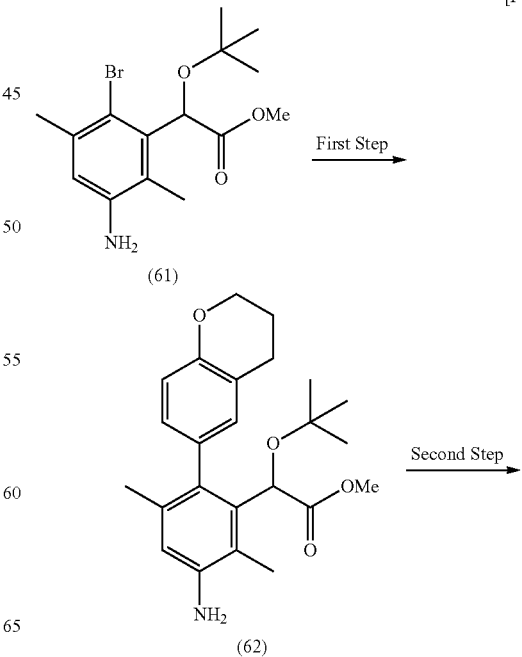

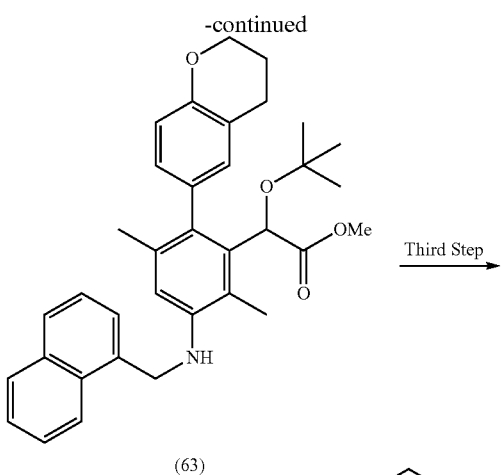

(63)

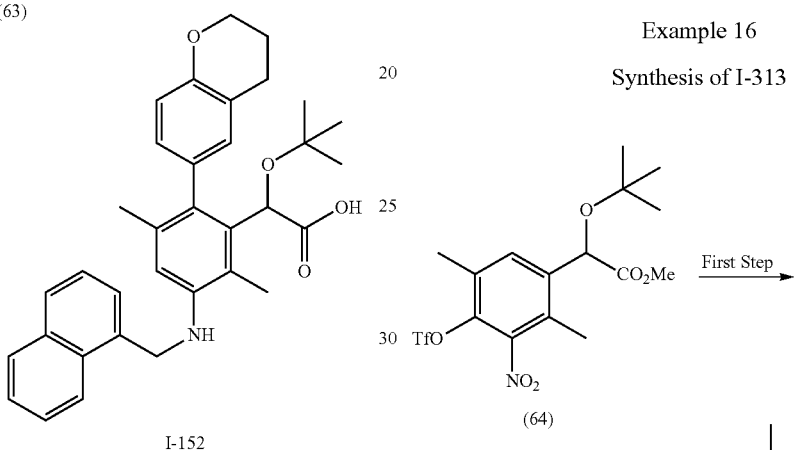

I-152

First Step Synthesis of Compound (62)

Compound (61) (689 mg, 2.00 mmol) obtained using a racemic source in the same manner as that for compound (58) was dissolved in N,N-dimethylformamide (7 mL), and chroman-6-ylboronic acid (713 mg, 4.00 mmol), potassium carbonate (1.11 g, 8.01 mmol), water (0.7 ml), and 1,1'-bis(di-tert-butylphosphino)ferrocene]palladium(II) dichloride (130 mg, 0.200 mmol) were added. The mixture was stirred under a nitrogen atmosphere, at 120° C. for 15 minutes. The reaction solution was poured into water, and extracted with ethyl acetate, and the organic layer was washed with water and then dried over anhydrous sodium sulfate. The crude product obtained by evaporating the solvent under reduced pressure was purified by silica gel column chromatography (hexane-ethyl acetate), to give 541 mg of a colorless foam substance of compound (62) (68% yield).

MS: m/z=398 [M+H]+

Second Step Synthesis of Compound (63)

Compound (62) was dissolved in 1,2-dichloroethane (1.5 ml), and 1-naphthaldehyde (37.2 mg, 0.238 mmol), and sodium triacetoxy boron hydride (138 mg, 0.649 mmol) and acetic acid (0.0120 ml, 0.126 mmol) were added, and then the mixture was stirred at room temperature for 3 hours. The reaction solution was poured into a saturated aqueous sodium bicarbonate solution, extracted with ethyl acetate, and the organic layer was washed with saturated saline and then dried over anhydrous sodium sulfate. The crude product obtained by evaporating the solvent under reduced pressure was purified by silica gel column chromatography (hexane-ethyl acetate), to give 121 mg of a colorless foam substance of compound (63) (100% yield).

MS: m/z=538 [M+H]+

Third Step Synthesis of Compound I-152

Methanol (2 ml), tetrahydrofuran (1 mL) and 2 mol/L sodium hydroxide (1.10 ml, 2.20 mmol) were added to compound (63) (118 mg, 0.219 mmol), and the mixture was stirred at 80° C. for 1.5 hours. The reaction solution was poured into a saturated aqueous ammonium chloride solution, extracted with ethyl acetate, and then dried over anhydrous sodium sulfate. The crude product obtained by evaporating the solvent under reduced pressure was purified by silica gel column chromatography (chloroform-methanol), to give 33 mg of colorless solid of compound I-152 (29% yield).

MS: m/z=524 [M+H]+

$^1$H-NMR (CDCl$_3$) δ: 1.01 (s, 9H), 2.06 (m, 2H), 2.07 (s, 6H), 2.71-2.85 (m, 2H), 4.22 (s, 2H), 4.76 (s, 2H), 5.23 (s, 1H), 6.71 (s, 1H), 6.85 (m, 2H), 7.18 (d, J=8.8 Hz, 1H), 7.49-7.54 (m, 4H), 7.84 (d, J=8.1 Hz, 1H), 7.91 (d, J=6.8 Hz, 1H), 8.11 (d, J=6.8 Hz, 1H).

Example 16

Synthesis of I-313

[Formula 167]

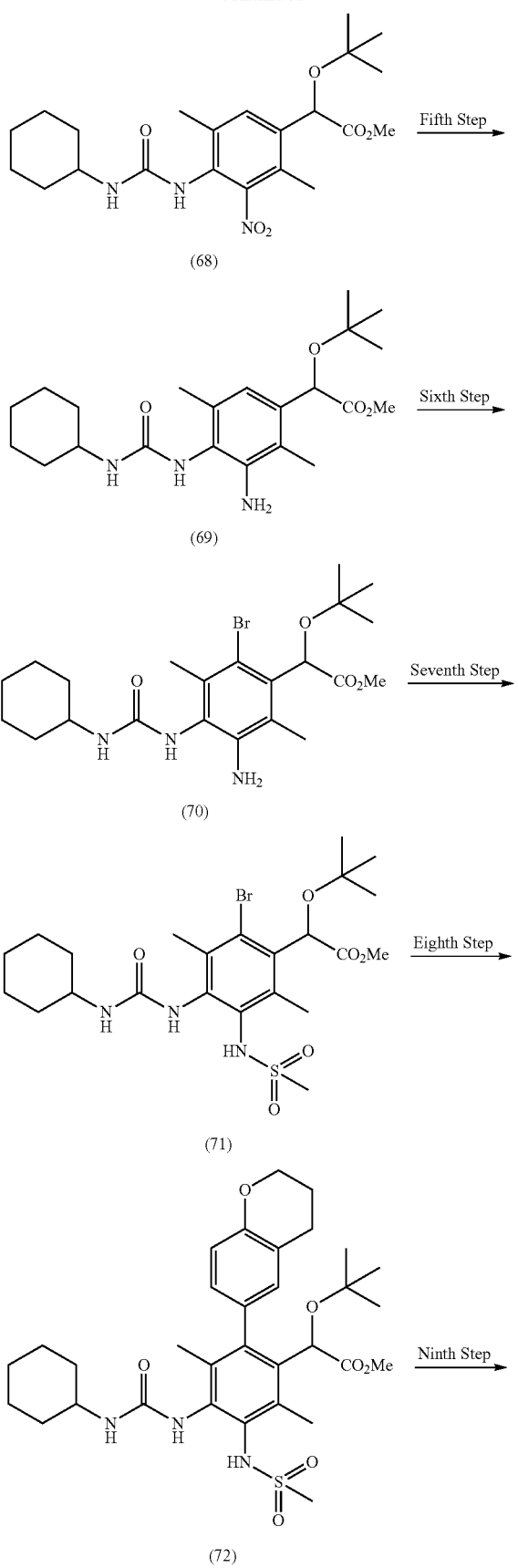

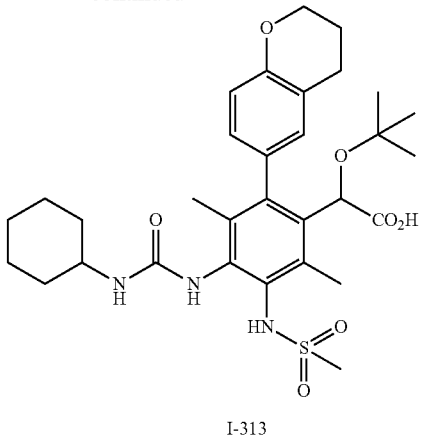 [SMILES: Cc1c(NC(=O)NC2CCCCC2)c(NS(C)(=O)=O)c(C)c(C(OC(C)(C)C)C(=O)O)c1-c1ccc2c(c1)CCCO2]

I-313

First Step Synthesis of Compound (65)

Compound (64) (4.43 g, 10.0 mmol) and (E)-styrylboronic acid (2.22 g, 15.0 mmol) were dissolved in dioxane (150 mL), a 2 mol/L aqueous potassium carbonate solution (15.0 mL, 30.0 mmol) was added, and then the operation of degassing and nitrogen substitution was repeated three times. $PdCl_2$ (dppf) (408 mg, 0.500 mmol) was added, the operation of degassing and nitrogen substitution was again repeated three times, and then the mixture was stirred at 80° C. for 2.75 hours. The reaction solution was cooled to room temperature and poured into ice water and a 2 mol/L aqueous hydrochloric acid solution, and the mixture was extracted with ethyl acetate. The organic layer was sequentially washed with a saturated aqueous sodium bicarbonate solution and a saturated aqueous sodium chloride solution, dried over anhydrous sodium sulfate, and then the solvent was evaporated under reduced pressure using an evaporator. The resulting residue was purified by silica gel chromatography (hexane-ethyl acetate) to give compound (65) as yellow foam (3.22 g, 80.9%).

$^1$H-NMR (CDCl$_3$) δ: 1.25 (s, 9H), 2.31 (s, 3H), 2.38 (s, 3H), 3.70 (s, 3H), 5.22 (s, 1H), 6.72 (d, J=16 Hz, 1H), 6.91 (d, J=16 Hz, 1H), 7.26-7.48 (m, 5H), 7.54 (s, 1H).

Second Step Synthesis of Compound (66)

Compound (65) (3.21 g, 8.08 mmol) was dissolved in a mixed solution of dichloromethane (40.0 mL) and methanol (20.0 mL), and the solution was cooled to an internal temperature of −78° C. in a dry ice bath. An ozone gas was bubbled for 25 minutes until the color of the reaction solution turned blue. Next, an oxygen gas was bubbled for 10 minutes until the blue color of the reaction solution disappeared. Moreover, dimethylsulfide (5.97 mL, 81.0 mmol) was added, and the dry ice bath was removed, and then the mixture was heated to room temperature, and stirred for 35 minutes. The reaction solution was poured into ice water and a 2 mol/L aqueous hydrochloric acid solution, and extracted with ethyl acetate. The organic layer was sequentially washed with a saturated aqueous sodium bicarbonate solution and a saturated aqueous sodium chloride solution, dried over anhydrous sodium sulfate, and then the solvent was evaporated under reduced pressure using an evaporator. The resulting residue was purified by silica gel chromatography (hexane-ethyl acetate) to give compound (66) as a pale yellow oily substance (1.87 g, 71.5%).

$^1$H-NMR (CDCl$_3$) δ: 1.25 (s, 9H), 2.31 (s, 3H), 2.67 (s, 3H), 3.70 (s, 3H), 5.23 (s, 1H), 7.65 (s, 1H), 10.19 (s, 1H).

Third Step Synthesis of Compound (67)

Compound (66) (2.00 g, 6.19 mmol) was dissolved in acetone (30.0 mL), and the solution was cooled in an ice bath, and an aqueous solution obtained by dissolving potassium permanganate (1.47 g, 9.28 mmol) in water (15.0 mL) was added. The ice bath was removed, and the mixture was stirred at room temperature for 1 hour and 40 minutes. The reaction solution was poured into an aqueous sodium sulfite solution, and ice water and a 2 mol/L aqueous hydrochloric acid solution were added, and then the mixture was extracted with ethyl acetate. The organic layer was washed with a saturated aqueous sodium chloride solution, and dried over anhydrous sodium sulfate, and then the solvent was evaporated under reduced pressure using an evaporator. The resulting residue was purified by silica gel chromatography (chloroform-methanol) to give compound (67) as a white solid (1.84 g, 87.6%).

$^1$H-NMR (DMSO-$d_6$) δ: 1.18 (s, 9H), 2.22 (s, 3H), 2.40 (s, 3H), 3.63 (s, 3H), 5.41 (s, 1H), 7.63 (s, 1H).

Fourth Step Synthesis of Compound (68)

Compound (67) (339 mg, 1.00 mmol) was dissolved in toluene (4.00 mL), and DPPA (0.430 g, 2.00 mmol) and triethylamine (0.277 mL, 2.00 mmol) were sequentially added, and then stirring was started at 100° C. After stirring for 1.5 hours, cyclohexylamine (0.229 mL, 2.00 mmol) was added, and the mixture was further stirred at 100° C. for 1 hour and 16 minutes. The reaction solution was cooled to room temperature and poured into ice water and a 2 mol/L aqueous hydrochloric acid solution, and the mixture was extracted with ethyl acetate. The organic layer was sequentially washed with a saturated aqueous sodium bicarbonate solution and a saturated aqueous sodium chloride solution, and dried over anhydrous sodium sulfate, and then the solvent was evaporated under reduced pressure using an evaporator. The resulting residue was purified by silica gel chromatography (hexane-ethyl acetate) to give compound (68) as a pale yellow solid (389 mg, 89.3%).

MS (ESI) m/z: 436.25 [M+H]+

Fifth Step Synthesis of Compound (69)

Compound (68) (386 mg, 0.886 mmol) was dissolved in a mixed solution of methanol (10.0 mL) and acetic acid (1.00 mL), and palladium hydroxide (249 mg) was added. The mixture was stirred under pressure under a hydrogen atmosphere all night. The reaction solution was filtered through celite, and the filtrate was poured into ice water and a saturated aqueous sodium bicarbonate solution, and extracted with ethyl acetate. The organic layer was washed with a saturated aqueous sodium chloride solution, and dried over anhydrous sodium sulfate, and then the solvent was evaporated under reduced pressure using an evaporator. The resulting residue was purified by silica gel chromatography (hexane-ethyl acetate) to give compound (69) as a pale yellow solid (303 mg, 84.3%).

MS (ESI) m/z: 406.25 [M+H]+

Sixth Step Synthesis of Compound (70)

Compound (69) (300 mg, 0.740 mmol) was dissolved in DMF (6.00 mL), and the solution was cooled in an ice bath. NBS (133 mg, 0.740 mmol) was added, and the mixture was stirred for 1 hour and 17 minutes under ice cooling. The reaction solution was poured into ice water and a saturated aqueous sodium bicarbonate solution, and extracted with ethyl acetate. The organic layer was washed with a saturated aqueous sodium chloride solution, and dried over anhydrous sodium sulfate, and then the solvent was evaporated under reduced pressure using an evaporator. The resulting residue was purified by silica gel chromatography (hexane-ethyl acetate) to give compound (70) as a brown solid (214 mg, 59.7%).

MS (ESI) m/z: 486.10 [M+H]+

Seventh Step Synthesis of Compound (71)

Compound (70) (214 mg, 0.442 mmol) was dissolved in pyridine (4.00 mL), and methanesulfonyl chloride (0.052 mL, 0.663 mmol) was added, and then the mixture was stirred at room temperature overnight. The reaction solution was poured into ice water and a 2 mol/L aqueous hydrochloric acid solution, and extracted with ethyl acetate. The organic layer was sequentially washed with a saturated aqueous sodium bicarbonate solution and a saturated aqueous sodium chloride solution, and dried over anhydrous sodium sulfate, and then the solvent was evaporated under reduced pressure using an evaporator. The resulting residue was purified by silica gel chromatography (hexane-ethyl acetate) to give compound (71) as pale yellow foam (110 mg, 44.3%).

MS (ESI) m/z: 563.90 [M+H]+

Eighth Step Synthesis of Compound (72)

Compound (71) (110 mg, 0.196 mmol) and 6-chromanboronic acid (52.2 mg, 0.293 mmol) were dissolved in a mixed solution of DMF (1.10 mL) and water (0.110 mL), and potassium carbonate (108 mg, 0.782 mmol) was added, and then the operation of degassing and nitrogen substitution was repeated three times. $Pd_2(dtbpf)Cl_2$ (25.2 mg, 0.0390 mmol) was added, and the operation of degassing and nitrogen substitution was again repeated three times, and then the mixture was stirred at 120° C. for 8 hours. The reaction solution was cooled to room temperature and poured into ice water and a 2 mol/L aqueous hydrochloric acid solution, and the mixture was extracted with ethyl acetate. The organic layer was sequentially washed with a saturated aqueous sodium bicarbonate solution and a saturated aqueous sodium chloride solution, and dried over anhydrous sodium sulfate, and then the solvent was evaporated under reduced pressure using an evaporator. The resulting residue was purified by silica gel chromatography (hexane-ethyl acetate) to give compound (72) as brown foam (20.0 mg, 16.6%).

MS (ESI) m/z: 616.30 [M+H]+

Ninth Step Synthesis of Compound I-313

Compound (72) (20.0 mg, 0.032 mmol) was dissolved in ethanol (0.648 mL), and a 2 mol/L aqueous sodium hydroxide solution (0.162 mL, 0.325 mmol) was added, and then the mixture was stirred at 100° C. for 2.5 hours. The reaction solution was cooled to room temperature and poured into ice water, and the pH of the aqueous layer was adjusted to around 3 with a 2 mol/L aqueous hydrochloric acid solution, and the mixture was extracted with ethyl acetate. The organic layer was washed with a saturated aqueous sodium chloride solution, and dried over anhydrous sodium sulfate, and then the solvent was evaporated under reduced pressure using an evaporator. The resulting residue was purified by silica gel chromatography (chloroform-methanol) and dried under reduced pressure at 60° C., thereby obtaining compound I-313 as pale yellow powder (5.00 mg, 25.6%).

MS (ESI) m/z: 602.4 [M+H]+

Example 17

Synthesis of Compound II-1 and Compound II-2

[Formula 168]

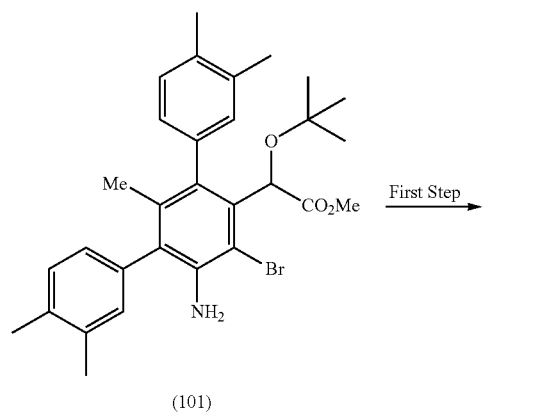

Third Step Synthesis of Compound II-2

First Step Synthesis of Compound (102)

Compound (101) (220 mg, 0.409 mmol) was dissolved in acetone (4 mL), and a solution of benzoyl isothiocyanate (98%, 82 mg, 0.490 mmol) in acetone (0.5 mL) was added dropwise, and then the mixture was stirred at room temperature for 0.5 hours. The concentrated residue was purified by silica gel chromatography (hexane-ethyl acetate) to give compound (102) (232 mg, 81% yield).

MS: m/z=701 [M+H]$^+$

Second Step Synthesis of Compound (103)

Compound (102) (50 mg, 0.071 mmol) was dissolved in DMF (1 mL), and sodium hydride (60%, 6.9 mg, 0.171 mmol) was added, and then the mixture was stirred at 100° C. for 3 hours. After cooling to room temperature, water and ethyl acetate were added, and the organic layer was washed with water and saturated saline, and then dried over magnesium sulfate. The concentrated residue containing compound (103) was used for next reaction without purification. (50 mg, 113% yield)

MS: m/z=621 [M+H]$^+$

Third Step Synthesis of Compound II-2

Compound (103) (50 mg, 0.071 mmol) was dissolved in a mixed solvent of THF (0.6 mL) and methanol (0.2 mL), and a 5 mol/L aqueous sodium hydroxide solution (0.14 mL, 0.70 mmol) was added, and then the mixture was stirred at room temperature for 2 hours. The half amount of the reaction solution was neutralized with a 2 mol/L hydrochloric acid, and then water and ethyl acetate were added. The organic layer was washed with water and saturated saline, and then dried over magnesium sulfate. The concentrated residue was separated and purified by liquid chromatography, thereby obtaining compound II-2 (8.6 mg).

285

MS: m/z=607 [M+H]$^+$ $^1$H-NMR (CDCl$_3$) δ: 1.15 (s, 9H), 1.87 (d, J=2.1 Hz, 3H), 2.11 (s, 3H), 2.28 (s, 3H), 2.30 (s, 3H), 2.32 (s, 3H), 5.17 (s, 1H), 6.8-7.8 (m, 11H)

Fourth Step Synthesis of Compound II-1

The remaining half amount of the reaction solution in the third step was stirred at 90° C. for 9 hours. About half amount was separated and purified by liquid chromatography, thereby obtaining compound 2 (8.6 mg). The resulting product was neutralized with a 2 mol/L hydrochloric acid, and then water and ethyl acetate were added. The organic layer was washed with water and saturated saline, and then dried over magnesium sulfate. The concentrated residue was separated and purified by liquid chromatography, thereby obtaining compound II-1 (3.6 mg).

MS: m/z=503 [M+H]$^+$ $^1$H-NMR (CDCl$_3$) δ: 1.08 (s, 9H), 1.78 (d, J=3.6 Hz, 3H), 2.28-2.31 (m, 9H), 5.04 (s, 1H), 6.8-7.4 (m, 6H)

Example 18

Synthesis of Compound II-3

[Formula 169]

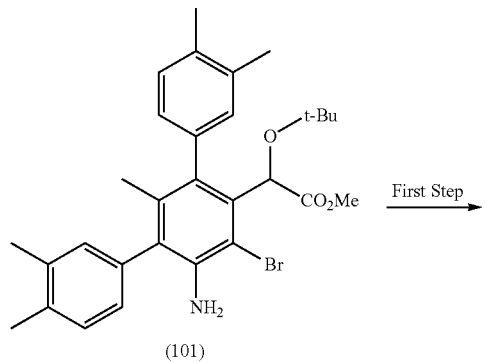

First Step Synthesis of Compound (104)

Compound (101) (200 mg, 0.371 mmol) was dissolved in DMA (2 mL), and ethyl (E)-3-(4,4,5,5-tetramethyl-1,3,2-dioxaborolan-2-yl)acrylate (126 mg, 0.557 mmol), [1,1'-bis(di-tert-butylphosphino)ferrocene]palladium dichloride (48.4 mg, 0.074 mmol), and a 2 mol/L aqueous potassium carbonate solution (0.371 mL, 0.743 mmol) were added, and the mixture was sealed and stirred at 130° C. for 2 hours. Water was added, and the mixture was extracted with ethyl acetate. The organic layer was washed with water, and then dried over anhydrous magnesium sulfate. The solvent was evaporated under reduced pressure, and the resulting residue was purified by silica gel chromatography (hexane-ethyl acetate) to give compound (104) (143 mg, 69% yield).

MS: m/z=580.4 [M+H]$^+$.

Second Step Synthesis of Compound (105)

10% palladium carbon (53.4 mg, 0.050 mmol) was added to a tetrahydrofuran-methanol (1:1, 3 mL) solution of compound (104) (140 mg, 0.251 mmol), and the mixture was stirred under a hydrogen atmosphere at room temperature for 1.5 hours. The solid was removed by filtration, and the filtrate was evaporated under reduced pressure to obtain compound (105) (134 mg).

MS: m/z=514.3 [M+H]$^+$.

Third Step Synthesis of Compound II-3

A 2 mol/L aqueous sodium hydroxide solution (0.403 mL, 0.806 mmol) was added to a tetrahydrofuran-methanol (1:1, 1 mL) solution of compound (105) (41.4 mg, 0.081 mmol), and the mixture was stirred at 50° C. for 2 hours. An aqueous hydrochloric acid solution was added, and the mixture was extracted with ethyl acetate. The organic layer was washed with an aqueous hydrochloric acid solution and saturated saline, and then the solvent dried over anhydrous magnesium sulfate was evaporated under reduced pressure, and the resulting residue was purified by silica gel chromatography (chloroform-methanol) to give compound II-3 (40.3 mg, 100% yield).

MS: m/z=500.4 [M+H]$^+$.

Example 19

Synthesis of Compound II-4

[Formula 170]

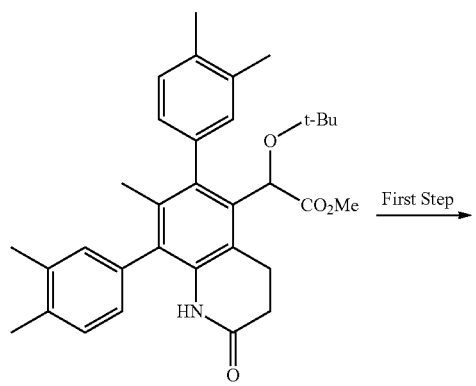
(105)

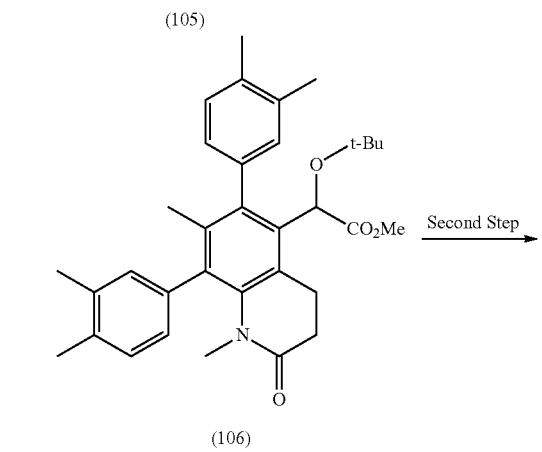
(106)

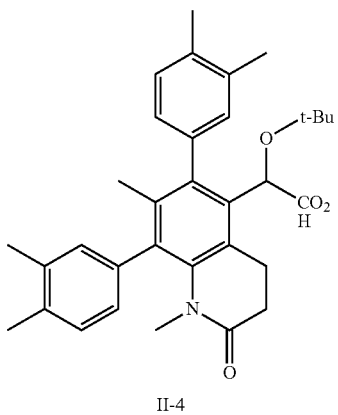
II-4

First Step Synthesis of Compound (106)

Compound (105) (400 mg, 0.779 mmol) was dissolved in DMF (4 mL), and sodium hydride (46.7 mg, 1.17 mmol) and methyl iodide (0.243 mL, 3.89 mmol) were added at 0° C., and then the mixture was stirred at room temperature for 2 hours. Water was added, and the mixture was extracted with ethyl acetate. The organic layer was washed with an aqueous hydrochloric acid solution and saturated saline, and then dried over anhydrous magnesium sulfate. The solvent was evaporated under reduced pressure, and the resulting residue was purified by silica gel chromatography (hexane-ethyl acetate) to give compound (106) (378 mg, 85% yield).

MS: m/z=528.3 [M+H]$^+$.

Second Step Synthesis of Compound II-4

A 4 mol/L aqueous sodium hydroxide solution (1.03 mL, 4.13 mmol) was added to a tetrahydrofuran-methanol (1:1, 2 mL) solution of compound (106) (109 mg, 0.207 mmol), and the mixture was stirred at 50° C. for 2 hours. An aqueous hydrochloric acid solution was added, and the mixture was extracted with ethyl acetate. The organic layer was washed with an aqueous hydrochloric acid solution and saturated saline, and then the solvent dried over anhydrous magnesium sulfate was evaporated under reduced pressure, and the resulting residue was purified by silica gel chromatography (chloroform-methanol) to give compound II-4 (41.2 mg, 39% yield).

$^1$H-NMR (CDCl$_3$) δ: 1.01-1.04 (m, 9H), 1.72-1.79 (m, 3H), 2.22-2.33 (m, 12H), 2.44-2.79 (m, 6H), 2.91-3.10 (m, 1H), 5.12-5.15 (m, 1H), 6.79-7.29 (m, 6H).

Example 20

Synthesis of Compound II-5

[Formula 171]

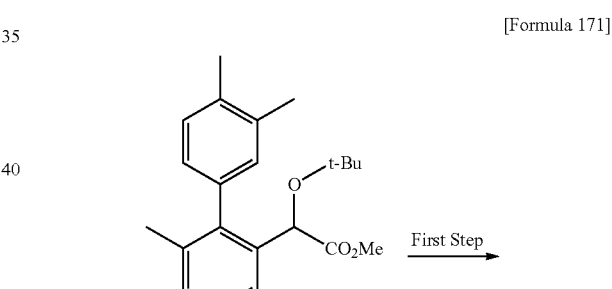
(105)

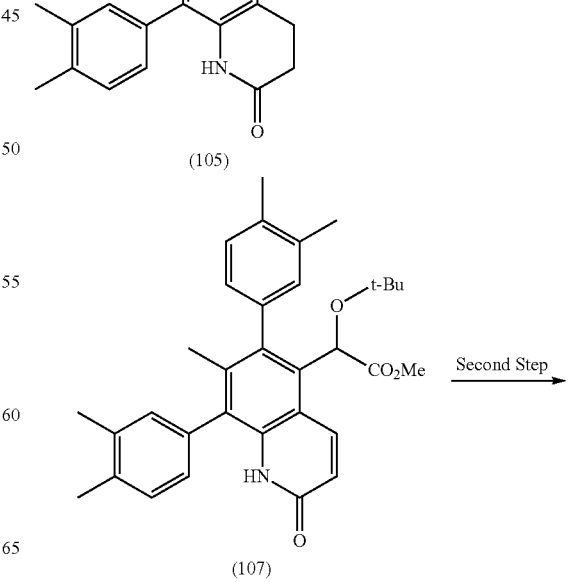
(107)

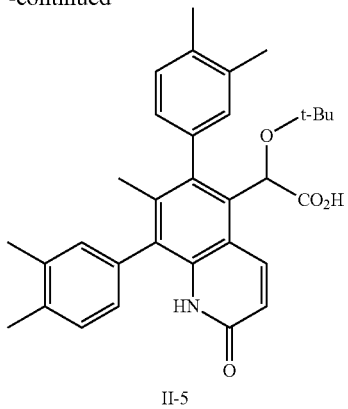

II-5

First Step Synthesis of Compound (107)

Compound (105) (28.8 mg, 0.056 mmol) was dissolved in dioxane (0.57 mL), and 2,3-dichloro-5,6-dicyano-p-benzoquinone (19.09 mg, 0.084 mmol) was added, and then the mixture was sealed and stirred at 120° C. for 13 hours. Water was added, and the mixture was extracted with ethyl acetate. The organic layer was washed with a saturated aqueous sodium bicarbonate solution and saturated saline, and then dried over anhydrous magnesium sulfate. The solvent was evaporated under reduced pressure, and the resulting residue was purified by silica gel chromatography (hexane-ethyl acetate) to give compound (107) (12.8 mg, 45% yield).

MS: m/z=512.5 [M+H]$^+$.

Second Step Synthesis of Compound II-5

A 2 mol/L aqueous sodium hydroxide solution (0.313 mL, 0.626 mmol) was added to a tetrahydrofuran-methanol (1:1, 1 mL) solution of compound (107) (32.0 mg, 0.063 mmol), and the mixture was stirred at 50° C. for 2 hours. An aqueous hydrochloric acid solution was added, and the mixture was extracted with ethyl acetate. The organic layer was washed with an aqueous hydrochloric acid solution and saturated saline, and then the solvent dried over anhydrous magnesium sulfate was evaporated under reduced pressure to give compound II-5 (31.1 mg, 100% yield).

$^1$H-NMR (CDCl$_3$) δ: 1.04 (s, 9H), 1.77-1.81 (m, 3H), 2.27-2.35 (m, 12H), 5.24-5.29 (m, 1H), 6.61-6.68 (m, 1H), 6.93-7.03 (m, 3H), 7.15-7.29 (m, 3H), 8.43-8.59 (m, 2H).

Example 21

Synthesis of Compound II-6

[Formula 172]

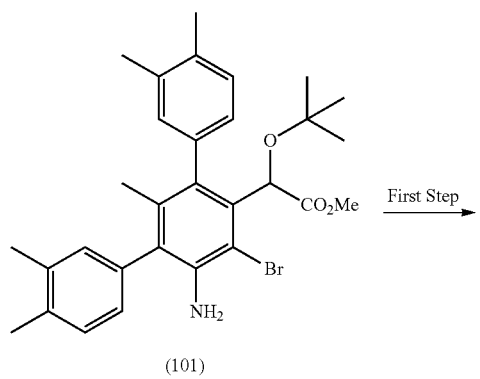

(101)

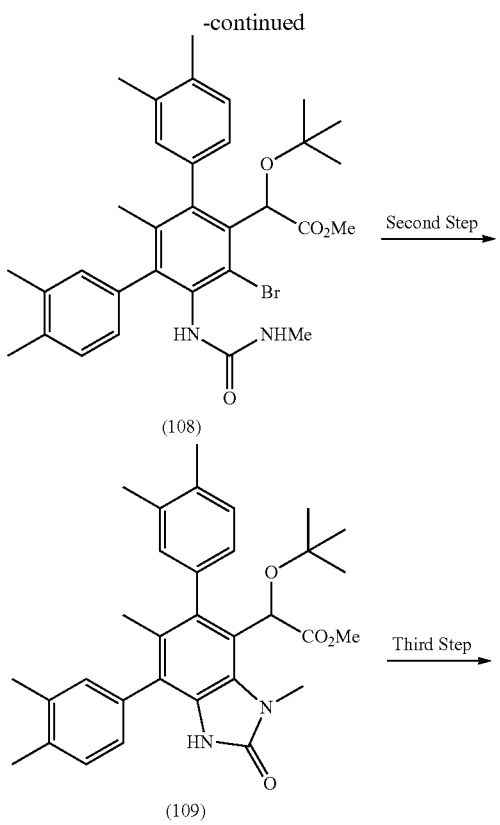

First Step Synthesis of Compound (108)

Compound (101) (300 mg, 0.557 mmol) was dissolved in 1,2-dichloroethane (3 mL), and diisopropylethylamine (0.195 mL, 1.11 mmol) and triphosgene (83 mL, 0.279 mmol) were added, and then the mixture was stirred at room temperature for 2 hours. Thereafter, a methylamine-tetrahydrofuran solution (0.84 mL, 1.67 mmol) was added, and the mixture was further stirred at room temperature for 1 hour. Saturated aqueous sodium bicarbonate was added, and the mixture was extracted with ethyl acetate. The organic layer was washed with saturated saline, and then dried over anhydrous sodium sulfate. The solvent was evaporated under reduced pressure, and the resulting residue was purified by silica gel chromatography (hexane-ethyl acetate) to give compound (108) (300 mg, 90% yield).

MS: m/z=596 [M+H]$^+$.

Second Step Synthesis of Compound (109)

Compound (108) (50 mg, 0.084 mmol) was dissolved in DMF (1 mL), and diisopropylethylamine (0.022 mL, 0.126 mmol) and copper iodide (4.8 mL, 0.025 mmol) were added, and then the mixture was sealed and stirred under a nitrogen atmosphere at 140° C. for 5 hours. 1 mol/L hydrochloric acid was added, and the mixture was extracted with ethyl acetate. The organic layer was washed with saturated aqueous sodium bicarbonate and saturated saline, and then dried over anhydrous sodium sulfate. The solvent was evaporated under reduced pressure, and the resulting residue was purified by silica gel chromatography (hexane-ethyl acetate) to give compound (109) (30 mg, 69% yield).

MS: m/z=515 [M+H]$^+$.

Third Step Synthesis of Compound II-6

Compound (109) (30 mg, 0.058 mmol) was dissolved in methanol (1 mL) and a 2 mol/L aqueous sodium hydroxide solution (0.146 mL, 0.291 mmol) was added, and the mixture was stirred at 70° C. for 4 hours. An aqueous hydrochloric acid solution was added, and the mixture was extracted with ethyl acetate. The organic layer was washed with saturated saline, and then dried over anhydrous sodium sulfate. The solvent was evaporated under reduced pressure, and the resulting residue was purified by silica gel chromatography (ethyl acetate-methanol) to give compound II-6 (21 mg, 72% yield).

MS: m/z=501 [M+H]$^+$.

$^1$H NMR (CDCl$_3$) δ: 1.06 (s, 9H), 1.88 (s, 3H), 2.26 (s, 3H), 2.27 (s, 3H), 2.31 (s, 3H), 2.32 (s, 3H), 2.99 (s, 3H), 5.09 (s, 1H), 6.94-7.52 (m, 6H).

Example 22

Synthesis of Compound II-8

[Formula 173]

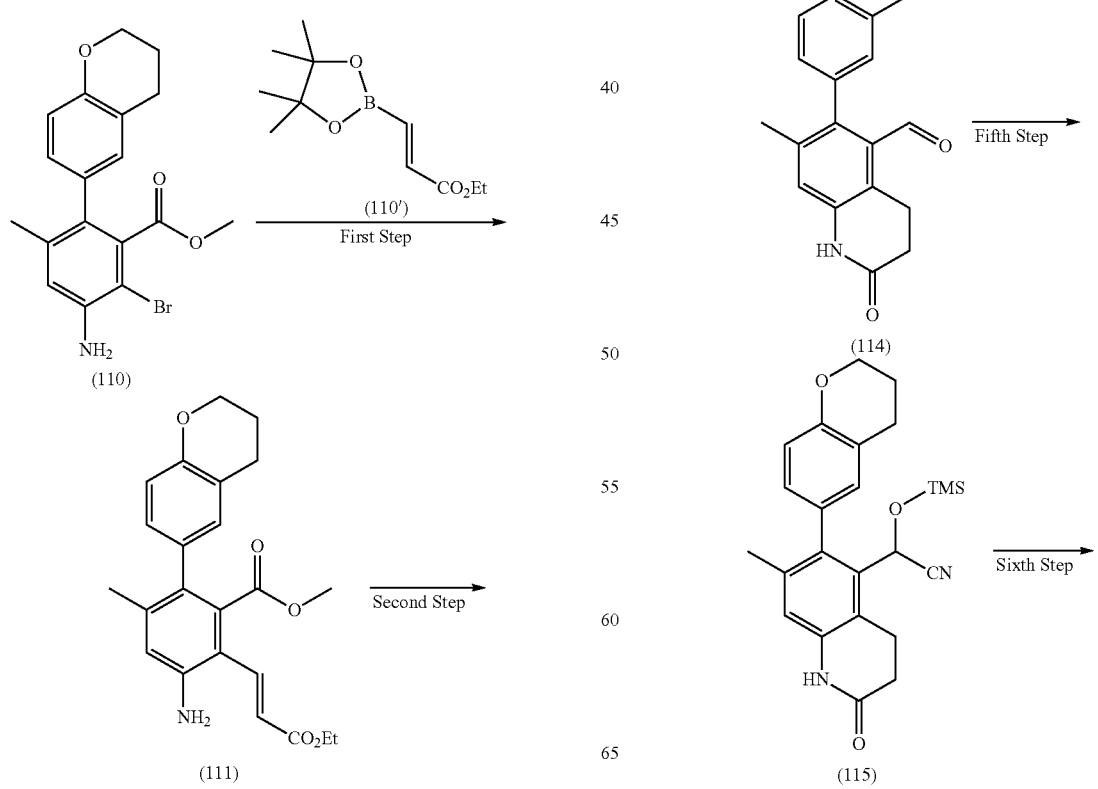

[Formula 174]

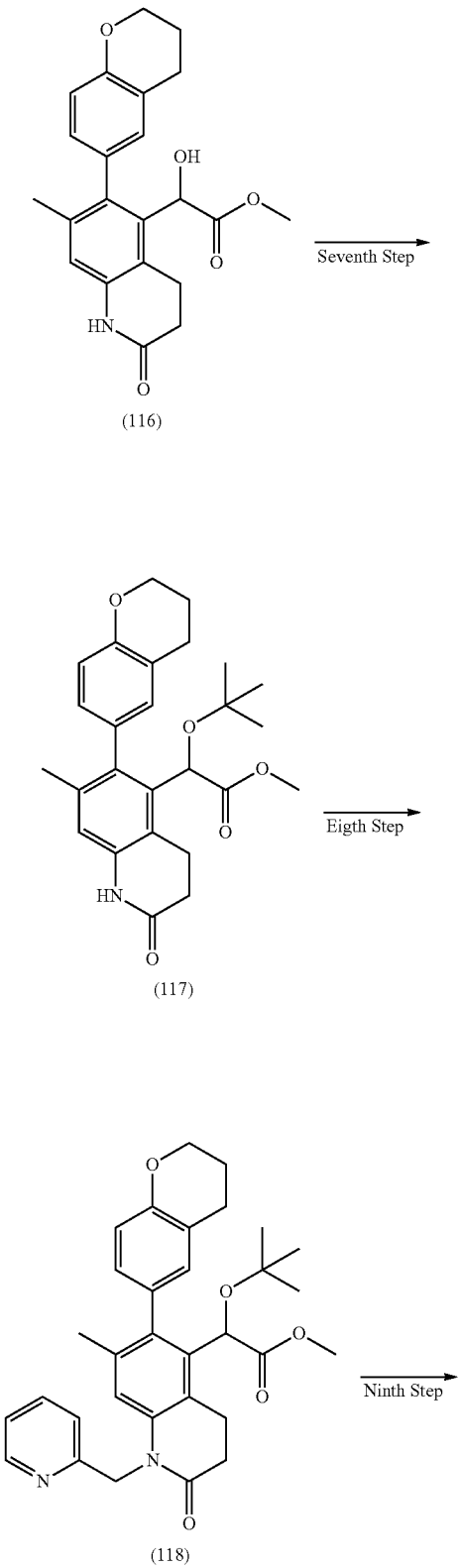

(116) →Seventh Step→ (117) →Eigth Step→ (118) →Ninth Step→

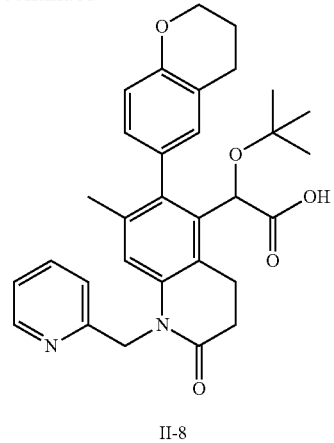

II-8

First Step Synthesis of Compound (111)

Cesium carbonate (48.5 g, 149 mmol) and Pd(dppf)Cl$_2$ were added to a 1,4-dioxane/water (100 mL/10 mL) solution of compound (110), and after nitrogen substitution, compound (110') (15.7 g, 69.4 mmol) was added, and then the mixture was stirred at 85° C. for 14 hours. After cooling to room temperature, ethyl acetate and water were added, and the organic layer was dried over sodium sulfate, and then the concentrated residue was purified by silica gel column chromatography, thereby obtaining compound (111) (15.0 g).

LC/MS (ESI): m/z=396 [M+H]$^+$

Second Step Synthesis of Compound (112)

Compound (111) (15.0 g, 38 mmol) was dissolved in ethanol (500 mL), and 10% palladium carbon (7 g) was added, and then the mixture was stirred under a hydrogen atmosphere at 40° C. for 4 hours, and further stirred at 80° C. After cooling to room temperature, palladium carbon was filtered, and the mixture was washed with dichloromethane (200 mL×3 times). The filtrate was dried over sodium sulfate, and then concentrated and dried, thereby obtaining compound (112) (9.5 g). The compound was used for next reaction without purification.

LC/MS (ESI): m/z=351 [M+H]$^+$

Third Step Synthesis of Compound (113)

Compound (112) (9.5 g, 27 mmol) was dissolved in dichloromethane, and a toluene solution (81 mL, 81 mmol) of 1 M diisobutylaluminum hydride was added dropwise at −60° C., and after stirring for 2 hours, the mixture was heated to room temperature. 1 M hydrochloric acid was added, and the organic layer was separated, and then the aqueous layer was extracted with ethyl acetate (300 mL×3 times). The organic layer was washed with water and saturated saline, dried over sodium sulfate and concentrated, and then purified by silica gel column chromatography to give compound (113) (4.8 g).

LC/MS (ESI): m/z=323 [M+H]$^+$

Fourth Step Synthesis of Compound (114)

Compound (113) (4.8 g, 14.9 mmol) was dissolved in DMSO, and 2-iodoxybenzoic acid (8.3 g, 29.7 mmol) was added, and then the mixture was stirred at 45° C. Ethyl acetate and water were added, and the organic layer was washed with water and saturated saline, dried over sodium sulfate and concentrated, and then purified by silica gel column chromatography to give compound (114) (3.5 g).

LC/MS (ESI): m/z=321 [M+H]$^+$

Fifth Step Synthesis of Compound (115)

Compound (114) (3.5 g, 10.9 mmol) was dissolved in dichloromethane (200 mL), and zinc iodide (3.5 g, 11.0 mmol) was added. TMSCN (3.3 g, 32.7 mmol) was added under ice cooling, and the mixture was stirred. Water (100 mL) was added, and the mixture was extracted with dichloromethane (100 mL×2 times), dried over sodium sulfate, and concentrated and dried, thereby obtaining compound (115) (5.0 g). The compound was used for next reaction without purification.

Sixth Step Synthesis of Compound (116)

Compound (115) (5 g, 10.9 mmol) was dissolved in methanol (250 mL), and hydrogen chloride gas was blown, and then the mixture was stirred at 60° C. for 14 hours. After cooling to room temperature, water was added, and the mixture was extracted with ethyl acetate (100 mL×3 times), dried over sodium sulfate, and concentrated and dried, thereby obtaining compound (116) (2.6 g). The compound was used for next reaction without purification.

Seventh Step Synthesis of Compound (117)

Compound (116) (2.6 g, 6.8 mmol) was dissolved in tert-butyl acetate (100 mL), and perchloric acid (70%, 8.0 g, 80 mmol) was added under a nitrogen stream little by little, and then the mixture was stirred at room temperature for 30 minutes. The reaction solution was flown into saturated saline, and the mixture was extracted with ethyl acetate (100 mL×3 times), dried over sodium sulfate and concentrated, and then purified by silica gel column chromatography, thereby obtaining compound (117) (2.4 g).

1H-NMR (400 MHz, DMSO-d6) δ: 10.01 (s, 1H), 6.88-6.73 (m, 4H), 4.95 (d, 1H, J=5.6 Hz), 4.18 (s, 2H), 3.62-3.58 (m, 3H), 3.07 (m, 1H), 2.83-2.76 (m, 3H), 2.35-2.31 (m, 3H), 1.99-1.89 (m, 5H), 0.90 (s, 9H).

Eighth Step Synthesis of Compound (118)

Compound (117) (132 mg, 0.3 mmol) was dissolved in DMF (10 mL), and 2-chloromethylpyridine (100 mg, 0.45 mmol) and cesium carbonate (300 mg, 0.9 mmol) were added, and then the mixture was stirred at 40° C. for 14 hours. After cooling to room temperature, water was added, and the mixture was extracted with diethyl ether (20 mL×2 times), dried over sodium sulfate, and concentrated and dried, thereby obtaining compound (118). The compound was used for next reaction without purification.

LC/MS (ESI): m/z=529 [M+H]$^+$

Ninth Step Synthesis of Compound II-8

Compound (118) was dissolved in methanol (10 mL), and a 1 M aqueous sodium hydroxide solution (10 mL, 10 mM) was added, and then the mixture was stirred at 50° C. for 14 hours. After cooling to room temperature, the mixture was concentrated, and fractionated by HPLC, thereby obtaining compound II-8 (60 mg).

LC/MS (ESI): m/z=515 [M+H]$^+$

1H-NMR (DMSO-d6) δ: 0.897 (s, 9H), 1.85 (s, 3H), 1.93-1.94 (m, 2H), 2.51-2.75 (m, 4H), 2.92-2.94 (m, 1H), 3.16-3.20 (m, 1H), 4.13-4.17 (m, 1H), 4.91 (s, 1H), 5.20-5.25 (m, 2H), 6.76-6.96 (m, 4H), 7.37-7.44 (m, 2H), 7.89-7.93 (m, 1H), 8.61 (d, 1H)

Example 23

Synthesis of II-21

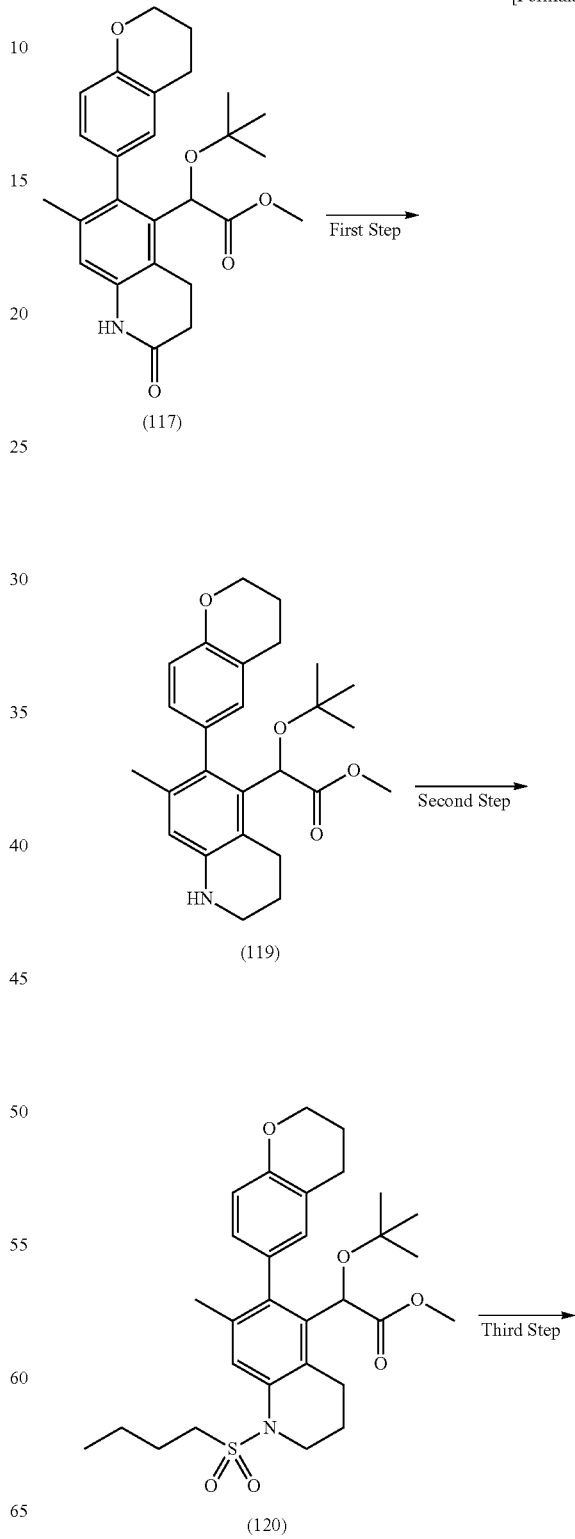

[Formula 175]

Example 24

Synthesis of II-53

[Formula 176]

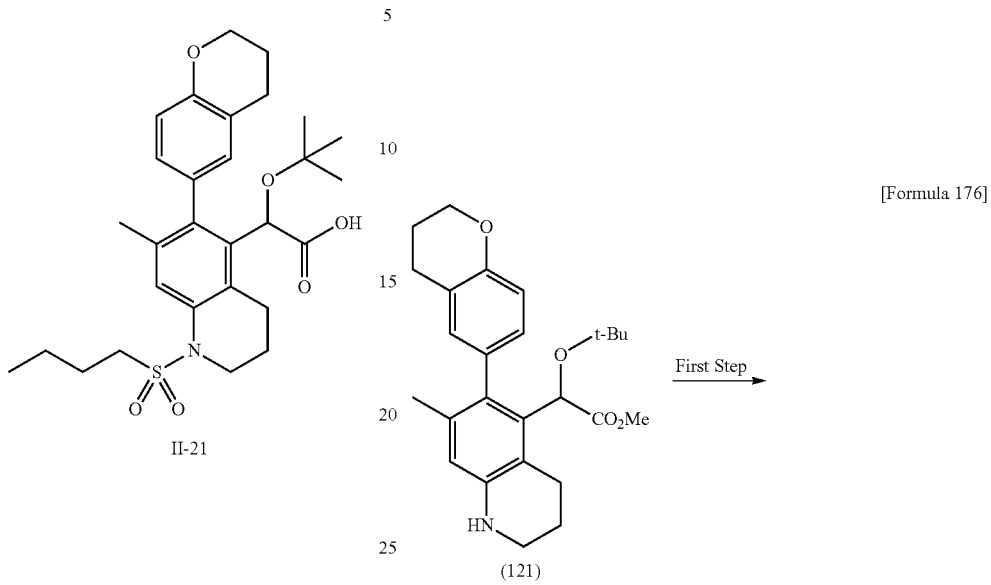

II-21

First Step Synthesis of Compound (119)

Compound (117) (600 mg, 1.3 mmol) was dissolved in THF (10 mL), and a 1 M BH3/THF solution (6.8 mL, 6.8 mmol) was added, and then the mixture was stirred at 50° C. for 14 hours. After cooling to room temperature, the pH of the mixture was adjusted to 7 with a 1 N aqueous sodium hydroxide solution. The mixture was concentrated and fractionated by HPLC, thereby obtaining compound (119) (500 mg).

LC-MS (ESI): m/z=424 [M+H]$^+$.

Second Step Synthesis of Compound (120)

Compound (119) (60 mg, 0.14 mmol) was dissolved in pyridine (2 mL), and butane-1-sulfonyl chloride (0.44 mg, 0.28 mmol) was added, and the mixture was stirred at room temperature for 5 hours. The pH of the mixture was adjusted to 3 with a 1 N aqueous hydrochloric acid solution, and the mixture was extracted with ethyl acetate (10 mL×3). Then the mixture was dried over sodium sulfate to be concentrated and dried, thereby obtaining compound (120) (77 mg). The compound was used for next reaction without purification.

LC-MS (ESI): m/z=544 [M+H]$^+$.

Third Step Synthesis of Compound II-21

Compound (120) (77 mg, 0.14 mmol) was dissolved in methanol (2 mL), and a 1 N aqueous sodium hydroxide solution (5 mL, 5 mmol) was added, and then the mixture was stirred at 45° C. for 14 hours. After cooling to room temperature, the pH was adjusted to 3 with a 1 N aqueous hydrochloric acid solution, and then the mixture was extracted with ethyl acetate (10 mL×3) to be concentrated and fractionated by HPLC, thereby obtaining compound II-21 (60 mg).

LC-MS (ESI): m/z=528 [M−H]−

1H-NMR (CDCl3) δ: 0.85-0.93 (m, 3H), 0.99 (s, 9H), 1.39-1.45 (m, 2H), 1.77-1.81 (m, 2H), 1.90 (s, 1H), 2.01-2.08 (m, 7H), 2.58 (s, 1H), 2.75-2.81 (m, 2H), 3.02-3.11 (m, 3H), 3.73-3.77 (m, 2H), 4.22-4.24 (m, 2H), 5.23 (s, 1H), 6.80-6.89 (m, 2H), 7.12 (s, 1H), 7.52 (s, 1H)

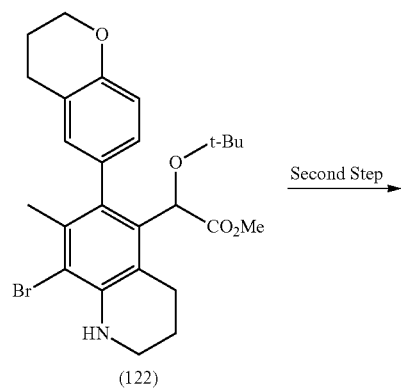

(121)

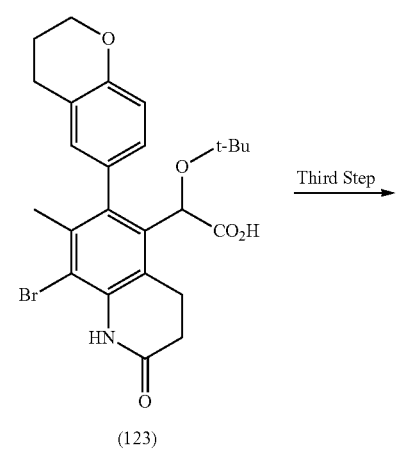

(122)

(123)

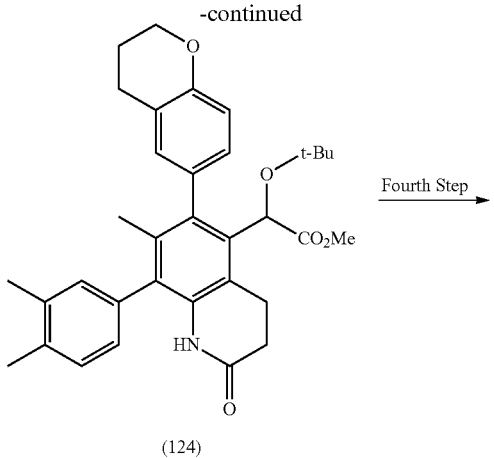

(124)

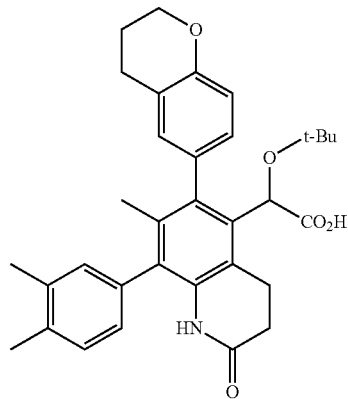

II-53

First Step Synthesis of Compound (122)

Compound (121) (43.0 mg, 0.102 mmol) was dissolved in DMF (1.5 mL). NBS (18.1 mg, 0.102 mmol) was added under ice cooling, and the mixture was stirred under ice cooling for 1.5 hours. Water (30 mL) was added, and the mixture was extracted with ethyl acetate (50 mL). The organic layer was washed with water (30 mL×2 times) and saturated saline (30 mL), dried over anhydrous magnesium sulfate and concentrated, and then purified by silica gel column chromatography (hexane-ethyl acetate), thereby obtaining compound (122) (47.8 mg, 94% yield) as a colorless foam substance.

MS: m/z=502.2, 504.2 [M+H]$^+$

Second Step Synthesis of Compound (123)

Compound (122) (47.0 mg, 0.094 mmol) was dissolved in a mixed solvent of tert-butanol and water (3:1, 1 mL), and acetic acid (0.016 mL, 0.281 mmol) and potassium permanganate (37.0 mg, 0.234 mmol) were added at room temperature, and then the mixture was stirred for 30 minutes. Ethanol (9 mL) and a 2 mol/L aqueous sodium hydroxide solution (15 mL) were added, and unwanted matters were removed by filtration. 1 mol/L hydrochloric acid (30 mL) was added, and the mixture was extracted with ethyl acetate (50 mL). The organic layer was washed with water (50 mL), saturated sodium bicarbonate (50 mL) and saturated saline (30 mL), dried over anhydrous magnesium sulfate and concentrated, and then purified by silica gel column chromatography (hexane-ethyl acetate), thereby obtaining compound (123) (13.8 mg, 29% yield) as a colorless foam substance.

MS: m/z=516.2, 518.2 [M+H]$^+$

Third Step Synthesis of Compound (124)

Compound (123) (14.0 mg, 0.027 mmol) was dissolved in DMA (0.28 mL), and 3,4-dimethylphenylboronic acid (6.10 mg, 0.041 mmol), [1,1'-bis(di-tert-butylphosphino)ferrocene]palladium dichloride (3.53 mg, 0.005 mmol), and a 2 mol/L aqueous potassium carbonate solution (0.027 mL, 0.054 mmol) were added, and the mixture was sealed and stirred at 110° C. for 1 hour. 1 mol/L hydrochloric acid (30 mL) was added, and the mixture was extracted with ethyl acetate (30 mL). The organic layer was washed with 1 mol/L hydrochloric acid (30 mL) and saturated saline (30 mL), and then dried over anhydrous magnesium sulfate. The mixture was concentrated, and then purified by silica gel chromatography (hexane-ethyl acetate), thereby obtaining compound (124) (9.4 mg, 64% yield) as a brown foam substance.

MS: m/z=542.3 [M+H]$^+$

Fourth Step Synthesis of Compound II-53

Compound (124) (9.0 mg, 0.017 mmol) was dissolved in ethanol (0.8 mL). A 2 mol/L aqueous sodium hydroxide solution (0.2 mL, 0.400 mmol) was added at room temperature, and the mixture was stirred under heat reflux for 4 hours. 1 mol/L hydrochloric acid (30 mL) was added, and the mixture was extracted with ethyl acetate (30 mL). The organic layer was washed with saturated saline (30 mL), and then dried over anhydrous magnesium sulfate. The mixture was concentrated, and then purified by silica gel column chromatography (chloroform-methanol), thereby obtaining compound II-53 (7.5 mg, 86% yield) as a colorless foam substance.

MS: m/z=528.3 [M+H]$^+$

Example 25

Synthesis of II-52

[Formula 177]

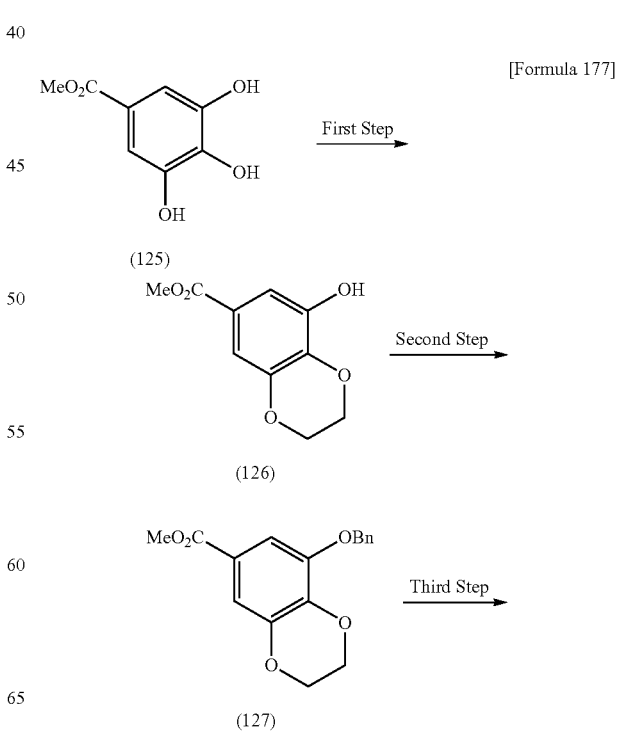

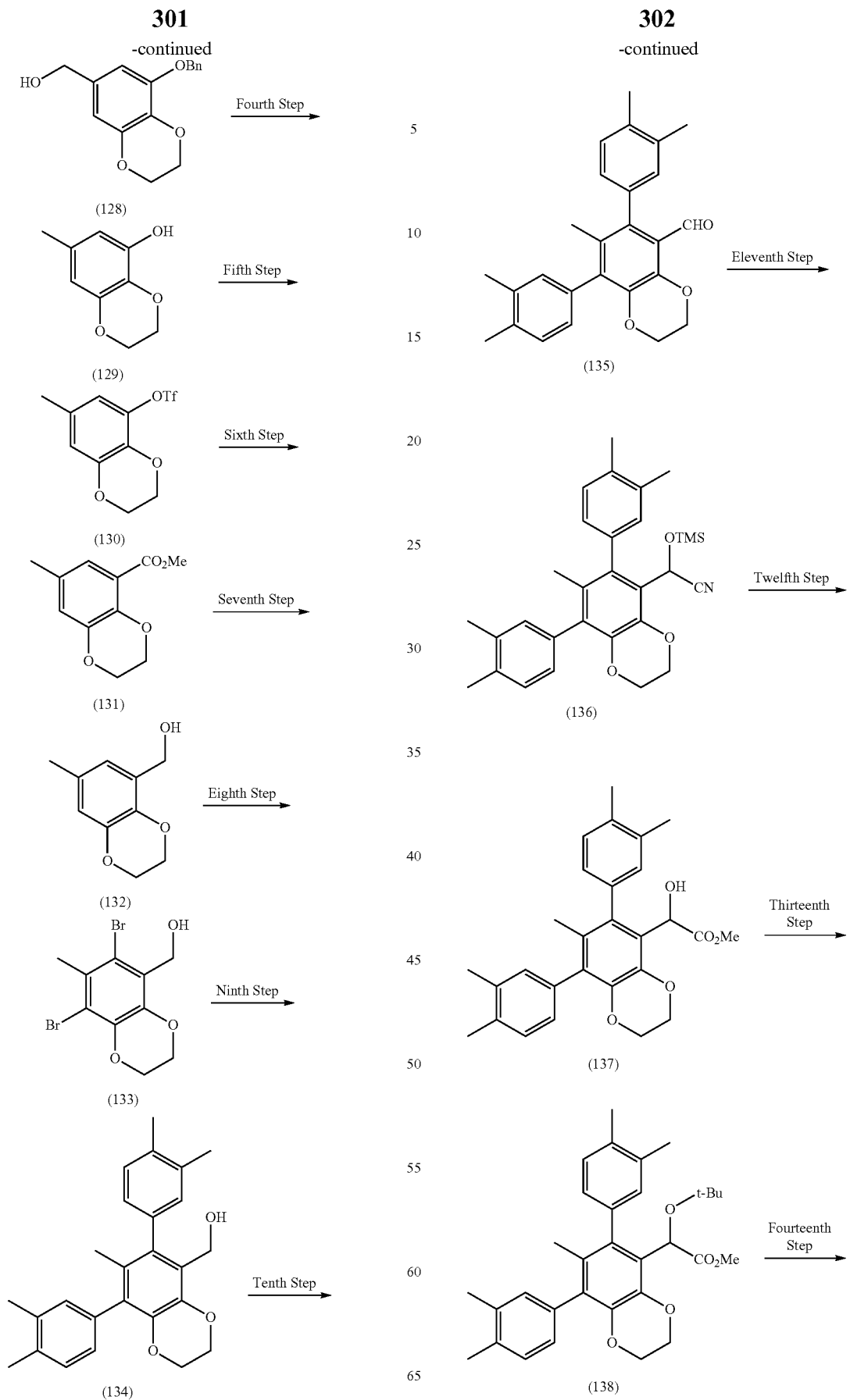

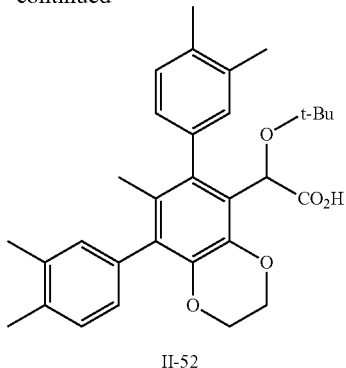

II-52

First Step Synthesis of Compound (126)

Compound (125) (12.5 g, 67.9 mmol) was dissolved in DMF (350 mL), and cesium carbonate (44.2 g, 136 mmol) was added at room temperature. Under heating and stirring of the mixture at 100° C., a DMF solution (50 mL) of 1,2-dibromoethane (5.87 mL, 68.1 mmol) was added dropwise in 50 minutes, and the mixture was stirred at 100° C. for 6.5 hours. The mixture was concentrated and 2 mol/L hydrochloric acid (200 mL) was added, and the mixture was extracted with ethyl acetate (300 mL). The organic layer was washed with 2 mol/L hydrochloric acid (100 mL) and saturated saline (100 mL), and then dried over anhydrous magnesium sulfate. The mixture was concentrated, and then purified by silica gel chromatography (hexane-ethyl acetate), thereby obtaining compound (126) (3.56 g, 25% yield) as a white solid.

$^1$H-NMR (CDCl$_3$) δ: 3.87 (s, 3H), 4.28-4.32 (m, 2H), 4.35-4.39 (m, 2H), 5.38 (s, 1H), 7.20 (d, J=1.9 Hz, 1H), 7.23 (d, J=1.9 Hz, 1H)

Second Step Synthesis of Compound (127)

Compound (126) (3.34 g, 15.9 mmol) was dissolved in DMF (33.4 mL), and potassium carbonate (3.29 g, 23.8 mmol) was added at room temperature, and then the mixture was stirred for 5 minutes. Benzyl bromide (2.27 mL, 19.1 mmol) was added at room temperature, and the mixture was stirred at room temperature for 2.5 hours. Water (50 mL) was added, and the mixture was extracted with ethyl acetate (150 mL). The organic layer was washed with 2 mol/L hydrochloric acid (75 mL×2 times) and saturated saline (50 mL), and then dried over anhydrous magnesium sulfate. The mixture was concentrated, and then hexane was added to solidify the mixture, thereby obtaining compound (127) (4.65 g, 97% yield) as a white solid.

$^1$H NMR-(CDCl$_3$) δ: 3.86 (s, 3H), 4.26-4.30 (m, 2H), 4.34-4.38 (m, 2H), 5.16 (s, 2H), 7.27-7.42 (m, 5H), 7.44-7.49 (m, 2H)

Third Step Synthesis of Compound (128)

Compound (127) (4.64 g, 15.5 mmol) was dissolved in THF (46 mL), and lithium aluminum hydride (1.17 g, 30.9 mmol) was added under ice cooling, and the mixture was stirred under ice cooling for 30 minutes. A saturated aqueous ammonium chloride solution (50 mL) was added at 0° C., and the mixture was extracted with ethyl acetate (200 mL). The organic layer was washed with water (100 mL) and saturated saline (50 mL), and then dried over anhydrous magnesium sulfate. The mixture was concentrated and solidified, thereby obtaining compound (128) (4.08 g, 97% yield) as a white solid.

$^1$H-NMR (CDCl$_3$) δ: 4.24-4.28 (m, 2H), 4.29-4.34 (m, 2H), 4.52 (d, J=3.0 Hz, 2H), 5.13 (s, 2H), 6.55 (d, J=1.9 Hz, 1H), 6.58 (d, J=1.9 Hz, 1H), 7.29-7.40 (m, 3H), 7.42-7.48 (m, 2H)

Fourth Step Synthesis of Compound (129)

Compound (128) (3.75 g, 13.8 mmol) was dissolved in acetic acid (37.5 mL), and 10% by weight palladium hydroxide (1.47 g, 1.38 mmol) was added, and then the mixture was stirred under a hydrogen atmosphere at room temperature for 16 hours. The reaction solution was filtered through celite, and then the filtrate was evaporated under reduced pressure using an evaporator. The resulting residue was purified by silica gel chromatography (chloroform-methanol) to give compound (129) (2.22 g, 97% yield) as a white solid.

$^1$H-NMR (CDCl$_3$) δ: 2.21 (s, 3H), 4.25-4.28 (m, 4H), 5.21 (s, 1H), 6.27 (d, J=1.6 Hz, 1H), 6.36 (d, J=1.6 Hz, 1H)

Fifth Step Synthesis of Compound (130)

Compound (129) (2.10 g, 12.6 mmol) was dissolved in dichloromethane (21 mL), and pyridine (2.04 mL, 25.3 mmol) was added at room temperature. The mixture was cooled to −78° C., and trifluoromethanesulfonic anhydride (3.20 mL, 19.0 mmol) was added dropwise in 5 minutes, and then the mixture was stirred for 2.5 hours while heating from −78° C. to −25° C. Water (100 mL) was added at −20° C., and the mixture was extracted with ethyl acetate (150 mL). The organic layer was washed with saturated saline (100 mL), and then dried over anhydrous magnesium sulfate. The mixture was concentrated, and then purified by silica gel chromatography (hexane-ethyl acetate), thereby obtaining compound (130) (3.99 g, 100% yield) as a white solid.

$^1$H-NMR (CDCl$_3$) δ: 2.26 (s, 3H), 4.29-4.31 (m, 4H), 6.62 (s, 1H), 6.70 (s, 1H)

Sixth Step Synthesis of Compound (131)

Compound (130) (3.50 g, 11.7 mmol) was dissolved in DMF (70 mL) and methanol (28 mL), and palladium acetate (263 mg, 1.17 mmol) and triethylamine (6.13 mL, 58.7 mmol) were added at room temperature, and then the mixture was stirred under a carbon monoxide atmosphere (1 atmosphere) at 70° C. for 52 hours. The reaction mixture was filtered through celite, 1 mol/L hydrochloric acid (100 mL) was added, and the mixture was extracted with ethyl acetate (400 mL). The organic layer was washed with 2 mol/L hydrochloric acid (100 mL) and saturated saline (100 mL), and then dried over anhydrous magnesium sulfate. The mixture was concentrated, and then purified by silica gel chromatography (hexane-ethyl acetate), thereby obtaining compound (131) (1.88 g, 77% yield) as a yellow oily substance.

$^1$H-NMR (CDCl$_3$) δ: 2.25 (s, 3H), 3.88 (s, 3H), 4.25-4.29 (m, 2H), 4.31-4.34 (m, 2H), 6.84 (d, J=2.0 Hz, 1H), 7.20 (d, J=2.0 Hz, 1H).

Seventh Step Synthesis of Compound (132)

Lithium aluminum hydride (314 mg, 8.26 mmol) was suspended in THF (17 mL), and a THF solution (17 mL) of compound (131) (1.72 g, 8.26 mmol) was added dropwise under ice cooling, and then the mixture was stirred under ice cooling and a nitrogen atmosphere for 30 minutes. 1 mol/L hydrochloric acid (50 mL) was added, and the mixture was extracted with chloroform (50 mL×3 times). The organic layer was dried over magnesium sulfate to be concentrated and solidified, thereby obtaining compound (132) (1.49 g, 100% yield) as a white solid.

$^1$H-NMR (CDCl$_3$) δ: 2.08 (t, J=6.4 Hz, 1H), 2.24 (s, 3H), 4.23-4.26 (m, 2H), 4.27-4.30 (m, 2H), 4.63 (d, J=6.4 Hz, 2H), 6.65 (d, J=1.9 Hz, 1H), 6.67 (d, J=1.9 Hz, 1H)

Eighth and Ninth Steps Synthesis of Compound (134)

Compound (132) (1.48 g, 8.24 mmol) was dissolved in DMF (30 mL). NBS (3.08 g, 17.3 mmol) was added under ice cooling, and the mixture was stirred for 24 hours while heating to room temperature. Water (50 mL) was added, and the mixture was extracted with ethyl acetate (300 mL). The organic layer was washed with 1 mol/L hydrochloric acid (50 mL×2 times) and saturated saline (50 mL), and then dried over anhydrous magnesium sulfate. The mixture was concentrated, and then the crude product (2.87 g) of the resulting compound (133) was dissolved in DMA (30 mL), and 3,4-dimethylphenylboronic acid (3.18 g, 21.2 mmol), [1,1'-bis(di-tert-butylphosphino)ferrocene]palladium dichloride (553 mg, 0.849 mmol) and a 2 mol/L aqueous potassium carbonate solution (12.7 mL, 25.5 mmol) were added, and then the mixture was sealed and stirred at 110° C. for 2 hours. Water (150 mL) was added, and the mixture was extracted with ethyl acetate (150 mL). An insoluble matter was filtered using celite, and the organic layer was washed with 1 mol/L hydrochloric acid (75 mL×2 times) and saturated saline (50 mL), and then dried over anhydrous magnesium sulfate. The mixture was concentrated, and then purified by silica gel chromatography (hexane-ethyl acetate) to give compound (134) (2.61 g, 82% yield).

MS: m/z=371.2 [M-OH]$^+$

Tenth Step Synthesis of Compound (135)

Compound (134) (2.69 g, 6.92 mmol) was dissolved in dichloromethane (54 mL), and DMP (4.54 g, 10.4 mmol) was added under ice cooling, and then the mixture was stirred at room temperature for 2 hours. Water (100 mL) was added, and the mixture was extracted with ethyl acetate (300 mL). The organic layer was washed with a saturated aqueous sodium bicarbonate solution (100 mL) and saturated saline (100 mL), and then dried over anhydrous magnesium sulfate. The mixture was concentrated, and then purified by silica gel chromatography (hexane-ethyl acetate) to give compound (135) (1.81 g, 63% yield).

MS: m/z=387.2 [M+H]$^+$

Eleventh and Twelfth Steps Synthesis of Compound (137)

Compound (135) (1.75 g, 4.53 mmol) was dissolved in dichloromethane (20 mL), and zinc iodide (1.52 g, 4.53 mmol) and trimethylsilyl cyanide (1.90 mL, 13.6 mmol) were added under ice cooling, and then the mixture was stirred at room temperature for 2 hours. A saturated aqueous sodium bicarbonate solution (50 mL) was added, and the mixture was extracted with ethyl acetate (150 mL). The organic layer was washed with water (50 mL) and saturated saline (50 mL), and then dried over anhydrous magnesium sulfate. The mixture was concentrated, and then the crude product (1.95 g) of resulting compound (136) was dissolved in methanol (10 mL), and concentrated sulfuric acid (2.14 mL, 40.1 mmol) was added at room temperature, and then the mixture was stirred under heat reflux for 3 hours. Water (50 mL) was added, and the mixture was extracted with ethyl acetate (150 mL). The organic layer was washed with a saturated aqueous sodium bicarbonate solution (50 mL) and saturated saline (50 mL), and then dried over anhydrous magnesium sulfate. The mixture was concentrated, and then purified by silica gel chromatography (hexane-ethyl acetate) to give compound (137) (125 mg, 6% yield).

MS: m/z=429.2 [M-OH]$^+$

Thirteenth Step Synthesis of Compound (138)

Compound (137) (125 mg, 0.280 mmol) was dissolved in tert-butyl acetate (3.74 mL), and a 70% aqueous perchloric acid solution (0.0505 mL, 0.588 mmol) was added, and then the mixture was stirred at room temperature for 45 hours. A saturated aqueous sodium bicarbonate solution (30 mL) was added, and the mixture was extracted with ethyl acetate (50 mL). The organic layer was washed with saturated saline (30 mL), and then dried over anhydrous magnesium sulfate. The mixture was concentrated, and then purified by silica gel chromatography (hexane-ethyl acetate) to give compound (138) (41.7 mg, 28% yield).

MS: m/z=525.2 [M+Na]$^+$

Fourteenth Step Synthesis of Compound II-52

Compound (138) (40.3 mg, 0.080 mmol) was dissolved in THF (1 mL) and methanol (1 mL), and a 2 mol/L aqueous sodium hydroxide solution (0.802 mL, 1.60 mmol) was added at room temperature, and then the mixture was stirred at 50° C. for 3.5 hours. Water (20 mL) and 1 mol/L hydrochloric acid (10 mL) were added, and the mixture was extracted with ethyl acetate (50 mL). The organic layer was washed with saturated saline (30 mL), and then dried over anhydrous magnesium sulfate. The mixture was concentrated, and then purified by reversed-phase high-performance liquid chromatography (0.1% formic acid in acetonitrile-water), thereby obtaining compound II-52 (22.5 mg, 57% yield) as a white solid.

MS: m/z=511.2 [M+Na]$^+$

Example 26

The following compounds were synthesized according to the above examples.

TABLE 1

| Compound No. | Structure | RT(min) | MS(M + H)+ |
|---|---|---|---|
| I-1 | 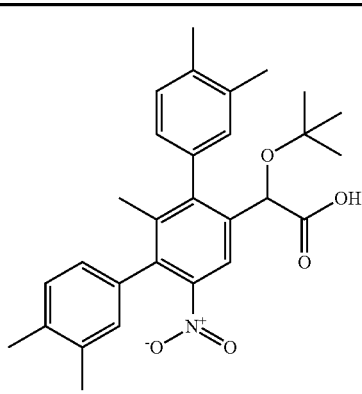 | *4 | 474 [M − H]− |

TABLE 1-continued

| Compound No. | Structure | RT(min) | MS(M + H)+ |
|---|---|---|---|
| I-2 | 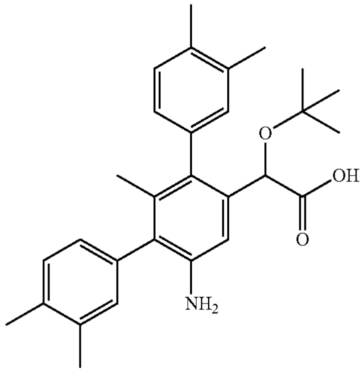 [SMILES: Cc1ccc(-c2c(N)cc(C(OC(C)(C)C)C(=O)O)c(-c3ccc(C)c(C)c3)c2C)cc1C] | 6.89 *1 | 446 |
| I-3 | 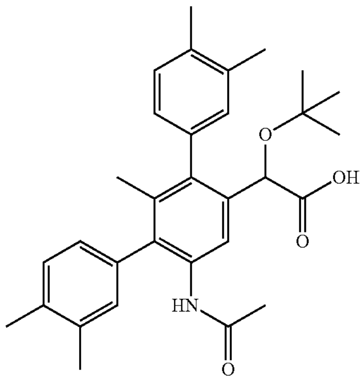 [SMILES: CC(=O)Nc1cc(C(OC(C)(C)C)C(=O)O)c(-c2ccc(C)c(C)c2)c(C)c1-c1ccc(C)c(C)c1] | 6.68 *1 | 488 |
| I-4 | 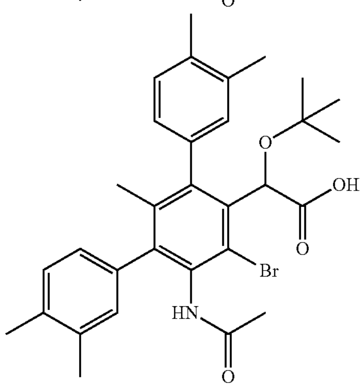 | *4 | 566 |

TABLE 2

| Compound No. | Structure | RT(min) | MS(M + H)+ |
|---|---|---|---|
| I-5 | 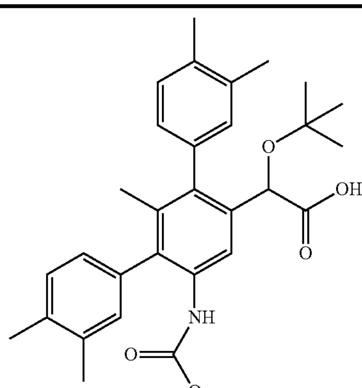 | *4 503 | M+. |

TABLE 2-continued

| Compound No. | Structure | RT(min) | MS(M + H)+ |
|---|---|---|---|
| I-7 | 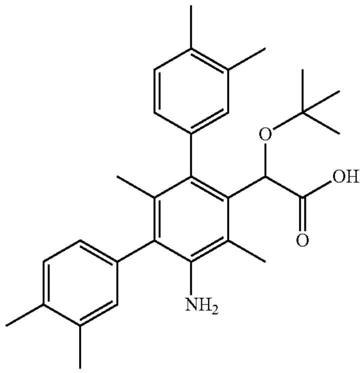 [SMILES: Cc1ccc(-c2c(C)c(-c3ccc(C)c(C)c3)c(C(OC(C)(C)C)C(=O)O)c(C)c2N)cc1C] | 3.08 | 460 |
| I-8 | 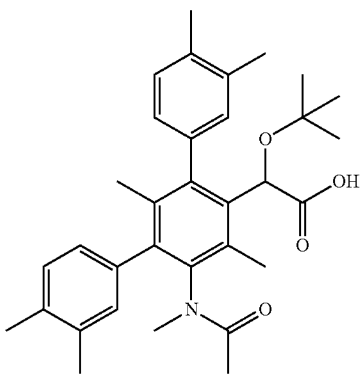 [SMILES: CC(=O)N(C)c1c(C)c(C(OC(C)(C)C)C(=O)O)c(-c2ccc(C)c(C)c2)c(C)c1-c1ccc(C)c(C)c1] | *4 | 516 |
| I-9 | 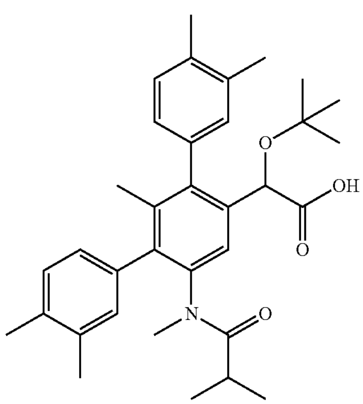 [SMILES: Cc1ccc(-c2c(C(OC(C)(C)C)C(=O)O)cc(N(C)C(=O)C(C)C)c(-c3ccc(C)c(C)c3)c2C)cc1C] | 3.12 | 531 |

TABLE 3

| Compound No. | Structure | RT(min) | MS(M + H)+ |
|---|---|---|---|
| I-10 | 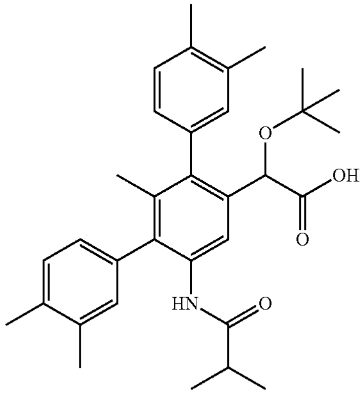 [SMILES: Cc1ccc(-c2c(NC(=O)C(C)C)cc(C(OC(C)(C)C)C(=O)O)c(-c3ccc(C)c(C)c3)c2C)cc1C] | 3.04 | 517 |
| I-13 | 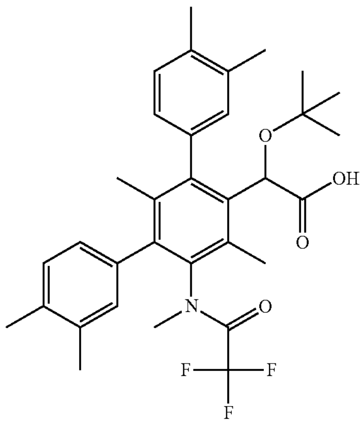 [SMILES: Cc1ccc(-c2c(C)c(-c3ccc(C)c(C)c3)c(N(C)C(=O)C(F)(F)F)c(C)c2C(OC(C)(C)C)C(=O)O)cc1C] | *4 | 570 |
| I-16 | 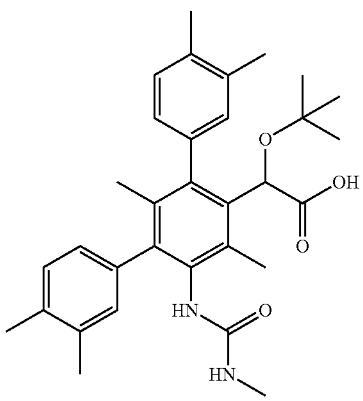 [SMILES: CNC(=O)Nc1c(C)c(C(OC(C)(C)C)C(=O)O)c(-c2ccc(C)c(C)c2)c(C)c1-c1ccc(C)c(C)c1] | *4 | 517 |
| I-17 | 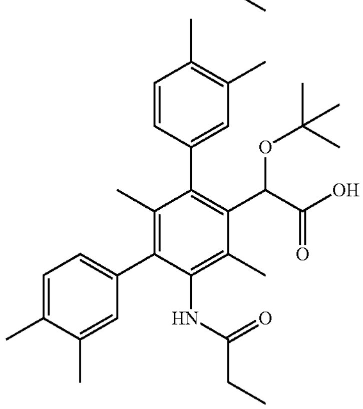 | 2.83 | 516 |

TABLE 4
| Compound No. | Structure | RT(min) | MS(M + H)+ |
|---|---|---|---|
| I-18 | 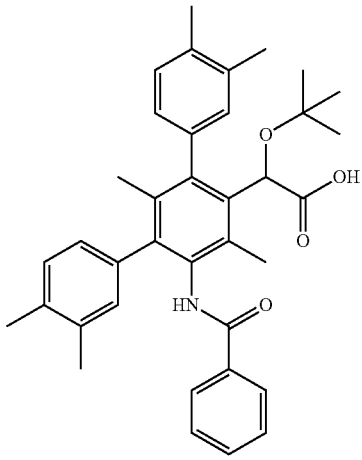 [SMILES: Cc1ccc(-c2c(C)c(-c3ccc(C)c(C)c3)c(C(OC(C)(C)C)C(=O)O)c(C)c2NC(=O)c2ccccc2)cc1C] | 2.97 | 564 |
| I-19 | 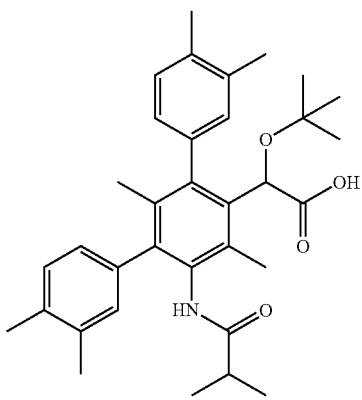 [SMILES: Cc1ccc(-c2c(C)c(-c3ccc(C)c(C)c3)c(C(OC(C)(C)C)C(=O)O)c(C)c2NC(=O)C(C)C)cc1C] | 2.92 | 530 |
| I-20 | 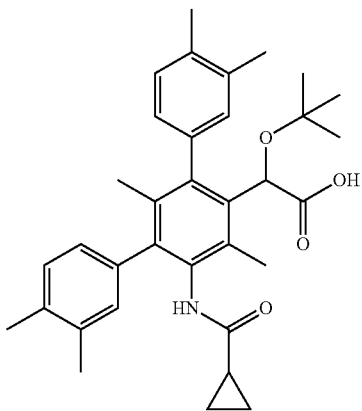 [SMILES: Cc1ccc(-c2c(C)c(-c3ccc(C)c(C)c3)c(C(OC(C)(C)C)C(=O)O)c(C)c2NC(=O)C2CC2)cc1C] | 2.88 | 528 |

TABLE 4-continued

| Compound No. | Structure | RT(min) | MS(M + H)+ |
|---|---|---|---|
| I-21 | 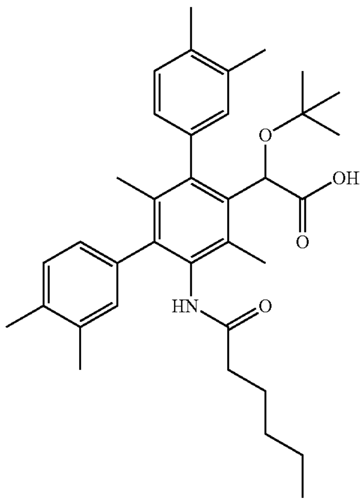 [SMILES: CCCCCC(=O)Nc1c(C)c(C(OC(C)(C)C)C(=O)O)c(-c2ccc(C)c(C)c2)c(C)c1-c1ccc(C)c(C)c1] | 3.13 | 558 |

TABLE 5

| Compound No. | Structure | RT(min) | MS(M + H)+ |
|---|---|---|---|
| I-22 | 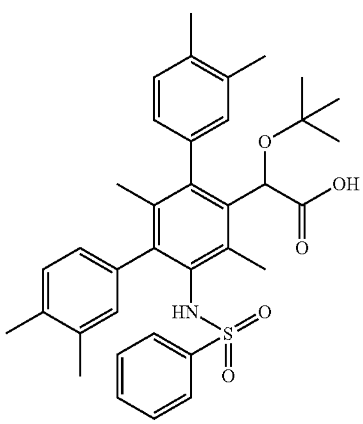 [SMILES: Cc1ccc(-c2c(C)c(-c3ccc(C)c(C)c3)c(C(OC(C)(C)C)C(=O)O)c(C)c2NS(=O)(=O)c2ccccc2)cc1C] | 3.12 | 600 |
| I-23 | 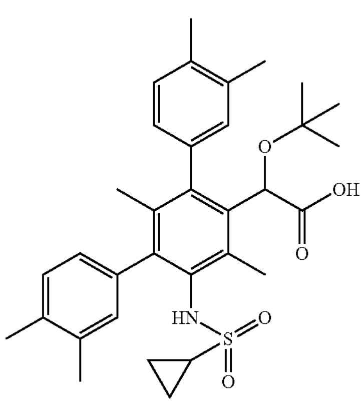 | 2.99 | 564 |

TABLE 5-continued

| Compound No. | Structure | RT(min) | MS(M + H)+ |
|---|---|---|---|
| I-24 | 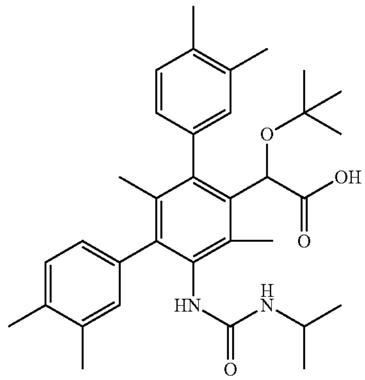 [SMILES: Cc1ccc(-c2c(C)c(-c3ccc(C)c(C)c3)c(C(OC(C)(C)C)C(=O)O)c(C)c2NC(=O)NC(C)C)cc1C] | 2.89 | 545 |
| I-25 | 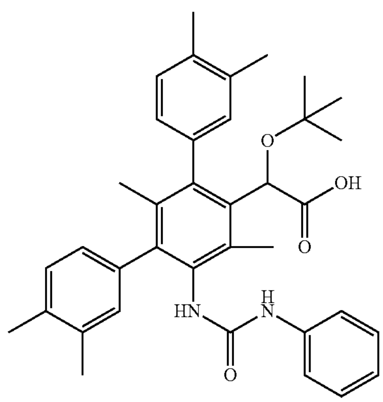 [SMILES: Cc1ccc(-c2c(C)c(-c3ccc(C)c(C)c3)c(C(OC(C)(C)C)C(=O)O)c(C)c2NC(=O)Nc2ccccc2)cc1C] | 3.00 | 579 |

TABLE 6

| Compound No. | Structure | RT(min) | MS(M + H)+ |
|---|---|---|---|
| I-26 | 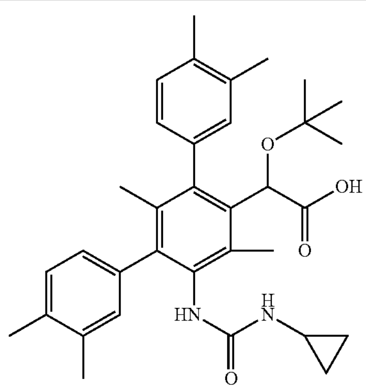 [SMILES: Cc1ccc(-c2c(C)c(-c3ccc(C)c(C)c3)c(C(OC(C)(C)C)C(=O)O)c(C)c2NC(=O)NC2CC2)cc1C] | 2.85 | 543 |

TABLE 6-continued
| Compound No. | Structure | RT(min) | MS(M + H)+ |
|---|---|---|---|
| I-27 | 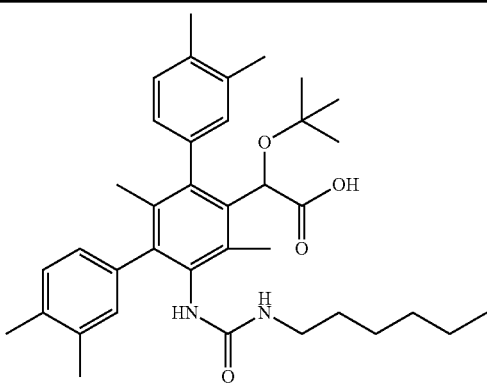 | 3.20 | 587 |
| I-28 | 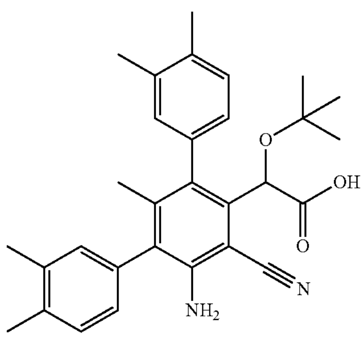 [SMILES: Cc1ccc(-c2c(C)c(-c3ccc(C)c(C)c3)c(C(OC(C)(C)C)C(=O)O)c(C#N)c2N)cc1C] | 3.09 | 471 |
TABLE 7
| Compound No. | Structure | RT (min) | MS (M + H)+ |
|---|---|---|---|
| I-29 | 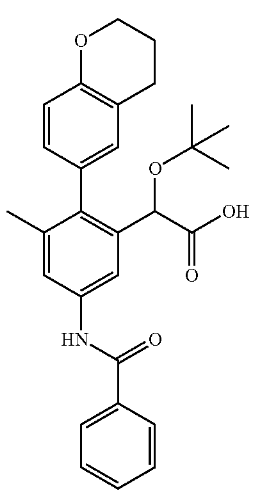 [SMILES: Cc1cc(NC(=O)c2ccccc2)cc(C(OC(C)(C)C)C(=O)O)c1-c1ccc2c(c1)CCCO2] | 2.47 | 473 |
TABLE 7-continued
| Compound No. | Structure | RT (min) | MS (M + H)+ |
|---|---|---|---|
| I-30 | 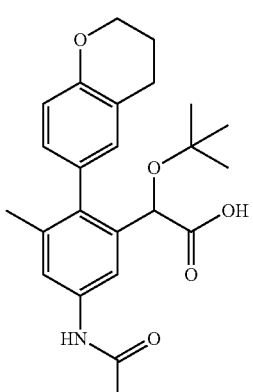 | 2.47 | 487 |

TABLE 7-continued

| Compound No. | Structure | RT (min) | MS (M + H)+ |
|---|---|---|---|
| I-31 | 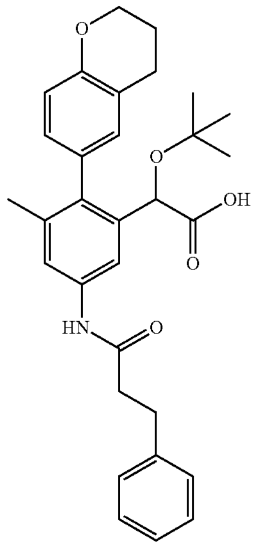 [SMILES: Cc1cc(NC(=O)CCc2ccccc2)cc(C(OC(C)(C)C)C(=O)O)c1-c1ccc2c(c1)CCCO2] | 2.55 | 501 |
| I-32 | 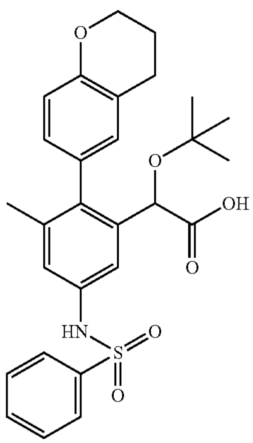 [SMILES: Cc1cc(NS(=O)(=O)c2ccccc2)cc(C(OC(C)(C)C)C(=O)O)c1-c1ccc2c(c1)CCCO2] | 2.42 | 509 |

TABLE 8

| Compound No. | Structure | RT (min) | MS (M + H)+ |
|---|---|---|---|
| I-33 | 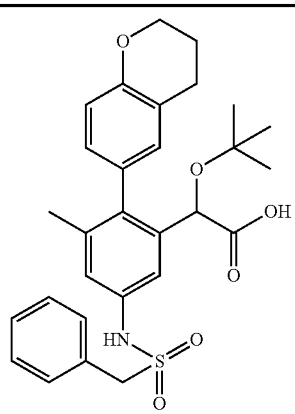 | 2.50 | 523 |

TABLE 8-continued

| Compound No. | Structure | RT (min) | MS (M + H)+ |
|---|---|---|---|
| I-34 | 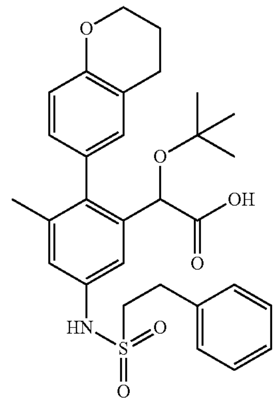 [SMILES: Cc1cc(NS(=O)(=O)CCc2ccccc2)cc(C(OC(C)(C)C)C(=O)O)c1-c1ccc2c(c1)CCCO2] | 2.60 | 537 |
| I-35 | 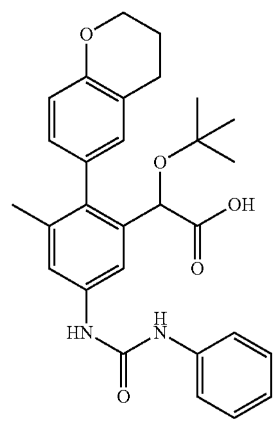 [SMILES: Cc1cc(NC(=O)Nc2ccccc2)cc(C(OC(C)(C)C)C(=O)O)c1-c1ccc2c(c1)CCCO2] | 2.45 | 488 |
| I-36 | 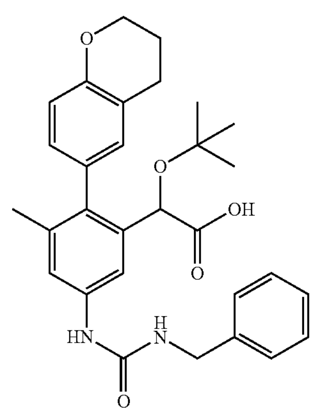 [SMILES: Cc1cc(NC(=O)NCc2ccccc2)cc(C(OC(C)(C)C)C(=O)O)c1-c1ccc2c(c1)CCCO2] | 2.39 | 502 |

TABLE 9
| Compound No. | Structure | RT(min) | MS(M + H)+ |
|---|---|---|---|
| I-37 | 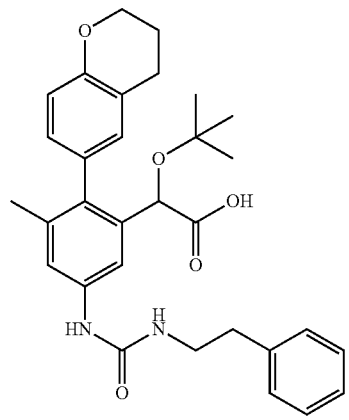 [SMILES: Cc1cc(NC(=O)NCCc2ccccc2)cc(C(OC(C)(C)C)C(=O)O)c1-c1ccc2c(c1)CCCO2] | 2.45 | 516 |
| I-39 | 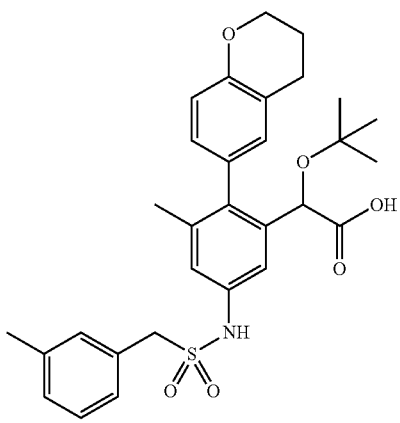 [SMILES: Cc1cccc(CS(=O)(=O)Nc2cc(C)c(-c3ccc4c(c3)CCCO4)c(C(OC(C)(C)C)C(=O)O)c2)c1] | 2.62 | 536 [M − H]− |
| I-40 | 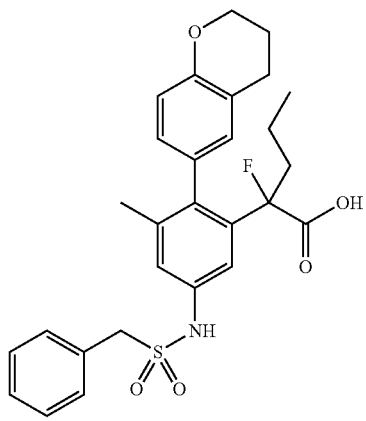 [SMILES: CCCC(F)(C(=O)O)c1cc(NS(=O)(=O)Cc2ccccc2)cc(C)c1-c1ccc2c(c1)CCCO2] | 2.42 | 510 [M − H]− |

TABLE 9-continued

| Compound No. | Structure | RT(min) | MS(M + H)+ |
|---|---|---|---|
| I-41 | 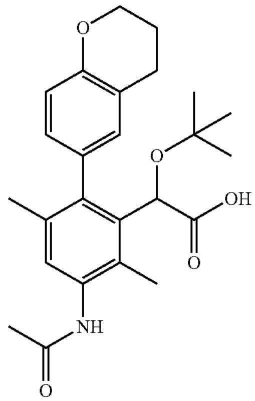 [SMILES: CC(=O)Nc1cc(C)c(-c2ccc3c(c2)CCCO3)c(C(OC(C)(C)C)C(=O)O)c1C] | 1.81 *3 | 448 [M + Na]+ |

TABLE 10

| Compound No. | Structure | RT(min) | MS(M + H)+ |
|---|---|---|---|
| I-42 | 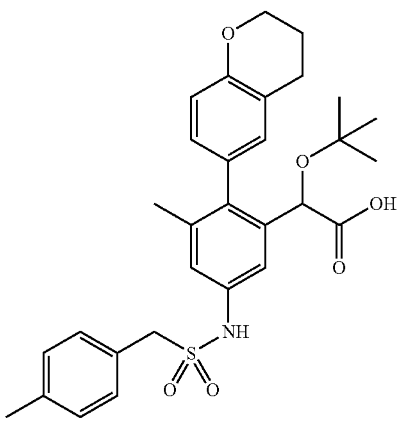 [SMILES: Cc1ccc(CS(=O)(=O)Nc2cc(C)c(-c3ccc4c(c3)CCCO4)c(C(OC(C)(C)C)C(=O)O)c2)cc1] | 2.53 | 536 [M − H]− |
| I-43 | 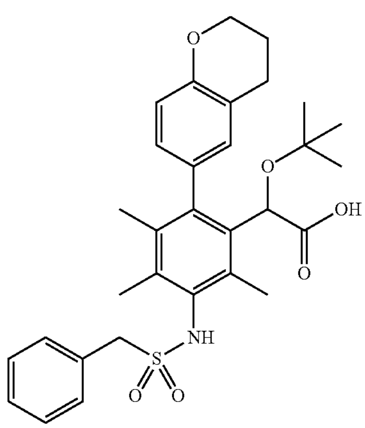 [SMILES: Cc1c(C)c(-c2ccc3c(c2)CCCO3)c(C(OC(C)(C)C)C(=O)O)c(C)c1NS(=O)(=O)Cc1ccccc1] | 2.52 | 550 [M − H]− |

TABLE 10-continued

| Compound No. | Structure | RT(min) | | MS(M + H)+ | |
|---|---|---|---|---|---|
| I-45 | 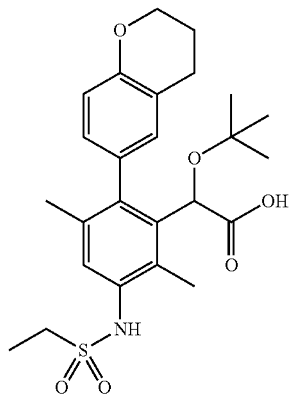 [SMILES: CCS(=O)(=O)Nc1cc(C)c(-c2ccc3c(c2)CCCO3)c(C(OC(C)(C)C)C(=O)O)c1C] | 1.91 | *3 | 973 | [2M + Na]+ |
| I-46 | 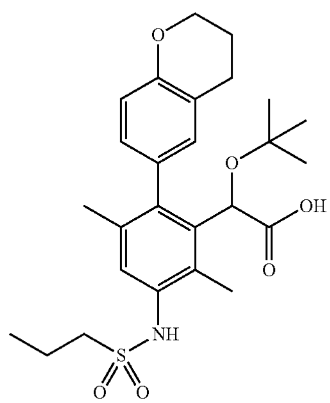 [SMILES: CCCS(=O)(=O)Nc1cc(C)c(-c2ccc3c(c2)CCCO3)c(C(OC(C)(C)C)C(=O)O)c1C] | 1.97 | *3 | 1001 | [2M + Na]+ |

TABLE 11

| Compound No. | Structure | RT(min) | | MS(M + H)+ | |
|---|---|---|---|---|---|
| I-47 | 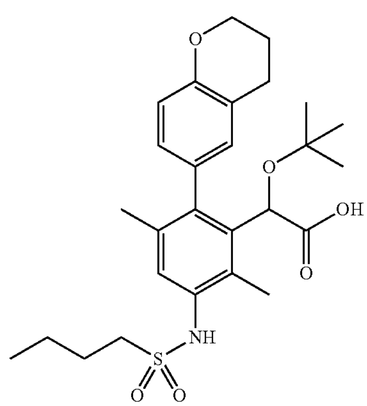 [SMILES: CCCCS(=O)(=O)Nc1cc(C)c(-c2ccc3c(c2)CCCO3)c(C(OC(C)(C)C)C(=O)O)c1C] | 2.03 | *3 | 1029 | [2M + Na]+ |

TABLE 11-continued

| Compound No. | Structure | RT(min) | MS(M + H)+ |
|---|---|---|---|
| I-48 | 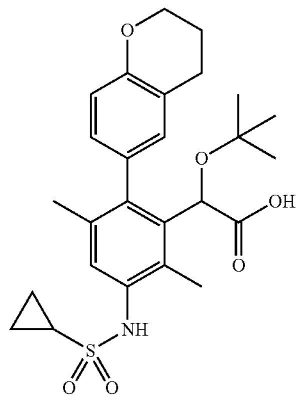 [SMILES: Cc1cc(NS(=O)(=O)C2CC2)c(C)c(C(OC(C)(C)C)C(=O)O)c1-c1ccc2c(c1)CCCO2] | 1.93 *3 | 997 [2M + Na]+ |
| I-50 | 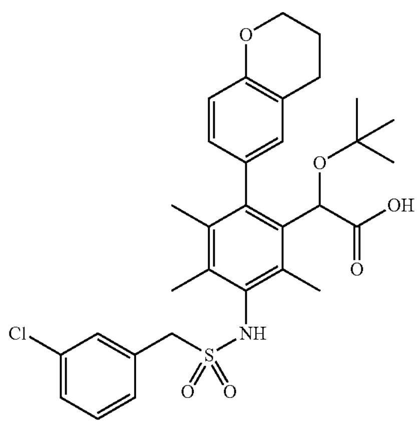 [SMILES: Cc1c(C)c(-c2ccc3c(c2)CCCO3)c(C(OC(C)(C)C)C(=O)O)c(C)c1NS(=O)(=O)Cc1cccc(Cl)c1] | 2.60 *2 | 586 |
| I-51 | 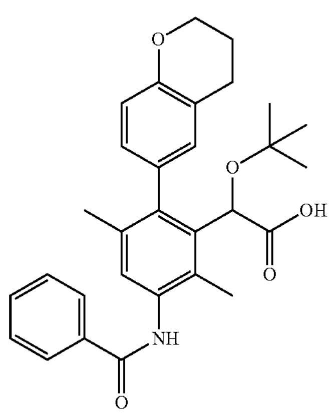 [SMILES: Cc1cc(NC(=O)c2ccccc2)c(C)c(C(OC(C)(C)C)C(=O)O)c1-c1ccc2c(c1)CCCO2] | 1.99 *3 | 997 [2M + Na]+ |

TABLE 12

| Compound No. | Structure | RT(min) | | MS(M + H)+ | |
| --- | --- | --- | --- | --- | --- |
| I-52 | 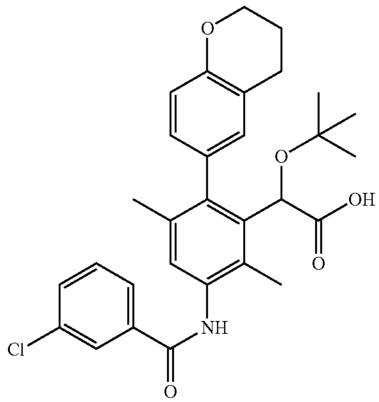 [SMILES: Cc1cc(NC(=O)c2cccc(Cl)c2)c(C)c(C(OC(C)(C)C)C(=O)O)c1-c1ccc2c(c1)CCCO2] | 2.08 | *3 | 1065 | [2M + Na]+ |
| I-53 | 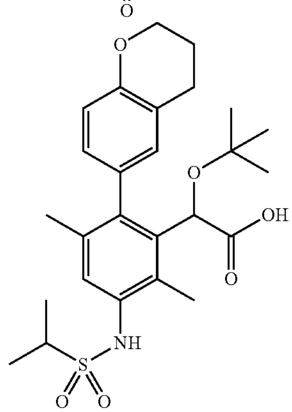 | 1.97 | *3 | 1001 | [2M + Na]+ |
| I-54 | 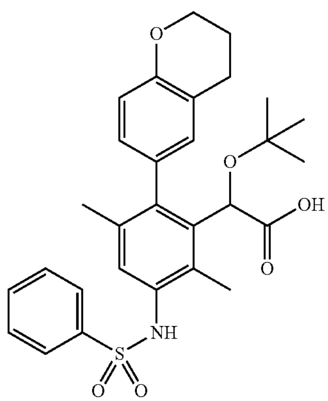 [SMILES: Cc1cc(NS(=O)(=O)c2ccccc2)c(C)c(C(OC(C)(C)C)C(=O)O)c1-c1ccc2c(c1)CCCO2] | 2.03 | *3 | 1069 | [2M + Na]+ |
| I-55 | 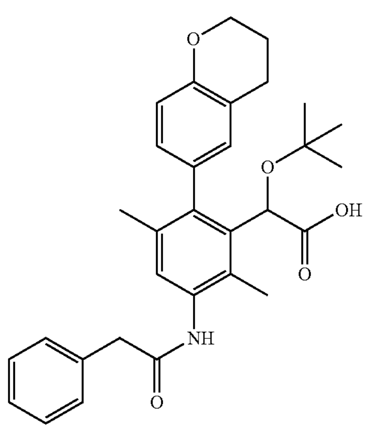 [SMILES: Cc1cc(NC(=O)Cc2ccccc2)c(C)c(C(OC(C)(C)C)C(=O)O)c1-c1ccc2c(c1)CCCO2] | 2.02 | *3 | 1026 | [2M + Na]+ |

TABLE 13

| Compound No. | Structure | RT(min) | MS(M + H)+ |
| --- | --- | --- | --- |
| I-56 | 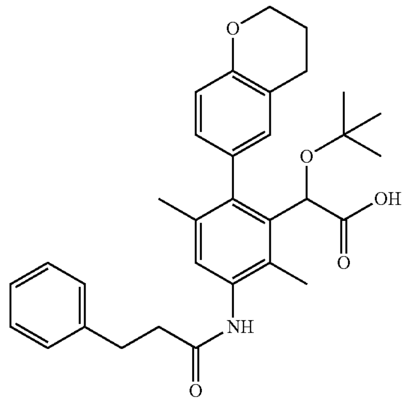 [SMILES: Cc1cc(NC(=O)CCc2ccccc2)c(C)c(C(OC(C)(C)C)C(=O)O)c1-c1ccc2c(c1)CCCO2] | 2.05 *3 | 1053 [2M + Na]+ |
| I-57 | 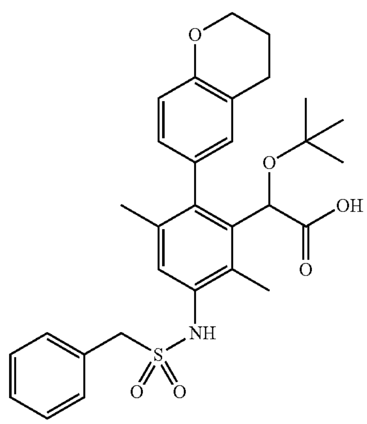 [SMILES: Cc1cc(NS(=O)(=O)Cc2ccccc2)c(C)c(C(OC(C)(C)C)C(=O)O)c1-c1ccc2c(c1)CCCO2] | 2.04 *3 | 1097 [2M + Na]+ |
| I-58 | 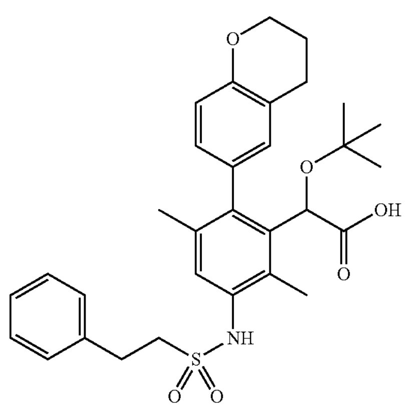 [SMILES: Cc1cc(NS(=O)(=O)CCc2ccccc2)c(C)c(C(OC(C)(C)C)C(=O)O)c1-c1ccc2c(c1)CCCO2] | 2.09 *3 | 1125 [2M + Na]+ |

TABLE 13-continued
| Compound No. | Structure | RT(min) | MS(M + H)+ |
|---|---|---|---|
| I-59 | 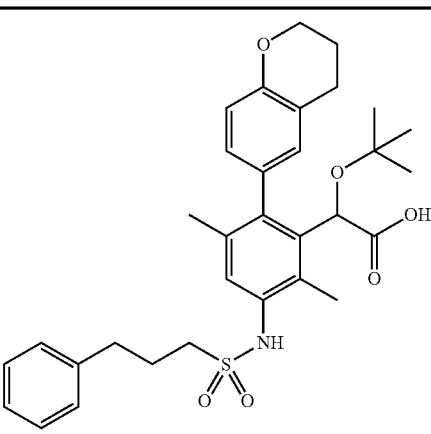 | 2.11 *3 | 1154 [2M + Na]+ |
TABLE 14
| Compound No. | Structure | RT(min) | MS(M + H)+ |
|---|---|---|---|
| I-60 | 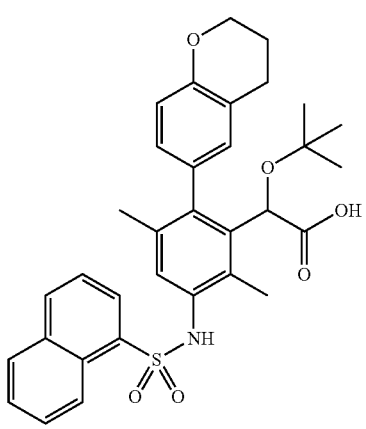 [SMILES: Cc1cc(NS(=O)(=O)c2cccc3ccccc23)c(C)c(C(OC(C)(C)C)C(=O)O)c1-c1ccc2c(c1)CCCO2] | 2.11 *3 | 1169 [2M + Na]+ |
| I-61 | 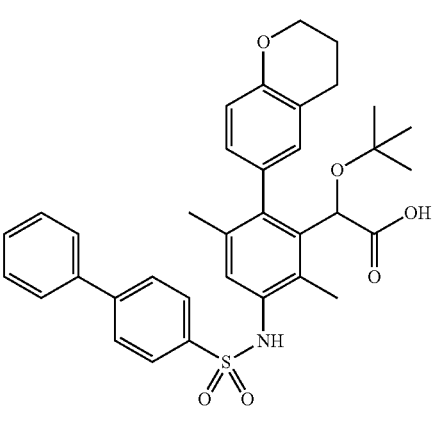 [SMILES: Cc1cc(NS(=O)(=O)c2ccc(-c3ccccc3)cc2)c(C)c(C(OC(C)(C)C)C(=O)O)c1-c1ccc2c(c1)CCCO2] | 2.89 | 598 [M − H]− |

TABLE 14-continued
| Compound No. | Structure | RT(min) | | MS(M + H)+ | |
|---|---|---|---|---|---|
| I-62 | 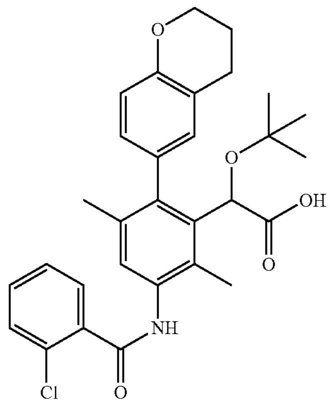 [SMILES: Cc1cc(NC(=O)c2ccccc2Cl)c(C)c(C(OC(C)(C)C)C(=O)O)c1-c1ccc2c(c1)CCCO2] | 2.02 | *3 | 1065 | [2M + Na]+ |
| I-63 | 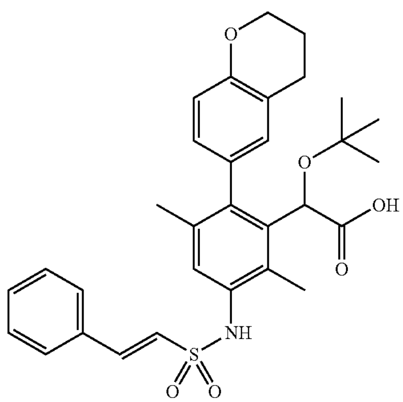 [SMILES: Cc1cc(NS(=O)(=O)/C=C/c2ccccc2)c(C)c(C(OC(C)(C)C)C(=O)O)c1-c1ccc2c(c1)CCCO2] | 2.07 | *3 | 1121 | [2M + Na]+ |
TABLE 15
| Compound No. | Structure | RT(min) | | MS(M + H)+ | |
|---|---|---|---|---|---|
| I-64 | 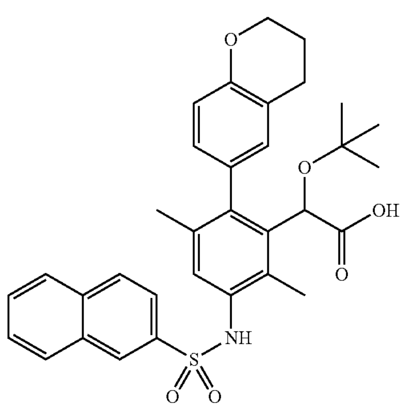 [SMILES: Cc1cc(NS(=O)(=O)c2ccc3ccccc3c2)c(C)c(C(OC(C)(C)C)C(=O)O)c1-c1ccc2c(c1)CCCO2] | 1.97 | *3 | 1169 | [2M + Na]+ |
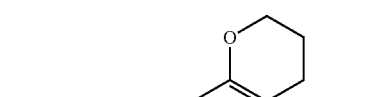

TABLE 15-continued

| Compound No. | Structure | RT(min) | MS(M + H)+ |
|---|---|---|---|
| I-65 | 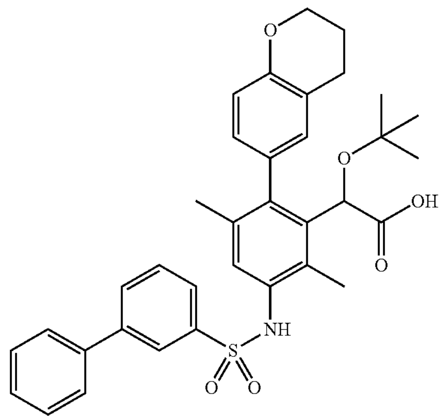 [SMILES: Cc1cc(NS(=O)(=O)c2cccc(-c3ccccc3)c2)c(C)c(C(OC(C)(C)C)C(=O)O)c1-c1ccc2c(c1)CCCO2] | 2.01 *3 | 1221 [2M + Na]+ |
| I-66 | 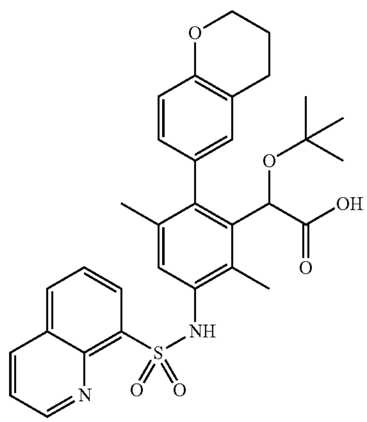 [SMILES: Cc1cc(NS(=O)(=O)c2cccc3cccnc23)c(C)c(C(OC(C)(C)C)C(=O)O)c1-c1ccc2c(c1)CCCO2] | 2.01 *3 | 575 |
| I-67 | 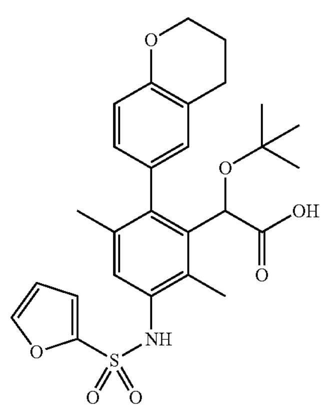 [SMILES: Cc1cc(NS(=O)(=O)c2ccco2)c(C)c(C(OC(C)(C)C)C(=O)O)c1-c1ccc2c(c1)CCCO2] | 1.96 *3 | 1049 [2M + Na]+ |

TABLE 16

| Compound No. | Structure | RT(min) | MS(M + H)+ |
|---|---|---|---|
| I-69 | 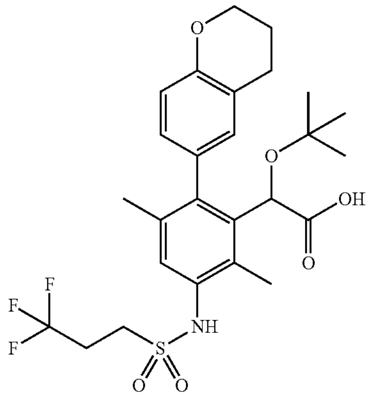 [SMILES: Cc1cc(NS(=O)(=O)CCC(F)(F)F)c(C)c(C(OC(C)(C)C)C(=O)O)c1-c1ccc2c(c1)CCCO2] | 2.54 | 542 [M − H]− |
| I-70 | 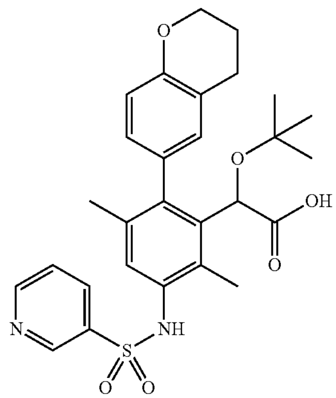 [SMILES: Cc1cc(NS(=O)(=O)c2cccnc2)c(C)c(C(OC(C)(C)C)C(=O)O)c1-c1ccc2c(c1)CCCO2] | 1.52 *5 | 575 |
| I-71 | 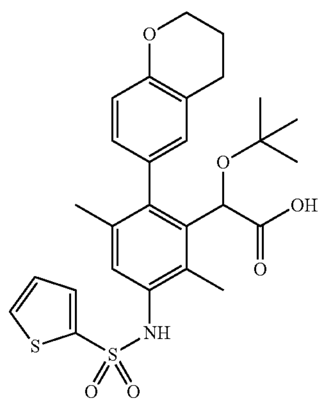 [SMILES: Cc1cc(NS(=O)(=O)c2cccs2)c(C)c(C(OC(C)(C)C)C(=O)O)c1-c1ccc2c(c1)CCCO2] | 1.61 *5 | 547 [M + NH4]+ |
| I-72 | 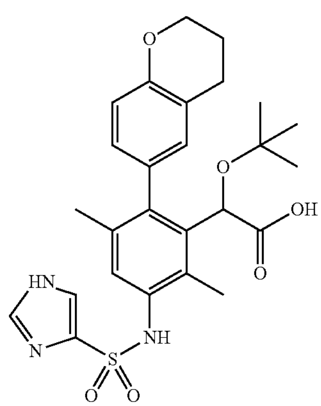 [SMILES: Cc1cc(NS(=O)(=O)c2c[nH]cn2)c(C)c(C(OC(C)(C)C)C(=O)O)c1-c1ccc2c(c1)CCCO2] | 1.44 *5 | 514 |

TABLE 17

| Compound No. | Structure | RT(min) | MS(M + H)+ |
| --- | --- | --- | --- |
| I-73 | 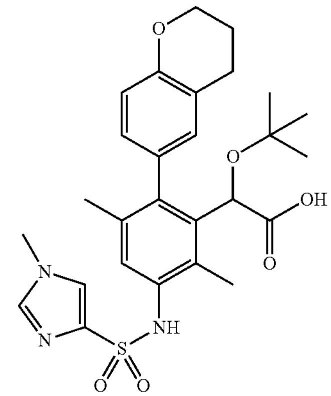 [SMILES: Cc1cc(NS(=O)(=O)c2cn(C)cn2)c(C)c(C(OC(C)(C)C)C(=O)O)c1-c1ccc2c(c1)CCCO2] | 1.47 *5 | 528 |
| I-74 | 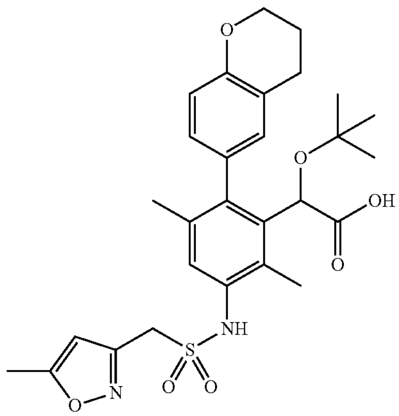 [SMILES: Cc1cc(CS(=O)(=O)Nc2cc(C)c(-c3ccc4c(c3)CCCO4)c(C(OC(C)(C)C)C(=O)O)c2C)no1] | 2.28 | 543 |
| I-75 | 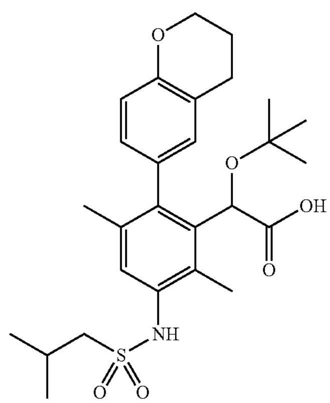 [SMILES: Cc1cc(NS(=O)(=O)CC(C)C)c(C)c(C(OC(C)(C)C)C(=O)O)c1-c1ccc2c(c1)CCCO2] | 2.04 *3 | 1029 [2M + Na]+ |
| I-77 | 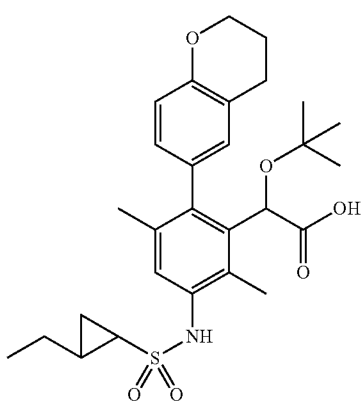 [SMILES: CCC1CC1S(=O)(=O)Nc1cc(C)c(-c2ccc3c(c2)CCCO3)c(C(OC(C)(C)C)C(=O)O)c1C] | 2.52 | 514 [M − H]− |

TABLE 18

| Compound No. | Structure | RT(min) | MS(M + H)+ |
|---|---|---|---|
| I-79 | 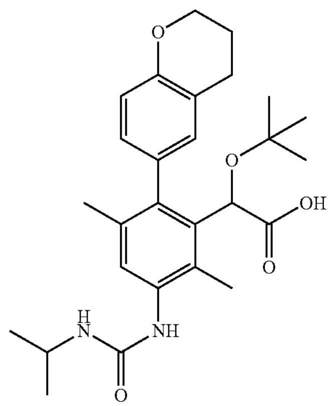 | 1.91 *3 | 469 |
| I-80 | 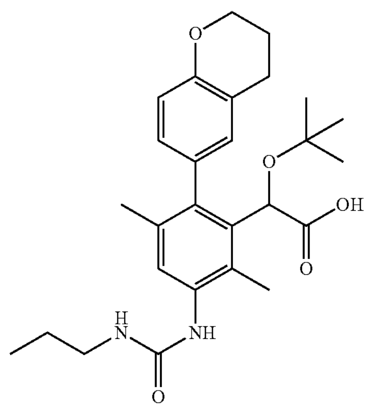 [SMILES: CCCNC(=O)Nc1cc(C)c(-c2ccc3c(c2)CCCO3)c(C(OC(C)(C)C)C(=O)O)c1C] | 1.90 *3 | 469 |
| I-81 | 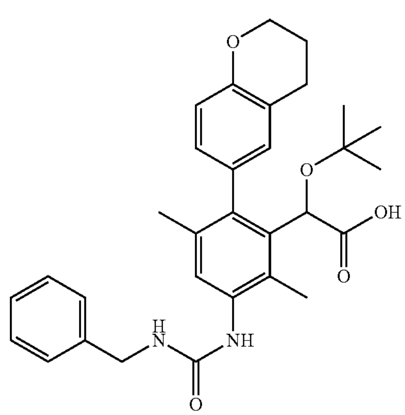 [SMILES: Cc1cc(NC(=O)NCc2ccccc2)c(C)c(C(OC(C)(C)C)C(=O)O)c1-c1ccc2c(c1)CCCO2] | 1.97 *3 | 517 |

TABLE 18-continued

| Compound No. | Structure | RT(min) | MS(M + H)+ |
|---|---|---|---|
| I-82 | 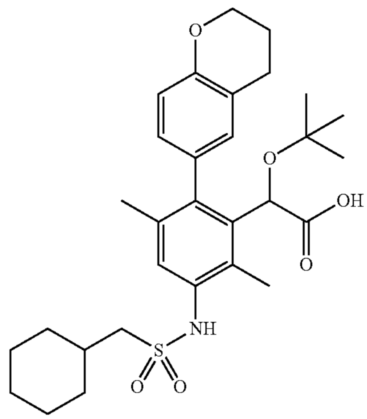 [SMILES: Cc1cc(NS(=O)(=O)CC2CCCCC2)c(C)c(C(OC(C)(C)C)C(=O)O)c1-c1ccc2c(c1)CCCO2] | 2.14 *3 | 1109 [2M + Na]+ |

TABLE 19

| Compound No. | Structure | RT(min) | MS(M + H)+ |
|---|---|---|---|
| I-83 | 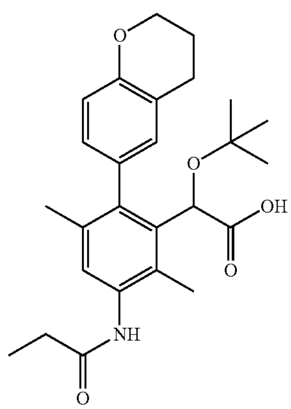 [SMILES: CCC(=O)Nc1cc(C)c(-c2ccc3c(c2)CCCO3)c(C(OC(C)(C)C)C(=O)O)c1C] | 1.88 *3 | 901 [2M + Na]+ |
| I-84 | 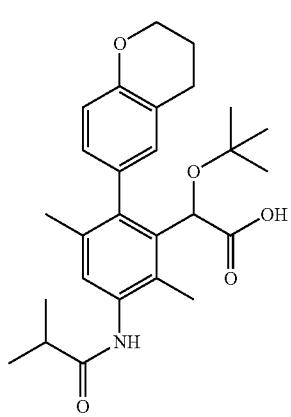 [SMILES: Cc1cc(NC(=O)C(C)C)c(C)c(C(OC(C)(C)C)C(=O)O)c1-c1ccc2c(c1)CCCO2] | 1.66 *3 | 929 [2M + Na]+ |

TABLE 19-continued
| Compound No. | Structure | RT(min) | MS(M + H)+ |
| --- | --- | --- | --- |
| I-85 | 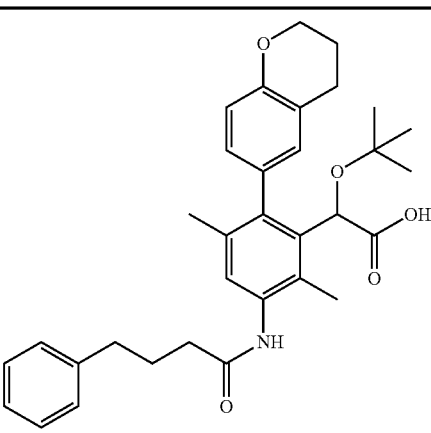 | 2.08 *3 | 1081 [2M + Na]+ |
| I-86 | 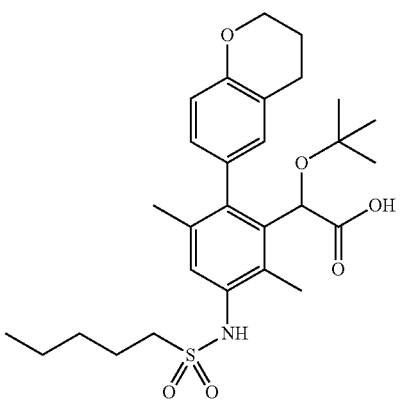 [SMILES: CCCCCS(=O)(=O)Nc1cc(C)c(-c2ccc3c(c2)CCCO3)c(C(OC(C)(C)C)C(=O)O)c1C] | 2.08 *3 | 1058 [2M + Na]+ |
TABLE 20
| Compound No. | Structure | RT(min) | MS(M + H)+ |
| --- | --- | --- | --- |
| I-87 | 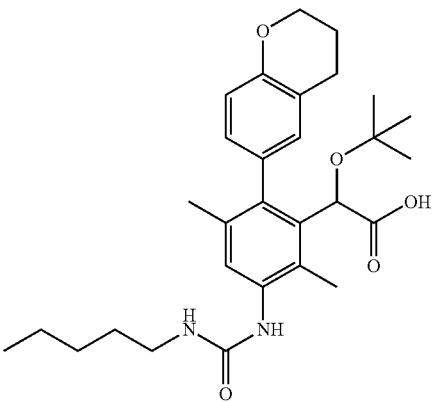 [SMILES: CCCCCNC(=O)Nc1cc(C)c(-c2ccc3c(c2)CCCO3)c(C(OC(C)(C)C)C(=O)O)c1C] | 2.03 *3 | 497 |

TABLE 20-continued

| Compound No. | Structure | RT(min) | MS(M + H)+ |
| --- | --- | --- | --- |
| I-88 | 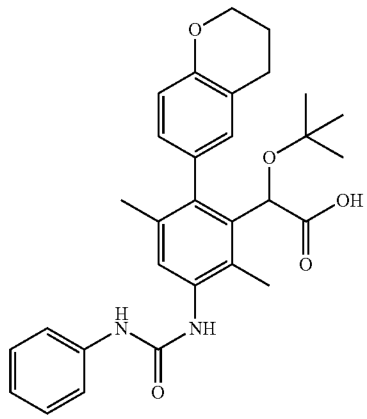 [SMILES: Cc1cc(NC(=O)Nc2ccccc2)c(C)c(C(OC(C)(C)C)C(=O)O)c1-c1ccc2c(c1)CCCO2] | 2.01 *3 | 503 |
| I-89 | 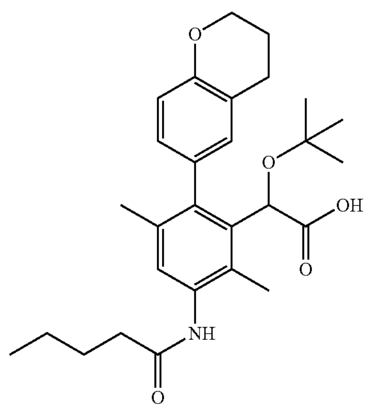 [SMILES: CCCCC(=O)Nc1cc(C)c(-c2ccc3c(c2)CCCO3)c(C(OC(C)(C)C)C(=O)O)c1C] | 2.00 *3 | 957 [2M + Na]+ |
| I-90 | 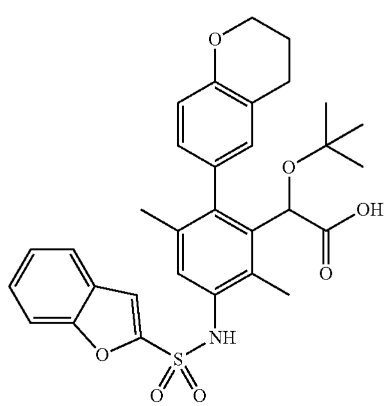 [SMILES: Cc1cc(NS(=O)(=O)c2cc3ccccc3o2)c(C)c(C(OC(C)(C)C)C(=O)O)c1-c1ccc2c(c1)CCCO2] | 2.07 *3 | 1149 [2M + Na]+ |

TABLE 21

| Compound No. | Structure | RT(min) | MS(M + H)+ |
|---|---|---|---|
| I-91 | 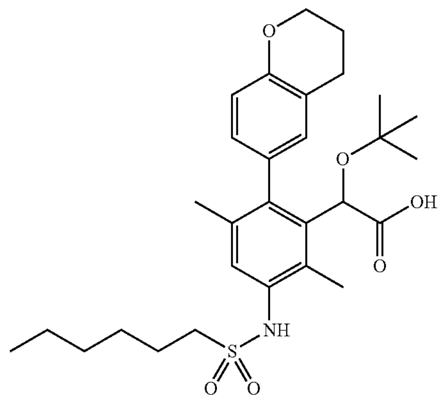 [SMILES: CCCCCCS(=O)(=O)Nc1cc(C)c(-c2ccc3c(c2)CCCO3)c(C(OC(C)(C)C)C(=O)O)c1C] | 2.14  *3 | 1085  [2M + Na]+ |
| I-92 | 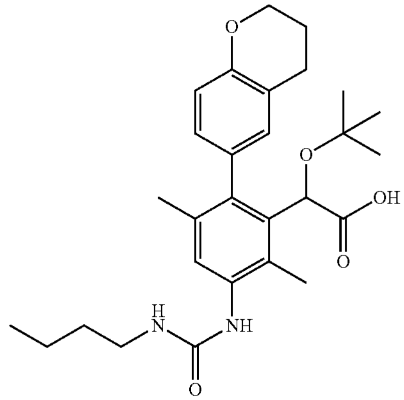 [SMILES: CCCCNC(=O)Nc1cc(C)c(-c2ccc3c(c2)CCCO3)c(C(OC(C)(C)C)C(=O)O)c1C] | 1.97  *3 | 483 |
| I-93 | 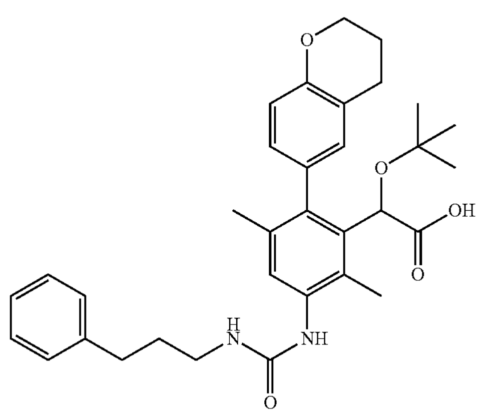 [SMILES: Cc1cc(NC(=O)NCCCc2ccccc2)c(C)c(C(OC(C)(C)C)C(=O)O)c1-c1ccc2c(c1)CCCO2] | 2.04  *3 | 545 |

TABLE 21-continued

| Compound No. | Structure | RT(min) | MS(M + H)+ |
|---|---|---|---|
| I-94 | 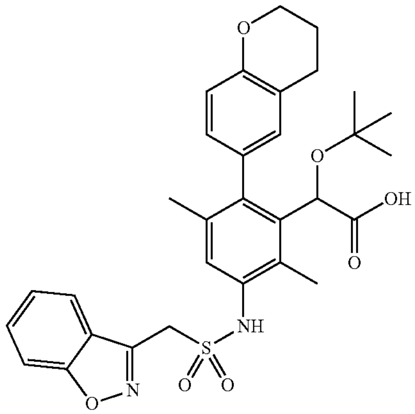 [SMILES: Cc1cc(NS(=O)(=O)Cc2noc3ccccc23)c(C)c(C(OC(C)(C)C)C(=O)O)c1-c1ccc2c(c1)CCCO2] | 2.49 | 579 |

TABLE 22

| Compound No. | Structure | RT(min) | MS(M + H)+ |
|---|---|---|---|
| I-95 | 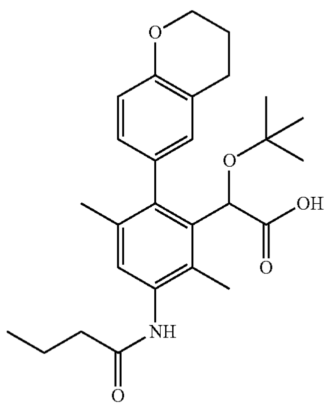 [SMILES: CCCC(=O)Nc1cc(C)c(-c2ccc3c(c2)CCCO3)c(C(OC(C)(C)C)C(=O)O)c1C] | 1.94 *3 | 929 [2M + Na]+ |
| I-96 | 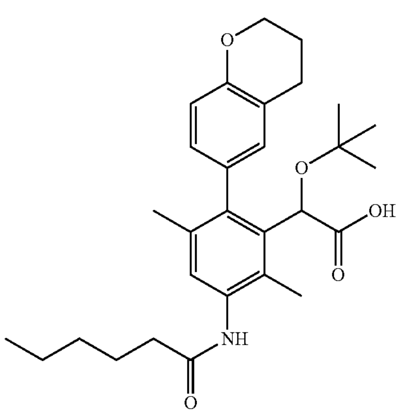 [SMILES: CCCCCC(=O)Nc1cc(C)c(-c2ccc3c(c2)CCCO3)c(C(OC(C)(C)C)C(=O)O)c1C] | 2.06 *3 | 985 [2M + Na]+ |

TABLE 22-continued

| Compound No. | Structure | RT(min) | MS(M + H)+ |
|---|---|---|---|
| I-97 | 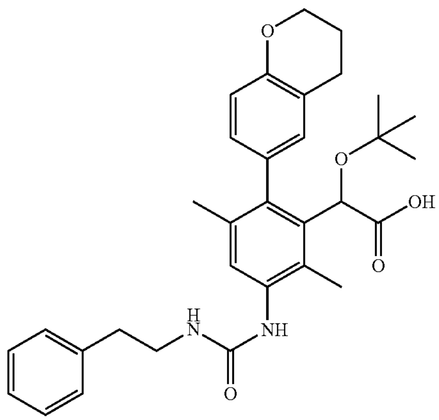 [SMILES: Cc1cc(NC(=O)NCCc2ccccc2)c(C)c(C(OC(C)(C)C)C(=O)O)c1-c1ccc2c(c1)CCCO2] | 2.01 *3 | 531 |
| I-98 | 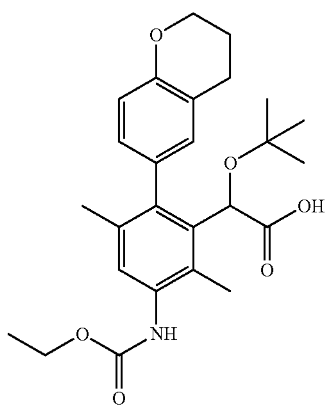 [SMILES: CCOC(=O)Nc1cc(C)c(-c2ccc3c(c2)CCCO3)c(C(OC(C)(C)C)C(=O)O)c1C] | 1.99 *3 | 933 [2M + Na]+ |

TABLE 23

| Compound No. | Structure | RT(min) | MS(M + H)+ |
|---|---|---|---|
| I-100 | 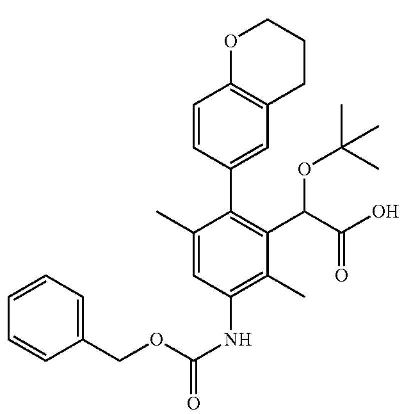 [SMILES: Cc1cc(NC(=O)OCc2ccccc2)c(C)c(C(OC(C)(C)C)C(=O)O)c1-c1ccc2c(c1)CCCO2] | 2.10 *3 | 1058 [2M + Na]+ |

TABLE 23-continued

| Compound No. | Structure | RT(min) | MS(M + H)+ |
|---|---|---|---|
| I-101 | 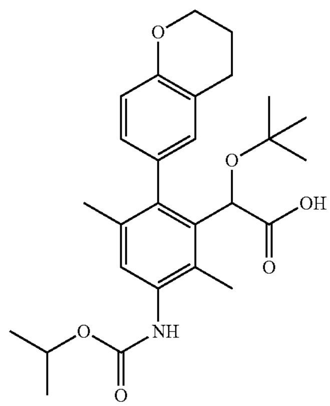 [SMILES: Cc1cc(NC(=O)OC(C)C)c(C)c(C(OC(C)(C)C)C(=O)O)c1-c1ccc2c(c1)CCCO2] | 2.07 *3 | 961 [2M + Na]+ |
| I-102 | 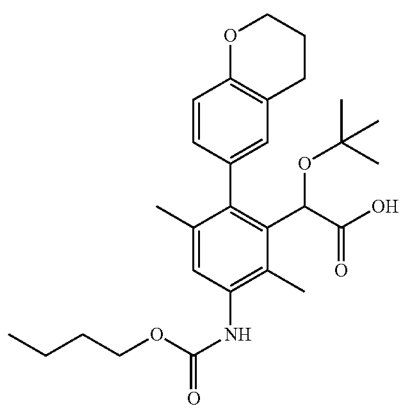 | 2.13 *3 | 989 [2M + Na]+ |
| I-103 | 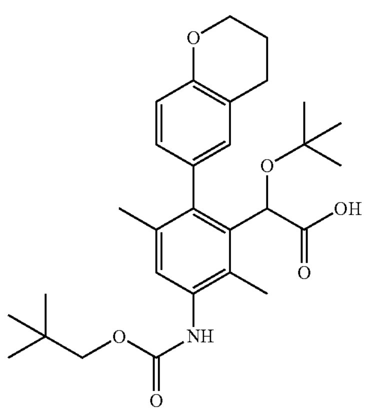 [SMILES: Cc1cc(NC(=O)OCC(C)(C)C)c(C)c(C(OC(C)(C)C)C(=O)O)c1-c1ccc2c(c1)CCCO2] | 2.18 *3 | 1017 [2M + Na]+ |

TABLE 24

| Compound No. | Structure | RT(min) | MS(M + H)+ |
| --- | --- | --- | --- |
| I-105 | 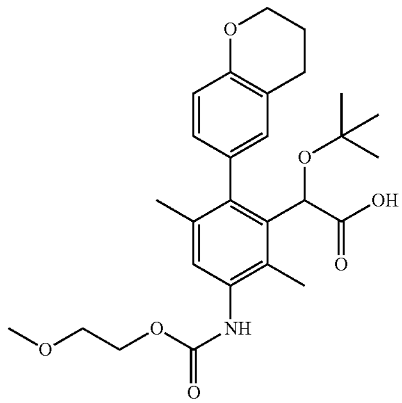 | 1.93 *3 | 993 [2M + Na]+ |
| I-106 | 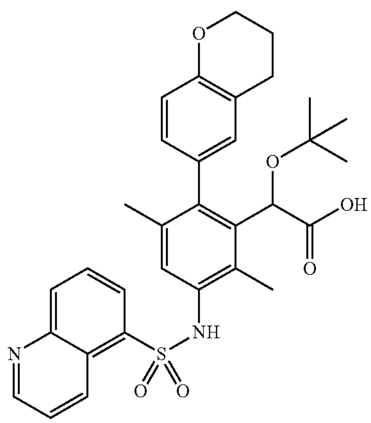 [SMILES: Cc1cc(NS(=O)(=O)c2cccc3ncccc23)c(C)c(C(OC(C)(C)C)C(=O)O)c1-c1ccc2c(c1)CCCO2] | 2.27 | 575 |
| I-107 | 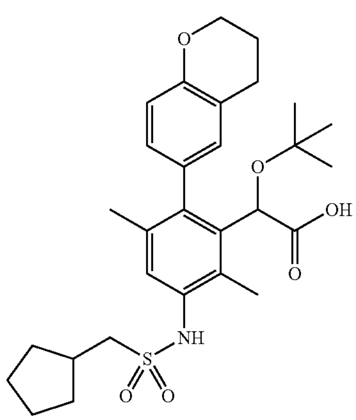 [SMILES: Cc1cc(NS(=O)(=O)CC2CCCC2)c(C)c(C(OC(C)(C)C)C(=O)O)c1-c1ccc2c(c1)CCCO2] | 1.89 *3 | 552 [M + Na]+ |

TABLE 24-continued

| Compound No. | Structure | RT(min) | MS(M + H)+ |
|---|---|---|---|
| I-108 | 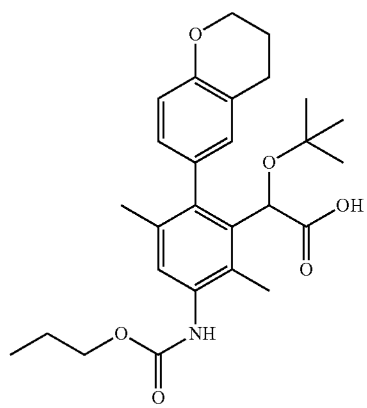 [SMILES: CCCOC(=O)Nc1cc(C)c(-c2ccc3c(c2)CCCO3)c(C(OC(C)(C)C)C(=O)O)c1C] | 1.85 *3 | 961 [2M + Na]+ |

TABLE 25

| Compound No. | Structure | RT(min) | MS(M + H)+ |
|---|---|---|---|
| I-109 | 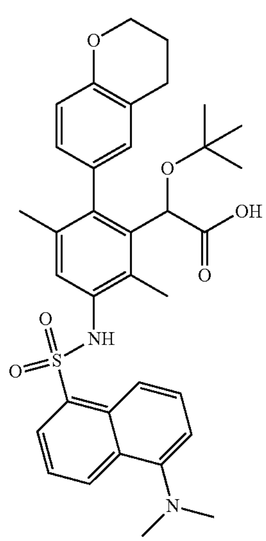 [SMILES: Cc1cc(NS(=O)(=O)c2cccc3c(N(C)C)cccc23)c(C)c(C(OC(C)(C)C)C(=O)O)c1-c1ccc2c(c1)CCCO2] | 2.91 | 616 |
| I-110 | | 2.54 | 548 |

TABLE 25-continued
| Compound No. | Structure | RT(min) | MS(M + H)+ |
|---|---|---|---|
| I-111 | 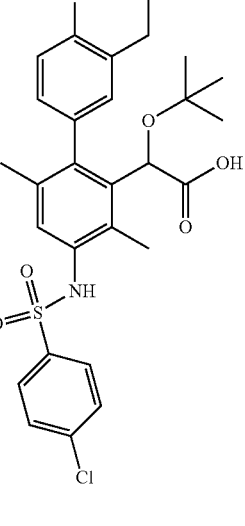 | 2.77 | 557 |
| I-112 | 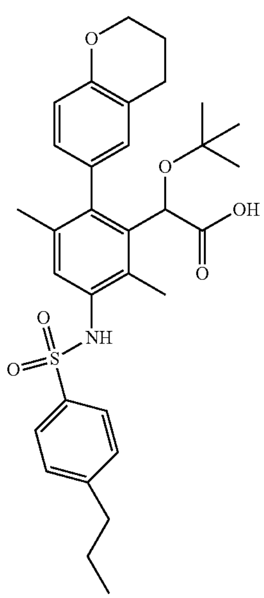 [SMILES: CCCc1ccc(S(=O)(=O)Nc2cc(C)c(-c3ccc4c(c3)CCCO4)c(C(OC(C)(C)C)C(=O)O)c2C)cc1] | 2.95 | 565 |
TABLE 26
| Compound No. | Structure | RT(min) | MS(M + H)+ |
|---|---|---|---|
| I-113 | 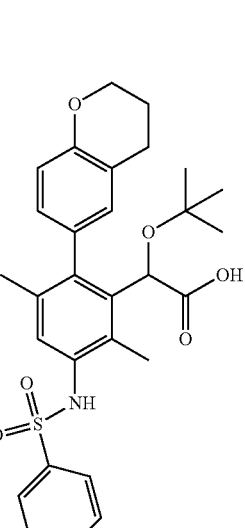 | 2.52 | 565 |
| I-114 | 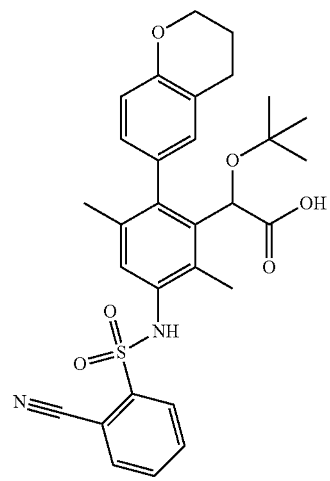 [SMILES: Cc1cc(NS(=O)(=O)c2ccccc2C#N)c(C)c(C(OC(C)(C)C)C(=O)O)c1-c1ccc2c(c1)CCCO2] | 2.47 | 548 |
| I-115 | 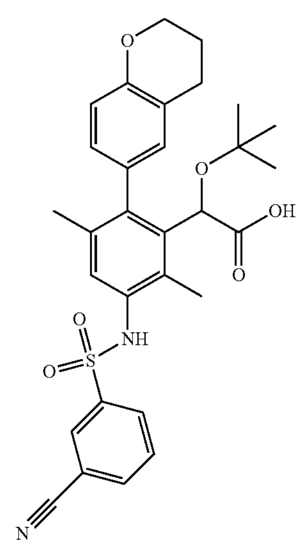 [SMILES: Cc1cc(NS(=O)(=O)c2cccc(C#N)c2)c(C)c(C(OC(C)(C)C)C(=O)O)c1-c1ccc2c(c1)CCCO2] | 2.52 | 548 |

TABLE 26-continued

| Compound No. | Structure | RT(min) | MS(M+H)+ |
|---|---|---|---|
| I-116 | 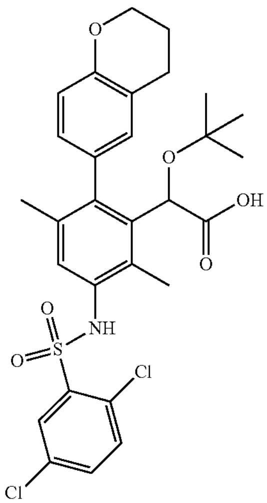 [SMILES: Cc1cc(NS(=O)(=O)c2cc(Cl)ccc2Cl)c(C)c(C(OC(C)(C)C)C(=O)O)c1-c1ccc2c(c1)CCCO2] | 2.85 | 591 |

TABLE 27

| Compound No. | Structure | RT (min) | MS (M+H)+ |
|---|---|---|---|
| I-117 | | 2.95 | 591 |
| I-118 | 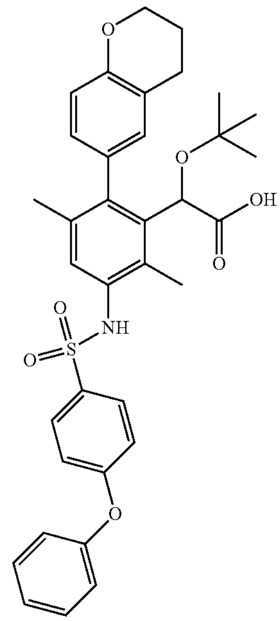 [SMILES: Cc1cc(NS(=O)(=O)c2ccc(Oc3ccccc3)cc2)c(C)c(C(OC(C)(C)C)C(=O)O)c1-c1ccc2c(c1)CCCO2] | 2.94 | 615 |
| I-119 | 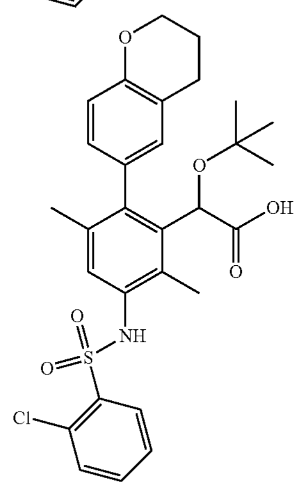 | 2.65 | 557 |
| I-120 | 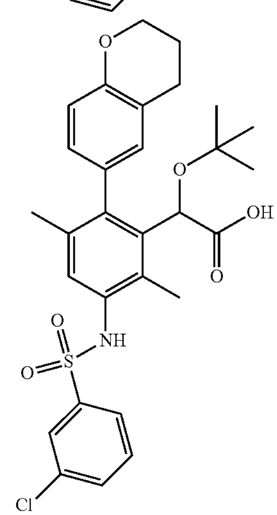 | 2.77 | 557 |

TABLE 28

| Compound No. | Structure | RT (min) | MS (M + H)+ |
| --- | --- | --- | --- |
| I-121 | 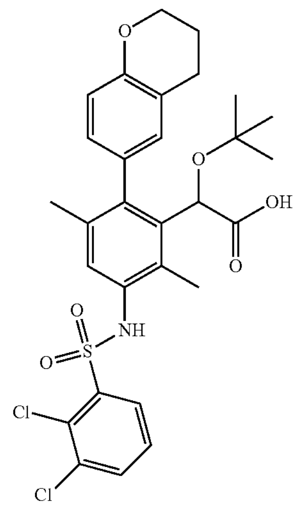 [SMILES: Cc1cc(NS(=O)(=O)c2cccc(Cl)c2Cl)c(C)c(C(OC(C)(C)C)C(=O)O)c1-c1ccc2c(c1)CCCO2] | 2.79 | 591 |
| I-122 | 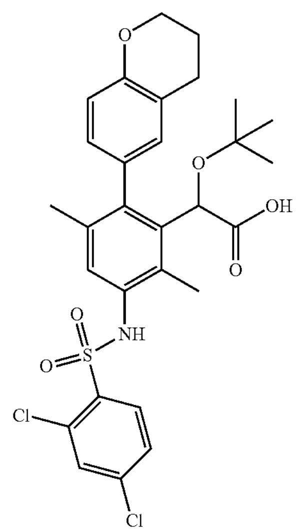 [SMILES: Cc1cc(NS(=O)(=O)c2ccc(Cl)cc2Cl)c(C)c(C(OC(C)(C)C)C(=O)O)c1-c1ccc2c(c1)CCCO2] | 2.87 | 591 |
| I-123 | 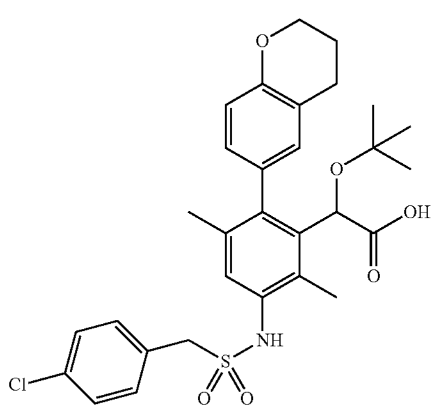 [SMILES: Cc1cc(NS(=O)(=O)Cc2ccc(Cl)cc2)c(C)c(C(OC(C)(C)C)C(=O)O)c1-c1ccc2c(c1)CCCO2] | 2.76 | 571 |

TABLE 28-continued
| Compound No. | Structure | RT (min) | MS (M + H)+ |
|---|---|---|---|
| I-124 | 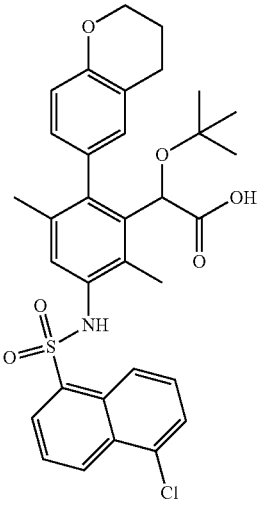 [SMILES: Cc1cc(NS(=O)(=O)c2cccc3c(Cl)cccc23)c(C)c(C(OC(C)(C)C)C(=O)O)c1-c1ccc2c(c1)CCCO2] | 3.02 | 607 |
TABLE 29
| Compound No. | Structure | RT (min) | MS (M + H)+ |
|---|---|---|---|
| I-125 | 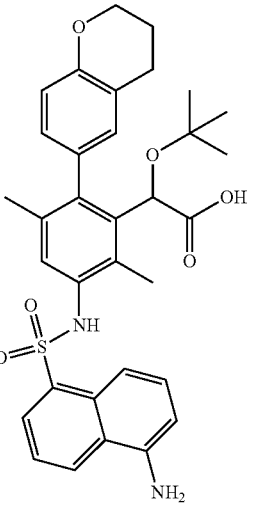 | 2.44 | 588 |
| I-126 | 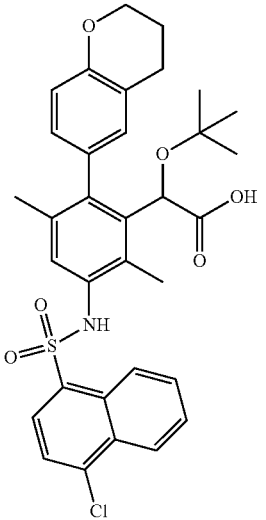 [SMILES: Cc1cc(NS(=O)(=O)c2ccc(Cl)c3ccccc23)c(C)c(C(OC(C)(C)C)C(=O)O)c1-c1ccc2c(c1)CCCO2] | 3.04 | 607 |

TABLE 29-continued

| Compound No. | Structure | RT (min) | MS (M + H)+ |
| --- | --- | --- | --- |
| I-127 | 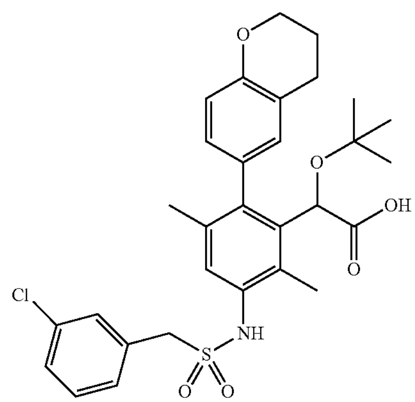 [SMILES: Cc1cc(NS(=O)(=O)Cc2cccc(Cl)c2)c(C)c(C(OC(C)(C)C)C(=O)O)c1-c1ccc2c(c1)CCCO2] | 2.74 | 571 |
| I-128 | 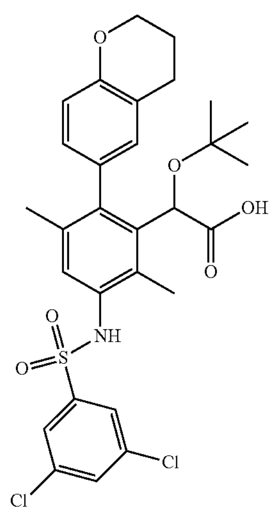 [SMILES: Cc1cc(NS(=O)(=O)c2cc(Cl)cc(Cl)c2)c(C)c(C(OC(C)(C)C)C(=O)O)c1-c1ccc2c(c1)CCCO2] | 2.99 | 591 |

TABLE 30

| Compound No. | Structure | RT (min) | MS (M + H)+ |
| --- | --- | --- | --- |
| I-129 | 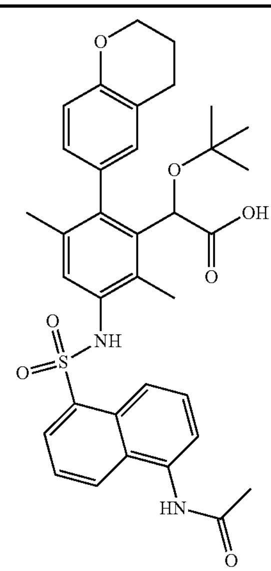 | 2.37 | 630 |

TABLE 30-continued

| Compound No. | Structure | RT (min) | MS (M + H)+ |
|---|---|---|---|
| I-130 | 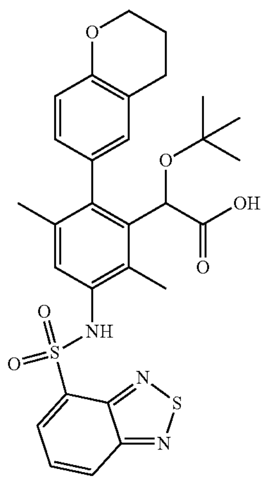 [SMILES: Cc1cc(NS(=O)(=O)c2cccc3nsnc23)c(C)c(C(OC(C)(C)C)C(=O)O)c1-c1ccc2c(c1)CCCO2] | 2.53 | 581 |
| I-131 | 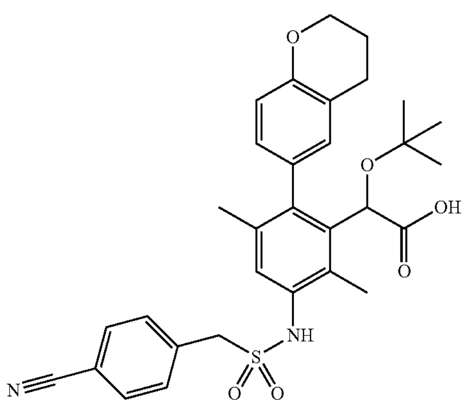 [SMILES: Cc1cc(NS(=O)(=O)Cc2ccc(C#N)cc2)c(C)c(C(OC(C)(C)C)C(=O)O)c1-c1ccc2c(c1)CCCO2] | 2.50 | 562 |
| I-132 | 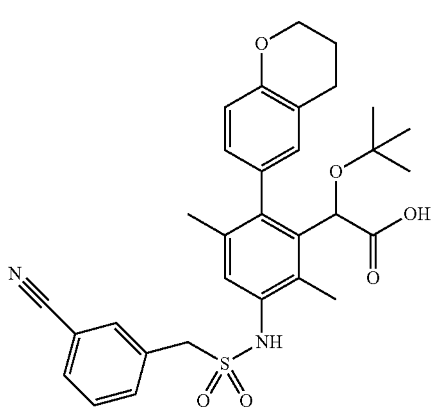 [SMILES: Cc1cc(NS(=O)(=O)Cc2cccc(C#N)c2)c(C)c(C(OC(C)(C)C)C(=O)O)c1-c1ccc2c(c1)CCCO2] | 2.49 | 562 |

TABLE 31

| Compound No. | Structure | RT (min) | MS (M + H)+ |
|---|---|---|---|
| I-133 | 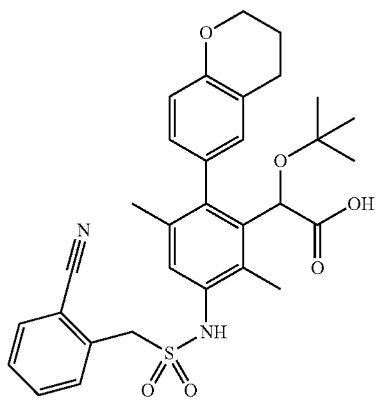 [SMILES: Cc1cc(NS(=O)(=O)Cc2ccccc2C#N)c(C)c(C(OC(C)(C)C)C(=O)O)c1-c1ccc2c(c1)CCCO2] | 2.51 | 562 |
| I-134 | 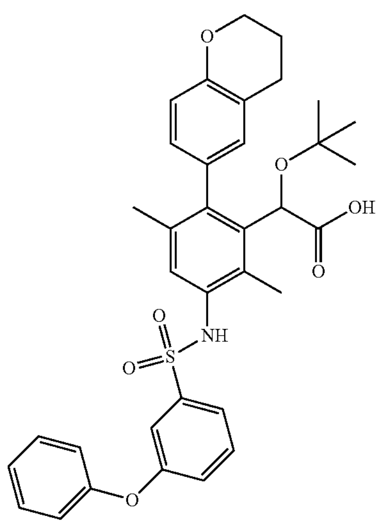 [SMILES: Cc1cc(NS(=O)(=O)c2cccc(Oc3ccccc3)c2)c(C)c(C(OC(C)(C)C)C(=O)O)c1-c1ccc2c(c1)CCCO2] | 2.92 | 615 |
| I-135 | 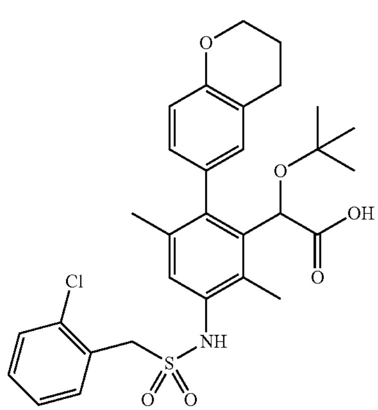 [SMILES: Cc1cc(NS(=O)(=O)Cc2ccccc2Cl)c(C)c(C(OC(C)(C)C)C(=O)O)c1-c1ccc2c(c1)CCCO2] | 2.71 | 571 |

TABLE 31-continued

| Compound No. | Structure | RT (min) | MS (M + H)+ |
|---|---|---|---|
| I-136 | 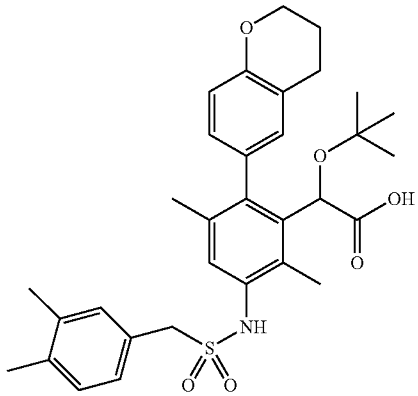 [SMILES: Cc1ccc(CS(=O)(=O)Nc2cc(C)c(-c3ccc4c(c3)CCCO4)c(C(OC(C)(C)C)C(=O)O)c2C)cc1C] | 2.82 | 565 |

TABLE 32

| Compound No. | Structure | RT (min) | MS (M + H)+ |
|---|---|---|---|
| I-137 | 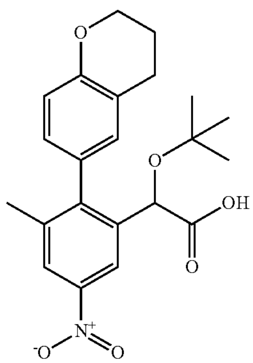 | 2.21 | 398 [M − H]− |
| I-138 | 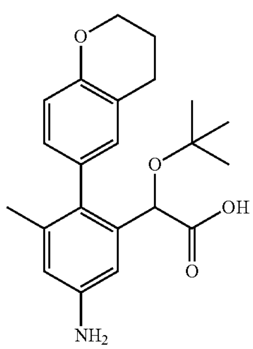 [SMILES: Cc1cc(N)cc(C(OC(C)(C)C)C(=O)O)c1-c1ccc2c(c1)CCCO2] | 1.89 | 370 |

TABLE 32-continued

| Compound No. | Structure | RT (min) | MS (M + H)+ |
|---|---|---|---|
| I-140 | 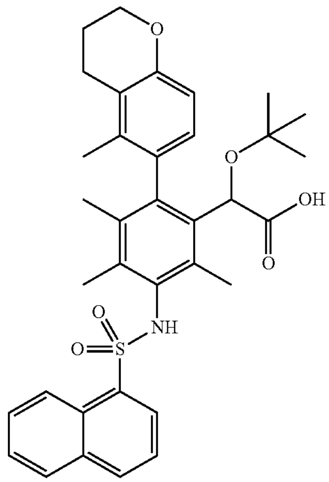 [SMILES: Cc1c(-c2c(C)c(C)c(NS(=O)(=O)c3cccc4ccccc34)c(C)c2C(OC(C)(C)C)C(=O)O)ccc2c1CCCO2] | 2.73 | 600 [M − H]− |
| I-141 | 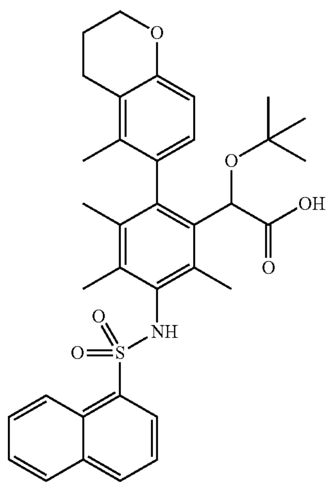 [SMILES: Cc1c(-c2c(C)c(C)c(NS(=O)(=O)c3cccc4ccccc34)c(C)c2C(OC(C)(C)C)C(=O)O)ccc2c1CCCO2] | 2.73 | 600 [M − H]− |

TABLE 33

| Compound No. | Structure | RT (min) | MS (M + H)+ |
|---|---|---|---|
| I-142 | 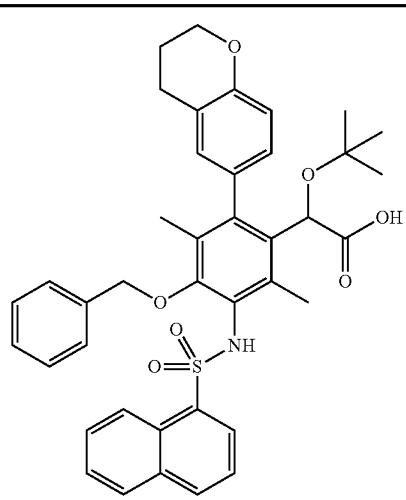 | 2.93 | 678 [M − H]− |

TABLE 33-continued

| Compound No. | Structure | RT (min) | MS (M + H)+ |
|---|---|---|---|
| I-143 | 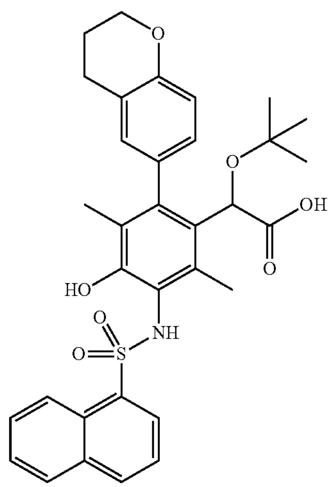 [SMILES: Cc1c(O)c(NS(=O)(=O)c2cccc3ccccc23)c(C)c(C(OC(C)(C)C)C(=O)O)c1-c1ccc2c(c1)CCCO2] | 2.53 | 588 [M − H]− |
| I-144 | 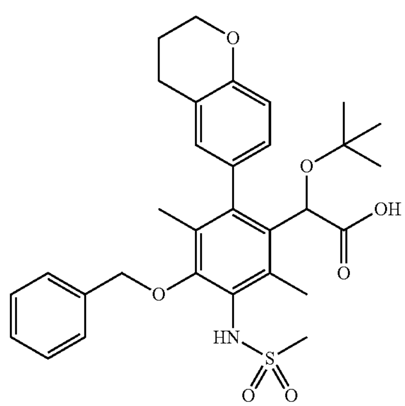 | 2.54 | 566 [M − H]− |
| I-145 | 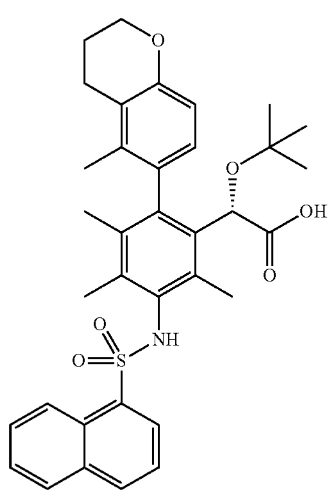 [SMILES: Cc1c(-c2c(C)c(C)c(NS(=O)(=O)c3cccc4ccccc34)c(C)c2[C@H](OC(C)(C)C)C(=O)O)ccc2c1CCCO2] | 2.76 | 600 [M − H]− |

TABLE 34
| Compound No. | Structure | RT (min) | MS (M + H)+ |
|---|---|---|---|
| I-146 | 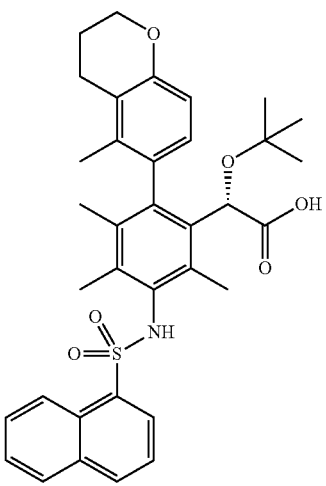 [SMILES: Cc1c(-c2c(C)c(C)c(NS(=O)(=O)c3cccc4ccccc34)c(C)c2[C@H](OC(C)(C)C)C(=O)O)ccc2c1CCCO2] | 2.76 | 600 [M − H]− |
| I-147 | 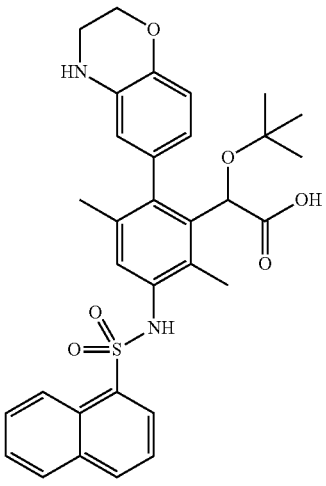 [SMILES: Cc1cc(NS(=O)(=O)c2cccc3ccccc23)c(C)c(C(OC(C)(C)C)C(=O)O)c1-c1ccc2c(c1)NCCO2] | 2.21, 2.46 | 575, 575 |
| I-148 | 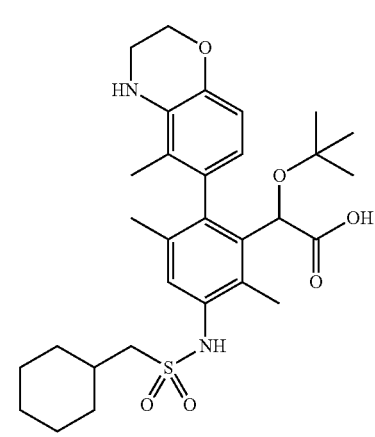 [SMILES: Cc1cc(NS(=O)(=O)CC2CCCCC2)c(C)c(C(OC(C)(C)C)C(=O)O)c1-c1ccc2c(c1C)NCCO2] | 2.37 *2 | 557 [M − H]− |

TABLE 34-continued

| Compound No. | Structure | RT (min) | MS (M + H)+ |
|---|---|---|---|
| I-149 | 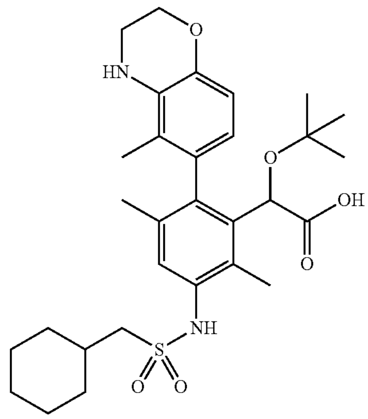 [SMILES: Cc1cc(NS(=O)(=O)CC2CCCCC2)c(C)c(C(OC(C)(C)C)C(=O)O)c1-c1ccc2c(c1C)NCCO2] | 2.56 *2 | 556 [M − H]− |

TABLE 35

| Compound No. | Structure | RT (min) | MS (M + H)+ |
|---|---|---|---|
| I-150 | 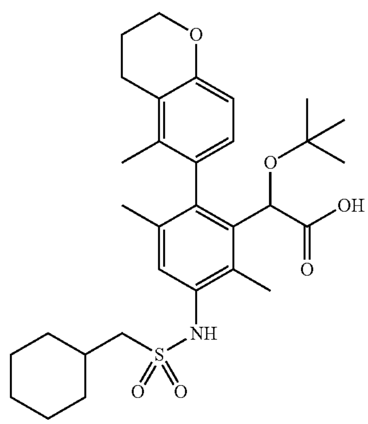 [SMILES: Cc1cc(NS(=O)(=O)CC2CCCCC2)c(C)c(C(OC(C)(C)C)C(=O)O)c1-c1ccc2c(c1C)CCCO2] | 2.76 *2 | 556 [M − H]− |
| I-151 | 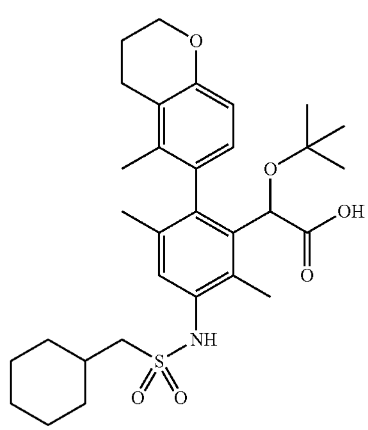 [SMILES: Cc1cc(NS(=O)(=O)CC2CCCCC2)c(C)c(C(OC(C)(C)C)C(=O)O)c1-c1ccc2c(c1C)CCCO2] | 2.77 *2 | 556 [M − H]− |

TABLE 35-continued

| Compound No. | Structure | RT (min) | MS (M + H)+ |
| --- | --- | --- | --- |
| I-153 | 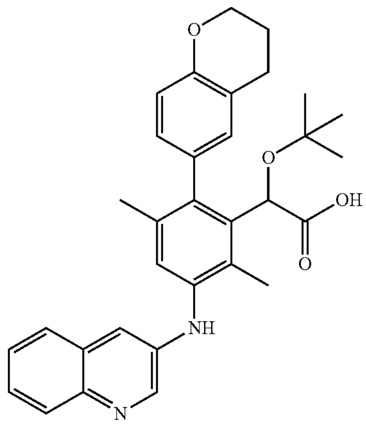 [SMILES: Cc1cc(Nc2cnc3ccccc3c2)c(C)c(C(OC(C)(C)C)C(=O)O)c1-c1ccc2c(c1)CCCO2] | 2.20 *2 | 511 |
| I-154 | 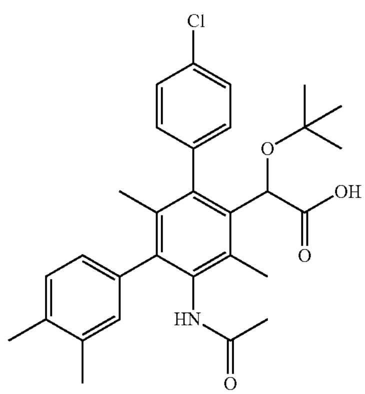 [SMILES: CC(=O)Nc1c(C)c(C(OC(C)(C)C)C(=O)O)c(-c2ccc(Cl)cc2)c(C)c1-c1ccc(C)c(C)c1] | 3.18 *7 | 508 |

TABLE 36

| Compound No. | Structure | RT (min) | MS (M + H)+ |
| --- | --- | --- | --- |
| I-155 | 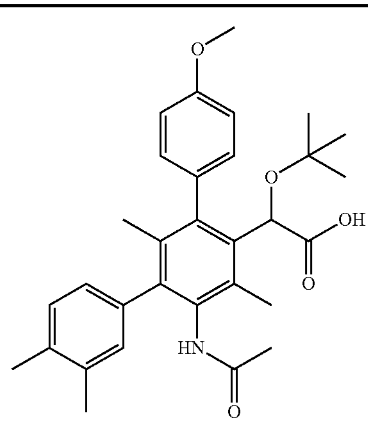 | 3.00 *7 | 504 [M + NH4]+ |

TABLE 36-continued

| Compound No. | Structure | RT (min) | MS (M + H)+ |
| --- | --- | --- | --- |
| I-156 | 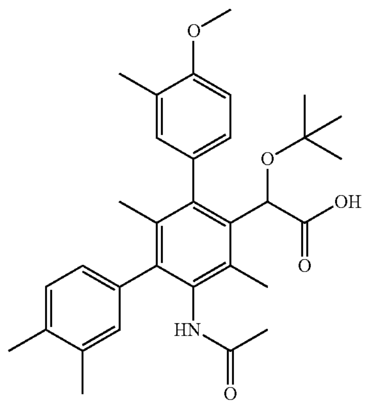 [SMILES: COc1ccc(-c2c(C)c(-c3ccc(C)c(C)c3)c(NC(C)=O)c(C)c2C(OC(C)(C)C)C(=O)O)cc1C] | 3.22, *7<br>3.31 | 518,<br>518 |
| I-157 | 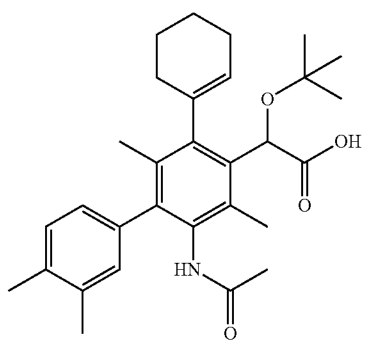 [SMILES: CC(=O)Nc1c(C)c(C(OC(C)(C)C)C(=O)O)c(C2=CCCCC2)c(C)c1-c1ccc(C)c(C)c1] | 3.20 *7 | 482 |
| I-158 | 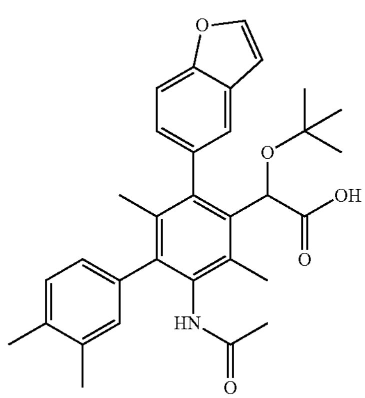 [SMILES: CC(=O)Nc1c(C)c(C(OC(C)(C)C)C(=O)O)c(-c2ccc3occc3c2)c(C)c1-c1ccc(C)c(C)c1] | 3.00, *7<br>3.07 | 513,<br>513 |

TABLE 37

| Compound No. | Structure | RT (min) | MS (M + H)+ |
|---|---|---|---|
| I-159 | 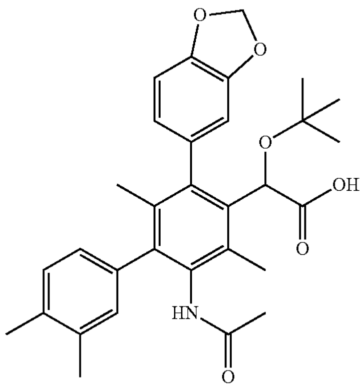 [SMILES: CC(=O)Nc1c(C)c(C(OC(C)(C)C)C(=O)O)c(-c2ccc3c(c2)OCO3)c(C)c1-c1ccc(C)c(C)c1] | 2.91, *7<br>3.00 | 518,<br>518 |
| I-160 | 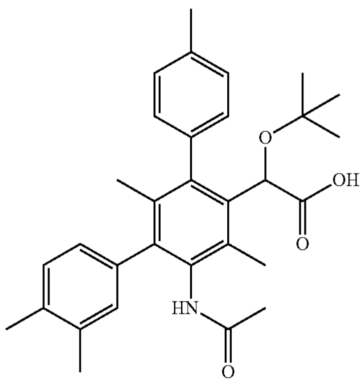 [SMILES: CC(=O)Nc1c(C)c(C(OC(C)(C)C)C(=O)O)c(-c2ccc(C)cc2)c(C)c1-c1ccc(C)c(C)c1] | 1.68 *5 | 505 [M + NH4]+ |
| I-161 | 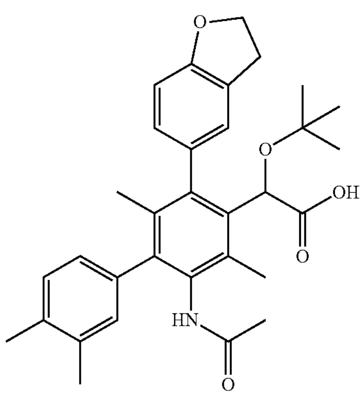 [SMILES: CC(=O)Nc1c(C)c(C(OC(C)(C)C)C(=O)O)c(-c2ccc3c(c2)CCO3)c(C)c1-c1ccc(C)c(C)c1] | 1.62 *5 | 533 [M + NH4]+ |
| I-162 | 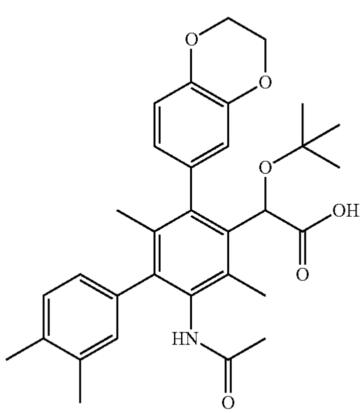 [SMILES: CC(=O)Nc1c(C)c(C(OC(C)(C)C)C(=O)O)c(-c2ccc3c(c2)OCCO3)c(C)c1-c1ccc(C)c(C)c1] | 2.91, *7<br>3.05 | 532,<br>532 |

TABLE 38

| Compound No. | Structure | RT (min) | MS (M + H)+ |
|---|---|---|---|
| I-163 | 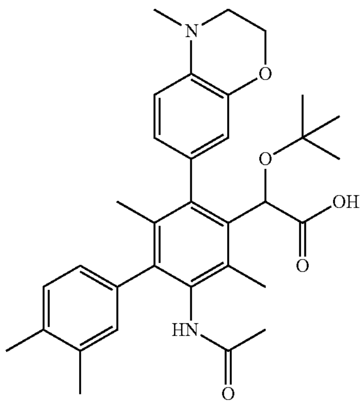 [SMILES: CC(=O)Nc1c(C)c(C(OC(C)(C)C)C(=O)O)c(-c2ccc3c(c2)OCCN3C)c(C)c1-c1ccc(C)c(C)c1] | 1.61 *5 | 562 [M + NH4]+ |
| I-166 | 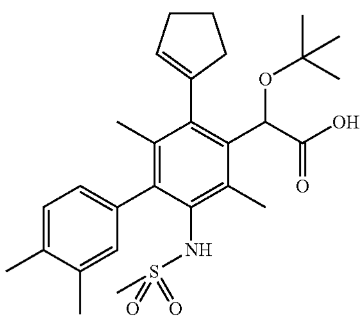 [SMILES: Cc1ccc(-c2c(C)c(C3=CCCC3)c(C(OC(C)(C)C)C(=O)O)c(C)c2NS(C)(=O)=O)cc1C] | 2.84 | 499 |
| I-167 | 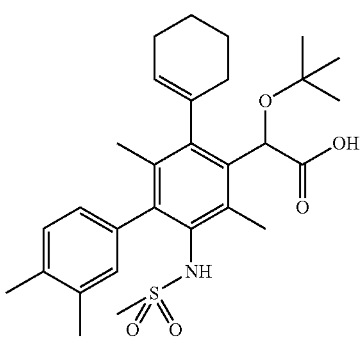 [SMILES: Cc1ccc(-c2c(C)c(C3=CCCCC3)c(C(OC(C)(C)C)C(=O)O)c(C)c2NS(C)(=O)=O)cc1C] | 2.98 | 513 |
| I-168 | 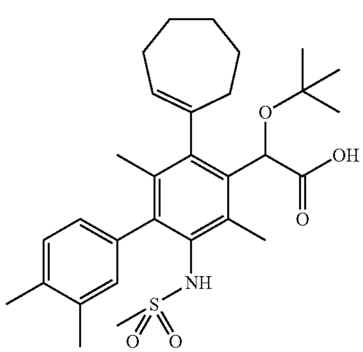 [SMILES: Cc1ccc(-c2c(C)c(C3=CCCCCC3)c(C(OC(C)(C)C)C(=O)O)c(C)c2NS(C)(=O)=O)cc1C] | 3.09 | 527 |

TABLE 39

| Compound No. | Structure | RT (min) | MS (M + H)+ |
|---|---|---|---|
| I-169 | 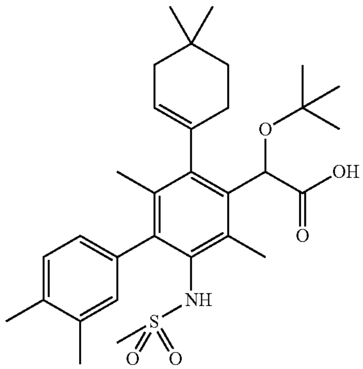 [SMILES: Cc1ccc(-c2c(C)c(C3=CCC(C)(C)CC3)c(C(OC(C)(C)C)C(=O)O)c(C)c2NS(C)(=O)=O)cc1C] | 3.17 | 541 |
| I-170 | 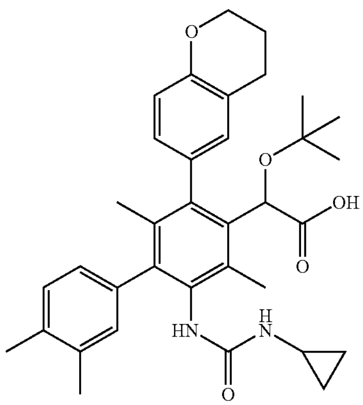 [SMILES: Cc1ccc(-c2c(C)c(-c3ccc4c(c3)CCCO4)c(C(OC(C)(C)C)C(=O)O)c(C)c2NC(=O)NC2CC2)cc1C] | 2.65 | 571 |
| I-171 | 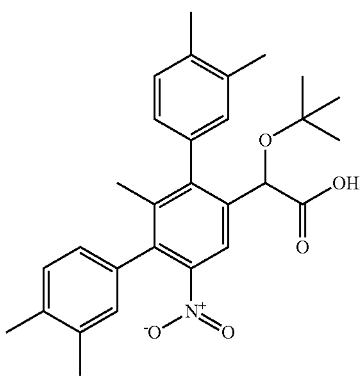 | *4 | 474 [M − H]− |
| I-172 | 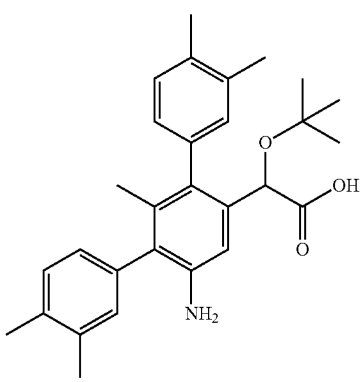 [SMILES: Cc1ccc(-c2c(N)cc(C(OC(C)(C)C)C(=O)O)c(-c3ccc(C)c(C)c3)c2C)cc1C] | 6.89 *6 | 446 |

TABLE 40

| Compound No. | Structure | RT (min) | MS (M + H)+ |
| --- | --- | --- | --- |
| I-173 | 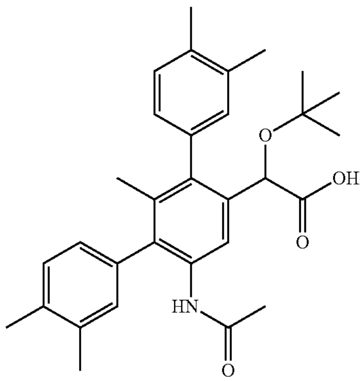 [SMILES: CC(=O)Nc1cc(C(OC(C)(C)C)C(=O)O)c(-c2ccc(C)c(C)c2)c(C)c1-c1ccc(C)c(C)c1] | 6.68 *6 | 488 |
| I-174 | 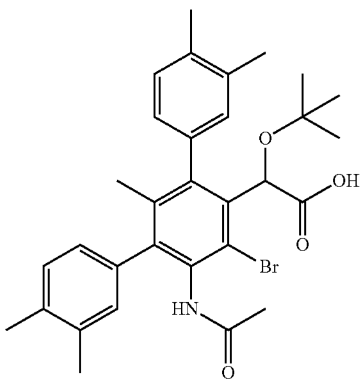 [SMILES: CC(=O)Nc1c(Br)c(C(OC(C)(C)C)C(=O)O)c(-c2ccc(C)c(C)c2)c(C)c1-c1ccc(C)c(C)c1] | *4 | 566 |
| I-175 | 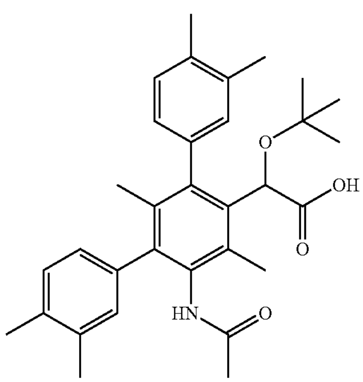 [SMILES: CC(=O)Nc1c(C)c(C(OC(C)(C)C)C(=O)O)c(-c2ccc(C)c(C)c2)c(C)c1-c1ccc(C)c(C)c1] | *4 | 502 |
| I-176 | 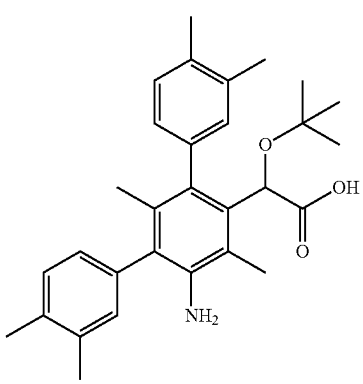 [SMILES: Cc1ccc(-c2c(C)c(-c3ccc(C)c(C)c3)c(C(OC(C)(C)C)C(=O)O)c(C)c2N)cc1C] | 3.08 *4 | 460 |

TABLE 41

| Compound No. | Structure | RT (min) | MS (M + H)+ |
| --- | --- | --- | --- |
| I-177 | 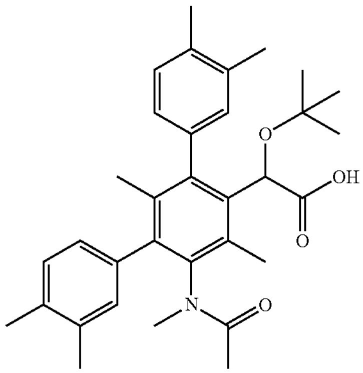 [SMILES: CC(=O)N(C)c1c(C)c(C(OC(C)(C)C)C(=O)O)c(-c2ccc(C)c(C)c2)c(C)c1-c1ccc(C)c(C)c1] | *4 | 516 |
| I-178 | 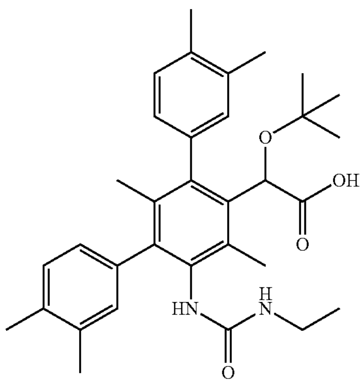 [SMILES: CCNC(=O)Nc1c(C)c(C(OC(C)(C)C)C(=O)O)c(-c2ccc(C)c(C)c2)c(C)c1-c1ccc(C)c(C)c1] | *4 | 531 |
| I-179 | 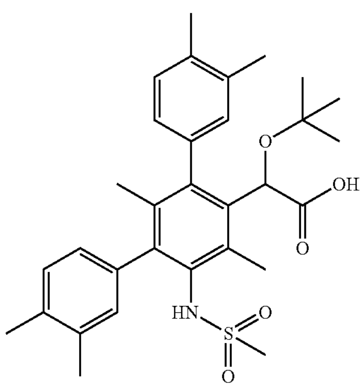 [SMILES: Cc1ccc(-c2c(C)c(-c3ccc(C)c(C)c3)c(C(OC(C)(C)C)C(=O)O)c(C)c2NS(C)(=O)=O)cc1C] | *4 | 537  M + • |
| I-180 | 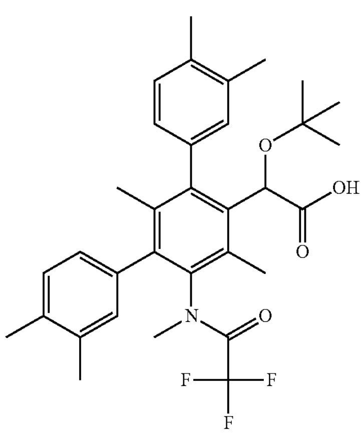 [SMILES: Cc1ccc(-c2c(C)c(-c3ccc(C)c(C)c3)c(N(C)C(=O)C(F)(F)F)c(C)c2C(OC(C)(C)C)C(=O)O)cc1C] | *4 | 570 |

TABLE 42
| Compound No. | Structure | RT (min) | MS (M + H)+ |
|---|---|---|---|
| I-181 | 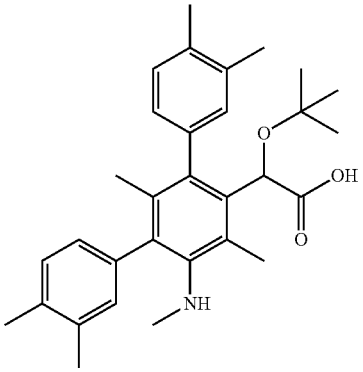 [SMILES: CNc1c(C)c(C(OC(C)(C)C)C(=O)O)c(-c2ccc(C)c(C)c2)c(C)c1-c1ccc(C)c(C)c1] | *4 | 474 |
| I-182 | 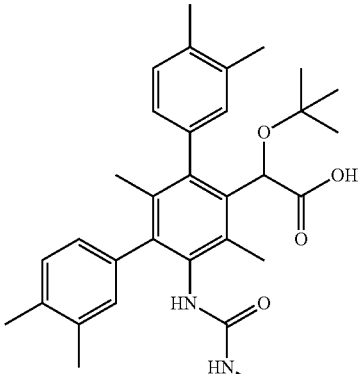 | *4 | 517 |
| I-183 | 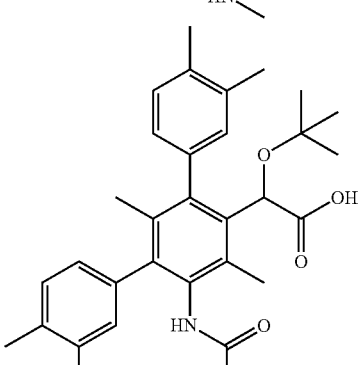 | 2.83 | 516 |
| I-184 | 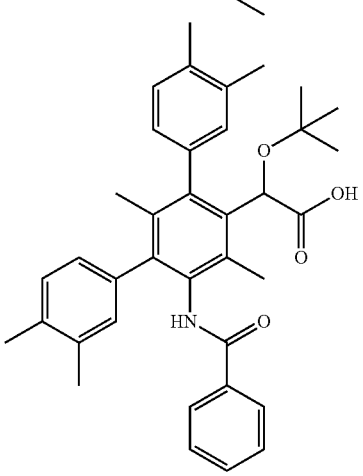 | 2.97 | 564 |
TABLE 43
| Compound No. | Structure | RT (min) | MS (M + H)+ |
|---|---|---|---|
| I-185 | 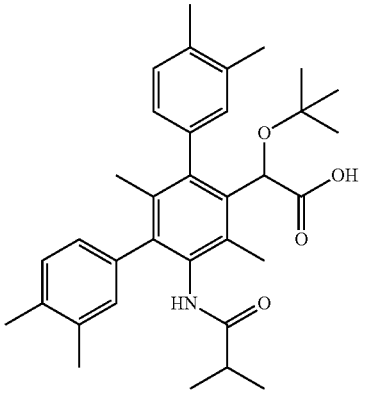 [SMILES: Cc1ccc(-c2c(C)c(-c3ccc(C)c(C)c3)c(C(OC(C)(C)C)C(=O)O)c(C)c2NC(=O)C(C)C)cc1C] | 2.92 | 530 |
| I-186 | 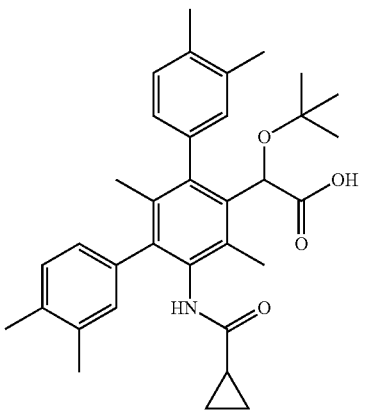 [SMILES: Cc1ccc(-c2c(C)c(-c3ccc(C)c(C)c3)c(C(OC(C)(C)C)C(=O)O)c(C)c2NC(=O)C2CC2)cc1C] | 2.88 | 528 |
| I-187 | 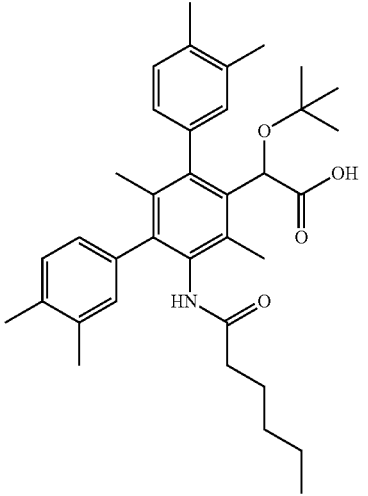 [SMILES: CCCCCC(=O)Nc1c(C)c(C(OC(C)(C)C)C(=O)O)c(-c2ccc(C)c(C)c2)c(C)c1-c1ccc(C)c(C)c1] | 3.13 | 558 |

TABLE 43-continued

| Compound No. | Structure | RT (min) | MS (M + H)+ |
|---|---|---|---|
| I-188 | 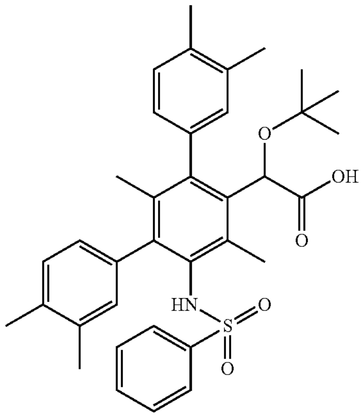 [SMILES: Cc1ccc(-c2c(C)c(-c3ccc(C)c(C)c3)c(C(OC(C)(C)C)C(=O)O)c(C)c2NS(=O)(=O)c2ccccc2)cc1C] | 3.12 | 600 |

TABLE 44

| Compound No. | Structure | RT(min) | MS(M + H)+ |
|---|---|---|---|
| I-189 | 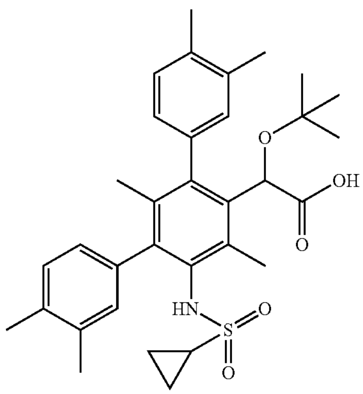 [SMILES: Cc1ccc(-c2c(C)c(-c3ccc(C)c(C)c3)c(C(OC(C)(C)C)C(=O)O)c(C)c2NS(=O)(=O)C2CC2)cc1C] | 2.99 | 564 |
| I-190 | 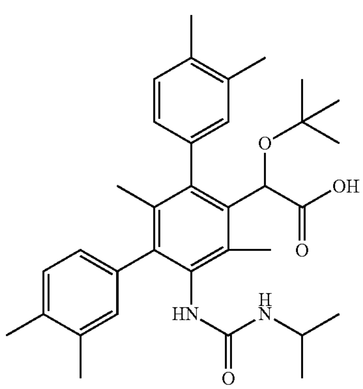 [SMILES: Cc1ccc(-c2c(C)c(-c3ccc(C)c(C)c3)c(C(OC(C)(C)C)C(=O)O)c(C)c2NC(=O)NC(C)C)cc1C] | 2.89 | 545 |

TABLE 44-continued

| Compound No. | Structure | RT(min) | MS(M + H)+ |
|---|---|---|---|
| I-191 | 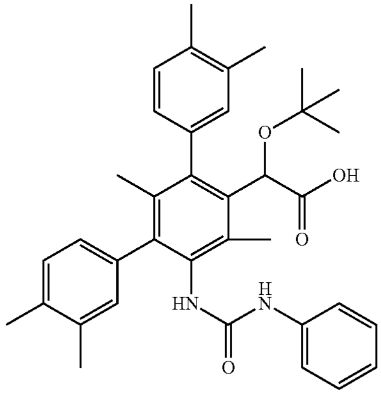 [SMILES: Cc1ccc(-c2c(C)c(-c3ccc(C)c(C)c3)c(C(OC(C)(C)C)C(=O)O)c(C)c2NC(=O)Nc2ccccc2)cc1C] | 3.00 | 579 |
| I-192 | 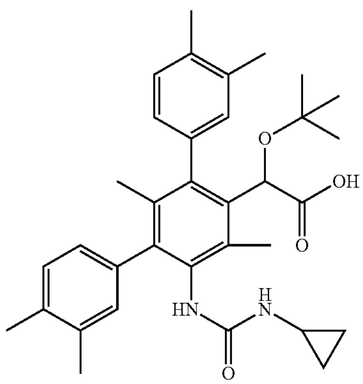 [SMILES: Cc1ccc(-c2c(C)c(-c3ccc(C)c(C)c3)c(C(OC(C)(C)C)C(=O)O)c(C)c2NC(=O)NC2CC2)cc1C] | 2.85 | 543 |

TABLE 45

| Compound No. | Structure | RT(min) | MS(M + H)+ |
|---|---|---|---|
| I-193 | 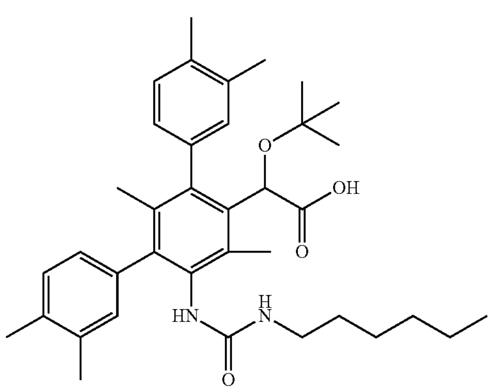 [SMILES: CCCCCCNC(=O)Nc1c(C)c(C(OC(C)(C)C)C(=O)O)c(-c2ccc(C)c(C)c2)c(C)c1-c1ccc(C)c(C)c1] | 3.20 | 587 |

TABLE 45-continued

| Compound No. | Structure | RT(min) | MS(M + H)+ |
|---|---|---|---|
| I-194 | 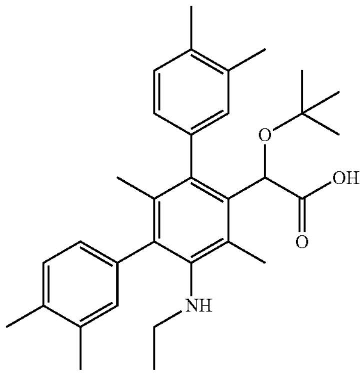 [SMILES: CCNc1c(C)c(C(OC(C)(C)C)C(=O)O)c(-c2ccc(C)c(C)c2)c(C)c1-c1ccc(C)c(C)c1] | 2.57 | 488 |
| I-195 | 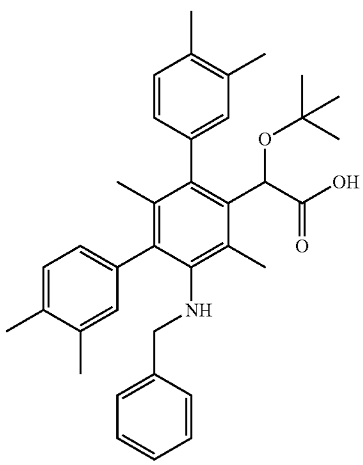 [SMILES: Cc1ccc(-c2c(C)c(-c3ccc(C)c(C)c3)c(C(OC(C)(C)C)C(=O)O)c(C)c2NCc2ccccc2)cc1C] | 3.49 | 550 |
| I-196 | 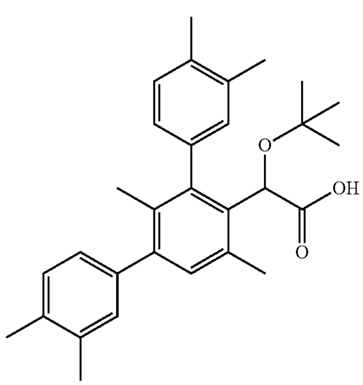 [SMILES: Cc1ccc(-c2cc(C)c(C(OC(C)(C)C)C(=O)O)c(-c3ccc(C)c(C)c3)c2C)cc1C] | *4 | 467 [M + Na]+ |

TABLE 46

| Compound No. | Structure | RT(min) | MS(M + H)+ |
|---|---|---|---|
| I-197 | 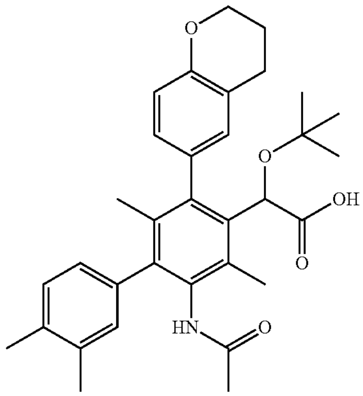 [SMILES: CC(=O)Nc1c(C)c(C(OC(C)(C)C)C(=O)O)c(-c2ccc3c(c2)CCCO3)c(C)c1-c1ccc(C)c(C)c1] | *4 | 530 |
| I-198 | 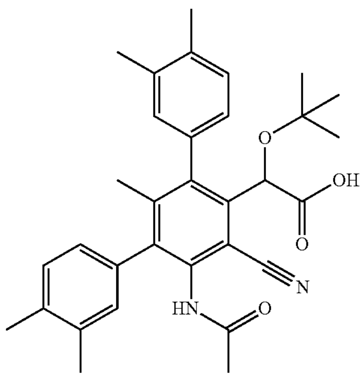 [SMILES: CC(=O)Nc1c(C#N)c(C(OC(C)(C)C)C(=O)O)c(-c2ccc(C)c(C)c2)c(C)c1-c1ccc(C)c(C)c1] | 2.64 *2 | 513 |
| I-199 | 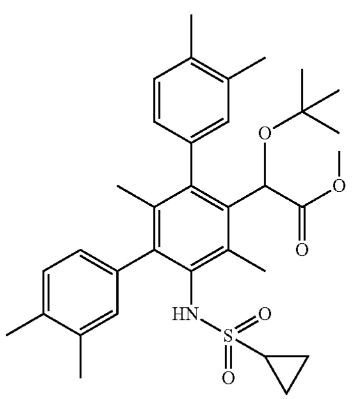 | 6.63 *2 | 576 [M − H]− |
| I-200 | 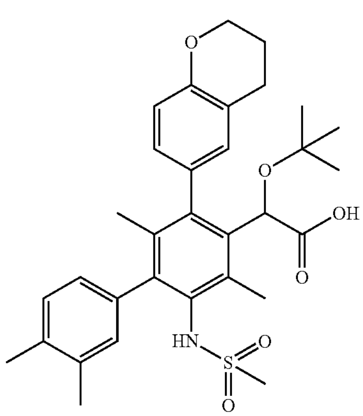 [SMILES: Cc1ccc(-c2c(C)c(-c3ccc4c(c3)CCCO4)c(C(OC(C)(C)C)C(=O)O)c(C)c2NS(C)(=O)=O)cc1C] | *4 | 565 M+• |

TABLE 47

| Compound No. | Structure | RT(min) | MS(M + H)+ |
|---|---|---|---|
| I-201 | 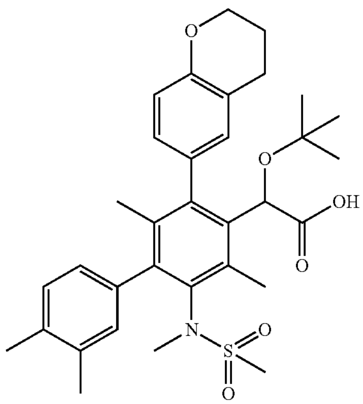 [SMILES: Cc1ccc(-c2c(C)c(-c3ccc4c(c3)CCCO4)c(C(OC(C)(C)C)C(=O)O)c(C)c2N(C)S(C)(=O)=O)cc1C] | 5.59, 5.66, 5.90, 5.96 | *2  578  [M − H]− |
| I-202 | 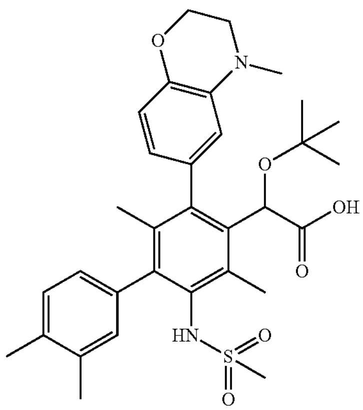 [SMILES: Cc1ccc(-c2c(C)c(-c3ccc4c(c3)N(C)CCO4)c(C(OC(C)(C)C)C(=O)O)c(C)c2NS(C)(=O)=O)cc1C] | | *4  580  M+ • |
| I-203 | 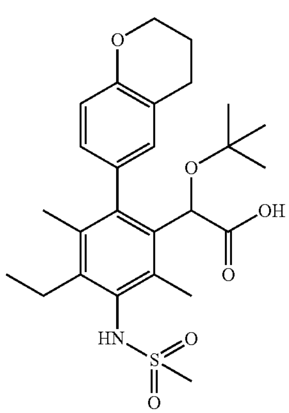 [SMILES: CCc1c(C)c(-c2ccc3c(c2)CCCO3)c(C(OC(C)(C)C)C(=O)O)c(C)c1NS(C)(=O)=O] | | *4  489  M+ • |

TABLE 47-continued

| Compound No. | Structure | RT(min) | MS(M + H)+ |
|---|---|---|---|
| I-204 | 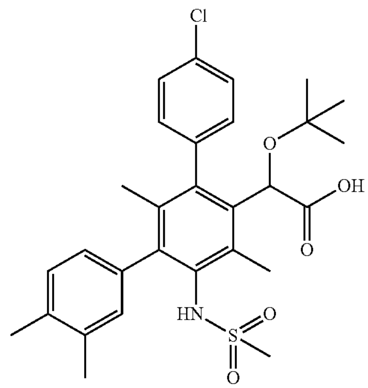 [SMILES: Cc1ccc(-c2c(C)c(-c3ccc(Cl)cc3)c(C(OC(C)(C)C)C(=O)O)c(C)c2NS(C)(=O)=O)cc1C] | *4 | 566 [M + Na]+ |

TABLE 48

| Compound No. | Structure | RT(min) | MS(M + H)+ |
|---|---|---|---|
| I-206 | 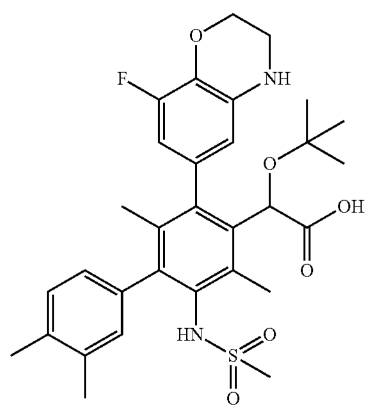 [SMILES: Cc1ccc(-c2c(C)c(-c3cc(F)c4c(c3)NCCO4)c(C(OC(C)(C)C)C(=O)O)c(C)c2NS(C)(=O)=O)cc1C] | *4 | 585 |
| I-207 | 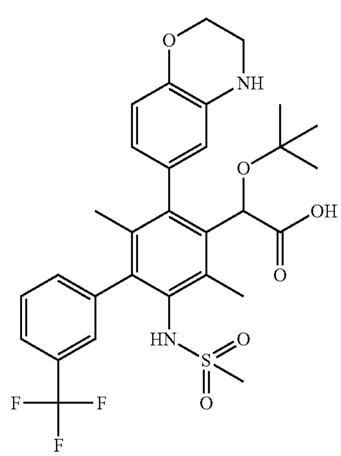 [SMILES: Cc1c(-c2cccc(C(F)(F)F)c2)c(NS(C)(=O)=O)c(C)c(C(OC(C)(C)C)C(=O)O)c1-c1ccc2c(c1)NCCO2] | 2.23, 2.46 | 607 |

TABLE 48-continued

| Compound No. | Structure | RT(min) | MS(M + H)+ |
|---|---|---|---|
| I-208 | 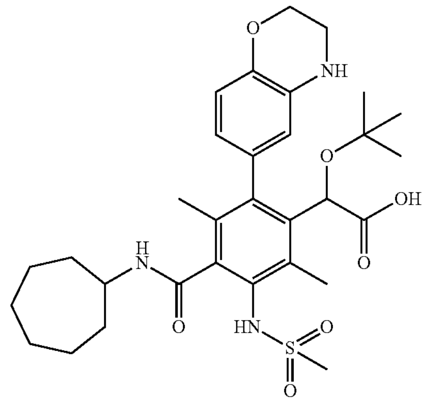 [SMILES: Cc1c(C(=O)NC2CCCCCC2)c(NS(C)(=O)=O)c(C)c(C(OC(C)(C)C)C(=O)O)c1-c1ccc2c(c1)NCCO2] | 2.02, 2.21 | 602 |
| I-209 | 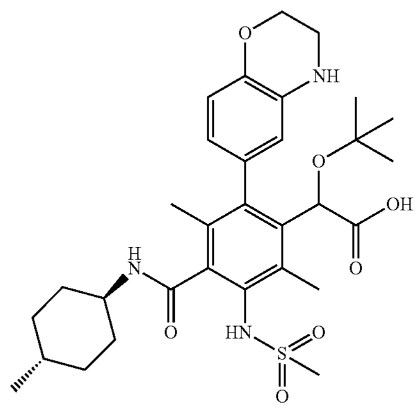 [SMILES: Cc1c(C(=O)N[C@H]2CC[C@H](C)CC2)c(NS(C)(=O)=O)c(C)c(C(OC(C)(C)C)C(=O)O)c1-c1ccc2c(c1)NCCO2] | 2.06, 2.25 | 602 |

TABLE 49

| Compound No. | Structure | RT(min) | MS(M + H)+ |
|---|---|---|---|
| I-211 | 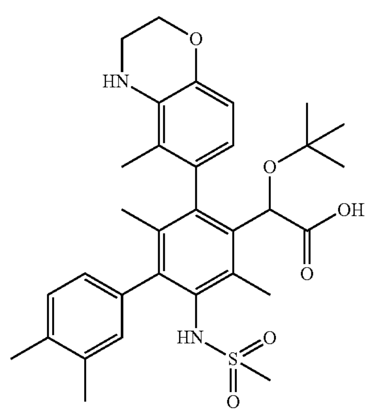 | 2.29 *2 | 579 [M − H]− |

TABLE 49-continued

| Compound No. | Structure | RT(min) | MS(M + H)+ |
|---|---|---|---|
| I-212 | 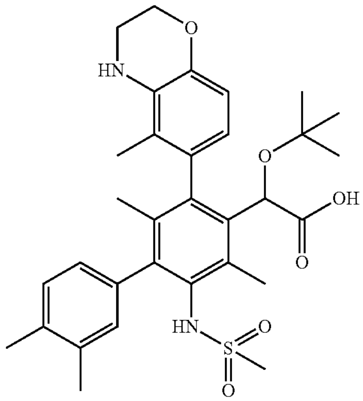 | 2.47 *2 | 579 [M − H]− |
| I-213 | 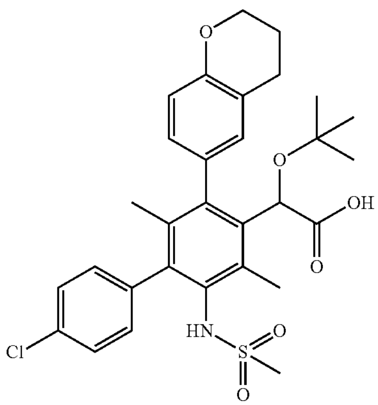 [SMILES: Cc1c(-c2ccc(Cl)cc2)c(NS(C)(=O)=O)c(C)c(C(OC(C)(C)C)C(=O)O)c1-c1ccc2c(c1)CCCO2] | 2.64 | 570 [M − H]− |
| I-214 | 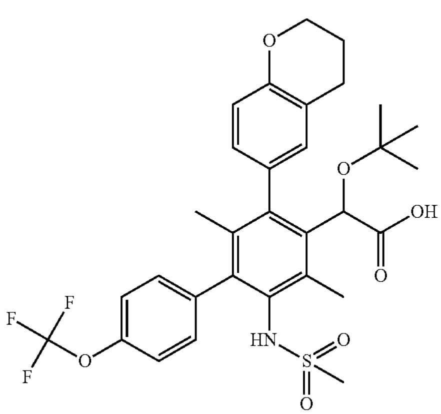 [SMILES: Cc1c(-c2ccc(OC(F)(F)F)cc2)c(NS(C)(=O)=O)c(C)c(C(OC(C)(C)C)C(=O)O)c1-c1ccc2c(c1)CCCO2] | 2.71 | 620 [M − H]− |

TABLE 50

| Compound No. | Structure | RT(min) | MS(M + H)+ |
|---|---|---|---|
| I-215 | 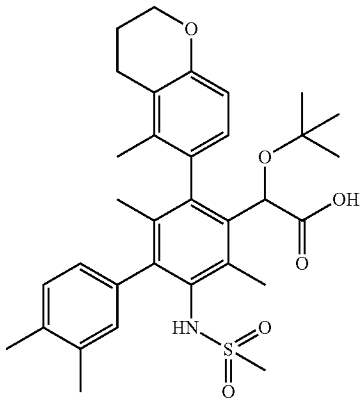 [SMILES: Cc1ccc(-c2c(C)c(-c3ccc4c(c3C)CCCO4)c(C(OC(C)(C)C)C(=O)O)c(C)c2NS(C)(=O)=O)cc1C] | 2.74 | 578 [M − H]− |
| I-216 | 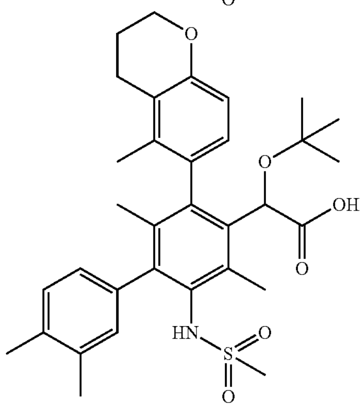 | 2.73 | 578 [M − H]− |
| I-217 | 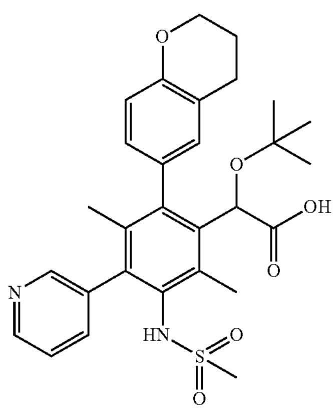 [SMILES: Cc1c(-c2cccnc2)c(NS(C)(=O)=O)c(C)c(C(OC(C)(C)C)C(=O)O)c1-c1ccc2c(c1)CCCO2] | 1.64 | 539 |
| I-218 | 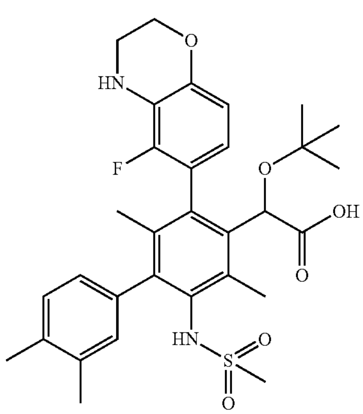 [SMILES: Cc1ccc(-c2c(C)c(-c3ccc4c(c3F)NCCO4)c(C(OC(C)(C)C)C(=O)O)c(C)c2NS(C)(=O)=O)cc1C] | 2.33 *2 | 583 [M − H]− |

TABLE 51

| Compound No. | Structure | RT(min) | MS(M + H)+ |
|---|---|---|---|
| I-219 | 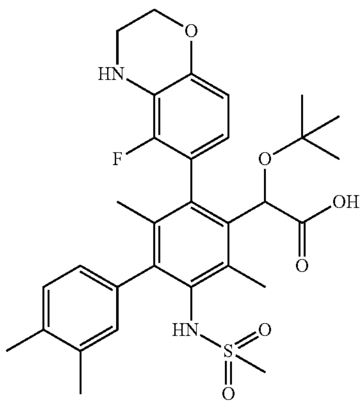 | 2.45 *2 | 583 [M − H]− |
| I-220 | 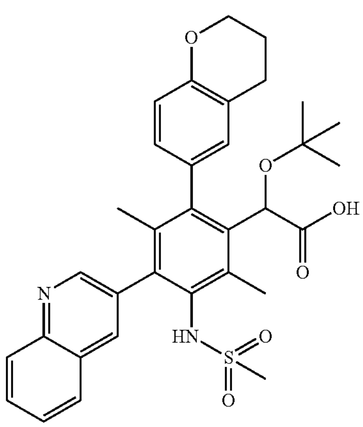 [SMILES: Cc1c(-c2cnc3ccccc3c2)c(NS(C)(=O)=O)c(C)c(C(OC(C)(C)C)C(=O)O)c1-c1ccc2c(c1)CCCO2] | 2.11 | 589 |
| I-221 | 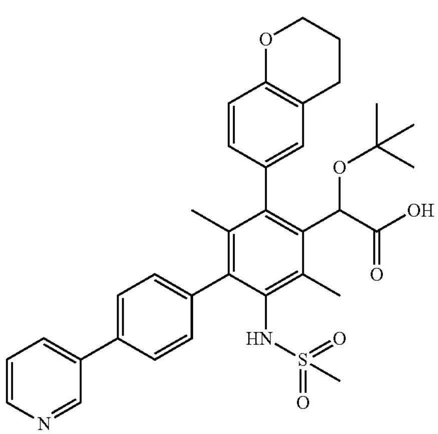 [SMILES: Cc1c(-c2ccc(-c3cccnc3)cc2)c(NS(C)(=O)=O)c(C)c(C(OC(C)(C)C)C(=O)O)c1-c1ccc2c(c1)CCCO2] | 1.90 | 616 |

TABLE 51-continued

| Compound No. | Structure | RT(min) | MS(M + H)+ |
|---|---|---|---|
| I-222 | 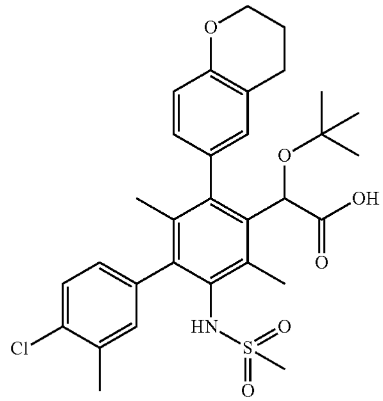 [SMILES: Cc1cc(-c2c(C)c(-c3ccc4c(c3)CCCO4)c(C(OC(C)(C)C)C(=O)O)c(C)c2NS(C)(=O)=O)ccc1Cl] | 2.73 | 584 [M − H]− |

TABLE 52

| Compound No. | Structure | RT(min) | MS(M + H)+ |
|---|---|---|---|
| I-223 | 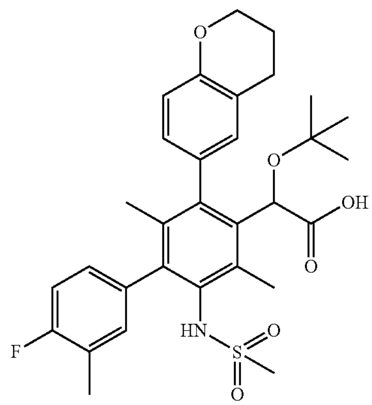 | 2.64 | 568 [M − H]− |
| I-224 | 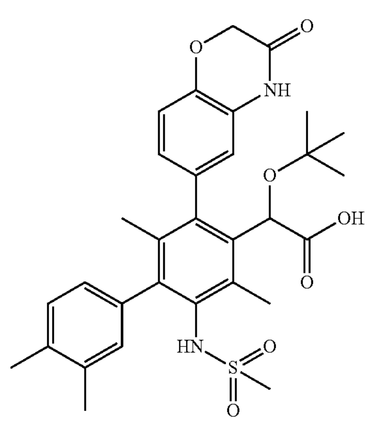 [SMILES: Cc1ccc(-c2c(C)c(-c3ccc4c(c3)NC(=O)CO4)c(C(OC(C)(C)C)C(=O)O)c(C)c2NS(C)(=O)=O)cc1C] | 2.31 | 579 [M − H]− |

TABLE 52-continued

| Compound No. | Structure | RT(min) | MS(M + H)+ |
|---|---|---|---|
| I-225 | 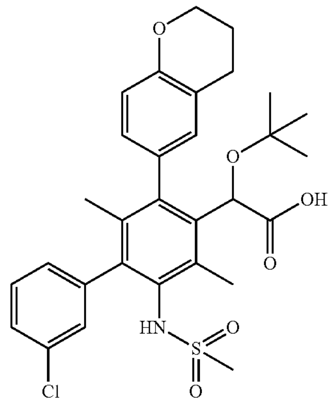 [SMILES: Cc1c(-c2cccc(Cl)c2)c(NS(C)(=O)=O)c(C)c(C(OC(C)(C)C)C(=O)O)c1-c1ccc2c(c1)CCCO2] | 2.57 | 570 [M − H]− |
| I-226 | 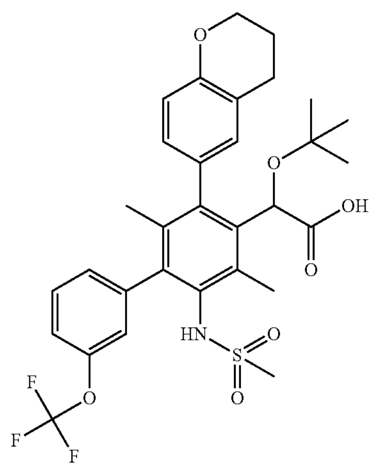 [SMILES: Cc1c(-c2cccc(OC(F)(F)F)c2)c(NS(C)(=O)=O)c(C)c(C(OC(C)(C)C)C(=O)O)c1-c1ccc2c(c1)CCCO2] | 2.71 | 620 [M − H]− |

TABLE 53

| Compound No. | Structure | RT(min) | MS(M + H)+ |
|---|---|---|---|
| I-227 | 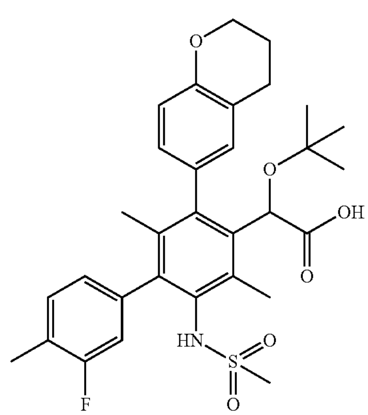 | 2.57 | 568 [M − H]− |

TABLE 53-continued

| Compound No. | Structure | RT(min) | MS(M + H)+ |
|---|---|---|---|
| I-228 | 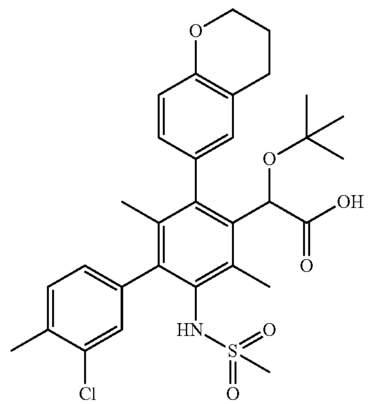 | 2.73 | 584 [M − H]− |
| I-229 | 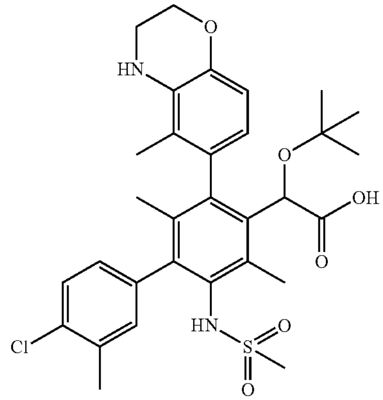 [SMILES: Cc1cc(-c2c(C)c(-c3ccc4c(c3C)NCCO4)c(C(OC(C)(C)C)C(=O)O)c(C)c2NS(C)(=O)=O)ccc1Cl] | 2.57 | 599 [M − H]− |
| I-230 | 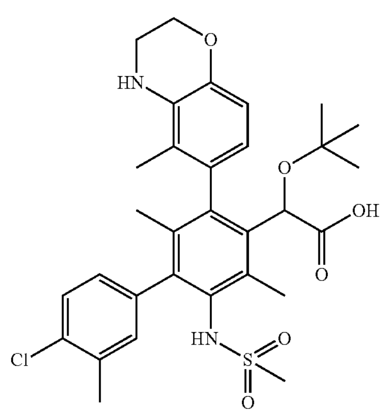 [SMILES: Cc1cc(-c2c(C)c(-c3ccc4c(c3C)NCCO4)c(C(OC(C)(C)C)C(=O)O)c(C)c2NS(C)(=O)=O)ccc1Cl] | 2.84 | 599 [M − H]− |

TABLE 54

| Compound No. | Structure | RT(min) | MS(M + H)+ |
|---|---|---|---|
| I-231 | 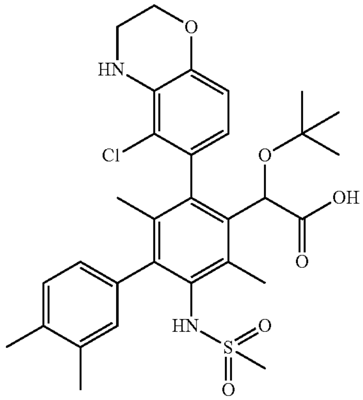 | 2.41 | 599 [M − H]− |
| I-232 | 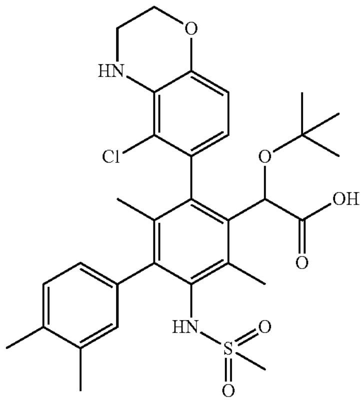 | 2.52 | 599 [M − H]− |
| I-233 | 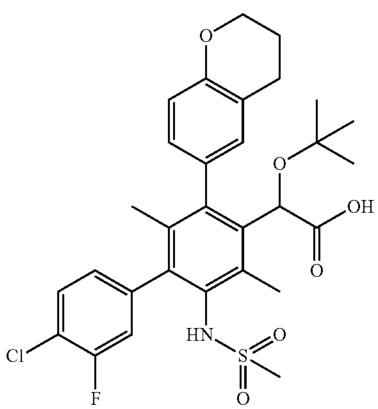 | 2.67 | 568 [M − H]− |
| I-234 | 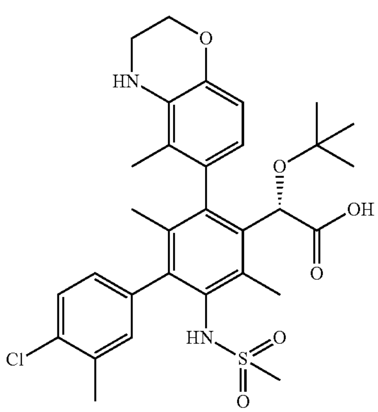 | 2.53 | 601 |

TABLE 55

| Compound No. | Structure | RT(min) | MS(M + H)+ | |
|---|---|---|---|---|
| I-235 | 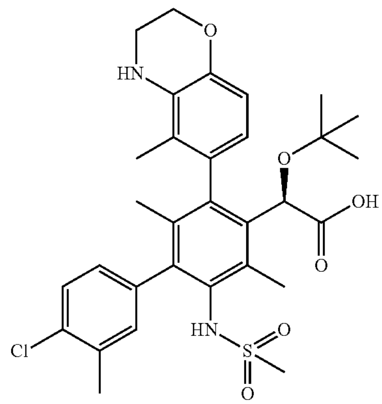 [SMILES: Cc1cc(-c2c(C)c(-c3ccc4c(c3C)NCCO4)c([C@@H](OC(C)(C)C)C(=O)O)c(C)c2NS(C)(=O)=O)ccc1Cl] | 2.53 | 601 | |
| I-236 | 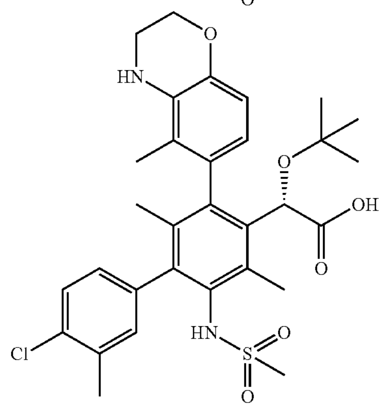 | 2.34 | 601 | |
| I-237 | 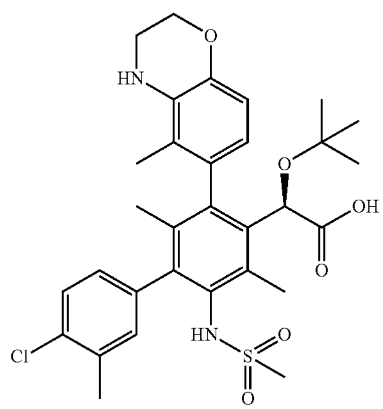 [SMILES: Cc1cc(-c2c(C)c(-c3ccc4c(c3C)NCCO4)c([C@@H](OC(C)(C)C)C(=O)O)c(C)c2NS(C)(=O)=O)ccc1Cl] | 2.34 | 601 | |
| I-238 | 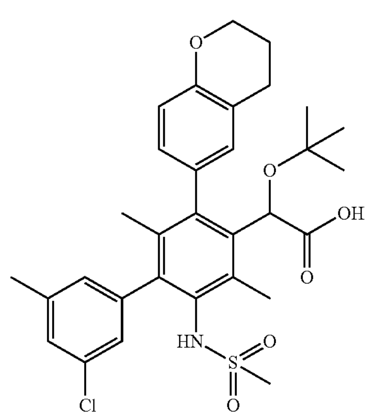 [SMILES: Cc1cc(Cl)cc(-c2c(C)c(-c3ccc4c(c3)CCCO4)c(C(OC(C)(C)C)C(=O)O)c(C)c2NS(C)(=O)=O)c1] | 2.73 | 584 | [M − H]− |

TABLE 56

| Compound No. | Structure | RT(min) | MS(M + H)+ |
|---|---|---|---|
| I-239 | 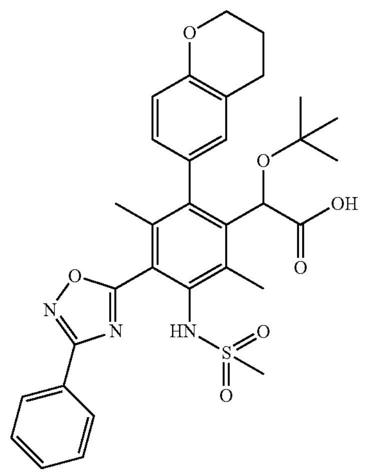 [SMILES: Cc1c(-c2nc(-c3ccccc3)no2)c(NS(C)(=O)=O)c(C)c(C(OC(C)(C)C)C(=O)O)c1-c1ccc2c(c1)CCCO2] | 2.58 | 606 |
| I-240 | 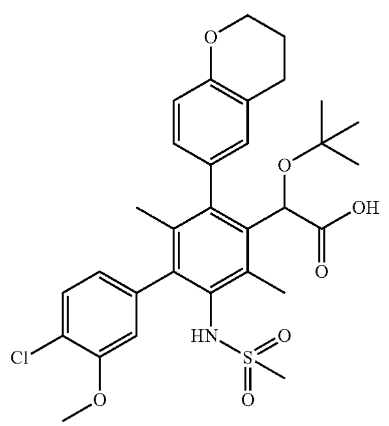 [SMILES: COc1cc(-c2c(C)c(-c3ccc4c(c3)CCCO4)c(C(OC(C)(C)C)C(=O)O)c(C)c2NS(C)(=O)=O)ccc1Cl] | 2.59 | 600 [M − H]− |
| I-241 | 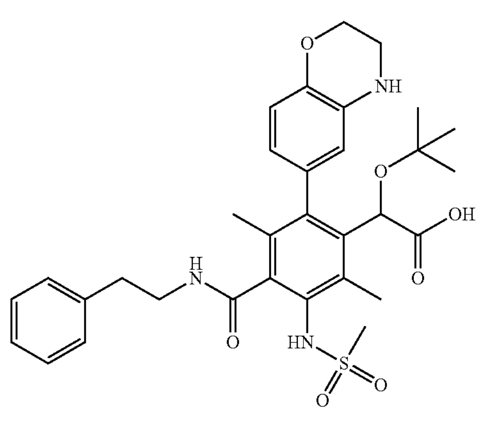 [SMILES: Cc1c(C(=O)NCCc2ccccc2)c(NS(C)(=O)=O)c(C)c(C(OC(C)(C)C)C(=O)O)c1-c1ccc2c(c1)NCCO2] | 1.93, 2.07 | *2 610, 610 |

TABLE 56-continued
| Compound No. | Structure | RT(min) | | MS(M + H)+ |
|---|---|---|---|---|
| I-242 | 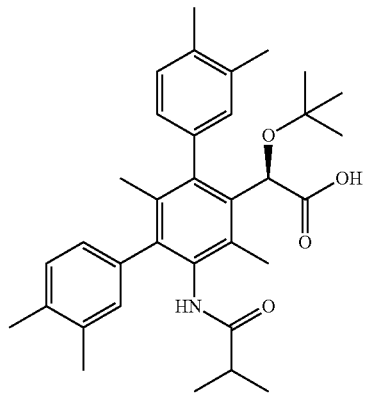 [SMILES: Cc1ccc(-c2c(C)c(-c3ccc(C)c(C)c3)c([C@@H](OC(C)(C)C)C(=O)O)c(C)c2NC(=O)C(C)C)cc1C] | 1.88, 1.93, 2.11 | *2 | 608, 608, 608 |
TABLE 57
| Compound No. | Structure | RT (min) | MS (M + H)+ |
|---|---|---|---|
| I-243 | 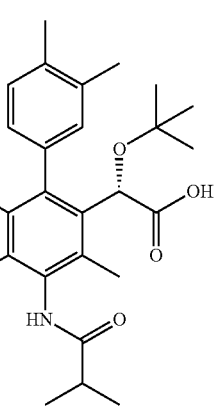 | 3.02 | 530 |
| I-244 | 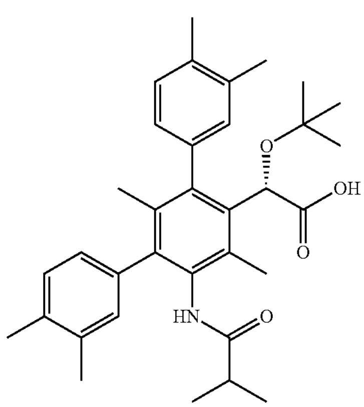 | 3.02 | 530 |
TABLE 57-continued
| Compound No. | Structure | RT (min) | MS (M + H)+ |
|---|---|---|---|
| I-245 | 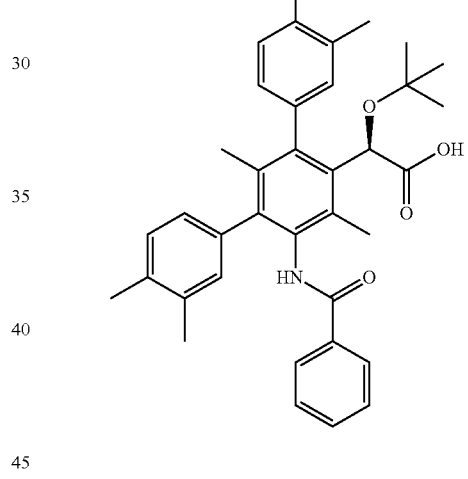 | 3.07 | 564 |
| I-246 | 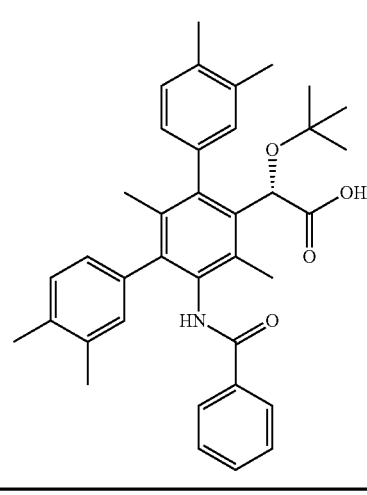 | 3.07 | 564 |

TABLE 58

| Compound No. | Structure | RT (min) | MS (M + H)+ |
|---|---|---|---|
| I-247 | 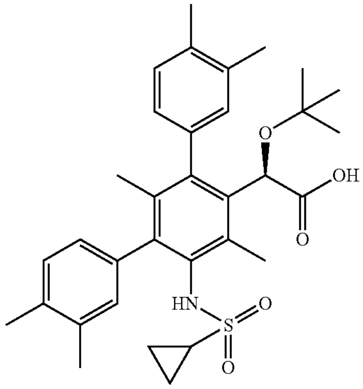 [SMILES: Cc1ccc(-c2c(C)c(-c3ccc(C)c(C)c3)c([C@@H](OC(C)(C)C)C(=O)O)c(C)c2NS(=O)(=O)C2CC2)cc1C] | 3.09 | 562 [M − H]− |
| I-248 | 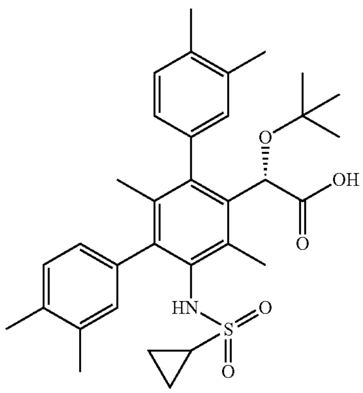 | 3.08 | 562 [M − H]− |
| I-249 | 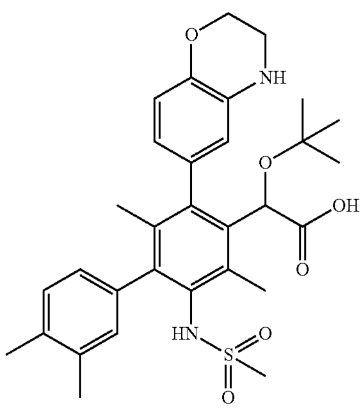 [SMILES: Cc1ccc(-c2c(C)c(-c3ccc4c(c3)NCCO4)c(C(OC(C)(C)C)C(=O)O)c(C)c2NS(C)(=O)=O)cc1C] | 2.24, *2 2.45 | 567, 567 |
| I-250 | 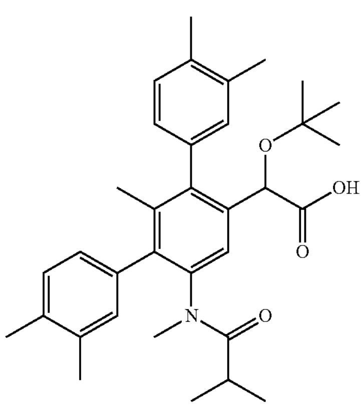 [SMILES: Cc1ccc(-c2c(C(OC(C)(C)C)C(=O)O)cc(N(C)C(=O)C(C)C)c(-c3ccc(C)c(C)c3)c2C)cc1C] | 3.12 | 530 |

TABLE 59

| Compound No. | Structure | RT (min) | MS (M + H)+ |
| --- | --- | --- | --- |
| I-251 | 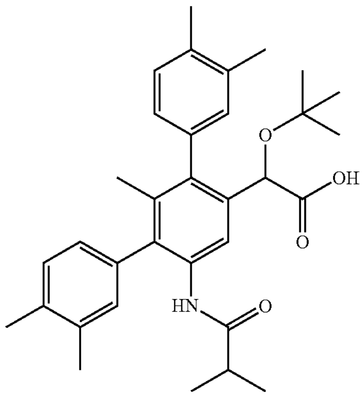 | 3.04 | 516 |
| I-252 | 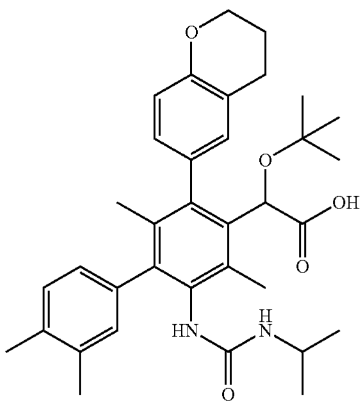 [SMILES: Cc1ccc(-c2c(C)c(-c3ccc4c(c3)CCCO4)c(C(OC(C)(C)C)C(=O)O)c(C)c2NC(=O)NC(C)C)cc1C] | 2.67, 2.70 | 573, 573 |
| I-253 | 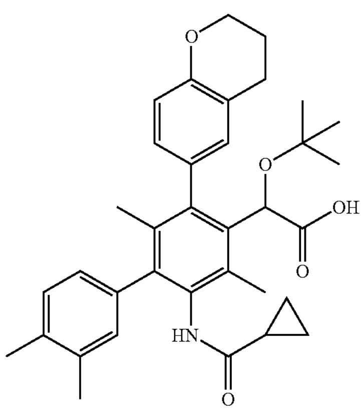 [SMILES: Cc1ccc(-c2c(C)c(-c3ccc4c(c3)CCCO4)c(C(OC(C)(C)C)C(=O)O)c(C)c2NC(=O)C2CC2)cc1C] | 2.69 | 556 |
| I-254 | 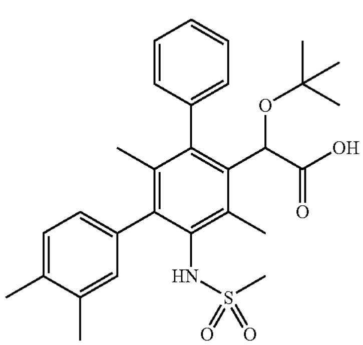 [SMILES: Cc1ccc(-c2c(C)c(-c3ccccc3)c(C(OC(C)(C)C)C(=O)O)c(C)c2NS(C)(=O)=O)cc1C] | 2.65 | 508 [M − H]− |

TABLE 60

| Compound No. | Structure | RT (min) | MS (M + H)+ |
|---|---|---|---|
| I-255 | 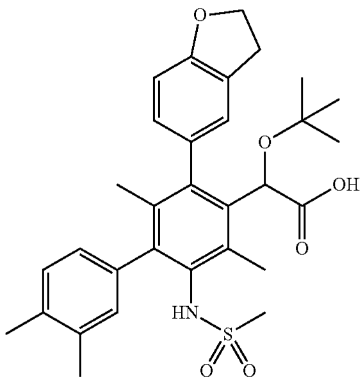 [SMILES: Cc1ccc(-c2c(C)c(-c3ccc4c(c3)CCO4)c(C(OC(C)(C)C)C(=O)O)c(C)c2NS(C)(=O)=O)cc1C] | 2.54, 2.59 | 550, 550 [M − H]− |
| I-256 | 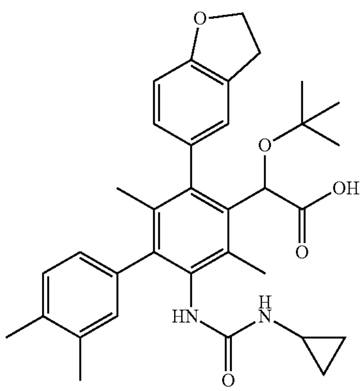 [SMILES: Cc1ccc(-c2c(C)c(-c3ccc4c(c3)CCO4)c(C(OC(C)(C)C)C(=O)O)c(C)c2NC(=O)NC2CC2)cc1C] | 2.50, 2.55 | 555, 555 [M − H]− |
| I-257 | 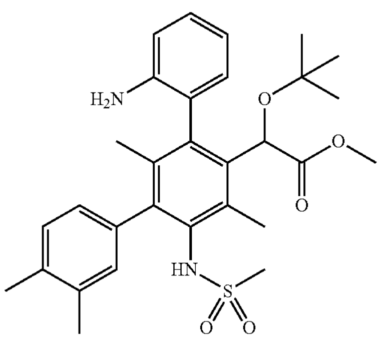 | 2.62 | 537 [M − H]− |
| I-258 | 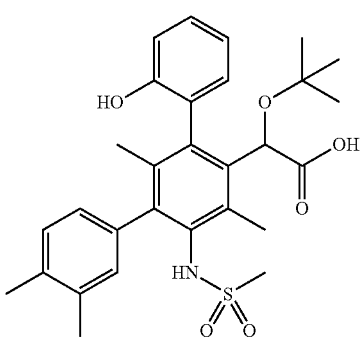 [SMILES: Cc1ccc(-c2c(C)c(-c3ccccc3O)c(C(OC(C)(C)C)C(=O)O)c(C)c2NS(C)(=O)=O)cc1C] | 2.18 | 524 [M − H]− |

TABLE 61
| Compound No. | Structure | RT (min) | MS (M + H)+ |
|---|---|---|---|
| I-259 | 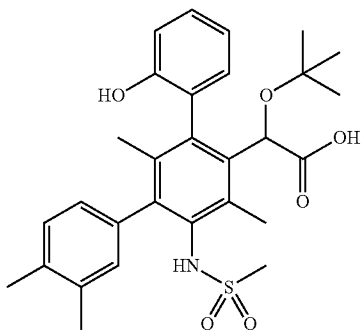 [SMILES: Cc1ccc(-c2c(C)c(-c3ccccc3O)c(C(OC(C)(C)C)C(=O)O)c(C)c2NS(C)(=O)=O)cc1C] | 2.46 | 524 [M − H]− |
| I-260 | 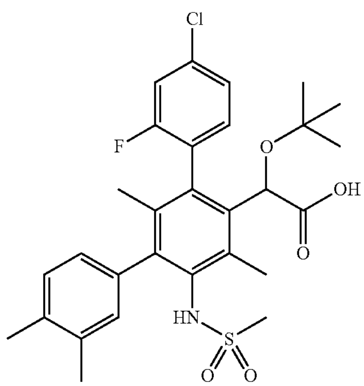 [SMILES: Cc1ccc(-c2c(C)c(-c3ccc(Cl)cc3F)c(C(OC(C)(C)C)C(=O)O)c(C)c2NS(C)(=O)=O)cc1C] | 2.75 | 560 [M − H]− |
| I-261 | 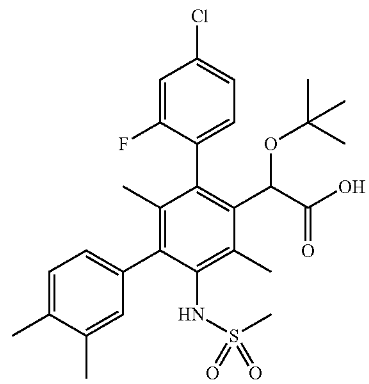 [SMILES: Cc1ccc(-c2c(C)c(-c3ccc(Cl)cc3F)c(C(OC(C)(C)C)C(=O)O)c(C)c2NS(C)(=O)=O)cc1C] | 2.81 | 560 [M − H]− |
| I-262 | 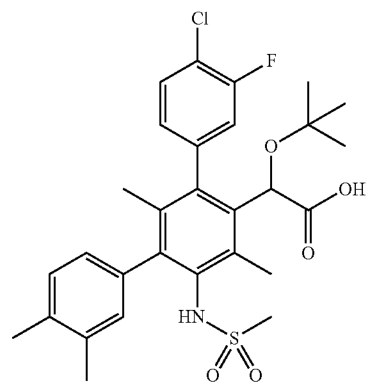 [SMILES: Cc1ccc(-c2c(C)c(-c3ccc(Cl)c(F)c3)c(C(OC(C)(C)C)C(=O)O)c(C)c2NS(C)(=O)=O)cc1C] | 2.81 | 560 [M − H]− |
TABLE 62
| Compound No. | Structure | RT (min) | MS (M + H)+ |
|---|---|---|---|
| I-263 | 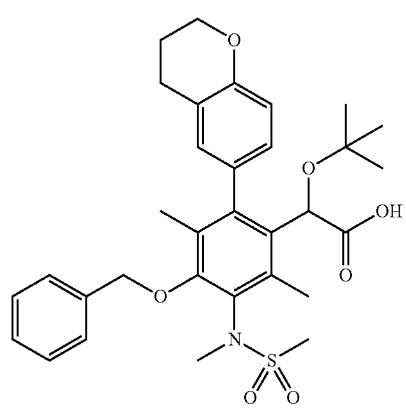 [SMILES: Cc1c(OCc2ccccc2)c(N(C)S(C)(=O)=O)c(C)c(C(OC(C)(C)C)C(=O)O)c1-c1ccc2c(c1)CCCO2] | 2.81 | 580 [M − H]− |
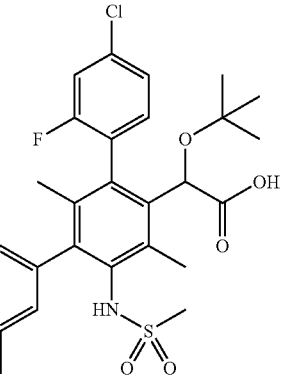
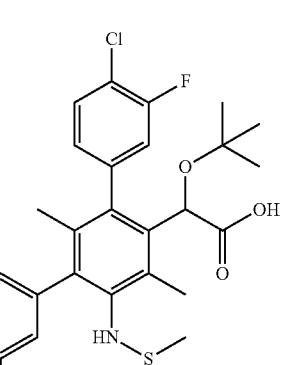

TABLE 62-continued

| Compound No. | Structure | RT (min) | MS (M + H)+ |
|---|---|---|---|
| I-264 | 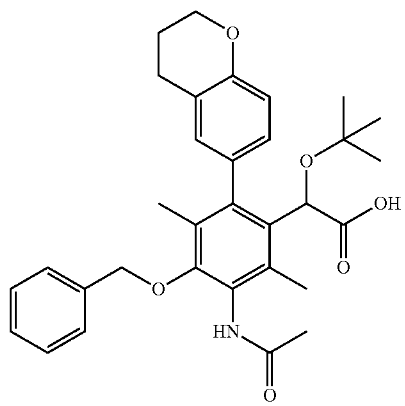 [SMILES: CC(=O)Nc1c(C)c(C(OC(C)(C)C)C(=O)O)c(-c2ccc3c(c2)CCCO3)c(C)c1OCc1ccccc1] | 2.37 | 532 |
| I-265 | 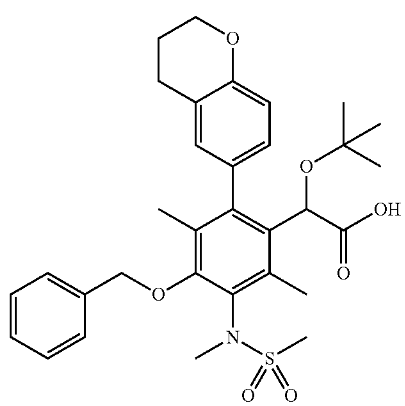 [SMILES: Cc1c(OCc2ccccc2)c(N(C)S(C)(=O)=O)c(C)c(C(OC(C)(C)C)C(=O)O)c1-c1ccc2c(c1)CCCO2] | 2.70 | 580 [M − H]− |
| I-266 | 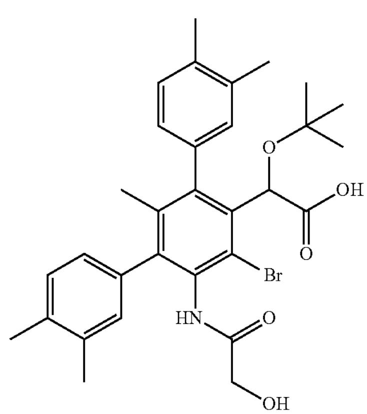 [SMILES: Cc1ccc(-c2c(C)c(-c3ccc(C)c(C)c3)c(C(OC(C)(C)C)C(=O)O)c(Br)c2NC(=O)CO)cc1C] | 2.61 | 581 [M − H]− |

TABLE 63

| Compound No. | Structure | RT (min) | MS (M+H)+ |
|---|---|---|---|
| I-267 | 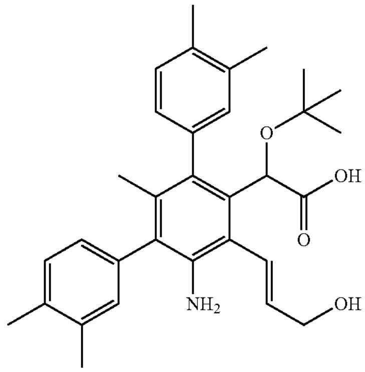 [SMILES: Cc1ccc(-c2c(C)c(-c3ccc(C)c(C)c3)c(C(OC(C)(C)C)C(=O)O)c(/C=C/CO)c2N)cc1C] | 2.90 | 502 |
| I-268 | 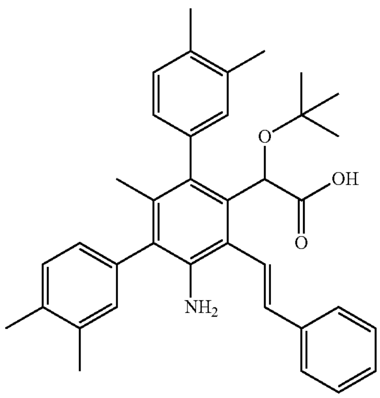 [SMILES: Cc1ccc(-c2c(C)c(-c3ccc(C)c(C)c3)c(C(OC(C)(C)C)C(=O)O)c(/C=C/c3ccccc3)c2N)cc1C] | 3.47 | 548 |
| I-270 | 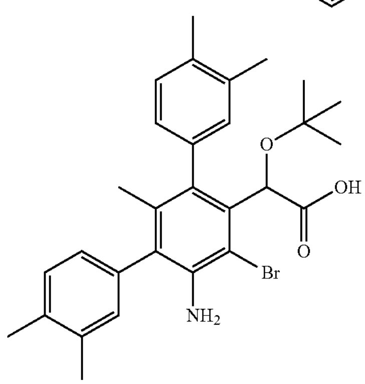 | 3.25 | 526 |
| I-271 | 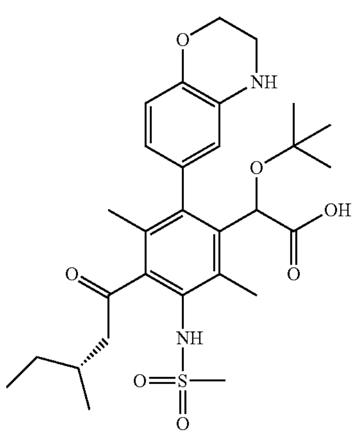 [SMILES: CC[C@@H](C)CC(=O)c1c(C)c(-c2ccc3c(c2)NCCO3)c(C(OC(C)(C)C)C(=O)O)c(C)c1NS(C)(=O)=O] | 1.69, 1.88 | 562, 562 |

TABLE 64

| Compound No. | Structure | RT (min) | MS (M+H)+ |
|---|---|---|---|
| I-272 | 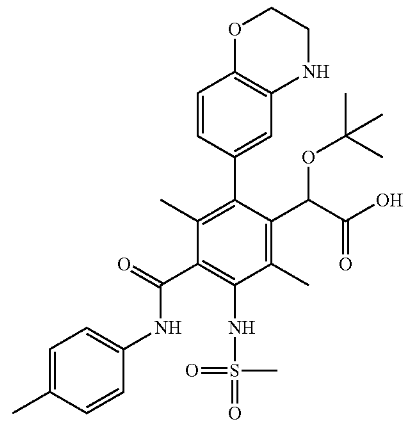 [SMILES: Cc1ccc(NC(=O)c2c(C)c(-c3ccc4c(c3)NCCO4)c(C(OC(C)(C)C)C(=O)O)c(C)c2NS(C)(=O)=O)cc1] | 1.99, 2.16 | 596, 596 |
| I-273 | 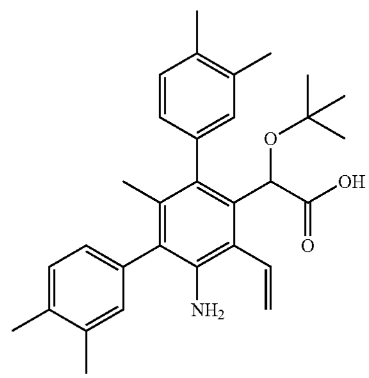 [SMILES: C=Cc1c(N)c(-c2ccc(C)c(C)c2)c(C)c(-c2ccc(C)c(C)c2)c1C(OC(C)(C)C)C(=O)O] | 3.22 | 472 |
| I-274 | 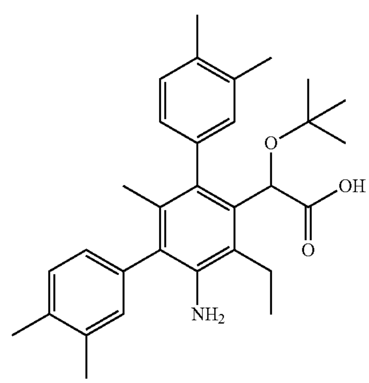 [SMILES: CCc1c(N)c(-c2ccc(C)c(C)c2)c(C)c(-c2ccc(C)c(C)c2)c1C(OC(C)(C)C)C(=O)O] | 3.21 | 474 |

TABLE 65

| Compound No. | Structure | RT (min) | MS (M + H)+ |
|---|---|---|---|
| I-275 | 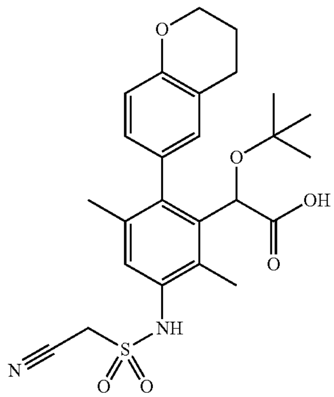 [SMILES: Cc1cc(NS(=O)(=O)CC#N)c(C)c(C(OC(C)(C)C)C(=O)O)c1-c1ccc2c(c1)CCCO2] | 2.27 | 485 [M − H]− |
| I-276 | 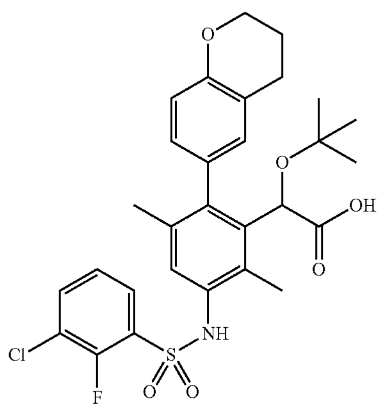 [SMILES: Cc1cc(NS(=O)(=O)c2cccc(Cl)c2F)c(C)c(C(OC(C)(C)C)C(=O)O)c1-c1ccc2c(c1)CCCO2] | 2.69 | 574 [M − H]− |
| I-277 | 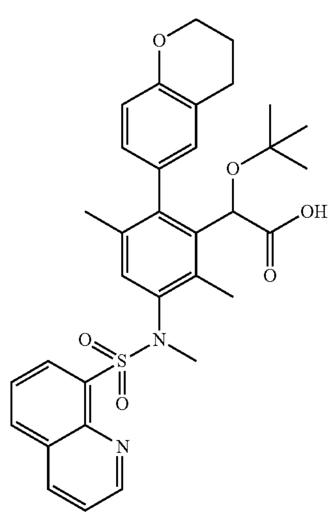 [SMILES: Cc1cc(N(C)S(=O)(=O)c2cccc3cccnc23)c(C)c(C(OC(C)(C)C)C(=O)O)c1-c1ccc2c(c1)CCCO2] | 2.56 | 589 |

TABLE 65-continued

| Compound No. | Structure | RT (min) | MS (M + H)+ |
|---|---|---|---|
| I-278 | 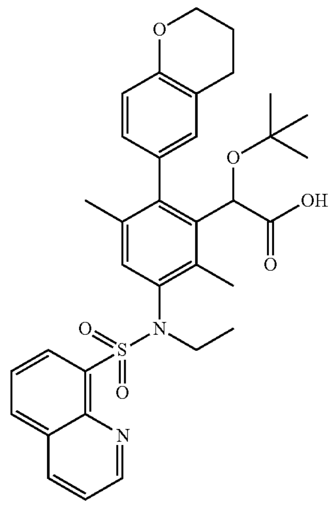 [SMILES: CCN(c1cc(C)c(-c2ccc3c(c2)CCCO3)c(C(OC(C)(C)C)C(=O)O)c1C)S(=O)(=O)c1cccc2cccnc12] | 2.65 | 603 |

TABLE 66

| Compound No. | Structure | RT (min) | MS (M + H)+ |
|---|---|---|---|
| I-279 | 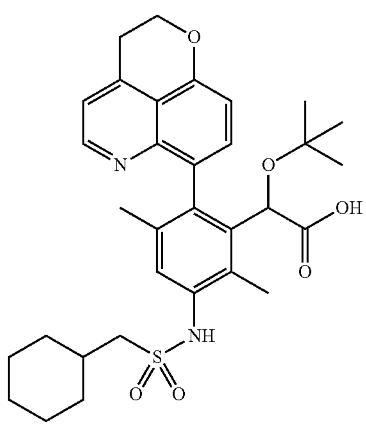 [SMILES: Cc1cc(NS(=O)(=O)CC2CCCCC2)c(C)c(C(OC(C)(C)C)C(=O)O)c1-c1ccc2c3c(ccnc13)CCO2] | 2.10 *2 | 581 |
| I-280 | 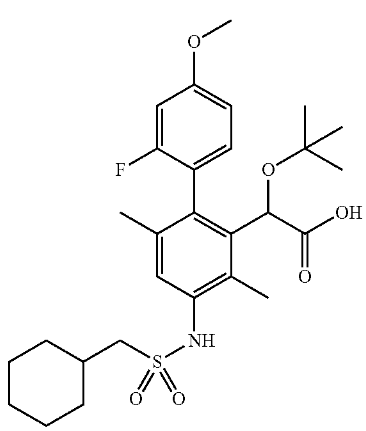 [SMILES: COc1ccc(-c2c(C)cc(NS(=O)(=O)CC3CCCCC3)c(C)c2C(OC(C)(C)C)C(=O)O)c(F)c1] | 2.61 *2 | 534 [M − H]− |

TABLE 66-continued

| Compound No. | Structure | RT (min) | MS (M + H)+ |
|---|---|---|---|
| I-281 | 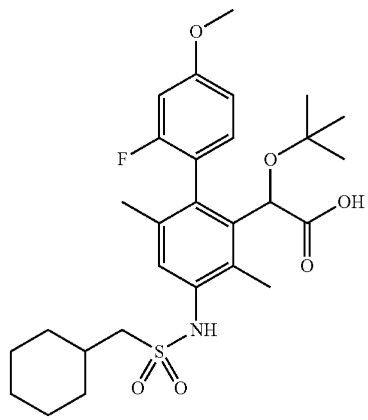 [SMILES: COc1ccc(-c2c(C)cc(NS(=O)(=O)CC3CCCCC3)c(C)c2C(OC(C)(C)C)C(=O)O)c(F)c1] | 2.58 *2 | 534 [M − H]− |
| I-282 | 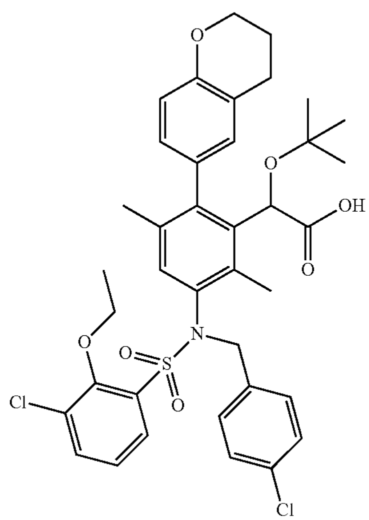 [SMILES: CCOc1c(Cl)cccc1S(=O)(=O)N(Cc1ccc(Cl)cc1)c1cc(C)c(-c2ccc3c(c2)CCCO3)c(C(OC(C)(C)C)C(=O)O)c1C] | 3.40 | 724 [M − H]− |

TABLE 67

| Compound No. | Structure | RT (min) | MS (M + H)+ |
|---|---|---|---|
| I-285 | 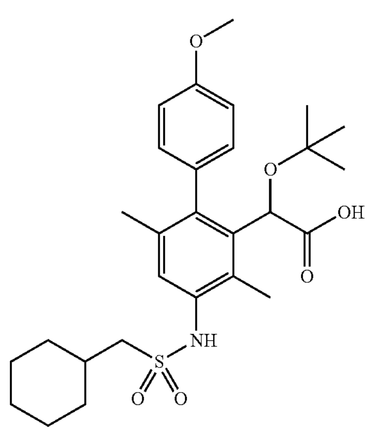 [SMILES: COc1ccc(-c2c(C)cc(NS(=O)(=O)CC3CCCCC3)c(C)c2C(OC(C)(C)C)C(=O)O)cc1] | 2.62 *2 | 516 [M − H]− |

TABLE 67-continued
| Compound No. | Structure | RT (min) | MS (M + H)+ |
|---|---|---|---|
| I-286 | 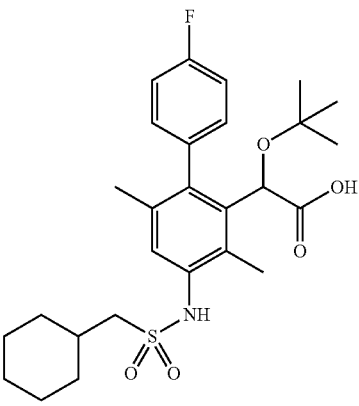 [SMILES: Cc1cc(NS(=O)(=O)CC2CCCCC2)c(C)c(C(OC(C)(C)C)C(=O)O)c1-c1ccc(F)cc1] | 2.66 | *2 504 [M − H]− |
| I-287 | 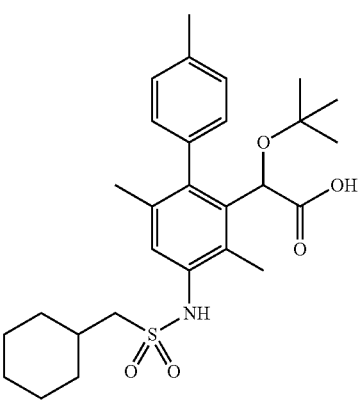 [SMILES: Cc1ccc(-c2c(C)cc(NS(=O)(=O)CC3CCCCC3)c(C)c2C(OC(C)(C)C)C(=O)O)cc1] | 2.77 | *2 500 [M − H]− |
| I-288 | 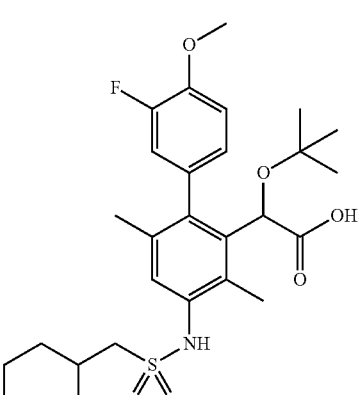 | 2.59 | *2 534 [M − H]− |

TABLE 68
| Compound No. | Structure | RT (min) | MS (M + H)+ |
|---|---|---|---|
| I-289 | 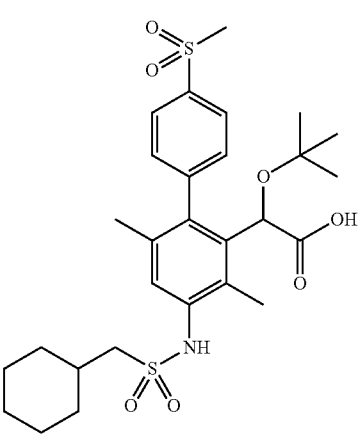 [SMILES: Cc1cc(NS(=O)(=O)CC2CCCCC2)c(C)c(C(OC(C)(C)C)C(=O)O)c1-c1ccc(S(C)(=O)=O)cc1] | 2.26 | *2 564 [M − H]− |
| I-290 | 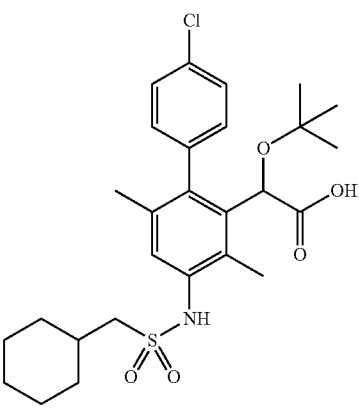 [SMILES: Cc1cc(NS(=O)(=O)CC2CCCCC2)c(C)c(C(OC(C)(C)C)C(=O)O)c1-c1ccc(Cl)cc1] | 2.78 | *2 520 [M − H]− |
| I-291 | 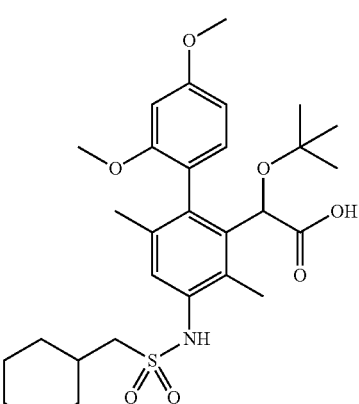 | 2.55 | *2 546 [M − H]− |

TABLE 68-continued

| Compound No. | Structure | RT (min) | MS (M + H)+ |
|---|---|---|---|
| I-292 | 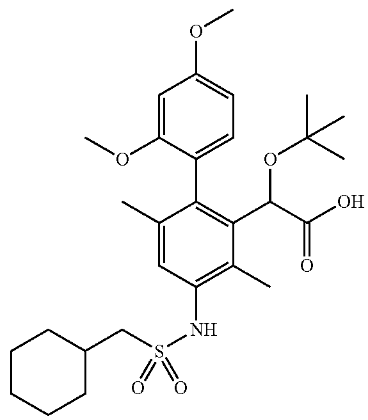 [SMILES: COc1ccc(-c2c(C)cc(NS(=O)(=O)CC3CCCCC3)c(C)c2C(OC(C)(C)C)C(=O)O)c(OC)c1] | 2.60 | *2 546 [M − H]− |

TABLE 69

| Compound No. | Structure | RT (min) | MS (M + H)+ |
|---|---|---|---|
| I-293 | 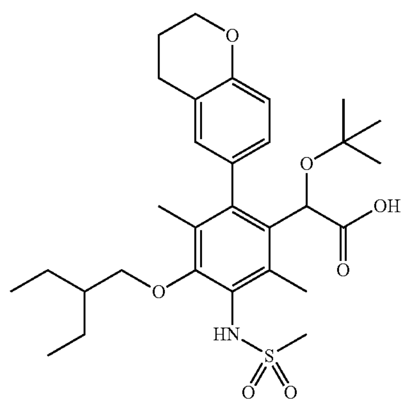 [SMILES: CCC(CC)COc1c(C)c(-c2ccc3c(c2)CCCO3)c(C(OC(C)(C)C)C(=O)O)c(C)c1NS(C)(=O)=O] | 2.86 | 560 [M − H]− |
| I-294 | 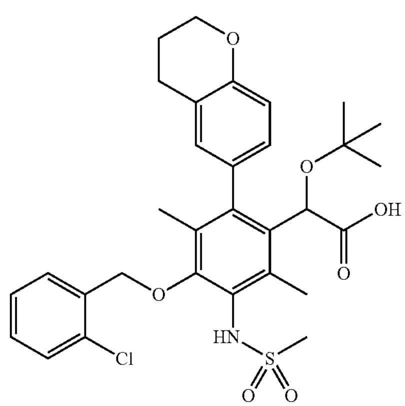 [SMILES: Cc1c(OCc2ccccc2Cl)c(NS(C)(=O)=O)c(C)c(C(OC(C)(C)C)C(=O)O)c1-c1ccc2c(c1)CCCO2] | 2.67 | 600 [M − H]− |

TABLE 69-continued

| Compound No. | Structure | RT (min) | MS (M + H)+ |
|---|---|---|---|
| I-295 | 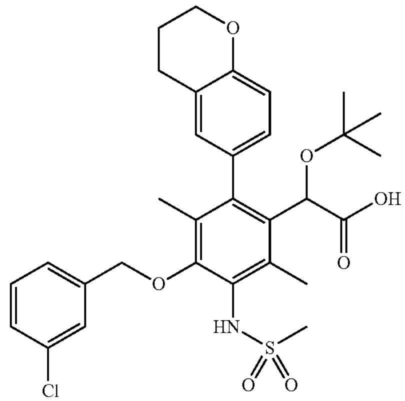 [SMILES: Cc1c(OCc2cccc(Cl)c2)c(NS(C)(=O)=O)c(C)c(C(OC(C)(C)C)C(=O)O)c1-c1ccc2c(c1)CCCO2] | 2.68 | 600 [M − H]− |
| I-297 | 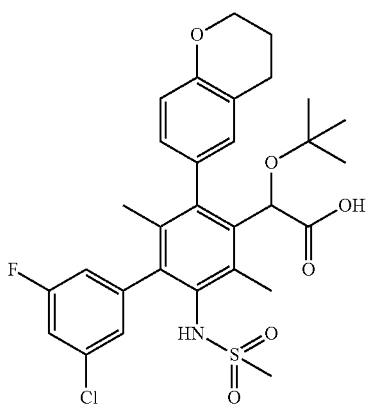 [SMILES: Cc1c(-c2cc(F)cc(Cl)c2)c(NS(C)(=O)=O)c(C)c(C(OC(C)(C)C)C(=O)O)c1-c1ccc2c(c1)CCCO2] | 2.66 | 588 [M − H]− |

TABLE 70

| Compound No. | Structure | RT (min) | MS (M + H)+ |
|---|---|---|---|
| I-298 | 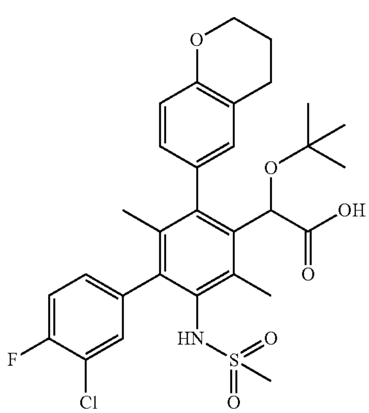 [SMILES: Cc1c(-c2ccc(F)c(Cl)c2)c(NS(C)(=O)=O)c(C)c(C(OC(C)(C)C)C(=O)O)c1-c1ccc2c(c1)CCCO2] | 2.60 | 588 [M − H]− |

TABLE 70-continued

| Compound No. | Structure | RT (min) | MS (M + H)+ |
|---|---|---|---|
| I-299 | 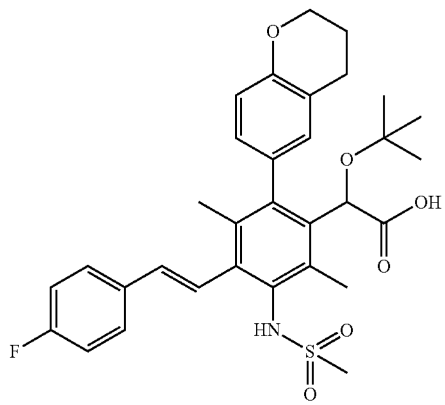 [SMILES: Cc1c(/C=C/c2ccc(F)cc2)c(NS(C)(=O)=O)c(C)c(C(OC(C)(C)C)C(=O)O)c1-c1ccc2c(c1)CCCO2] | 2.59 | 580 [M − H]− |
| I-302 | 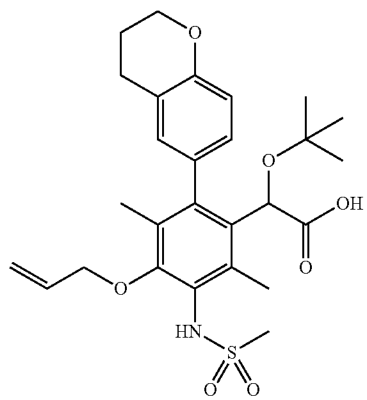 [SMILES: C=CCOc1c(C)c(-c2ccc3c(c2)CCCO3)c(C(OC(C)(C)C)C(=O)O)c(C)c1NS(C)(=O)=O] | 2.34 | 516 [M − H]− |
| I-303 | 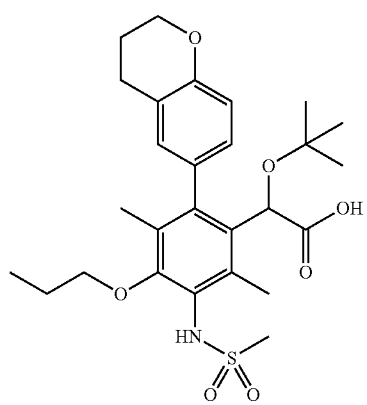 [SMILES: CCCOc1c(C)c(-c2ccc3c(c2)CCCO3)c(C(OC(C)(C)C)C(=O)O)c(C)c1NS(C)(=O)=O] | 2.43 | 518 [M − H]− |

TABLE 71

| Compound No. | Structure | RT (min) | | MS (M + H)+ |
|---|---|---|---|---|
| I-304 | 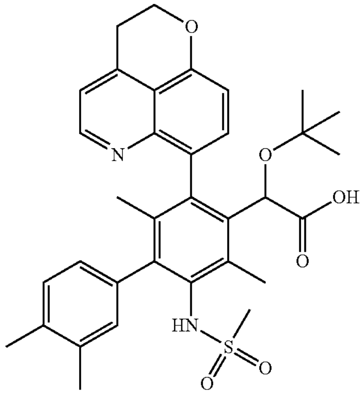 [SMILES: Cc1ccc(-c2c(C)c(-c3ccc4c5c(ccnc35)CCO4)c(C(OC(C)(C)C)C(=O)O)c(C)c2NS(C)(=O)=O)cc1C] | 2.05 | *2 | 603 |
| I-305 | 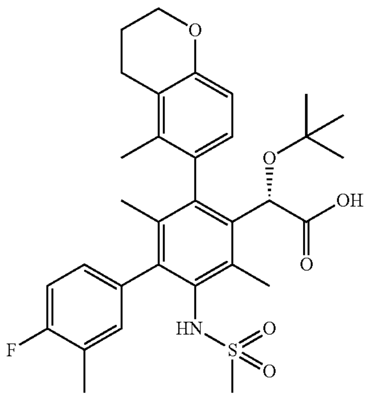 [SMILES: Cc1cc(-c2c(C)c(-c3ccc4c(c3C)CCCO4)c([C@H](OC(C)(C)C)C(=O)O)c(C)c2NS(C)(=O)=O)ccc1F] | 2.66 | *2 | 582 [M − H]− |
| I-306 | 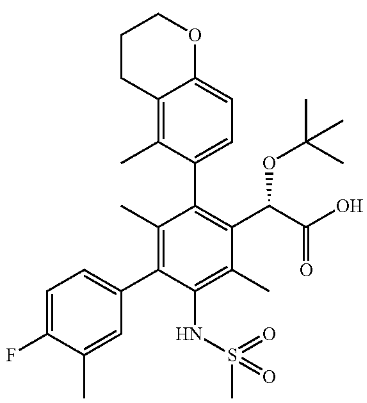 [SMILES: Cc1cc(-c2c(C)c(-c3ccc4c(c3C)CCCO4)c([C@H](OC(C)(C)C)C(=O)O)c(C)c2NS(C)(=O)=O)ccc1F] | 2.33 | *2 | 582 [M − H]− |
| I-307 | 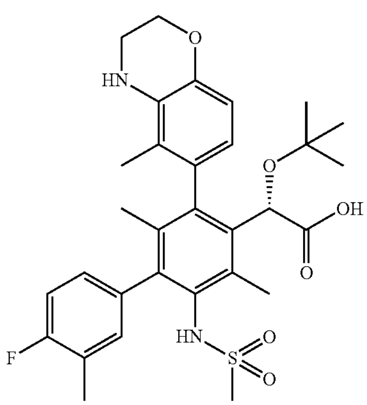 [SMILES: Cc1cc(-c2c(C)c(-c3ccc4c(c3C)NCCO4)c([C@H](OC(C)(C)C)C(=O)O)c(C)c2NS(C)(=O)=O)ccc1F] | 2.24 | *2 | 583 [M − H]− |

TABLE 72
| Compound No. | Structure | RT(min) | MS(M + H)+ |
| --- | --- | --- | --- |
| I-308 | 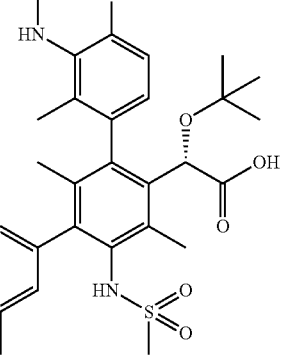 | 2.40 *2 | 583 [M − H]− |
| I-309 | 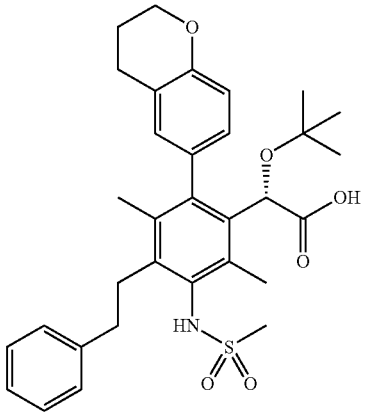 [SMILES: Cc1c(CCc2ccccc2)c(NS(C)(=O)=O)c(C)c([C@H](OC(C)(C)C)C(=O)O)c1-c1ccc2c(c1)CCCO2] | 2.61 | 564 [M − H]− |
| I-310 | 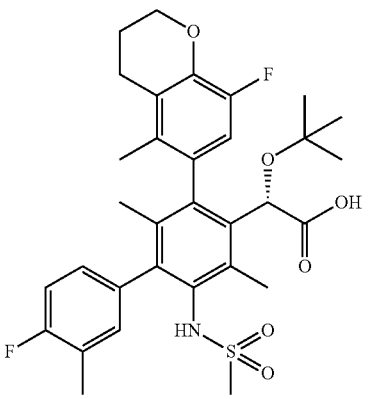 | 2.61 *2 | 600 [M − H]− |
| I-311 | 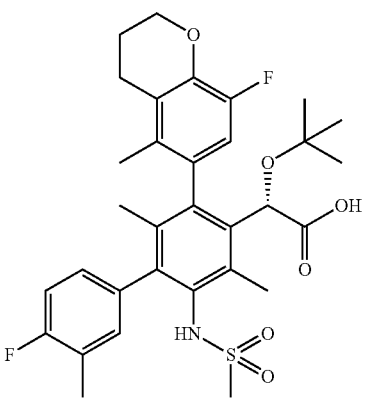 | 2.59 *2 | 600 [M − H]− |

TABLE 73

| Compound No. | Structure | RT(min) | MS(M + H)+ |
|---|---|---|---|
| I-312 | 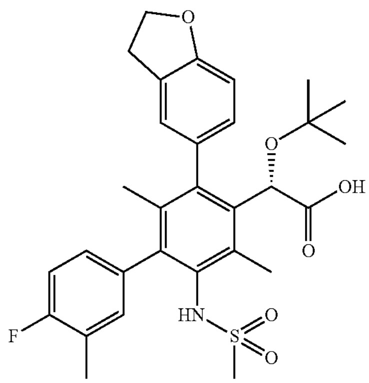 [SMILES: Cc1cc(-c2c(C)c(-c3ccc4c(c3)CCO4)c([C@H](OC(C)(C)C)C(=O)O)c(C)c2NS(C)(=O)=O)ccc1F] | 2.47, 2.51 *2 | 554, [M − H]− 554 |

TABLE 74

| Compound No. | Structure | RT(min) | MS(M + H)+ |
|---|---|---|---|
| II-7 | 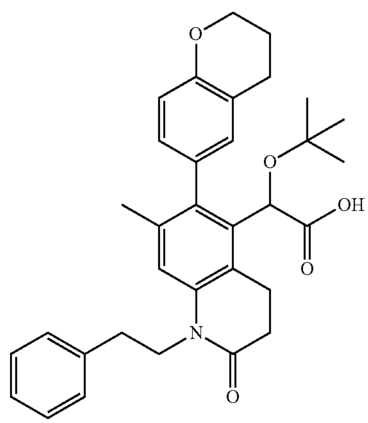 [SMILES: Cc1cc2c(c(C(OC(C)(C)C)C(=O)O)c1-c1ccc3c(c1)CCCO3)CCC(=O)N2CCc1ccccc1] | 2.73 | 528 |
| II-9 | 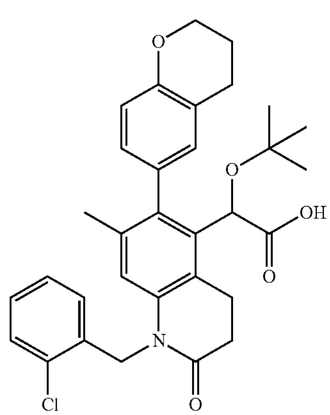 [SMILES: Cc1cc2c(c(C(OC(C)(C)C)C(=O)O)c1-c1ccc3c(c1)CCCO3)CCC(=O)N2Cc1ccccc1Cl] | 2.21 *3 | 548 |

TABLE 74-continued
| Compound No. | Structure | RT(min) | MS(M + H)+ |
|---|---|---|---|
| II-10 | 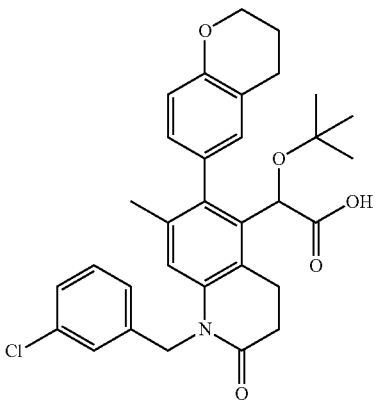 [SMILES: Cc1cc2c(c(C(OC(C)(C)C)C(=O)O)c1-c1ccc3c(c1)CCCO3)CCC(=O)N2Cc1cccc(Cl)c1] | 2.21 *3 | 548 |
| II-11 | 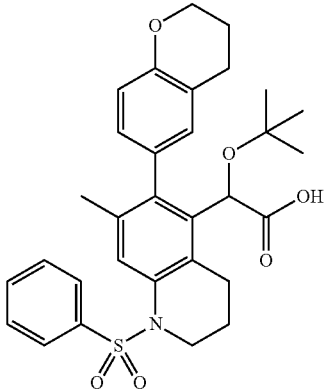 [SMILES: Cc1cc2c(c(C(OC(C)(C)C)C(=O)O)c1-c1ccc3c(c1)CCCO3)CCCN2S(=O)(=O)c1ccccc1] | 2.77 | 548 [M − H]− |
TABLE 75
| Compound No. | Structure | RT(min) | MS(M + H)+ |
|---|---|---|---|
| II-12 | 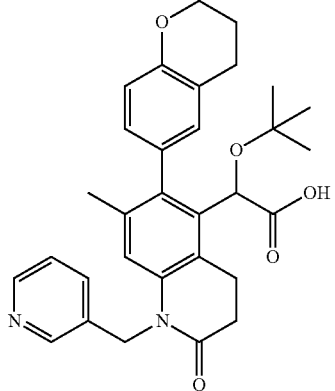 | 1.43 *3 | 515 |

TABLE 75-continued
| Compound No. | Structure | RT(min) | MS(M + H)+ |
|---|---|---|---|
| II-13 | 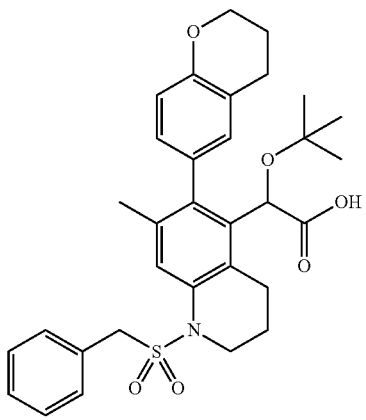 [SMILES: Cc1cc2c(c(C(OC(C)(C)C)C(=O)O)c1-c1ccc3c(c1)CCCO3)CCCN2S(=O)(=O)Cc1ccccc1] | 2.77 | 562 [M − H]− |
| II-14 | 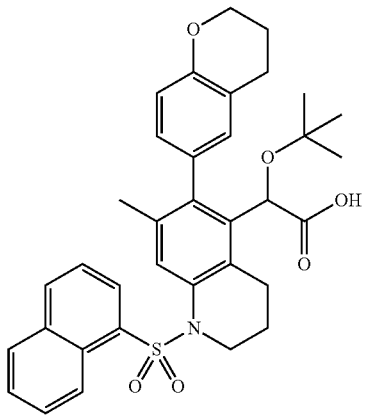 [SMILES: Cc1cc2c(c(C(OC(C)(C)C)C(=O)O)c1-c1ccc3c(c1)CCCO3)CCCN2S(=O)(=O)c1cccc2ccccc12] | 2.96 | 598 [M − H]− |
| II-15 | 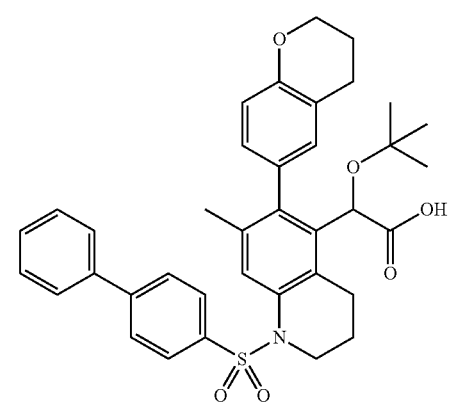 [SMILES: Cc1cc2c(c(C(OC(C)(C)C)C(=O)O)c1-c1ccc3c(c1)CCCO3)CCCN2S(=O)(=O)c1ccc(-c2ccccc2)cc1] | 2.27 *3 | 626 |

TABLE 76
| Compound No. | Structure | RT(min) | MS(M + H)+ |
|---|---|---|---|
| II-16 | 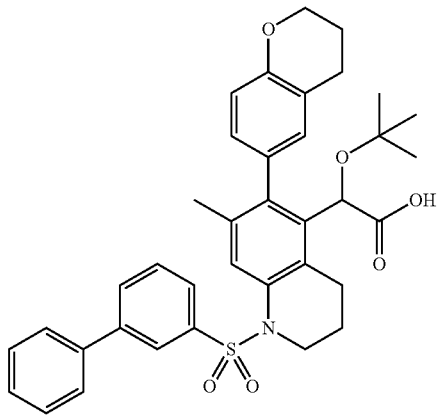 [SMILES: Cc1cc2c(c(C(OC(C)(C)C)C(=O)O)c1-c1ccc3c(c1)CCCO3)CCCN2S(=O)(=O)c1cccc(-c2ccccc2)c1] | 2.24  *3 | 626 |
| II-17 | 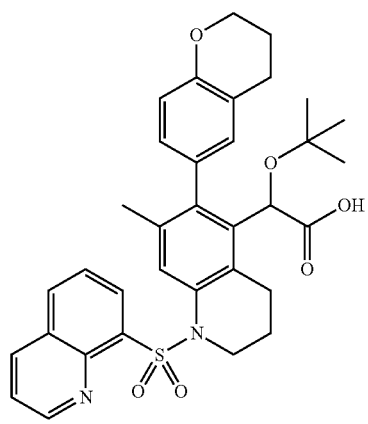 [SMILES: Cc1cc2c(c(C(OC(C)(C)C)C(=O)O)c1-c1ccc3c(c1)CCCO3)CCCN2S(=O)(=O)c1cccc2cccnc12] | 2.08  *3 | 601 |
| II-18 | 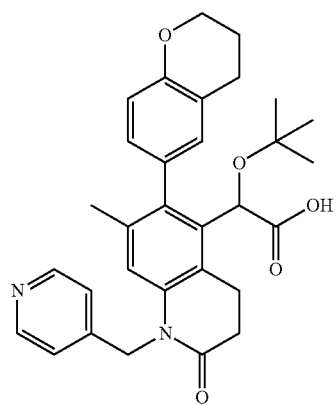 [SMILES: Cc1cc2c(c(C(OC(C)(C)C)C(=O)O)c1-c1ccc3c(c1)CCCO3)CCC(=O)N2Cc1ccncc1] | 1.70  *3 | 515 |

TABLE 76-continued

| Compound No. | Structure | RT(min) | | MS(M + H)+ |
|---|---|---|---|---|
| II-19 | 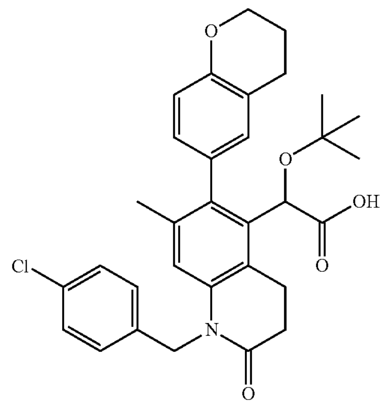 [SMILES: Cc1cc2c(c(C(OC(C)(C)C)C(=O)O)c1-c1ccc3c(c1)CCCO3)CCC(=O)N2Cc1ccc(Cl)cc1] | 1.93 | *3 | 548 |

TABLE 77

| Compound No. | Structure | RT(min) | | MS(M + H)+ |
|---|---|---|---|---|
| II-20 | 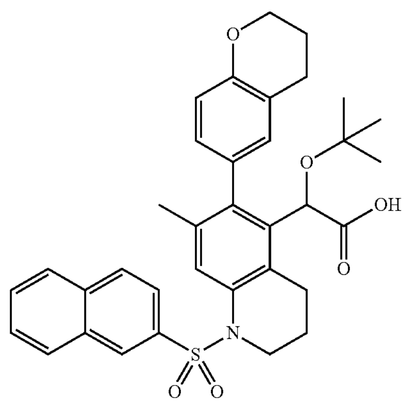 [SMILES: Cc1cc2c(c(C(OC(C)(C)C)C(=O)O)c1-c1ccc3c(c1)CCCO3)CCCN2S(=O)(=O)c1ccc2ccccc2c1] | 2.23 | *3 | 600 |
| II-22 | 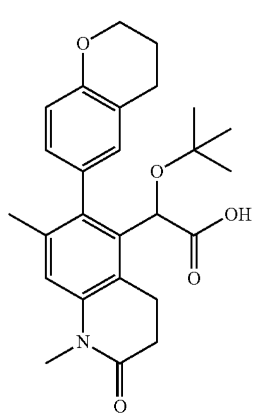 [SMILES: Cc1cc2c(c(C(OC(C)(C)C)C(=O)O)c1-c1ccc3c(c1)CCCO3)CCC(=O)N2C] | 2.30 | | 438 |

TABLE 77-continued

| Compound No. | Structure | RT(min) | MS(M + H)+ |
|---|---|---|---|
| II-23 | 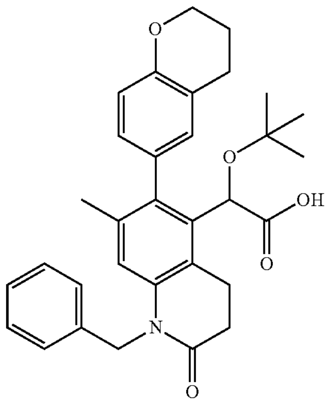 [SMILES: Cc1cc2c(c(C(OC(C)(C)C)C(=O)O)c1-c1ccc3c(c1)CCCO3)CCC(=O)N2Cc1ccccc1] | 2.67 | 514 |
| II-24 | 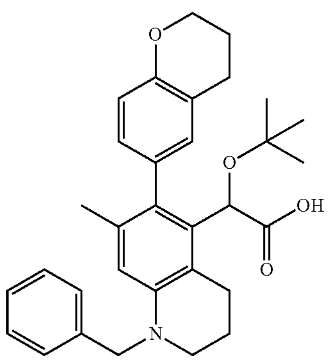 [SMILES: Cc1cc2c(c(C(OC(C)(C)C)C(=O)O)c1-c1ccc3c(c1)CCCO3)CCCN2Cc1ccccc1] | 3.04 | 501 |

TABLE 78

| Compound No. | Structure | RT(min) | MS(M + H)+ |
|---|---|---|---|
| II-25 | 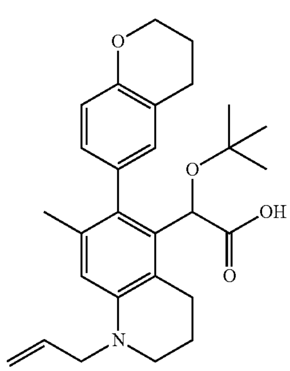 [SMILES: C=CCN1CCCc2c1cc(C)c(-c1ccc3c(c1)CCCO3)c2C(OC(C)(C)C)C(=O)O] | 2.85 | 450 |

TABLE 78-continued

| Compound No. | Structure | RT(min) | MS(M + H)+ |
|---|---|---|---|
| II-26 | 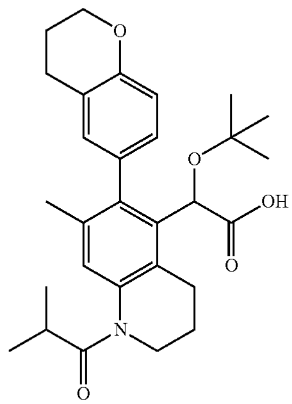 [SMILES: Cc1cc2c(c(C(OC(C)(C)C)C(=O)O)c1-c1ccc3c(c1)CCCO3)CCCN2C(=O)C(C)C] | 2.49 | 480 |
| II-27 | 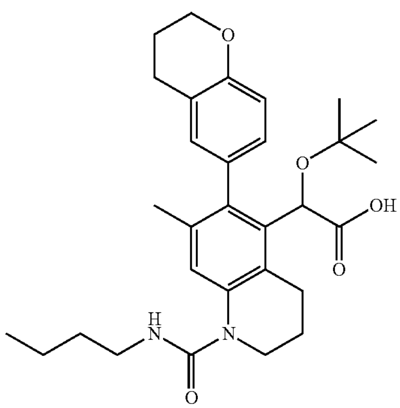 [SMILES: CCCCNC(=O)N1CCCc2c1cc(C)c(-c1ccc3c(c1)CCCO3)c2C(OC(C)(C)C)C(=O)O] | 2.51 | 509 |
| II-28 | 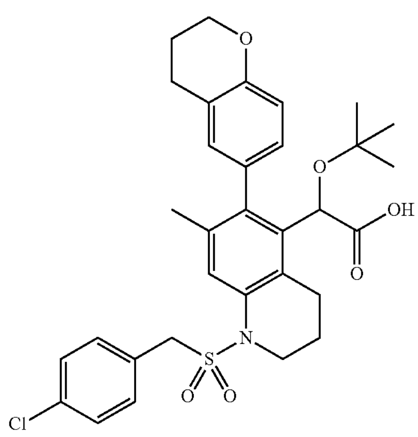 [SMILES: Cc1cc2c(c(C(OC(C)(C)C)C(=O)O)c1-c1ccc3c(c1)CCCO3)CCCN2S(=O)(=O)Cc1ccc(Cl)cc1] | 2.92 | 596 [M − H]− |

TABLE 79
| Compound No. | Structure | RT(min) | MS(M + H)+ |
|---|---|---|---|
| II-29 | 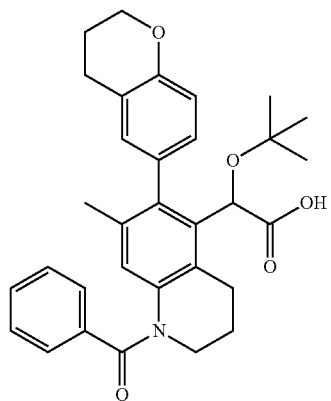 [SMILES: Cc1cc2c(c(C(OC(C)(C)C)C(=O)O)c1-c1ccc3c(c1)CCCO3)CCCN2C(=O)c1ccccc1] | 2.60 | 514 |
| II-30 | 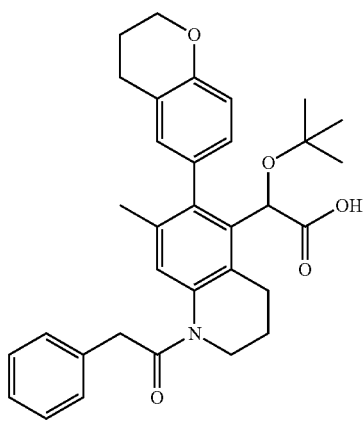 [SMILES: Cc1cc2c(c(C(OC(C)(C)C)C(=O)O)c1-c1ccc3c(c1)CCCO3)CCCN2C(=O)Cc1ccccc1] | 2.70 | 528 |
| II-31 | 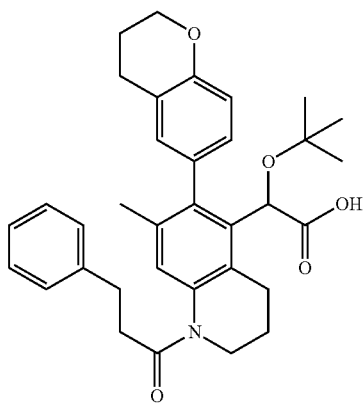 [SMILES: Cc1cc2c(c(C(OC(C)(C)C)C(=O)O)c1-c1ccc3c(c1)CCCO3)CCCN2C(=O)CCc1ccccc1] | 2.77 | 542 |

TABLE 79-continued
| Compound No. | Structure | RT(min) | MS(M + H)+ |
|---|---|---|---|
| II-32 | 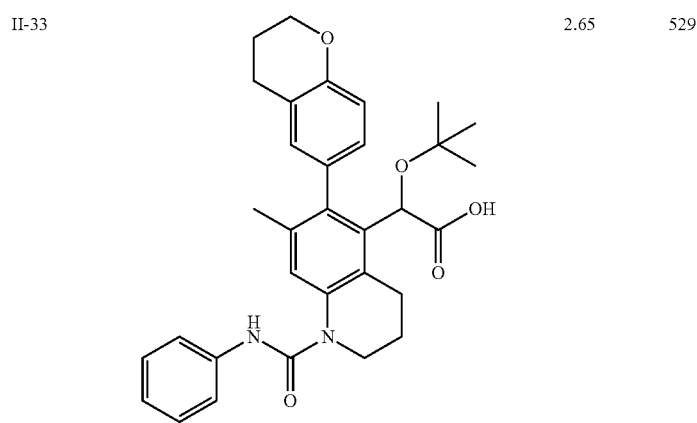 | 2.87 | 520 |
TABLE 80
| Compound No. | Structure | RT(min) | MS(M + H)+ |
|---|---|---|---|
| II-33 | 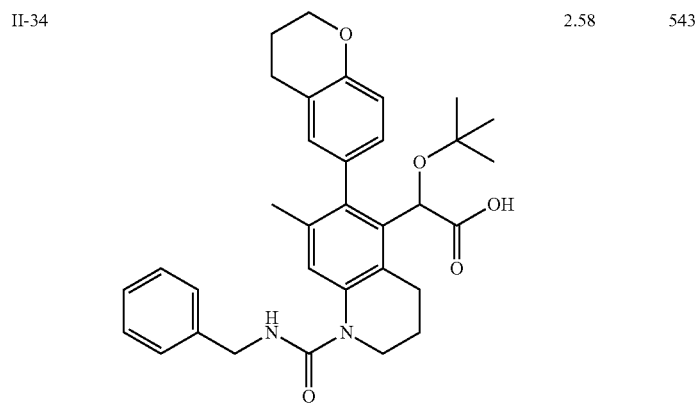 | 2.65 | 529 |
| II-34 | 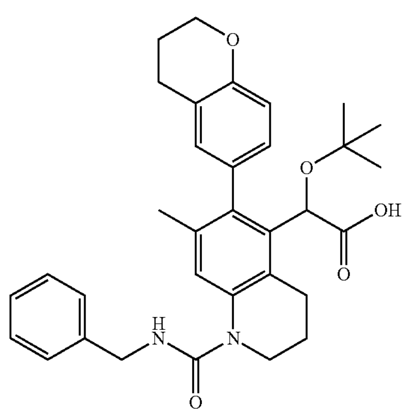 [SMILES: Cc1cc2c(c(C(OC(C)(C)C)C(=O)O)c1-c1ccc3c(c1)CCCO3)CCCN2C(=O)NCc1ccccc1] | 2.58 | 543 |

TABLE 80-continued

| Compound No. | Structure | RT(min) | MS(M + H)+ |
|---|---|---|---|
| II-35 | 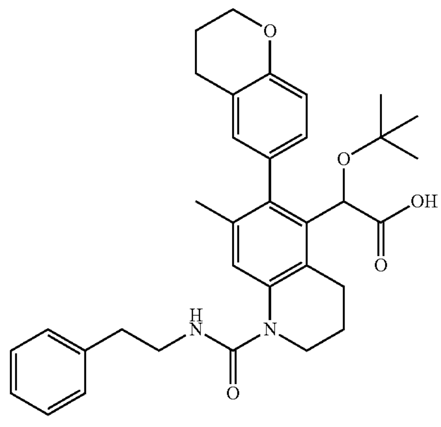 [SMILES: Cc1cc2c(c(C(OC(C)(C)C)C(=O)O)c1-c1ccc3c(c1)CCCO3)CCCN2C(=O)NCCc1ccccc1] | 2.66 | 557 |
| II-36 | 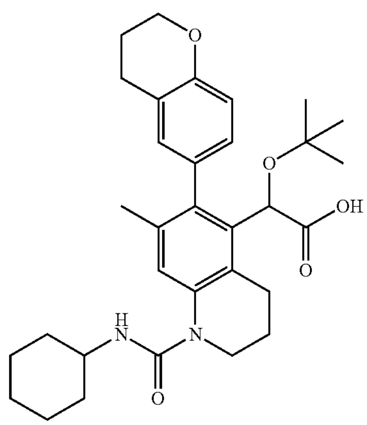 [SMILES: Cc1cc2c(c(C(OC(C)(C)C)C(=O)O)c1-c1ccc3c(c1)CCCO3)CCCN2C(=O)NC1CCCCC1] | 2.76 | 535 |

TABLE 81

| Compound No. | Structure | RT(min) | MS(M + H)+ |
|---|---|---|---|
| II-37 | 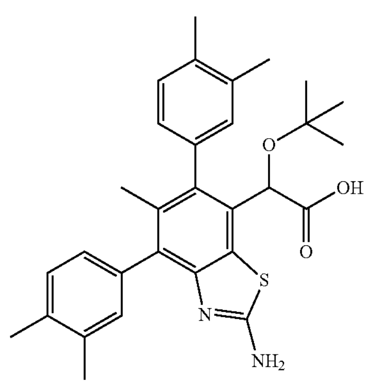 [SMILES: Cc1ccc(-c2c(C)c(-c3ccc(C)c(C)c3)c3nc(N)sc3c2C(OC(C)(C)C)C(=O)O)cc1C] | 2.48 | 503 |

TABLE 81-continued

| Compound No. | Structure | RT(min) | MS(M + H)+ |
|---|---|---|---|
| II-38 | 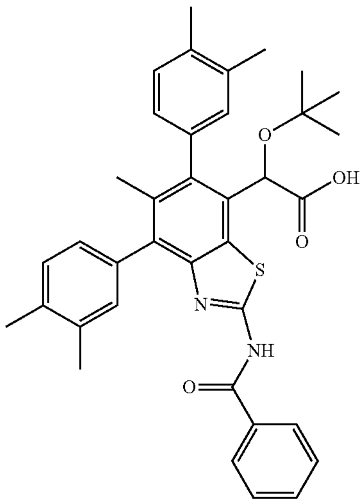 [SMILES: Cc1ccc(-c2c(C)c(-c3ccc(C)c(C)c3)c3nc(NC(=O)c4ccccc4)sc3c2C(OC(C)(C)C)C(=O)O)cc1C] | 3.34 | 607 |
| II-39 | 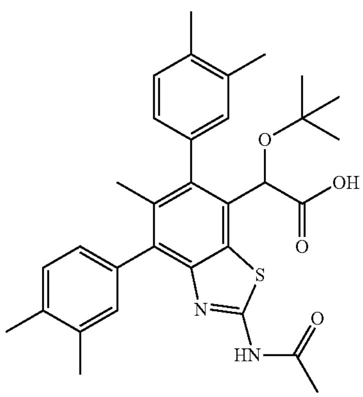 [SMILES: CC(=O)Nc1nc2c(-c3ccc(C)c(C)c3)c(C)c(-c3ccc(C)c(C)c3)c(C(OC(C)(C)C)C(=O)O)c2s1] | 3.18 | 545 |
| II-40 | 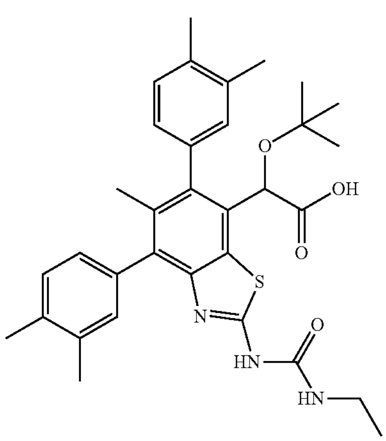 [SMILES: CCNC(=O)Nc1nc2c(-c3ccc(C)c(C)c3)c(C)c(-c3ccc(C)c(C)c3)c(C(OC(C)(C)C)C(=O)O)c2s1] | 3.28 | 574 |

TABLE 82

| Compound No. | Structure | RT(min) | MS(M + H)+ |
| --- | --- | --- | --- |
| II-41 | 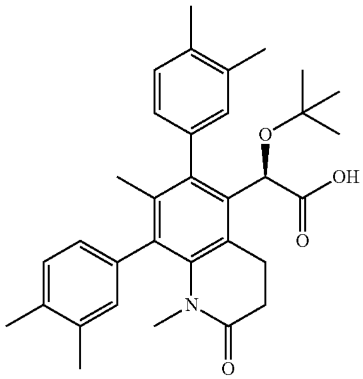 [SMILES: Cc1ccc(-c2c(C)c(-c3ccc(C)c(C)c3)c3c(c2[C@@H](OC(C)(C)C)C(=O)O)CCC(=O)N3C)cc1C] | 3.20 | 514 |
| II-42 | 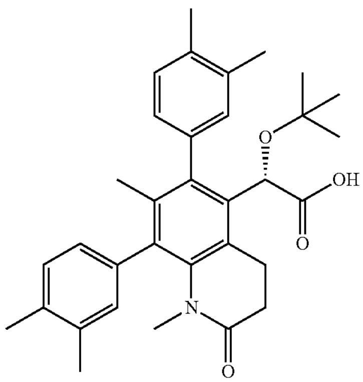 [SMILES: Cc1ccc(-c2c(C)c(-c3ccc(C)c(C)c3)c3c(c2[C@H](OC(C)(C)C)C(=O)O)CCC(=O)N3C)cc1C] | 3.20 | 514 |
| II-43 | 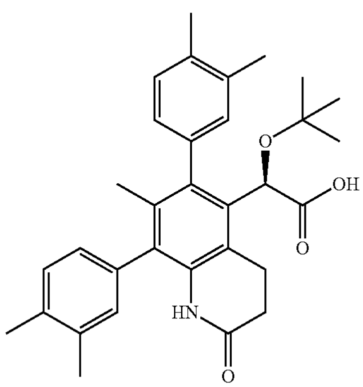 | 3.12 | 500 |
| II-44 | 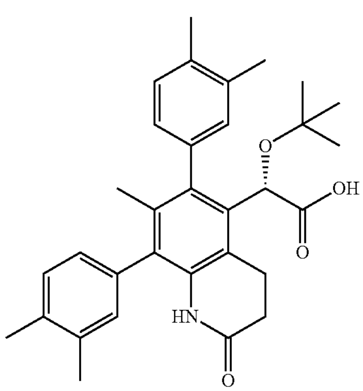 | 3.12 | 500 |

TABLE 83

| Compound No. | Structure | RT(min) | MS(M + H)+ |
|---|---|---|---|
| II-45 | 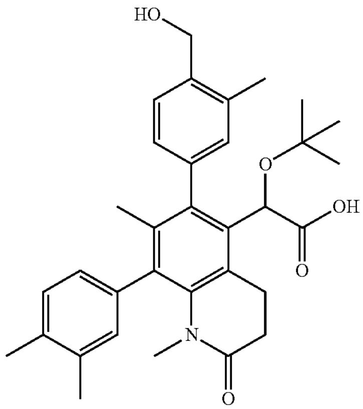 [SMILES: Cc1ccc(-c2c(C)c(-c3ccc(CO)c(C)c3)c(C(OC(C)(C)C)C(=O)O)c3c2N(C)C(=O)CC3)cc1C] | 2.40, 2.51 | 530, 530 |
| II-46 | 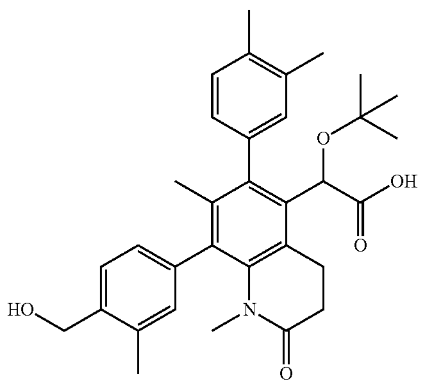 [SMILES: Cc1ccc(-c2c(C)c(-c3ccc(CO)c(C)c3)c3c(c2C(OC(C)(C)C)C(=O)O)CCC(=O)N3C)cc1C] | 2.55 | 530 |
| II-47 | 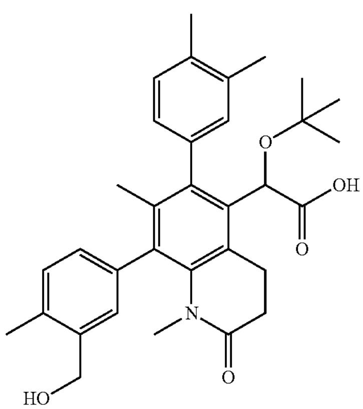 [SMILES: Cc1ccc(-c2c(C)c(-c3ccc(C)c(CO)c3)c3c(c2C(OC(C)(C)C)C(=O)O)CCC(=O)N3C)cc1C] | 2.65 | 530 |
| II-48 | 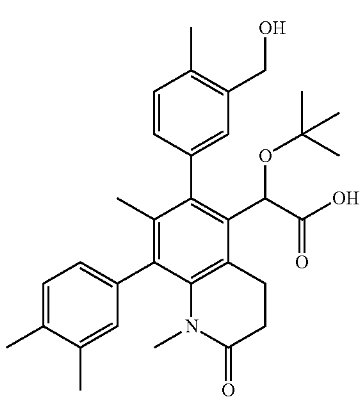 [SMILES: Cc1ccc(-c2c(C)c(-c3ccc(C)c(CO)c3)c(C(OC(C)(C)C)C(=O)O)c3c2N(C)C(=O)CC3)cc1C] | 2.22, 2.59 | 530, 530 |

TABLE 84

| Compound No. | Structure | RT(min) | MS(M + H)+ |
|---|---|---|---|
| II-49 | 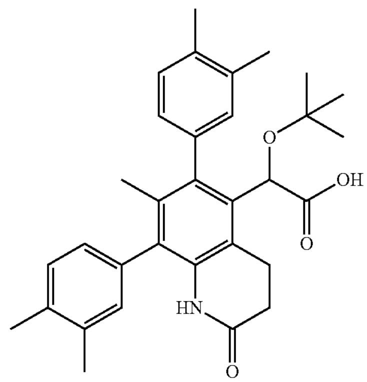 [SMILES: Cc1ccc(-c2c(C)c(-c3ccc(C)c(C)c3)c(C(OC(C)(C)C)C(=O)O)c3c2NC(=O)CC3)cc1C] | 3.00 | 500 |
| II-50 | 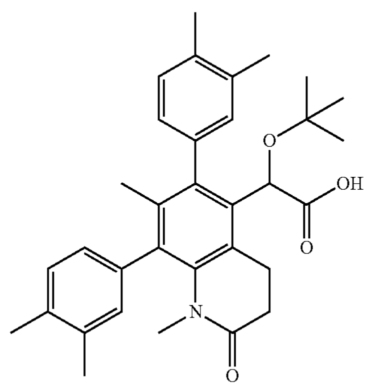 | 3.07 | 514 |
| II-51 | 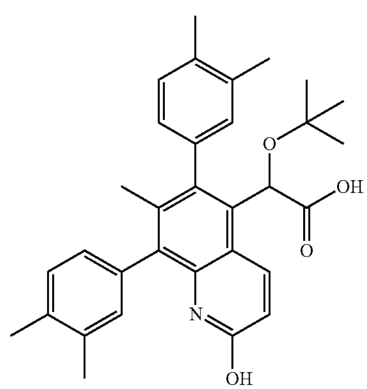 [SMILES: Cc1ccc(-c2c(C)c(-c3ccc(C)c(C)c3)c3nc(O)ccc3c2C(OC(C)(C)C)C(=O)O)cc1C] | 2.93 | 498 |
| II-54 | 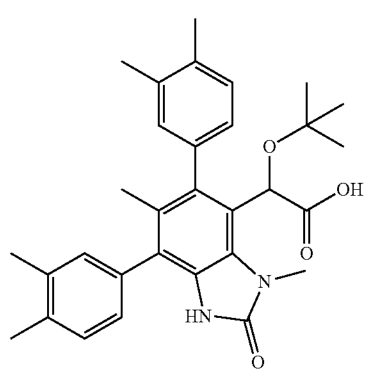 [SMILES: Cc1ccc(-c2c(C)c(-c3ccc(C)c(C)c3)c3[nH]c(=O)n(C)c3c2C(OC(C)(C)C)C(=O)O)cc1C] | 2.96 | 501 |

TABLE 85

| Compound No. | Structure | RT(min) | MS(M + H)+ |
|---|---|---|---|
| II-55 | 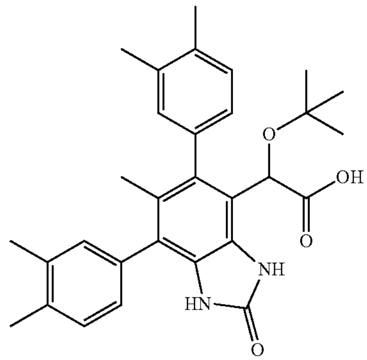 [SMILES: Cc1ccc(-c2c(C)c(-c3ccc(C)c(C)c3)c3[nH]c(=O)[nH]c3c2C(OC(C)(C)C)C(=O)O)cc1C] | 2.78 *2 | 487 |
| II-56 | 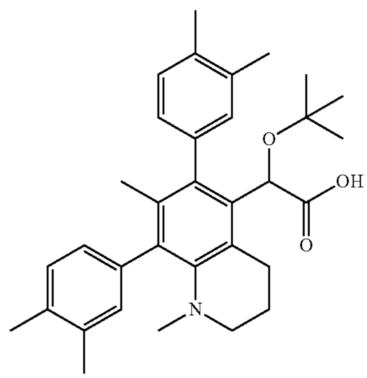 [SMILES: Cc1ccc(-c2c(C)c(-c3ccc(C)c(C)c3)c3c(c2C(OC(C)(C)C)C(=O)O)CCCN3C)cc1C] | 2.44 | 500 |
| II-57 | 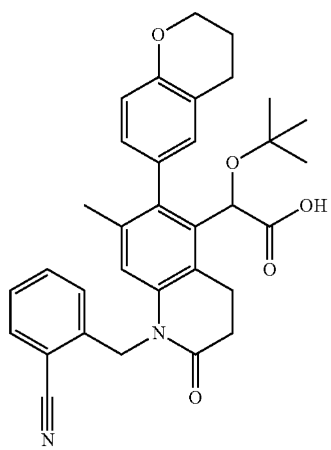 [SMILES: Cc1cc2c(c(C(OC(C)(C)C)C(=O)O)c1-c1ccc3c(c1)CCCO3)CCC(=O)N2Cc1ccccc1C#N] | 2.05 *3 | 539 |
| II-58 | 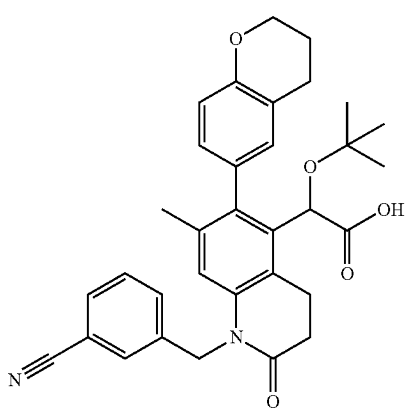 [SMILES: Cc1cc2c(c(C(OC(C)(C)C)C(=O)O)c1-c1ccc3c(c1)CCCO3)CCC(=O)N2Cc1cccc(C#N)c1] | 2.04 *3 | 539 |

TABLE 86

| Compound No. | Structure | RT(min) | MS(M + H)+ |
|---|---|---|---|
| II-59 | 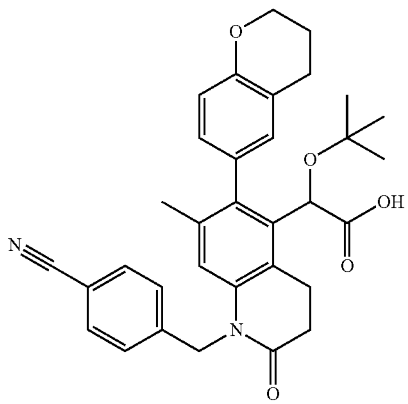 [SMILES: Cc1cc2c(c(C(OC(C)(C)C)C(=O)O)c1-c1ccc3c(c1)CCCO3)CCC(=O)N2Cc1ccc(C#N)cc1] | 2.04 *3 | 539 |

For those described as *1 to *7 in RT result, measurement was performed by changing the measurement conditions to the following LC/MS measurement conditions or MS measurement conditions.
*1: Column: ACQUITY UPLC BEH C18 (1.7 µm, i.d. 2.1×50 mm) (Waters)
Flow rate: 0.4 mL/min
UV detection wavelength: 200 to 400 nm
Mobile phase: [A]: 0.1% water, [B]: a 0.1% formic acid-containing acetonitrile solution
Gradient: a linear gradient of 10% to 90% solvent [B] was carried out in 8 minutes.
*2: Column: Shim-pack XR-ODS (2.2 µm, i.d. 50×3.0 mm) (Shimadzu)
Flow rate: 1.6 mL/min
UV detection wavelength: 254 nm
Mobile phase: [A]: a 0.1% formic acid-containing aqueous solution, [B]: a 0.1% formic acid-containing acetonitrile solution
Gradient: a linear gradient of 10% to 100% solvent [B] was carried out in 3 minutes, and 100% solvent [B] was kept for 0.5 minutes.
*3: Column: Waters X Bridge C18 (3.5 µM, i.d. 50×4.6 mm) (Waters)
Flow rate: 2.0 mL/min
UV detection wavelength: 254 nm
Mobile phase: [A]: a 0.05% TFA-containing aqueous solution, [B]: a 0.05%
TFA-containing acetonitrile solution
Gradient: a linear gradient of 5% to 100% solvent [B] was carried out in 1.6 minutes, and 100% solvent [B] was kept for 1.4 minutes.
Column Temperature: 40° C.
*4: FAB-MS measurement was only performed.
*5: Column: Waters X Bridge C18 (3.5 µm, i.d. 50×4.6 mm) (Waters)
Flow rate: 2.0 mL/min
UV detection wavelength: 254 nm
Mobile phase: [A]: a 0.01 M $NH_4HCO_3$ aqueous solution, [B]: acetonitrile
Gradient: a linear gradient of 5% to 100% solvent [B] was carried out in 1.6 minutes, and 100% solvent [B] was kept for 1.4 minutes.
Column Temperature: 40° C.
*6: Column: ACQUITY UPLC(R)BEH C18 (1.7 µm i.d. 2.1×50 mm) (Waters)
Flow rate: 0.4 mL/min
UV detection wavelength: 200 to 400 nm
Mobile phase: [A]: water, [B]: a 0.1% formic acid-containing acetonitrile solution
A linear gradient of 10% to 90% solvent [B] was carried out in 8 minutes.
*7: Column: Waters X Bridge C18 (3.5 µm, i.d. 50×4.6 mm) (Waters)
Flow rate: 2.0 mL/min
UV detection wavelength: 254 nm
Mobile phase: [A]: a 0.01 M $NH_4HCO_3$ aqueous solution, [B]: acetonitrile
Gradient: a linear gradient of 5% to 100% solvent [B] was carried out in 5 minutes, and 100% solvent [B] was kept for 1 minute.
Column Temperature: 40° C.
The biology assay of the compound of the present invention is described below.

Experimental Example 1

HIV Replication Inhibition Assay

HIV (HTLV-III B strain) persistent infected human T cell strain Molt-4 clone 8 was cultured in 10% Fetal Bovine Serum-containing RPMI-1640 medium and the supernatant was filtrated, then the virus titer was measured and the solution was stored at −80° C. Each anti-human immunodeficiency virus active substance was diluted with the above cultured medium to the designated concentration, which was dispensed into 96 well micro plate by 50 µL. Next, a MT-4 cell suspended liquid was dispensed by 100 µL ($2.5×10^4$ cells), then the above HIV-containing supernatant diluted with the above cultured medium was added thereto by 50 µL (60 pfu (plaque forming unit)).

The obtained mixture was cultured at 37° C. in $CO_2$ incubator for four days, then 3-(4,5-dimehylthiazole-2-yl)-2,5-diphenyltetrazolynium bromide (MTT) 5 mg/mL in PBS was added to each well by 30 µL, followed by 1 hr-cultivation. In this step, as formazan was precipitated by reduction of MTT in living cells, the cell supernatant was removed from all well by 150 µL, then a 150 µL of solution (10% Triton X-100 and 0.4% (v/v)-containing isopropanol) was added thereto, followed by shaking with a plate mixer, to elute formazan. The formazan was measured with a microreader at OD: 560 nm and 690 nm (wavelength) and the result was compared with the reference. EC50 means the compound concentration at which cell cytotoxicity by virus is inhibited 50%.

The result is shown below.

TABLE 87

| Compound No | EC50 (nM) |
|---|---|
| I-4 | 13 |
| I-6 | 7.8 |
| I-7 | 18 |
| I-11 | 21 |
| I-12 | 6.4 |
| I-14 | 19 |
| I-60 | 4 |
| I-66 | 4.5 |
| I-82 | 4.1 |
| I-121 | 5.2 |
| I-140 | 1.9 |
| I-145 | 1.2 |
| I-150 | 2.3 |
| I-168 | 3.9 |
| I-215 | 2.2 |
| I-263 | 2.5 |
| I-285 | 4.5 |
| I-300 | 1.7 |
| I-305 | 2 |
| I-310 | 4 |
| II-4 | 10 |
| II-5 | 38 |
| II-14 | 4.8 |
| II-17 | 2.5 |
| II-42 | 4.4 |

Experimental Example 2

CYP Inhibition Assay

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenedine hydroxylation (CYP3A4) as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 μmol/L ethoxyresorufin (CYP1A2), 100 μmol/L tolbutamide (CYP2C9), 50 μmol/L S-mephenytoin (CYP2C19), 5 μmol/L dextromethorphan (CYP2D6), 1 μmol/L terfenedine (CYP3A4); reaction time, 15 minutes; reaction temperature, 37° C.; enzyme, pooled human hepatic microsome 0.2 mg protein/mL; test drug concentration, 1, 5, 10, 20 μmol/L (four points).

Each five kinds of substrates, human hepatic microsome, and a test drug in 50 mmol/L Hepes buffer as a reaction solution was added to a 96-well plate as the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tolbutamide hydroxide (CYP2C9 metabolite), mephenytoin 4' hydroxide (CYP2C19 metabolite), dextrorphan (CYP2D6 metabolite), and terfenadine alcohol (CYP3A4 metabolite) were quantified by LC/MS/MS.

A reaction system containing only DMSO which is a solvent for dissolving a drug was adopted as a control (100%), and the remaining activity (%) was calculated, then $IC_{50}$ was calculated by reverse presumption with a logistic model using a concentration and an inhibition rate.

As a result, all $IC_{50}$ of Compound I-2 to I-10 and II-4 for the activity of CYP1A2, CYP2C19, CYP2D6, CYP3A4 was 20 μM or more Experimental Example 3

CYP3A4 Fluorescent MBI Test

The CYP3A4 fluorescent MBI test is to investigate the enhancement of CYP3A4 inhibition of a compound by a metabolism reaction. 7-Benzyloxytrifluoromethylcoumarin (7-BFC) is debenzylated by the CYP3A4 enzyme to produce 7-hydroxytrifluoromethylcoumarin (HFC), a metabolite emitting fluorescent light. The test was performed using 7-HFC-producing reaction as an index, The reaction conditions were as follows: substrate 5.6 μmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 pmol/mL, at reaction 6.25 pmol/mL (at 10-fold dilution); test drug concentration, 0.625, 1.25, 2.5, 5, 10, 20 μmol/L (six points).

An enzyme in a K-Pi buffer (pH 7.4) and a test drug solution as a pre-reaction solution were added to a 96-well plate at the composition of the pre-reaction, a part of it was transferred to another 96-well plate so that it was 1/10 diluted by a substrate in a K-Pi buffer, NADPH as a co-factor was added to initiate a reaction as an index (without preincubation) and, after a predetermined time of a reaction, acetonitrile/0.5 mol/L Tris (trishydroxyaminomethane)=4/1 was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane)=4/1 was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving a drug to a reaction system was adopted as a control (100%), remaining activity (%) was calculated at each concentration of a test drug added as the solution, and $IC_{50}$ was calculated by reverse presumption by a logistic model using a concentration and an inhibition rate. A case where the difference of $IC_{50}$ values is 5 μM or more was defined as (+) and, a case where the difference is 3 μM or less was defined as (−).

As a result, compound I-31, I-9 and II-4 were (−).

Experimental Example 4

Metabolism Stability Test

Commercially available pooled human hepatic microsomes and a test compound were reacted for a constant time, then a remaining rate was calculated by comparing a reacted sample and an unreacted sample, thereby a degree of metabolism of the test compound in liver was assessed.

A reaction was performed (oxidative reaction) at 37° C. for 0 minute or 30 minutes in the presence of 1 mmol/L NADPH in 0.2 mL of a buffer (50 mmol/L Tris-HCl, pH 7.4, 150 mmol/L potassium chloride, 10 mmol/L magnesium chloride) containing 0.5 mg protein/mL of human liver microsomes. After the reaction, 50 μl, of the reaction solution was added to 100 μL of a methanol/acetonitrile=1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%. Hydrolysis reaction was performed in the absence of NADPH and glucuronidation reaction was in the presence of 5 mM UDP-glucuronic acid in place of NADPH, followed by similar operations.

As a result, the amount of compound I-6 in liver microsomes of human and rat was 79% and 58%, respectively.

Experimental Example 5

Solubility Test

The solubility of each compound was determined under 1% DMSO addition conditions. A 10 mmol/L solution of the compound was prepared with DMSO, and 6 μL of the solution was added to 594 μL of an artificial intestinal juice (water and a 118 mL solution of 0.2 mol/L NaOH reagent are added to 250 mL of 0.2 mol/L potassium dihydrogen phosphate reagent to reach 1000 mL) with a pH of 6.8. The mixture is left standing for 16 hours at 25° C., and the mixture is vacuum-filtered. The filtrate is two-fold diluted with methanol/water=1/1 (v/v), and the compound concentration in the filtrate is measured with HPLC or LC/MS/MS by the absolute calibration method.

As a result, the solubility of each compound I-2 to I-4, I-6, I-10 and II-4 in the artificial intestinal juice was 50 μM or more.

Experimental Example 6

Fluctuation Ames Test

The mutagenicity of the compound of the present invention was assayed.

20 μL of freezing-stored rat typhoid bacillus (*Salmonella typhimurium* TA98 strain, TA100 strain) was inoculated on 10 mL of a liquid nutrient medium (2.5% Oxoid nutrient broth No. 2), and this was cultured before shaking at 37° C. for 10 hours. 9 mL of a bacterial solution of the TA98 strain was centrifuged (2000×g, 10 minutes) to remove a culturing solution. The bacteria was suspended in F buffer ($K_2HPO_4$: 3.5 g/L, $KH_2PO_4$: 1 g/L, $(NH_4)_2SO_4$: 1 g/L, trisodium citrate dehydrate: 0.25 g/L, $MgSO_4.7H_2O$: 0.1 g/L), and the suspension was added to 110 mL of an Exposure medium (Micro F buffer containing Biotin: 8 μg/mL, histidine: 0.2 μg/mL, glucose: 8 mg/mL). The TA100 strain was added to 120 mL of the Exposure medium per 3.16 mL of the bacterial solution to prepare a test bacterial solution. Each 12 μL of a test substance DMSO solution (several stage dilution from maximum dose 50 mg/mL at 2- to 3-fold ratio), DMSO as a negative control, 50 μg/mL of 4-nitroquinoline-1-oxide DMSO solution for the TA98 strain, 0.25 μg/mL of 2-(2-furyl)-3-(5-nitro-2-furyl) acrylamide DMSO solution for the TA100 strain each under the non-metabolism activating condition, 40 μg/mL of 2-aminoanthracene DMSO solution for the TA98 strain, 20 μg/mL of 2-aminoanthracene DMSO solution for the TA100 strain each under the metabolism activating condition all as a positive control, and 588 μL of the test bacterial solution (a mixed solution of 498 μL of the test bacterial solution and 90 μL of S9 mix under the metabolism activating condition) were mixed, and this was shaking-cultured at 37° C. for 90 minutes. 460 μL of the bacterial solution exposed to the test substance was mixed with 2300 μL of an Indicator medium (Micro F buffer containing biotin: 8 μg/mL, histidine 0.2 μg/mL, glucose: 8 mg/mL, Bromo Cresol Purple: 37.5 μg/mL), each 50 μL was dispensed into microplate 48 wells/ dose, and this was subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and was assessed by comparing with a negative control group. (−) means that mutagenicity is negative and (+) is positive.

As a result, the mutagenicity of compound I-6, I-11, I-12, and II-3 was negative.

Experimental Example 7

BA Test

Materials and methods for studies on oral absorption
(1) Animal: mouse or SD rats are used.
(2) Breeding conditions: mouse or SD rats are allowed to freely take solid feed and sterilized tap water.
(3) Dose and grouping: orally or intravenously administered at a predetermined dose; grouping is as follows (Dose depends on the compound)
Oral administration: 1 to 30 mg/kg (n=2 to 3)
Intravenous administration: 0.5 to 10 mg/kg (n=2 to 3)
(4) Preparation of dosing solution: for oral administration, in a solution or a suspension state; for intravenous administration, in a solubilized state
(5) Administration method: in oral administration, forcedly administer into ventriculus with oral probe; in intravenous administration, administer from caudal vein with a needle-equipped syringe
(6) Evaluation items: blood is collected over time, and the plasma concentration of drug is measured by LC/MS/MS
(7) Statistical analysis: regarding the transition of the plasma concentration, the area under the plasma concentration-time curve (AUC) is calculated by non-linear least squares program WinNonlin (Registered trademark), and the bioavailability (BA) is calculated from the AUCs of the oral administration group and intravenous administration group Experimental Example 8 hERG Test

For the purpose of assessing risk of an electrocardiogram QT interval prolongation, effects on delayed rectifier K+ current ($I_{Kr}$), which plays an important role in the ventricular repolarization process of the compound of the present invention, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds was recorded. After the generated current was stabilized, extracellular solution (NaCl: 135 mmol/L, KCl: 5.4 mmol/L, $NaH_2PO_4$: 0.3 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazineethanesulfonic acid): 10 mmol/L, pH=7.4) in which the test compound had been dissolved at an objective concentration was applied to the cell under the room temperature condition for 10 minutes. From the recording $I_{Kr}$, an absolute value of the tail peak current was measured based on the current value at the resting membrane potential using an analysis software (DataXpress ver. 1, Molecular Devices Corporation). Further, the inhibition relative to the tail peak current before application of the test substance was calculated, and compared with the vehicle-applied group (0.1% dimethyl sulfoxide solution) to assess influence of the test substance on $I_{Kr}$.

As a result, the inhibition ratio of compound I-6 and II-4 was 3.5% and 3.8%, respectively.

Test Example 9

Powder Solubility Test

Appropriate amounts of the test substances are put into appropriate containers. To the respective containers are added 200 µL of JP-1 fluid (sodium chloride 2.0 g, hydrochloric acid 7.0 mL and water to reach 1000 mL), 200 µL of JP-2 fluid (phosphate buffer (pH 6.8) 500 mL and water 500 mL), and 200 µl of 20 mmol/L TCA (sodium taurocholate)/JP-2 fluid (TCA 1.08 g and JP-2 fluid to reach 100 mL). In the case that all amount of the test compound is dissolved after the addition of the test fluid, the test compound is added as appropriate. The containers are sealed, and shaken for 1 hour at 37° C. The mixtures are filtered, and 1004 of methanol is added to each of the filtrate (100 µL) so that the filtrates are two-fold diluted. The dilution ratio may be changed if necessary. The dilutions are observed for bubbles and precipitates, and then the containers are sealed and shaken. Quantification is performed by HPLC with an absolute calibration method.

Formulation Example 1

Tablet

| Compound of the present invention | 15 mg |
|---|---|
| Lactose | 15 mg |
| Calcium Stearate | 3 mg |

The above ingredients other than Calcium Stearate are uniformly mixed, crushed, granule, dried to prepare granules of suitable size. After addition of Calcium Stearate, the mixture is compressed to prepare tables.

Formulation Example 2

Capsules

| Compound of the present invention | 10 mg |
|---|---|
| Magnecium Stearate | 10 mg |
| Lactose | 80 mg |

The above ingredients are uniformly mixed to prepare powdered medicine as powder or fine particles, which are put into capsule containers to prepare capsules.

Formulation Example 3

Granules

| Compound of the present invention | 30 g |
|---|---|
| Lactose | 265 g |
| Magnecium Stearate | 5 g |

The above ingredients are fully mixed, compressed, crushed, selected the size to prepare granules of suitable size.

Industrial Applicability

The compound of the present invention may be a medicament useful as a therapeutic agent for virus infection disease such as AIDS.

The invention claimed is:
1. A compound of formula (II) or a pharmaceutically acceptable salt thereof:

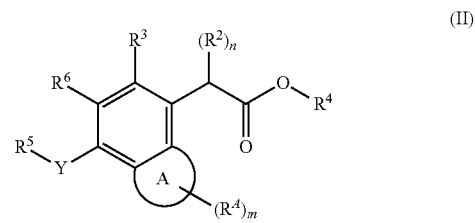

wherein
$R^2$ is tert-Butoxy,
n is 1,
$R^3$ is a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group,
$R^4$ is a hydrogen atom,
$R^5$ is a hydrogen atom, hydroxy, formyl, carboxy, carbamoyl, carbamoyloxy, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted monoalkylcarbamoyl, substituted or unsubstituted dialkylcarbamoyl, substituted or unsubstituted monoalkylcarbamoyloxy, substituted or unsubstituted dialkylcarbamoyloxy, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclicoxy, substituted or unsubstituted nonaromatic carbocyclicoxy, substituted or unsubstituted aromatic heterocyclicoxy, substituted or unsubstituted nonaromatic heterocyclicoxy, substituted or unsubstituted aromatic carbocyclic sulfanyl, substituted or unsubstituted nonaromatic carbocyclic sulfanyl, substituted or unsubstituted aromatic heterocyclic sulfanyl, substituted or unsubstituted nonaromatic heterocyclic sulfanyl, substituted or unsubstituted aromatic carbocyclic carbonyl, substituted or unsubstituted nonaromatic carbocyclic carbonyl, substituted or unsubstituted aromatic heterocyclic carbonyl, substituted or unsubstituted nonaromatic heterocyclic carbonyl, substituted or unsubstituted aromatic carbocyclic oxycarbonyl, substituted or unsubstituted nonaromatic carbocyclic oxycarbonyl, substituted or unsubstituted aromatic heterocyclic oxycarbonyl, substituted or unsubstituted nonaromatic heterocyclic oxycarbonyl, substituted or unsubstituted aromatic carbocyclic carbamoyl, substituted or unsubstituted nonaromatic carbocyclic carbamoyl, substituted or unsubstituted aromatic heterocyclic carbamoyl, substituted or unsubstituted nonaromatic heterocyclic carbamoyl, or —$NR^{51}R^{52}$ ($R^{51}$ and $R^{52}$ are each independently a hydrogen atom, formyl, carbamoyl, carboxy, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkylcarbamoyl, substituted or unsubstituted alkenylcarbamoyl, substituted or unsubstituted alkynylcarbamoyl, substituted or unsubstituted alkyloxycarbonyl, substituted or unsubstituted alkenyloxycarbonyl, substituted or unsubstituted alkynyloxycarbonyl, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclic carbonyl, substituted or unsubstituted nonaromatic carbocyclic carbonyl, substituted or unsubstituted aromatic heterocyclic carbonyl, substituted or unsubstituted nonaromatic heterocyclic carbonyl, substituted or unsubstituted aromatic carbocyclic carbamoyl, substituted or unsubstituted nonaromatic carbocyclic carbamoyl, substituted or unsubstituted aromatic heterocyclic carbamoyl, substituted or unsubstituted nonaromatic heterocyclic carbamoyl, substituted or unsubstituted aromatic carbocyclic oxycarbonyl, substituted or unsubstituted nonaromatic carbocyclic oxycarbonyl, substituted or unsubstituted aromatic heterocyclic oxycarbonyl, or substituted or unsubstituted nonaromatic heterocyclic oxycarbonyl), Y is a single bond, alkylene, alkenylene, or alkynylene, when $R^5$ is a hydrogen atom, substituted or unsubstituted alkyl, substituted or unsubstituted alkenyl, or substituted or unsubstituted alkynyl, Y is a single bond, $R^6$ is a hydrogen atom, halogen, cyano, substituted or unsubstituted alkyl, substituted or unsubstituted alkenyl, substituted or unsubstituted alkynyl, a substituted or unsubstituted nonaromatic carbocyclic group, or substituted or unsubstituted alkyloxy, ring A is an aromatic heterocyclic ring, or a nonaromatic heterocyclic ring, m is an integer of 0 to 4, $R^A$ is each independently halogen, cyano, nitro, oxo, or —$X^A$—$R^{A1}$, wherein $X^A$ is a single bond, —O—, —S—, —$NR^{A2}$—, —CO—, —$SO_2$—, —O—CO—, —CO—O—, —$NR^{A2}$—CO—, —CO—$NR^{A2}$—, —$NR^{A2}$—CO—O—, —CO—O—$NR^{A2}$—, —O—CO—$NR^{A2}$—, —$NR^{A2}$—O—CO—, —CO—$NR^{A2}$—O—, —O—$NR^{A2}$—CO—, —$NR^{A2}$—CO—$NR^{A3}$—, —$NR^{A2}$—$SO_2$—, or —$SO_2$—$NR^{A2}$—, $R^{A1}$ is a hydrogen atom, substituted or unsubstituted alkyl, substituted or unsubstituted alkenyl, substituted or unsubstituted alkynyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, $R^{A2}$ and $R^{A3}$ are each independently a hydrogen atom, substituted or unsubstituted alkyl, substituted or unsubstituted alkenyl, or substituted or unsubstituted alkynyl, and when $X^A$ is —$NR^{A2}$—, —CO—$NR^{A2}$—, CO—O—$NR^{A2}$—, —O—CO—$NR^{A2}$—, or —$SO_2$—$NR^{A2}$—, $R^{A1}$ and $R^{A2}$ may be taken together with an adjacent nitrogen atom to form a substituted or unsubstituted aromatic heterocyclic group, or a substituted or unsubstituted nonaromatic heterocyclic group.

2. The compound or pharmaceutically acceptable salt to claim 1, wherein ring A is a five-membered ring or a six-membered ring.

3. The compound or pharmaceutically acceptable salt according to claim 1, wherein $R^A$ is halogen, cyano, oxo or —$X^A$—$R^{A1}$, where $X^A$ is a single bond, —O—, —S—, —$NR^{A2}$—, —CO—, —$SO_2$—, $NR^{A2}$—CO—, —CO—$NR^{A2}$—, —$NR^{A2}$—CO—$NR^{A3}$—, —$NR^{A2}$—$SO_2$—, or —$SO_2$—$NR^{A2}$—, $R^{A1}$ is a hydrogen atom, substituted or unsubstituted alkyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, and $R^{A2}$ and $R^{A3}$ are each independently a hydrogen atom or substituted or unsubstituted alkyl.

4. The compound or pharmaceutically acceptable salt according to claim 1, wherein $R^6$ is substituted or unsubstituted alkyl, and ring A is a five-membered or six-membered aromatic heterocyclic ring or nonaromatic heterocyclic ring.

5. The compound or pharmaceutically acceptable salt according to claim 1, wherein $R^6$ is substituted or unsubstituted alkyl, ring A is a five-membered or six-membered aromatic heterocyclic ring or nonaromatic heterocyclic ring, and m is any integer of 0 to 4, $R^5$ is a hydrogen atom, substituted or unsubstituted alkyl, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclic carbamoyl, substituted or unsubstituted nonaromatic carbocyclic carbamoyl, or —$NR^{51}R^{52}$, where $R^{51}$ is substituted or unsubstituted aromatic carbocyclic carbonyl or substituted or unsubstituted nonaromatic carbocyclic carbonyl, and $R^{52}$ is a hydrogen atom, Y is a single bond, $R^A$ is each independently halogen, cyano, oxo or $X^A$—$R^{A1}$, where $X^A$ is a single bond, —O—, —S—,—$NR^{A2}$—, —CO—, —$SO_2$—, $NR^{A2}$—CO—, —CO—$NR^{A2}$—, —$NR^{A2}$—CO—$NR^{A3}$—, —$NR^{A2}$—$SO_2$—, or —$SO_2$—$NR^{A2}$—, $R^{A1}$ is a hydrogen atom, substituted or unsubstituted alkyl, a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group, and $R^{42}$ and $R^{43}$ are each independently a hydrogen atom or substituted or unsubstituted alkyl, and $R^3$ is substituted or unsubstituted phenyl, substituted or unsubstituted cycloalkenyl, substituted or unsubstituted benzofuryl, substituted or unsubstituted benzodioxolyl, substituted or unsubstituted benzodioxanyl, substituted or unsubstituted dihydrobenzofuryl, substituted or unsubstituted chromanyl, or substituted or unsubstituted benzomorpholinyl.

6. The compound or pharmaceutically acceptable salt according to claim 1, wherein $R^6$ is substituted or unsubstituted alkyl.

7. The compound or pharmaceutically acceptable salt according to claim 1, wherein $R^5$ is a hydrogen atom, substituted or unsubstituted alkyl, a substituted or unsubstituted aromatic carbocyclic group, a substituted or unsubstituted nonaromatic carbocyclic group, a substituted or unsubstituted aromatic heterocyclic group, a substituted or unsubstituted nonaromatic heterocyclic group, substituted or unsubstituted aromatic carbocyclic carbamoyl, or —$NR^{51}H$, where $R^{51}$ is substituted or unsubstituted aromatic carbocyclic carbonyl.

8. The compound or pharmaceutically acceptable salt according to claim 7, wherein $R^5$ is a substituted or unsubstituted aromatic carbocyclic group, a substituted or unsubstituted nonaromatic carbocyclic group, a substituted or unsubstituted aromatic heterocyclic group, or a substituted or unsubstituted nonaromatic heterocyclic group.

9. The compound or pharmaceutically acceptable salt according to claim 1, wherein Y is a single bond.

10. The compound or pharmaceutically acceptable salt according to claim 1, wherein $R^3$ is substituted or unsubstituted phenyl, substituted or unsubstituted cycloalkenyl, substituted or unsubstituted benzofuryl, substituted or unsubstituted benzodioxolyl, substituted or unsubstituted benzodioxanyl, substituted or unsubstituted dihydrobenzofuryl, substituted or unsubstituted chromanyl, or substituted or unsubstituted benzomorpholinyl.

11. A pharmaceutical composition, comprising:
the compound or pharmaceutically acceptable salt according to claim 1; and
a pharmaceutically acceptable excipient.

12. The pharmaceutical composition according to claim 11, having anti-HIV action.

* * * * *